(12) United States Patent
Diedrich et al.

(10) Patent No.: US 11,795,226 B2
(45) Date of Patent: Oct. 24, 2023

(54) BISPECIFIC CD16-BINDING MOLECULES AND THEIR USE IN THE TREATMENT OF DISEASE

(71) Applicant: MacroGenics, Inc., Rockville, MD (US)

(72) Inventors: Gundo Diedrich, North Potomac, MD (US); Liqin Liu, Germantown, MD (US); Hua Watson Li, Clarksburg, MD (US); Leslie S. Johnson, Rockville, MD (US)

(73) Assignee: MacroGenics, Inc., Rockville, MD (US)

( * ) Notice: Subject to any disclaimer, the term of this patent is extended or adjusted under 35 U.S.C. 154(b) by 531 days.

(21) Appl. No.: 16/771,377

(22) PCT Filed: Dec. 6, 2018

(86) PCT No.: PCT/US2018/064204
§ 371 (c)(1),
(2) Date: Jun. 10, 2020

(87) PCT Pub. No.: WO2019/118266
PCT Pub. Date: Jun. 20, 2019

(65) Prior Publication Data
US 2021/0171630 A1    Jun. 10, 2021

Related U.S. Application Data

(60) Provisional application No. 62/597,800, filed on Dec. 12, 2017.

(51) Int. Cl.
C07K 16/00 (2006.01)
C12P 21/08 (2006.01)
A61K 39/395 (2006.01)
A61K 39/40 (2006.01)
C07K 16/28 (2006.01)
A61P 31/18 (2006.01)
A61P 35/00 (2006.01)
C07K 16/10 (2006.01)
C07K 16/32 (2006.01)

(52) U.S. Cl.
CPC ............ *C07K 16/283* (2013.01); *A61P 31/18* (2018.01); *A61P 35/00* (2018.01); *C07K 16/1027* (2013.01); *C07K 16/1063* (2013.01); *C07K 16/2803* (2013.01); *C07K 16/32* (2013.01); *C07K 2317/20* (2013.01); *C07K 2317/24* (2013.01); *C07K 2317/31* (2013.01); *C07K 2317/33* (2013.01); *C07K 2317/35* (2013.01); *C07K 2317/52* (2013.01); *C07K 2317/565* (2013.01); *C07K 2317/626* (2013.01); *C07K 2317/732* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,565,332 A | 10/1996 | Hoogenboom et al. |
| 5,580,717 A | 12/1996 | Dower et al. |
| 5,733,743 A | 3/1998 | Johnson et al. |
| 5,807,715 A | 9/1998 | Morrison et al. |
| 5,821,337 A | 10/1998 | Carter et al. |
| 5,843,749 A | 12/1998 | Maisonpierre et al. |

(Continued)

FOREIGN PATENT DOCUMENTS

| | | |
|---|---|---|
| EP | 0519596 A1 | 12/1992 |
| EP | 1868650 B1 | 12/2007 |

(Continued)

OTHER PUBLICATIONS

Janeway Jr et al., Immunology, 3rd Edition, 1997 Garland Publishing Inc., pp. 3:1-3:11. (Year: 1997).*

(Continued)

*Primary Examiner* — Chun W Dahle
(74) *Attorney, Agent, or Firm* — MEDLER FERRO WOODHOUSE & MILLS

(57) ABSTRACT

The present invention is directed to molecules (e.g., an antibody, a diabody, an scFv, an antibody, a TandAb, etc.) capable of binding an epitope of human CD16 (a "CD16 Binding Molecule"). The present invention is further directed to CD 16 Binding Molecules that are capable of binding an epitope of human CD16 and one or more epitope(s) of a Disease Antigen ("DA") (e.g., a "CD16×DA Binding Molecule"). The present invention is particularly directed to such CD16×DA Binding Molecules that are antibodies, or that comprise an Epitope Binding Domain thereof, or are diabodies (including DART® diabodies), bispecific antibodies, TandAbs, other multispecific binding molecules (e.g., trivalent TRIDENT™ molecules), etc. The invention particularly concerns CD16×DA Binding Molecules that are capable of binding a Disease Antigen that is a Cancer Antigen or a Pathogen-Associated Antigen in addition to being able to bind CD 16. The invention particularly concerns the use of such CD16 and CD16×DA Binding Molecules in the treatment of cancer and pathogen-associated diseases. The present invention is also directed to pharmaceutical compositions that comprise such molecule(s).

20 Claims, 38 Drawing Sheets
Specification includes a Sequence Listing.

(56) References Cited

U.S. PATENT DOCUMENTS

| | | |
|---|---|---|
| 5,866,692 A | 2/1999 | Shitara et al. |
| 5,997,867 A | 12/1999 | Waldmann et al. |
| 6,054,297 A | 4/2000 | Carter et al. |
| 6,180,377 B1 | 1/2001 | Morgan et al. |
| 6,265,150 B1 | 7/2001 | Terstappen et al. |
| 6,277,375 B1 | 8/2001 | Ward |
| 6,331,415 B1 | 12/2001 | Cabilly et al. |
| 7,083,784 B2 | 8/2006 | Dall'Acqua et al. |
| 7,112,324 B1 | 9/2006 | Dorken et al. |
| 7,148,038 B2 | 12/2006 | Mather |
| 7,217,797 B2 | 5/2007 | Hinton et al. |
| 7,405,061 B2 | 7/2008 | Mather et al. |
| 7,527,969 B2 | 5/2009 | Mather et al. |
| 7,569,672 B2 | 8/2009 | Mather et al. |
| 7,572,895 B2 | 8/2009 | Mather et al. |
| 7,572,896 B2 | 8/2009 | Mather et al. |
| 7,666,424 B2 | 2/2010 | Cheung et al. |
| 7,737,258 B2 | 6/2010 | Cheung |
| 7,740,845 B2 | 6/2010 | Cheung |
| 7,892,554 B2 | 2/2011 | Marks et al. |
| 8,044,180 B2 | 10/2011 | Koenig et al. |
| 8,088,376 B2 | 1/2012 | Chamberlain et al. |
| 8,133,982 B2 | 3/2012 | Johnson et al. |
| 8,148,154 B2 | 4/2012 | Cheung et al. |
| 8,173,424 B2 | 5/2012 | Marks et al. |
| 8,187,593 B2 | 5/2012 | Koenig et al. |
| 8,193,318 B2 | 6/2012 | Koenig et al. |
| 8,350,011 B2 | 1/2013 | Cartlidge et al. |
| 8,414,892 B2 | 4/2013 | Cheung |
| 8,501,471 B2 | 8/2013 | Cheung |
| 8,530,627 B2 | 9/2013 | Koenig et al. |
| 8,669,349 B2 | 3/2014 | Johnson et al. |
| 8,778,339 B2 | 7/2014 | Tuaillon et al. |
| 8,779,098 B2 | 7/2014 | Mather et al. |
| 8,784,808 B2 | 7/2014 | Johnson et al. |
| 8,795,667 B2 | 8/2014 | Johnson et al. |
| 8,802,091 B2 | 8/2014 | Johnson et al. |
| 8,802,093 B2 | 8/2014 | Johnson et al. |
| 8,858,942 B2 | 10/2014 | Cartlidge et al. |
| 8,946,387 B2 | 2/2015 | Koenig et al. |
| 8,968,730 B2 | 3/2015 | Koenig et al. |
| 8,974,792 B2 | 3/2015 | Marks et al. |
| 8,993,730 B2 | 3/2015 | Johnson et al. |
| 9,062,110 B2 | 6/2015 | Cheung |
| 2002/0147311 A1 | 10/2002 | Gillies et al. |
| 2003/0049607 A1 | 3/2003 | Greener et al. |
| 2003/0175273 A1 | 9/2003 | Shitara et al. |
| 2006/0166291 A1 | 7/2006 | Mather |
| 2006/0172349 A1 | 8/2006 | Mather et al. |
| 2006/0172350 A1 | 8/2006 | Mather et al. |
| 2007/0004909 A1 | 1/2007 | Johnson et al. |
| 2007/0071675 A1 | 3/2007 | Wu et al. |
| 2007/0071763 A1 | 3/2007 | Burnie et al. |
| 2007/0148164 A1 | 6/2007 | Farrington et al. |
| 2009/0041789 A1 | 2/2009 | Elsaesser-Beile et al. |
| 2009/0060910 A1 | 3/2009 | Johnson et al. |
| 2009/0265797 A1 | 10/2009 | Goetsch et al. |
| 2010/0143245 A1 | 6/2010 | Cheung |
| 2010/0174053 A1 | 7/2010 | Johnson et al. |
| 2011/0081347 A1 | 4/2011 | Gorlatov |
| 2011/0097323 A1 | 4/2011 | Johnson et al. |
| 2011/0117089 A1 | 5/2011 | Johnson et al. |
| 2011/0206672 A1 | 8/2011 | Little et al. |
| 2011/0311522 A1 | 12/2011 | Chen et al. |
| 2012/0009186 A1 | 1/2012 | Koenig et al. |
| 2012/0034221 A1 | 2/2012 | Bonvini et al. |
| 2012/0141476 A1 | 6/2012 | Johnson et al. |
| 2012/0294796 A1 | 11/2012 | Johnson et al. |
| 2013/0149236 A1 | 6/2013 | Johnson et al. |
| 2013/0295121 A1 | 11/2013 | Johnson et al. |
| 2014/0017237 A1 | 1/2014 | Johnson et al. |
| 2014/0099318 A1 | 4/2014 | Huang et al. |
| 2014/0255407 A1 | 9/2014 | Koenig |
| 2015/0175697 A1 | 6/2015 | Bonvini et al. |
| 2016/0280795 A1 | 9/2016 | Wang |

FOREIGN PATENT DOCUMENTS

| | | |
|---|---|---|
| EP | 2158221 B1 | 3/2010 |
| EP | 2247304 B1 | 11/2010 |
| EP | 2252631 B1 | 11/2010 |
| EP | 2282770 B1 | 2/2011 |
| EP | 2371866 B1 | 10/2011 |
| EP | 2376109 B1 | 10/2011 |
| EP | 2542256 B1 | 1/2013 |
| EP | 2601216 B1 | 6/2013 |
| EP | 2714079 B2 | 4/2014 |
| EP | 2714733 B1 | 4/2014 |
| EP | 2786762 B1 | 10/2014 |
| EP | 2839842 A1 | 2/2015 |
| EP | 2840091 A1 | 2/2015 |
| WO | WO 1991/003493 | 3/1991 |
| WO | WO 1992/022583 | 12/1992 |
| WO | WO 1993/011161 | 6/1993 |
| WO | WO 1995/015171 | 6/1995 |
| WO | WO 1998/002463 | 1/1998 |
| WO | WO 1998/023289 | 6/1998 |
| WO | WO 1999/055367 | 11/1999 |
| WO | WO 1999/057150 | 11/1999 |
| WO | WO 2001/000245 | 1/2001 |
| WO | WO 2001/077342 | 10/2001 |
| WO | WO 2002/002781 | 1/2002 |
| WO | WO 2003/012069 | 2/2003 |
| WO | WO 2003/024191 | 3/2003 |
| WO | WO 2003/025018 | 3/2003 |
| WO | WO 2003/032814 | 4/2003 |
| WO | WO 2003/087340 | 10/2003 |
| WO | WO 2003/093443 | 11/2003 |
| WO | WO 2004/001381 | 12/2003 |
| WO | WO 2004/043239 | 5/2004 |
| WO | WO 2004/106381 | 12/2004 |
| WO | WO 2005/028498 | 3/2005 |
| WO | WO 2005/070966 | 8/2005 |
| WO | WO 2005/121179 | 12/2005 |
| WO | WO 2006/044410 | 4/2006 |
| WO | WO 2006/076584 | 7/2006 |
| WO | WO 2006/083852 | 8/2006 |
| WO | WO 2006/084075 | 8/2006 |
| WO | WO 2006/084078 | 8/2006 |
| WO | WO 2006/084092 | 8/2006 |
| WO | WO 2006/084226 | 8/2006 |
| WO | WO 2006/107617 | 10/2006 |
| WO | WO 2006/107786 | 10/2006 |
| WO | WO 2006/113665 | 10/2006 |
| WO | WO 2007/024715 | 3/2007 |
| WO | WO 2007/046893 | 4/2007 |
| WO | WO 2007/075270 | 7/2007 |
| WO | WO 2007/110205 | 10/2007 |
| WO | WO 2007/146968 | 12/2007 |
| WO | WO 2008/003103 | 1/2008 |
| WO | WO 2008/003116 | 1/2008 |
| WO | WO 2008/019290 | 2/2008 |
| WO | WO 2008/024188 | 2/2008 |
| WO | WO 2008/027236 | 3/2008 |
| WO | WO 2008/116219 | 9/2008 |
| WO | WO 2008/146911 | 12/2008 |
| WO | WO 2008/157379 | 12/2008 |
| WO | WO 2009/018386 | 2/2009 |
| WO | WO 2010/027797 | 3/2009 |
| WO | WO 2009/058492 | 5/2009 |
| WO | WO 2009/123894 | 10/2009 |
| WO | WO 2009/132876 | 11/2009 |
| WO | WO 2009/151717 | 12/2009 |
| WO | WO 2010/028795 | 3/2010 |
| WO | WO 2010/028796 | 3/2010 |
| WO | WO 2010/028797 | 3/2010 |
| WO | WO 2010/033279 | 3/2010 |
| WO | WO 2010/080538 | 7/2010 |
| WO | WO 2010/108127 | 9/2010 |
| WO | WO 2010/136172 | 12/2010 |
| WO | WO 2011/034660 | 3/2011 |
| WO | WO 2011/086091 | 7/2011 |
| WO | WO 2011/109400 | 9/2011 |
| WO | WO 2011/133886 | 10/2011 |
| WO | WO 2011/143545 | 11/2011 |

(56) References Cited

FOREIGN PATENT DOCUMENTS

| | | |
|---|---|---|
| WO | WO 2011/147986 | 12/2011 |
| WO | WO 2012/009544 | 1/2012 |
| WO | WO 2012/018687 | 2/2012 |
| WO | WO 2012/030904 | 3/2012 |
| WO | WO 2012/058768 | 5/2012 |
| WO | WO 2012/143524 | 10/2012 |
| WO | WO 2012/147713 | 11/2012 |
| WO | WO 2012/156430 | 11/2012 |
| WO | WO 2012/162067 | 11/2012 |
| WO | WO 2012/162068 | 11/2012 |
| WO | WO 2012/162583 | 11/2012 |
| WO | WO 2013/003652 | 1/2013 |
| WO | WO 2013/006544 | 1/2013 |
| WO | WO 2013/006867 | 1/2013 |
| WO | WO 2013/013700 | 1/2013 |
| WO | WO 2013/041687 | 3/2013 |
| WO | WO 2013/070565 | 5/2013 |
| WO | WO 2013/119903 | 8/2013 |
| WO | WO 2013/163427 | 10/2013 |
| WO | WO 2013/174873 | 11/2013 |
| WO | WO 2013/192589 | 12/2013 |
| WO | WO 2014/022540 | 2/2014 |
| WO | WO 2014/063059 | 4/2014 |
| WO | WO 2014/072888 | 5/2014 |
| WO | WO 2014/159940 | 10/2014 |
| WO | WO 2015/021089 | 2/2015 |
| WO | WO 2015/026892 | 2/2015 |
| WO | WO 2015/026894 | 2/2015 |
| WO | WO 2015/184207 | 3/2015 |
| WO | WO 2015/048610 | 4/2015 |
| WO | WO 2015/184203 | 12/2015 |
| WO | WO 2016/036937 | 3/2016 |
| WO | WO 2016/154101 | 4/2016 |
| WO | WO 2016/109668 | 7/2016 |
| WO | WO 2016/149695 | 9/2016 |
| WO | WO 2016/149698 | 9/2016 |
| WO | WO 2016/149710 | 9/2016 |
| WO | WO 2016/196975 | 12/2016 |
| WO | WO 2017/011413 | 1/2017 |
| WO | WO 2017/011414 | 1/2017 |
| WO | WO 2017/062604 | 4/2017 |
| WO | WO 2017/165464 | 9/2017 |
| WO | WO 2019/118266 | 6/2019 |
| WO | WO 2019/222104 | 11/2019 |

OTHER PUBLICATIONS

Edwards et al. J. Mol. Biol., 2003, 334:103-118. (Year: 2003).*
Lloyd et al. Protein Engineering Design & Selection 2009, 22;3:159-168. (Year: 2009).*
Goel et al. The Journal of Immunology, 2004, 173:7358-7367. (Year: 2004).*
Kanyavuz et al. Nature Review Immunology, 19: 355-368. (Year: 2019).*
Abdulghani, J. et al. (2010) "TRAIL Receptor Signaling and Therapeutics," Expert Opin. Ther. Targets 14(10):1091-1108.
Adenis, A. et al. (2003) "Inhibitors of Epidermal Growth Factor Receptor and Colorectal Cancer," Bull. Cancer, 90 Spec No. S228-S232 (Abstract Only).
Akcakanat, A. et al. (2006) "Heterogeneous Expression Of GAGE, NY-ESO-1, MAGE-A and SSX Proteins in Esophageal Cancer: Implications for Immunotherapy," Int. J. Cancer, 118(1):123-128.
Alhussaini, M. et al. (2015) "Targeting CD123 In AML Using A T-Cell Directed Dual-Affinity Re-Targeting (DART®) Platform," Blood pii: blood-2014-05-575704.
Almqvist, Y. (2006) "In vitro and in vivo Characterization of 177Lu-huA33: A Radioimmunoconjugate Against Colorectal Cancer," Nucl. Med. Biol. 33(8):991-998.
Alt, M.et al. (1999) "Novel tetravalent and bispecific IgG-like antibody molecules combining single-chain diabodies with the immunoglobulin yl Fc or CH3 region," FEBS Lett. 454(1-2):90-94.
Andera, L. (2009) "Signaling Activated by The Death Receptors of The TNFR Family," Biomed. Pap. Med. Fac. Univ, Palacky Olomouc Czech, Repub. 153(3):173-180.
Asano, R. et al. (2004) "A Diabody For Cancer Immunotherapy and Its Functional Enhancement by Fusion Of Human Fc Domain," Abstract 3P-683, J. Biochem. 76(8):992.
Asano, R. et al. (2013) "Domain Order Of A Bispecific Diabody Dramatically Enhances Its Antitumor Activity Beyond Structural Format Conversions The Case Of The hEx3 Diabody," Prot. Engineer. Des. Select. 26(5):359-367.
Atwell, S. et al. (1997) "Stable Heterodimers from Remodeling the Domain Interface Of A Homodimer Using A Phage Display Library," J. Mol. Biol. 270: 26-35.
Bachanova, V. et al. (2014) "NK Cells In Therapy Of Cancer," Crit. Rev. Oncog. 19(1-2):133-141.
Baeuerle, P.A. et al. (2009) "Bispecific T cell Engaging Antibodies For Cancer Therapy," Cancer Res. 69(12):4941-4944.
Barderas, R. et al. (2012) "High Expression Of IL-13 Receptor A2 In Colorectal Cancer Is Associated With Invasion, Liver Metastasis, And Poor Prognosis," Cancer Res. 72(11):2780-2790.
Bast, R.C. Jr. et al. (2005) "New Tumor Markers: CA125 And Beyond," Int. J. Gynecol. Cancer 15(Suppl 3):274-281.
Bataille, R. (2006) "The Phenotype Of Normal, Reactive And Malignant Plasma Cells. Identification Of "Many And Multiple Myelomas" And Of New Targets For Myeloma Therapy," Haematologica 91(9):1234-1240.
Bauer, S. et al. (1999) "Activation Of NK Cells And T Cells By NKG2D, A Receptor For Stress-Inducible MICA," Science 285(5428):727-729.
Bhattacharya-Chatterjee et al. (1988) "Idiotype Vaccines Against Human T Cell Leukemia. II. Generation And Characterization Of A Monoclonal Idiotype Cascade (Ab1, Ab2, and Ab3)," J. Immunol. 141:1398-1403.
Bird, R.E. et al. (1988) "Single-Chain Antigen-Binding Proteins," Science 242:423-426.
Blumenthal, R.D. et al. (2007) "Expression Patterns Of CEACAM5 And CEACAM6 In Primary And Metastatic Cancers," BMC Cancer, 7:2, pp. 1-15.
Bodey, B. (2002) "Cancer-Testis Antigens: Promising Targets For Antigen Directed Antineoplastic Immunotherapy," Expert Opin. Biol. Ther. 2(6):577-584.
Boghaert, E.R. et al. (2008) "The Oncofetal Protein, 5T4, Is A Suitable Target For Antibody-Guided Anti-Cancer Chemotherapy With Calicheamicin," Int. J. Oncol. 32(1):221-234.
Bou-Assaly, W. et al. (2010) "Cetuximab (Erbitux)," Am. J. Neuroradiol. 31(4):626-627.
Boumazos, S. et al. (2010) "Fcγ Receptor IIIb (CD16b) Polymorphisms Are Associated With Susceptibility To Idiopathic Pulmonary Fibrosis," Lung 188(6):475-481.
Bozinov, O. et al. (2010) "Decreasing Expression Of The Interleukin-13 Receptor IL-13Ralpha2 In Treated Recurrent Malignant Gliomas," Neurol. Med. Chir. (Tokyo) 50(8):617-621.
Brandsma, A.M. (2015) "Fc Receptor Inside-Out Signaling And Possible Impact On Antibody Therapy," Immunol Rev. 268(1):74-87 (Abstract Only).
Brown, B.A. et al. (1987) "Tumor-Specific Genetically Engineered Murine/Human Chimeric Monoclonal Antibody," Cancer Res. 47:3577-3583.
Brown, C.E. et al. (2013) "Glioma IL13Ra2 Is Associated With Mesenchymal Signature Gene Expression And Poor Patient Prognosis," PLoS One. 18;8(10):e77769.
Bruhns, P. et al. (2009) "Specificity And Affinity Of Human Fcgamma Receptors And Their Polymorphic Variants For Human IgG Subclasses," Blood. 113(16):3716-3725.
Buchacher, A. et al. (1994) "Generation Of Human Monoclonal Antibodies Against HIV-1 Proteins; Electrofusion And Epstein-Barr Virus Transformation For Peripheral Blood Lymphocyte Immortalization," AIDS Res. Hum. Retroviruses 10(4):359-369.
Calin, G.A. et al. (2006) "Genomics Of Chronic Lymphocytic Leukemia MicroRNAs As New Players With Clinical Significance," Semin. Oncol. 33(2):167-173.

(56) References Cited

OTHER PUBLICATIONS

Cameron, S. et al. (2012) "Focal Overexpression Of CEACAM6 Contributes To Enhanced Tumourigenesis In Head And Neck Cancer via Suppression Of Apoptosis," Mol. Cancer 11:74, pp. 1-11.
Cao, Y. et al. (2003) "Bispecific Antibody Conjugates In Therapeutics," Adv. Drug. Deliv. Rev. 55:171-197.
Carlo-Stella, C. et al. (2007) "Targeting TRAIL Agonistic Receptors for Cancer Therapy," Clin, Cancer 13(8):2313-2317.
Carter, P. et al. (1992) "Humanization Of An Anti-p185her2 Antibody For Human Cancer Therapy," Proc. Natl. Acad. Sci. (U.S.A.) 89:4285-4289.
Castelli, C. et al. (2000) "T-Cell Recognition Of Melanoma-Associated Antigens," J. Cell. Physiol. 182(3):323-331.
Castillo, J. et al. (2008) "Newer Monoclonal Antibodies For Hematological Malignancies," Exp. Hematol. 36(7):755-768.
Chan, C.E. et al. (2009) "The Use Of Antibodies In The Treatment Of Infectious Diseases," Singapore Med. J. 50(7):663-666.
Chang, K. et al. (1996) "Molecular Cloning Of Mesothelin, A Differentiation Antigen Present On Mesothelium, Mesotheliomas, And Ovarian Cancers," Proc. Natl. Acad. Sci. (U.S.A.) 93:136-140.
Chapin, C. et al. (2012) "Distribution And Surfactant Association Of Carcinoembryonic Cell Adhesion Molecule 6 In Human Lung," Amer. J. Physiol. Lung Cell. Mol. Physiol. 302(2):L216-L25.
Chapoval, A. et al. (2001) "B7—H3: A Costimulatory Molecule For T Cell Activation and IFN-γ Production," Nature Immunol. 2:269-274.
Chaudhari, B.R. et al. (2006) "Following the TRAIL to Apoptosis," Immunologic Res. 35(3):249-262.
Chen, P. et al. (2014) "EphA2 Enhances The Proliferation And Invasion Ability Of LnCap Prostate Cancer Cells," Oncol. Lett. 8(1):41-46.
Cheson, B.D. et al. (2008) "Monoclonal Antibody Therapy For B-Cell Non-Hodgkin's Lymphoma," N. Engl. J. Med. 359(6):613-626.
Chichili, G.R. et al. (2015) "A CD3xCD123 Bispecific DART For Redirecting Host T Cells To Myelogenous Leukemia: Preclinical Activity And Safety In Nonhuman Primates," Sci. Transl. Med. 7(289):289ra82.
Chothia, C. et al. (1987) "Canonical Structures For The Hypervariable Regions Of Immunoglobulins," J. Mol. Biol. 196:901-917.
Chu, P.G. et al. (2001) "CD79: A Review," Appl. Immunohistochem. Mol. Morphol. 9(2):97-106.
Co, M.S. et al. (1991) "Humanized Antibodies For Antiviral Therapy," Proc. Natl. Acad. Sci. (U.S.A.) 88:2869-2873.
Co, MS. et al. (1992) "Chimeric And Humanized Antibodies With Specificity For The CD33 Antigen," J. Immunol. 148:1149-1154.
Collins, M. et al. (2005) "The B7 Family Of Immune-Regulatory Ligands," Genome Biol. 6:223.1-223.7.
Coudert, J.D. et al. (2005) "Altered NKG2D Function In NK Cells Induced By Chronic Exposure To Altered NKG2D Ligand-Expressing Tumor Cells," Blood 106:1711-1717.
Cracco, C.M. et al. (2005) "Immune Response In Prostate Cancer," Minerva Urol. Nefrol. 57(4):301-311.
Dall'Acqua, W.F. et al. (2006) "Properties of Human IgG1s Engineered for Enhanced Binding to the Neonatal Fc Receptor (FcRn)," J. Biol. Chem. 281(33):23514-23524.
Daugherty, B.L. et al. (1991) "Polymerase Chain Reaction Facilitates The Cloning, CDR-Grafting, And Rapid Expression Of A Murine Monoclonal Antibody Directed Against The CD18 Component Of Leukocyte Integrins," Nucl. Acids Res. 19:2471-2476.
Davis, T.A. et al. (1999) "Therapy of B-cell Lymphoma With Anti-CD20 Antibodies Can Result In The Loss Of CD20 Antigen Expression." Clin Cancer Res, 5:611-615, 1999.
Deng, X. et al. (2014) "Expression Profiling Of CEACAM6 Associated With The Tumorigenesis And Progression In Gastric Adenocarcinoma," Genet. Mol. Res. 13(3):7686-7697.
Dennis, J.W. (1999) "Glycoprotein Glycosylation And Cancer Progression," Biochim. Biophys. Acta. 6;1473(1):21-34.

DiBartolomeo, M. et al. (2015) "Bevacizumab Treatment In The Elderly Patient With Metastatic Colorectal Cancer," Clin. Interv. Aging 10:127-133.
DiMaio, D. et al. (2006) "Human Papillomaviruses And Cervical Cancer," Adv. Virus Res. 66:125-59.
Dong, C. et al. (2003) "Immune Regulation by Novel Costimulatory Molecules," Immunolog. Res. 28(1):39-48.
Dougall, W.C. et al. (1994) "The Neu-Oncogene: Signal Transduction Pathways, Transformation Mechanisms and Evolving Therapies," Oncogene 9:2109-2123 (Abstract Only).
Edelson, R.L (1998) "Cutaneous T-Cell Lymphoma: A Model For Selective Immunotherapy," Cancer J. Sci. Am. 4:62-71.
Egloff, A.M. et al. (2006) "Cyclin B1 And Other CyclinsAs Tumor Antigens In Immunosurveillance And Immunotherapy Of Cancer," Cancer Res. 66(1):6-9.
Eisen, T. et al. (2014) "Naptumomab Estafenatox: Targeted Immunotherapy with a Novel Immunotoxin," Curr. Oncol. Rep. 16:370, pp. 1-6.
Eketorp, S.S. et al. (2014) "Alemtuzumab (Anti-CD52 Monoclonal Antibody) As Single-Agent Therapy In Patients With Relapsed/Refractory Chronic Lymphocytic Leukaemia (CLL)-A Single Region Experience On Consecutive Patients," Ann Hematol. 93(10):1725-1733.
EP 18889206.1 Extended Search Report (dated 2021) 17 pages.
Estin, C.D. et al. (1989) "Transfected Mouse Melanoma Lines That Express Various Levels Of Human Melanoma-Associated Antigen p97," J. Natl. Cancer Instit. 81(6):445-454.
Feizi, T. (1985) "Demonstration By Monoclonal Antibodies That Carbohydrate Structures Of Glycoproteins And Glycolipids Are Onco-Developmental Antigens," Nature 314:53-57.
Fernandes, M.J. (2005) "Signaling Through CD 16b In Human Neutrophils Involves The Tec Family Of Tyrosine Kinases," J. Leukoc. Biol. 78(2):524-532.
Fernandes, M.J. et al. (2006) "CD16b Associates With High-Density, Detergent-Resistant Membranes In Human Neutrophils," Biochem. J. 393(Pt 1):351-359.
Ferrari, G. et al. (2011) "An HIV-1 gp120 Envelope Human Monoclonal Antibody That Recognizes a C1 Conformational Epitope Mediates Potent Antibody-Dependent Cellular Cytotoxicity (ADCC) Activity and Defines a Common ADCC Epitope in Human HIV-1 Serum," J. Virol. 85(14):7029-7036.
Field, K.M. (2015) "Bevacizumab And Glioblastoma: Scientific Review, Newly Reported Updates, And Ongoing Controversies," Cancer 121(7):997-1007.
Fijen, C.A. (2000) "The Role Of Fcgamma Receptor Polymorphisms And C3 In The Immune Defence Against Neisseria Meningitidis In Complement-Deficient Individuals," Clin. Exp. Immunol. 120(2):338-345.
Fitzgerald et al. (1997) "Improved Tumour Targeting By Disulphide Stabilized Diabodies Expressed In Pichia pastoris," Protein Eng. 10:1221-1225.
Foon et al. (1995) "Immune Response To The Carcinoembryonic Antigen In Patients Treated With An Anti-Idiotype Antibody Vaccine," J. Clin. Invest. 96(1):334-42.
Foon, K.A. et al. (2004) "Preclinical And Clinical Evaluations Of ABX-EGF, A Fully Human Anti-Epidermal Growth Factor Receptor Antibody," Int. J. Radiat. Oncol. Biol. Phys. 58(3):984-990.
Fujisawa, T. et al. (2009) "A Novel Role Of Interleukin-13 Receptor Alpha2 In Pancreatic Cancer Invasion And Metastasis," Cancer Res. 69(22):8678-8685.
Fukushima, A. et al. (2007) "B7—H3 Regulates The Development Of Experimental Allergic Conjunctivitis In Mice," Immunol. Lett. 113:52-57.
Ganesan, A. (2006) "Solid-Phase Synthesis In The Twenty-First Century," Mini Rev. Med. Chem. 6(1):3-10.
Gardnerova, M. et al. (2000) "The Use Of TNF Family Ligands And Receptors And Agents Which Modify Their Interaction As Therapeutic Agents," Curr. Drug Targets 1(4):327-364.
Ge, Y. (2005) "CD36: A Multiligand Molecule," Lab Hematol. 11(1):31-37 (Abstract Only).
Ghetie et al. (1994) "Anti-CD19 Inhibits The Growth Of Human B-Cell Tumor Lines In Vitro And Of Daudi Cells In SCID Mice By Inducing Cell Cycle Arrest," Blood 83:1329-1336.

(56) References Cited

OTHER PUBLICATIONS

Gil, J. et al. (2006) "*Regulation Of The INK4b-ARF-INK4a Tumour Suppressor Locus: All For One Or One For All,*" Nat. Rev. Mol. Cell Biol. 7(9):667-677.

Gill, S. et al. (2014) "*Efficacy Against Human Acute Myeloid Leukemia And Myeloablation Of Normal Hematopoiesis In A Mouse Model Using Chimeric Antigen Receptor-Modified T Cells,*" Blood 123(15): 2343-2354.

Gonzales, N.R. et al. (2004) "*SDR Grafting Of A Murine Antibody Using Multiple Human Germline Templates To Minimize Its Immunogenicity,*" Mol. Immunol. 41:863-872.

Gorman, S. D. et al. (1991) "*Reshaping A Therapeutic CD4 Antibody,*" Proc. Natl. Acad. Sci. (U.S.A.) 88:4181-4185.

Govindan R. (2004) "*Cetuximab In Advanced Non-Small Cell Lung Cancer,*" Clin. Cancer Res. 10(12 Pt 2):4241s-4244s.

Grabowski, J.P. (2015) "*Current Management Of Ovarian Cancer,*" Minerva Med. 106(3):151-156 (Abstract Only).

Groh, V. et al. (2001) "*Costimulation Of CD8αβ T Cells By NKG2D via Engagement By MIC Induced On Virus-Infected Cells,*" Nat. Immunol. 2(3):255-260.

Guo, S. et al. (2012) "*Role of ADAM10 and ADAM17 in CD16b Shedding Mediated By Different Stimulators,*" Chin. Med. Sci. J. 27(2):73-79.

Guy, C.S. et al. (2009) "*Organization of Proximal Signal Initiation at the TCR:CD3 Complex,*" Immunol Rev. 232(1):7-21.

Hall, R.D. et al. (2015) "*Angiogenesis Inhibition As A Therapeutic Strategy In Non-Small Cell Lung Cancer (NSCLC),*" Transl. Lung Cancer Res. 4(5):515-523.

Harris, A. et al. (2011) "*Trimeric HIV-1 Glycoprotein Gp140 Immunogens And Native HIV-1 Envelope Glycoproteins Display The Same Closed And Open Quaternary Molecular Architectures,*" Proc. Natl. Acad. Sci. (U.S.A.) 108(28):11440-11445.

Hartmann, F. et al. (2001) "*Anti-CD16/CD30 Bispecific Antibody Treatment for Hodgkin's Disease: Role of Infusion Schedule and Costimulation with Cytokines,*" Clin. Canc. Res. 7:1873-1881.

Heath, J.K. et al. (1997) "*The Human A33 Antigen Is A Transmembrane Glycoprotein And A Novel Member Of The Immunoglobulin Superfamily,*" Proc. Natl. Acad. Sci. (U.S.A.) 94(2):469-474.

Hellström, I. et al. (1985) "*Monoclonal Antibodies To Cell Surface Antigens Shared By Chemically Induced Mouse Bladder Carcinomas,*" Cancer. Res. 45:2210-2188.

Hellström et al. (1986) "*Monoclonal Mouse Antibodies Raised Against Human Lung Carcinoma,*" Cancer Res. 46:3917-3923).

Henttu, P. et al. (1989) "*cDNA Coding For The Entire Human Prostate Specific Antigen Shows High Homologies To The Human Tissue Kallikrein Genes,*" Biochem. Biophys. Res. Comm. 10(2):903-910.

Herlyn, M. et al. (1982) "*Monoclonal Antibody Detection Of A Circulating Tumor-Associated Antigen. I. Presence Of Antigen In Sera Of Patients With Colorectal, Gastric, And Pancreatic Carcinoma,*" J. Clin. Immunol. 2:135-140.

Hilkens, J. et al. (1992) "*Cell Membrane-Associated Mucins And Their Adhesion-Modulating Property,*" Trends in Biochem. Sci. 17:359-363.

Hofmeyer, K. et al. (2008) "*The Contrasting Role of B7—H3,*" Proc. Natl. Acad. Sci. (U.S.A.) 105(30):10277-10278.

Holliger, P. et al. (1993) "*'Diabodies': Small Bivalent and Bispecific Antibody Fragments,*" Proc. Natl. Acad. Sci. (U.S.A.) 90:6444-6448.

Holliger, P. et al. (1996) "*Specific Killing of Lymphoma Cells by Cytotoxic T-Cells Mediated by A Bispecific Diabody,*" Protein Eng. 9:299-305 (Abstract Only).

Holliger, P. et al. (1999) "*Carcinoembryonic Antigen (CEA)-Specific T cell Activation In Colon Carcinoma Induced By Anti-CD3 X Anti-CEA Bispecific Diabodies And B7 X Anti-CEA Bispecific Fusion Proteins,*" Cancer Res. 59:2909-2916.

Holmberg, L.A. (2001) "*Theratope Vaccine (STn-KLH),*" Expert Opin. Biol. Ther. 1(5):881-91.

Hoon D. et al. (1993) "*Molecular Cloning Of A Human Monoclonal Antibody Reactive To Ganglioside GM3 Antigen On Human Cancers,*" Cancer Res. 53:5244-5250.

Houghten, R.A. (1985) "*General Method For The Rapid Solid-Phase Synthesis Of Large Numbers Of Peptides: Specificity Of Antigen-Antibody Interaction At The Level Of Individual Amino Acids,*" Proc. Natl. Acad. Sci. (U.S.A.) 82(15):5131-5135.

Hynes, N.E. et al. (1994) "*The Biology of erbB-2/neu/HER-2 and its Role in Cancer,*" Biochim. Biophys. Acta 1198:165-184.

Israeli, R.S. et al. (1993) "*Molecular Cloning of a Complementary DNA Encoding A Prostate-Specific Membrane Antigen,*" Cancer Res. 53:227-230.

Jamieson, A.M. et al. (2002) "*The Role Of The NKG2D Immunoreceptor In Immune Cell Activation And Natural Killing,*" Immunity 17(1):19-29.

Jennings, V.M. (1995) "*Review of Selected Adjuvants Used in Antibody Production,*" ILAR J. 37(3):119-125.

Johansson, M.U. et al. (2002) "*Structure, Specificity, And Mode Of Interaction For Bacterial Albumin-Binding Modules,*" J. Biol. Chem. 277(10):8114-8120.

Johnson, S. et al. (2010) "*Effector Cell Recruitment With Novel Fv-Based Dual-Affinity Re-Targeting Protein Leads To Potent Tumor Cytolysis And In Vivo B-Cell Depletion,*" J. Molec. Biol. 399(3):436-449.

Jones, P.T. et al. (1986) "*Replacing The Complementarity-Determining Regions In A Human Antibody With Those From A Mouse,*" Nature 321:522-525.

Jurcic, J.G. (2005) "*Immunotherapy For Acute Myeloid Leukemia,*" Curr. Oncol. Rep. 7(5):339-346.

Kasaian, M.T. et al. (2011) "*IL-13 Antibodies Influence IL-13 Clearance In Humans By Modulating Scavenger Activity Of IL-13Ra2,*" J. Immunol. 187(1):561-569.

Kashmiri, S.V. et al. (2005) "*SDR Grafting—A New Approach To Antibody Humanization,*" Methods 36(1):25-34.

Kawai, S. et al. (2008) "*Interferon-A Enhances CD8 17 Expression And The Antitumor Activity Of Anti-CD317 Monoclonal Antibody In Renal Cell Carcinoma Xenograft Models,*" Cancer Science 99(12):2461-2466.

Kettleborough, C. A. et al. (1991) "*Humanization Of A Mouse Monoclonal Antibody By CDR-Grafting: The Importance Of Framework Residues On Loop Conformation,*" Protein Engineering 4:773-3783.

Kim, K.S. et al. (2010) "*Construction Of A Humanized Antibody To Hepatitis B Surface Antigen By Specificity-Determining Residues (SDR)-Grafting And De-Immunization,*" Biochem. Biophys. Res. Commun. 396(2):231-237.

Kim, J.H. et al. (2012) "*Humanization By CDR Grafting And Specificity-Determining Residue Grafting,*" Methods Mol. Biol. 907:237-245.

Koene, H.R. et al. (1997) "*FcγRIIIa-158V/F Polymorphism Influences the Binding of IgG by Natural Killer Cell FcγRIIIa, Independently of the FcγRIIIa-48L/R/H Phenotype,*" Blood, 90(3):1109-1114.

Kohler, G et al. (1975) "*Continuous Cultures Of Fused Cells Secreting Antibody Of Predefined Specificity,*" Nature 256:495-497.

Korman, AJ et al. (2007) "*Checkpoint Blockade in Cancer Immunotherapy,*" Adv. Immunol. 90:297-339.

Kounalakis, N. et al. (2005) "*Tumor Cell And Circulating Markers In Melanoma: Diagnosis, Prognosis, And Management,*" Curr. Oncol. Rep. 7(5):377-382.

Kreitman, R.J. (2006) "*Immunotoxins For Targeted Cancer Therapy,*" AAPS J. 8(3):E532-51.

Kwong, KY et al. (2008) "*Generation, Affinity Maturation, And Characterization Of A Human Anti-Human NKG2D Monoclonal Antibody With Dual Antagonistic And Agonistic Activity,*" J. Mol. Biol. 384:1143-1156.

Langer (1990) "*New Methods Of Drug Delivery,*" Science 249:1527-1533.

Lee, K.-F. et al. (1995) "*Requirement for Neuregulin Receptor erbB2 in Neural and Cardiac Development*", Nature 378:394-398.

Lee, Y.M. et al. (2006) "*Targeting Cyclins And Cyclin-Dependent Kinases In Cancer: Lessons From Mice, Hopes For Therapeutic Applications In Human,*" Cell Cycle 5(18):2110-2114.

(56) References Cited

OTHER PUBLICATIONS

Lefranc, G. et al. (1979) "Gm, Am and Km Immunoglobulin Allotypes of Two Populations in Tunisia," Hum. Genet.: 50, 199-211.
Lewis-Wambi, J.S. et al. (2008) "Overexpression Of CEACAM6 Promotes Migration And Invasion Of Oestrogen-Deprived Breast Cancer Cells," Eur. J. Cancer 44(12):1770-1779.
Liu, K.J. et al. (2015) "Bevacizumab In Combination With Anticancer Drugs For Previously Treated Advanced Non-Small Cell Lung Cancer," Tumour Biol. 36(3):1323-1327 (diff ref in server).
Livingston, P.O. et al. (1994) "Improved Survival In Stage III Melanoma Patients With GM2 Antibodies: A Randomized Trial Of Adjuvant Vaccination With GM2 Ganglioside," J. Clin. Oncol. 12:1036-1044.
Livingston, P.O. et al. (2005) "Selection Of GM2, Fucosyl GM1, Globo H And Polysialic Acid As Targets On Small Cell Lung Cancers For Antibody-Mediated Immunotherapy," Cancer Immunol. Immunother. 54(10):1018-1025.
LoBuglio, A.F. et al. (1989) "Mouse/Human Chimeric Monoclonal Antibody In Man: Kinetics And Immune Response," Proc. Natl. Acad. Sci. (U.S.A.) 86:4220-4224.
Lonberg, N. et al. (1995) "Human Antibodies From Transgenic Mice," Int. Rev. Immunol 13:65-93.
Loo, D. et al. (2012) "Development Of An Fc-Enhanced Anti-B7—H3 Monoclonal Antibody With Potent Antitumor Activity," Clin. Cancer Res. 18(14):3834-3845.
Lotem, M. et al. (2006) "Presentation Of Tumor Antigens By Dendritic Cells Genetically Modified With Viral And Nonviral Vectors," J. Immunother. 29(6):616-27 (Manuscript only).
Lu, D. et al. (2005) "A Fully Human Recombinant IgG-Like Bispecific Antibody To Both The Epidermal Growth Factor Receptor And The Insulin-Like Growth Factor Receptor For Enhanced Antitumor Activity," J. Biol. Chem. 280(20):19665-19672.
Lu, S. et al. (2015) "Structural Mechanism Of High Affinity FcγRI recognition Of Immunoglobulin G," Immuno. Rev. 268(1):192-200 (Abstract Only).
Maeda, H. et al. (1991) "Construction Of Reshaped Human Antibodies With HIV-Neutralizing Activity," Human Antibodies Hybridoma 2:124-134.
Mardiros, A. et al. (2013) "T Cells Expressing CD123-Specific Chimeric Antigen Receptors Exhibit Specific Cytolytic Effector Functions And Antitumor Effects Against Human Acute Myeloid Leukemia," Blood 122:3138-3148.
Marvin et al. (2005) "Recombinant Approaches To IgG-Like Bispecific Antibodies," Acta Pharmacol. Sin. 26:649-658.
Mathelin C. (2006) "Circulating Proteinic Biomarkers And Breast Cancer," Gynecol. Obstet. Fertil. 34(7-8):638-646 (in French).
Meknache, N. et al. (2009) "Human Basophils Express The Glycosylphosphatidylinositol-Anchored Low-Affinity IgG Receptor FcgammaRIIIB (CD16B)," J. Immunol. 182(4):2542-2550.
Merrifield, B. (1986) "Solid Phase Synthesis," Science 232(4748):341-347.
Messmer, D. et al. (2005) "CD154 Gene Therapy For Human B-Cell Malignancies," Ann N. Y. Acad. Sci. 1062:51-60.
Miao, B. et al. (2014) "EphA2 is a Mediator of Vemurafenib Resistance and a Novel Therapeutic Target in Melanoma," Cancer Discov. DOI: 10.1158/2159-8290.CD-14-0295 (15 pages).
Midgley, R. et al. (2005) "Bevacizumab—Current Status And Future Directions," Ann. Oncol. 16(7):999-1004.
Miller, J.S. (2013) "Therapeutic Applications: Natural Killer Cells In The Clinic," Hematology Am. Soc. Hematol. Educ. Program. 2013:247-253.
Mittelman et al. (1990) "Active Specific Immunotherapy In Patients With Melanoma. A Clinical Trial With Mouse Antiidiotypic Monoclonal Antibodies Elicited With Syngeneic Anti-High-Molecular-Weight-Melanoma-Associated Antigen Monoclonal Antibodies," J. Clin. Invest. 86:2136-2144.
Möller et al. (1991) "Bispecific-Monoclonal-Antibody-Directed Lysis Of Ovarian Carcinoma Cells By Activated Human T Lymphocytes," Cancer Immunol. Immunother. 33(4):210-216.

Moore, P.A. et al. (2011) "Application Of Dual Affinity Retargeting Molecules To Achieve Optimal Redirected T cell Killing Of B-Cell Lymphoma," Blood 117(17):4542-4551.
Muñoz, L. et al. (2001) "Interleukin-3 Receptor Alpha Chain (CD123) Is Widely Expressed In Hematologic Malignancies," Haematologica 86(12):1261-1269.
Narita, Y. (2015) "Bevacizumab For Glioblastoma," Ther. Clin. Risk Manag. 11:1759-1765.
Natali et al. (1987) "Immunohistochemical Detection Of Antigen In Human Primary And Metastatic Melanomas By The Monoclonal Antibody 140.240 And Its Possible Prognostic Significance," Cancer 59:55-63.
O'Dwyer. P.J. (2006) "The Present And Future Of Angiogenesis-Directed Treatments Of Colorectal Cancer," Oncologist 11(9):992-998.
Olafsen et al. (2004) "Covalent Disulfide-Linked Anti-CEA Diabody Allows Site-Specific Conjugation And Radiolabeling For Tumor Targeting Applications," Prot. Engr. Des. Sel. 17:21-27.
Pal, S.K. et al. (2006) "Targeting HER2 Epitopes," Semin. Oncol. 33(4):386-391.
PCT Written Opinion WO 2019/118266 (2021) 10 pages.
Peeters et al. (2001) "Production Of Antibodies And Antibody Fragments In Plants," Vaccine 19:2756.
Peggs, K.S. et al. (2006) "Principles And Use Of Anti-CTLA4 Antibody In Human Cancer Immunotherapy," Curr. Opin. Immunol. 18(2):206-13.
Peipp, M. et al. (2002) "Bispecific Antibodies Targeting Cancer Cells," Biochem. Soc. Trans. 30(4):507-511.
Peltz, G.A. et al. (1989) "Human Fc Gamma RIII: Cloning, Expression, And Identification Of The Chromosomal Locus Of Two Fc Receptors For IgG," Proc. Natl. Acad. Sci. (U.S.A.) 86(3):1013-1017.
Perez et al. (1989) "Isolation And Characterization Of A cDNA Encoding The Ks1/4 Epithelial Carcinoma Marker," J. Immunol. 142:3662-3667.
Pietrantonio, F. et al. (2015) "Bevacizumab-Based Neoadjuvant Chemotherapy For Colorectal Cancer Liver Metastases: Pitfalls And Helpful Tricks In A Review For Clinicians," Crit. Rev. Oncol. Hematol. 95(3):272-281.
Pincus, S.H. et al. (2003) "In Vivo Efficacy Of Anti-Glycoprotein 41, But Not Anti-Glycoprotein 120, Immunotoxins In A Mouse Model Of HIV Infection," J. Immunol. 170(4):2236-2241.
Pizzitola, I. et al. (2014) "Chimeric Antigen Receptors Against CD33/CD123 Antigens Efficiently Target Primary Acute Myeloid Leukemia Cells in vivo," Leukemia doi:10.1038/leu.2014.62.
Pollock et al. (1999) "Transgenic Milk As A Method For The Production Of Recombinant Antibodies," J. Immunol. Methods 231:147-157.
Portolés, P. et al. (2009) "The TCR/CD3 Complex: Opening the Gate to Successful Vaccination," Current Pharmaceutical Design 15:3290-3300.
Prange W. et al. (2003) "Beta-Catenin Accumulation In The Progression Of Human Hepatocarcinogenesis Correlates With Loss Of E-Cadherin And Accumulation Of P53, But Not With Expression Of Conventional WNT-1 Target Genes," J. Pathol. 201(2):250-259.
Prasad, D.V. et al. (2004) "Murine B7—H3 Is A Negative Regulator Of T Cells," J. Immunol. 173:2500-2506.
Ragnhammar et al. (1993) "Effect Of Monoclonal Antibody 17-1A And GM-CSF In Patients With Advanced Colorectal Carcinoma—Long-Lasting, Complete Remissions Can Be Induced," Int. J. Cancer 53:751-758.
Ragupathi, G. (2005) "Antibody Inducing Polyvalent Cancer Vaccines," Cancer Treat. Res. 123:157-180.
Raulet D.H. (2003) "Roles Of The NKG2D Immunoreceptor And Its Ligands," Nature Rev. Immunol. 3:781-790.
Ravetch, J. V. et al. (1989) "Alternative Membrane Forms Of FcγRIII(CD 16) On Human Natural Killer Cells And Neutrophils," J. Exper. Med. 170:481-497.
Reff et al. (1994) "Depletion Of B Cells In Vivo By A Chimeric Mouse Human Monoclonal Antibody To CD20," Blood 83:435-445.
Ridgway et al. (1996) "'Knobs-Into-Holes' Engineering Of Antibody CH3 Domains For Heavy Chain Heterodimerization," Protein Engr. 9:617-621.

(56) References Cited

OTHER PUBLICATIONS

Riechmann, L. et al. (1988) "Reshaping Human Antibodies for Therapy," Nature 332:323-327.
Riley, C.J. et al. (2009) "Design And Activity Of A Murine And Humanized Anti-CEACAM6 Single-Chain Variable Fragment In The Treatment Of Pancreatic Cancer," Cancer Res. 69(5):1933-1940.
Rimon, E. et al. (2004) "Gonadotropin-Induced Gene Regulation In Human Granulosa Cells Obtained From IVF Patients: Modulation Of Genes Coding For Growth Factors And Their Receptors And Genes Involved In Cancer And Other Diseases," Int. J. Oncol. 24(5):1325-1338.
Ritter, G. et al. (1997) "Characterization Of Posttranslational Modifications Of Human A33 Antigen, A Novel Palmitoylated Surface Glycoprotein Of Human Gastrointestinal Epithelium," Biochem. Biophys. Res. Commun. 236(3):682-686.
Rosati, S. et al. (2005) "Chronic Lymphocytic Leukaemia: A Review Of The Immuno-Architecture," Curr. Top. Microbiol. Immunol. 294:91-107.
Rouard, H. et al. (1997) "Fc Receptors As Targets For Immunotherapy," Int. Rev. Immunol. 16(1-2):147-185 (Abstract Only).
Sadraeian, M. et al. (2017) "Selective Cytotoxicity Of A Novel Immunotoxin Based On Pulchellin A Chain For Cells Expressing HIV Envelope," Sci. Rep. 7(1):7579 doi: 10.1038/s41598-017-08037-3 (12 pages).
Saleh et al. (1993) "Generation Of A Human Anti-Idiotypic Antibody That Mimics The GD2 Antigen," J. Immunol. 151:3390-3398.
Santra, S. et al. (2015) "Human Non-neutralizing HIV-1 Envelope Monoclonal Antibodies Limit the Number of Founder Viruses during SHIV Mucosal Infection in Rhesus Macaques," PLoS Pathog. 11(8):e1005042. doi: 10.1371/ioumal.ppat.1005042 (38 pages).
Sato, K. et al. (1993) "Reshaping a Human Antibody to Inhibit the Interleukin 6-dependent Tumor Cell Growth," Cancer Res 53:851-856.
Sayeed, A. et al. (2013) "Aberrant Regulation Of The BST2 (Tetherin) Promoter Enhances Cell Proliferation And Apoptosis Evasion In High Grade Breast Cancer Cells," PLoS ONE 8(6)e67191, pp. 1-10.
Selvaraj, P. et al. (2004) "Functional Regulation Of Human Neutrophil Fc Gamma Receptors," Immunol Res. 29(1-3):219-230.
Sgouros et al. (1993) "Modeling And Dosimetry Of Monoclonal Antibody M195 (Anti-CD33) In Acute Myelogenous Leukemia," J. Nucl. Med. 34:422-430.
Sharpe, A.H. et al. (2002) "The B7-CD28 Superfamily," Nature Rev. Immunol. 2:116-126.
Shaw, D.R. et al. (1987) "Characterization Of A Mouse/Human Chimeric Monoclonal Antibody (17-1A) To A Colon Cancer Tumor-Associated Antigen," J. Immunol. 138:4534-4538.
Shen, R. (2010) "GP41-Specific Antibody Blocks Cell-Free HIV Type 1 Transcytosis Through Human Rectal Mucosa And Model Colonic Epithelium," J. Immunol. 184(7):3648-3655.
Shitara, K. et al. (1993) "A Mouse/Human Chimeric Anti-(Ganglioside GD3) Antibody With Enhanced Antitumor Activities," Cancer Immunol. Immunother. 36:373-380.
Sloan, D.D. et al. (2015) "Targeting HIV Reservoir in Infected CD4 T Cells by Dual-Affinity Re-targeting Molecules (DARTs) that Bind HIV Envelope and Recruit Cytotoxic T Cells," PLoS Pathog. 11(11):el005233. doi: 10.1371/joumal.ppat.1005233 (29 pages).
Staerz, U.D. et al. (1985) "Hybrid Antibodies Can Target Sites For Attack By T Cells," Nature 314:628-631.
Stavenhagen, J.B. et al. (2007) "Fc Optimization Of Therapeutic Antibodies Enhances Their Ability To Kill Tumor Cells In Vitro And Controls Tumor Expansion In Vivo Via Low-Affinity Activating Fcgamma Receptors," Cancer Res. 57(18):8882-8890.
Stomski, F.C. et al. (1996) "Human Interleukin-3 (IL-3) Induces Disulfide-Linked IL-3 Receptor Alpha- And Beta-Chain Heterodimerization, Which Is Required For Receptor Activation But Not High-Affinity Binding," Mol. Cell. Biol. 16(6):3035-3046.

Stopforth, R.J. et al. (2016) "Regulation of Monoclonal Antibody Immunotherapy by FcγRIIB," J. Clin. Immunol. [Feb. 27, 2016 Epub], pp. 1-7.
Suh, D.H. et al. (2015) "Major Clinical Research Advances In Gynecologic Cancer In 2014," J. Gynecol. Oncol. 26(2):156-167.
Sun, M. et al. (2002) "Characterization of Mouse and Human B7—H3 Genes," J. Immunol. 168:6294-6297.
Suresh, T. et al. (2014) "New Antibody Approaches To Lymphoma Therapy," J. Hematol. Oncol. 7:58; Hoelzer, D. (2013) "Targeted Therapy With Monoclonal Antibodies In Acute Lymphoblastic Leukemia," Curr. Opin. Oncol. 25(6):701-706.
Swisher, J.F. et al. (2015) "The Many Faces Of FcγRI: Implications For Therapeutic Antibody Function," Immunol. Rev. 268(1):160-174 (Abstract Only).
Tailor et al. (1990) "Nucleotide Sequence Of Human Prostatic Acid Phosphatase Determined From A Full-Length cDNA Clone," Nucl. Acids Res. 18(16):4928).
Takemura, S. et al. (2000) "Construction Of A Diabody (Small Recombinant Bispecific Antibody) Using A Refolding System," Protein Eng. 13(8):583-588.
Tamm, A. et al. (1996) "The Binding Epitopes Of Human CD 16 (Fc Gamma RIII) Monoclonal Antibodies. Implications For Ligand Binding," J. Immunol. 157(4):1576-1581 (Abstract Only).
Tamm, A. et al. (1996) "The IgG Binding Site Of Human FcgammaRIIIB Receptor Involves CC'And FG Loops Of The Membrane-Proximal Domain," J. Biol. Chem. 271(7):3659-3666.
Tay, M.Z. et al. (2016) "Antibody-Mediated Internalization of Infectious HIV-1 Virions Differs among Antibody Isotypes and Subclasses," PLoS Pathog. 12(8):e1005817, doi: 10.1371/journal.ppat.1005817.
Tedder (2009) "CD19: A Promising B Cell Target For Rheumatoid Arthritis," Nat. Rev. Rheumatol. 5:572-577.
Tellez-Avila, F.I. et al. (2005) "The Carcinoembryonic Antigen: Apropos Of An Old Friend," Rev. Invest. Clin. 57(6):814-819 (Spanish; English Abstract).
Tempest, P.R. et al. (1991) "Reshaping A Human Monoclonal Antibody to Inhibit Human Respiratory Syncytial Virus Infection in vivo," Bio/Technology 9:266-271.
Tettamanti, S. et al. (2013) "Targeting Of Acute Myeloid Leukaemia By Cytokine-Induced Killer Cells Redirected With A Novel CD123-Specific Chimeric Antigen Receptor," Br. J. Haematol. 161:389-401.
Thepen, T. et al. (2009) "Fcgamma Receptor 1 (CD64), A Target Beyond Cancer," Curr. Pharm. Des. 15(23):2712-2718 (Abstract Only).
Thomas, DA. et al. (2006) "Monoclonal Antibody Therapy for Hairy Cell Leukemia," Hematol Oncol Clin North Am, 20(5):1125-1136 (Abstract Only).
Thompson, JA. et al. (1991) "Carcinoembryonic Antigen Gene Family: Molecular Biology and Clinical Perspectives," J. Clin. Lab. Anal. 5:344-366.
Topalian, S.L. et al. (2015) "Immune Checkpoint Blockade: A Common Denominator Approach to Cancer Therapy," Cancer Cell 27:450-461.
Trauth, B.C. et al. (1989) "Monoclonal Antibody-Mediated Tumor Regression by Induction Of Apoptosis," Science 245:301-304.
Troussard, X. et al. (1998) "Hairy Cell Leukemia. What Is Nev Forty Years After the First Description?" Hematol. Cell. Ther, 40(4):139-148 (abstract only).
Unkeless, J.C. et al. (1995) "Function of Human Fc Gamma RIIA And Fc Gamma RIIIB," Semin. Immunol. 7(1):37-44.
Van Horssen, R. et al. (2006) "TNF-Alpha in Cancer Treatment: Molecular Insights, Antitumor Effects, And Clinical Utility," Oncologist 11(4):397-408.
Van Sorge, NM. (2003) "FcgammaR Polymorphisms: Implications for Function, Disease Susceptibility And Immunotherapy," Tissue Antigens 61(3):189-202.
Verhoeyen, M. et al. (1988) "Reshaping Human Antibodies: Grafting an Antilysozyme Activity," Science 239:1534-1536.
Veri, M.C. et al. (2010) "Therapeutic Control of B Cell Activation Via Recruitment Of Fcgamma Receptor IIB (CD32B) Inhibitory Function With A Novel Bispecific Antibody Scaffold," Arthritis Rheum. 62(7):1933-1943.

(56) References Cited

OTHER PUBLICATIONS

Viglietta, V. et al. (2007) "*Modulating Co-Stimulation*," Neurotherapeutics 4:666-675.

Vijayasardahl et al. (1990) "*The Melanoma Antigen Gp75 Is the Human Homologue Of The Mouse B (Brown) Locus Gene Product,*" J. Exp. Med. 171(4):1375-1380.

Wang, W. et al. (2009) "*Chimeric and Humanized Anti-HM1.24 Antibodies Mediate Antibody-Dependent Cellular Cytotoxicity Against Lung Cancer Cells. Lung Cancer,*" 63(1):23-31.

Wang, W. et al. (2009) *HM1.24 (CD317) Is A Novel Target Against Lung Cancer for Immunotherapy Using Anti-HM1.24 Antibody*, Cancer Immunology, Immunotherapy 58(6):967-976.

Wang, Y. et al. (2013) "*ADAM17 Cleaves CD16b (FcγRIIIb) In Human Neutrophils,*" Biochim. Biophys. Acta 1833(3):680-685.

White, A.L. et al. (2014) "*FcγRIIB As A Key Determinant Of Agonistic Antibody Efficacy,*" Curr. Top. Microbiol. Immunol. 382:355-372.

Winter et al. (1991) "*Man-Made Antibodies,*" Nature 349:293-299.

Winter, G. et al. (1994) "*Making Antibodies By Phage Display Technology,*" Annu. Rev. Immunol. 12.433-455.

Wong, N.A. et al. (2006) "*EpCAM and gpA3 3 Are Markers Of Barrett's Metaplasia,*" J. Clin. Pathol. 59(3):260-263.

Wu, A. et al. (2001) "*Multimerization Of A Chimeric Anti-CD20 Single Chain Fv-Fv Fusion Protein Is Mediated Through Variable Domain Exchange,*" Protein Engineering 14(2):1025-1033.

Wu, J. et al. (1997) "*A Novel Polymorphism of FcγRIIIa (CD16) Alters Receptor Function and Predisposes to Autoimmune Disease,*" J. Clin.Invest. 100(5):1059-1070.

Wu, J. et al. (2015) "*AFM13: A First-In-Class Tetravalent Bispecific Anti-CD30/CD16A Antibody For NK Cell-Mediated Immunotherapy,*" J. Hematol. Oncol. 8:96:1-4.

Wyatt et al. (1995) "*Involvement of The V1/V2 Variable Loop Structure In The Exposure Of Human Immunodeficiency Virus Type 1 gp120 Epitopes Induced By Receptor Binding,*" J. Virol. 69:5723-5733.

Xie et al. (2005) "*A New Format of Bispecific Antibody: Highly Efficient Heterodimerization, Expression and Tumor Cell Lysis,*" J. Immunol. Methods 296:95-101.

Xu, J. et al. (2014) "*High EphA2 Protein Expression in Renal Cell Carcinoma Is Associated With A Poor Disease Outcome,*" Oncol. Lett. Aug. 2014; 8(2): 687-692.

Yazdi, M.H. et al. (2015) "*A Comprehensive Review of Clinical Trials on EGFR Inhibitors Such as Cetuximab and Panitumumab as Monotherapy and in Combination for Treatment of Metastatic Colorectal Cancer,*" Avicenna J. Med. Biotechnol. 7(4):134-144.

Yi, KH. et al. (2009) "Fine *Tuning the Immune Response Through B7—H3 And B7—H4,*" Immunol. Rev. 229:145-151.

Yokota, T. et al. (1992) "*Rapid Tumor Penetration of A Single-Chain Fv And Comparison With Other Immunoglobulin Forms,*" Cancer Res. 52:3402-3408.

Youinou, P. et al. (2002) "*Pathogenic Effects of Anti-Fc Gamma Receptor IIIB (CD16) On Polymorphonuclear Neutrophils In Non-Organ-Specific Autoimmune Diseases,*" Autoimmun Rev. 1(1-2):13-19.

Yu YH. et al. (1991) "*Coexpression Of Different Antigenic Markers on Moieties That Bear CA 125 Determinants,*" Cancer Res. 51(2):468-475.

Zang, X. et al. (2007) "*The B7 Family and Cancer Therapy: Costimulation And Coinhibition,*" Clin. Cancer Res. 13:5271-5279.

Zheng, C. et al. (2011) "*A Novel Anti-CEACAM5 Monoclonal Antibody, CC4, Suppresses Colorectal Tumor Growth and Enhances NK Cells-Mediated Tumor Immunity,*" PLoS One 6(6):e21146, pp. 1-11.

Zhou, H. et al. (2002) "Lung Tumorigenesis Associated with Erb-B-2 And Erb-B-3 Overexpression In Human Erb-B-3 Transgenic Mice Is Enhanced By Methylnitrosourea," Oncogene 21(57):8732-8740.

Mariuzza, R.A. et al. (1987) "*The Structural Basis Of Antigen-Antibody Recognition,*" Annu. Rev. Biophys. Biophys. Chem. 16:139-159.

Pan, Q. et al. (2007) "*Blocking Neuropilin-1 Function Has An Additive Effect With Anti-VEGF To Inhibit Tumor Growth,*" Cancer Cell. 11(1):53-67.

Ellwanger, K. et al. (2016) "*Highly Cytotoxic EGFR/CD16A TandAbs Specifically Recruit NK Cells to Potently Kill Various Types of Solid Tumors,*" Cancer Res. 76(14_supplement):593 (1 page).

\* cited by examiner

|              | 10         | 20         | 30         | 40         |
|--------------|------------|------------|------------|------------|
| huCD16A_158F_ECD | GMRTEDLPKA | VVFLEPQWYR | VLEKDSVTLK | CQGAYSPEDN |
| huCD16A_158V_ECD | GMRTEDLPKA | VVFLEPQWYR | VLEKDSVTLK | CQGAYSPEDN |
| huCD16B_NA1_ECD  | GMRTEDLPKA | VVFLEPQWYR | VLEKDSVTLK | CQGAYSPEDN |
| huCD16B_NA2_ECD  | GMRTEDLPKA | VVFLEPQWYS | VLEKDSVTLK | CQGAYSPEDN |
| cyCD16_ECD       | GMRAEDLPRA | VVFLEPQWYR | VLEKDRVTLK | CQGAYSPEDN |

|              | 50         | 60         | 70         | 80         |
|--------------|------------|------------|------------|------------|
| huCD16A_158F_ECD | STQWFHNESL | ISSQASSYFI | DAATVDDSGE | YRCQTNLSTL |
| huCD16A_158V_ECD | STQWFHNESL | ISSQASSYFI | DAATVDDSGE | YRCQTNLSTL |
| huCD16B_NA1_ECD  | STQWFHNNSL | ISSQASSYFI | DAATVDDSGE | YRCQTNLSTL |
| huCD16B_NA2_ECD  | STQWFHNESL | ISSQASSYFI | DAATNDDSGE | YRCQTNLSTL |
| cyCD16_ECD       | STRWFHNESL | ISSQTSSYFI | AAARVNNSGE | YRCQTSLSTL |

|              | 90         | 100        | 110        | 120        |
|--------------|------------|------------|------------|------------|
| huCD16A_158F_ECD | SDPVQLEVHI | GWLLLQAPRW | VFKEEDPIHL | RCHSWKNTAL |
| huCD16A_158V_ECD | SDPVQLEVHI | GWLLLQAPRW | VFKEEDPIHL | RCHSWKNTAL |
| huCD16B_NA1_ECD  | SDPVQLEVHV | GWLLLQAPRW | VFKEEDPIHL | RCHSWKNTAL |
| huCD16B_NA2_ECD  | SDPVQLEVHI | GWLLLQAPRW | VFKEEDPIHL | RCHSWKNTAL |
| cyCD16_ECD       | SDPVQLEVHI | GWLLLQAPRW | VFKEEESIHL | RCHSWKNTLL |

|              | 130        | 140        | 150        | 160        |
|--------------|------------|------------|------------|------------|
| huCD16A_158F_ECD | HKVTYLQNGK | GRKYFHHNSD | FYIPKATLKD | SGSYFCRGLF |
| huCD16A_158V_ECD | HKVTYLQNGK | GRKYFHHNSD | FYIPKATLKD | SGSYFCRGLV |
| huCD16B_NA1_ECD  | HKVTYLQNGK | DRKYFHHNSD | FHIPKATLKD | SGSYFCRGLV |
| huCD16B_NA2_ECD  | HKVTYLQNGK | DRKYFHHNSD | FHIPKATLKD | SGSYFCRGLV |
| cyCD16_ECD       | HKVTYLQNGK | GRKYFHQNSD | FYIPKATLKD | SGSYFCRGLI |

|              | 170        | 180        | 190        |     | SEQ ID NO: |
|--------------|------------|------------|------------|-----|------------|
| huCD16A_158F_ECD | GSKNVSSETV | NITITQGLAV | STISSFFPPG | YQ | 146 |
| huCD16A_158V_ECD | GSKNVSSETV | NITITQGLAV | STISSFFPPG | YQ | 147 |
| huCD16B_NA1_ECD  | GSKNVSSETV | NITITQGLAV | STIS       |    | 148 |
| huCD16B_NA2_ECD  | GSKNVSSETV | NITITQGLAV | STIS       |    | 149 |
| cyCD16_ECD       | GSKNVSSETV | NITITQDLAV | SSIS       |    | 150 |

Figure 7

|  | 10 | 20 | 30 | 40 |
|---|---|---|---|---|
| huCD16A_176V.pro | MWQL------ | --------LL | P--TALLLLV | SAGMRTEDLP |
| cyCD16.pro | MWQL------ | --------LL | P--TALLLLV | SAGMRAEDLP |
| muCD16.pro | M-TLDTQMFQ | NAHSGSQWLL | PPLTILLLFA | FADRQSAALP |

|  | 50 | 60 | 70 | 80 |
|---|---|---|---|---|
| huCD16A_176V.pro | KAVVFLEPQW | YRVLEKDSVT | LKCQGAYSPE | DNSTQWFHNE |
| cyCD16.pro | RAVVFLEPQW | YRVLEKDRVT | LKCQGAYSPE | DNSTRWFHNE |
| muCD16.pro | KAVVKLDPPW | IQVLKEDMVT | LMCEGTHNPG | NSSTQWFHNW |

|  | 90 | 100 | 110 | 120 |
|---|---|---|---|---|
| huCD16A_176V.pro | SLISSQASSY | FIDAATVDDS | GEYRCQTNLS | TLSDPVQLEV |
| cyCD16.pro | SLISSQTSSY | FIAAARVNNS | GEYRCQTSLS | TLSDPVQLEV |
| muCD16.pro | SSIRSQVQSS | YTFKATVNDS | GEYRCQMEQT | RLSDPVDLGV |

|  | 130 | 140 | 150 | 160 |
|---|---|---|---|---|
| huCD16A_176V.pro | HIGWLLLQAP | RWVFKEEDPI | HLRCHSWKNT | ALHKVTYLQN |
| cyCD16.pro | HIGWLLLQAP | RWVFKEEESI | HLRCHSWKNT | ALHKVTYLQN |
| muCD16.pro | ISDWLLLQTP | QRVFLEGETI | TLRCHSWRNK | LLNRISFFHN |

|  | 170 | 180 | 190 | 200 |
|---|---|---|---|---|
| huCD16A_176V.pro | GKGRKYFHHN | SDFYIPKATL | KDSGSYFCRG | LVGSKNVSSE |
| cyCD16.pro | GKGRKYFHQN | SDFYIPKATL | KDSGSYFCRG | LIGSKNVSSE |
| muCD16.pro | EKSVRYHHYK | SNFSIPKANH | SHSGDYYCKG | SLGSTQHQSK |

|  | 210 | 220 | 230 | 240 |
|---|---|---|---|---|
| huCD16A_176V.pro | TVNITITQGL | AVSTISSFFP | PGYQVSFCLV | MVLLFAVDTG |
| cyCD16.pro | TVNITITQDL | AVSSISSFFP | PGYQVSFCLV | MVLLFAVDTG |
| muCD16.pro | PVTITVQDPA | TTSSISLVW- | --YHTAFSLV | MCLLFAVDTG |

|  | 250 | 260 | 270 |  | SEQ ID NO: |
|---|---|---|---|---|---|
| huCD16A_176V.pro | LYFSVKTNIR | SSTRDW-KDH | KFKWRKDPQD | K | 183 |
| cyCD16.pro | LYFSMKKSIP | SSTRDW-EDH | KFKWSKDPQD | K | 184 |
| muCD16.pro | LYFYVRRNIQ | TPRDYWRKSL | SIRKHQAPQD | K | 185 |

Figure 13

BISPECIFIC CD16-BINDING MOLECULES AND THEIR USE IN THE TREATMENT OF DISEASE

CROSS-REFERENCE TO RELATED APPLICATIONS

This application is a § 371 National Stage Application of PCT/US2018/064204 (filed Dec. 6, 2018), which application claims priority to U.S. Patent Application Serial No. 62/597,800 (filed Dec. 12, 2017), each of which applications is herein incorporated by reference in its entirety.

REFERENCE TO SEQUENCE LISTING

This application includes one or more Sequence Listings pursuant to 37 C.F.R. 1.821 et seq., which are disclosed in computer-readable media (file name: 1301_0153PCT_Sequence_Listing_ST25.txt, created on Dec. 4, 2018, and having a size of 276,384 bytes), which file is herein incorporated by reference in its entirety.

FIELD OF THE INVENTION

The present invention is directed to molecules (e.g., an antibody, a diabody, an scFv, an antibody, a TandAb, etc.) capable of binding an epitope of human CD16 (a "CD16 Binding Molecule"). The present invention is further directed to CD16 Binding Molecules that are capable of binding an epitope of human CD16 and one or more epitope(s) of a Disease Antigen ("DA") (e.g., a "CD16×DA Binding Molecule"). The present invention is particularly directed to such CD16×DA Binding Molecules that are antibodies, or that comprise an Epitope Binding Domain thereof, or are diabodies (including DART® diabodies), bispecific antibodies, TandAbs, other multispecific binding molecules (e.g., trivalent TRIDENT™ molecules), etc. The invention particularly concerns CD16×DA Binding Molecules that are capable of binding a Disease Antigen that is a Cancer Antigen or a Pathogen-Associated Antigen in addition to being able to bind CD16. The invention particularly concerns the use of such CD16 and CD16×DA Binding Molecules in the treatment of cancer and pathogen-associated diseases. The present invention is also directed to pharmaceutical compositions that comprise such molecule(s).

BACKGROUND OF THE INVENTION

The mammalian immune system serves as a defense against a variety of conditions, including, e.g., injury, infection and neoplasia. The efficiency with which humans and other mammals develop an immunological response to pathogens, foreign substances and cancer antigens rests on two characteristics: the exquisite specificity of the immune response for antigen recognition, and the immunological memory that allows for faster and more vigorous responses upon re-activation with the same antigen (Portolés, P. et al. (2009) "*The TCR/CD3 Complex: Opening the Gate to Successful Vaccination*," Current Pharmaceutical Design 15:3290-3300; Guy, C. S. et al. (2009) "*Organization of Proximal Signal Initiation at the TCR:CD3 Complex*," Immunol Rev. 232(1):7-21; Topalian, S. L. et al. (2015) "*Immune Checkpoint Blockade: A Common Denominator Approach to Cancer Therapy*," Cancer Cell 27:450-461).

In healthy individuals, the immune system is in a quiescent state, inhibited by a repertoire of diverse inhibitory receptors and receptor ligands. Upon recognition of a cancer antigen, microbial pathogen, or an allergen, an array of activating receptors and receptor ligands are triggered to induce the activation of the immune system. Such activation leads to the activation of macrophages, Natural Killer (NK) cells and antigen-specific, cytotoxic, T-cells, and promotes the release of various cytokines, all of which act to counter the perceived threat to the health of the subject (Dong, C. et al. (2003) "*Immune Regulation by Novel Costimulatory Molecules*," Immunolog. Res. 28(1):39-48; Viglietta, V. et al. (2007) "*Modulating Co-Stimulation*," Neurotherapeutics 4:666-675; Korman, A. J. et al. (2007) "*Checkpoint Blockade in Cancer Immunotherapy*," Adv. Immunol. 90:297-339). The immune system is capable of returning to its normal quiescent state when the countervailing inhibitory immune signals outweigh the activating immune signals.

Thus, the disease state of cancer (and indeed the disease states of infectious diseases) may be considered to reflect a failure to adequately activate a subject's immune system. Such failure may reflect an inadequate presentation of activating immune signals, or it may reflect an inadequate ability to alleviate inhibitory immune signals in the subject. In some instances, researchers have determined that cancer cells can co-opt the immune system to evade being detected by the immune system (Topalian, S. L. et al. (2015) "*Immune Checkpoint Blockade: A Common Denominator Approach to Cancer Therapy*," Cancer Cell 27:450-461).

Among the receptors involved in the activation of the immune system are the Fc Receptors:CD16, CD32 and CD64. These Fc receptors are found on the surfaces of multiple types of immune system cells (e.g., B lymphocytes, follicular dendritic cells, natural killer cells, macrophages, neutrophils, eosinophils, basophils and mast cells). Such receptors have an "extracellular" portion (which is thus capable of ligating to an Fc Domain), a "transmembrane" portion (which extends through the cellular membrane), and a "cytoplasmic" portion (positioned inside the cell). Multiple types of FcγRs have been identified: CD16A (FcγRIIIA), CD16B (FcγRIIIB), CD32A (FcγRIIA), CD32B (FcγRIIB), and CD64 (FcγRI). These receptors bind the Fc portion of IgG antibodies, thereby triggering the transduction of activating or inhibitory signals to the immune system.

CD16 is a generic name for the activating Fc receptors, FcγRIIIA (CD16A) and FcγRIIIB (CD16B). These receptors bind the Fc portion of IgG antibodies, thereby triggering the release of cytokines. If such antibodies are bound to a Disease Antigen that is expressed on the surface of a cell (e.g., a cancer cell, pathogen-infected cell, etc.), then such release mediates the killing of the targeted cell.

CD16A is expressed by Natural Killer (NK) cells and tissue macrophages that bind aggregated but not monomeric human IgG (Selvaraj, P. et al. (2004) "*Functional Regulation Of Human Neutrophil Fc Gamma Receptors*," Immunol Res. 29(1-3):219-230; Peltz, G. A. et al. (1989) "*Human Fc Gamma RIII: Cloning, Expression, And Identification Of The Chromosomal Locus Of Two Fc Receptors For IgG*," Proc. Natl. Acad. Sci. (U.S.A.) 86(3):1013-1017; Bachanova, V. et al. (2014) "*NK Cells In Therapy Of Cancer*," Crit. Rev. Oncog. 19(1-2): 133-141; Miller, J. S. (2013) "*Therapeutic Applications: Natural Killer Cells In The Clinic*," Hematology Am. Soc. Hematol. Educ. Program. 2013:247-253; Youinou, P. et al. (2002) "*Pathogenic Effects Of Anti-Fc Gamma Receptor IIIB (CD16) On Polymorphonuclear Neutrophils In Non-Organ-Specific Autoimmune Diseases*," Autoimmun Rev. 1(1-2):13-19; Peipp, M. et al. (2002) "*Bispecific Antibodies Targeting Cancer Cells*," Biochem. Soc. Trans. 30(4):507-511; Unkeless, J. C. et al.

(1995) "*Function Of Human Fc Gamma RIIA And Fc Gamma RIIIB*," Semin. Immunol. 7(1):37-44).

The expression of CD16A by Natural Killer (NK) cells has particular relevance to the present invention, since such cells release cytokines when their CD16 molecules bind to the Fc Domain of an antibody. Thus, when a natural antibody binds to a Disease Antigen of a target cell, its Fc Domain can be recognized by a CD16 molecule of a Natural Killer cell, which then mediates the killing of the target cell. Since such killing is antibody-dependent, it is termed antibody-dependent cell-mediated cytotoxicity (ADCC). ADCC thus depends on a prior antibody response, and, as stated, requires the presence and participation of an FcγR-expressing effector cell (typically natural killer (NK) cells, but also macrophages, neutrophils and eosinophils). CD16A signals ADCC through interactions with the CD ξ protein of NK cells, and signals macrophage-mediated killing through interactions with macrophage FcγR chains.

CD16A possesses two major polymorphic forms, F158 and V158, which differ by possessing a phenylalanine or a valine at residue 158 (shown as residue 160 of the extracellular domain of CD16A (FIG. 7), which corresponds to residue 176 of the full-length protein (Wu, J. et al. (1997) "*A Novel Polymorphism of FcγRIIIa (CD16) Alters Receptor Function and Predisposes to Autoimmune Disease*," J. Clin. Invest. 100(5):1059-1070; Ravetch, J. V. et al. (1989) "*Alternative Membrane Forms Of FcγRIII(CD16) On Human Natural Killer Cells And Neutrophils*," J. Exper. Med. 170:481-497; Koene, H. R. et al. (1997) "*FcγRIIIa-158V/F Polymorphism Influences the Binding of IgG by Natural Killer Cell FcγRIIIa, Independently of the FcγRIIIa-48L/R/H Phenotype*," Blood, 90(3):1109-1114; van Sorge, N. M. (2003) "*FcgammaR Polymorphisms: Implications For Function, Disease Susceptibility And Immunotherapy*," Tissue Antigens 61(3):189-202; Fijen, C. A. (2000) "*The Role Of Fcgamma Receptor Polymorphisms And C3 In The Immune Defence Against Neisseria Meningitidis In Complement-Deficient Individuals*," Clin. Exp. Immunol. 120(2): 338-345). 50% of Caucasians are homozygous for the phenylalanine polymorphism (F158/F158), whereas 39% of Caucasians are heterozygous for this polymorphism (F158/V158) and 11% of Caucasians are homozygous for the valine polymorphism (V158/V158).

CD16B is expressed on neutrophils, and is anchored to glycophosphatidylinositol ("GPI-anchored") (Meknache, N. et al. (2009) "*Human Basophils Express The Glycosylphosphatidylinositol-Anchored Low Affinity IgG Receptor FcgammaRIIIB (CD16B)*," J. Immunol. 182(4):2542-2550 Fernandes, M. J. et al. (2006) "*CD16b Associates With High-Density, Detergent-Resistant Membranes In Human Neutrophils*," Biochem. J. 393(Pt 1):351-359; Selvaraj, P. et al. (2004) "*Functional Regulation Of Human Neutrophil Fc Gamma Receptors*," Immunol Res. 29(1-3):219-230; Unkeless, J. C. et al. (1995) "*Function Of Human Fc Gamma RIIA And Fc Gamma RIIIB*," Semin. Immunol. 7(1):37-44). Although thought to be a decoy receptor, it can also transmit signals (Fernandes, M. J. (2005) "*Signaling Through CD16b In Human Neutrophils Involves The Tec Family Of Tyrosine Kinases*," J. Leukoc. Biol. 78(2):524-532), and is downregulated/cleaved by ADAM17 after cell activation (Wang, Y. et al. (2013) "*ADAM17 Cleaves CD16b (FcγRIIIb) In Human Neutrophils*," Biochim. Biophys. Acta 1833(3):680-685; Guo, S. et al. (2012) "*Role of ADAM10 and ADAM17 in CD16b Shedding Mediated By Different Stimulators*," Chin. Med. Sci. J. 27(2):73-79).

CD16B possesses two major polymorphic forms, NA1 and NA2, which exhibit different binding affinities for IgG1 and IgG3 subclasses (Bournazos, S. et al. (2010) "*Fcγ Receptor IIIb (CD16b) Polymorphisms Are Associated With Susceptibility To Idiopathic Pulmonary Fibrosis*," Lung 188 (6):475-481; van Sorge, N. M. (2003) "*FcgammaR Polymorphisms: Implications For Function, Disease Susceptibility And Immunotherapy*," Tissue Antigens 61(3):189-202). 13% of Caucasians and 16% of Indians are homozygous for the NA1 polymorphism (NA1/NA1), whereas 55% of Caucasians and 28% of Indians are heterozygous for this polymorphism (NA1/NA2) and 32% of Caucasians and 55% of Indians are homozygous for the NA2 polymorphism (NA2/NA2). The alignment of human CD16A and CD16B allotypes is shown in FIG. 7.

CD32A (FcγRIIA) (Brandsma, A. M. (2015) "*Fc Receptor Inside-Out Signaling And Possible Impact On Antibody Therapy*," Immunol Rev. 268(1):74-87; van Sorge, N. M. et al. (2003) "*FcgammaR Polymorphisms: Implications For Function, Disease Susceptibility And Immunotherapy*," Tissue Antigens 61(3):189-202; Selvaraj, P. et al. (2004) "*Functional Regulation Of Human Neutrophil Fc Gamma Receptors*," Immunol. Res. 29(1-3):219-230) and CD64 (FcγRI) (Lu, S. et al. (2015) "*Structural Mechanism Of High Affinity FcγRI recognition Of Immunoglobulin G*," Immunol. Rev. 268(1):192-200; Swisher, J. F. et al. (2015) "*The Many Faces Of FcγRI: Implications For Therapeutic Antibody Function*," Immunol. Rev. 268(1):160-174; Thepen, T. et al. (2009) "*Fcgamma Receptor 1 (CD64), A Target Beyond Cancer*," Curr. Pharm. Des. 15(23):2712-2718; Rouard, H. et al. (1997) "*Fc Receptors As Targets For Immunotherapy*," Int. Rev. Immunol. 16(1-2):147-185) are activating Fc receptors that are expressed on macrophages, neutrophils, eosinophils and dendritic cells (and for CD32A, also on platelets and Langerhan cells). In contrast, CD32B (FcγRIIB) is an inhibiting Fc receptor on B lymphocytes (macrophages, neutrophils, and eosinophils) (Stopforth, R. J. et al. (2016) "*Regulation of Monoclonal Antibody Immunotherapy by FcγRIIB*," J. Clin. Immunol. [2016 Feb. 27 Epub], pp. 1-7; Bruhns, P. et al. (2009) "*Specificity And Affinity Of Human Fcgamma Receptors And Their Polymorphic Variants For Human IgG Subclasses*," Blood. 113(16): 3716-3725; White, A. L. et al. (2014) "*FcγRIIB As A Key Determinant Of Agonistic Antibody Efficacy*," Curr. Top. Microbiol. Immunol. 382:355-372; Selvaraj, P. et al. (2004) "*Functional Regulation Of Human Neutrophil Fc Gamma Receptors*," Immunol. Res. 29(1-3):219-230).

The ability of the different FcγRs to mediate diametrically opposing functions reflects their structural differences, and in particular whether the FcγR possesses an immunoreceptor tyrosine-based activation motif ("ITAM") or an immunoreceptor tyrosine-based inhibitory motif ("ITIM"). The recruitment of different cytoplasmic enzymes to these structures dictates the outcome of the FcγR-mediated cellular responses. ITAM-containing FcγRs include FcγRT, FcγRIIA, FcγRIIIA, and activate the immune system when bound to Fc Domains (e.g., aggregated Fc Domains present in an immune complex). FcγRIIB is the only currently known natural ITIM-containing FcγR; it acts to dampen or inhibit the immune system when bound to aggregated Fc Domains.

Although natural IgG antibodies directed to an epitope of a particular Disease Antigen possess Fc Domains that can interact with CD16 molecules to activate a subject's immune response, in the case of many diseases and many subjects, such immune system activation is not sufficient to provide an effective therapy for the disease. Thus, despite prior advances in identifying the molecules involved in mammalian immune responses, a need remains for improved therapies for treating cancers and infectious diseases. The CD16-Binding Molecules of the present invention, and particularly, the CD16×DA Binding Molecules of the present invention that comprise a CD16 Binding Domain and a Binding Domain specific for a Disease Antigen expressed on a target cell are capable of co-localizing CD16-expressing cells to the site(s) of cells expressing the Disease Antigen. Such co-localization enhances the ADCC-mediated killing of target cells by increasing the likelihood that an Fc portion of an antibody directed against an epitope of the Disease Antigen will bind to a CD16-expressing effector cell and, via such Fc-CD16 interaction, trigger immune system activation and the release of cytokines against the target cell. Thus, the present invention is directed to improving the activation of a subject's immune response to a Disease antigen and other goals.

SUMMARY OF THE INVENTION

The present invention is directed to molecules (e.g., an antibody, a diabody, an scFv, an antibody, a TandAb, etc.) capable of binding an epitope of human CD16 (a "CD16 Binding Molecule"). The present invention is further directed to CD16 Binding Molecules that are capable of binding an epitope of human CD16 and one or more epitope(s) of a Disease Antigen ("DA") (e.g., a "CD16×DA Binding Molecule"). The present invention is particularly directed to such CD16×DA Binding Molecules that are antibodies, or that comprise an Epitope Binding Domain thereof, or are diabodies (including DART® diabodies), bispecific antibodies, TandAbs, other multispecific binding molecules (e.g., trivalent TRIDENT™ molecules), etc. The invention particularly concerns CD16×DA Binding Molecules that are capable of binding a Disease Antigen that is a Cancer Antigen or a Pathogen-Associated Antigen in addition to being able to bind CD16. The invention particularly concerns the use of such CD16 and CD16×DA Binding Molecules in the treatment of cancer and pathogen-associated diseases. The present invention is also directed to pharmaceutical compositions that comprise such molecule(s).

In detail, the invention provides a CD16×Disease Antigen (CD16×DA) Binding Molecule comprising a CD16 Binding Domain capable of binding an epitope of CD16 and also a Disease Antigen-Binding Domain capable of binding an epitope of a Disease Antigen, wherein the CD16 Binding Domain comprises one or more of:

(I) (A) a $CDR_H1$ Domain comprising the amino acid sequence of SEQ ID NO:66;
(B) a $CDR_H2$ Domain comprising the amino acid sequence of SEQ ID NO:67;
(C) a $CDR_H3$ Domain comprising the amino acid sequence of SEQ ID NO:68 or SEQ ID NO:60;
(D) a $CDR_L1$ Domain comprising the amino acid sequence of SEQ ID NO:69 or SEQ ID NO:74;
(E) a $CDR_L2$ Domain comprising the amino acid sequence of SEQ ID NO:70; and
(F) a $CDR_L3$ Domain comprising the amino acid sequence of SEQ ID NO:71 or SEQ ID NO:61;
(II) (A) a $CDR_H1$ Domain comprising the amino acid sequence of SEQ ID NO:77;
(B) a $CDR_H2$ Domain comprising the amino acid sequence of SEQ ID NO:78;
(C) a $CDR_H3$ Domain comprising the amino acid sequence of SEQ ID NO:79;
(D) a $CDR_L1$ Domain comprising the amino acid sequence of SEQ ID NO:80;
(E) a $CDR_L2$ Domain comprising the amino acid sequence of SEQ ID NO:81; and
(F) a $CDR_L3$ Domain comprising the amino acid sequence of SEQ ID NO:82;
(III) a VH Domain comprising the amino acid sequence of SEQ ID NO:72, SEQ ID NO:83, SEQ ID NO:84, or SEQ ID NO:58;
(IV) a VL Domain comprising the amino acid sequence of SEQ ID NO:73, SEQ ID NO:85, or SEQ ID NO:59;
(V) a VH Domain comprising the amino acid sequence of SEQ ID NO:72 and a VL Domain comprising the amino acid sequence of SEQ ID NO:73; and
(VI) a VH Domain comprising the amino acid sequence of SEQ ID NO:83 or SEQ ID NO:84 and a VL Domain comprising the amino acid sequence of SEQ ID NO:85
(VII) a VH Domain comprising the amino acid sequence of SEQ ID NO:58 and a VL Domain comprising the amino acid sequence of SEQ ID NO:73;
(VIII) a VH Domain comprising the amino acid sequence of SEQ ID NO:72 and a VL Domain comprising the amino acid sequence of SEQ ID NO:59; and
(IX) a VH Domain comprising the amino acid sequence of SEQ ID NO:58 and a VL Domain comprising the amino acid sequence of SEQ ID NO:59.

The invention additionally concerns the embodiment of such CD16×Disease Antigen Binding Molecule, wherein the Molecule is a bispecific antibody, a bispecific diabody, a bispecific TandAb, a bispecific trivalent molecule, or a bispecific CAR.

The invention additionally concerns the embodiment of such CD16×Disease Antigen Binding Molecules, wherein the Molecule is capable of binding more than one Disease Antigen and/or more than one epitope of CD16.

The invention additionally concerns the embodiment of such CD16×Disease Antigen Binding Molecules, wherein the CD16 Binding Domain comprises:

(A) a $CDR_H1$ Domain comprising the amino acid sequence of SEQ ID NO:66;
(B) a $CDR_H2$ Domain comprising the amino acid sequence of SEQ ID NO:67;
(C) a $CDR_H3$ Domain comprising the amino acid sequence of SEQ ID NO:68, or SEQ ID NO:60;
(D) a $CDR_L1$ Domain comprising the amino acid sequence of SEQ ID NO:69 or SEQ ID NO:74;
(E) a $CDR_L2$ Domain comprising the amino acid sequence of SEQ ID NO:70; and
(F) a $CDR_L3$ Domain comprising the amino acid sequence of SEQ ID NO:71, or SEQ ID NO:61.

The invention additionally concerns the embodiment of such CD16×Disease Antigen Binding Molecules, wherein the CD16 Binding Domain comprises:

(A) a VH Domain comprising the amino acid sequence of SEQ ID NO:72, or SEQ ID NO:58;
(B) a VL Domain comprising the amino acid sequence of SEQ ID NO:73, or SEQ ID NO:59; or
(C) a VH Domain comprising the amino acid sequence of SEQ ID NO:72 and a VL Domain comprising the amino acid sequence of SEQ ID NO:73
(D) a VH Domain comprising the amino acid sequence of SEQ ID NO:58 and a VL Domain comprising the amino acid sequence of SEQ ID NO:73;
(E) a VH Domain comprising the amino acid sequence of SEQ ID NO:72 and a VL Domain comprising the amino acid sequence of SEQ ID NO:59; or
(F) a VH Domain comprising the amino acid sequence of SEQ ID NO:58 and a VL Domain comprising the amino acid sequence of SEQ ID NO:59.

The invention additionally concerns the embodiment of such CD16×Disease Antigen Binding Molecules, wherein the CD16 Binding Domain comprises:
(A) a $CDR_H1$ Domain comprising the amino acid sequence of SEQ ID NO:77;
(B) a $CDR_H2$ Domain comprising the amino acid sequence of SEQ ID NO:78;
(C) a $CDR_H3$ Domain comprising the amino acid sequence of SEQ ID NO:79;
(D) a $CDR_L1$ Domain comprising the amino acid sequence of SEQ ID NO:80;
(E) a $CDR_L2$ Domain comprising the amino acid sequence of SEQ ID NO:81; and
(F) a $CDR_L3$ Domain comprising the amino acid sequence of SEQ ID NO:82.

The invention additionally concerns the embodiment of such CD16×Disease Antigen Binding Molecules, wherein the CD16 Binding Domain comprises:
(A) a VH Domain comprising the amino acid sequence of SEQ ID NO:83, or SEQ ID NO:84;
(B) a VL Domain comprising the amino acid sequence of or SEQ ID NO:85; or
(C) a VH Domain comprising the amino acid sequence of SEQ ID NO:83 or SEQ ID NO:84 and a VL Domain comprising the amino acid sequence of SEQ ID NO:85.

The invention additionally concerns the embodiment of such CD16×Disease Antigen Binding Molecules, wherein the Disease Antigen is a Cancer Antigen and the disease is cancer.

The invention additionally concerns the embodiment of such CD16×Disease Antigen Binding Molecules, wherein the cancer is selected from the group consisting of adrenal cancer, bladder cancer, breast cancer, colorectal cancer, gastric cancer, glioblastoma, kidney cancer, non-small-cell lung cancer, acute lymphocytic leukemia, acute myeloid leukemia, chronic lymphocytic leukemia, chronic myeloid leukemia, hairy cell leukemia, Burkett's lymphoma, diffuse large B cell lymphoma, follicular lymphoma, mantle cell lymphoma, marginal zone lymphoma, non-Hodgkin's lymphoma, small lymphocytic lymphoma, multiple myeloma, melanoma, ovarian cancer, pancreatic cancer, prostate cancer, skin cancer, renal cell carcinoma, testicular cancer, and uterine cancer.

The invention additionally concerns the embodiment of such CD16×Disease Antigen Binding Molecules, wherein the Cancer Antigen is selected from the group consisting of the Cancer Antigens: 19.9, 4.2, A33, ADAM-9, AH6, ALCAM, B1, B7-H3, BAGE, beta-catenin, blood group $ALe^b/Le^y$, Burkitt's lymphoma antigen-38.13, C14, CA125, Carboxypeptidase M, CD5, CD19, CD20, CD22, CD23, CD25, CD27, CD28, CD33, CD36, CD40/CD154, CD45, CD56, CD46, CD52, CD56, CD79a/CD79b, CD103, CD123, CD317, CDK4, CEA, CEACAM5/CEACAM6, CO17-1A, CO-43, CO-514, CTA-1, CTLA-4, Cytokeratin 8, D1.1, Di56-22, DR5, $E_1$ series, EGFR, an Ephrin receptor, EphA2, Erb, GAGE, a GD2/GD3/GM2 ganglioside, GICA 19-9, gp100, Gp37, gp75, gpA33, HER2/neu, HMFG, human papillomavirus-E6/human papillomavirus-E7, HMW-MAA, I antigen, IL13Rα2, Integrin (36, JAM-3, KID3, KID31, KS 1/4 pan-carcinoma antigen, L6,L20, LEA, LUCA-2, M1:22:25:8, M18, M39, MAGE, MART, mesothelin, MUC-1, MUM-1, Myl, N-acetylglucosaminyl-transferase, neoglycoprotein, NS-10, OFA-1, OFA-2, Oncostatin M, p15, p97, PEM, PEMA, PIPA, PSA, PSMA, prostatic acid phosphate, $R_{24}$, ROR1, a sphingolipid, SSEA-1, SSEA-3, SSEA-4, sTn, the T cell receptor derived peptide, $T_5A_7$, TAG-72, TL5, TNF-receptor, TNF-γ receptor, TRA-1-85, a Transferrin Receptor, 5T4, TSTA, VEGF, a VEGF Receptor, VEP8, VEP9, VIM-D5, and Y hapten, $Le^y$.

The invention additionally concerns the embodiment of such CD16×Disease Antigen Binding Molecules, wherein the Disease Antigen is 5T4, B7-H3, CEACAM5/CEACAM6, CD19, CD123, EGRF, EphA2, HER2/neu, IL13Rα2 or VEGF.

The invention additionally concerns the embodiment of such CD16×Disease Antigen Binding Molecules, wherein the Disease Antigen is a Pathogen-Associated Antigen.

The invention additionally concerns the embodiment of such CD16×Disease Antigen Binding Molecules, wherein the Pathogen-Associated Antigen is selected from the group consisting of the Pathogen-Associated Antigens: Herpes Simplex Virus infected cell protein (ICP)47, Herpes Simplex Virus gD, Epstein-Barr Virus LMP-1, Epstein-Barr Virus LMP-2A, Epstein-Barr Virus LMP-2B, Human Immunodeficiency Virus gp160, Human Immunodeficiency Virus gp120, Human Immunodeficiency Virus gp41, etc.), Human Papillomavirus E6, Human Papillomavirus E7, human T-cell leukemia virus gp64, human T-cell leukemia virus gp46, and human T-cell leukemia virus gp21.

The invention additionally concerns the embodiment of such CD16×Disease Antigen Binding Molecules, wherein the Disease Antigen is an HIV env antigen.

The invention additionally concerns the embodiment of such CD16×Disease Antigen Binding Molecules, wherein the molecule is:
(A) a diabody, said diabody being a covalently bonded complex that comprises two, or three, four or five polypeptide chains; or
(B) a trivalent binding molecule, said trivalent binding molecule being a covalently bonded complex that comprises three, four or five polypeptide chains, or
(C) a bispecific antibody.

The invention additionally concerns the embodiment of such CD16×Disease Antigen Binding Molecules, wherein the molecule comprises an Fc Region.

The invention additionally concerns the embodiment of such CD16×Disease Antigen Binding Molecules, wherein the Fc Region, is of the IgG1, IgG2, IgG3, or IgG4 isotype.

The invention additionally concerns the embodiment of such CD16×Disease Antigen Binding Molecules, wherein the Fc Region is a variant Fc Region that comprises:
(A) one or more amino acid modifications that reduces the affinity of the variant Fc Region for an FcγR; and/or
(B) one or more amino acid modifications that enhances the serum half-life of the variant Fc Region.

The invention additionally concerns the embodiment of such CD16×Disease Antigen Binding Molecules:
(A) said modifications that reduces the affinity of the variant Fc Region for an FcγR comprise the substitution of L234A; L235A; or L234A and L235A; and
(B) said modifications that that enhances the serum half-life of the variant Fc Region comprise the substitution of M252Y; M252Y and S254T; M252Y and T256E; M252Y, S254T and T256E; or K288D and H435K, wherein said numbering is that of the EU index as in Kabat.

The invention additionally concerns a CD16 Binding Molecule, that comprises:
(A) a $CDR_H1$ Domain comprising the amino acid sequence of SEQ ID NO:66;
(B) a $CDR_H2$ Domain comprising the amino acid sequence of SEQ ID NO:67;
(C) a $CDR_H3$ Domain comprising the amino acid sequence of SEQ ID NO:68, or SEQ ID NO:60;

(D) a $CDR_L1$ Domain comprising the amino acid sequence of SEQ ID NO:69 or SEQ ID NO:74;
(E) a $CDR_L2$ Domain comprising the amino acid sequence of SEQ ID NO:70; and
(F) a $CDR_L3$ Domain comprising the amino acid sequence of SEQ ID NO:71, or SEQ ID NO:61.

The invention additionally concerns the embodiment of such a CD16 Binding Molecule wherein the molecule comprises:
(A) a VH Domain comprising the amino acid sequence of SEQ ID NO:72, or SEQ ID NO:58;
(B) a VL Domain comprising the amino acid sequence of SEQ ID NO:73, or SEQ ID NO:59;
(C) a VH Domain comprising the amino acid sequence of SEQ ID NO:72 and a VL Domain comprising the amino acid sequence of SEQ ID NO:73; or
(D) a VH Domain comprising the amino acid sequence of SEQ ID NO:58 and a VL Domain comprising the amino acid sequence of SEQ ID NO:73;
(E) a VH Domain comprising the amino acid sequence of SEQ ID NO:72 and a VL Domain comprising the amino acid sequence of SEQ ID NO:59; or
(F) a VH Domain comprising the amino acid sequence of SEQ ID NO:58 and a VL Domain comprising the amino acid sequence of SEQ ID NO:59.

The invention additionally concerns a CD16 Binding Molecule that comprises:
(A) a $CDR_H1$ Domain comprising the amino acid sequence of SEQ ID NO:77;
(B) a $CDR_H2$ Domain comprising the amino acid sequence of SEQ ID NO:78;
(C) a $CDR_H3$ Domain comprising the amino acid sequence of SEQ ID NO:79;
(D) a $CDR_L1$ Domain comprising the amino acid sequence of SEQ ID NO:80;
(E) a $CDR_L2$ Domain comprising the amino acid sequence of SEQ ID NO:81; and
(F) a $CDR_L3$ Domain comprising the amino acid sequence of SEQ ID NO:82.

The invention additionally concerns the embodiment of such CD16 Binding Molecule wherein the molecule comprises:
(A) a VH Domain comprising the amino acid sequence of SEQ ID NO:83 or SEQ ID NO:84;
(B) a VL Domain comprising the amino acid sequence of or SEQ ID NO:85; or (C) a VH Domain comprising the amino acid sequence of SEQ ID NO:83 or SEQ ID NO:84 and a VL Domain comprising the amino acid sequence of SEQ ID NO:85.

The invention additionally concerns the embodiment of such CD16 Binding Molecules wherein the molecule is selected from the group consisting of: an antibody, a multispecific antibody, a Fab' fragment, a F(ab')$_2$ fragment, a (Fv) fragment, a single-chain (scFv), a single-chain antibody, a disulfide-linked bispecific Fv (sdFv), a diabody, a trivalent binding molecule, and a CAR-T molecule.

The invention additionally concerns a pharmaceutical composition that comprises any of the above-described CD16×Disease Antigen Binding Molecules, or CD16 Binding Molecules, and a pharmaceutically acceptable carrier.

The invention additionally concerns the use of the above-described pharmaceutical composition in the treatment of a disease characterized by the expression of the Disease Antigen.

The invention additionally concerns a method for the treatment of a disease characterized by the expression of the Disease Antigen, comprising administering to a subject in need thereof a therapeutically effective amount of the above-described pharmaceutical composition.

The invention additionally concerns the embodiment of such use or method wherein the CD16×Disease Antigen Binding Molecule is capable of binding more than one Disease Antigen and/or more than one epitope of CD16.

The invention additionally concerns such use or method wherein the CD16×Disease Antigen Binding Molecule, wherein the Disease Antigen is a Cancer Antigen, and the disease is cancer.

The invention additionally concerns such use or method wherein the cancer is selected from the group consisting of adrenal cancer, bladder cancer, breast cancer, colorectal cancer, gastric cancer, glioblastoma, kidney cancer, non-small-cell lung cancer, acute lymphocytic leukemia, acute myeloid leukemia, chronic lymphocytic leukemia, chronic myeloid leukemia, hairy cell leukemia, Burkett's lymphoma, diffuse large B cell lymphoma, follicular lymphoma, mantle cell lymphoma, marginal zone lymphoma, non-Hodgkin's lymphoma, small lymphocytic lymphoma, multiple myeloma, melanoma, ovarian cancer, pancreatic cancer, prostate cancer, skin cancer, renal cell carcinoma, testicular cancer, and uterine cancer.

The invention additionally concerns such use or method wherein the Cancer Antigen is selected from the group consisting of the Cancer Antigens: 19.9, 4.2, A33, ADAM-9, AH6, ALCAM, B1, B7-H3, BAGE, beta-catenin, blood group $ALe^b/Le^y$, Burkitt's lymphoma antigen-38.13, C14, CA125, Carboxypeptidase M, CD5, CD19, CD20, CD22, CD23, CD25, CD27, CD28, CD33, CD36, CD40/CD154, CD45, CD56, CD46, CD52, CD56, CD79a/CD79b, CD103, CD123, CD317, CDK4, CEA, CEACAM5/CEACAM6, CO17-1A, CO-43, CO-514, CTA-1, CTLA-4, Cytokeratin 8, D1.1, $D_1$56-22, DR5, $E_1$ series, EGFR, an Ephrin receptor, EphA2, Erb, GAGE, a GD2/GD3/GM2 ganglioside, GICA 19-9, gp100, Gp37, gp75, gpA33, HER2/neu, HMFG, human papillomavirus-E6/human papillomavirus-E7, HMW-MAA, I antigen, IL13Rα2, Integrin β6, JAM-3, KID3, KID31, KS 1/4 pan-carcinoma antigen, L6,L20, LEA, LUCA-2, M1:22:25:8, M18, M39, MAGE, MART, mesothelin, MUC-1, MUM-1, Myl, N-acetylglucosaminyl-transferase, neoglycoprotein, NS-10, OFA-1, OFA-2, Oncostatin M, p15, p97, PEM, PEMA, PIPA, PSA, PSMA, prostatic acid phosphate, $R_{24}$, ROR1, a sphingolipid, SSEA-1, SSEA-3, SSEA-4, sTn, the T cell receptor derived peptide, $T_5A_7$, TAG-72, TL5, TNF-receptor, TNF-γ receptor, TRA-1-85, a Transferrin Receptor, 5T4, TSTA, VEGF, a VEGF Receptor, VEP8, VEP9, VIM-D5, and Y hapten, $Le^y$.

The invention additionally concerns such use or method wherein the Disease Antigen is 5T4, B7-H3, CEACAM5/CEACAM6, CD19, CD123, EGRF, EphA2, HER2/neu, IL13Rα2 or VEGF.

The invention additionally concerns such use or method wherein the CD16×Disease Antigen Binding Molecule, wherein the Disease Antigen is a Pathogen-Associated Antigen.

The invention additionally concerns such use or method wherein the Pathogen-Associated Antigen is selected from the group consisting of the Pathogen-Associated Antigens: Herpes Simplex Virus infected cell protein (ICP)47, Herpes Simplex Virus gD, Epstein-Barr Virus LMP-1, Epstein-Barr Virus LMP-2A, Epstein-Barr Virus LMP-2B, Human Immunodeficiency Virus gp160, Human Immunodeficiency Virus gp120, Human Immunodeficiency Virus gp41, etc.), Human Papillomavirus E6, Human Papillomavirus E7, human T-cell leukemia virus gp64, human T-cell leukemia virus gp46, and human T-cell leukemia virus gp21.

The invention additionally concerns such use or method wherein the Disease Antigen is an HIV env antigen.

BRIEF DESCRIPTION OF THE DRAWINGS

FIG. 3A shows an Fc Region-containing diabody which contains a peptide Heterodimer-Promoting Domain comprising a cysteine residue. FIG. 3B shows an Fc Region-containing diabody, which contains E-coil and K-coil Heterodimer-Promoting Domains comprising a cysteine residue and a linker (with an optional cysteine residue). FIG. 3C, shows an Fc-Region-Containing diabody, which contains antibody CH1 and CL domains. FIGS. 3D-3E illustrate how selection of the binding domains shown in FIG. 3B can result in a CD16×DA Binding Molecule having two binding sites specific for an epitope of CD16 and two binding sites specific for an epitope of a DA. FIGS. 3D-3E illustrate non-limiting examples of how domains may be selected to yield CD16×DA Binding Molecules having differing orientations (i.e., FIG. 3D employs, a VL CD16 Domain as the VL1 Domain of the Binding Molecule, a VH CD16 Domain as the VH1 Domain of the Binding Molecule, a VL DA Domain as the VL2 Domain of the Binding Molecule, and a VH DA Domain as the VH2 Domain of the Binding Molecule. In contrast, FIG. 3E employs, a VL DA Domain as the VL1 Domain of the Binding Molecule, a VH DA Domain as the VH1 Domain of the Binding Molecule, a VL CD16 Domain as the VL2 Domain of the Binding Molecule, and a VH CD16 Domain as the VH2 Domain of the Binding Molecule). As provided below, the VL/VH binding sites formed by the association of the polypeptide chains may be the same or different so as to permit tetravalent binding that is monospecific, bispecific, trispecific or tetraspecific.

FIG. 5A shows the general structure of such a CD16×DA Binding Molecule. Two of the polypeptide chains possess a CH2 and CH3 Domain, such that the associated chains form an Fc Region that comprises all or part of an Fc Region. The polypeptide chains comprising the linked VL and VH Domains further comprise a Heterodimer-Promoting Domain. VL and VH Domains that recognize the same epitope are shown using the same shading or fill pattern. FIG. 5B shows the structure of an alternative CD16×DA Binding Molecule in which the variable domains shown in FIG. 5A have been selected to yield a resultant CD16×DA Binding Molecule that possesses two non-diabody type binding domains specific for an illustrative DA, HER2/neu, and two diabody-type binding domains specific for CD16. FIG. 5C shows the structure of an alternative CD16×DA Binding Molecule in which the variable domains shown in FIG. 5A have been selected to yield a resultant CD16×DA Binding Molecule that possesses two non-diabody type binding domains specific for CD16 and two diabody-type binding domains specific for HER2/neu. FIG. 5D shows the structure of an alternative CD16×DA Binding Molecule in which the variable domains shown in FIG. 5A have been selected to yield a resultant CD16×DA Binding Molecule that possesses two non-diabody type binding domains specific for an epitope of CD16, one diabody-type binding domains specific for an epitope of HER2/neu and a second diabody-type binding domain specific for an epitope of CD16. Such CD16 epitopes may be the same or different. As will be appreciated, by proper selection of the binding domains shown in FIG. 5A, any three of the binding domains could have been selected to bind an epitope of CD16. Likewise, any three of the binding domains could have been selected to bind an epitope of HER2/neu. As provided below, the VL/VH binding sites formed by the association of the polypeptide chains may be the same or different so as to permit tetravalent binding that is monospecific, bispecific, trispecific or tetraspecific.

FIG. 6A schematically the domains of trivalent binding molecules comprising two diabody-type binding domains and a Fab-type binding domain having different domain orientations in which the diabody-type binding domains are N-terminal or C-terminal to an Fc Region. FIGS. 6B-6C show the structure of illustrative non-limiting examples of CD16×DA Binding Molecules in which the variable domains shown in FIG. 6A have been selected to yield a resultant CD16×DA Binding Molecule that possesses a non-diabody type binding domains specific for CD16, a diabody-type binding domain that is specific for an illustrative DA, HER2/neu, and a second diabody-type binding domain that is specific for CD16. FIG. 6D illustrates schematically the domains of trivalent binding molecules comprising two diabody-type binding domains and a Fab-type binding domain having different domain orientations in which the diabody-type binding domains are N-terminal or C-terminal to an Fc Region. The molecules in FIGS. 6A-6D comprise four chains. FIGS. 6E and 6F, respectively, illustrate schematically the domains of trivalent binding molecules comprising two diabody-type binding domains N-terminal to an Fc Region, and a Fab-type binding domain in which the light chain and heavy chain are linked via a polypeptide spacer, or an scFv-type binding domain. The trivalent binding molecules in FIGS. 6G and 6H, respectively, illustrate schematically the domains of trivalent binding molecules comprising two diabody-type binding domains C-terminal to an Fc Region, and a Fab-type binding domain in which the light chain and heavy chain are linked via a polypeptide spacer, or an scFv-type binding domain. The trivalent binding molecules in FIGS. 6E-6H comprise three chains. VL and VH Domains that recognize the same epitope are shown using the same shading or fill pattern.

FIG. 7 shows an alignment of the extracellular domains (ECD) of the 158F allotype of human CD16A (SEQ ID NO:146), the 158V allotype of human CD16A (SEQ ID NO:147), the NA1 allotype of human CD16B (SEQ ID NO:148), the NA2 allotype of human CD16B (SEQ ID NO:149), and the CD16 of cynomolgus monkey (SEQ ID NO:150). Differences in sequence relative to that of the 158F allotype of human CD16A are shown in underlined boldface. In the portion of the human CD16A molecule presented, the 158F/158V polymorphism is found at position 160.

FIG. 13 presents an alignment of the amino acid sequences of human CD16 (SEQ ID NO:183), cynomolgus monkey CD16 (SEQ ID NO:184) and murine CD16 (SEQ ID NO:185). Differences in sequence relative to that of human CD16 are shown in underlined boldface.

FIG. 14A: N87 HER2/neu target cells (HER2/neu expression: +++)/NK cells; CD16A allotype 158F/158F; FIG. 14B: MCF7 HER2/neu target cells (HER2/neu expression: +/−)/NK cells; CD16A allotype 158F/158F; FIG. 14C: MDA-MB-231 HER2/neu target cells (HER2/neu expression: +/−)/PBMCs; CD16A allotype not assessed; FIG. 14D: N87 HER2/neu target cells (HER2/neu expression: +++)/PBMCs; CD16A allotype 158F/158V; FIG. 14E: Hs700T HER2/neu target cells (HER2/neu expression: +/−)/PBMCs; CD16A allotype 158F/158V.

FIG. 15A: 293HEK D371 target cells/ PBMCs; CD16A allotype 158F/158V; FIG. 15B: 293HEK D371 target cells/PBMCs; CD16A allotype 158F/158F; FIG. 15C: 293HEK D371 target cells/NK cells; CD16A allotype 158F/158V.

DETAILED DESCRIPTION OF THE INVENTION

Figure 1A:
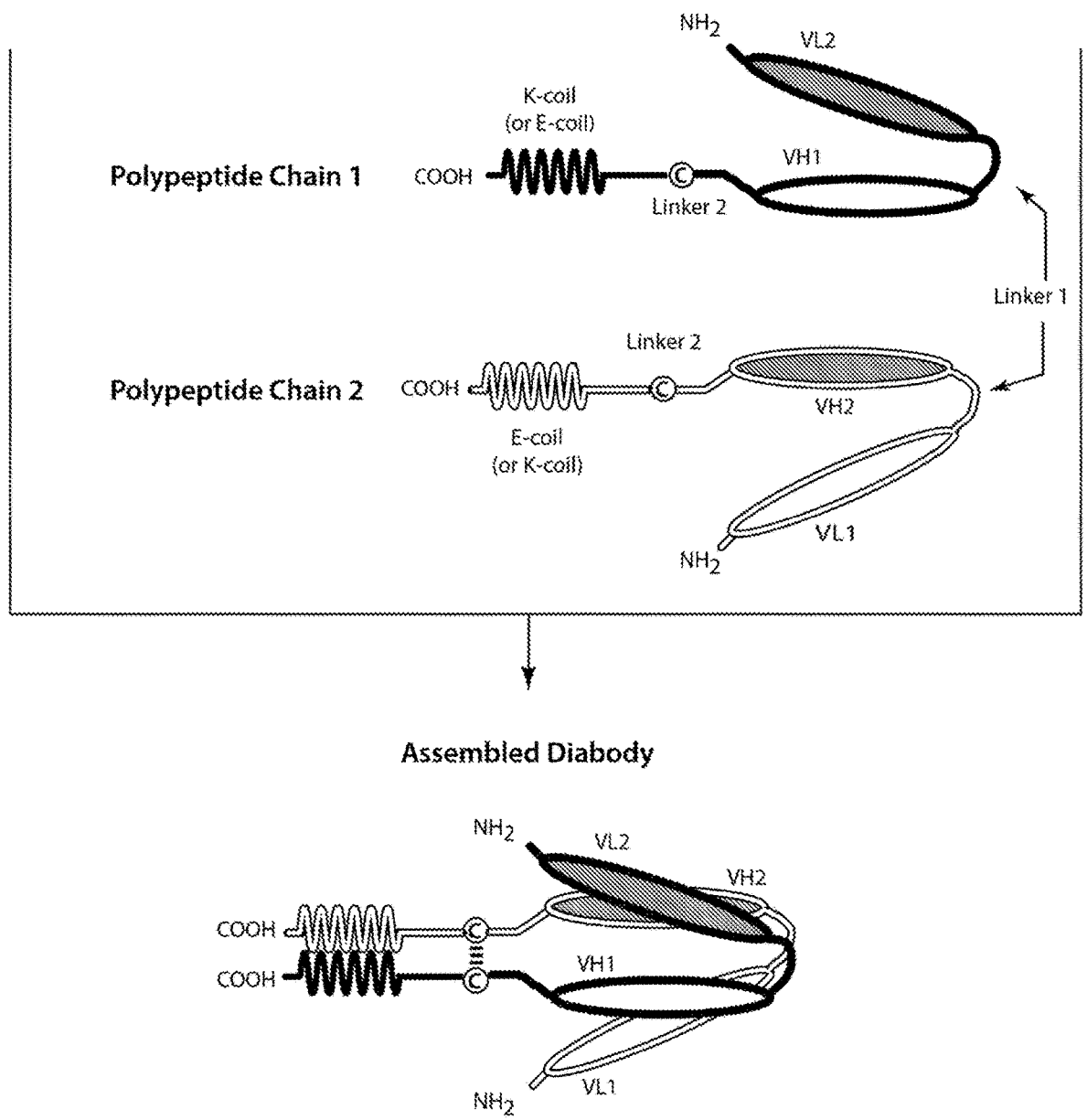
FIGS. 1A-1B provide a schematic of a representative covalently bonded diabody having two epitope-binding sites composed of two polypeptide chains, each having an E-coil or K-coil Heterodimer-Promoting Domain (alternative Heterodimer-Promoting Domains are provided below). A cysteine residue may be present in a linker (FIG. 1A) and/or in the Heterodimer-Promoting Domain (FIG. 1B). VL and VH Domains that recognize the same epitope are shown using the same shading or fill pattern. The wavy line (VWWV) in this and all of the Figures providing schematic presentations of binding molecule domains represents one or more optional Heterodimer-Promoting Domains, that is/are preferably present.

The present invention is directed to molecules (e.g., an antibody, a diabody, an scFv, an antibody, a TandAb, etc.) capable of binding an epitope of human CD16 (a "CD16 Binding Molecule"). The present invention is further directed to CD16 Binding Molecules that are capable of binding an epitope of human CD16 and one or more epitope(s) of a Disease Antigen ("DA") (e.g., a "CD16×DA Binding Molecule"). The present invention is particularly directed to such CD16×DA Binding Molecules that are antibodies, or that comprise an Epitope Binding Domain thereof, or are diabodies (including DART® diabodies), bispecific antibodies, TandAbs, other multispecific binding molecules (e.g., trivalent TRIDENT™ molecules), etc. The invention particularly concerns CD16×DA Binding Molecules that are capable of binding a Disease Antigen that is a Cancer Antigen or a Pathogen-Associated Antigen in addition to being able to bind CD16. The invention particularly concerns the use of such CD16 and CD16×DA Binding Molecules in the treatment of cancer and pathogen-associated diseases. The present invention is also directed to pharmaceutical compositions that comprise such molecule(s).

I. Antibodies and Other Binding Molecules

A. Antibodies

The CD16×DA Binding Molecules of the present invention may be antibodies, or be derivable from antibodies (e.g., by fragmentation, cleavage, etc. of antibody polypeptides, or from use of the amino acid sequences of antibody molecules or of polynucleotides (or their sequences) that encode such polynucleotides, etc.).

Antibodies are immunoglobulin molecules capable of specific binding to a particular domain or moiety or conformation (an "epitope") of a molecule, such as a carbohydrate, polynucleotide, lipid, polypeptide, etc. An epitope-containing molecule may have immunogenic activity, such that it elicits an antibody production response in an animal; such molecules are termed "antigens." As used herein, the terms "antibody" and "antibodies" refer to monoclonal antibodies, multispecific antibodies, human antibodies, humanized antibodies, synthetic antibodies, chimeric antibodies, polyclonal antibodies, camelized antibodies, single-chain Fvs (scFv), single-chain antibodies, Fab fragments, F(ab') fragments, disulfide-linked bispecific Fvs (sdFv), intrabodies, and Epitope Binding Domains of any of the above. Such Immunoglobulin molecules can be of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass.

The term "monoclonal antibody" refers to a homogeneous antibody population wherein the monoclonal antibody is comprised of amino acids (naturally occurring or non-naturally occurring) that are involved in the selective binding of an antigen. Monoclonal antibodies are highly specific, being directed against a single epitope (or antigenic site). The term "monoclonal antibody" encompasses not only intact monoclonal antibodies and full-length monoclonal antibodies, but also fragments thereof (such as Fab, Fab', F(ab')$_2$, (Fv), single-chain (scFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody." Methods of making monoclonal antibodies are known in the art. One method which may be employed is the method of Kohler, G. et al. (1975) "*Continuous Cultures Of Fused Cells Secreting Antibody Of Predefined Specificity,*" Nature 256:495-497 or a modification thereof. Typically, monoclonal antibodies are developed in mice, rats or rabbits. The antibodies are produced by immunizing an animal with an immunogenic amount of cells, cell extracts, or protein preparations that contain the desired epitope. The immunogen can be, but is not limited to, primary cells, cultured cell lines, cancerous cells, proteins, peptides, nucleic acids, or tissue. Cells used for immunization may be cultured for a period of time (e.g., at least 24 hours) prior to their use as an immunogen. Cells may be used as immunogens by themselves or in combination with a non-denaturing adjuvant, such as Ribi (see, e.g., Jennings, V. M. (1995) "*Review of Selected Adjuvants Used in Antibody Production*," ILAR J. 37(3):119-125). In general, cells should be kept intact and preferably viable when used as immunogens. Intact cells may allow antigens to be better detected than ruptured cells by the immunized animal. Use of denaturing or harsh adjuvants, e.g., Freund's adjuvant, may rupture cells and therefore is discouraged. The immunogen may be administered multiple times at periodic intervals such as, bi weekly, or weekly, or may be administered in such a way as to maintain viability in the animal (e.g., in a tissue recombinant). Alternatively, existing monoclonal antibodies and any other equivalent antibodies that are immunospecific for a desired pathogenic epitope can be sequenced and produced recombinantly by any means known in the art. In one embodiment, such an antibody is sequenced and the polynucleotide sequence is then cloned into a vector for expression or propagation. The sequence encoding the antibody of interest may be maintained in a vector in a host cell and the host cell can then be expanded and frozen for future use. The polynucleotide sequence of such antibodies may be used for genetic manipulation to generate the monospecific or multispecific (e.g., bispecific, trispecific and tetraspecific) molecules of the invention as well as an affinity optimized, a chimeric antibody, a humanized antibody, and/or a caninized antibody, to improve the affinity, or other characteristics of the antibody as detailed below.

Antibodies and the Binding Molecules of the present invention bind epitopes via their Binding Domains in an "immunospecific" manner. As used herein, a molecule is said to bind an epitope of another molecule in an immunospecific manner (or "immunospecifically") if it binds or associates more frequently, more rapidly, with greater duration and/or with greater affinity with that epitope relative to alternative epitopes. For example, an antibody that immunospecifically binds to a viral epitope is an antibody that binds this viral epitope with greater affinity, avidity, more readily, and/or with greater duration than it immunospecifically binds to other viral epitopes or non-viral epitopes. It is also understood by reading this definition that, for example, an antibody (or moiety or epitope) that immunospecifically binds to a first target may or may not specifically or preferentially bind a second target. As such, "immunospecific binding" does not necessarily require (although it can include) exclusive binding. Generally, but not necessarily, reference to binding means "immunospecific" binding. Natural antibodies are capable of binding to only one epitope species (i.e., they are "monospecific"), although they can immunospecifically bind multiple copies of that species (i.e., exhibiting "bivalency" or "multivalency"). Two molecules are said to be capable of binding one another in a "physiospecific" manner, if such binding exhibits the specificity with which receptors bind their respective ligands.

The last few decades have seen a revival of interest in the therapeutic potential of antibodies, and antibodies have become one of the leading classes of biotechnology-derived drugs (Chan, C. E. et al. (2009) "*The Use Of Antibodies In The Treatment Of Infectious Diseases*," Singapore Med. J. 50(7):663-666). Over 200 antibody-based drugs have been approved for use or are under development.

1. General Structural Attributes of Antibodies

The basic structural unit of naturally occurring immunoglobulins (e.g., IgG) is a tetramer composed of two shorter "Light Chains" complexed with two longer "Heavy Chains" and is usually expressed as a glycoprotein of about 150,000 Da. Each chain is composed of an amino-terminal ("N-terminal") portion that comprises a "Variable Domain" and a carboxy-terminal ("C-terminal") portion that comprises at least one "Constant Domain." An IgG Light Chain is composed of a single "Light Chain Variable Domain" ("VL") and a single "Light Chain Constant Domain" ("CL"). Thus, the structure of the light chains of an IgG molecule is n-VL-CL-c (where n and c represent, respectively, the N-terminus and the C-terminus of the polypeptide). An IgG Heavy Chain is composed of a single "Heavy Chain Variable Domain" ("VH"), three "Heavy Chain Constant Domains" ("CH1," "CH2" and "CH3"), and a "Hinge" Region ("H"), located between the CH1 and CH2 Domains. Thus, the structure of an IgG heavy chain is n-VH—CH1-H—CH2-CH3-c (where n and c represent, respectively, the N-terminus and the C-terminus of the polypeptide). The ability of an intact, unmodified antibody (e.g., an IgG antibody) to bind an epitope of an antigen depends upon the presence and sequences of the Variable Domains. Unless specifically noted, the order of domains of the protein molecules described herein is in the "N-terminal to C-terminal" direction.

(a) Constant Domains (i) Light Chain Constant Domain

A preferred CL Domain is a human IgG CL Kappa Domain. The amino acid sequence of an exemplary human CL Kappa Domain is (SEQ ID NO:1):

```
RTVAAPSVFI FPPSDEQLKS GTASVVCLLN NFYPREAKVQ

WKVDNALQSG NSQESVTEQD SKDSTYSLSS TLTLSKADYE

KHKVYACEVT HQGLSSPVTK SFNRGEC
```

Alternatively, an exemplary CL Domain is a human IgG CL Lambda Domain. The amino acid sequence of an exemplary human CL Lambda Domain is (SEQ ID NO:2):

```
QPKAAPSVTL FPPSSEELQA NKATLVCLIS DFYPGAVTVA

WKADSSPVKA GVETTPSKQS NNKYAASSYL SLTPEQWKSH

RSYSCQVTHE GSTVEKTVAP TECS
```

(ii) Heavy Chain CH1 Domains

The CH1 Domains of the two Heavy Chains of an antibody complex with the antibody's Light Chain's "CL" constant region, and are attached to the Heavy Chains CH2 Domains via an intervening Hinge Domain.

An exemplary CH1 Domain is a human IgG1 CH1 Domain. The amino acid sequence of an exemplary human IgG1 CH1 Domain is (SEQ ID NO:3):

```
ASTKGPSVFP LAPSSKSTSG GTAALGCLVK

DYFPEPVTVS WNSGALTSGV HTFPAVLQSS

GLYSLSSVVT VPSSSLGTQT YICNVNHKPS

NTKVDKRV
```

An exemplary CH1 Domain is a human IgG2 CH1 Domain. The amino acid sequence of an exemplary human IgG2 CH1 Domain is (SEQ ID NO:4):

```
ASTKGPSVFP LAPCSRSTSE STAALGCLVK

DYFPEPVTVS WNSGALTSGV HTFPAVLQSS

GLYSLSSVVT VPSSNFGTQT YTCNVDHKPS

NTKVDKTV
```

An exemplary CH1 Domain is a human IgG3 CH1 Domain. The amino acid sequence of an exemplary human IgG3 CH1 Domain is (SEQ ID NO:5):

```
ASTKGPSVFP LAPCSRSTSG GTAALGCLVK

DYFPEPVTVS WNSGALTSGV HTFPAVLQSS

GLYSLSSVVT VPSSSLGTQT YTCNVNHKPS

NTKVDKRV
```

An exemplary CH1 Domain is a human IgG4 CH1 Domain. The amino acid sequence of an exemplary human IgG4 CH1 Domain is (SEQ ID NO:6):

```
ASTKGPSVFP LAPCSRSTSE STAALGCLVK

DYFPEPVTVS WNSGALTSGV HTFPAVLQSS

GLYSLSSVVT VPSSSLGTKT YTCNVDHKPS

NTKVDKRV
```

(b) Heavy Chain Hinge Regions

One exemplary Hinge Domain is a human IgG1 Hinge Domain. The amino acid sequence of an exemplary human IgG1 Hinge Domain is (SEQ ID NO:7):

```
EPKSCDKTHTCPPCP.
```

Another exemplary Hinge Domain is a human IgG2 Hinge Domain. The amino acid sequence of an exemplary human IgG2 Hinge Domain is (SEQ ID NO:8):

```
ERKCCVECPPCP.
```

Another exemplary Hinge Domain is a human IgG3 Hinge Domain. The amino acid sequence of an exemplary human IgG2 Hinge Domain is (SEQ ID NO:9):

```
ELKTPLGDTT HTCPRCPEPK SCDTPPPCPR CPEPKSCDTP

PPCPRCPEPK SCDTPPPCPR CP.
```

Another exemplary Hinge Domain is a human IgG4 Hinge Domain. The amino acid sequence of an exemplary human IgG4 Hinge Domain is (SEQ ID NO:10):

```
ESKYGPPCPSCP.
```

As described herein, an IgG4 Hinge Domain may comprise a stabilizing mutation such as the S228P substitution. The amino acid sequence of an exemplary S228P-stabilized human IgG4 Hinge Domain is (SEQ ID NO:11):

```
ESKYGPPCPPCP.
```

(c) Heavy Chain CH2 and CH3 Domains

The CH2 and CH3 Domains of the two heavy chains interact to form the "Fc Domain" of IgG antibodies that is recognized by cellular Fc Receptors, including but not limited to Fc gamma Receptors (FcγRs). As used herein, the term "Fc Region" is used to define a C-terminal region of an IgG heavy chain. A portion of an Fc Region (including a portion that encompasses an entire Fc Region) is referred to herein as an "Fc Domain." An Fc Region is said to be of a particular IgG isotype, class or subclass if its amino acid sequence is most homologous to that isotype relative to other IgG isotypes. In addition to their known uses in diagnostics, antibodies have been shown to be useful as therapeutic agents.

The amino acid sequence of the CH2-CH3 Domain of an exemplary human IgG1 is (SEQ ID NO:12):

```
        231        240        250        260        270
        APELLGGPSV FLFPPKPKDT LMISRTPEVT CVVVDVSHED 280        290        300        310
        PEVKFNWYVD GVEVHNAKTK PREEQYNSTY RVVSVLTVLH 320        330        340        350
        QDWLNGKEYK CKVSNKALPA PIEKTISKAK GQPREPQVYT 360        370        380        390
        LPPSREEMTK NQVSLTCLVK GFYPSDIAVE WESNGQPENN 400        410        420        430
        YKTTPPVLDS DGSFFLYSKL TVDKSRWQQG NVFSCSVMHE 440        447
        ALHNHYTQKS LSLSPGX
``` as numbered by the EU index as set forth in Kabat, wherein X is lysine (K) or is absent.

The amino acid sequence of the CH2-CH3 Domain of an exemplary human IgG2 is (SEQ ID NO:13):

```
        231        240        250        260        270
        APPVA-GPSV FLFPPKPKDT LMISRTPEVT CVVVDVSHED 280        290        300        310
        PEVQFNWYVD GVEVHNAKTK PREEQFNSTF RVVSVLTVVH 320        330        340        350
        QDWLNGKEYK CKVSNKGLPA PIEKTISKTK GQPREPQVYT 360        370        380        390
        LPPSREEMTK NQVSLTCLVK GFYPSDISVE WESNGQPENN 400        410        420        430
        YKTTPPMLDS DGSFFLYSKL TVDKSRWQQG NVFSCSVMHE 440        447
        ALHNHYTQKS LSLSPGX
``` as numbered by the EU index as set forth in Kabat, wherein X is lysine (K) or is absent.

The amino acid sequence of the CH2-CH3 Domain of an exemplary human IgG3 is (SEQ ID NO:14):

```
        231        240        250        260        270
        APELLGGPSV FLFPPKPKDT LMISRTPEVT CVVVDVSHED 280        290        300        310
        PEVQFKWYVD GVEVHNAKTK PREEQYNSTF RVVSVLTVLH 320        330        340        350
        QDWLNGKEYK CKVSNKALPA PIEKTISKTK GQPREPQVYT
```

-continued

```
         360        370        380        390
LPPSREEMTK NQVSLTCLVK GFYPSDIAVE WESSGQPENN 400        410        420        430
YNTTPPMLDS DGSFFLYSKL TVDKSRWQQG NIFSCSVMHE 440   447
ALHNRFTQKS LSLSPGX
``` as numbered by the EU index as set forth in Kabat, wherein X is lysine (K) or is absent.

The amino acid sequence of the CH2-CH3 Domain of an exemplary human IgG4 is (SEQ ID NO:15):

```
    231        240        250        260        270
APEFLGGPSV FLFPPKPKDT LMISRTPEVT CVVVDVSQED 280        290        300        310
PEVQFNWYVD GVEVHNAKTK PREEQFNSTY RVVSVLTVLH 320        330        340        350
QDWLNGKEYK CKVSNKGLPS SIEKTISKAK GQPREPQVYT 360        370        380        390
LPPSQEEMTK NQVSLTCLVK GFYPSDIAVE WESNGQPENN 400        410        420        430
YKTTPPVLDS DGSFFLYSRL TVDKSRWQEG NVFSCSVMHE 440   447
ALHNHYTQKS LSLSLGX
``` as numbered by the EU index as set forth in Kabat, wherein X is lysine (K) or is absent.

Throughout the present specification, the numbering of the residues in the constant region of an IgG heavy chain is that of the EU index as in Kabat et al., SEQUENCES OF PROTEINS OF IMMUNOLOGICAL INTEREST, 5$^{th}$ Ed. Public Health Service, NH1, MD (1991) ("Kabat"), expressly incorporated herein by reference. The term "EU index as in Kabat" refers to the numbering of the constant domains of human IgG1 EU antibody. Amino acids from the Variable Domains of the mature heavy and light chains of immunoglobulins are also designated by the position of an amino acid in the chain. Kabat described numerous amino acid sequences for antibodies, identified an amino acid consensus sequence for each subgroup, and assigned a residue number to each amino acid, and the CDRs are identified as defined by Kabat (it will be understood that $CDR_H1$ as defined by Chothia, C. & Lesk, A. M. ((1987) "Canonical Structures For The Hypervariable Regions Of Immunoglobulins," J. Mol. Biol. 196: 901-917) begins five residues earlier). Kabat's numbering scheme is extendible to antibodies not included in his compendium by aligning the antibody in question with one of the consensus sequences in Kabat by reference to conserved amino acids. This method for assigning residue numbers has become standard in the field and readily identifies amino acids at equivalent positions in different antibodies, including chimeric or humanized variants. For example, an amino acid at position 50 of a human antibody light chain occupies the equivalent position to an amino acid at position 50 of a mouse antibody light chain.

Polymorphisms have been observed at a number of different positions within antibody constant regions (e.g., Fc positions, including but not limited to positions 270, 272, 312, 315, 356, and 358 as numbered by the EU index as set forth in Kabat), and thus slight differences between the presented sequence and sequences in the prior art can exist. Polymorphic forms of human immunoglobulins have been well-characterized. At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b3, b0, b3, b4, s, t, g1, c5, u, v, g5) (Lefranc et al., "The Human IgG Subclasses: Molecular Analysis Of Structure, Function And Regulation." Pergamon, Oxford, pp. 43-78 (1990); Lefranc, G. et al., 1979, Hum. Genet.: 50, 199-211). It is specifically contemplated that the antibodies of the present invention may incorporate any allotype, isoallotype, or haplotype of any immunoglobulin gene, and are not limited to the allotype, isoallotype or haplotype of the sequences provided herein. Furthermore, in some expression systems the C-terminal amino acid residue (bolded above) of the CH3 Domain may be post-translationally removed. Accordingly, the C-terminal residue of the CH3 Domain is an optional amino acid residue in the CD16×DA Binding Molecules of the invention. Specifically encompassed by the instant invention are CD16×DA Binding Molecules lacking the C-terminal residue of the CH3 Domain. Also specifically encompassed by the instant invention are such constructs comprising the C-terminal lysine residue of the CH3 Domain.

(d) Variable Domains

The Variable Domains of an IgG molecule consist of three "complementarity determining regions" ("CDRs"), which contain the amino acid residues of the antibody that will be in contact with the epitope, as well as intervening non-CDR segments, referred to as "framework regions" ("FRs"), which, in general maintain the structure and determine the positioning of the CDR loops so as to permit such contacting (although certain framework residues may also contact the epitope). Thus, the VL and VH Domains have the structure n-FR1-CDR1-FR2-CDR2-FR3-CDR3-FR4-c. The amino acid sequences of the CDRs determine whether an antibody will be able to bind to a particular epitope. Interaction of an antibody light chain with an antibody heavy chain and, in particular, interaction of their VL and VH Domains, forms an epitope-binding site of the antibody.

Polypeptides that are (or may serve as) the first, second and third CDR of the Light Chain of an antibody are herein respectively designated as: $CDR_L1$ Domain, $CDR_L2$ Domain, and $CDR_L3$ Domain. Similarly, polypeptides that are (or may serve as) the first, second and third CDR of the Heavy Chain of an antibody are herein respectively designated as: $CDR_H1$ Domain, $CDR_H2$ Domain, and $CDR_H3$ Domain. Thus, the terms $CDR_L1$ Domain, $CDR_L2$ Domain, $CDR_L3$ Domain, $CDR_H1$ Domain, $CDR_H2$ Domain, and $CDR_H3$ Domain are directed to polypeptides that when incorporated into a protein cause that protein to be able to bind to a specific epitope regardless of whether such protein is an antibody having light and heavy chains or is a diabody or a single-chain binding molecule (e.g., an scFv, a BiTe, etc.), or is another type of protein.

The term "Epitope Binding Domain" denotes a fragment or portion of a binding molecule (or a polypeptide having the amino acid sequence of such a fragment or portion) that contributes to the ability of the binding molecule to immunospecifically bind to an epitope. An Epitope Binding Domain may contain a VL or VH Domain of an antibody, or any 1, 2, 3, 4, or 5 of the CDR Domains of an antibody, or may contain all 6 of the CDR Domains of an antibody and, although capable of immunospecifically binding such epitope, may exhibit an immunospecificity, affinity or selectivity towards such epitope that differs from that of such antibody. An Epitope Binding Domain may contain only part of a CDR, namely the subset of CDR residues required for binding, termed the SDRs (Kim, J. H. et al. (2012) "*Humanization By CDR Grafting And Specificity-Determining Residue Grafting*," Methods Mol. Biol. 907:237-245; Kim, K. S. et al. (2010) "*Construction Of A Humanized Antibody To Hepatitis B Surface Antigen By Specificity-Determining Residues (SDR)-Grafting And De Immunization*," Biochem. Biophys. Res. Commun. 396(2):231-237; Kashmiri, S. V. et al. (2005) "*SDR Grafting—A New Approach To Antibody Humanization*," Methods 36(1):25-34; Gonzales, N. R. et al. (2004) "*SDR Grafting Of A Murine Antibody Using Multiple Human Germline Templates To Minimize Its Immunogenicity*," Mol. Immunol. 41:863-872). Preferably, however, an Epitope Binding Domain will contain all 6 of the CDR Domains of such antibody. An Epitope Binding Domain may be a single polypeptide chain (e.g., an scFv), or may comprise two or more polypeptide chains, which may each have an amino terminus and a carboxy terminus (e.g., a diabody, a Fab fragment, an $Fab_2$ fragment, etc.), and which may be covalently bonded to one another via a disulfide bond.

2. Humanization of Antibodies

The invention also particularly encompasses Binding Molecules that comprise a VL or VH Domain of an antibody, and preferably both a VL and a VH Domain of an antibody. Preferably, such antibody is a humanized antibody. Monoclonal antibodies are typically prepared in non-human species, such as mouse or rabbit. The Variable and/or Constant Domains of such antibodies may be recognized as immunogens, thus provoking an immune response against them. Such molecules may however be "humanized" by introducing one or more amino acid substitutions in order to render such antibodies more like antibodies produced by humans, thereby reducing or eliminating their immunogenicity. The term "humanized" antibody refers to a chimeric molecule, generally prepared using recombinant techniques, having an epitope-binding site of an immunoglobulin from a non-human species and a remaining immunoglobulin structure of the molecule that is based upon the structure and/or sequence of a human immunoglobulin. The polynucleotide sequence of the variable domains of such antibodies may be used for genetic manipulation to generate such derivatives and to improve the affinity, or other characteristics of such antibodies. Application of this approach to various antibodies has been reported by LoBuglio, A. F. et al. (1989) "*Mouse/Human Chimeric Monoclonal Antibody In Man: Kinetics And Immune Response*," Proc. Natl. Acad. Sci. (U.S.A.) 86:4220-4224; Sato, K. et al. (1993) Cancer Res 53:851-856. Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, and/or six) which differ in sequence relative to the original antibody.

The general principle in humanizing an antibody involves retaining the basic sequence of the Epitope Binding Domain of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable domains (2) designing the humanized antibody or caninized antibody, i.e., deciding which antibody framework region to use during the humanizing or canonizing process (3) the actual humanizing or caninizing methodologies/techniques and (4) the transfection and expression of the humanized antibody. See, for example, U.S. Pat. Nos. 4,816,567; 5,807,715; 5,866,692; and 6,331,415.

A number of humanized antibody molecules comprising an Epitope Binding Domain derived from a non-human immunoglobulin have been described, including chimeric antibodies having rodent or modified rodent Variable Domain and their associated complementarity determining regions (CDRs) fused to human constant domains (see, for example, Winter et al. (1991) "*Man-made Antibodies*," Nature 349:293-299; Lobuglio et al. (1989) "*Mouse/Human Chimeric Monoclonal Antibody In Man: Kinetics And Immune Response*," Proc. Natl. Acad. Sci. (U.S.A.) 86:4220-4224 (1989), Shaw et al. (1987) "*Characterization Of A Mouse/Human Chimeric Monoclonal Antibody (17-1A) To A Colon Cancer Tumor Associated Antigen*," J. Immunol. 138:4534-4538, and Brown et al. (1987) "*Tumor-Specific Genetically Engineered Murine/Human Chimeric Monoclonal Antibody*," Cancer Res. 47:3577-3583). Other references describe rodent CDRs grafted into a human supporting framework region (FR) prior to fusion with an appropriate human antibody Constant Domain (see, for example, Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; and Jones et al. (1986) "*Replacing The Complementarity-Determining Regions In A Human Antibody With Those From A Mouse*," Nature 321:522-525). Another reference describes rodent CDRs supported by recombinantly veneered rodent framework regions. See, for example, European Patent Publication No. 519,596. These "humanized" molecules are designed to minimize unwanted immunological response towards rodent anti-human antibody molecules, which limits the duration and effectiveness of therapeutic applications of those moieties in human recipients. Other methods of humanizing antibodies that may also be utilized are disclosed by Daugherty et al. (1991) "*Polymerase Chain Reaction Facilitates The Cloning, CDR-Grafting, And Rapid Expression Of A Murine Monoclonal Antibody Directed Against The CD18 Component Of Leukocyte Integrins*," Nucl. Acids Res. 19:2471-2476 and in U.S. Pat. Nos. 6,180,377; 6,054,297; 5,997,867; and 5,866,692. The invention particularly encompasses binding molecules (including antibodies and diabodies) that comprise a VL and/or VH Domain of a "humanized" antibody.

Notwithstanding such successes, the production of stable, functional heterodimeric, non-monospecific diabodies optimized for therapeutic use can be further improved by the careful consideration and placement of the domains employed in the polypeptide chains. The present invention is thus directed to the provision of specific polypeptides that are particularly designed to form, via covalent bonding, stable and therapeutically useful heterodimeric diabodies and heterodimeric Fc diabodies that are capable of simultaneously binding CD16 and a Disease Antigen.

B. Bispecific Antibodies

As indicated above, natural antibodies are capable of binding to only one epitope species, although they can bind multiple copies of that species. The ability of an antibody to bind an epitope of an antigen depends upon the presence and amino acid sequence of the antibody's VL and VH Domains. Interaction of an antibody's Light Chain and Heavy Chain and, in particular, interaction of its VL and VH Domains forms one of the two Epitope Binding Domains of a natural antibody, such as an IgG. Natural antibodies are capable of binding only one epitope species (i.e., they are monospecific), although they can bind multiple copies of that species (i.e., exhibiting bi-valency or multi-valency).

The functionality of antibodies can be enhanced by generating multispecific antibody-based molecules that can simultaneously bind two separate and distinct antigens (or different epitopes of the same antigen) and/or by generating antibody-based molecule having higher valency (i.e., more than two Binding Domains) for the same epitope and/or antigen.

In order to provide molecules having greater capability than natural antibodies, a wide variety of recombinant bispecific antibody formats have been developed (see, e.g., PCT Publication Nos. WO 2008/003116, WO 2009/132876, WO 2008/003103, WO 2007/146968, WO 2009/018386, WO 2012/009544, WO 2013/070565). Most of such approaches use linker peptides to fuse a further binding domain (e.g. an scFv, VL, VH, etc.) to, or within the antibody core (IgA, IgD, IgE, IgG or IgM), or to fuse multiple antibody binding portions to one another (e.g. two Fab fragments or scFv). Alternative formats use linker peptides to fuse a binding protein (e.g., an scFv, VL, VH, etc.) to a dimerization domain such as the CH2-CH3 Domain or alternative polypeptides (WO 2005/070966, WO 2006/107786A WO 2006/107617A, WO 2007/046893). Typically, such approaches involve compromises and trade-offs. For example, PCT Publication Nos. WO 2013/174873, WO 2011/133886 and WO 2010/136172 disclose that the use of linkers may cause problems in therapeutic settings, and teaches a trispecific antibody in which the CL and CH1 Domains are switched from their respective natural positions and the VL and VH Domains have been diversified (WO 2008/027236; WO 2010/108127) to allow them to bind to more than one antigen. Thus, the molecules disclosed in these documents trade binding specificity for the ability to bind additional antigen species. PCT Publication Nos. WO 2013/163427 and WO 2013/119903 disclose modifying the CH2 Domain to contain a fusion protein adduct comprising a binding domain. The document notes that the CH2 Domain likely plays only a minimal role in mediating effector function. PCT Publication Nos. WO 2010/028797, WO2010028796 and WO 2010/028795 disclose recombinant antibodies whose Fc Regions have been replaced with additional VL and VH Domains, so as to form trivalent binding molecules. PCT Publication Nos. WO 2003/025018 and WO2003012069 disclose recombinant diabodies whose individual chains contain scFv domains. PCT Publication Nos. WO 2013/006544 discloses multi-valent Fab molecules that are synthesized as a single polypeptide chain and then subjected to proteolysis to yield heterodimeric structures. Thus, the molecules disclosed in these documents trade all or some of the capability of mediating effector function for the ability to bind additional antigen species. PCT Publication Nos. WO 2014/022540, WO 2013/003652, WO 2012/162583, WO 2012/156430, WO 2011/086091, WO 2008/024188, WO 2007/024715, WO 2007/075270, WO 1998/002463, WO 1992/022583 and WO 1991/003493 disclose adding additional Binding Domains or functional groups to an antibody or an antibody portion (e.g., adding a diabody to the antibody's light chain, or adding additional VL and VH Domains to the antibody's light and heavy chains, or adding a heterologous fusion protein or chaining multiple Fab Domains to one another). Thus, the molecules disclosed in these documents trade native antibody structure for the ability to bind additional antigen species.

C. Chimeric Antigen Receptors

The binding molecules of the present invention may be Chimeric Antigen Receptors ("CARs") that comprise a single chain variable fragment (scFv) capable of binding CD16 and a Disease Antigen. As indicated above, scFvs are made by linking Light and Heavy Chain Variable Domains together via a short linking peptide. First-generation CARs typically had the intracellular domain from the CD3 chain, which is the primary transmitter of signals from endogenous TCRs. Second-generation CARs possessed additional intracellular signaling domains from various costimulatory protein receptors (e.g., CD28, 41BB, ICOS, etc.) to the cytoplasmic tail of the CAR in order to provide additional signals to the T-cell. Third-generation CARs combine multiple signaling domains, such as CD3z-CD28-41BB or CD3z-CD28-OX40, in order to further augment potency (Tettamanti, S. et al. (2013) "*Targeting Of Acute Myeloid Leukaemia By Cytokine-Induced Killer Cells Redirected With A Novel CD123-Specific Chimeric Antigen Receptor,*" Br. J. Haematol. 161:389-401; Gill, S. et al. (2014) "*Efficacy Against Human Acute Myeloid Leukemia And Myeloablation Of Normal Hematopoiesis In A Mouse Model Using Chimeric Antigen Receptor Modified T Cells,*" Blood 123 (15): 2343-2354; Mardiros, A. et al. (2013) "*T Cells Expressing CD123-Specific Chimeric Antigen Receptors Exhibit Specific Cytolytic Effector Functions And Antitumor Effects Against Human Acute Myeloid Leukemia,*" Blood 122:3138-3148; Pizzitola, I. et al. (2014) "*Chimeric Antigen Receptors Against CD33/CD123 Antigens Efficiently Target Primary Acute Myeloid Leukemia Cells in vivo,*" Leukemia doi:10.1038/leu.2014.62.

The intracellular domain of the CARs of the present invention is preferably selected from the intracellular domain of any of: 41BB-CD3ζ, b2c-CD3ζ, CD28, CD28-4-1BB-CD3ζ, CD28-CD3ζ, CD28-FcεRIγ, CD28mut-CD3ζ, CD28-OX40-CD3ζ, CD28-OX40-CD3ζ, CD3, CD4-CD3ζ, CD4-FcεRIγ, CD8-CD3ζ, FcεRIγ, FcεRIγCAIX, Heregulin-CD3ζ, IL-13-CD3ζ, or Ly49H-CD3ζ (Tettamanti, S. et al. (2013) "*Targeting Of Acute Myeloid Leukaemia By Cytokine-Induced Killer Cells Redirected With A Novel CD123-Specific Chimeric Antigen Receptor,*" Br. J. Haematol. 161:389-401; Gill, S. et al.

(2014) "*Efficacy Against Human Acute Myeloid Leukemia And Myeloablation Of Normal Hematopoiesis In A Mouse Model Using Chimeric Antigen Receptor Modified T Cells*," Blood 123(15): 2343-2354; Mardiros, A. et al. (2013) "*T Cells Expressing CD123-Specific Chimeric Antigen Receptors Exhibit Specific Cytolytic Effector Functions And Anti-tumor Effects Against Human Acute Myeloid Leukemia*," Blood 122:3138-3148; Pizzitola, I. et al. (2014) "*Chimeric Antigen Receptors Against CD33/CD123 Antigens Efficiently Target Primary Acute Myeloid Leukemia Cells in vivo*," Leukemia doi:10.1038/leu.2014.62).

II. Bispecific Diabodies

The art has additionally noted the capability of producing diabodies that differ from natural antibodies in being capable of binding two or more different epitope species (i.e., exhibiting bispecificity or multispecificity in addition to bi-valency or multi-valency) (see, e.g., Holliger et al. (1993) "'*Diabodies': Small Bivalent And Bispecific Antibody Fragments*," Proc. Natl. Acad. Sci. (U.S.A.) 90:6444-6448; US 2004/0058400 (Hollinger et al.); US 2004/0220388 (Mertens et al.); Alt et al. (1999) FEBS Lett. 454(1-2):90-94; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20): 19665-19672; WO 02/02781 (Mertens et al.); Olafsen, T. et al. (2004) "*Covalent Disulfide-Linked Anti-CEA Diabody Allows Site-Specific Conjugation And Radiolabeling For Tumor Targeting Applications*," Protein Eng Des Sel. 17(1): 21-27; Wu, A. et al. (2001) "*Multimerization Of A Chimeric Anti-CD20 Single Chain Fv-Fv Fusion Protein Is Mediated Through Variable Domain Exchange*," Protein Engineering 14(2):1025-1033; Asano et al. (2004) "*A Diabody For Cancer Immunotherapy And Its Functional Enhancement By Fusion Of Human Fc Domain*," Abstract 3P-683, J. Biochem. 76(8):992; Takemura, S. et al. (2000) "*Construction Of A Diabody (Small Recombinant Bispecific Antibody) Using A Refolding System*," Protein Eng. 13(8):583-588; Baeuerle, P. A. et al. (2009) "*Bispecific T cell Engaging Antibodies For Cancer Therapy*," Cancer Res. 69(12):4941-4944).

The design of a diabody is based on the structure of the single-chain Variable Domain fragment (scFv), in which Light and Heavy Chain Variable Domains are linked to one another using a short linking peptide. Bird et al. (1988) ("*Single-Chain Antigen-Binding Proteins*," Science 242: 423-426) describes example of linking peptides which bridge approximately 3.5 nm between the carboxy terminus of one Variable Domain and the amino terminus of the other Variable Domain. Linkers of other sequences have been designed and used (Bird et al. (1988) "*Single-Chain Antigen Binding Proteins*," Science 242:423-426). Linkers can in turn be modified for additional functions, such as attachment of drugs or attachment to solid supports. The single-chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The provision of non-monospecific "diabodies" provides a significant advantage over antibodies: the capacity to co-ligate and co-localize cells that express different epitopes. Bispecific diabodies thus have wide-ranging applications including therapy and immunodiagnosis. Bispecificity allows for great flexibility in the design and engineering of the diabody in various applications, providing enhanced avidity to multimeric antigens, the cross-linking of differing antigens, and directed targeting to specific cell types relying on the presence of both target antigens. Due to their bivalency, low dissociation rates and rapid clearance from the circulation (for diabodies of small size, at or below ~50 kDa), diabody molecules known in the art have also shown particular use in the field of tumor imaging (Fitzgerald et al. (1997) "*Improved Tumour Targeting By Disulphide Stabilized Diabodies Expressed In Pichia pastoris*," Protein Eng. 10:1221-1225).

The ability to produce bispecific diabodies has led to their use (in "trans") to co-ligate two cells together, for example, by co-ligating receptors that are present on the surface of different cells (e.g., cross-linking cytotoxic T-cells to target cells, such as cancer cells or pathogen-infected cells, that express a Disease Antigen) (Staerz et al. (1985) "*Hybrid Antibodies Can Target Sites For Attack By T Cells*," Nature 314:628-631, and Holliger et al. (1996) "*Specific Killing Of Lymphoma Cells By Cytotoxic T-Cells Mediated By A Bispecific Diabody*," Protein Eng. 9:299-305; Marvin et al. (2005) "*Recombinant Approaches To IgG-Like Bispecific Antibodies*," Acta Pharmacol. Sin. 26:649-658; Sloan et al. (2015) "*Targeting HIV Reservoir in Infected CD4 T Cells by Dual-Affinity Re-targeting Molecules (DARTs) that Bind HIV Envelope and Recruit Cytotoxic T Cells*," PLoS Pathog 11(11): e1005233. doi:10.1371/journal.ppat.1005233)). Alternatively (or additionally), bispecific (or multispecific) diabodies can be used (in "cis") to co-ligate molecules, such as receptors, etc., that are present on the surface of the same cell. Co-ligation of different cells and/or receptors is useful to modulate effector functions and/or immune cell signaling. Multispecific molecules (e.g., bispecific diabodies) comprising Epitope Binding Domains may be directed to a surface determinant of any immune cell such as CD2, CD3, CD8, CD16, TCR, NKG2D, etc., which are expressed on T lymphocytes, Natural Killer (NK) cells, Antigen-Presenting Cells or other mononuclear cells, or to a surface determinant of a B cell, such as CD19, CD20, CD22, CD30, CD37, CD40, and CD74 (Moore, P. A. et al. (2011) "*Application Of Dual Affinity Retargeting Molecules To Achieve Optimal Redirected T cell Killing Of B-Cell Lymphoma*," Blood 117(17):4542-4551; Cheson, B. D. et al. (2008) "*Monoclonal Antibody Therapy For B-Cell Non Hodgkin's Lymphoma*," N. Engl. J. Med. 359(6):613-626; Castillo, J. et al. (2008) "*Newer Monoclonal Antibodies For Hematological Malignancies*," Exp. Hematol. 36(7):755-768). In particular, Epitope Binding Domains directed to a cell surface receptor that is present on immune effector cells, are useful in the generation of multispecific binding molecules capable of mediating redirected cell killing.

In many studies, diabody binding to effector cell determinants, e.g., Fcγ receptors (FcγR), was also found to activate the effector cell (Holliger et al. (1996) "*Specific Killing Of Lymphoma Cells By Cytotoxic T cells Mediated By A Bispecific Diabody*," Protein Eng. 9:299-305; Holliger et al. (1999) "*Carcinoembryonic Antigen (CEA)-Specific T cell Activation In Colon Carcinoma Induced By Anti-CD3× Anti-CEA Bispecific Diabodies And B7×Anti-CEA Bispecific Fusion Proteins*," Cancer Res. 59:2909-2916; WO 2006/113665; WO 2008/157379; WO 2010/080538; WO 2012/

018687; WO 2012/162068). Normally, effector cell activation is triggered by the binding of an antigen-bound antibody to an effector cell via an Fc Domain-FcγR interaction; thus, in this regard, diabody molecules may exhibit Ig-like functionality independent of whether they comprise an Fc Domain (e.g., as assayed in any effector function assay known in the art or exemplified herein (e.g., ADCC assay)). By cross-linking tumor and effector cells, the diabody not only brings the effector cell within the proximity of a tumor cell but leads to effective tumor killing (see e.g., Cao et al. (2003) "Bispecific Antibody Conjugates In Therapeutics," Adv. Drug. Deliv. Rev. 55:171-197).

However, the advantages of the above-described bispecific diabodies come at a salient cost. The formation of such non-mono-specific diabodies requires the successful assembly of two or more distinct and different polypeptides (i.e., such formation requires that the diabodies be formed through the heterodimerization of different polypeptide chain species). This fact is in contrast to mono-specific diabodies, which are formed through the homodimerization of identical polypeptide chains. Because at least two dissimilar polypeptides (i. e., two polypeptide species) must be provided in order to form a non-mono-specific diabody, and because homodimerization of such polypeptides leads to inactive molecules (Takemura, S. et al. (2000) "Construction Of A Diabody (Small Recombinant Bispecific Antibody) Using A Refolding System," Protein Eng. 13(8):583-588), the production of such polypeptides must be accomplished in such a way as to prevent covalent bonding between polypeptides of the same species (i. e., so as to prevent homodimerization) (Takemura, S. et al. (2000) "Construction Of A Diabody (Small Recombinant Bispecific Antibody) Using A Refolding System," Protein Eng. 13(8):583-588). The art has therefore taught the non-covalent association of such polypeptides (see, e.g., Olafsen et al. (2004) "Covalent Disulfide-Linked Anti-CEA Diabody Allows Site-Specific Conjugation And Radiolabeling For Tumor Targeting Applications," Prot. Engr. Des. Sel. 17:21-27; Asano et al. (2004) "A Diabody For Cancer Immunotherapy And Its Functional Enhancement By Fusion Of Human Fc Domain," Abstract 3P-683, J. Biochem. 76(8):992; Takemura, S. et al. (2000) "Construction Of A Diabody (Small Recombinant Bispecific Antibody) Using A Refolding System," Protein Eng. 13(8): 583-588; Lu, D. et al. (2005) "A Fully Human Recombinant IgG-Like Bispecific Antibody To Both The Epidermal Growth Factor Receptor And The Insulin-Like Growth Factor Receptor For Enhanced Antitumor Activity," J. Biol. Chem. 280(20):19665-19672).

However, the art has recognized that bispecific diabodies composed of non-covalently associated polypeptides are unstable and readily dissociate into non-functional single polypeptide chain monomers (see, e.g., Lu, D. et al. (2005) "A Fully Human Recombinant IgG-Like Bispecific Antibody To Both The Epidermal Growth Factor Receptor And The Insulin-Like Growth Factor Receptor For Enhanced Antitumor Activity," J. Biol. Chem. 280(20):19665-19672).

In the face of this challenge, the art has succeeded in developing stable, covalently bonded heterodimeric non-mono-specific diabodies, termed DART® diabodies, see, e.g., Sloan, D. D. et al. (2015) "Targeting HIV Reservoir in Infected CD4 T Cells by Dual-Affinity Re-targeting Molecules (DARTs) that Bind HIV Envelope and Recruit Cytotoxic T Cells," PLoS Pathog. 11(11):e1005233. doi: 10.1371/journal.ppat.1005233; Al Hussaini, M. et al. (2015) "Targeting CD123 In AML Using A T-Cell Directed Dual-Affinity Re-Targeting (DART®) Platform," Blood pii: blood-2014-05-575704; Chichili, G. R. et al. (2015) "A CD3xCD123 Bispecific DART For Redirecting Host T Cells To Myelogenous Leukemia: Preclinical Activity And Safety In Nonhuman Primates," Sci. Transl. Med. 7(289):289ra82; Johnson, S. et al. (2010) "Effector Cell Recruitment With Novel Fv-Based Dual-Affinity Re-Targeting Protein Leads To Potent Tumor Cytolysis And In Vivo B-Cell Depletion," J. Molec. Biol. 399(3):436-449; Veri, M. C. et al. (2010) "Therapeutic Control Of B Cell Activation Via Recruitment Of Fcgamma Receptor IIB (CD32B) Inhibitory Function With A Novel Bispecific Antibody Scaffold," Arthritis Rheum. 62(7):1933-1943; Moore, P. A. et al. (2011) "Application Of Dual Affinity Retargeting Molecules To Achieve Optimal Redirected T cell Killing Of B-Cell Lymphoma," Blood 117(17):4542-4551; U.S. Pat. Nos. 8,044,180; 8,133,982; 8,187,593; 8,193,318; 8,530,627; 8,669,349; 8,778,339; 8,784,808; 8,795,667; 8,802,091; 8,802,093; 8,946,387; 8,968,730; and 8,993,730; US Patent Publication Nos. 2009/0060910; 2010/0174053; 2011/0081347; 2011/0097323; 2011/0117089; 2012/0009186; 2012/0034221; 2012/0141476; 2012/0294796; 2013/0149236; 2013/0295121; 2014/0017237; and 2014/0099318; European Patent Documents No. EP 1868650; EP 2158221; EP 2247304; EP 2252631; EP 2282770; EP 2328934; EP 2376109; EP 2542256; EP 2601216; EP 2714079; EP 2714733; EP 2786762; EP 2839842; EP 2840091; and PCT Publication Nos. WO 2006/113665; WO 2008/157379; WO 2010/027797; WO 2010/033279; WO 2010/080538; WO 2011/109400; WO 2012/018687; WO 2012/162067; WO 2012/162068; WO 2014/159940; WO 2015/021089; WO 2015/026892; and WO 2015/026894). Such diabodies comprise two or more covalently complexed polypeptides and involve engineering one or more cysteine residues into each of the employed polypeptide species that permit disulfide bonds to form and thereby covalently bond one or more pairs of such polypeptide chains to one another. For example, the addition of a cysteine residue to the C-terminus of such constructs has been shown to allow disulfide bonding between the involved polypeptide chains, stabilizing the resulting diabody without interfering with the diabody's binding characteristics.

Figure 1B:
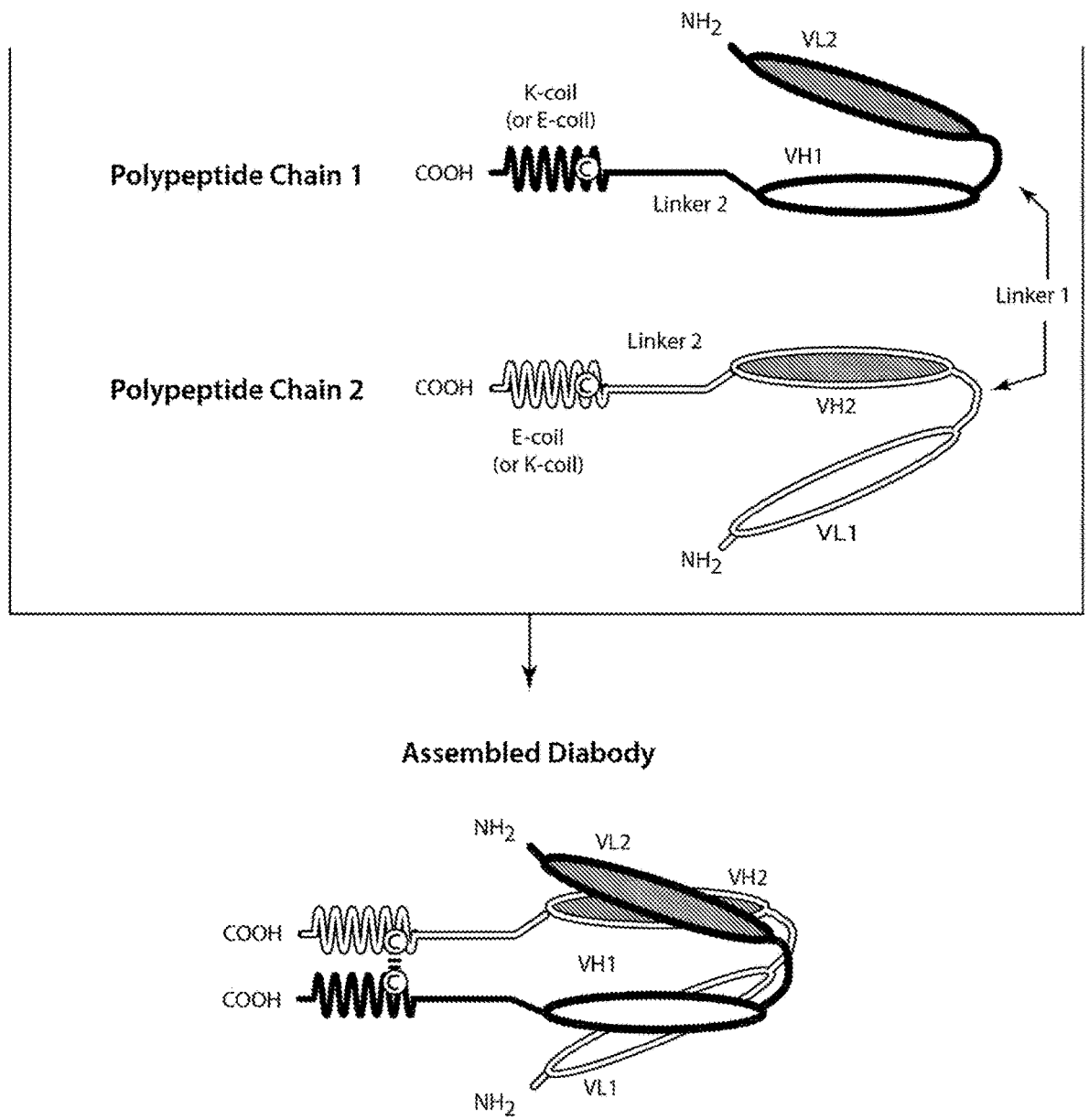

The simplest DART® diabody comprises two polypeptide chains each comprising three Domains (FIGS. 1A-1B). The first polypeptide chain comprises: (i) a Domain that comprises a binding region of a light chain variable Domain of the a first immunoglobulin (VL1), (ii) a second Domain that comprises a binding region of a heavy chain variable Domain of a second immunoglobulin (VH2), and (iii) a third Domain that serves to promote heterodimerization (a "Heterodimer-Promoting Domain") with the second polypeptide chain and to covalently bond the first polypeptide to the second polypeptide chain of the diabody. The second polypeptide chain contains a complementary first Domain (a VL2 Domain), a complementary second Domain (a VH1 Domain) and a third Domain that complexes with the third Domain of the first polypeptide chain in order to promote heterodimerization (a "Heterodimer-Promoting Domain") and covalent bonding with the first polypeptide chain. Such molecules are stable, potent and have the ability to simultaneously bind two or more antigens. In one embodiment, the third Domains of the first and second polypeptide chains each contain a cysteine ("©") residue, which serves to bind the polypeptides together via a disulfide bond. The third Domain of one or both of the polypeptide chains may additionally possess the sequence of a CH2-CH3 Domain, such that complexing of the diabody polypeptides forms an Fc Domain that is capable of binding to the Fc receptor of cells (such as B lymphocytes, dendritic cells, natural killer cells, macrophages, neutrophils, eosinophils, basophils and mast cells). Many variations of such molecules have been described (see, e.g., United States Patent Publication Nos. 2013-0295121; 2010-0174053; 2007-0004909; 2009-0060910; European Patent Publication No. EP 2714079; EP 2601216; EP 2376109; EP 2158221 and PCT Publication Nos. WO 2012/162068; WO 2012/018687; WO 2010/080538; WO 2006/113665) and are provided herein. Many variations of such molecules have been described (see, e.g., United States Patent Publication Nos. 2015/0175697; 2014/0255407; 2014/0099318; 2013/0295121; 2010/0174053; 2009/0060910; 2007-0004909; European Patent Publication Nos. EP 2714079; EP 2601216; EP 2376109; EP 2158221; EP 1868650; and PCT Publication Nos. WO 2012/162068; WO 2012/018687; WO 2010/080538; WO 2006/113665), and are provided herein.

Alternative constructs are known in the art for applications where a bispecific or tetravalent molecule is desirable but an Fc is not required including, but not limited to, Bispecific T cell Engager molecules, also referred to as "BITE® antibodies" (see, e.g., PCT Publication Nos: WO 1993/11161; and WO 2004/106381) and tetravalent tandem antibodies, also referred to as "TandAbs®" (see, e.g. United States Patent Publication No: 2011-0206672; European Patent Publication No. EP 2371866, and; PCT Publication Nos. WO 1999/057150, WO 2003/025018, and WO 2013/013700). BiTEs are formed from a single polypeptide chain comprising tandem linked scFvs, while TandAbs are formed by the homo-dimerization of two identical polypeptide chains, each possessing a VH1, VL2, VH2, and VL2 Domain.

The present invention provides bispecific binding molecules that are capable of enhancing an immune response directed to the killing of a target cell (e.g., a cancer cell or a pathogen-infected cell, a pathogen, etc.) expressing a Disease Antigen. Such bispecific binding molecules are capable of binding a "First Epitope" and a "Second Epitope," wherein one of such epitopes is an epitope of CD16 and the other of such epitopes is an epitope of a Disease Antigen ("DA"). It is irrelevant whether a particular epitope is designated as the first vs. the Second Epitope; such notation having relevance only with respect to the presence and orientation of the domains of the polypeptide chains of the binding molecules of the present invention. Thus, the bispecific molecules of the present invention comprise "$VL_{CD16}$"/"$VH_{CD16}$" Domains that are capable of binding an epitope of CD16, and "$VL_{DA}$"/"$VH_{DA}$" Domains that are capable of binding an epitope of a Disease Antigen. The instant invention particular encompasses bispecific diabodies, BiTEs, antibodies, and TandAbs produced using any of the methods provided herein.

A. Diabodies Lacking Fc Domains

In one embodiment, the CD16 Binding Molecules of the present invention will be bispecific diabodies and will comprise domains capable of binding both a first and a Second Epitope, but will lack an Fc Domain, and thus will be unable to bind FcγR molecules via an Fc-FcγR interaction. Such molecules are, however, able to bind to CD16 via the SDRs or CDRs of their CD16 Binding Domains. The absence of Fc domains thus serves to prevent the molecules from binding to non-CD16 FcγRs, such as the inhibitory receptor CD32B.

The first polypeptide chain of such an embodiment of bispecific diabodies preferably comprises, in the N-terminal to C-terminal direction: an N-terminus, the VL Domain of a monoclonal antibody capable of binding either the First or Second Epitope (i.e., either $VL_{CD16}$ or $VL_{DA}$), a first intervening spacer peptide (Linker 1), a VH Domain of a monoclonal antibody capable of binding the epitope of the Disease Antigen (if such first polypeptide chain contains $VL_{CD16}$) or a VH Domain of a monoclonal antibody capable of binding CD16 (if such first polypeptide chain contains $VL_{DA}$), a second intervening spacer peptide (Linker 2) optionally containing a cysteine residue, a Heterodimer-Promoting Domain and a C-terminus (FIGS. 1A-1B).

The second polypeptide chain of this embodiment of bispecific diabodies comprises, in the N-terminal to C-terminal direction: an N-terminus, the VL Domain of a monoclonal antibody capable of binding the First or Second Epitope (i.e., $VL_{CD16}$ or $VL_{DA}$, and being the VL Domain not selected for inclusion in the first polypeptide chain of the diabody), an intervening spacer peptide (Linker 1), a VH Domain of a monoclonal antibody capable of binding either the First or Second Epitope (i.e., $VH_{CD16}$ or $VH_{DA}$, and being the VH Domain not selected for inclusion in the first polypeptide chain of the diabody), a second intervening spacer peptide (Linker 2) optionally containing a cysteine residue, a Heterodimer-Promoting Domain and a C-terminus (FIGS. 1A-1B). The employed VL and VH Domains specific for a particular epitope are preferably obtained or derived from the same monoclonal antibody. However, such domains may be derived from different monoclonal antibodies provided that they associate to form a functional Binding Domain capable of immunospecifically binding such epitope. Such different antibodies are referred to herein as being "corresponding" antibodies.

The VL Domain of the first polypeptide chain interacts with the VH Domain of the second polypeptide chain to form a first functional Epitope Binding Domain that is specific for one of the epitopes (e.g., the First Epitope). Likewise, the VL Domain of the second polypeptide chain interacts with the VH Domain of the first polypeptide chain in order to form a second functional Epitope Binding Domain that is specific for the other epitope (i.e., the Second Epitope). Thus, the selection of the VL and VH Domains of the first and second polypeptide chains is "coordinated," such that the two polypeptide chains of the diabody collectively comprise VL and VH Domains capable of binding both the First Epitope and the Second Epitope (i.e., they collectively comprise $VL_{CD16}$/$VH_{CD16}$ and $VL_{DA}$/$VH_{DA}$).

Most preferably, the length of the intervening spacer peptide (i.e., "Linker 1," which separates such VL and VH Domains) is selected to substantially or completely prevent the VL and VH Domains of the polypeptide chain from binding one another (for example consisting of from 0, 1, 2, 3, 4, 5, 6, 7, 8 or 9 intervening linker amino acid residues). Thus, the VL and VH Domains of the first polypeptide chain are substantially or completely incapable of binding one another. Likewise, the VL and VH Domains of the second polypeptide chain are substantially or completely incapable of binding one another. A preferred intervening spacer peptide (Linker 1) has the sequence (SEQ ID NO:16):

GGGS GGGG.

The length and composition of the second intervening spacer peptide ("Linker 2") is selected based on the choice of one or more polypeptide domains that promote such dimerization (i.e., a "Heterodimer-Promoting Domain"). Typically, the second intervening spacer peptide (Linker 2) will comprise 3-20 amino acid residues. In particular, where the employed Heterodimer-Promoting Domain(s) do/does not comprise a cysteine residue a cysteine-containing second intervening spacer peptide (Linker 2) is utilized. A cysteine-containing second intervening spacer peptide (Linker 2) will contain 1, 2, 3 or more cysteines. A preferred cysteine-containing spacer peptide (Linker 2) has the sequence GGCGGG (SEQ ID NO:17). Alternatively, Linker 2 does not comprise a cysteine (e.g., GGG, GGGS (SEQ ID NO:18), LGGGSG (SEQ ID NO:19), GGGSGGGSGGG (SEQ ID NO:20), AS TKG (SEQ ID NO:21), LEPKSS (SEQ ID NO:22), APSSS (SEQ ID NO:23), etc.) and a cysteine-containing Heterodimer-Promoting Domain, as described below is used. Optionally, both a cysteine-containing Linker 2 and a cysteine-containing Heterodimer-Promoting Domain are used.

The Heterodimer-Promoting Domains may be GVEPKSC (SEQ ID NO:24) or VEPKSC (SEQ ID NO:25) or AEPKSC (SEQ ID NO:26) on one polypeptide chain and GFNRGEC (SEQ ID NO:27) or FNRGEC (SEQ ID NO:28) on the other polypeptide chain (US2007/0004909).

In a preferred embodiment, the Heterodimer-Promoting Domains will comprise tandemly repeated coil domains of opposing charge for example, an "E-coil" Heterodimer-Promoting Domain (SEQ ID NO:29: EVAALEK-EVAAL EK-EVAALEK-EVAALEK), whose glutamate residues will form a negative charge at pH 7, or a "K-coil" Heterodimer-Promoting Domain (SEQ ID NO:30: KVAALKE-KVAAL KE-KVAALKE KVAALKE), whose lysine residues will form a positive charge at pH 7. The presence of such charged domains promotes association between the first and second polypeptides, and thus fosters heterodimer formation. Heterodimer-Promoting Domains that comprise modifications of the above-described E-coil and K-coil sequences so as to include one or more cysteine residues may be utilized. The presence of such cysteine residues permits the coil present on one polypeptide chain to become covalently bonded to a complementary coil present on another polypeptide chain, thereby covalently bonding the polypeptide chains to one another and increasing the stability of the diabody. Examples of such particularly preferred are Heterodimer-Promoting Domains include a Modified E-Coil having the amino acid sequence EVAACEK-EVAALEK-EVAALEK-EVAALEK (SEQ ID NO:31), and a modified K-coil having the amino acid sequence KVAACKE-KVAALKE-KVAALKE-KVAALKE (SEQ ID NO:32).

As disclosed in WO 2012/018687, in order to improve the in vivo pharmacokinetic properties of diabodies, a diabody may be modified to contain a polypeptide portion of a serum-binding protein at one or more of the termini of the diabody. Most preferably, such polypeptide portion of a serum-binding protein will be installed at the C-terminus of a polypeptide chain of the diabody. Albumin is the most abundant protein in plasma and has a half-life of 19 days in humans. Albumin possesses several small molecule binding domains that permit it to non-covalently bind other proteins and thereby extend their serum half-lives. The Albumin-Binding Domain 3 (ABD3) of protein G of *Streptococcus* strain G148 consists of 46 amino acid residues forming a stable three-helix bundle and has broad albumin-binding specificity (Johansson, M. U. et al. (2002) "*Structure, Specificity, And Mode Of Interaction For Bacterial Albumin-Binding Modules*," J. Biol. Chem. 277(10):8114-8120). Thus, a particularly preferred polypeptide portion of a serum-binding protein for improving the in vivo pharmacokinetic properties of a diabody is the Albumin-Binding Domain (ABD) from streptococcal protein G, and more preferably, the Albumin-Binding Domain 3 (ABD3) of protein G of *Streptococcus* strain G148 (SEQ ID NO:33):

```
LAEAKVLANR ELDKYGVSDY YKNLIDNAKS
AEGVKALIDE ILAALP.
```

As disclosed in WO 2012/162068 (herein incorporated by reference), "deimmunized" variants of SEQ ID NO:33 have the ability to attenuate or eliminate MHC class II binding. Based on combinational mutation results, the following combinations of substitutions are considered to be preferred substitutions for forming such a deimmunized ABD: 66D/70S+71A; 66S/70S+71A; 66S/70S+79A; 64A/65A/71A; 64A/65A/71A+66S; 64A/65A/71A+66D; 64A/65A/71A+66E; 64A/65A/79A+66S; 64A/65A/79A+66D; 64A/65A/79A+66E. Variant ABDs having the modifications L64A, I65A and D79A or the modifications N66S, T7OS and D79A. Variant deimmunized ABD having the amino acid sequence:

```
                                         (SEQ ID NO: 34)
LAEAKVLANR ELDKYGVSDY YKNLID₆₆NAKS₇₀

A₇₁EGVKALIDE ILAALP,
``` or the amino acid sequence:

```
                                         (SEQ ID NO: 35)
LAEAKVLANR ELDKYGVSDY YKNA₆₄A₆₅NNAKT

VEGVKALIA₇₉E ILAALP,
``` or the amino acid sequence:

```
                                         (SEQ ID NO: 36)
LAEAKVLANR ELDKYGVSDY YKNLIS₆₆NAKS₇₀

VEGVKALIA₇₉E ILAALP,
``` are particularly preferred as such deimmunized ABD exhibit substantially wild-type binding while providing attenuated MHC class II binding. Thus, the first polypeptide chain of such a diabody having an ABD contains a third linker (Linker 3) preferably positioned C-terminally to the E-coil (or K-coil) Domain of such polypeptide chain so as to intervene between the E-coil (or K-coil) Domain and the ABD (which is preferably a deimmunized ABD). A preferred sequence for such Linker 3 is SEQ ID NO:18:

```
GGGS.
```

B. Diabodies Comprising Fc Domains

One embodiment of the present invention relates to multi-specific diabodies (e.g., bispecific, trispecific, tetraspecific, etc.) that comprise an Fc Domain and that are capable of simultaneously binding an epitope of CD16 and an epitope of a Disease Antigen. The Fc Domain of such molecules may be of any isotype (e.g., IgG1, IgG2, IgG3, or IgG4). The molecules may further comprise a CH1 Domain and/or a Hinge Domain. When present, the CH1 Domain and/or Hinge Domain may be of any isotype (e.g., IgG1, IgG2, IgG3, or IgG4), and is preferably of the same isotype as the desired Fc Domain.

Figure 2:
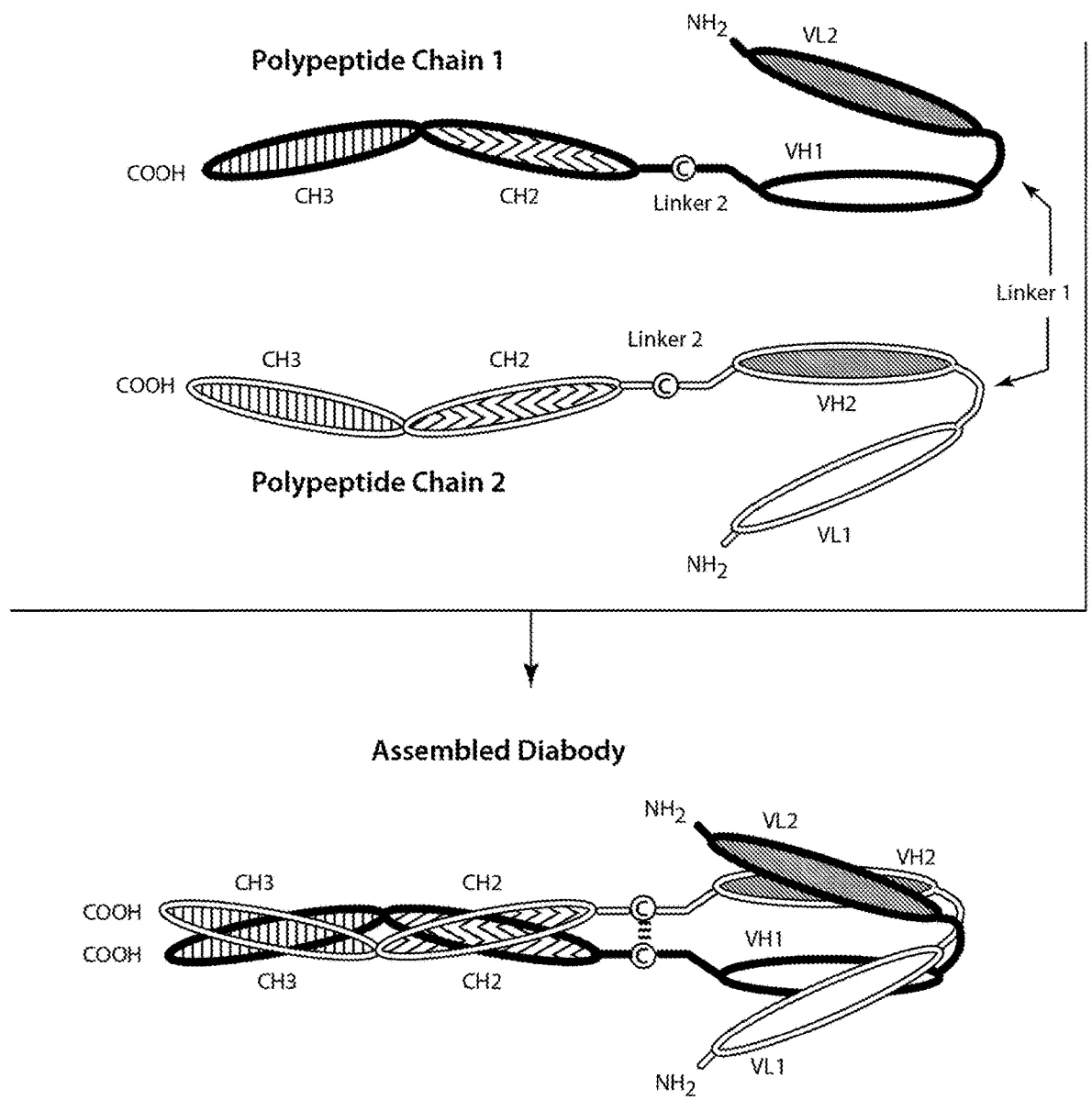
FIG. 2 provides a schematic of a representative covalently bonded diabody molecule having two epitope-binding sites composed of two polypeptide chains, each having a CH2 and CH3 Domain, such that the associated chains form all or part of an Fc Region. VL and VH Domains that recognize the same epitope are shown using the same shading or fill pattern.

The addition of an IgG CH2-CH3 Domain to one or both of the diabody polypeptide chains, such that the complexing of the diabody chains results in the formation of an Fc Domain, increases the biological half-life and/or alters the valency of the diabody. Such diabodies comprise, two or more polypeptide chains whose sequences permit the polypeptide chains to covalently bind each other to form a covalently associated diabody that is capable of simultaneously binding the First Epitope and the Second Epitope. Incorporating an IgG CH2-CH3 Domains onto both of the diabody polypeptides will permit a two-chain bispecific Fc Domain-containing diabody to form (FIG. 2).

Figure 3A:
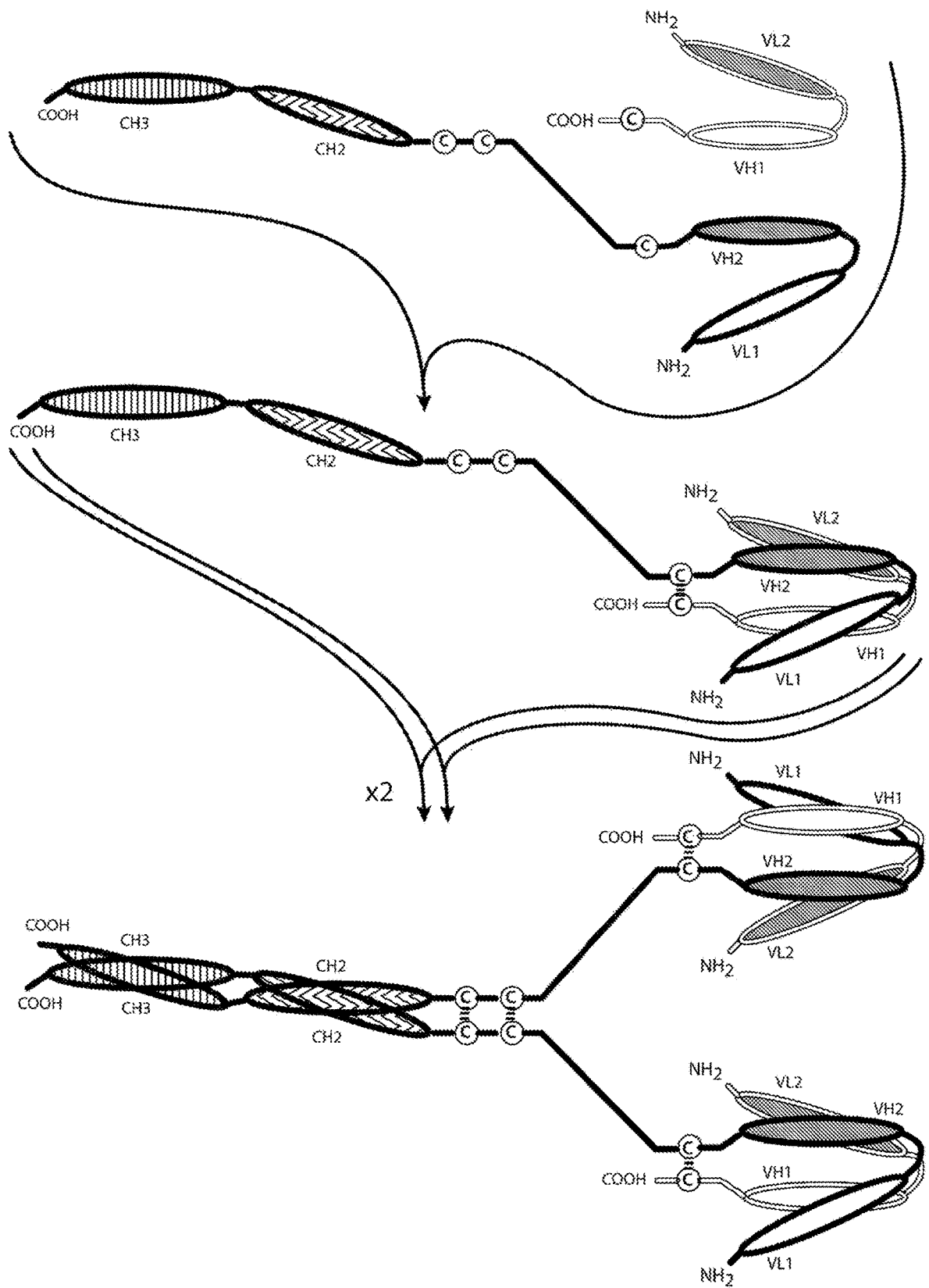
FIGS. 3A-3E provide schematics showing representative covalently bonded tetravalent diabodies having four epitope-binding sites composed of two pairs of polypeptide chains (i.e., four polypeptide chains in all). One polypeptide chain of each pair possesses a CH2 and CH3 Domain, such that the associated chains form all or part of an Fc Region. VL and VH Domains that recognize the same epitope are shown using the same shading or fill pattern. The two pairs of polypeptide chains may be same. In such embodiments, wherein the two pairs of polypeptide chains are the same and the VL and VH Domains recognize different epitopes (as shown in FIGS. 3A-3B), the resulting molecule possesses four epitope-binding sites and is bispecific and bivalent with respect to each bound epitope. In such embodiments, wherein the VL and VH Domains recognize the same epitope (e.g., the same VL Domain CDRs and the same VH Domain CDRs are used on both chains) the resulting molecule possesses four epitope-binding sites and is monospecific and tetravalent with respect to a single epitope. Alternatively, the two pairs of polypeptides may be different. In such embodiments, wherein the two pairs of polypeptide chains are different and the VL and VH Domains of each pair of polypeptides recognize different epitopes (as shown by the different shading and patterns in FIG. 3C), the resulting molecule possesses four epitope-binding sites and is tetraspecific and monovalent with respect to each bound epitope.
Figure 3B:
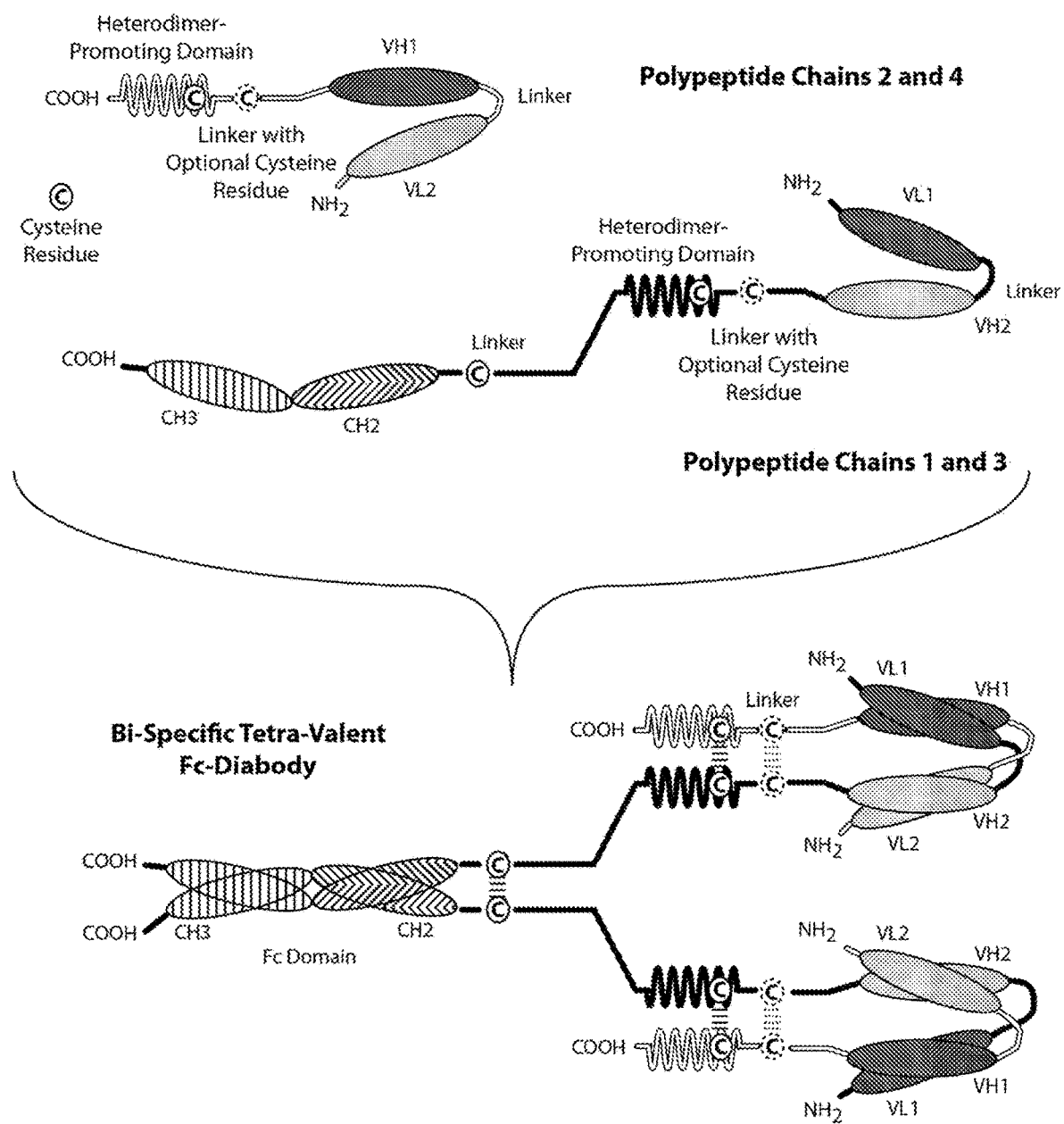
Figure 3C:
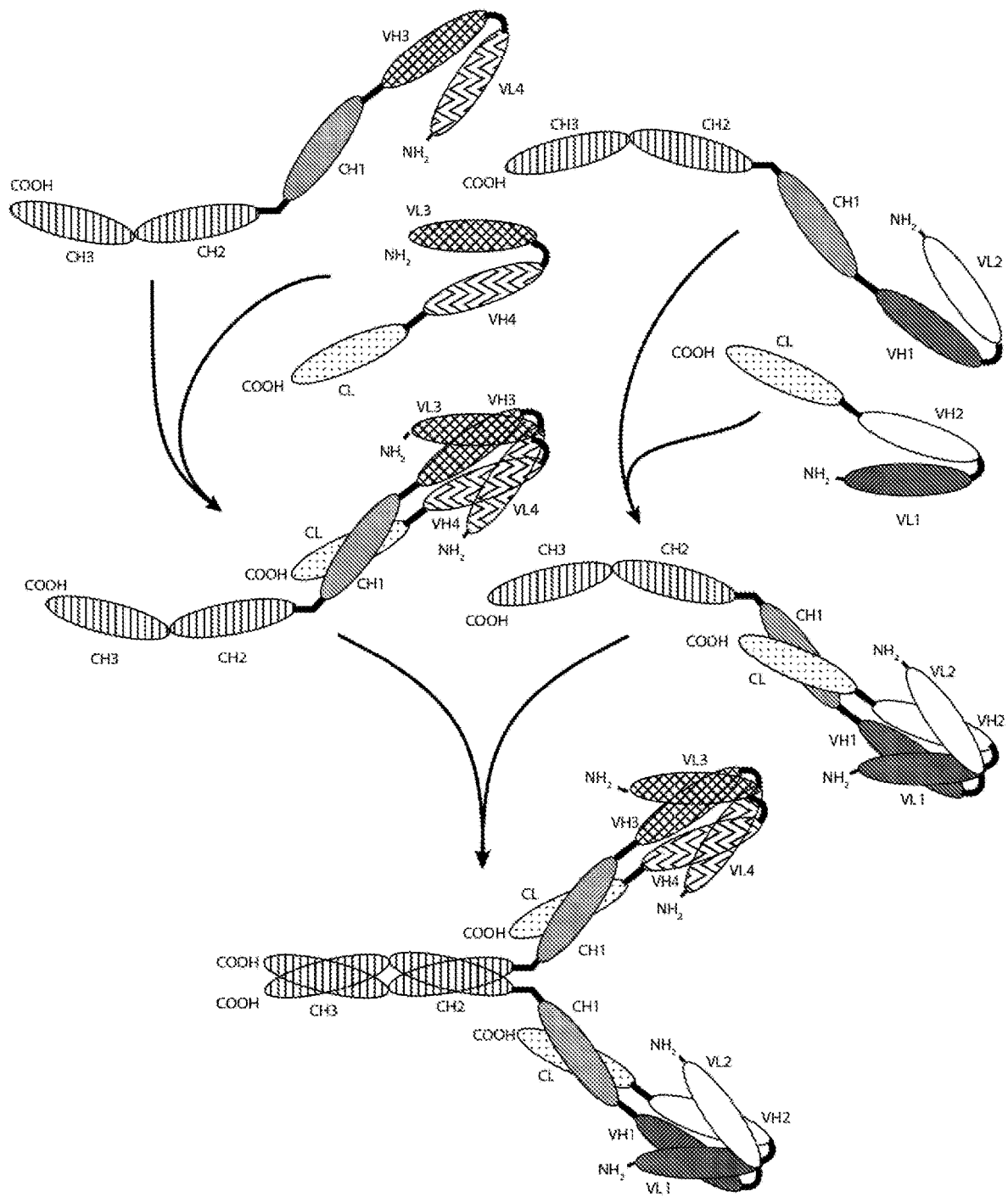
Figure 3D:
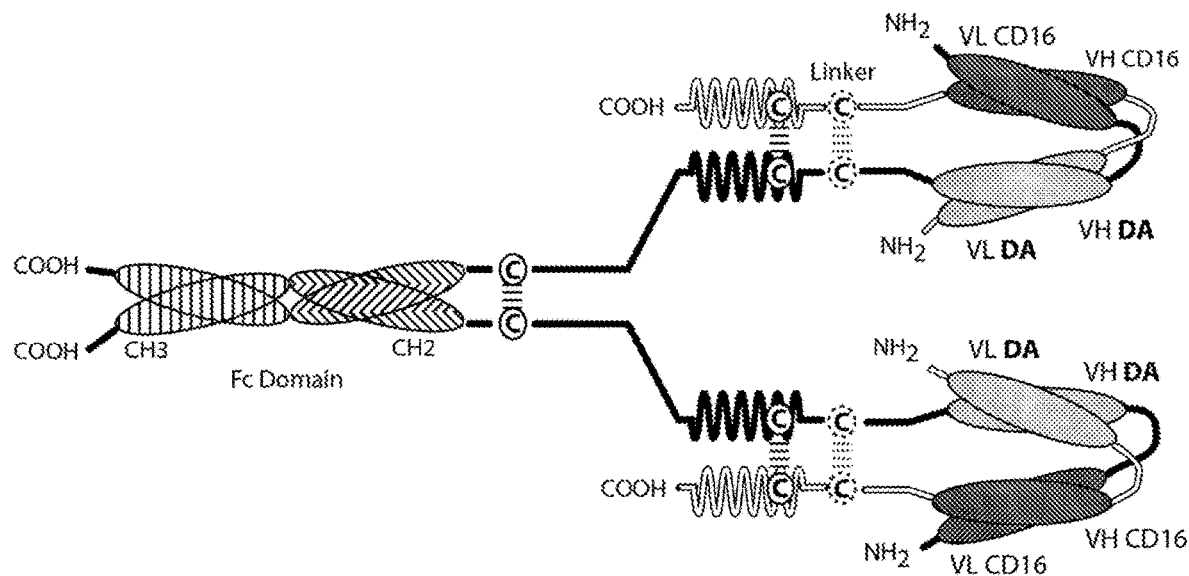
Figure 3E:
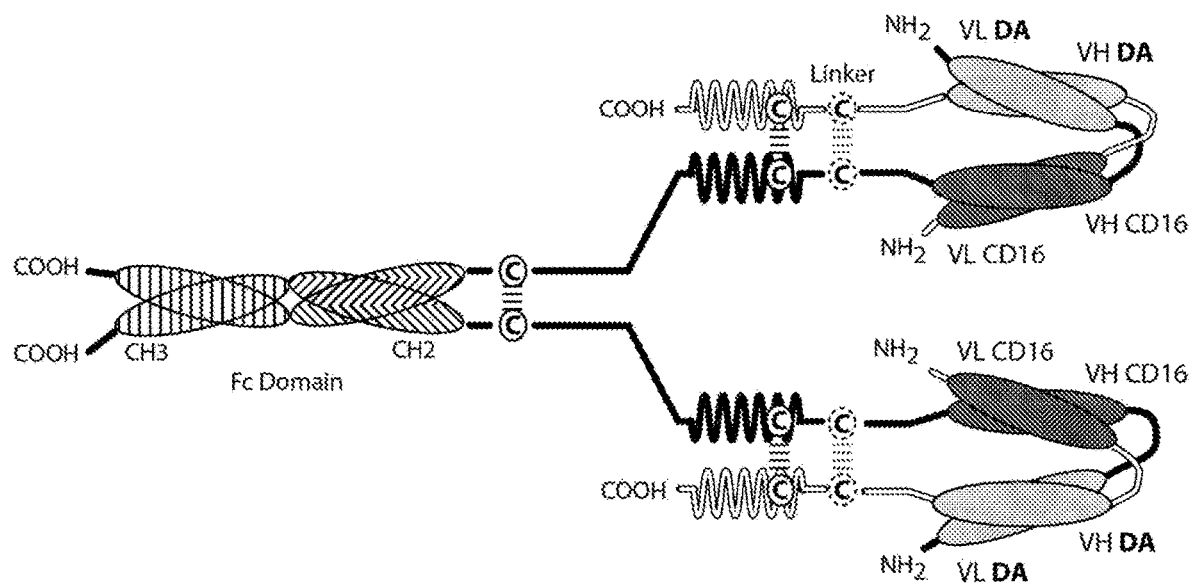

Alternatively, incorporating IgG CH2-CH3 Domains onto only one of the diabody polypeptides will permit a more complex four-chain bispecific Fc Domain-containing diabody to form (FIGS. 3A-3C). FIG. 3C shows a representative four-chain diabody possessing the Constant Light (CL) Domain and the Constant Heavy CH1 Domain, however fragments of such domains as well as other polypeptides may alternatively be employed (see, e.g., FIGS. 3A and 3B, United States Patent Publication Nos. 2013-0295121; 2010-0174053 and 2009-0060910; European Patent Publication No. EP 2714079; EP 2601216; EP 2376109; EP 2158221 and PCT Publication Nos. WO 2012/162068; WO 2012/018687; WO 2010/080538). Thus, for example, in lieu of the CH1 Domain, one may employ a peptide having the amino acid sequence GVEPKSC (SEQ ID NO:24), VEPKSC (SEQ ID NO:25), or AEPKSC (SEQ ID NO:26), derived from the Hinge Domain of a human IgG, and in lieu of the CL Domain, one may employ the C-terminal 6 amino acids of the human kappa Light Chain, GFNRGEC (SEQ ID NO:27) or FNRGEC (SEQ ID NO:28). A representative peptide containing four-chain diabody is shown in FIG. 3A. Alternatively, or in addition, one may employ a peptide comprising tandem coil domains of opposing charge such as the "E-coil" helical domains

```
(SEQ ID NO: 29:
EVAALEK-EVAALEK-EVAALEK-EVAALEK
or

SEQ ID NO: 31:
EVAACEK-EVAALEK-EVAALEK-EVAALEK);
and the "K-coil" domains
(SEQ ID NO: 30:
KVAALKE-KVAALKE-KVAALKE-KVAALKE
or

SEQ ID NO: 32:
KVAACKE-KVAALKE-KVAALKE-KVAALKE).
```

A representative coil domain containing four-chain diabody is shown in FIG. 3B.

Fc Domain-containing diabody molecules of the present invention may include additional intervening spacer peptides (Linkers), generally such Linkers will be incorporated between a Heterodimer-Promoting Domain (e.g., an E-coil or K-coil) and a CH2-CH3 Domain and/or between a CH2-CH3 Domain and a Variable Domain (i.e., VH or VL). Typically, the additional Linkers will comprise 3-20 amino acid residues and may optionally contain all or a portion of an IgG Hinge Domain (preferably a cysteine-containing portion of an IgG Hinge Domain possessing 1, 2, 3 or more cysteine residues). Linkers that may be employed in the bispecific Fc Domain-containing diabody molecules of the present invention include: GGGS (SEQ ID NO:18), LGGGSG (SEQ ID NO:19), GGGSGGGSGGG (SEQ ID NO:20), AS TKG (SEQ ID NO:21), LEPKSS (SEQ ID NO:22), APSSS (SEQ ID NO:23), APSSSPME (SEQ ID NO:37), VEPKSADKTHTCPPCP (SEQ ID NO:38), LEPKSADKTHTCPPCP (SEQ ID NO:39), DKTHTCPPCP (SEQ ID NO:40), the scFv linker: GGGGSGGGGSGGGGS (SEQ ID NO:41); the "long" linker: GGGGSGGGSGGG (SEQ ID NO:42), GGC, and GGG. LEPKSS (SEQ ID NO:22) may be used in lieu of GGG or GGC for ease of cloning. Additionally, the amino acids GGG, or LEPKSS (SEQ ID NO:22) may be immediately followed by DKTH-TCPPCP (SEQ ID NO:40) to form the alternate linkers: GGGDKTHTCPPCP (SEQ ID NO:43); and LEPKSSDKTHTCPPCP (SEQ ID NO:44).

Bispecific Fc Domain-containing molecules of the present invention may incorporate an IgG Hinge Domain in addition to or in place of a linker. Exemplary Hinge Domains include: EPKSCDKTHTCPPCP (SEQ ID NO:5) from IgG1, ERKCCVECPPCP (SEQ ID NO:6) from IgG2, ELKTPLGDTTHTCPRCPEPKSCDTPPPCPRC-PEPKSCDTPPPCPRCPEPKS CDTPPPCPRCP (SEQ ID NO:7) from IgG3, ESKYGPPCPSCP (SEQ ID NO:8) from IgG4, and ESKYGPPCPPCP (SEQ ID NO:9) an IgG4 Hinge variant comprising a stabilizing S228P substitution (as numbered by the EU index as set forth in Kabat) to reduce strand exchange.

As provided in FIG. 3A-3C, Fc Domain-containing diabodies of the invention may comprise four chains. The first and third polypeptide chains of such a diabody contain three domains: (i) a VL1-containing Domain, (ii) a VH2-containing Domain, (iii) a Heterodimer-Promoting Domain, and (iv) a Domain containing a CH2-CH3 sequence. The second and fourth polypeptide chains contain: (i) a VL2-containing Domain, (ii) a VH1-containing Domain, and (iii) a Heterodimer-Promoting Domain, where the Heterodimer-Promoting Domains promote the dimerization of the first/third polypeptide chains with the second/fourth polypeptide chains. The VL and/or VH Domains of the third and fourth polypeptide chains, and VL and/or VH Domains of the first and second polypeptide chains may be the same or different so as to permit tetravalent binding that is either mono-specific, bispecific or tetraspecific. The notation "VL3" and "VH3" denote respectively, the Light Chain Variable Domain and Variable Heavy Chain Domain that bind a "third" epitope of such diabody. Similarly, the notation "VL4" and "VH4" denote respectively, the Light Chain Variable Domain and Variable Heavy Chain Domain that bind a "fourth" epitope of such diabody. The general structure of the polypeptide chains of a representative four-chain bispecific Fc Domain-containing diabodies of invention is provided in Table 1:

TABLE 1

| | | |
|---|---|---|
| Bispecific | $2^{nd}$ Chain | NH$_2$-VL2-VH1-HPD-COOH |
| | $1^{st}$ Chain | NH$_2$-VL1-VH2-HPD-CH2-CH3-COOH |
| | $1^{st}$ Chain | NH$_2$-VL1-VH2-HPD-CH2-CH3-COOH |
| | $2^{nd}$ Chain | NH$_2$-VL2-VH1-HPD-COOH |
| Tetraspecific | $2^{nd}$ Chain | NH$_2$-VL2-VH1-HPD-COOH |
| | $1^{st}$ Chain | NH$_2$-VL1-VH2-HPD-CH2-CH3-COOH |
| | $3^{rd}$ Chain | NH$_2$-VL3-VH4-HPD-CH2-CH3-COOH |
| | $4^{th}$ Chain | NH$_2$-VL4-VH3-HPD-COOH |

HPD = Heterodimer-Promoting Domain

In a specific embodiment, diabodies of the present invention are bispecific, tetravalent (i.e., possess four Epitope Binding Domains), Fc-containing diabodies that are composed of four total polypeptide chains (FIGS. 3A-3C). The bispecific, tetravalent, Fc-containing diabodies of the invention comprise two First Epitope Binding Domains and two Second Epitope Binding Domains.

Figure 4A:
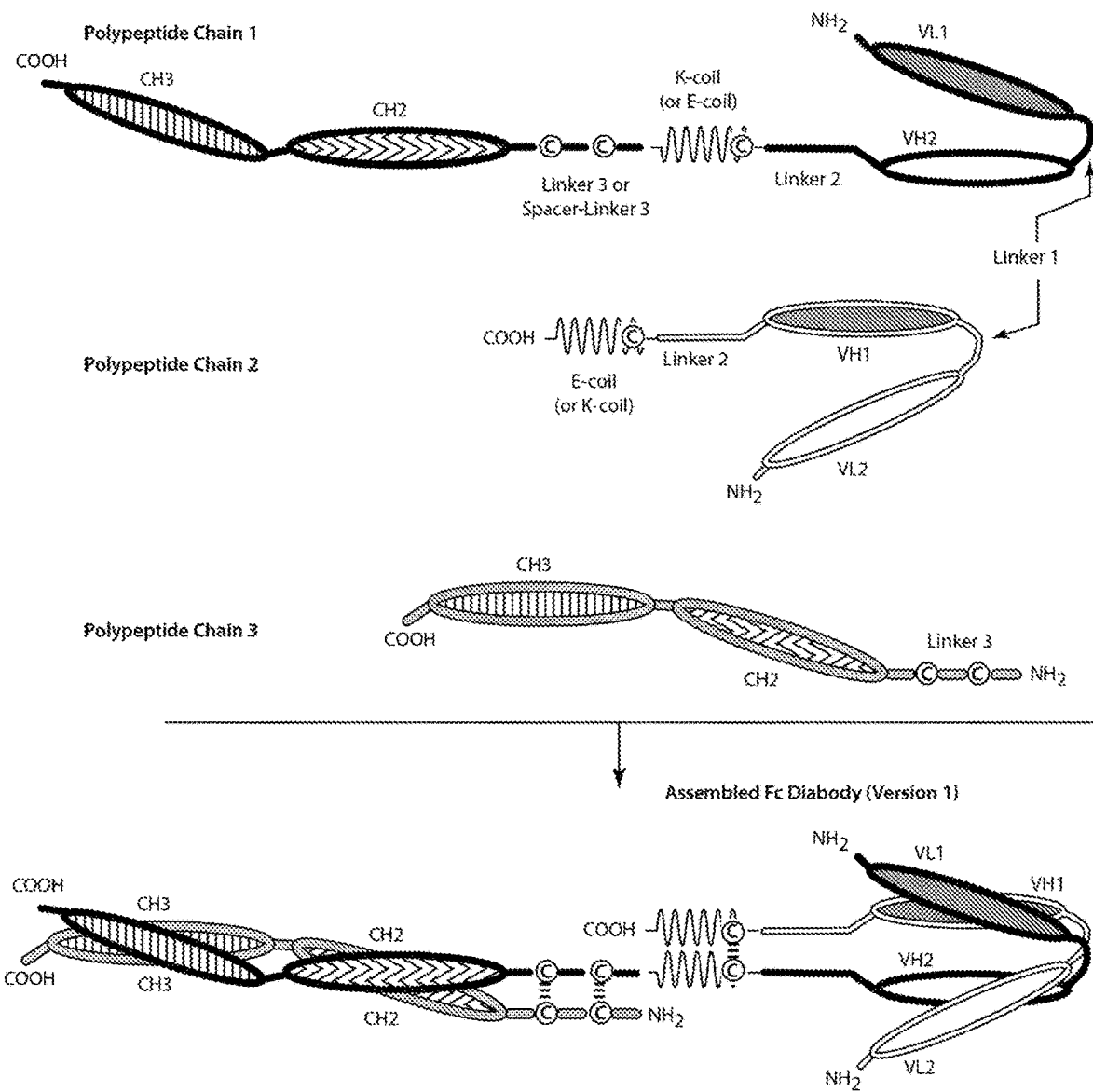
FIGS. 4A and 4B provide schematics of a representative covalently bonded diabody molecule having two epitope-binding sites composed of three polypeptide chains. Two of the polypeptide chains possess a CH2 and CH3 Domain, such that the associated chains form all or part of an Fc Region. The polypeptide chains comprising the VL and VH Domain further comprise a Heterodimer-Promoting Domain. VL and VH Domains that recognize the same epitope are shown using the same shading or fill pattern.
Figure 4B:
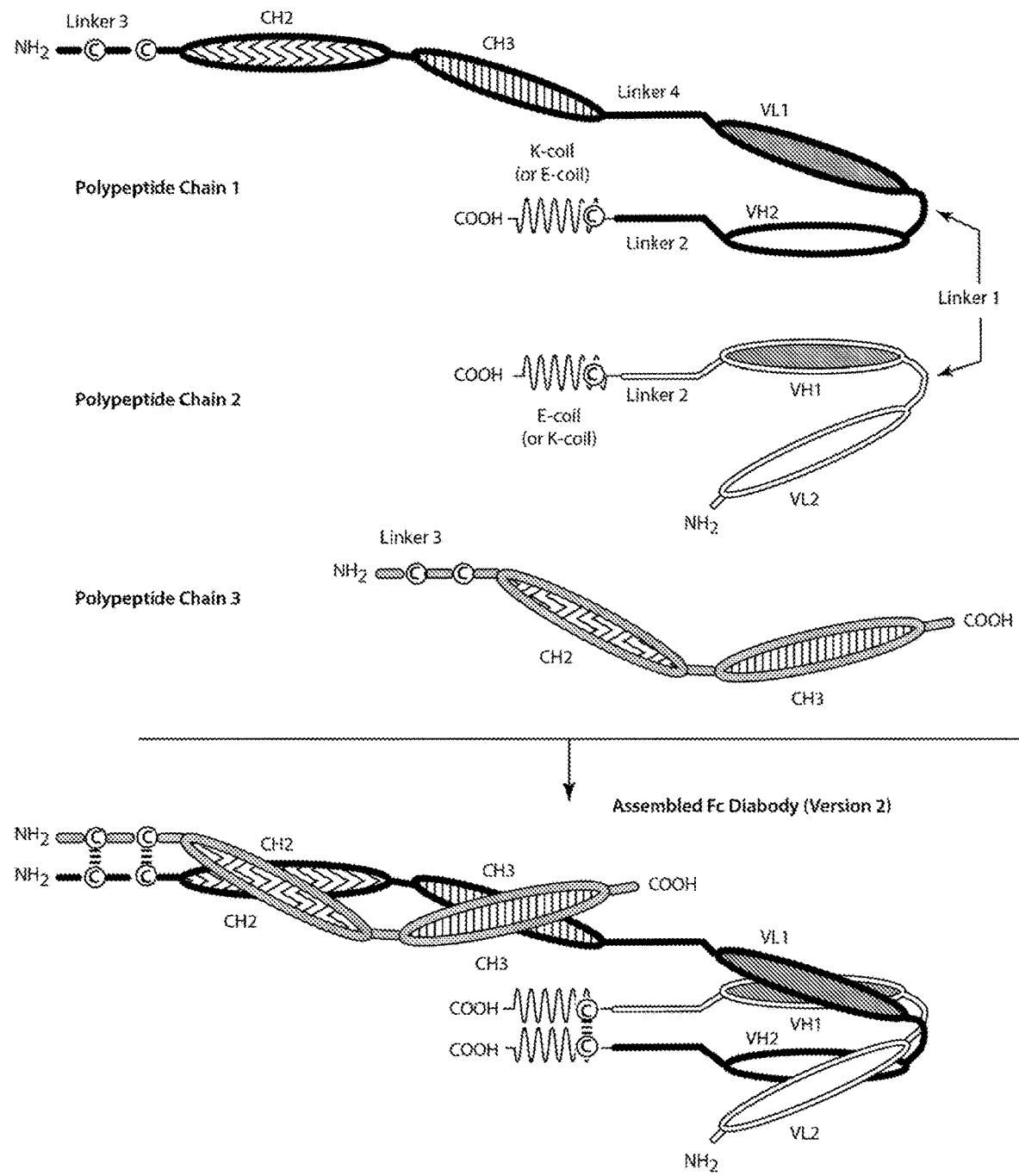
Figure 5A:
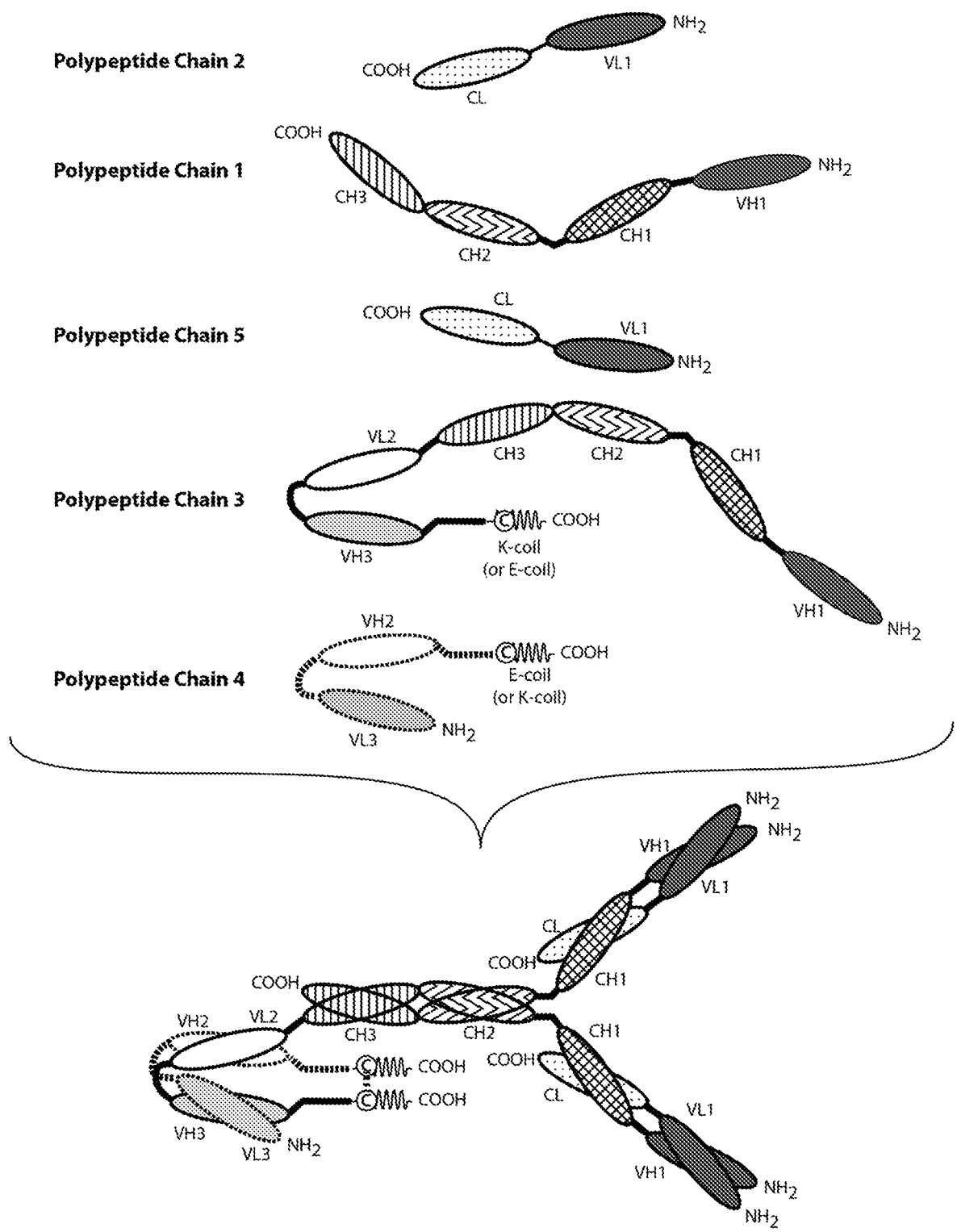
FIGS. 5A-5D provide schematics of a representative covalently bonded Binding Molecule having four epitope-binding sites composed of five polypeptide chains.
Figure 5B:
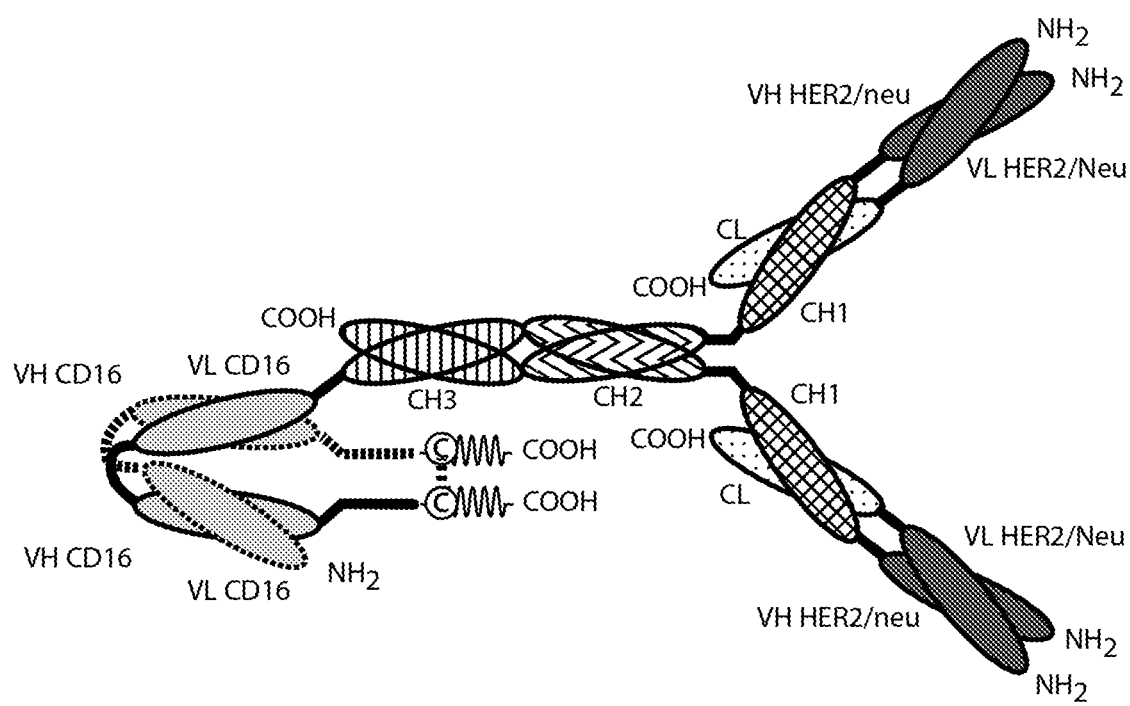
Figure 5C:
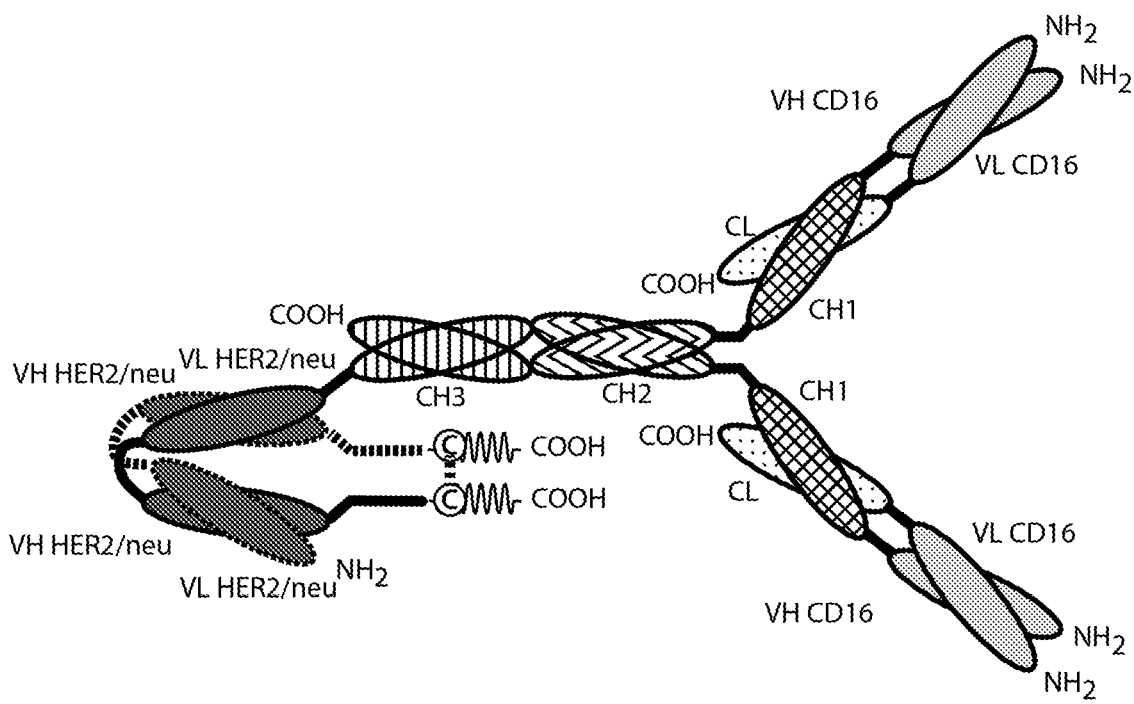
Figure 5D:
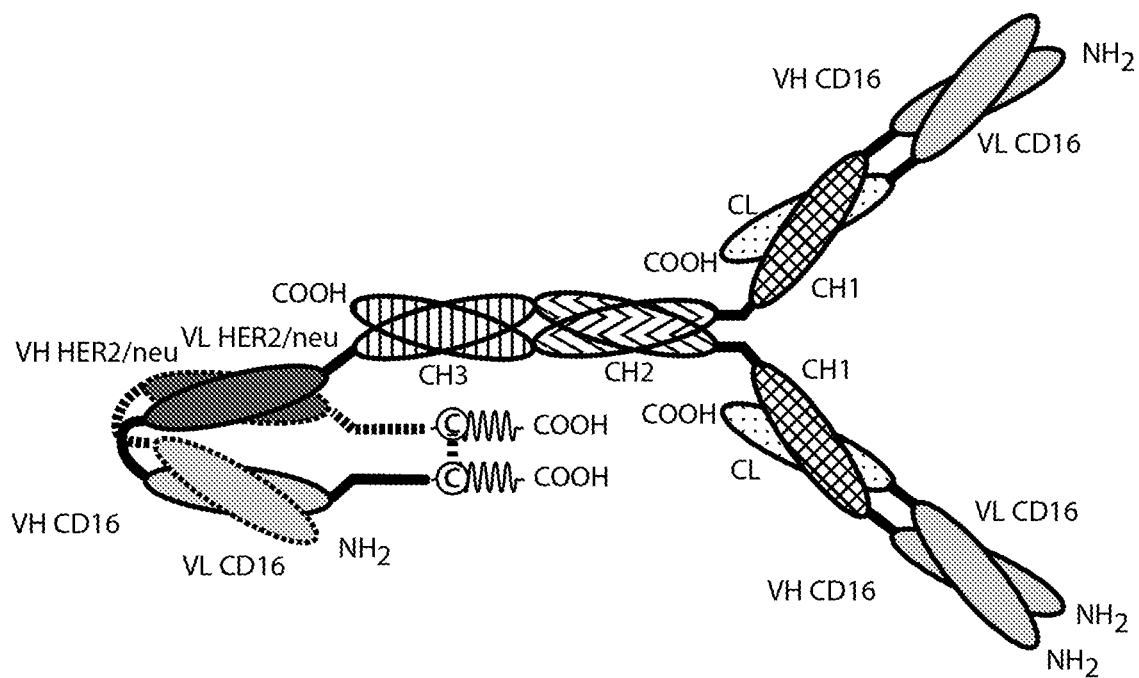

In a further embodiment, the Fc Domain-containing diabodies of the present invention may comprise three polypeptide chains. The first polypeptide of such a diabody contains three domains: (i) a VL1-containing Domain, (ii) a VH2-containing Domain and (iii) a Domain containing a CH2-CH3 sequence. The second polypeptide of such a diabody contains: (i) a VL2-containing Domain, (ii) a VH1-containing Domain and (iii) a Domain that promotes heterodimerization and covalent bonding with the diabody's first polypeptide chain. The third polypeptide of such a diabody comprises a CH2-CH3 sequence. Thus, the first and second polypeptide chains of such a diabody associate together to form a VL1/VH1 Epitope Binding Domain that is capable of binding either the First or Second Epitope, as well as a VL2/VH2 Epitope Binding Domain that is capable of binding the other of such epitopes. The first and second polypeptides are bonded to one another through a disulfide bond involving cysteine residues in their respective Third Domains. Notably, the first and third polypeptide chains complex with one another to form an Fc Domain that is stabilized via a disulfide bond. Such bispecific diabodies have enhanced potency. FIGS. 4A and 4B illustrate the structures of such diabodies. Such Fc Domain-containing diabodies may have either of two orientations (Table 2):

TABLE 2

| First Orientation | $3^{rd}$ Chain | NH$_2$-CH2-CH3-COOH |
|---|---|---|
| | $1^{st}$ Chain | NH$_2$-VL1-VH2-HPD-CH2-CH3-COOH |
| | $2^{nd}$ Chain | NH$_2$-VL2-VH1-HPD-COOH |
| Second Orientation | $3^{rd}$ Chain | NH$_2$-CH2-CH3-COOH |
| | $1^{st}$ Chain | NH$_2$-CH2-CH3-VL1-VH2-HPD-COOH |
| | $2^{nd}$ Chain | NH$_2$-VL2-VH1-HPD-COOH |

HPD = Heterodimer-Promoting Domain

In a specific embodiment, diabodies of the present invention are bispecific, bivalent (i.e., possess two Epitope Binding Domains), Fc-containing diabodies that are composed of three total polypeptide chains (FIGS. 4A-4B). The bispecific, bivalent Fc-containing diabodies of the invention comprise one Epitope Binding Domain immunospecific for either the First or Second Epitope, as well as a VL2/VH2 Epitope Binding Domain that is capable of binding the other of such epitopes.

In a further embodiment, the Fc Domain-containing diabodies may comprise a total of five polypeptide chains. In a particular embodiment, two of the five polypeptide chains have the same amino acid sequence. The first polypeptide chain of such a diabody contains: (i) a VH1-containing Domain, (ii) a CH1-containing Domain, and (iii) a Domain containing a CH2-CH3 sequence. The first polypeptide chain may be the Heavy Chain of an antibody that contains a VH1 and a Heavy Chain constant region. The second and fifth polypeptide chains of such a diabody contain: (i) a VL1-containing Domain, and (ii) a CL-containing Domain. The second and/or fifth polypeptide chains of such a diabody may be Light Chains of an antibody that contains a VL1 complementary to the VH1 of the first/third polypeptide chain. The first, second and/or fifth polypeptide chains may be isolated from a naturally occurring antibody. Alternatively, they may be constructed recombinantly. The third polypeptide chain of such a diabody contains: (i) a VH1-containing Domain, (ii) a CH1-containing Domain, (iii) a Domain containing a CH2-CH3 sequence, (iv) a VL2-containing Domain, (v) a VH3-containing Domain and (vi) a Heterodimer-Promoting Domain, where the Heterodimer-Promoting Domains promote the dimerization of the third chain with the fourth chain. The fourth polypeptide of such diabodies contains: (i) a VL3-containing Domain, (ii) a VH2-containing Domain and (iii) a Domain that promotes heterodimerization and covalent bonding with the diabody's third polypeptide chain.

Thus, the first and second, and the third and fifth, polypeptide chains of such diabodies associate together to form two VL1/VH1 Epitope Binding Domains capable of binding a First Epitope. The third and fourth polypeptide chains of such diabodies associate together to form a VL2/VH2 Epitope Binding Domain that is capable of binding a Second Epitope, as well as a VL3/VH3 Epitope Binding Domain that is capable of binding a Third Epitope. The first and third polypeptides are bonded to one another through a disulfide bond involving cysteine residues in their respective constant regions. Notably, the first and third polypeptide chains complex with one another to form an Fc Domain. Such multispecific diabodies have enhanced potency. FIG. 5 illustrates the structure of such diabodies. It will be understood that the VL1/VH1, VL2/VH2, and VL3/VH3 Domains may be the same or different so as to permit binding that is mono-specific, bispecific or trispecific.

The VL and VH Domains of the polypeptide chains are selected so as to form VL/VH Epitope Binding Domains specific for a desired epitope. The VL/VH Epitope Binding Domains formed by the association of the polypeptide chains may be the same or different so as to permit tetravalent binding that is mono-specific, bispecific, trispecific or tetraspecific. In particular, the VL and VH Domains maybe selected such that a multivalent diabody may comprise two Binding Domains for a First Epitope and two Binding Domains for a Second Epitope, or three Binding Domains for a First Epitope and one Binding Domain for a Second Epitope, or two Binding Domains for a First Epitope, one Binding Domain for a Second Epitope and one Binding Domain for a Third Epitope (as depicted in FIG. 5). The general structure of the polypeptide chains of representative five-chain Fc Domain-containing diabodies of invention is provided in Table 3:

TABLE 3

| Bispecific (2 × 2) | $2^{nd}$ Chain | NH$_2$-VL1-CL-COOH |
|---|---|---|
| | $1^{st}$ Chain | NH$_2$-VH1-CH1-CH2-CH3-COOH |
| | $3^{rd}$ Chain | NH$_2$-VH1-CH1-CH2-CH3-VL2-VH2-HPD-COOH |
| | $5^{nd}$ Chain | NH$_2$-VL1-CL-COOH |
| | $4t^{th}$ Chain | NH$_2$-VL2-VH2-HPD-COOH |
| Bispecific (3 × 1) | $2^{nd}$ Chain | NH$_2$-VL1-CL-COOH |
| | $1^{st}$ Chain | NH$_2$-VH1-CH1-CH2-CH3-COOH |
| | $3^{rd}$ Chain | NH$_2$-VH1-CH1-CH2-CH3-VL1-VH2-HPD-COOH |
| | $5^{nd}$ Chain | NH$_2$-VL1-CL-COOH |
| | $4^{th}$ Chain | NH$_2$-VL2-VH1-HPD-COOH |
| Trispecific (2 × 1 × 1) | $2^{nd}$ Chain | NH$_2$-VL1-CL-COOH |
| | $1^{st}$ Chain | NH$_2$-VH1-CH1-CH2-CH3-COOH |
| | $3^{rd}$ Chain | NH$_2$-VH1-CH1-CH2-CH3-VL2-VH3-HPD-COOH |
| | $5^{nd}$ Chain | NH$_2$-VL1-CL-COOH |
| | $4^{th}$ Chain | NH$_2$-VL3-VH2-HPD-COOH |

HPD = Heterodimer-Promoting Domain

In a specific embodiment, diabodies of the present invention are bispecific, tetravalent (i.e., possess four Epitope Binding Domains), Fc-containing diabodies that are composed of five total polypeptide chains having two Epitope Binding Domains immunospecific for the First Epitope, and two Epitope Binding Domains specific for the Second Epitope. In another embodiment, the bispecific, tetravalent, Fc-containing diabodies of the invention comprise three Epitope Binding Domains immunospecific for the First Epitope and one Epitope Binding Domain specific for the Second Epitope. As provided above, the VL and VH Domains may be selected to permit trispecific binding. Accordingly, the invention also encompasses trispecific, tetravalent, Fc-containing diabodies. The trispecific, tetravalent, Fc-containing diabodies of the invention comprise two Epitope Binding Domains immunospecific for the First Epitope, one Epitope Binding Domain immunospecific for the Second Epitope, and one Epitope Binding Domain immunospecific for the Third Epitope.

In traditional immune function, the interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All of these interactions are initiated through the binding of the Fc Domain of antibodies or immune complexes to specialized cell surface receptors on hematopoietic cells. As discussed above, the diversity of cellular responses triggered by antibodies and immune complexes results from the structural heterogeneity of the three Fc receptors: FcγRI (CD64), FcγRII (CD32), and FcγRIII (CD16). FcγRI (CD64), FcγRIIA (CD32A) and FcγRIII (CD16) are activating (i.e., immune system enhancing) receptors; FcγRIIB (CD32B) is an inhibiting (i.e., immune system dampening) receptor. In addition, interaction with the neonatal Fc Receptor (FcRn) mediates the recycling of IgG molecules from the endosome to the cell surface and release into the blood. The amino acid sequence of exemplary wild-type IgG1 (SEQ ID NO:12), IgG2 (SEQ ID NO:13), IgG3 (SEQ ID NO:14), and IgG4 (SEQ ID NO:15) are presented above.

Modification of the Fc Domain may lead to an altered phenotype, for example altered serum half-life, altered stability, altered susceptibility to cellular enzymes or altered effector function. It may therefore be desirable to modify an Fc Domain-containing binding molecule of the present invention with respect to effector function, for example, so as to enhance the effectiveness of such molecule in treating cancer. Reduction or elimination of Fc Domain-mediated effector function is desirable in certain cases, for example in the case of antibodies whose mechanism of action involves blocking or antagonism, but not killing of the cells bearing a target antigen. Increased effector function is generally desirable when directed to undesirable cells, such as tumor and foreign cells, where the FcγRs are expressed at low levels, for example, tumor-specific B cells with low levels of FcγRIIB (e.g., non-Hodgkin's lymphoma, CLL, and Burkitt's lymphoma). Molecules of the invention possessing such conferred or altered effector function activity are useful for the treatment and/or prevention of a disease, disorder or infection in which an enhanced efficacy of effector function activity is desired.

Accordingly, in certain embodiments, the Fc Domain of the Fc Domain-containing molecules of the present invention may be an engineered variant Fc Domain. Although the Fc Domain of the bispecific Fc Domain-containing molecules of the present invention may possess the ability to bind one or more Fc receptors (e.g., FcγR(s)), more preferably such variant Fc Domain have altered binding FcγRIA (CD64), FcγRIIA (CD32A), FcγRIIB (CD32B), FcγRIIIA (CD16a) or FcγRIIIB (CD16b) (relative to the binding exhibited by a wild-type Fc Domain), e.g., will have enhanced binding an activating receptor and/or will have substantially reduced or no ability to bind inhibitory receptor (s). Thus, the Fc Domain of the Fc Domain-containing molecules of the present invention may include some or all of the CH2 Domain and/or some or all of the CH3 Domain of a complete Fc Domain, or may comprise a variant CH2 and/or a variant CH3 sequence (that may include, for example, one or more insertions and/or one or more deletions with respect to the CH2 or CH3 domains of a complete Fc Domain). Such Fc Domains may comprise non-Fc polypeptide portions, or may comprise portions of non-naturally complete Fc Domains, or may comprise non-naturally occurring orientations of CH2 and/or CH3 Domains (such as, for example, two CH2 Domains or two CH3 Domains, or in the N-terminal to C-terminal direction, a CH3 Domain linked to a CH2 Domain, etc.).

Fc Domain modifications identified as altering effector function are known in the art, including modifications that increase binding activating receptors (e.g., FcγRIIA (CD16A) and reduce binding inhibitory receptors (e.g., FcγRIIB (CD32B) (see, e.g., Stavenhagen, J. B. et al. (2007) "*Fc Optimization Of Therapeutic Antibodies Enhances Their Ability To Kill Tumor Cells In Vitro And Controls Tumor Expansion In Vivo Via Low-Affinity Activating Fcgamma Receptors*," Cancer Res. 57(18):8882-8890). Table 4 lists exemplary single, double, triple, quadruple and quintuple substitutions (numbering (according to the EU index) and substitutions are relative to the amino acid sequence of SEQ ID NO:12 as presented above) of exemplary modification that increase binding activating receptors and/or reduce binding inhibitory receptors.

TABLE 4

Variations of Preferred Activating Fc Domains†

| Single-Site Variations | | | |
|---|---|---|---|
| F243L | R292G | D270E | R292P |
| Y300L | P396L | | |

| Double-Site Variations | | | |
|---|---|---|---|
| F243L and R292P | F243L and Y300L | F243L and P396L | R292P and Y300L |
| D270E and P396L | R292P and V305I | P396L and Q419H | P247L and N421K |
| R292P and P396L | Y300L and P396L | R255L and P396L | R292P and P305I |
| K392T and P396L | | | |

| Triple-Site Variations | |
|---|---|
| F243L, P247L and N421K | P247L, D270E and N421K |
| F243L, R292P and Y300L | R255L, D270E and P396L |
| F243L, R292P and V305I | D270E, G316D and R416G |
| F243L, R292P and P396L | D270E, K392T and P396L |
| F243L, Y300L and P396L | D270E, P396L and Q419H |
| V284M, R292L and K370N | R292P, Y300L and P396L |

| Quadruple-Site Variations | |
|---|---|
| L234F, F243L, R292P and Y300L | F243L, P247L, D270E and N421K |
| L234F, F243L, R292P and Y300L | F243L, R255L, D270E and P396L |
| L235I, F243L, R292P and Y300L | F243L, D270E, G316D and R416G |
| L235Q, F243L, R292P and Y300L | F243L, D270E, K392T and P396L |
| P247L, D270E, Y300L and N421K | F243L, R292P, Y300L, and P396L |
| R255L, D270E, R292G and P396L | F243L, R292P, V305I and P396L |
| R255L, D270E, Y300L and P396L | F243L, D270E, P396L and Q419H |
| D270E, G316D, P396L and R416G | |

| Quintuple-Site Variations | |
|---|---|
| L235V, F243L, R292P, Y300L and P396L | F243L, R292P, V305I, Y300L and P396L |
| L235P, F243L, R292P, Y300L and P396L | |

†numbering is according to the EU index as in Kabat

Exemplary variants of human IgG1 Fc Domains with reduced binding CD32B and/or increased binding CD16A contain F243L, R292P, Y300L, V305I or P396L substitutions, wherein the numbering is that of the EU index as in Kabat. These amino acid substitutions may be present in a human IgG1 Fc Domain in any combination. In one embodiment, the variant human IgG1 Fc Domain contains a F243L, R292P and Y300L substitution. In another embodiment, the variant human IgG1 Fc Domain contains a F243L, R292P, Y300L, V305I and P396L substitution.

In certain embodiments, it is preferred for the Fc Domains of the Fc Domain-containing binding molecules of the present invention to exhibit decreased (or substantially no) binding FcγRIA (CD64), FcγRIIA (CD32A), FcγRIIB (CD32B), FcγRIIIA (CD16a) or FcγRIIIB (CD16b) (relative to the binding exhibited by the wild-type IgG1 Fc Domain (SEQ ID NO:12). In a specific embodiment, the Fc Domain-containing binding molecules of the present invention comprise an IgG Fc Domain that exhibits reduced antibody-dependent cell-mediated cytotoxicity (ADCC) effector function. In a preferred embodiment, the CH2-CH3 Domains of such binding molecules include any 1, 2, 3, or 4 of the substitutions: L234A, L235A, D265A, N297Q, and N297G, wherein the numbering is that of the EU index as in Kabat. In another embodiment, the CH2-CH3 Domains contain an N297Q substitution, an N297G substitution, L234A and L235A substitutions or a D265A substitution, as these mutations abolish FcR binding. Alternatively, a CH2-CH3 Domain of a naturally occurring Fc Domain that inherently exhibits decreased (or substantially no) binding FcγRIIIA (CD16a) and/or reduced effector function (relative to the binding and effector function exhibited by the wild-type IgG1 Fc Domain (SEQ ID NO:12)) is utilized. In a specific embodiment, the Fc Domain-containing binding molecules of the present invention comprise an IgG2 Fc Domain (SEQ ID NO:13), an IgG3 Fc Domain (SEQ ID NO:14) or an IgG4 Fc Domain (SEQ ID NO:15). When an IgG4 Fc Domain is utilized, the instant invention also encompasses the introduction of a stabilizing mutation, such as the Hinge Region S228P substitution described above (see, e.g., SEQ ID NO:11). Since the N297G, N297Q, L234A, L235A and D265A substitutions abolish effector function, in circumstances in which effector function is desired, these substitutions would preferably not be employed.

A preferred IgG1 sequence for the CH2 and CH3 Domains of the Fc Domain-containing molecules of the present invention having reduced or abolished effector function will comprise the substitutions L234A/L235A (SEQ ID NO:45):

```
APEAAGGPSV FLFPPKPKDT LMISRTPEVT CVVVDVSHED
PEVKFNWYVD GVEVHNAKTK PREEQYNSTY RVVSVLTVLH
QDWLNGKEYK CKVSNKALPA PIEKTISKAK GQPREPQVYT
LPPSREEMTK NQVSLTCLVK GFYPSDIAVE WESNGQPENN
YKTTPPVLDS DGSFFLYSKL TVDKSRWQQG NVFSCSVMHE
ALHNHYTQKS LSLSPGX
``` wherein X is lysine (K) or is absent.

A second preferred IgG1 sequence for the CH2 and CH3 Domains of the Fc Region-containing molecules of the present invention comprises an S442C substitution (shown underlined), so as to permit two CH3 domains to be covalently bonded to one another via a disulfide bond or to permit conjugation of a drug moiety. The amino acid sequence of such molecule is (SEQ ID NO:46):

```
APELLGGPSV FLFPPKPKDT LMISRTPEVT CVVVDVSHED
PEVKFNWYVD GVEVHNAKTK PREEQYNSTY RVVSVLTVLH
QDWLNGKEYK CKVSNKALPA PIEKTISKAK GQPREPQVYT
LPPSREEMTK NQVSLTCLVK GFYPSDIAVE WESNGQPENN
YKTTPPVLDS DGSFFLYSKL TVDKSRWQQG NVFSCSVMHE
ALHNHYTQKS LCLSPGX
``` wherein X is lysine (K) or is absent.

A third preferred IgG1 sequence for the CH2 and CH3 Domains of the Fc Region-containing molecules of the present invention comprises the L234A/L235A substitutions (shown underlined) that reduce or abolish effector function and the S442C substitution (shown underlined) that permits two CH3 domains to be covalently bonded to one another via a disulfide bond or conjugation of a drug moiety. The amino acid sequence of such molecule is (SEQ ID NO:47):

```
APEAAGGPSV FLFPPKPKDT LMISRTPEVT CVVVDVSHED
PEVKFNWYVD GVEVHNAKTK PREEQYNSTY RVVSVLTVLH
QDWLNGKEYK CKVSNKALPA PIEKTISKAK GQPREPQVYT
LPPSREEMTK NQVSLTCLVK GFYPSDIAVE WESNGQPENN
YKTTPPVLDS DGSFFLYSKL TVDKSRWQQG NVFSCSVMHE
ALHNHYTQKS LCLSPGX
``` wherein X is lysine (K) or is absent.

The serum half-life of proteins comprising Fc Domains may be increased by increasing the binding affinity of the Fc Domain for FcRn. The term "half-life" as used herein means a pharmacokinetic property of a molecule that is a measure of the mean survival time of the molecules following their administration. Half-life can be expressed as the time required to eliminate fifty percent (50%) of a known quantity of the molecule from a subject's body (e.g., a human patient or other mammal) or a specific compartment thereof, for example, as measured in serum, i.e., circulating half-life, or in other tissues. In general, an increase in half-life results in an increase in mean residence time (MRT) in circulation for the molecule administered.

In some embodiments, the Fc Domain-containing binding molecules of the present invention comprise a variant Fc Domain that comprises at least one amino acid modification relative to a wild-type Fc Domain, such that the molecule has an increased half-life (relative to such molecule if comprising a wild-type Fc Domain). In some embodiments, the Fc Domain-containing binding molecules of the present invention comprise a variant IgG Fc Domain that comprises a half-life extending amino acid substitution at one or more positions selected from the group consisting of 238, 250, 252, 254, 256, 257, 256, 265, 272, 286, 288, 303, 305, 307, 308, 309, 311, 312, 317, 340, 356, 360, 362, 376, 378, 380, 382, 413, 424, 428, 433, 434, 435, and 436, wherein the numbering is that of the EU index as in Kabat. Numerous mutations capable of increasing the half-life of an Fc Domain-containing molecule are known in the art and include, for example M252Y, S254T, T256E, and combinations thereof. For example, see the mutations described in U.S. Pat. Nos. 6,277,375, 7,083,784; 7,217,797, 8,088,376; U.S. Publication Nos. 2002/0147311; 2007/0148164; and PCT Publication Nos. WO 98/23289; WO 2009/058492; and WO 2010/033279, which are herein incorporated by reference in their entireties.

In some embodiments, the Fc Domain-containing binding molecules of the present invention exhibiting enhanced half-life possess a variant Fc Domain comprising substitutions at two or more of Fc Domain residues 250, 252, 254, 256, 257, 288, 307, 308, 309, 311, 378, 428, 433, 434, 435 and 436. In particular, two or more substitutions selected from: T250Q, M252Y, S254T, T256E, K288D, T307Q, V308P, A378V, M428L, N434A, H435K, and Y436I, wherein the numbering is that of the EU index as in Kabat. In a specific embodiment, such molecules may possess a variant IgG Fc Domain comprising the substitution:
 (A) M252Y, S254T and T256E;
 (B) M252Y and S254T;
 (C) M252Y and T256E;
 (D) T250Q and M428L;
 (E) T307Q and N434A;
 (F) A378V and N434A;
 (G) N434A and Y436I;
 (H) V308P and N434A; or
 (I) K288D and H435K.

In a preferred embodiment, an Fc Domain-containing CD16×DA Binding Molecule of the present invention possesses a variant IgG Fc Region comprising any 1, 2, or 3 of the substitutions: M252Y, S254T and T256E. The invention further encompasses CD16×DA Binding Molecules possessing variant Fc Regions comprising:
 (A) one or more mutations which alter effector function and/or FcγR; and
 (B) one or more mutations which extend serum half-life.

An IgG1 sequence for the CH2 and CH3 Domains of the Fc Domain-containing molecules of the present invention that provides an increased half-life (and that has a 10-fold increase in binding to both cynomolgus monkey and human FcRn) (Dall'Acqua, W. F. et al. (2006) "*Properties of Human IgG1s Engineered for Enhanced Binding to the Neonatal Fc Receptor (FcRn)*," J. Biol. Chem. 281(33): 23514-23524) will comprise the substitutions M252Y/S254T/T256E (SEQ ID NO:48):

```
APELLGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGX
``` wherein X is lysine (K) or is absent.

An alternative IgG1 sequence for the CH2 and CH3 Domains of the Fc Domain-containing molecules of the present invention combining the reduced or abolished effector function provided by the substitutions L234A/L235A and the increased serum half-life provided by the substitutions M252Y/S254T/T256E is provided by SEQ ID NO: 49:

```
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGX
``` wherein X is lysine (K) or is absent.

A further preferred IgG1 sequence for the CH2 and CH3 Domains of the Fc Region-containing molecules of the present invention comprises the L234A/L235A substitutions (shown underlined) that reduce or abolish effector function and the M252Y, S254T and T256E substitutions (shown underlined), so as to extend the serum half-life and the S442C substitution (shown underlined), so as to permit two CH3 domains to be covalently bonded to one another via a disulfide bond or to permit conjugation of a drug moiety. The amino acid sequence of such molecule is (SEQ ID NO:50):

```
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LCLSPGX
``` wherein X is lysine (K) or is absent.

For certain antibodies, diabodies and trivalent binding molecules that are desired to have Fc-Domain-containing polypeptide chains of differing amino acid sequence (e.g., whose Fc Domain-containing polypeptide chains are desired to not be identical), it is desirable to reduce or prevent homodimerization from occurring between the CH2-CH3 Domains of identical chains (e.g., two first polypeptide chains or between the CH2-CH3 Domains of two third polypeptide chains). The CH2 and/or CH3 Domains of such polypeptide chains need not be identical in sequence, and advantageously are modified to foster heterodimer complexing between the two polypeptide chains. For example, an amino acid substitution (preferably a substitution with an amino acid comprising a bulky side group forming a "knob", e.g., tryptophan) can be introduced into the CH2 or CH3 Domain such that steric interference will prevent interaction with a similarly mutated domain and will obligate the mutated domain to pair with a domain into which a complementary, or accommodating mutation has been engineered, i.e., "the hole" (e.g., a substitution with glycine). Such sets of mutations can be engineered into any pair of polypeptides comprising CH2-CH3 Domains that forms an Fc Domain to foster heterodimerization. Methods of protein engineering to favor heterodimerization over homodimerization are well-known in the art, in particular with respect to the engineering of immunoglobulin-like molecules, and are encompassed herein (see e.g., Ridgway et al. (1996) "'*Knobs-Into-Holes' Engineering Of Antibody CH3 Domains For Heavy Chain Heterodimerization*," Protein Engr. 9:617-621, Atwell et al. (1997) "*Stable Heterodimers From Remodeling The Domain Interface Of A Homodimer Using A Phage Display Library*," J. Mol. Biol. 270: 26-35, and Xie et al. (2005) "*A New Format Of Bispecific Antibody: Highly Efficient Heterodimerization, Expression And Tumor Cell Lysis*," J. Immunol. Methods 296:95-101; each of which is hereby incorporated herein by reference in its entirety).

A preferred knob is created by modifying an IgG Fc Domain to contain the modification T366W. A preferred hole is created by modifying an IgG Fc Domain to contain the modification T366S, L368A and Y407V. To aid in purifying a hole-bearing polypeptide chain homodimer from the final bispecific heterodimeric Fc Domain-containing molecule, the Protein A Binding Domain of the hole-bearing CH2 and CH3 Domains of a polypeptide chain is preferably mutated by amino acid substitution at position 435 (H435R). Thus, the hole-bearing polypeptide chain homodimer will not bind protein A, whereas the bispecific heterodimer will retain its ability to bind protein A via the Protein A Binding Domain. In an alternative embodiment, the hole-bearing polypeptide chain may incorporate amino acid substitutions at positions 434 and 435 (N434A/N435K).

A preferred IgG1 amino acid sequence for the CH2 and CH3 Domains of one Fc Domain-containing polypeptide chain of an Fc Domain-containing molecule of the present invention will have the "knob-bearing" sequence (SEQ ID NO:51):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGX
``` wherein X is lysine (K) or is absent.

An alternative IgG1 amino acid sequence for the CH2 and CH3 Domains of one Fc Domain-containing polypeptide chain of an Fc Domain-containing molecule of the present invention having a M252Y/S254T/T256E substitution and a "knob-bearing" sequence is SEQ ID NO:52:

```
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSTWQQG NVFSCSVMHE

ALHNHYTQKS LSLSPGX
``` wherein X is lysine (K) or is absent.

A preferred IgG1 amino acid sequence for the CH2 and CH3 Domains of the other Fc Domain-containing polypeptide chain of an Fc Domain-containing molecule of the present invention having two polypeptide chains (or the third polypeptide chain of an Fc Domain-containing molecule having three, four, or five polypeptide chains) will have the "hole-bearing" sequence (SEQ ID NO:53):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSRWQQG NVFSCSVMHE

ALHNRYTQKS LSLSPGX
``` wherein X is lysine (K) or is absent.

An alternative IgG1 amino acid sequence for the CH2 and CH3 Domains of the other Fc Domain-containing polypeptide chain of an Fc Domain-containing molecule of the present invention having a M252Y/S254T/T256E substitution and a "hole-bearing" sequence is SEQ ID NO:54:

```
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSRWQQG NVFSCSVMHE

ALHNRYTQKS LSLSPGX
``` wherein X is lysine (K) or is absent.

As will be noted, the CH2-CH3 Domains of SEQ ID NO:51, SEQ ID NO:52, SEQ ID NO:53, and SEQ ID NO:54 include a substitution at position 234 with alanine and 235 with alanine, and thus form an Fc Domain exhibit decreased (or substantially no) binding FcγRIA (CD64), FcγRIIA (CD32A), FcγRIIB (CD32B), FcγRIIIA (CD16a) or FcγRIIIB (CD16b) (relative to the binding exhibited by the wild-type Fc Domain (SEQ ID NO:12). The invention also encompasses such CH2-CH3 Domains, which comprise the wild-type alanine residues, alternative and/or additional substitutions which modify effector function and/or FγR binding activity of the Fc Domain. The invention also encompasses such CH2-CH3 Domains, which further comprise one or more half-live extending amino acid substitutions. In particular, the invention encompasses such hole-bearing and such knob-bearing CH2-CH3 Domains which further comprise the M252Y/S254T/T256E.

An IgG4 amino acid sequence for the CH2 and CH3 Domains of the one Fc Domain-containing polypeptide chain of an Fc Domain-containing molecule of the present invention has enhanced serum half-life (relative to IgG1 CH2 and CH3 Domains) due to its possession of Y252/T254/E256 (SEQ ID NO:55):

```
APEFLGGPSV FLFPPKPKDT LYITREPEVT CVVVDVSQED

PEVQFNWYVD GVEVHNAKTK PREEQFNSTY RVVSVLTVLH

QDWLNGKEYK CKVSNKGLPS SIEKTISKAK GQPREPQVYT

LPPSQEEMTK NQVSLTCLVK GFYPSDIAVE WESNGQPENN

YKTTPPVLDS DGSFFLYSRL TVDKSRWQEG NVFSCSVMHE

ALHNHYTQKS LSLSLGX
``` wherein X is lysine (K) or is absent.

A "knob-bearing" variant of such an IgG4 CH2-CH3 amino acid sequence has the amino acid sequence of SEQ ID NO:56:

```
APEFLGGPSV FLFPPKPKDT LYITREPEVT CVVVDVSQED

PEVQFNWYVD GVEVHNAKTK PREEQFNSTY RVVSVLTVLH
```

```
QDWLNGKEYK CKVSNKGLPS SIEKTISKAK GQPREPQVYT

LPPSQEEMTK NQVSLWCLVK GFYPSDIAVE WESNGQPENN

YKTTPPVLDS DGSFFLYSRL TVDKSRWQEG NVFSCSVMHE

ALHNHYTQKS LSLSLGX
``` wherein X is lysine (K) or is absent.

A "hole-bearing" variant of such an IgG4 CH2-CH3 amino acid sequence has the amino acid sequence of SEQ ID NO:57:

```
APEFLGGPSV FLFPPKPKDT LYITREPEVT CVVVDVSQED

PEVQFNWYVD GVEVHNAKTK PREEQFNSTY RVVSVLTVLH

QDWLNGKEYK CKVSNKGLPS SIEKTISKAK GQPREPQVYT

LPPSQEEMTK NQVSLSCAVK GFYPSDIAVE WESNGQPENN

YKTTPPVLDS DGSFFLVSRL TVDKSRWQEG NVFSCSVMHE

ALHNRYTQKS LSLSLGX
``` wherein X is lysine (K) or is absent.

It is preferred that the first polypeptide chain will have a "knob-bearing" CH2-CH3 sequence, such as that of SEQ ID NO:51 or SEQ ID NO:52. However, as will be recognized, a "hole-bearing" CH2-CH3 Domain (e.g., SEQ ID NO:53 or SEQ ID NO:54) could be employed in the first polypeptide chain, in which case, a "knob-bearing" CH2-CH3 Domain (e.g., SEQ ID NO:51 or SEQ ID NO:52) would be employed in the second polypeptide chain of an Fc Domain-containing molecule of the present invention having two polypeptide chains (or in the third polypeptide chain of an Fc Domain-containing molecule having three, four, or five polypeptide chains).

In other embodiments, the invention encompasses Fc Domain-containing binding molecules comprising CH2 and/or CH3 Domains that have been engineered to favor heterodimerization over homodimerization using mutations known in the art, such as those disclosed in PCT Publication No. WO 2007/110205; WO 2011/143545; WO 2012/058768; WO 2013/06867, all of which are incorporated herein by reference in their entirety.

III. Trivalent Binding Molecules Containing Fc Domains

A further embodiment of the present invention relates to trivalent binding molecules comprising an Fc Domain capable of simultaneously binding a First Epitope, a Second Epitope and a Third Epitope, wherein at least one of such epitopes is not identical to another. Such trivalent binding molecules comprise three Epitope Binding Domains, two of which are Diabody-Type Binding Domains, which provide Binding Domain A and Binding Domain B, and one of which is a Fab-Type Binding Domain, or an scFv-Type Binding Domain, which provides Binding Domain C (see, e.g., FIGS. 6A-6H, PCT Publication Nos. WO 2015/184207 and WO 2015/184203). Such trivalent binding molecules thus comprise "VL1"/"V111" domains that are capable of binding the First Epitope and "VL2"/"VH2" domains that are capable of binding the Second Epitope and "VL3" and "VH3" domains that are capable of binding the "third" epitope of such trivalent binding molecule. A "Diabody-Type Binding Domain" is the type of Epitope Binding Domain present in a diabody, as described above. Each of a "Fab-Type Binding Domain" and an "scFv-Type Binding Domain" are Epitope Binding Domains that are formed by the interaction of the VL Domain of an immunoglobulin Light Chain and a complementing VH Domain of an immunoglobulin Heavy Chain. Fab-Type Binding Domains differ from Diabody-Type Binding Domains in that the two polypeptide chains that form a Fab-Type Binding Domain comprise only a single Epitope Binding Domain, whereas the two polypeptide chains that form a Diabody-Type Binding Domain comprise at least two Epitope Binding Domains. Similarly, scFv-Type Binding Domains also differ from Diabody-Type Binding Domains in that they comprise only a single Epitope Binding Domain. Thus, as used herein Fab-Type, and scFv-Type Binding Domains are distinct from Diabody-Type Binding Domains.

Figure 6A:
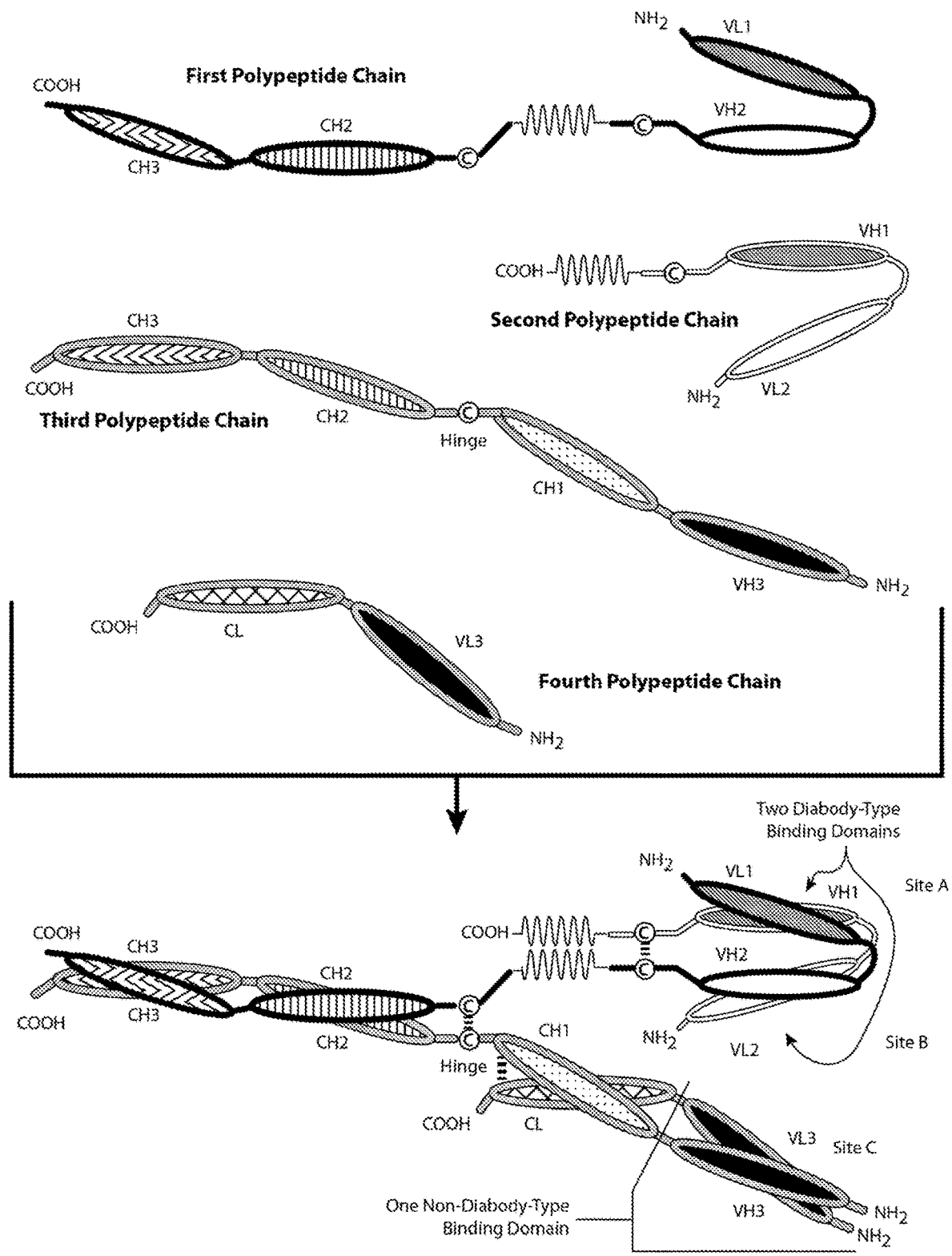
FIGS. 6A-6H provide schematics of representative Fc Region-containing trivalent binding molecules having three epitope-binding sites.
Figure 6B:
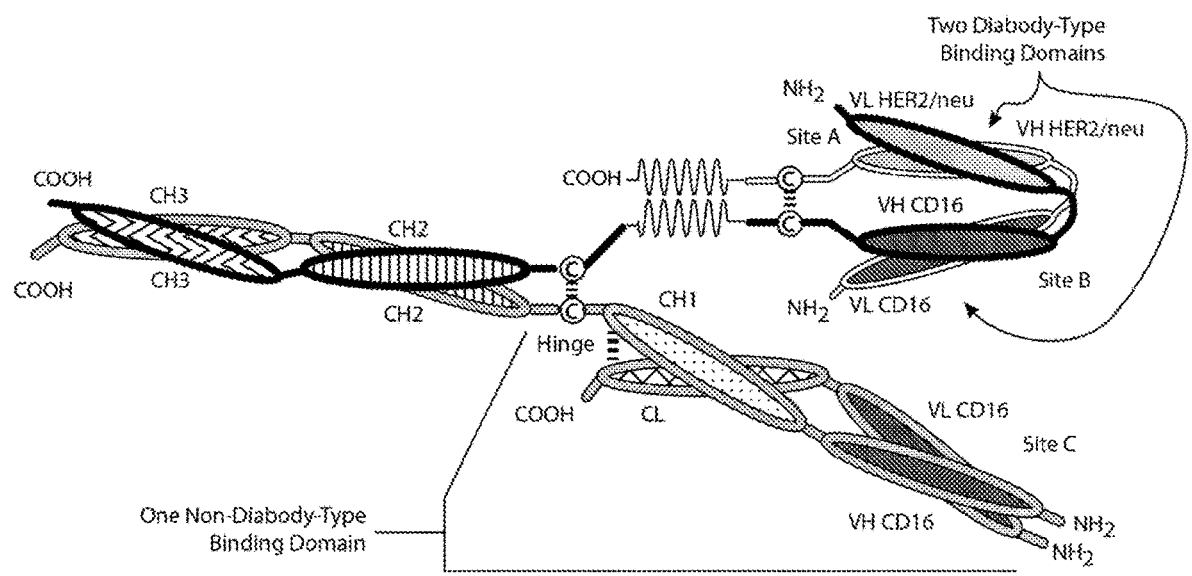
Figure 6C:
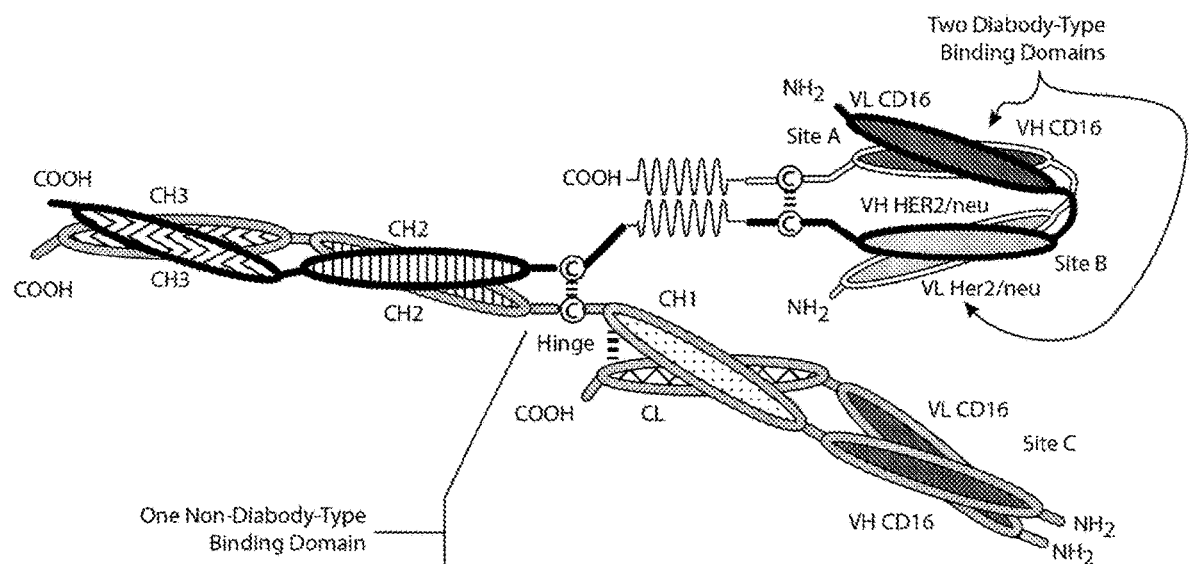
Figure 6D:
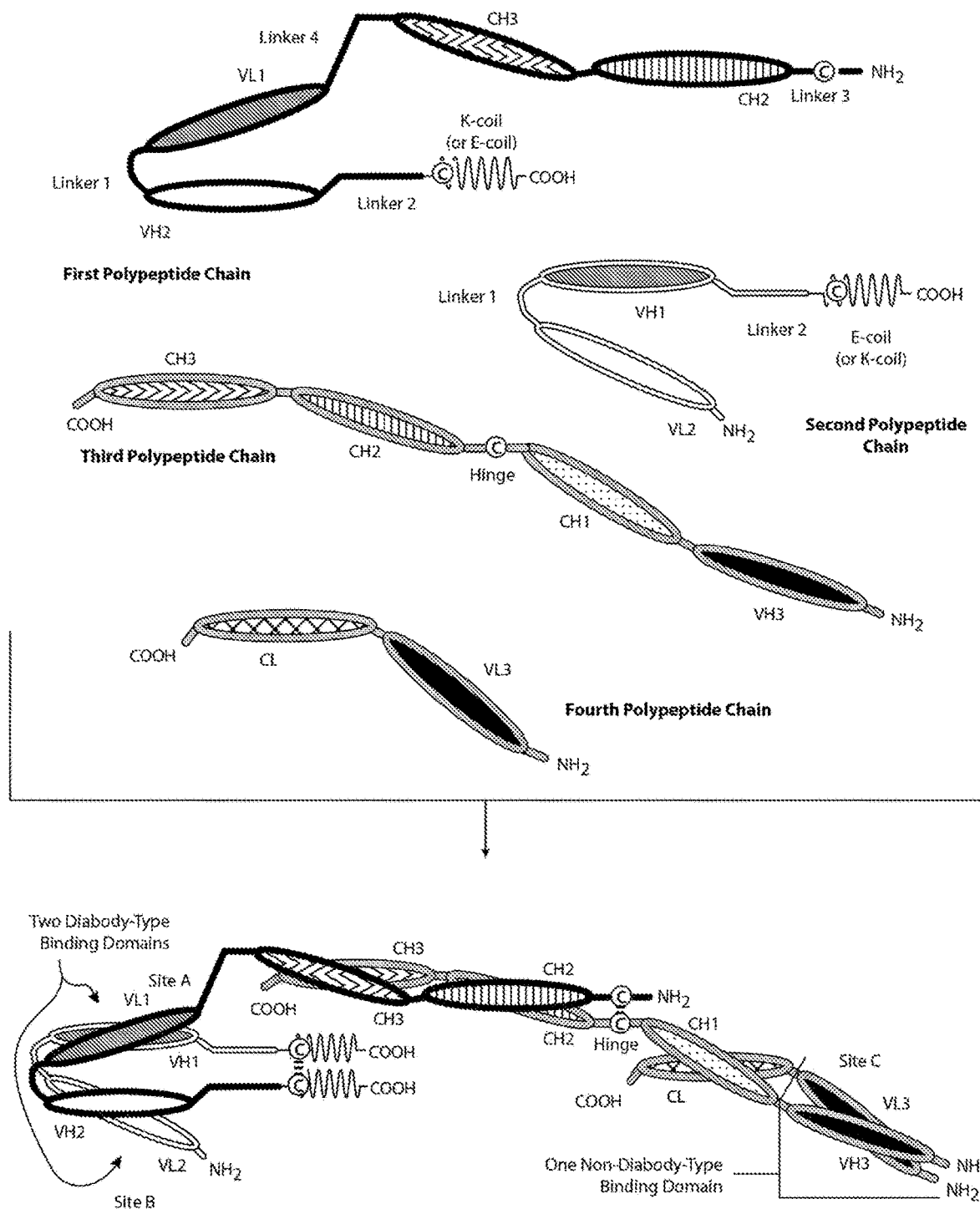
Figure 6E:
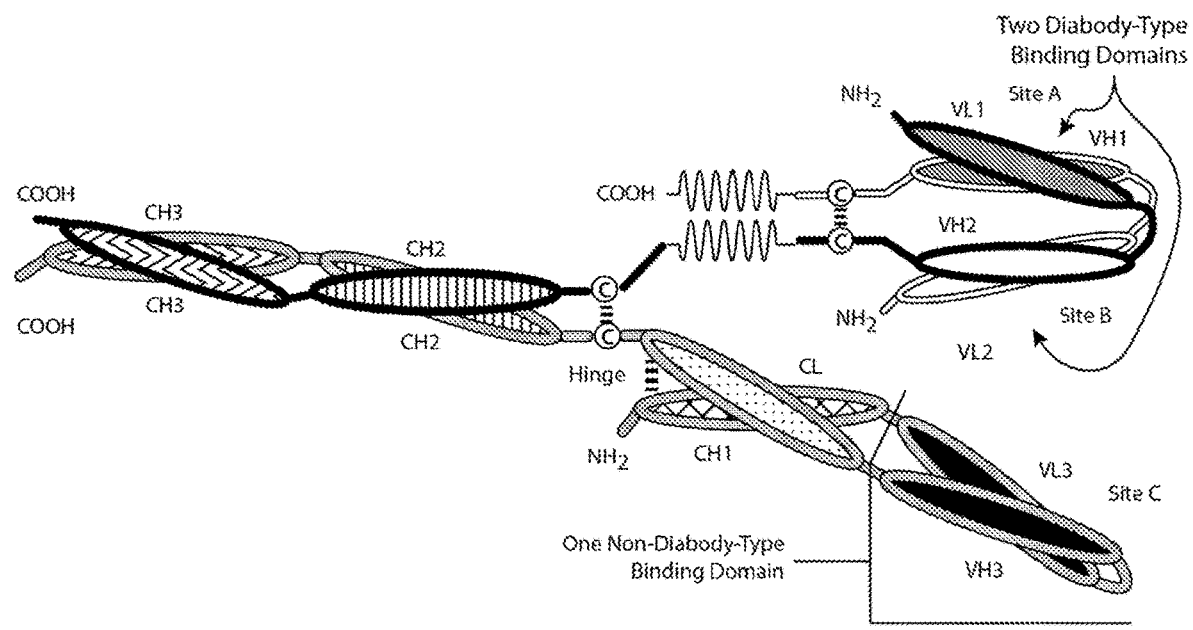
Figure 6F:
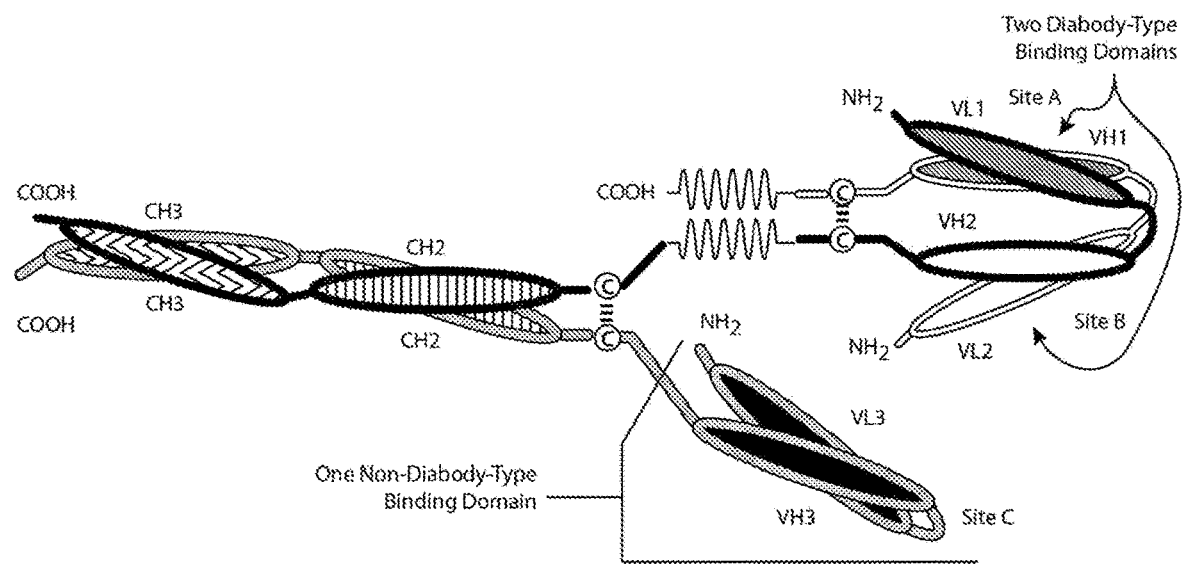
Figure 6G:
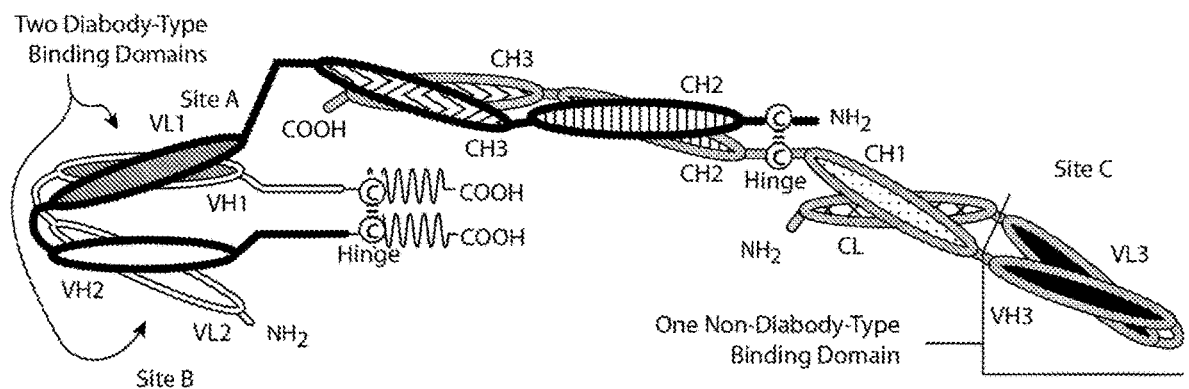
Figure 6H:
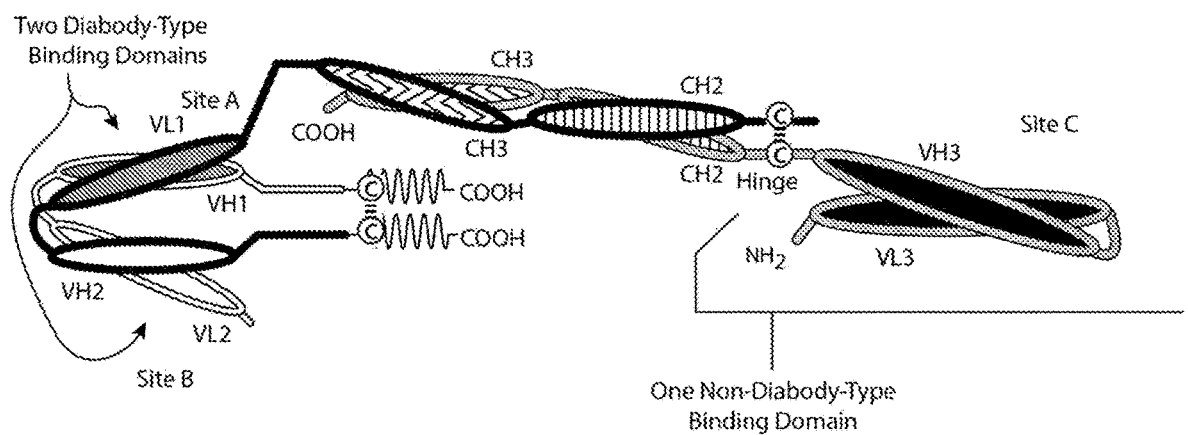

Typically, the trivalent Binding Molecules of the present invention will comprise four different polypeptide chains (see FIGS. 6A-6B), however, the molecules may comprise fewer or greater numbers of polypeptide chains, for example by fusing such polypeptide chains to one another (e.g., via a peptide bond) or by dividing such polypeptide chains to form additional polypeptide chains, or by associating fewer or additional polypeptide chains via disulfide bonds. FIGS. 6E-6F illustrate this aspect of the present invention by schematically depicting such molecules having three polypeptide chains. As provided in FIGS. 6A-6H, the trivalent binding molecules of the present invention may have alternative orientations in which the Diabody-Type Binding Domains are N-terminal (FIGS. 6A, 6B, 6C, 6E and 6F) or C-terminal (FIGS. 6D, 6G and 6H) to an Fc Domain. CH2 and CH3 Domains useful for the generation of trivalent binding molecules are provided above and include knob-bearing and hole-bearing domains.

In certain embodiments, the first polypeptide chain of such trivalent binding molecules of the present invention contains: (i) a VL1-containing Domain, (ii) a VH2-containing Domain, (iii) a Heterodimer-Promoting Domain, and (iv) a Domain containing a CH2-CH3 sequence. The VL1 and VL2 Domains are located N-terminal or C-terminal to the CH2-CH3-containing domain as presented in Table 4 (also see, FIGS. 6A and 6B). The second polypeptide chain of such embodiments contains: (i) a VL2-containing Domain, (ii) a VH1-containing Domain, and (iii) a Heterodimer-Promoting Domain. The third polypeptide chain of such embodiments contains: (i) a VH3-containing Domain, (ii) a CH1-containing Domain and (iii) a Domain containing a CH2-CH3 sequence. The third polypeptide chain may be the Heavy Chain of an antibody that contains a VH3 and a Heavy Chain constant region, or a polypeptide that contains such domains. The fourth polypeptide of such embodiments contains: (i) a VL3-containing Domain and (ii) a CL-containing Domain. The fourth polypeptide chains may be a Light Chain of an antibody that contains a VL3 complementary to the VH3 of the third polypeptide chain, or a polypeptide that contains such domains. The third or fourth polypeptide chains may be isolated from naturally occurring antibodies. Alternatively, they may be constructed recombinantly, synthetically or by other means.

The Light Chain Variable Domain of the first and second polypeptide chains are separated from the Heavy Chain Variable Domains of such polypeptide chains by an intervening spacer peptide having a length that is too short to permit their VL1/VH2 (or their VL2/VH1) domains to associate together to form an Epitope Binding Domain capable of binding either the First or Second Epitope. A preferred intervening spacer peptide (Linker 1) for this purpose has the sequence (SEQ ID NO:16):

GGGSGGGG.

Other Domains of the trivalent binding molecules may be separated by one or more intervening spacer peptides (Linkers), optionally comprising a cysteine residue. In particular, as provided above, such Linkers will typically be incorporated between Variable Domains (i.e., VH or VL) and peptide Heterodimer-Promoting Domains (e.g., an E-coil or K-coil) and between such peptide Heterodimer-Promoting Domains (e.g., an E-coil or K-coil) and CH2-CH3 Domains. Exemplary linkers useful for the generation of trivalent binding molecules are provided above and are also provided in PCT Application Nos: PCT/US15/33081; and PCT/US15/33076. Thus, the first and second polypeptide chains of such trivalent binding molecules associate together to form a VL1/VH1 Binding Domain capable of binding a First Epitope, as well as a VL2/VH2 Binding Domain that is capable of binding a Second Epitope. The third and fourth polypeptide chains of such trivalent binding molecules associate together to form a VL3/VH3 Binding Domain that is capable of binding a Third Epitope.

As described above, the trivalent binding molecules of the present invention may comprise three polypeptides. Trivalent binding molecules comprising three polypeptide chains may be obtained by linking the domains of the fourth polypeptide N-terminal to the VH3-containing Domain of the third polypeptide (e.g., using an intervening spacer peptide (Linker 4)). Alternatively, a third polypeptide chain of a trivalent binding molecule of the invention containing the following domains is utilized: (i) a VL3-containing Domain, (ii) a VH3-containing Domain, and (iii) a Domain containing a CH2-CH3 sequence, wherein the VL3 and VH3 are spaced apart from one another by an intervening spacer peptide that is sufficiently long (at least 9 or more amino acid residues) so as to allow the association of these domains to form an Epitope Binding Domain. One preferred intervening spacer peptide for this purpose has the sequence:

(SEQ ID NO: 41)
GGGGSGGGSGGGGS.

It will be understood that the VL1/VH1, VL2/VH2, and VL3/VH3 Domains of such trivalent binding molecules may be different so as to permit binding that is mono-specific, bispecific or trispecific. In particular, the VL and VH Domains may be selected such that a trivalent binding molecule comprises two Binding Domains for a First Epitope and one Binding Domains for a Second Epitope, or one Binding Domain for a First Epitope and two Binding Domains for a Second Epitope, or one Binding Domain for a First Epitope, one Binding Domain for a Second Epitope and one Binding Domain for a Third Epitope.

The general structure of the polypeptide chains of representative trivalent binding molecules of invention is provided in FIGS. 6A-6H and in Table 5:

TABLE 5

| Four Chain | $2^{nd}$ Chain | NH$_2$-VL2-VH1-HPD-COOH |
| $1^{st}$ | $1^{st}$ Chain | NH$_2$-VL1-VH2-HPD-CH2-CH3-COOH |
| Orientation | $3^{rd}$ Chain | NH$_2$-VH3-CH1-CH2-CH3-COOH |
| | $2^{nd}$ Chain | NH$_2$-VL3-CL-COOH |
| Four Chain | $2^{nd}$ Chain | NH$_2$-VL2-VH1-HPD-COOH |
| 2nd | $1^{st}$ Chain | NH$_2$-CH2-CH3-VL1-VH2-HPD-COOH |
| Orientation | $3^{rd}$ Chain | NH$_2$-VH3-CH1-CH2-CH3-COOH |
| | $2^{nd}$ Chain | NH$_2$-VL3-CL-COOH |

TABLE 5-continued

| Three Chain | $2^{nd}$ Chain | NH$_2$-VL2-VH1-HPD-COOH |
| 1st | $1^{st}$ Chain | NH$_2$-VL1-VH2-HPD-CH2-CH3-COOH |
| Orientation | $3^{rd}$ Chain | NH$_2$-VL3-VH3-HPD-CH2-CH3-COOH |
| Three Chain | $2^{nd}$ Chain | NH$_2$-VL2-VH1-HPD-COOH |
| $2^{nd}$ | $1^{st}$ Chain | NH$_2$-CH2-CH3-VL1-VH2-HPD-COOH |
| Orientation | $3^{rd}$ Chain | NH$_2$-VL3-VH3-HPD-CH2-CH3-COOH |

HPD = Heterodimer-Promoting Domain

As provided above, such trivalent binding molecules may comprise three, four, five, or more polypeptide chains.

IV. Embodiments of the Invention

As stated above, the present invention is directed to a CD16×DA Binding Molecule (e.g., an antibody, a diabody, an scFv, an antibody, a TandAb, etc.) comprising a Binding Domain capable of binding an epitope of CD16 (i.e., a "CD16-Binding Domain") and a Binding Domain capable of binding an epitope of a Disease Antigen (i.e., a "Disease Antigen-Binding Domain"). The invention thus encompasses binding molecules comprising one or more of the VH and/or VL Domains of an antibody that binds to CD16, or more preferably, the CDR$_H$1, CDR$_H$2, and CDR$_H$3, and the CDR$_L$1, CDR$_L$2 and CDR$_L$3 portions of such Domains. In a preferred embodiment of the invention, such binding molecules will additionally contain Binding Domains sufficient to permit such molecules to bind to epitopes of one, two, three or or more than three Disease Antigens. The present invention is also directed to pharmaceutical compositions that comprise such molecule(s).

By possessing Binding Domains sufficient to immunospecifically bind CD16 and a Disease Antigen, the molecules of the present invention have the ability to co-localize CD16-expressing cells (and especially Natural Killer cells) to the site(s) of cells expressing the Disease Antigen so as to enhance the likelihood of ADCC-mediated killing of the target cell. As discussed above, such molecules may be bispecific, or may be capable of binding more than two epitopes.

In one embodiment, such CD16-binding molecules of the present invention will be mono-specific so as to possess the ability to bind to only a single epitope of CD16 and only a single epitope of a Disease Antigen.

Alternatively, such molecules may be multi-specific, i.e., capable of binding one, two, three or four total epitopes, which may be apportioned in any manner to bind one, two or three epitope(s) of CD16 (which two or three CD16 epitopes may be the same or different) and three, two or one epitope(s) of one or more Disease Antigen(s).

Thus, where such molecules are capable of immunospecifically binding to only a single Disease Antigen, they may be capable of immunospecifically binding to only one CD16 epitope and to one, two or three epitope(s) of the Disease Antigen (which two Disease Antigen epitopes may be the same or different, and which three epitopes may be the same, or may be different, or may be two epitopes that are the same and one epitope that is different), or they may be capable of immunospecifically binding to only two CD16 epitopes (which two epitopes may be the same or different) and one or two epitope(s) of the Disease Antigen (which two Disease Antigen epitopes may be the same or different), or they may be capable of immunospecifically binding to three CD16 epitopes (which three epitopes may be the same, or may be different or may be two epitopes that are the same and one epitope that is different) and 1 epitope of the Disease Antigen.

Similarly, where such molecules are capable of immunospecifically binding to two different Disease Antigens (e.g., a First Disease Antigen and a Second Disease Antigen), they may be capable of immunospecifically binding to only one CD16 epitope and to one or two epitope(s) of the First Disease Antigen (which two First Disease Antigen epitopes may be the same or different) and two or one epitope(s) of the Second Disease Antigen (which two Second Disease Antigen epitopes may be the same or different), or they may be capable of immunospecifically binding to only two CD16 epitopes (which two epitopes may be the same or different) and one epitope of the First Disease Antigen and one epitope of the Second Disease Antigen.

Similarly, such molecules may be capable of immunospecifically binding to three different Disease Antigens (e.g., a First Disease Antigen, a Second Disease Antigen and a Third Disease Antigen) and only one CD16 epitope.

Thus, for example, such molecules may bind:
(1) a single epitope of CD16 and a single epitope of a Disease Antigen that is arrayed on the surface of the target cell;
(2) a single epitope of CD16 and two epitopes of a Disease Antigen that is arrayed on the surface of the target cell
(3) a single epitope of CD16 and three epitopes of a Disease Antigen that is arrayed on the surface of the target cell;
(4) a single epitope of CD16, one epitope of a First Disease Antigen that is arrayed on the surface of the target cell, and one epitope of a Second Disease Antigen that is arrayed on the surface of the target cell;
(5) a single epitope of CD16, two epitopes of a First Disease Antigen that is arrayed on the surface of the target cell, and one epitope of a Second Disease Antigen that is arrayed on the surface of the target cell;
(6) two epitopes of CD16 and a single epitope of a Disease Antigen that is arrayed on the surface of the target cell;
(7) two epitopes of CD16 and two epitopes of a Disease Antigen that is arrayed on the surface of the target cell;
(8) two epitopes of CD16 and one epitope of a First Disease Antigen that is arrayed on the surface of the target cell and one epitope of a Second Disease Antigen that is arrayed on the surface of the target cell;
(9) three epitopes of CD16 and one epitope of a Disease Antigen that is arrayed on the surface of the target cell;
in all cases in which binding is to more than one epitope of CD16 or a Disease Antigen, such epitopes may be the same or may be different or may be the same as one such epitope and different from another such epitope.

Table 6 illustrates possible combination binding specificities of exemplary molecules of the invention.

TABLE 6

Number of Epitopes Recognized by Exemplary CD16 × DA Binding Molecules of the Invention Possessing Two, Three or Four Epitope Binding Domains That Are Capable of Mediating the Redirected Killing of a Target Cell

| Total Number of Binding Domains | Number of CD16 Epitope(s) | Number of Epitopes of 1st Disease Antigen | Number of Epitopes of 2nd Disease Antigen | Number of Epitopes of 3rd Disease Antigen | Number of Epitopes of Non-CD16 Cell Surface Molecule |
|---|---|---|---|---|---|
| 2 | 1 | 1 | 0 | 0 | 0 |
| 3 | 1 | 1 | 1 | 0 | 0 |
| 3 | 1 | 1 | 0 | 0 | 1 |
| 3 | 1 | 2 | 0 | 0 | 0 |
| 3 | 2 | 1 | 0 | 0 | 0 |
| 4 | 1 | 1 | 1 | 0 | 1 |
| 4 | 1 | 1 | 1 | 1 | 0 |
| 4 | 1 | 2 | 0 | 0 | 1 |
| 4 | 1 | 2 | 1 | 0 | 0 |
| 4 | 2 | 1 | 1 | 0 | 0 |
| 4 | 2 | 1 | 0 | 0 | 1 |

By forming more complex molecules, one may obtain CD16-binding molecules that are capable of binding one or more Disease Antigens and that possess more than four epitope binding domains. Thus, no limitation is placed on the nature of epitopes or additional epitopes that may be bound by the molecules of the present invention other than that such additional binding capability does not prevent the molecule or Binding Domain thereof that is capable of binding to an epitope of CD16 from such binding and does not prevent the molecule or Binding Domain thereof that is capable of binding to an epitope of a Disease Antigen from such binding. Thus, the CD16 Binding molecules of the present invention may possess Epitope Binding Domains alternative or additional Epitope Binding Domains. As an example, the invention contemplates a binding molecule that comprises a First Epitope Binding Domain capable of immunospecifically binding an epitope of CD16 and a Second Epitope Binding Domain that is capable of immunospecifically binding an epitope of a Disease Antigen that is arrayed on the surface of such target cell and a Third Epitope Binding Domain capable of immunospecifically binding a different cell surface molecule, such as a non-CD16 cell surface molecule of a Natural Killer cell.

V. Exemplary Binding Molecules

The present invention is directed molecules (e.g., an antibody, a diabody, an scFv, an antibody, a TandAb, etc.) capable of binding human CD16 by virtue of their possession of a CD16 Binding Domain. The present invention is particularly directed to such CD-16 Binding Molecules that are CD16×DA Binding Molecules. Listed below are exemplary antibodies that may be used to produce the binding molecules and combination therapy of the present invention.

A. Exemplary Anti-Human CD16 Antibodies

1. CD16-M1 and CD16-M2 and Their Humanized Derivatives hCD16-M1 and hCD16-M2

The present invention provides murine anti-human CD16 monoclonal antibodies: CD16-M1 and CD16-M2, and their humanized derivatives: hCD16-M1 and hCD16-M2, which are novel, high affinity anti-human CD16 monoclonal antibodies that bind well to both the CD16 158F allotype and the CD16 158V allotype, and that bind CD16 at a site that does not block CD16-IgG binding. Such antibodies are particularly preferred for the purposes of the present invention since they can be readily employed in a patient population irrespective of its 158F/158V CD16A polymorphisms.

(a) Anti-Human CD16 Monoclonal Antibody CD16-M1

The amino acid sequence of the VH Domain of murine anti-human CD16 monoclonal antibody CD16-M1 (SEQ ID NO:64) is shown below (CDR$_H$ residues are shown underlined):

```
EVKLVESGGT LVKPGGSLKL SCAASGFTFN NYGMSWVRQT

PEKRLEWVAT ISGGGSYTFY PDSVKGRFTI SRDNAKNSLY

LQMSSLRSED TALYYCIRQS ARAPEPYWGQ GTLVTVSS
```

The amino acid sequence of the VL Domain of murine anti-human CD16 monoclonal antibody CD16-M1 (SEQ ID NO:65) is shown below (CDR$_L$ residues are shown underlined):

```
DIVMTQSQKF MSTSVGDRVS VTCKASQNVG THVAWYQQKS

GQSPKSLLYS ASYRYSGVPD RFSGSGSGTD FTLTISNVQS

EDLAEYFCQQ YKSYPLTFGA GTKLELK
```

The CDRs of anti-human CD16 monoclonal antibody CD16-M1 are shown in Table 7.

TABLE 7

| CDRs of Anti-Human CD16-Monoclonal Antibody CD16-M1 | | |
|---|---|---|
| CDR | Sequence | SEQ ID NO |
| CDR$_H$1 | NYGMS | SEQ ID NO: 66 |
| CDR$_H$2 | TISGGGSYTFYPDSVKG | SEQ ID NO: 67 |
| CDR$_H$3 | QSARAPEPY | SEQ ID NO: 68 |
| CDR$_L$1 | KASQNVGTHVA | SEQ ID NO: 69 |
| CDR$_L$2 | SASYRYS | SEQ ID NO: 70 |
| CDR$_L$3 | QQYKSYPLT | SEQ ID NO: 71 | hCD16-M1 is a humanized derivative of murine anti-human CD16 monoclonal antibody CD16-M1. The amino acid sequence of the VH Domain of hCD16-M1 (SEQ ID NO:72) is shown below (CDR$_H$ residues are shown underlined):

```
EVQLVESGGG LVKPGGSLRL SCAASGFTFS NYGMSWVRQA

PGKGLEWVAT ISGGGSYTFY PDSVKGRFTI SRDNAKNSLY

LQMNSLRTED TALYYCVRQS ARAPEPYWGQ GTLVTVSS
```

The amino acid sequence of the VL Domain of hCD16-M1 (SEQ ID NO:73) is shown below (CDR$_L$ residues are shown underlined):

```
DIQMTQSPSF LSASVGDRVT ITCRASQNVG THVAWYQQKP

GKAPKSLLYS ASYRYSGVPS RFSGSGSGTD FTLTISSLQS

EDIATYYCQQ YKSYPLTFGQ GTKLEIK
``` hCD16-M1A is an optimized derivative of the humanized anti-human CD16 monoclonal antibody hCD16-M1. hCD16-M1A comprises the VL Domain of hCD16-M1 (SEQ ID NO:73) and an optimized VH Domain comprising mutations in CDR$_H$3. The amino acid sequence of the optimized VH Domain of hCD16-M1A (SEQ ID NO:58) is shown below (the mutated CDR$_H$3 residues are shown underlined):

```
EVQLVESGGG LVKPGGSLRL SCAASGFTFS NYGMSWVRQA

PGKGLEWVAT ISGGGSYTFY PDSVKGRFTI SRDNAKNSLY

LQMNSLRTED TALYYCVRQS ANSPVPYWGQ GTLVTVSS
``` hCD16-M1B is an optimized derivative of the humanized anti-human CD16 monoclonal antibody hCD16-M1. hCD16-M1B comprises the VH Domain of hCD16-M1 (SEQ ID NO:72) and an optimized VL Domain comprising mutations in CDR$_L$3. The amino acid sequence of the optimized VL Domain of hCD16-M1B (SEQ ID NO:59) is shown below (the mutated CDR$_L$3 residues are shown underlined):

```
DIQMTQSPSF LSASVGDRVT ITCRASQNVG THVAWYQQKP

GKAPKSLLYS ASYRYSGVPS RFSGSGSGTD FTLTISSLQS

EDIATYYCQD YTNYPLTFGQ GTKLEIK
``` hCD16-M1AB is an optimized derivative of the humanized anti-human CD16 monoclonal antibody hCD16-M1. hCD16-M1AB comprises the optimized VH Domain of hCD16-M1A (SEQ ID NO:58) and the optimized VL Domain of hCD16-M1B (SEQ ID NO:59).

The CDRs of humanized anti-human CD16 monoclonal antibody hCD16-M1 and the optimized anti-human CD16 monoclonal antibodies hCD16-M1A, hCD16-M1B, hCD16-M1AB are shown in Table 8.

TABLE 8

| CDRs of Anti-Human CD16-Monoclonal Antibody hCD16-M1 | | |
|---|---|---|
| CDR | Sequence | SEQ ID NO |
| CDR$_H$1 | NYGMS | SEQ ID NO: 66 |
| CDR$_H$2 | TISGGGSYTFYPDSVKG | SEQ ID NO: 67 |
| CDR$_H$3 | QSARAPEPY | SEQ ID NO: 68 |
| CDR$_L$1 | RASQNVGTHVA | SEQ ID NO: 74 |
| CDR$_L$2 | SASYRYS | SEQ ID NO: 70 |
| CDR$_L$3 | QQYKSYPLT | SEQ ID NO: 71 |
| hCD16-M1A | | |
| CDR$_H$1 | NYGMS | SEQ ID NO: 66 |
| CDR$_H$2 | TISGGGSYTFYPDSVKG | SEQ ID NO: 67 |
| CDR$_H$3 | QSANSPVPY | SEQ ID NO: 60 |

TABLE 8-continued

| CDR | Sequence | SEQ ID NO |
|---|---|---|
| CDRs of Anti-Human CD16-Monoclonal Antibody hCD16-M1 | | |
| CDR$_L$1 | RASQNVGTHVA | SEQ ID NO: 74 |
| CDR$_L$2 | SASYRYS | SEQ ID NO: 70 |
| CDR$_L$3 | QQYKSYPLT | SEQ ID NO: 71 |
| hCD16-M1B | | |
| CDR$_H$1 | NYGMS | SEQ ID NO: 66 |
| CDR$_H$2 | TISGGGSYTFYPDSVKG | SEQ ID NO: 67 |
| CDR$_H$3 | QSARAPEPY | SEQ ID NO: 68 |
| CDR$_L$1 | RASQNVGTHVA | SEQ ID NO: 74 |
| CDR$_L$2 | SASYRYS | SEQ ID NO: 70 |
| CDR$_L$3 | QDYTNYPLT | SEQ ID NO: 61 |
| hCD16-M1AB | | |
| CDR$_H$1 | NYGMS | SEQ ID NO: 66 |
| CDR$_H$2 | TISGGGSYTFYPDSVKG | SEQ ID NO: 67 |
| CDR$_H$3 | QSANSPVPY | SEQ ID NO: 60 |
| CDR$_L$1 | RASQNVGTHVA | SEQ ID NO: 74 |
| CDR$_L$2 | SASYRYS | SEQ ID NO: 70 |
| CDR$_L$3 | QDYTNYPLT | SEQ ID NO: 61 |

As will be recognized, CDR$_L$1 of hCD16-M1, hCD16-M1A, hCD16-M1B, and hCD16-M1AB (RASQNVGTHVA; SEQ ID NO:74) differs from CDR$_L$1 of CD16-M1 (KASQNVGTHVA; SEQ ID NO:69) in its first residue. Either CDR$_L$1 may be employed interchangeably, and the present invention encompasses humanized, and optimized CD16 Binding Molecules that comprise a CD16 Epitope Binding Domain having the amino acid sequence of 1, 2 or 3 of the following CDR$_H$s, and/or 1, 2 or 3 of the such CDR$_L$s.

(b) Anti-Human CD16 Monoclonal Antibody CD16-M2

The amino acid sequence of the VH Domain of murine anti-human CD16 monoclonal antibody CD16-M2 (SEQ ID NO:75) is shown below (CDR$_H$ residues are shown underlined):

```
EVQLQQSGPE LVKPGASVKM SCKASGYTFT SSAMHWVKKN
PGQGLEWIGY INHYNDGIKY NERFKGKATL TSDKSSSTAY
MELSSLTSED SAVYYCATGY RYASWFASWG QGTLVTVSS
```

The amino acid sequence of the VL Domain of murine anti-human CD16 monoclonal antibody CD16-M2 (SEQ ID NO:76) is shown below (CDR$_L$ residues are shown underlined):

```
DILLTQSPAI LSVSPGERVS FSCRASQNIG TSIHWYQQRT
DGSPRLLIKS VSESISGIPS RFSGSGSGTD FTLTINGVES
GDISDYYCQQ SNSWPLTFGA GTKLELK
```

The CDRs of anti-human CD16 monoclonal antibody CD16-M2 are shown in Table 9:

TABLE 9

| CDR | Sequence | SEQ ID NO |
|---|---|---|
| CDRs of Anti-Human CD16 Monoclonal Antibody CD16-M2 | | |
| CDR$_H$1 | SSAMH | SEQ ID NO: 77 |
| CDR$_H$2 | YINHYNDGIKYNERFKG | SEQ ID NO: 78 |
| CDR$_H$3 | GYRYASWFAS | SEQ ID NO: 79 |
| CDR$_L$1 | RASQNIGTSIH | SEQ ID NO: 80 |
| CDR$_L$2 | SVSESIS | SEQ ID NO: 81 |
| CDR$_L$3 | QQSNSWPLT | SEQ ID NO: 82 | hCD16-M2 is a humanized derivative of murine anti-human CD16 monoclonal antibody CD16-M2. Humanization resulted in two suitable VH Domains (hCD16-M2 VH1 and hCD16-M2 VH2), either of which may be employed with the obtained humanized VL Domain (hCD16-M2 VL1).

The amino acid sequence of VH Domain hCD16-M2 VH1 (SEQ ID NO:83) is shown below (CDR$_H$ residues are shown underlined):

```
QVQLVQSGAE VKKPGASVKV SCKASGYTFT
SSAMHWVRQA PGQGLEWMGY INHYNDGIKY
NERFKGRVTI TADKSTSTAY MELSSLRSED
TAVYYCATGY RYASWFASWG QGTLVTVSS
```

The amino acid sequence of VH Domain hCD16-M2 VH2 (SEQ ID NO:84) is shown below (CDR$_H$ residues are shown underlined):

```
QVQLVQSGAE VKKPGASVKV SCKASGYTFT
SSAMHWVRQA PGQGLEWMGY INHYNDGIKY
NERFKGRVTI TADKSTSTAY MELSSLRSED
TAVYYCARGY RYASWFASWG QGTLVTVSS
```

As will be recognized, the amino acid sequence of hCD16-M2 VH1 (SEQ ID NO:83) differs from that of hCD16-M2 VH2 (SEQ ID NO:84) in possessing a T98R substitution in the residue that immediately precedes CDR$_H$3 (shown boxed above).

The amino acid sequence of the VL Domain hCD16-M2 VL1 (SEQ ID NO:85) is shown below (CDR$_L$ residues are shown underlined):

```
EIVLTQSPAT LSVSPGERAT LSCRASQNIG

TSIHWYQQKP DQSPKLLIKS VSESISGVPS

RFSGSGSGTD FTLTINSLEA EDFATYYCQQ

SNSWPLTFGQ GTKLEIK
```

The CDRs of humanized anti-human CD16 monoclonal antibody hCD16-M2 are shown in Table 10.

TABLE 10

| \multicolumn{3}{c}{CDRs of Anti-Human CD16 Monoclonal Antibody hCD16-M2} | | |
|---|---|---|
| CDR | Sequence | SEQ ID NO |
| CDR$_H$1 | SSAMH | SEQ ID NO: 77 |
| CDR$_H$2 | YINHYNDGIKYNERFKG | SEQ ID NO: 78 |
| CDR$_H$3 | GYRYASWFAS | SEQ ID NO: 79 |
| CDR$_L$1 | RASQNIGTSIH | SEQ ID NO: 80 |
| CDR$_L$2 | SVSESIS | SEQ ID NO: 81 |
| CDR$_L$3 | QQSNSWPLT | SEQ ID NO: 82 |

B. Exemplary Antibodies that Bind to the Cell Surface of Effector Cells

The CD16×DA Binding Molecules of the present invention, and particularly the trispecific CD16×DA Binding Molecules of the present invention may comprise a binding site for a non-CD16 cell surface molecule of an effector cell. As used herein, the term "effector cell" denotes a cell that directly or indirectly mediates the killing of target cells (e.g., foreign cells, infected cells or cancer cells). Examples of effector cells include helper T Cells, cytotoxic T Cells, Natural Killer (NK) cells, plasma cells (antibody-secreting B cells), macrophages and granulocytes. Preferred cell surface molecules of such cells include CD2, CD3, CD8, CD16, TCR, and the NKG2D receptor. Accordingly, molecules capable of immunospecifically binding an epitope of such molecules, or to other effector cell surface molecules may be used in accordance with the principles of the present invention. Exemplary antibodies, whose VH and VL Domains may be used to construct molecules capable of mediating the redirected killing of a target cell are provided below.

1. Exemplary Anti-NKG2D Antibodies

A preferred non-CD16 cell surface molecule of a Natural Killer effector cell is the NKG2D receptor. The NKG2D receptor is expressed on all human (and other mammalian) Natural Killer cells (Bauer, S. et al. (1999) "*Activation Of NK Cells And T Cells By NKG2D, A Receptor For Stress-Inducible MICA*," Science 285(5428):727-729; Jamieson, A. M. et al. (2002) "*The Role Of The NKG2D Immunoreceptor In Immune Cell Activation And Natural Killing*," Immunity 17(1):19-29) as well as on all CD8$^+$ T cells (Groh, V. et al. (2001) "*Costimulation Of CD8αβ T Cells By NKG2D Via Engagement By MIC Induced On Virus-Infected Cells*," Nat. Immunol. 2(3):255-260; Jamieson, A. M. et al. (2002) "*The Role Of The NKG2D Immunoreceptor In Immune Cell Activation And Natural Killing*," Immunity 17(1):19-29). Such binding ligands, and particularly those which are not expressed on normal cells, include the histocompatibility 60 (H60) molecule, the product of the retinoic acid early inducible gene-1 (RAE-1), and the murine UL16-binding proteinlike transcript 1 (MULTI) (Raulet D. H. (2003) "*Roles Of The NKG2D Immunoreceptor And Its Ligands*," Nature Rev. Immunol. 3:781-790; Coudert, J. D. et al. (2005) "*Altered NKG2D Function In NK Cells Induced By Chronic Exposure To Altered NKG2D Ligand-Expressing Tumor Cells*," Blood 106:1711-1717). Molecules that specifically bind to the NKG2D Receptor include the anti-NKG2D antibodies "KYK-1.0" and "KYK-2.0" (Kwong, K Y et al. (2008) "*Generation, Affinity Maturation, And Characterization Of A Human Anti-Human NKG2D Monoclonal Antibody With Dual Antagonistic And Agonistic Activity*," J. Mol. Biol. 384:1143-1156).

The amino acid sequence of the VH Domain of KYK-1.0 (SEQ ID NO:86) is shown below (CDR$_H$ residues are shown underlined):

```
EVQLVESGGG VVQPGGSLRL SCAASGFTFS

SYGMHWVRQA PGKGLEWVAF IRYDGSNKYY

ADSVKGRFTI SRDNSKNTKY LQMNSLRAED

TAVYYCAKDR FGYYLDYWGQ GTLVTVSS
```

The amino acid sequence of the VL Domain of KYK-1.0 (SEQ ID NO:87) is shown below (CDR$_L$ residues are shown underlined):

```
QPVLTQPSSV SVAPGETARI PCGGDDIETK

SVHWYQQKPG QAPVLVIYDD DDRPSGIPER

FFGSNSGNTA TLSISRVEAG DEADYYCQVW

DDNNDEWVFG GGTQLTVL
```

The amino acid sequence of a VH Domain of KYK-2.0 (SEQ ID NO:88) is shown below (CDR$_H$ residues are shown underlined):

```
QVQLVESGGG LVKPGGSLRL SCAASGFTFS

SYGMHWVRQA PGKGLEWVAF IRYDGSNKYY

ADSVKGRFTI SRDNSKNTLY LQMNSLRAED

TAVYYCAKDR GLGDGTYFDY WGQGTTVTVS

S
```

The amino acid sequence of a VL Domain of KYK-2.0 (SEQ ID NO:89) is shown below (CDR$_L$ residues are shown underlined):

```
QSALTQPASV SGSPGQSITI SCSGSSSNIG

NNAVNWYQQL PGKAPKLLIY YDDLLPSGVS

DRFSGSKSGT SAFLAISGLQ SEDEADYYCA

AWDDSLNGPV FGGGTKLTVL
```

Other exemplary antibodies that bind to the cell surface of a Natural Killer cell include antibodies: A1, AC2, EPR3678 (2), EPR20461, EPR20627 and IMG17B5F11 (which bind CD39); TB01, HNK-1/Leu-7 and NK1 (which bind CD57);

FN50 (which binds CD69); 5B5, B-L2, TS82b and C33 (which bind CD82); 3B3, B199.2 and EP7169 (which bind CD161); 17D9 (which binds CLEC1B); 2F9 (which binds KIR2DL1); EPR8825 (which binds KIR2DL2); mAb 33 (which binds KIR2DL4); 11E3, 17B4, EPR4392(2), EPR20261 and EPR 20627 (which bind Lymphocyte Activation Gene 3); A10, C7, CX5, 1D11 and MM0489-10R27 (which bind NKG2D); BMK13 (which binds PRG2); EPR9916 (which binds SLAMF6); etc. Antibodies capable of binding to each of such exemplary non-CD16 cell surface molecule are commercially available from Abcam plc and other sources, and may be readily adapted to the purposes of the present invention.

2. Exemplary Anti-CD2 Antibodies

In one embodiment, the molecules of the present invention that are capable of mediating the redirected killing of a target cell will bind an effector cell by immunospecifically binding an epitope of CD2 present on the surface of such effector cell. Molecules that specifically bind CD2 include the anti-CD2 antibody "CD2 mAb Lo-CD2a."

The amino acid sequence of the VH Domain of CD2 mAb Lo-CD2a (ATCC Accession No: 11423); SEQ ID NO:90) is shown below (CDR$_H$ residues are shown underlined):

```
EVQLQQSGPE LQRPGASVKL SCKASGYIFT

EYYMYWVKQR PKQGLELVGR IDPEDGSIDY

VEKFKKKATL TADTSSNTAY MQLSSLTSED

TATYFCARGK FNYRFAYWGQ GTLVTVSS
```

The amino acid sequence of the VL Domain of CD2 mAb Lo-CD2a (ATCC Accession No: 11423; SEQ ID NO:91) is shown below (CDR$_L$ residues are shown underlined):

```
DVVLTQTPPT LLATIGQSVS ISCRSSQSLL

HSSGNTYLNW LLQRTGQSPQ PLIYLVSKLE

SGVPNRFSGS GSGTDFTLKI SGVEAEDLGV

YYCMQFTHYP YTFGAGTKLE LK
```

3. Exemplary Anti-CD8 Antibodies

In one embodiment, the molecules of the present invention that are capable of mediating the redirected killing of a target cell will bind an effector cell by immunospecifically binding an epitope of CD8 present on the surface of such effector cell. Antibodies that specifically bind CD8 include the anti-CD8 antibodies "OKT8" and "TRX2."

The amino acid sequence of the VH Domain of OKT8 (SEQ ID NO:92) is shown below (CDR$_H$ residues are shown underlined):

```
QVQLLESGPE LLKPGASVKM SCKASGYTFT

DYNMHWVKQS HGKSLEWIGY IYPYTGGTGY

NQKFKNKATL TVDSSSSTAY MELRSLTSED

SAVYYCARNF RYTYWYFDVW GQGTTVTVSS
```

The amino acid sequence of the VL Domain of OKT8 (SEQ ID NO:93) is shown below (CDR$_L$ residues are shown underlined):

```
DIVMTQSPAS LAVSLGQRAT ISCRASESVD

SYDNSLMHWY QQKPGQPPKV LIYLASNLES

GVPARFSGSG SRTDFTLTID PVEADDAATY

YCQQNNEDPY TFGGGTKLEI KR
```

The amino acid sequence of the VH Domain of TRX2 (SEQ ID NO:94) is shown below (CDR$_H$ residues are shown underlined):

```
QVQLVESGGG VVQPGRSLRL SCAASGFTFS

DFGMNWVRQA PGKGLEWVAL IYYDGSNKFY

ADSVKGRFTI SRDNSKNTLY LQMNSLRAED

TAVYYCAKPH YDGYYHFFDS WGQGTLVTVS

S
```

The amino acid sequence of the VL Domain of TRX2 (SEQ ID NO:95) is shown below (CDR$_L$ residues are shown underlined):

```
DIQMTQSPSS LSASVGDRVT ITCKGSQDIN

NYLAWYQQKP GKAPKLLIYN TDILHTGVPS

RFSGSGSGTD FTFTISSLQP EDIATYYCYQ

YNNGYTFGQG TKVEIK
```

VI. Exemplary Disease Antigens

The Disease Antigens of the present invention comprise cell surface antigens that are characteristic of a cancer cell ("Cancer Antigens") as well as cell surface antigens that are characteristic of a pathogen cell or a cell infected by a pathogen (Pathogen-Associated Antigens").

A. Exemplary Cancer Antigens Arrayed on the Surface of Cancer Cells

As used herein, the term "Cancer Antigen" denotes an antigen that is characteristically expressed on the surface of a cancer cell, and that may thus be treated with an Antibody-Based Molecule or an Immunomodulatory Molecule. Examples of Cancer Antigens include, but are not limited to: 19.9 as found in colon cancer, gastric cancer mucins; 4.2; A33 (a colorectal carcinoma antigen; Almqvist, Y. (2006) "*In vitro and in vivo Characterization of 177Lu-huA33: A Radioimmunoconjugate Against Colorectal Cancer,*" Nucl. Med. Biol. 33(8):991-998); ADAM-9 (United States Patent Publication No. 2006/0172350; PCT Publication No. WO 06/084075); AH6 as found in gastric cancer; ALCAM (PCT Publication No. WO 03/093443); APO-1 (malignant human lymphocyte antigen) (Trauth, B. C. et al. (1989) "*Monoclonal Antibody-Mediated Tumor Regression By Induction Of Apoptosis,*" Science 245:301-304); B1 (Egloff, A. M. et al. (2006) "*Cyclin B1 And Other Cyclins As Tumor Antigens In Immunosurveillance And Immunotherapy Of Cancer,*" Cancer Res. 66(1):6-9); B7-H3 (Collins, M. et al. (2005) "*The B7 Family Of Immune-Regulatory Ligands,*" Genome Biol. 6:223.1-223.7). Chapoval, A. et al. (2001) "*B7-H3: A Costimulatory Molecule For T Cell Activation and IFN-γ Production,*" Nature Immunol. 2:269-274; Sun, M. et al.

(2002) "Characterization of Mouse and Human B7-H3 Genes," J. Immunol. 168:6294-6297); BAGE (Bodey, B. (2002) "Cancer-Testis Antigens: Promising Targets For Antigen Directed Antineoplastic Immunotherapy," Expert Opin. Biol. Ther. 2(6):577-584); beta-catenin (Prange W. et al. (2003) "Beta-Catenin Accumulation In The Progression Of Human Hepatocarcinogenesis Correlates With Loss Of E-Cadherin And Accumulation Of P53, But Not With Expression Of Conventional WNT-1 Target Genes," J. Pathol. 201(2):250-259); blood group $ALe^b/Le^y$ as found in colonic adenocarcinoma; Burkitt's lymphoma antigen-38.13; C14 as found in colonic adenocarcinoma; CA125 (ovarian carcinoma antigen) (Bast, R. C. Jr. et al. (2005) "New Tumor Markers: CA125 And Beyond," Int. J. Gynecol. Cancer 15(Suppl 3):274-281; Yu et al. (1991) "Coexpression Of Different Antigenic Markers On Moieties That Bear CA 125 Determinants," Cancer Res. 51(2):468-475); Carboxypeptidase M (United States Patent Publication No. 2006/0166291); CD5 (Calin, G. A. et al. (2006) "Genomics Of Chronic Lymphocytic Leukemia MicroRNAs As New Players With Clinical Significance," Semin. Oncol. 33(2):167-173; CD19 (Ghetie et al. (1994) "Anti-CD19 Inhibits The Growth Of Human B-Cell Tumor Lines In Vitro And Of Daudi Cells In SCID Mice By Inducing Cell Cycle Arrest," Blood 83:1329-1336; Troussard, X. et al. 1998 Hematol Cell Ther. 40(4):139-48; CD20 (Reff et al. (1994) "Depletion Of B Cells In Vivo By A Chimeric Mouse Human Monoclonal Antibody To CD20," Blood 83:435-445; Thomas, D. A. et al. 2006 Hematol Oncol Clin North Am. 20(5):1125-36); CD22 (Kreitman, R. J. (2006) "Immunotoxins For Targeted Cancer Therapy," AAPS J. 8(3):E532-51); CD23 (Rosati, S. et al. (2005) "Chronic Lymphocytic Leukaemia: A Review Of The Immuno-Architecture," Curr. Top. Microbiol. Immunol. 294:91-107); CD25 (Troussard, X. et al. (1998) "Hairy Cell Leukemia. What Is New Forty Years After The First Description?" Hematol. Cell. Ther. 40(4):139-148); CD27 (Bataille, R. (2006) "The Phenotype Of Normal, Reactive And Malignant Plasma Cells. Identification Of "Many And Multiple Myelomas" And Of New Targets For Myeloma Therapy," Haematologica 91(9):1234-1240); CD28 (Bataille, R. (2006) "The Phenotype Of Normal, Reactive And Malignant Plasma Cells. Identification Of "Many And Multiple Myelomas" And Of New Targets For Myeloma Therapy," Haematologica 91(9):1234-1240); CD33 (Sgouros et al. (1993) "Modeling And Dosimetry Of Monoclonal Antibody M195 (Anti-CD33) In Acute Myelogenous Leukemia," J. Nucl. Med. 34:422-430); CD36 (Ge, Y. (2005) "CD36: A Multiligand Molecule," Lab Hematol. 11(1):31-7); CD40/CD154 (Messmer, D. et al. (2005) "CD154 Gene Therapy For Human B-Cell Malignancies," Ann. N. Y. Acad. Sci. 1062: 51-60); CD45 (Jurcic, J. G. (2005) "Immunotherapy For Acute Myeloid Leukemia," Curr. Oncol. Rep. 7(5):339-346); CD56 (Bataille, R. (2006) "The Phenotype Of Normal, Reactive And Malignant Plasma Cells. Identification Of "Many And Multiple Myelomas" And Of New Targets For Myeloma Therapy," Haematologica 91(9):1234-1240); CD46 (U.S. Pat. No. 7,148,038; PCT Publication No. WO 03/032814); CD52 (Eketorp, S. S. et al. (2014) "Alemtuzumab (Anti-CD52 Monoclonal Antibody) As Single-Agent Therapy In Patients With Relapsed/Refractory Chronic Lymphocytic Leukaemia (CLL)-A Single Region Experience On Consecutive Patients," Ann Hematol. 93(10):1725-1733; Suresh, T. et al. (2014) "New Antibody Approaches To Lymphoma Therapy," J. Hematol. Oncol. 7:58; Hoelzer, D. (2013) "Targeted Therapy With Monoclonal Antibodies In Acute Lymphoblastic Leukemia," Curr. Opin. Oncol. 25(6):701-706); CD56 (Bataille, R. (2006) "The Phenotype Of Normal, Reactive And Malignant Plasma Cells. Identification Of "Many And Multiple Myelomas" And Of New Targets For Myeloma Therapy," Haematologica 91(9):1234-1240); CD79a/CD79b (Troussard, X. et al. (1998) "Hairy Cell Leukemia. What Is New Forty Years After The First Description?" Hematol. Cell. Ther. 40(4): 139-148; Chu, P. G. et al. (2001) "CD79: A Review," Appl. Immunohistochem. Mol. Morphol. 9(2):97-106); CD103 (Troussard, X. et al. (1998) "Hairy Cell Leukemia. What Is New Forty Years After The First Description?" Hematol. Cell. Ther. 40(4):139-148); CD317 (Kawai, S. et al. (2008) "Interferon-A Enhances CD317 Expression And The Antitumor Activity Of Anti-CD317 Monoclonal Antibody In Renal Cell Carcinoma Xenograft Models," Cancer Science 99(12):2461-2466; Wang, W. et al. (2009) HM1.24 (CD317) Is A Novel Target Against Lung Cancer For Immunotherapy Using Anti-HM1.24 Antibody," Cancer Immunology, Immunotherapy 58(6):967-976; Wang, W. et al. (2009) "Chimeric And Humanized Anti-HM1.24 Antibodies Mediate Antibody-Dependent Cellular Cytotoxicity Against Lung Cancer Cells. Lung Cancer," 63(1):23-31; Sayeed, A. et al. (2013) "Aberrant Regulation Of The BST2 (Tetherin) Promoter Enhances Cell Proliferation And Apoptosis Evasion In High Grade Breast Cancer Cells," PLoS ONE 8(6)e67191, pp. 1-10); CDK4 (Lee, Y. M. et al. (2006) "Targeting Cyclins And Cyclin-Dependent Kinases In Cancer: Lessons From Mice, Hopes For Therapeutic Applications In Human," Cell Cycle 5(18):2110-2114); CEA (carcinoembryonic antigen; Foon et al. (1995) "Immune Response To The Carcinoembryonic Antigen In Patients Treated With An Anti-Idiotype Antibody Vaccine," J. Clin. Invest. 96(1):334-42); Mathelin, C. (2006) "Circulating Proteinic Biomarkers And Breast Cancer," Gynecol. Obstet. Fertil. 34(7-8):638-646; Tellez-Avila, F. I. et al. (2005) "The Carcinoembryonic Antigen: Apropos Of An Old Friend," Rev. Invest. Clin. 57(6):814-819); CEACAM5/CEACAM6 (Zheng, C. et al. (2011) "A Novel Anti-CEACAM5 Monoclonal Antibody, CC4, Suppresses Colorectal Tumor Growth and Enhances NK Cells-Mediated Tumor Immunity," PLoS One 6(6):e21146, pp. 1-11); CO17-1A (Ragnhammar et al. (1993) "Effect Of Monoclonal Antibody 17-1A And GM-CSF In Patients With Advanced Colorectal Carcinoma—Long-Lasting, Complete Remissions Can Be Induced," Int. J. Cancer 53:751-758); CO-43 (blood group $Le^b$); CO-514 (blood group $Le^a$) as found in adenocarcinoma; CTA-1; CTLA-4 (Peggs, K. S. et al. (2006) "Principles And Use Of Anti-CTLA4 Antibody In Human Cancer Immunotherapy," Curr. Opin. Immunol. 18(2):206-13); Cytokeratin 8 (PCT Publication No. WO 03/024191); D1.1; $D_1$56-22; DR5 (Abdulghani, J. et al. (2010) "TRAIL Receptor Signaling And Therapeutics," Expert Opin. Ther. Targets 14(10): 1091-1108; Andera, L. (2009) "Signaling Activated By The Death Receptors Of The TNFR Family," Biomed. Pap. Med. Fac. Univ. Palacky Olomouc Czech. Repub. 153(3): 173-180; Carlo-Stella, C. et al. (2007) "Targeting TRAIL Agonistic Receptors for Cancer Therapy," Clin, Cancer 13(8):2313-2317; Chaudhari, B. R. et al. (2006) "Following the TRAIL to Apoptosis," Immunologic Res. 35(3):249-262); $E_1$ series (blood group B) as found in pancreatic cancer; EGFR (Epidermal Growth Factor Receptor; Adenis, A. et al. (2003) "Inhibitors Of Epidermal Growth Factor Receptor And Colorectal Cancer," Bull. Cancer. 90 Spec No: 5228-5232); Ephrin receptors (and in particular EphA2 (U.S. Pat. No. 7,569,672; PCT Publication No. WO 06/084226); Erb (ErbB1; ErbB3; ErbB4; Zhou, H. et al. (2002) "Lung Tumorigenesis Associated With Erb-B-2 And Erb-B-3 Overexpression In Human Erb-B-3 Transgenic Mice Is Enhanced By Methylnitrosourea," Oncogene 21(57):8732-8740; Rimon, E. et al. (2004) "Gonadotropin Induced Gene Regulation In Human Granulosa Cells Obtained From IVF Patients: Modulation Of Genes Coding For Growth Factors And Their Receptors And Genes Involved In Cancer And Other Diseases," Int. J. Oncol. 24(5):1325-1338); GAGE (GAGE-1; GAGE-2; Akcakanat, A. et al. (2006) "Heterogeneous Expression Of GAGE, NY-ESO-1, MAGE-A and SSX Proteins In Esophageal Cancer: Implications For Immunotherapy," Int. J. Cancer. 118(1): 123-128); GD2/GD3/GM2 (Livingston, P. O. et al. (2005) "Selection Of GM2, Fucosyl GML Globo H And Polysialic Acid As Targets On Small Cell Lung Cancers For Antibody Mediated Immunotherapy," Cancer Immunol. Immunother. 54(10):1018-1025); ganglioside GD2 (GD2; Saleh et al. (1993) "Generation Of A Human Anti-Idiotypic Antibody That Mimics The GD2 Antigen," J. Immunol., 151, 3390-3398); ganglioside GD3 ($G_{D3}$; Shitara et al. (1993) "A Mouse/Human Chimeric Anti-(Ganglioside GD3) Antibody With Enhanced Antitumor Activities," Cancer Immunol. Immunother. 36:373-380); ganglioside GM2 ($G_{M2}$; Livingston et al. (1994) "Improved Survival In Stage III Melanoma Patients With GM2 Antibodies: A Randomized Trial Of Adjuvant Vaccination With GM2 Ganglioside," J. Clin. Oncol. 12:1036-1044); ganglioside GM3 (GM3; Hoon et al. (1993) "Molecular Cloning Of A Human Monoclonal Antibody Reactive To Ganglioside GM3 Antigen On Human Cancers," Cancer Res. 53:5244-5250); GICA 19-9 (Herlyn et al. (1982) "Monoclonal Antibody Detection Of A Circulating Tumor Associated Antigen. I. Presence Of Antigen In Sera Of Patients With Colorectal, Gastric, And Pancreatic Carcinoma," J. Clin. Immunol. 2:135-140); gp100 (Lotem, M. et al. (2006) "Presentation Of Tumor Antigens By Dendritic Cells Genetically Modified With Viral And Nonviral Vectors," J. Immunother. 29(6):616-27); Gp37 (human leukemia T cell antigen; Bhattacharya-Chatterjee et al. (1988) "Idiotype Vaccines Against Human T Cell Leukemia. II. Generation And Characterization Of A Monoclonal Idiotype Cascade (Ab1, Ab2, and Ab3)," J. Immunol. 141:1398-1403); gp75 (melanoma antigen; Vijayasardahl et al. (1990) "The Melanoma Antigen Gp75 Is The Human Homologue Of The Mouse B (Brown) Locus Gene Product," J. Exp. Med. 171(4):1375-1380); gpA33 (Heath, J. K. et al. (1997) "The Human A33 Antigen Is A Transmembrane Glycoprotein And A Novel Member Of The Immunoglobulin Superfamily," Proc. Natl. Acad. Sci. (U.S.A.) 94(2):469-474; Ritter, G. et al. (1997) "Characterization Of Posttranslational Modifications Of Human A33 Antigen, A Novel Palmitoylated Surface Glycoprotein Of Human Gastrointestinal Epithelium," Biochem. Biophys. Res. Commun. 236(3):682-686; Wong, N. A. et al. (2006) "EpCAM and gpA33 Are Markers Of Barrett's Metaplasia," J. Clin. Pathol. 59(3):260-263); HER2 antigen (HER2/neu, p185$^{HER2}$; Pal, S. K. et al. (2006) "Targeting HER2 Epitopes," Semin. Oncol. 33(4):386-391); HMFG (human milk fat globule antigen; WO1995015171); human papillomavirus-E6/human papillomavirus-E7 (DiMaio, D. et al. (2006) "Human Papillomaviruses And Cervical Cancer," Adv. Virus Res. 66:125-59; HMW-MAA (high molecular weight melanoma antigen; Natali et al. (1987) "Immunohistochemical Detection Of Antigen In Human Primary And Metastatic Melanomas By The Monoclonal Antibody 140.240 And Its Possible Prognostic Significance," Cancer 59:55-63; Mittelman et al. (1990) "Active Specific Immunotherapy In Patients With Melanoma. A Clinical Trial With Mouse Antiidiotypic Monoclonal Antibodies Elicited With Syngeneic Anti-High-Molecular-Weight-Melanoma-Associated Antigen Monoclonal Antibodies," J. Clin. Invest. 86:2136-2144); I antigen (differentiation antigen; Feizi (1985) "Demonstration By Monoclonal Antibodies That Carbohydrate Structures Of Glycoproteins And Glycolipids Are Onco-Developmental Antigens," Nature 314:53-57); IL13Rα2 (PCT Publication No. WO 2008/146911; Brown, C. E. et al. (2013) "Glioma IL13Rα2 Is Associated With Mesenchymal Signature Gene Expression And Poor Patient Prognosis," PLoS One. 18; 8(10):e77769; Barderas, R. et al. (2012) "High Expression Of IL-13 Receptor A2 In Colorectal Cancer Is Associated With Invasion, Liver Metastasis, And Poor Prognosis," Cancer Res. 72(11):2780-2790; Kasaian, M. T. et al. (2011) "IL-13 Antibodies Influence IL-13 Clearance In Humans By Modulating Scavenger Activity Of IL-13Rα2," J. Immunol. 187(1): 561-569; Bozinov, O. et al. (2010) "Decreasing Expression Of The Interleukin-13 Receptor IL-13Ralpha2 In Treated Recurrent Malignant Gliomas," Neurol. Med. Chir. (Tokyo) 50(8):617-621; Fujisawa, T. et al. (2009) "A novel role of interleukin-13 receptor alpha2 in pancreatic cancer invasion and metastasis," Cancer Res. 69(22):8678-8685); Integrin β6 (PCT Publication No. WO 03/087340); JAM-3 (PCT Publication No. WO 06/084078); KID3 (PCT Publication No. WO 05/028498); KID31 (PCT Publication No. WO 06/076584); KS 1/4 pan-carcinoma antigen (Perez et al. (1989) "Isolation And Characterization Of A cDNA Encoding The Ks1/4 Epithelial Carcinoma Marker," J. Immunol. 142:3662-3667; Möller et al. (1991) "Bispecific-Monoclonal-Antibody-Directed Lysis Of Ovarian Carcinoma Cells By Activated Human T Lymphocytes," Cancer Immunol. Immunother. 33(4):210-216; Ragupathi, G. 2005 Cancer Treat Res. 123:157-80); L6 and L20 (human lung carcinoma antigens; Hellström et al. (1986) "Monoclonal Mouse Antibodies Raised Against Human Lung Carcinoma," Cancer Res. 46:3917-3923); LEA; LUCA-2 (United States Patent Publication No. 2006/0172349; PCT Publication No. WO 06/083852); M1:22:25:8; M18; M39; MAGE (MAGE-1; MAGE-3; (Bodey, B. (2002) "Cancer-Testis Antigens: Promising Targets For Antigen Directed Antineoplastic Immunotherapy," Expert Opin. Biol. Ther. 2(6):577-584); MART (Kounalakis, N. et al. (2005) "Tumor Cell And Circulating Markers In Melanoma: Diagnosis, Prognosis, And Management," Curr. Oncol. Rep. 7(5):377-382; mesothelin (Chang, K. et al. (1996) "Molecular Cloning Of Mesothelin, A Differentiation Antigen Present On Mesothelium, Mesotheliomas, And Ovarian Cancers," Proc. Natl. Acad. Sci. (U.S.A.) 93:136-140); MUC-1 (Mathelin, C. (2006) "Circulating Proteinic Biomarkers And Breast Cancer," Gynecol. Obstet. Fertil. 34(7-8):638-646); MUM-1 (Castelli, C. et al. (2000) "T-Cell Recognition Of Melanoma-Associated Antigens," J. Cell. Physiol. 182(3):323-331); Myl; N-acetylglucosaminyltransferase (Dennis, J. W. (1999) "Glycoprotein Glycosylation And Cancer Progression," Biochim. Biophys. Acta. 6; 1473(1):21-34); neoglycoprotein; NS-10 as found in adenocarcinomas; OFA-1; OFA-2; Oncostatin M (Oncostatin Receptor Beta; U.S. Pat. No. 7,572,896; PCT Publication No. WO 06/084092); p15 (Gil, J. et al. (2006) "Regulation Of The INK4b-ARF-INK4a Tumour Suppressor Locus: All For One Or One For All," Nat. Rev. Mol. Cell Biol. 7(9):667-677); p97 (melanoma-associated antigen; Estin et al. (1989) "Transfected Mouse Melanoma Lines That Express Various Levels Of Human Melanoma-Associated Antigen p97," J. Natl. Cancer Instit. 81(6):445-454); PEM (polymorphic epithelial mucin; Hilkens et al. (1992) "Cell Membrane-Associated Mucins And Their Adhesion Modulating Property," Trends in Biochem. Sci. 17:359-363); PEMA (polymorphic epithelial mucin antigen); PIPA (U.S. Pat. No. 7,405,061; PCT Publication No. WO 04/043239); PSA (prostate-specific antigen; Henttu et al. (1989) "cDNA Coding For The Entire Human Prostate Specific Antigen Shows High Homologies To The Human Tissue Kallikrein Genes," Biochem. Biophys. Res. Comm. 10(2):903-910; Israeli et al. (1993) "Molecular Cloning Of A Complementary DNA Encoding A Prostate-Specific Membrane Antigen," Cancer Res. 53:227-230; Cracco, C. M. et al. (2005) "Immune Response In Prostate Cancer," Minerva Urol. Nefrol. 57(4):301-311); PSMA (prostate-specific membrane antigen; Ragupathi, G. (2005) "Antibody Inducing Polyvalent Cancer Vaccines," Cancer Treat. Res. 123: 157-180); prostatic acid phosphate (Tailor et al. (1990) "Nucleotide Sequence Of Human Prostatic Acid Phosphatase Determined From A Full-Length cDNA Clone," Nucl. Acids Res. 18(16):4928); R24 as found in melanoma; ROR1 (U.S. Pat. No. 5,843,749); sphingolipids; SSEA-1; SSEA-3; SSEA-4; sTn (Holmberg, L. A. (2001) "Theratope Vaccine (STn-KLH)," Expert Opin. Biol. Ther. 1(5):881-91); T cell receptor derived peptide from a cutaneous T cell lymphoma (see Edelson (1998) "Cutaneous T-Cell Lymphoma: A Model For Selective Immunotherapy," Cancer J. Sci. Am. 4:62-71); $T_5A_7$ found in myeloid cells; TAG-72 (Yokota et al. (1992) "Rapid Tumor Penetration Of A Single-Chain Fv And Comparison With Other Immunoglobulin Forms," Cancer Res. 52:3402-3408); TL5 (blood group A); TNF-receptor (TNF-α receptor, TNF-β receptor; TNF-γ receptor (van Horssen, R. et al. (2006) "TNF-Alpha In Cancer Treatment: Molecular Insights, Antitumor Effects, And Clinical Utility," Oncologist 11(4):397-408; Gardnerova, M. et al. (2000) "The Use Of TNF Family Ligands And Receptors And Agents Which Modify Their Interaction As Therapeutic Agents," Curr. Drug Targets 1(4):327-364); TRA-1-85 (blood group H); Transferrin Receptor (U.S. Pat. No. 7,572,895; PCT Publication No. WO 05/121179); 5T4 (TPBG, trophoblast glycoprotein; Boghaert, E. R. et al. (2008) "The Oncofetal Protein, 5T4, Is A Suitable Target For Antibody-Guided Anti-Cancer Chemotherapy With Calicheamicin," Int. J. Oncol. 32(1):221-234; Eisen, T. et al. (2014) "Naptumomab Estafenatox: Targeted Immunotherapy with a Novel Immunotoxin," Curr. Oncol. Rep. 16:370, pp. 1-6); TSTA (tumor-specific transplantation antigen) such as virally-induced tumor antigens including T-antigen DNA tumor viruses and envelope antigens of RNA tumor viruses, oncofetal antigen-alpha-fetoprotein such as CEA of colon, bladder tumor oncofetal antigen (Hellström et al. (1985) "Monoclonal Antibodies To Cell Surface Antigens Shared By Chemically Induced Mouse Bladder Carcinomas," Cancer. Res. 45:2210-2188); VEGF (Pietrantonio, F. et al. (2015) "Bevacizumab Based Neoadjuvant Chemotherapy For Colorectal Cancer Liver Metastases: Pitfalls And Helpful Tricks In A Review For Clinicians," Crit. Rev. Oncol. Hematol. 95(3): 272-281; Grabowski, J. P. (2015) "Current Management Of Ovarian Cancer," Minerva Med. 106(3):151-156; Field, K. M. (2015) "Bevacizumab And Glioblastoma: Scientific Review, Newly Reported Updates, And Ongoing Controversies," Cancer 121(7):997-1007; Suh, D. H. et al. (2015) "Major Clinical Research Advances In Gynecologic Cancer In 2014," J. Gynecol. Oncol. 26(2): 156-167; Liu, K. J. et al. (2015) "Bevacizumab In Combination With Anticancer Drugs For Previously Treated Advanced Non-Small Cell Lung Cancer," Tumour Biol. 36(3):1323-1327; Di Bartolomeo, M. et al. (2015) "Bevacizumab Treatment In The Elderly Patient With Metastatic Colorectal Cancer," Clin. Interv. Aging 10:127-133); VEGF Receptor (O'Dwyer. P. J. (2006) "The Present And Future Of Angiogenesis-Directed Treatments Of Colorectal Cancer," Oncologist 11(9):992-998); VEP8; VEP9; VIM-D5; and Y hapten, $Le^y$ as found in embryonal carcinoma cells. Additional Cancer Antigens, and molecules (e.g., antibodies) that bind them are disclosed in Table 11. 5T4, B7-H3, CEACAM5/CEACAM6, CD123, DR5, EGFR, an Ephrin receptor, gpA33, HER2/neu, IL13Rα2, ROR1, and VEGF are particularly preferred "Cancer Antigens" of the present invention.

TABLE 11

Antibody and Antibody-Based Molecules

| Antibody Name | Cancer Antigens | Therapeutic Target Application |
|---|---|---|
| 3F8 | Gd2 | Neuroblastoma |
| 8H9 | B7-H3 | Neuroblastoma, Sarcoma, Metastatic Brain Cancers |
| Abagovomab | CA-125 | Ovarian Cancer |
| Adecatumumab | Epcam | Prostate and Breast Cancer |
| Afutuzumab | CD20 | Lymphoma |
| Alacizumab | VEGFR2 | Cancer |
| Altumomab | CEA | Colorectal Cancer |
| Amatuximab | Mesothelin | Cancer |
| Anatumomab Mafenatox | TAG-72 | Non-Small Cell Lung Carcinoma |
| Anifrolumab | Interferon A/B Receptor | Systemic Lupus Erythematosus |
| Anrukinzumab | IL-13 | Cancer |
| Apolizumab | HLA-DR | Hematological Cancers |
| Arcitumomab | CEA | Gastrointestinal Cancer |
| Atinumab | RTN4 | Cancer |
| Bectumomab | CD22 | Non-Hodgkin's Lymphoma (Detection) |
| Belimumab | BAFF | Non-Hodgkin Lymphoma |
| Bevacizumab | VEGF-A | Metastatic Cancer, Retinopathy of Prematurity |
| Bivatuzumab | CD44 V6 | Squamous Cell Carcinoma |
| Blinatumomab | CD19 | Cancer |
| Brentuximab | CD30 (TNFRSF8) | Hematologic Cancers |
| Cantuzumab | MUC1 | Cancers |
| Cantuzumab Mertansine | Mucin Canag | Colorectal Cancer |
| Caplacizumab | VWF | Cancers |
| Capromab | Prostatic Carcinoma Cells | Prostate Cancer (Detection) |
| Carlumab | MCP-1 | Oncology/Immune Indications |
| Catumaxomab | Epcam, CD3 | Ovarian Cancer, Malignant Ascites, Gastric Cancer |
| Cc49 | Tag-72 | Tumor Detection |
| Cetuximab | EGFR | Metastatic Colorectal Cancer and Head and Neck Cancer |
| Ch.14.18 | Undetermined | Neuroblastoma |
| Citatuzumab | Epcam | Ovarian Cancer and other Solid Tumors |
| Cixutumumab | IGF-1 Receptor | Solid Tumors |
| Clivatuzumab | MUC1 | Pancreatic Cancer |
| Conatumumab | TRAIL-R2 | Cancer |
| Dacetuzumab | CD40 | Hematologic Cancers |
| Dalotuzumab | Insulin-Like Growth Factor I Receptor | Cancer |
| Daratumumab | CD38 | Cancer |
| Demcizumab | DLL4 | Cancer |
| Detumomab | B-Lymphoma Cell | Lymphoma |
| Drozitumab | DR5 | Cancer |
| Duligotumab | HER3 | Cancer |
| Dusigitumab | ILGF2 | Cancer |
| Ecromeximab | GD3 | Ganglioside Malignant Melanoma |
| Eculizumab | C5 | Paroxysmal Nocturnal Hemoglobinuria |
| Edrecolomab | Epcam | Colorectal Carcinoma |
| Elotuzumab | SLAMF7 | Multiple Myeloma |
| Elsilimomab | IL-6 | Cancer |
| Enavatuzumab | TWEAK Receptor | Cancer |
| Enlimomab | ICAM-1 (CD54) | Cancer |
| Enokizumab | IL9 | Asthma |
| Enoticumab | DLL4 | Cancer |
| Ensituximab | 5AC | Cancer |

TABLE 11-continued

Antibody and Antibody-Based Molecules

| Antibody Name | Cancer Antigens | Therapeutic Target Application |
| --- | --- | --- |
| Epitumomab Cituxetan | Episialin | Cancer |
| Epratuzumab | CD22 | Cancer, SLE |
| Ertumaxomab | HER2/neu, CD3 | Breast Cancer |
| Etaracizumab | Integrin A,β₃ | Melanoma, Prostate Cancer, Ovarian Cancer |
| Faralimomab | Interferon Receptor | Cancer |
| Farletuzumab | Folate Receptor 1 | Ovarian Cancer |
| Fasinumab | HNGF | Cancer |
| Fbta05 | CD20 | Chronic Lymphocytic Leukaemia |
| Ficlatuzumab | HGF | Cancer |
| Figitumumab | IGF-1 Receptor | Adrenocortical Carcinoma, Non-Small Cell Lung Carcinoma |
| Flanvotumab | TYRP1 (Glycoprotein 75) | Melanoma |
| Fontolizumab | IFN-γ | Crohn's Disease |
| Fresolimumab | TGF-B | Idiopathic Pulmonary Fibrosis, Focal Segmental Glomerulosclerosis, Cancer |
| Futuximab | EGFR | Cancer |
| Galiximab | CD80 | B Cell Lymphoma |
| Ganitumab | IGF-I | Cancer |
| Gemtuzumab Ozogamicin | CD33 | Acute Myelogenous Leukemia |
| Gevokizumab | IL-β | Diabetes |
| Girentuximab | Carbonic Anhydrase 9 (CA-IX) | Clear Cell Renal Cell Carcinoma |
| Glembatumumab Vedotin | GPNMB | Melanoma, Breast Cancer |
| Golimumab | TNF-A | Rheumatoid Arthritis, Psoriatic Arthritis, Ankylosing Spondylitis |
| Ibritumomab Tiuxetan | CD20 | Non-Hodgkin's Lymphoma |
| Icrucumab | VEGFR-1 | Cancer |
| Igovomab | CA-125 | Ovarian Cancer (Diagnosis) |
| Imab362 | Cldn18.2 | Gastrointestinal Adenocarcinomas and Pancreatic Tumor |
| Imgatuzumab | EGFR | Cancer |
| Inclacumab | Selectin P | Cancer |
| Indatuximab Ravtansine | SDC1 | Cancer |
| Inotuzumab Ozogamicin | CD22 | Cancer |
| Intetumumab | CD51 | Solid Tumors (Prostate Cancer, Melanoma) |
| Ipilimumab | CD152 | Melanoma |
| Iratumumab | CD30 (TNFRSF8) | Hodgkin's Lymphoma |
| Itolizumab | CD6 | Cancer |
| Labetuzumab | CEA | Colorectal Cancer |
| Lambrolizumab | PDCD1 | Antineoplastic Agent |
| Lampalizumab | CFD | Cancer |
| Lexatumumab | TRAIL-R2 | Cancer |
| Libivirumab | Hepatitis B Surface Antigen | Hepatitis B |
| Ligelizumab | IGHE | Cancer |
| Lintuzumab | CD33 | Cancer |
| Lirilumab | KIR2D | Cancer |
| Lorvotuzumab | CD56 | Cancer |
| Lucatumumab | CD40 | Multiple Myeloma, Non-Hodgkin's Lymphoma, Hodgkin's Lymphoma |
| Lumiliximab | CD23 | Chronic Lymphocytic Leukemia |
| Mapatumumab | TRAIL-R1 | Cancer |
| Margetuximab | Ch4d5 | Cancer |
| Matuzumab | EGFR | Colorectal, Lung and Stomach Cancer |
| Milatuzumab | CD74 | Multiple Myeloma and Other Hematological Malignancies |
| Minretumomab | TAG-72 | Cancer |
| Mitumomab | GD3 Ganglioside | Small Cell Lung Carcinoma |
| Mogamulizumab | CCR4 | Cancer |
| Morolimumab | Rhesus Factor | Cancer |
| Moxetumomab Pasudotox | CD22 | Cancer |
| Nacolomab Tafenatox | C242 Antigen | Colorectal Cancer |
| Namilumab | C SF2 | Cancer |
| Naptumomab Estafenatox | 5T4 | Non-Small Cell Lung Carcinoma, Renal Cell Carcinoma |
| Narnatumab | RON | Cancer |
| Nebacumab | Endotoxin | Sepsis |
| Necitumumab | EGFR | Non-Small Cell Lung Carcinoma |
| Nerelimomab | TNF-A | Cancer |
| Nesvacumab | Angiopoietin 2 | Cancer |
| Nimotuzumab | EGFR | Squamous Cell Carcinoma, Head and Neck Cancer, Nasopharyngeal Cancer, Glioma |
| Nivolumab | PD-1 | Cancer |
| Nofetumomab Merpentan | Undetermined | Cancer |
| Ocaratuzumab | CD20 | Cancer |
| Ofatumumab | CD20 | Chronic Lymphocytic Leukemia |
| Olaratumab | PDGF-R A | Cancer |
| Olokizumab | IL6 | Cancer |
| Onartuzumab | Human Scatter Factor Receptor Kinase | Cancer |
| Ontuxizumab | TEM1 | Cancer |
| Oportuzumab Monatox | Epcam | Cancer |
| Oregovomab | CA-125 | Ovarian Cancer |
| Orticumab | Oxldl | Cancer |
| Otlertuzumab | CD37 | Cancer |
| Panitumumab | EGFR | Colorectal Cancer |
| Pankomab | Tumor Specific Glycosylation of MUC1 | Ovarian Cancer |
| Parsatuzumab | EGFL7 | Cancer |
| Patritumab | HER3 | Cancer |
| Pembrolizumab | PD-1 | Cancer |
| Pemtumomab | MUC1 | Cancer |
| Perakizumab | IL17A | Arthritis |
| Pertuzumab | HER2/neu | Cancer |
| Pidilizumab | PD-1 | Cancer and Infectious Diseases |
| Pinatuzumab Vedotin | CD22 | Cancer |
| Pintumomab | Adenocarcinoma Antigen | Adenocarcinoma |
| Placulumab | Human TNF | Cancer |
| Polatuzumab Vedotin | CD79B | Cancer |
| Pritoxaximab | E. Coli Shiga Toxin Type-1 | Cancer |
| Pritumumab | Vimentin | Brain Cancer |
| Quilizumab | IGHE | Cancer |
| Racotumomab | N-Glycolylneuraminic Acid | Cancer |
| Radretumab | Fibronectin Extra Domain-B | Cancer |
| Ramucirumab | VEGFR2 | Solid Tumors |
| Rilotumumab | HGF | Solid Tumors |
| Rituximab | CD20 | Lymphomas, Leukemias, Some Autoimmune Disorders |
| Robatumumab | IGF-1 Receptor | Cancer |
| Roledumab | RHD | Cancer |
| Samalizumab | CD200 | Cancer |
| Satumomab Pendetide | TAG-72 | Cancer |
| Seribantumab | ERBB3 | Cancer |
| Setoxaximab | E. Coli Shiga Toxin Type-1 | Cancer |

TABLE 11-continued

Antibody and Antibody-Based Molecules

| Antibody Name | Cancer Antigens | Therapeutic Target Application |
|---|---|---|
| Sgn-CD19a | CD19 | Acute Lymphoblastic Leukemia and B Cell Non-Hodgkin Lymphoma |
| Sgn-CD33 a | CD33 | Acute Myeloid Leukemia |
| Sibrotuzumab | FAP | Cancer |
| Siltuximab | IL-6 | Cancer |
| Solitomab | Epcam | Cancer |
| Sontuzumab | Episialin | Cancer |
| Tab alumab | BAFF | B Cell Cancers |
| Tacatuzumab Tetraxetan | Alpha-Fetoprotein | Cancer |
| Taplitumomab Paptox | CD19 | Cancer |
| Telimomab | Undetermined | Cancer |
| Tenatumomab | Tenascin C | Cancer |
| Teneliximab | CD40 | Cancer |
| Teprotumumab | CD221 | Hematologic Tumors |
| Ticilimumab | CTLA-4 | Cancer |
| Tigatuzumab | TRAIL-R2 | Cancer |
| Tnx-650 | Il-13 | Hodgkin's Lymphoma |
| Tositumomab | CD20 | Follicular Lymphoma |
| Tovetumab | CD140a | Cancer |
| Trastuzumab | HER2/neu | Breast Cancer |
| Trbs07 | Gd2 | Melanoma |
| Tremelimumab | CTLA-4 | Cancer |
| Tucotuzumab Celmoleukin | Epcam | Cancer |
| Ublituximab | MS4A1 | Cancer |
| Urelumab | 4-1BB | Cancer |
| Vantictumab | Frizzled Receptor | Cancer |
| Vapaliximab | AOC3 (VAP-1) | Cancer |
| Vatelizumab | ITGA2 | Cancer |
| Veltuzumab | CD20 | Non-Hodgkin's Lymphoma |
| Vesencumab | NRP1 | Cancer |
| Volociximab | Integrin A5β1 | Solid Tumors |
| Vorsetuzumab | CD70 | Cancer |
| Votumumab | Tumor Antigen CTAA16.88 | Colorectal Tumors |
| Zalutumumab | EGFR | Squamous Cell Carcinoma of The Head And Neck |
| Zatuximab | HER1 | Cancer |
| Ziralimumab | CD147 | Cancer |

Exemplary antibodies, whose VH and VL Domains may be used to construct the binding molecules of the present invention that are capable of binding a Cancer Antigen arrayed on the surface of a cancer cell and mediating the redirected killing of such cancer cells are listed in Table 11, additional antibodies that may be used to construct molecules capable of binding a Cancer Antigen arrayed on the surface of a cancer cell and mediating the redirected killing of such cancer cells are provided below.

1. Exemplary Anti-B7-H3 Antibodies

B7-H3 is a Cancer Antigen that is over-expressed on a wide variety of solid tumor types and is a member of the B7 family of molecules that are involved in immune regulation (see, U.S. Pat. No. 8,802,091; US 2014/0328750; US 2013/0149236; Loo, D. et al. (2012) "*Development Of An Fc-Enhanced Anti-B7-H3Monoclonal Antibody With Potent Antitumor Activity*," Clin. Cancer Res. 18(14):3834-3845). In particular, several independent studies have shown that human malignant cancer cells (e.g., cancer cells of neuroblastomas and gastric, ovarian and non-small cell lung cancers) exhibit a marked increase in expression of B7-H3 protein and that this increased expression was associated with increased disease severity (Zang, X. et al. (2007) "*The B7 Family And Cancer Therapy: Costimulation And Coinhibition*," Clin. Cancer Res. 13:5271-5279), suggesting that B7-H3 is exploited by tumors as an immune evasion pathway (Hofmeyer, K. et al. (2008) "*The Contrasting Role Of B7-H3*," Proc. Natl. Acad. Sci. (U.S.A.) 105(30):10277-10278).

B7-H3 has also been found to co-stimulate CD4+ and CD8+ T-cell proliferation. B7-H3 also stimulates IFN-γ production and CD8+ lytic activity (Chapoval, A. et al. (2001) "*B7-H3: A Costimulatory Molecule For T Cell Activation and IFN-γ Production*," Nature Immunol. 2:269-274; Sharpe, A. H. et al. (2002) "*The B7-CD28 Superfamily*," Nature Rev. Immunol. 2:116-126). However, the protein also possibly acts through NFAT (nuclear factor for activated T cells), NF-κB (nuclear factor kappa B), and AP-1 (Activator Protein-1) factors to inhibit T-cell activation (Yi. K. H. et al. (2009) "Fine *Tuning The Immune Response Through B7-H3 And B7-H4*," Immunol. Rev. 229:145-151). B7-H3 is also believed to inhibit Th1, Th2, or Th17 in vivo (Prasad, D. V. et al. (2004) "*Murine B7-H3 Is A Negative Regulator Of T Cells*," J. Immunol. 173:2500-2506; Fukushima, A. et al. (2007) "B7-H3 Regulates The Development Of Experimental Allergic Conjunctivitis In Mice," Immunol. Lett. 113:52-57; Yi. K. H. et al. (2009) "*Fine Tuning The Immune Response Through B7-H3 And B7-H4*," Immunol. Rev. 229:145-151).

Preferred B7-H3-binding molecules possess the VL and/or VH Domains, of humanized anti-human B7-H3 monoclonal antibody "B7-H3 mAb-B," "B7-H3 mAb-C," "B7-H3 mAb-D," and more preferably possess 1, 2 or all 3 of the $CDR_L$s of the VL Region and/or 1, 2 or all 3 of the $CDR_H$s of the VH Domain of such anti-B7-H3 monoclonal antibodies.

Upon humanization, antibody B7-H3 mAb-B yielded two variant VH Domains, B7-H3 mAb-B VH1 and B7-H3 mAb-B VH2; and two variant VL Domains B7-113 mAb-B VL1 and B7-H3 mAb-B VL2, which may be used in any combination of VH/VL Domains to yield a functional B7-H3 Binding Domain.

The amino acid sequence of the VH Domain of B7-H3 mAb-B VH1 (SEQ ID NO:96) is shown below ($CDR_H$ residues are shown underlined):

```
QVQLVQSGAE VKKPGASVKV SCKASGYTFT

SYWMQWVRQA PGQGLEWMGT IYPGDGDTRY

TQKFKGRVTI TADKSTSTAY MELSSLRSED

TAVYYCARRG IPRLWYFDVW GQGTTVTVSS
```

The amino acid sequence of the VH Domain of B7-H3 mAb-B VH2 (SEQ ID NO:97) is shown below ($CDR_H$ residues are shown underlined):

```
QVQLVQSGAE VKKPGASVKV SCKASGYTFT

SYWMQWVRQA PGQGLEWMGT IYPGGGDTRY

TQKFQGRVTI TADKSTSTAY MELSSLRSED

TAVYYCARRG IPRLWYFDVW GQGTTVTVSS
```

The amino acid sequence of the VL Domain of B7-H3 mAb-B VL1 (SEQ ID NO:98) is shown below ($CDR_L$ residues are shown underlined).

```
DIQMTQSPSS LSASVGDRVT ITCRASQDIS

NYLNWYQQKP GKAPKLLIYY TSRLHSGVPS

RFSGSGSGTD FTLTISSLQP EDIATYYCQQ

GNTLPPTFGG GTKLEIK
```

The amino acid sequence of the VL Domain of B7-H3 mAb-B VL2 (SEQ ID NO:99) is shown below (CDR$_L$ residues are shown underlined).

```
DIQMTQSPSS LSASVGDRVT ITCRASQSIS

SYLNWYQQKP GKAPKLLIYY TSRLQSGVPS

RFSGSGSGTD FTLTISSLQP EDIATYYCQQ

GNTLPPTFGG GTKLEIK
```

The amino acid sequence of the VH Domain of humanized B7-H3 mAb-C (SEQ ID NO:100) is shown below (CDR$_H$ residues are shown underlined):

```
EVQLVESGGG LVKPGGSLRL SCAASGFTFS

SYGMSWVRQA PGKGLEWVAT INSGGSNTYY

PDSLKGRFTI SRDNAKNSLY LQMNSLRAED

TAVYYCARHD GGAMDYWGQG TTVTVSS
```

The amino acid sequence of the VL Domain of humanized B7-H3 mAb-C (SEQ ID NO:101) is shown below (CDR$_L$ residues are shown underlined).

```
DIQMTQSPSS LSASVGDRVT ITCRASESIY

SYLAWYQQKP GKAPKLLVYN TKTLPEGVPS

RFSGSGSGTD FTLTISSLQP EDFATYYCQH

HYGTPPWTFG QGTRLEIK
```

The amino acid sequence of the VH Domain of B7-H3 mAb-D (SEQ ID NO:102) is shown below (CDR$_H$ residues are shown underlined).

```
EVQLVESGGG LVQPGGSLRL SCAASGFTFS

SFGMHWVRQA PGKGLEWVAY ISSGSGTIYY

ADTVKGRFTI SRDNAKNSLY LQMNSLRAED

TAVYYCARHG YRYEGFDYWG QGTTVTVSS
```

The amino acid sequence of the VL Domain of B7-H3 mAb-D (SEQ ID NO:103) is shown below (CDR$_L$ residues are shown underlined).

```
DIQMTQSPSF LSASVGDRVT ITCKASQNVD

TNVAWYQQKP GKAPKALIYS ASYRYSGVPS

RFSGSGSGTD FTLTISSLQP EDFAEYFCQQ

YNNYPFTFGQ GTKLEIK
```

Particularly preferred, are B7-H3-binding molecules which possess a humanized VH and/or VL Domain including but not limited to "Enoblituzumab" (also known as MGA271; CAS Reg No. 1353485-38-7). Enoblituzumab is an Fc-optimized monoclonal antibody that binds to HER2/neu and mediates enhanced ADCC activity. The amino acid sequences of the complete Heavy and Light Chains of Enoblituzumab are known in the art (see., e.g., WHO Drug Information, 2017, Recommended INN: List 77, 31(1):49).

The amino acid sequence of the VH Domain of Enoblituzumab (SEQ ID NO:104) is shown below (CDR$_H$ residues are shown underlined):

```
EVQLVESGGG LVQPGGSLRL SCAASGFTFS

SFGMHWVRQA PGKGLEWVAY ISSDSSAIYY

ADTVKGRFTI SRDNAKNSLY LQMNSLRDED

TAVYYCGRGR ENIYYGSRLD YWGQGTTVTV

SS
```

The amino acid sequence of the VL Domain of Enoblituzumab (SEQ ID NO:105) is shown below (CDR$_L$ residues are shown underlined):

```
DIQLTQSPSF LSASVGDRVT ITCKASQNVD

TNVAWYQQKP GKAPKALIYS ASYRYSGVPS

RFSGSGSGTD FTLTISSLQP EDFATYYCQQ

YNNYPFTFGQ GTKLEIK
```

In addition to the above-identified preferred anti-B7-H3 Binding Molecules, the invention contemplates the use of any of the following anti-B7-H3 Binding Molecules: LUCA1; BLA8; PA20; or SKN2 (see, U.S. Pat. Nos. 7,527,969; 8,779,098 and PCT Patent Publication WO 2004/001381); M30; cM30; M30-H1-L1; M30-H1-L2; M30-H1-L3; M30-H1-L4; M30-H1-L5; M30-H1-L6; M30-H1-L7; M30-H4-L1; M30-H4-L2; M30-H4-L3; and M30-H4-L4 (see, US Patent Publication 2013/0078234 and PCT Patent Publication WO 2012/147713); and 8119 (see U.S. Pat. Nos. 7,666,424; 7,737,258; 7,740,845; 8,148,154; 8,414,892; 8,501,471; 9,062,110; US Patent Publication 2010/0143245 and PCT Patent Publication WO 2008/116219).

The present invention specifically includes and encompasses CD16×B7-H3 Binding Molecules that comprise the VL and/or VH Domain, and/or 1, 2 or all 3 of the CDR$_L$s of the VL Region and/or 1, 2 or all 3 of the CDR$_H$s of the VH Domain of any of B7-H3 mAb-B, B7-H3 mAb-B VH1, B7-H3 mAb-B VH2, B7-H3 mAb-B VL1, B7-H3 mAb-B VL2, B7-H3 mAb-C, B7-H3 mAb-D, or Enoblituzumab, or any of the other anti-B7-H3 antibodies provided herein; and more preferably possess 1, 2 or all 3 of the CDR$_L$s of the VL Region and/or 1, 2 or all 3 of the CDR$_H$s of the VH Domain of such anti-B7-H3 monoclonal antibodies.

2. Exemplary Anti-CEACAM5 and Anti-CEACAM6 Antibodies

Carcinoembryonic Antigen-Related Cell Adhesion Molecules 5 (CEACAM5) and 6 (CEACAM6) have been found to be associated with various types of cancers including medullary thyroid cancer, colorectal cancer, pancreatic cancer, hepatocellular carcinoma, gastric cancer, lung cancer, head and neck cancers, urinary bladder cancer, prostate cancer, uterine cancer, endometrial cancer, breast cancer, hematopoietic cancer, leukemia and ovarian cancer (PCT Pubmication No. WO 2011/034660), and particularly colorectal, gastrointestinal, pancreatic, non-small cell lung cancer (NSCL), breast, thyroid, stomach, ovarian and uterine carcinomas (Zheng, C. et al. (2011) "*A Novel Anti-CEACAM5 Monoclonal Antibody, CC4, Suppresses Colorectal Tumor Growth and Enhances NK Cells-Mediated Tumor Immunity*," PLoS One 6(6):e21146, pp. 1-11).

CEACAM5 has been found to be overexpressed in 90% of gastrointestinal, colorectal and pancreatic cancers, 70% of non-small cell lung cancer cells and 50% of breast cancers (Thompson, J. A. et al. (1991) "*Carcinoembryonic Antigen Gene Family: Molecular Biology And Clinical Perspectives*," J. Clin. Lab. Anal. 5:344-366). Overexpressed carcinoembryonic antigen-related cellular adhesion molecule 6 (CEACAM6) plays important roles in the invasion and metastasis of a variety of human cancers, including medullary thyroid cancer, colorectal cancer, pancreatic cancer, hepatocellular carcinoma, gastric cancer, lung cancer, head and neck cancers, urinary bladder cancer, prostate cancer, uterine cancer, endometrial cancer, breast cancer, hematopoietic cancer, leukemia and ovarian cancer (PCT Pubmication No. WO 2011/034660; Deng, X. et al. (2014) "*Expression Profiling Of CEACAM6 Associated With The Tumorigenesis And Progression In Gastric Adenocarcinoma*," Genet. Mol. Res. 13(3):7686-7697; Cameron, S. et al. (2012) "*Focal Overexpression Of CEACAM6 Contributes To Enhanced Tumourigenesis In Head And Neck Cancer Via Suppression Of Apoptosis*," Mol. Cancer 11:74, pp. 1-11; Chapin, C. et al. (2012) "*Distribution And Surfactant Association Of Carcinoembryonic Cell Adhesion Molecule 6 In Human Lung*," Amer. J. Physiol. Lung Cell. Mol. Physiol. 302(2):L216-L25; Riley, C. J. et al. (2009) "*Design And Activity Of A Murine And Humanized Anti-CEACAM6 Single-Chain Variable Fragment In The Treatment Of Pancreatic Cancer*," Cancer Res. 69(5): 1933-1940; Lewis-Wambi, J. S. et al. (2008) "*Overexpression Of CEACAM6 Promotes Migration And Invasion Of Oestrogen-Deprived Breast Cancer Cells*," Eur. J. Cancer 44(12):1770-1779; Blumenthal, R. D. et al. (2007) "*Expression Patterns Of CEACAM5 And CEACAM6 In Primary And Metastatic Cancers*," BMC Cancer. 7:2, pp. 1-15). Antibodies that immunospecifically bind CEACAM5 and CEACAM6 are commercially available (Santa Cruz Biotechnology, Inc., Novus Biologicals LLC; Abnova Corporation).

The amino acid sequence of the VH Domain of the humanized anti-CEACAM5/ANTI-CEACAM6 antibody 16C3 (EP 2585476) (SEQ ID NO:106) is shown below (CDR$_H$ residues are shown underlined):

```
QVQLQQSGPE VVRPGVSVKI SCKGSGYTFT

DYAMHWVKQS HAKSLEWIGL ISTYSGDTKY

NQNFKGKATM TVDKSASTAY MELSSLRSED

TAVYYCARGD YSGSRYWFAY WGQGTLVTVS

S
```

The amino acid sequence of the VL Domain of the humanized anti-CEACAM5/ANTI-CEACAM6 antibody 16C3 (EP 2585476) (SEQ ID NO:107) is shown below (CDR$_L$ residues are shown underlined):

```
DIQMTQSPSS LSASVGDRVT ITCGASENIY

GALNWYQRKP GKSPKLLIWG ASNLADGMPS
```

```
RFSGSGSGRQ YTLTISSLQP EDVATYYCQN

VLSSPYTFGG GTKLEIK
```

The amino acid sequence of the VH Domain of the humanized anti-CEACAM5/CEACAM6 antibody hMN15 (WO 2011/034660) (SEQ ID NO:108) is shown below (CDR$_H$ residues are shown underlined):

```
QVQLVESGGG VVQPGRSLRL SCSSSGFALT

DYYMSWVRQA PGKGLEWLGF IANKANGHTT

DYSPSVKGRF TISRDNSKNT LFLQMDSLRP

EDTGVYFCAR DMGIRWNFDV WGQGTPVTVS

S
```

The amino acid sequence of the VL Domain of the humanized anti-CEACAM5/CEACAM6 antibody hMN15 (WO 2011/034660) (SEQ ID NO:109) is shown below (CDR$_L$ residues are shown underlined):

```
DIQLTQSPSS LSASVGDRVT MTCSASSRVS

YIHWYQQKPG KAPKRWIYGT STLASGVPAR

FSGSGSGTDF TFTISSLQPE DIATYYCQQW

SYNPPTFGQG TKVEIKR
```

The present invention specifically includes and encompasses CD16×CEACAM5/CEACAM6 Binding Molecules that comprise the VL and/or VH Domain, and/or 1, 2 or all 3 of the CDR$_L$s of the VL Region and/or 1, 2 or all 3 of the CDR$_H$s of the VH Domain of the anti-CEACAM5/CEACAM6 monoclonal antibodies 16C3 or hMN15.

3. Exemplary Anti-EGRF Antibodies

Epidermal Growth Factor Receptor (EGFR) is a Cancer Antigen of certain metastatic colorectal cancer, metastatic non-small cell lung cancer and head and neck cancer. Exemplary antibodies that bind human EGRF are "Cetuximab" and "Panitumumab." Cetuximab is a recombinant human-mouse chimeric epidermal growth factor receptor (EGFR) IgG1 monoclonal antibody (Govindan R. (2004) "*Cetuximab In Advanced Non-Small Cell Lung Cancer*," Clin. Cancer Res. 10(12 Pt 2):42415-4244s; Bou-Assaly, W. et al. (2010) "*Cetuximab (Erbitux)*," Am. J. Neuroradiol. 31(4):626-627). Panitumumab (Vectibix®, Amgen) is a fully humanized epidermal growth factor receptor (EGFR) IgG2 monoclonal antibody (Foon, K. A. et al. (2004) "*Preclinical And Clinical Evaluations Of ABX-EGF, A Fully Human Anti-Epidermal Growth Factor Receptor Antibody*," Int. J. Radiat. Oncol. Biol. Phys. 58(3):984-990; Yazdi, M. H. et al. (2015) "*A Comprehensive Review of Clinical Trials on EGFR Inhibitors Such as Cetuximab and Panitumumab as Monotherapy and in Combination for Treatment of Metastatic Colorectal Cancer*," Avicenna J. Med. Biotechnol. 7(4):134-144).

The amino acid sequence of the VH Domain of the chimeric anti-EGFR antibody Cetuximab (SEQ ID NO:110) is shown below (CDR$_H$ residues are shown underlined):

```
QVQLKQSGPG LVQPSQSLSI TCTVSGFSLT

NYGVHWVRQS PGKGLEWLGV IWSGGNTDYN

TPFTSRLSIN KDNSKSQVFF KMNSLQSNDT

AIYYCARALT YYDYEFAYWG QGTLVTVSA
```

The amino acid sequence of the VL Domain of the chimeric anti-EGFR antibody Cetuximab (SEQ ID NO:111) is shown below (CDR$_L$ residues are shown underlined):

```
DILLTQSPVI LSVSPGERVS FSCRASQSIG TNIHWYQQRT

NGSPRLLIKY ASESISGIPS RFSGSGSGTD FTLSINSVES

EDIADYYCQQ NNNWPTTFGA GTKLELKR
```

The amino acid sequence of the VH Domain of Panitumumab (SEQ ID NO:112) is shown below (CDR$_H$ residues are shown underlined):

```
QVQLQESGPG LVKPSETLSL TCTVSGGSVS SGDYYWTWIR

QSPGKGLEWI GHIYYSGNTN YNPSLKSRLT ISIDTSKTQF

SLKLSSVTAA DTAIYYCVRD RVTGAFDIWG QGTMVTVSS
```

The amino acid sequence of the VL Domain of Panitumumab (SEQ ID NO:113) is shown below (CDR$_L$ residues are shown underlined):

```
DIQMTQSPSS LSASVGDRVT ITCQASQDIS NYLNWYQQKP

GKAPKLLIYD ASNLETGVPS RFSGSGSGTD FTFTISSLQP

EDIATYFCQH FDHLPLAFGG GTKVEIKR
```

The present invention specifically includes and encompasses CD16×EGFR Binding Molecules that comprise the VL and/or VH Domain, and/or 1, 2 or all 3 of the CDR$_L$s of the VL Region and/or 1, 2 or all 3 of the CDR$_H$s of the VH Domain of the anti-EGFR monoclonal antibodies Cetuximab or Panitumumab.

4. Exemplary Anti-EphA2 Antibodies

The receptor tyrosine kinase, Ephrin type-A receptor 2 (EphA2) is normally expressed at sites of cell-to-cell contact in adult epithelial tissues, however, recent studies have shown that it is also overexpressed in various types of epithelial carcinomas, with the greatest level of EphA2 expression observed in metastatic lesions. High expression levels of EphA2 have been found in a wide range of cancers and in numerous cancer cell lines, including prostate cancer, breast cancer, non-small cell lung cancer and melanoma (Xu, J. et al. (2014) "*High EphA2 Protein Expression In Renal Cell Carcinoma Is Associated With A Poor Disease Outcome*," Oncol. Lett. August 2014; 8(2): 687-692; Miao, B. et al. (2014) "*EphA2 is a Mediator of Vemurafenib Resistance and a Novel Therapeutic Target in Melanoma*," Cancer Discov. pii: CD-14-0295). EphA2 does not appear to be merely a marker for cancer, but rather appears to be persistently overexpressed and functionally changed in numerous human cancers (Chen, P. et al. (2014) "*EphA2 Enhances The Proliferation And Invasion Ability Of LnCap Prostate Cancer Cells*," Oncol. Lett. 8(1):41-46). Exemplary antibodies that bind human EphA2 are "EphA2 mAb 1," "EphA2 mAb 2" and "EphA2 mAb 3."

The amino acid sequence of the VH Domain of EphA2 mAb 1 (SEQ ID NO:114) is shown below (CDR$_H$ residues are shown underlined):

```
QVQLKESGPG LVAPSQSLSI TCTVSGFSLS RYSVHWVRQP

PGKGLEWLGM IWGGGSTDYN SALKSRLSIS KDNSKSQVFL

KMNSLQTDDT AMYYCARKHG NYYTMDYWGQ GTSVTVSS
```

The amino acid sequence of the VL Domain of EphA2 mAb 1 (SEQ ID NO:115) is shown below (CDR$_L$ residues are shown underlined):

```
DIQMTQTTSS LSASLGDRIT ISCRASQDIS NYLNWYQQKP

DGTVKLLIYY TSRLHSGVPS RFSGSGSGTD YSLTISNLEQ

EDIATYFCQQ GYTLYTFGGG TKLEIK
```

The amino acid sequence of the VH Domain of EphA2 mAb 2 (SEQ ID NO:116) is shown below (CDR$_H$ residues are shown underlined):

```
QIQLVQSGPE LKKPGETVKI SCKASGFTFT NYGMNWVKQA

PGKGLKWMGW INTYIGEPTY ADDFKGRFVF SLETSASTAY

LQINNLKNED MATYFCAREL GPYYFDYWGQ GTTLTVSS
```

The amino acid sequence of the VL Domain of EphA2 mAb 2 (SEQ ID NO:117) is shown below (CDR$_L$ residues are shown underlined):

```
DVVMTQTPLS LPVSLGDQAS ISCRSSQSLV HSSGNTYLHW

YLQKPGQSPK LLIYKVSNRF SGVPDRFSGS GSGTDFTLKI

SRVEAEDLGV YFCSQSTHVP TFGSGTKLEI K
```

The amino acid sequence of the VH Domain of EphA2 mAb 3 (SEQ ID NO:118) is shown below (CDR$_H$ residues are shown underlined):

```
EVQLVESGGG SVKPGGSLKL SCAASGFTFT DHYMYWVRQT

PEKRLEWVAT ISDGGSFTSY PDSVKGRFTI SRDIAKNNLY

LQMSSLKSED TAMYYCTRDE SDRPFPYWGQ GTLVTVSS
```

The amino acid sequence of the VL Domain of EphA2 mAb 3 (SEQ ID NO:119) is shown below (CDR$_L$ residues are shown underlined):

```
DIVLTQSHRS MSTSVGDRVN ITCKASQDVT TAVAWYQQKP

GQSPKLLIFW ASTRHAGVPD RFTGSGSGTD FTLTISSVQA

GDLALYYCQQ HYSTPYTFGG GTKLEIK
```

The present invention specifically includes and encompasses CD16×EphA2 Binding Molecules that comprise the VL and/or VH Domain, and/or 1, 2 or all 3 of the CDR$_L$5 of the VL Region and/or 1, 2 or all 3 of the CDR$_H$s of the VH Domain of anti-EphA2 monoclonal antibodies EphA2 mAb 1, EphA2 mAb 2 and EphA2 mAb 3.

5. Exemplary Anti-gpA33 Antibodies

The 43 kD transmembrane glycoprotein A33 (gpA33) is expressed in >95% of all colorectal carcinomas (Heath, J. K. et al. (1997) "*The Human A33 Antigen Is A Transmembrane Glycoprotein And A Novel Member Of The Immunoglobulin Superfamily*," Proc. Natl. Acad. Sci. (U.S.A.) 94(2):469-474; Ritter, G. et al. (1997) "*Characterization Of Posttranslational Modifications Of Human A33 Antigen, A Novel Palmitoylated Surface Glycoprotein Of Human Gastrointestinal Epithelium*," Biochem. Biophys. Res. Commun. 236 (3):682-686; Wong, N. A. et al. (2006) "*EpCAM and gpA33 Are Markers Of Barrett's Metaplasia*," J. Clin. Pathol. 59(3):260-263). An exemplary antibody that binds to human gpA33 is "gpA33 mAb 1."

The amino acid sequence of the VH Domain of gpA33 mAb 1 (SEQ ID NO:120) is shown below (CDR$_H$ residues are shown underlined):

```
QVQLVQSGAE VKKPGASVKV SCKASGYTFT GSWMNWVRQA

PGQGLEWIGR IYPGDGETNY NGKFKDRVTI TADKSTSTAY

MELSSLRSED TAVYYCARIY GNNVYFDVWG QGTTVTVSS
```

The amino acid sequence of the VL Domain of gpA33 mAb 1 (SEQ ID NO:121) is shown below (CDR$_L$ residues are shown underlined):

```
DIQLTQSPSF LSASVGDRVT ITCSARSSIS FMYWYQQKPG

KAPKLLIYDT SNLASGVPSR FSGSGSGTEF TLTISSLEAE

DAATYYCQQW SSYPLTFGQG TKLEIK
```

The present invention specifically includes and encompasses CD16×gpA33 Binding Molecules that comprise the VL and/or VH Domain, and/or 1, 2 or all 3 of the CDR$_L$s of the VL Region and/or 1, 2 or all 3 of the CDR$_H$s of the VH Domain of anti-gpA33 monoclonal antibodies gpA33 mAb 1, or of any of the anti-gpA33 monoclonal antibodies provided in WO 2015/026894.

6. Exemplary Anti HER2/Neu Antibodies

HER2/neu is a 185 kDa receptor protein that was originally identified as the product of the transforming gene from neuroblastomas of chemically treated rats. HER2/neu has been extensively investigated because of its role in several human carcinomas and in mammalian development (Hynes et al. (1994) Biochim. Biophys. Acta 1198:165-184; Dougall et al. (1994) Oncogene 9:2109-2123; Lee et al. (1995) Nature 378:394-398). Exemplary antibodies that bind human HER2/neu include "Margetuximab," "Trastuzumab" and "Pertuzumab." Margetuximab (also known as MGAH22; CAS Reg No. 1350624-75-7) is an Fc-optimized monoclonal antibody that binds to HER2/neu and mediates enhanced ADCC activity. Trastuzumab (also known as rhuMAB4D5, and marketed as HERCEPTIN®; CAS Reg No 180288-69-1; see, U.S. Pat. No. 5,821,337) is the humanized version of antibody 4D5, having IgG1/kappa constant regions. Pertuzumab (also known as rhuMAB2C4, and marketed as PERJETA™; CAS Reg No 380610-27-5; see for example, WO2001/000245) is a humanized version of antibody 2C4 having IgG1/kappa constant regions.

The present invention specifically includes and encompasses CD16×HER2/neu Binding Molecules that comprise the VL and/or VH Domain, and/or 1, 2 or all 3 of the CDR$_L$s of the VL Region and/or 1, 2 or all 3 of the CDR$_H$s of the VH Domain of the anti-HER2/neu monoclonal antibodies Margetuximab, Trastuzumab or Pertuzumab.

The amino acid sequence of the VH Domain of Margetuximab (SEQ ID NO:122 is shown below (CDR$_H$ residues are shown underlined):

```
QVQLQQSGPE LVKPGASLKL SCTASGFNIK DTYIHWVKQR

PEQGLEWIGR IYPTNGYTRY DPKFQDKATI TADTSSNTAY

LQVSRLTSED TAVYYCSRWG GDGFYAMDYW GQGASVTVSS
```

The amino acid sequence of the VL Domain of Margetuximab (SEQ ID NO:123) is shown below (CDR$_L$ residues are shown underlined):

```
DIVMTQSHKF MSTSVGDRVS ITCKASQDVN TAVAWYQQKP

GHSPKLLIYS ASFRYTGVPD RFTGSRSGTD FTFTISSVQA

EDLAVYYCQQ HYTTPPTFGG GTKVEIK
```

The amino acid sequences of the complete Heavy and Light Chains of Margetuximab are known in the art (see., e.g., WHO Drug Information, 2014, Recommended INN: List 71, 28(1):93-94).

The amino acid sequence of the VH Domain of Trastuzumab (SEQ ID NO:124) is shown below (CDR$_H$ residues are shown underlined):

```
EVQLVESGGG LVQPGGSLRL SCAASGFNIK DTYIHWVRQA

PGKGLEWVAR IYPTNGYTRY ADSVKGRFTI SADTSKNTAY

LQMNSLRAED TAVYYCSRWG GDGFYAMDYW GQGTLVTVSS
```

The amino acid sequence of the VL Domain of Trastuzumab (SEQ ID NO:125) is shown below (CDR$_L$ residues are shown underlined):

```
DIQMTQSPSS LSASVGDRVT ITCRASQDVN TAVAWYQQKP

GKAPKLLIYS ASFLYSGVPS RFSGSRSGTD FTLTISSLQP

EDFATYYCQQ HYTTPPTFGQ GTKVEIK
```

The amino acid sequence of the VH Domain of Pertuzumab (SEQ ID NO:126) is shown below (CDR$_H$ residues are shown underlined):

```
EVQLVESGGG LVQPGGSLRL SCAASGFTFT DYTMDWVRQA

PGKGLEWVAD VNPNSGGSIY NQRFKGRFTL SVDRSKNTLY

LQMNSLRAED TAVYYCARNL GPSFYFDYWG QGTLVTVSS
```

The amino acid sequence of the VL Domain of Pertuzumab (SEQ ID NO:127) is shown below (CDR$_L$ residues are shown underlined):

```
DIQMTQSPSS LSASVGDRVT ITCKASQDVS IGVAWYQQKP

GKAPKLLIYS ASYRYTGVPS RFSGSGSGTD FTLTISSLQP

EDFATYYCQQ YYIYPYTFGQ GTKVEIK
```

In addition to the above-identified preferred anti-HER2/neu Binding Molecules, the invention includes and encompasses CD16×HER2/neu Binding Molecules that comprise the VL and/or VH Domain, and/or 1, 2 or all 3 of the $CDR_L$s of the VL Region and/or 1, 2 or all 3 of the $CDR_H$s of the VH Domain of any of the following anti-HER2/neu Binding Molecules: 1.44.1; 1.140; 1.43; 1.14.1; 1.100.1; 1.96; 1.18.1; 1.20; 1.39; 1.24; and 1.71.3 (U.S. Pat. Nos. 8,350,011; 8,858,942; and PCT Patent Publication WO 2008/019290); F5 and C1 (U.S. Pat. Nos. 7,892,554; 8,173,424; 8,974,792; and PCT Patent Publication WO 99/55367); and also the anti-HER2/neu Binding Molecules of US Patent Publication US2013017114 and PCT Patent Publications WO2011/147986 and WO 2012/143524).

The present invention specifically includes and encompasses CD16×HER2/neu Binding Molecules that comprise the VL and/or VH Domain, and/or 1, 2 or all 3 of the $CDR_L$s of the VL Region and/or 1, 2 or all 3 of the $CDR_H$s of the VH Domain of any of Margetuximab, Trastuzumab or Pertuzumab, or any of the other anti-HER2/neu antibodies provided herein; and more preferably possess 1, 2 or all 3 of the $CDR_L$s of the VL Region and/or 1, 2 or all 3 of the $CDR_H$s of the VH Domain of such anti-HER2/neu monoclonal antibodies.

7. Exemplary Anti-VEGF Antibodies

VEGF-A is a chemical signal that stimulates angiogenesis in a variety of diseases, especially in certain metastatic cancers such as metastatic colon cancer, and in certain lung cancers, renal cancers, ovarian cancers, and glioblastoma multiforme of the brain. An exemplary antibody that binds to human VEGF-A is "Bevacizumab" (Avastin®). Bevacizumab is a recombinant humanized IgG1 monoclonal antibody (Midgley, R. et al. (2005) "*Bevacizumab—Current Status And Future Directions,*" Ann. Oncol. 16(7):999-1004; Hall, R. D. et al. (2015) "*Angiogenesis Inhibition As A Therapeutic Strategy In Non-Small Cell Lung Cancer (NSCLC),*" Transl. Lung Cancer Res. 4(5):515-523; Narita, Y. (2015) "Bevacizumab For Glioblastoma," Ther. Clin. Risk Manag. 11:1759-1765).

The amino acid sequence of the VH Domain of Bevacizumab (SEQ ID NO:128) is shown below ($CDR_H$ residues are shown underlined):

```
EVQLVESGGG LVQPGGSLRL SCAASGYTFT NYGMNWVRQA

PGKGLEWVGW INTYTGEPTY AADFKRRFTF SLDTSKSTAY

LQMNSLRAED TAVYYCAKYP HYYGSSHWYF DVWGQGTLVT VSS
```

The amino acid sequence of the VL Domain of Bevacizumab (SEQ ID NO:129) is shown below ($CDR_L$ residues are shown underlined):

```
    DIQMTQSPSS LSASVGDRVT ITCSASQDIS NYLNWYQQKP

GKAPKVLIYF TSSLHSGVPS RFSGSGSGTD FTLTISSLQP

EDFATYYCQQ YSTVPWTFGQ GTKVEIKR
```

The present invention specifically includes and encompasses CD16×VEGF Binding Molecules that comprise the VL and/or VH Domain, and/or 1, 2 or all 3 of the $CDR_L$5 of the VL Region and/or 1, 2 or all 3 of the $CDR_H$s of the VH Domain of the anti-VEGF monoclonal antibody Bevacizumab.

8. Exemplary Anti-5T4 Antibodies

The oncofetal protein, 5T4, is a tumor-associated protein displayed on the cell membrane of many carcinomas, including kidney, colon, prostate, lung, carcinoma and in acute lymphoblastic leukemia (see, Boghaert, E. R. et al. (2008) "*The Oncofetal Protein, 5T4, Is A Suitable Target For Antibody-Guided Anti-Cancer Chemotherapy With Calicheamicin,*" Int. J. Oncol. 32(1):221-234; Eisen, T. et al. (2014) "*Naptumomab Estafenatox: Targeted Immunotherapy with a Novel Immunotoxin,*" Curr. Oncol. Rep. 16:370, pp. 1-6). Exemplary antibodies that bind to human 5T4 include "5T4 mAb 1" and "5T4 mAb 2."

The amino acid sequence of the VH Domain of 5T4 mAb 1 (SEQ ID NO:130) is shown below (CDR residues are shown underlined):

```
QVQLVQSGAE VKKPGASVKV SCKASGYTFT SFWMHWVRQA

PGQGLEWMGR IDPNRGGTEY NEKAKSRVTM TADKSTSTAY

MELSSLRSED TAVYYCAGGN PYYPMDYWGQ GTTVTVSS
```

The amino acid sequence of the VL Domain of an 5T4 mAb 1 (SEQ ID NO:131) is shown below (CDR residues are shown underlined):

```
DIQMTQSPSS LSASVGDRVT ITCRASQGIS NYLAWFQQKP

GKAPKSLIYR ANRLQSGVPS RFSGSGSGTD FTLTISSLQP

EDVATYYCLQ YDDFPWTFGQ GTKLEIK
```

The amino acid sequence of the VH Domain of 5T4 mAb 2 (SEQ ID NO:132) is shown below (CDR residues are shown underlined):

```
QVQLQQPGAE LVKPGASVKM SCKASGYTFT SYWITWVKQR

PGQGLEWIGD IYPGSGRANY NEKFKSKATL TVDTSSSTAY

MQLSSLTSED SAVYNCARYG PLFTTVVDPN SYAMDYWGQG TSVTVSS
```

The amino acid sequence of the VL Domain of 5T4 mAb 2 (SEQ ID NO:133) is shown below (CDR residues are shown underlined):

```
DVLMTQTPLS LPVSLGDQAS ISCRSSQSIV YSNGNTYLEW

YLQKPGQSPK LLIYKVSNRF SGVPDRFSGS GSGTDFTLKI

SRVEAEDLGV YYCFQGSHVP FTFGSGTKLE IK
```

The present invention specifically includes and encompasses CD16×5T4 Binding Molecules that comprise the VL and/or VH Domain, and/or 1, 2 or all 3 of the $CDR_L$s of the VL Region and/or 1, 2 or all 3 of the $CDR_H$s of the VH Domain of the anti-5T4 monoclonal antibodies 5T4 mAb 1 or 5T4 mAb 2, or of any of the anti-5T4 antibodies provided in WO 2013/041687 or WO 2015/184203.

The present application additionally specifically includes and encompasses CD16×5T4 Trispecific Binding Molecules that are capable of binding to 5T4, to CD16 and to CD8, and particularly such trispecific binding molecules that comprise the VL and/or VH Domain, and/or 1, 2 or all 3 of the $CDR_L$s of the VL Region and/or 1, 2 or all 3 of the $CDR_H$s of the VH Domain of the anti-5T4 monoclonal antibodies 5T4 mAb 1 or 5T4 mAb 2 or of any of the anti-5T4 monoclonal antibodies provided in WO 2015/184203, and/or the VL and/or VH Domain, and/or 1, 2 or all 3 of the CDR$_L$s of the VL Region and/or 1, 2 or all 3 of the CDR$_H$s of the VH Domain of any of the anti-CD8 monoclonal antibodies provided herein.

9. Exemplary Anti-IL13Rα2 Antibodies

Interleukin-13 Receptor α2 (IL13Rα2) is overexpressed in a variety of cancers, including glioblastoma, colorectal cancer, cervical cancer, pancreatic cencer, multiple melanoma, osteosarcoma, leukemia, lymphoma, prostate cancer and lung cancer (PCT Pubmication No. WO 2008/146911; Brown, C. E. et al. (2013) "*Glioma IL13Rα2 Is Associated With Mesenchymal Signature Gene Expression And Poor Patient Prognosis*," PLoS One. 18; 8(10):e77769; Barderas, R. et al. (2012) "*High Expression Of IL-13 Receptor A2 In Colorectal Cancer Is Associated With Invasion, Liver Metastasis, And Poor Prognosis*," Cancer Res. 72(11):2780-2790; Kasaian, M. T. et al. (2011) "*IL-13 Antibodies Influence IL-13 Clearance In Humans By Modulating Scavenger Activity Of IL-13Rα2*," J. Immunol. 187(1):561-569; Bozinov, O. et al. (2010) "*Decreasing Expression Of The Interleukin-13 Receptor IL-13Ralpha2 In Treated Recurrent Malignant Gliomas*," Neurol. Med. Chir. (Tokyo) 50(8): 617-621; Fujisawa, T. et al. (2009) "*A Novel Role Of Interleukin-13 Receptor Alpha2 In Pancreatic Cancer Invasion And Metastasis*," Cancer Res. 69(22):8678-8685). Antibodies that immunospecifically bind to IL13Rα2 are commercially available and have been described in the art (Abnova Corporation, Biorbyt, LifeSpan BioSciences, United States Biologicals; see also PCT Publication No. WO 2008/146911). Exemplary antibodies that bind to human IL13Rα2 include "hu08" (see, e.g., PCT Publication No. WO 2014/072888).

The amino acid sequence of the VH Domain of hu08 (SEQ ID NO:134) is shown below (CDR residues are shown underlined):

```
EVQLVESGGG LVQPGGSLRL SCAASGFTFS RNGMSWVRQA

PGKGLEWVAT VSSGGSYIYY ADSVKGRFTI SRDNAKNSLY

LQMNSLRAED TAVYYCARQG TTALATRFFD VWGQGTLVTV SS
```

The amino acid sequence of the VL Domain of hu08 (SEQ ID NO:135) is shown below (CDR residues are shown underlined):

```
DIQMTQSPSS LSASVGDRVT ITCKASQDVG TAVAWYQQKP

GKAPKLLIYS ASYRSTGVPS RFSGSGSGTD FTLTISSLQP

EDFATYYCQH HYSAPWTFGG GTKVEIK
```

The present invention specifically includes and encompasses CD16×IL13Rα2 Binding Molecules that comprise the VL and/or VH Domain, and/or 1, 2 or all 3 of the CDR$_L$s of the VL Region and/or 1, 2 or all 3 of the CDR$_H$s of the VH Domain of the anti-IL13Rα2 monoclonal antibody hu08.

10. Exemplary Anti-CD123 Antibodies

CD123 (interleukin 3 receptor alpha, IL-3Ra) is a 40 kDa molecule and is part of the interleukin 3 receptor complex (Stomski, F. C. et al. (1996) "*Human Interleukin-3 (IL-3) Induces Disulfide-Linked IL-3 Receptor Alpha-And Beta-Chain Heterodimerization, Which Is Required For Receptor Activation But Not High-Affinity Binding*," Mol. Cell. Biol. 16(6):3035-3046). Interleukin 3 (IL-3) drives early differentiation of multipotent stem cells into cells of the erythroid, myeloid and lymphoid progenitors. CD123 has been reported to be overexpressed on malignant cells in a wide range of hematologic malignancies including acute myeloid leukemia (AML) and myelodysplastic syndrome (MDS) (Muñoz, L. et al. (2001) "*Interleukin-3 Receptor Alpha Chain (CD123) Is Widely Expressed In Hematologic Malignancies*," Haematologica 86(12):1261-1269). Overexpression of CD123 is associated with poorer prognosis in AML (Tettamanti, M. S. et al. (2013) "*Targeting Of Acute Myeloid Leukaemia By Cytokine-Induced Killer Cells Redirected With A Novel CD123-Specific Chimeric Antigen Receptor*," Br. J. Haematol. 161:389-401).

An exemplary antibody that binds to human CD123, and that may be employed in the present invention, is "CD123 mAb 1" (see, e.g., PCT Patent Publication WO 2015/026892).

The amino acid sequence of the VH Domain of CD123 mAb 1 (SEQ ID NO:136) is shown below (CDR$_H$ residues are shown underlined):

```
EVQLVQSGAE LKKPGASVKV SCKASGYTFT DYYMKWVRQA

PGQGLEWIGD IIPSNGATFY NQKFKGRVTI TVDKSTSTAY

MELSSLRSED TAVYYCARSH LLRASWFAYW GQGTLVTVSS
```

The amino acid sequence of the VL Domain of CD123 mAb 1 (SEQ ID NO:137) is shown below (CDR$_L$ residues are shown underlined):

```
DFVMTQSPDS LAVSLGERVT MSCKSSQSLL NSGNQKNYLT

WYQQKPGQPP KLLIYWASTR ESGVPDRFSG SGSGTDFTLT

ISSLQAEDVA VYYCQNDYSY PYTFGQGTKL EIK
```

The present invention specifically includes and encompasses CD16×CD123 Binding Molecules that comprise the VL and/or VH Domain, and/or 1, 2 or all 3 of the CDR$_L$s of the VL Region and/or 1, 2 or all 3 of the CDR$_H$s of the VH Domain of the anti-CD123 monoclonal antibody CD123 mAb 1 or any of the anti-CD123 antibodies disclosed in US 2017/081424 and WO 2016/036937.

11. Exemplary Anti-CD19 Antibodies

CD19 (B lymphocyte surface antigen B4, Genbank accession number M28170) is a component of the B cell-receptor (BCR) complex, and is a positive regulator of B cell signaling that modulates the threshold for B cell activation and humoral immunity. CD19 is one of the most ubiquitously expressed antigens in the B cell lineage and is expressed on >95% of B cell malignancies, including acute lymphoblastic leukemia (ALL), chronic lymphocytic leukemia (CLL), and non-Hodgkin's Lymphoma (NHL). Notably, CD19 expression is maintained on B cell lymphomas that become resistant to anti-CD20 therapy (Davis et al. (1999) "*Therapy of B-cell Lymphoma With Anti-CD20 Antibodies Can Result In The Loss Of CD20 Antigen Expression*." Clin Cancer Res, 5:611-615, 1999). CD19 has also been suggested as a target to treat autoimmune diseases (Tedder (2009) "*CD19: A Promising B Cell Target For Rheumatoid Arthritis*," Nat. Rev. Rheumatol. 5:572-577).

An exemplary antibody that binds to human CD19, and that may be employed in the present invention, is the anti-CD19 antibody disclosed in WO 2016/048938 (referred to herein as "CD19 mAb 1").

The amino acid sequence of the VH Domain of CD19 mAb 1 SEQ ID NO:138) is shown below (CDR$_H$ residues are shown underlined):

```
QVTLRESGPA LVKPTQTLTL TCTFSGFSLS TSGMGVGWIR

QPPGKALEWL AHIWWDDDKR YNPALKSRLT ISKDTSKNQV

FLTMTNMDPV DTATYYCARM ELWSYYFDYW GQGTTVTVSS
```

The amino acid sequence of the VL Domain of CD19 mAb 1 (SEQ ID NO:139) is shown below (CDR$_L$ residues are shown underlined):

```
ENVLTQSPAT LSVTPGEKAT ITCRASQSVS YMHWYQQKPG

QAPRLLIYDA SNRASGVPSR FSGSGSGTDH TLTISSLEAE

DAATYYCFQG SVYPFTFGQG TKLEIK
```

The present invention specifically includes and encompasses CD16×CD19 Binding Molecules that comprise the VL and/or VH Domain, and/or 1, 2 or all 3 of the CDR$_L$s of the VL Region and/or 1, 2 or all 3 of the CDR$_H$s of the VH Domain of the anti-CD19 monoclonal antibody CD19 mAb 1, or any of the anti-CD19 antibodies disclosed in U.S. Pat. No. 7,112,324.

B. Exemplary Pathogen-Associated Antigens

As used herein, the term "Pathogen-Associated Antigen" denotes an antigen that is characteristically expressed on the surface of a pathogen-infected cell, and that may thus be treated with an Antibody-Based Molecule or an Immunomodulatory Molecule. Examples of Pathogen-Associated Antigens include, but are not limited to antigens expressed on the surface of a cell infected with: a Herpes Simplex Virus (e.g., infected cell protein (ICP)47, gD, etc.), a varicella-zoster virus, a Kaposi's sarcoma-associated herpesvirus, an Epstein-Barr Virus (e.g., LMP-1, LMP-2A, LMP-2B, etc.), a Cytomegalovirus (e.g., UL11, etc.), Human Immunodeficiency Virus (e.g., env proteins gp160, gp120, gp41, etc.), a Human Papillomavirus (e.g., E6, E7, etc.), a human T-cell leukemia virus (e.g., env proteins gp64, gp46, gp21, etc.), Hepatitis A Virus, Hepatitis B Virus, Hepatitis C Virus, Vesicular Stomatitis Virus (VSV), Bacilli, *Citrobacter*, Cholera, Diphtheria, *Enterobacter*, Gonococci, *Helicobacter pylori*, *Klebsiella*, *Legionella*, Meningococci, mycobacteria, *Pseudomonas*, Pneumonococci, *rickettsia* bacteria, *Salmonella*, *Serratia*, Staphylococci, Streptococci, Tetanus, *Aspergillus* (*fumigatus, niger*, etc.), *Blastomyces dermatitidis*, *Candida* (*albicans, krusei, glabrata, tropicalis*, etc.), *Cryptococcus neoformans*, Genus Mucorales (*mucor, absidia, rhizopus*), *Sporothrix schenkii*, *Paracoccidioides brasiliensis*, *Coccidioides immitis*, *Histoplasma capsulatum*, Leptospirosis, *Borrelia burgdorferi*, helminth parasite (hookworm, tapeworms, flukes, flatworms (e.g. Schistosomia), Giardia Zambia, *trichinella, Dientamoeba Fragilis, Trypanosoma brucei, Trypanosoma cruzi*, and *Leishmania donovani*). Such antibodies are available commercially from a wide number of sources, or can be obtained by immunizing mice or other animals (including for the production of monoclonal antibodies) with such antigens.

Exemplary antibodies, whose VH and VL Domains may be used to construct molecules capable of binding a Pathogen-Associated Antigen arrayed on the surface of a pathogen-infected cell are antibodies are provided below, additional antibodies are known in the art.

1. Exemplary Anti-HIV Antibodies

The env protein of HIV is an exemplary Pathogen-Associated Antigen, and antibodies that bind the env protein of HIV are exemplary of antibodies capable of binding a Pathogen-Associated Antigen.

The initial step in HIV-1 infection occurs with the binding of cell surface CD4 to trimeric HIV-1 envelope glycoproteins (env), a heterodimer of a transmembrane glycoprotein (gp41) and a surface glycoprotein (gp120). The gp120 and gp41 glycoproteins are initially synthesized as a single gp160 polypeptide that is subsequently cleaved to generate the non-covalently associated gp120/gp41 complex. The ectodomain of env is a heterodimer with mass of approximately 140 kDa, composed of the entire gp120 component, and approximately 20 kDa of gp41 (Harris, A. et al. (2011) "*Trimeric HIV-1 Glycoprotein Gp140 Immunogens And Native HIV-1 Envelope Glycoproteins Display The Same Closed And Open Quaternary Molecular Architectures*," Proc. Natl. Acad. Sci. (U.S.A.) 108(28):11440-11445). Antibodies that that immunospecifically bind to env proteins are commercially available and have been described in the art (see, e.g., GenBank Accession No. AFQ31503; Buchacher, A. et al. (1994) "*Generation Of Human Monoclonal Antibodies Against HIV-1 Proteins; Electrofusion And Epstein-Barr Virus Transformation For Peripheral Blood Lymphocyte Immortalization*," AIDS Res. Hum. Retroviruses 10(4): 359-369; Shen, R. (2010) "*GP41-Specific Antibody Blocks Cell-Free HIV Type 1 Transcytosis Through Human Rectal Mucosa And Model Colonic Epithelium*," J. Immunol. 184 (7):3648-3655; WO 2012/162068; and WO 2016/054101). Exemplary antibodies that bind to HIV env include "7B2" (GenBank Accession No. AFQ31503) and "A32" (PCT Publication No. WO 2014/159940).

Antibody 7B2 (Genbank accession numbers JX188438 and JX188439) is an anti-HIV env human IgG1 antibody that binds HIV gp41 at 598-604 in the immunodominant helix-loop-helix region of the molecule (Sadraeian, M. et al. (2017) "*Selective Cytotoxicity Of A Novel Immunotoxin Based On Pulchellin A Chain For Cells Expressing HIV Envelope*," Sci. Rep. 7(1):7579 doi: 10.1038/s41598-017-08037-3). The antibody was isolated from an HIV-1 chronically infected subject using Epstein-Barr (EB) virus B cell transformation and heterohybridoma production (Pincus, S. H. et al. (2003) "*In Vivo Efficacy Of Anti-Glycoprotein 41, But Not Anti-Glycoprotein 120, Immunotoxins In A Mouse Model Of HIV Infection*," J. Immunol. 170(4):2236-2241). Antibody 7B2 has been found to be capable of recognizing both virus particles and infected cells (Santra, S. et al. (2015) "*Human Non-neutralizing HIV-1 Envelope Monoclonal Antibodies Limit the Number of Founder Viruses during SHIV Mucosal Infection in Rhesus Macaques*," PLoS Pathog. 11(8):e1005042. doi: 10.1371/journal.ppat.1005042; Tay, M. Z. et al. (2016) "*Antibody-Mediated Internalization of Infectious HIV-1 Virions Differs among Antibody Isotypes and Subclasses*," PLoS Pathog. 12(8):e1005817. doi: 10.1371/journal.ppat.1005817).

The amino acid sequence of the VH Domain of 7B2 (SEQ ID NO:140) is shown below (CDR residues are shown underlined):

```
QVQLVQSGGG VFKPGGSLRL SCEASGFTFT EYYMTWVRQA

PGKGLEWLAY ISKNGEYSKY SPSSNGRFTI SRDNAKNSVF

LQLDRLSADD TAVYYCARAD GLTYFSELLQ YIFDLWGQGA RVTVSS
```

The amino acid sequence of the VL Domain of 7B2 (SEQ ID NO:141) is shown below (CDR residues are shown underlined):

```
DIVMTQSPDS LAVSPGERAT IHCKSSQTLL YSSNNRHSIA

WYQQRPGQPP KLLLYWASMR LSGVPDRFSG SGSGTDFTLT

INNLQAEDVA IYYCHQYSSH PPTFGHGTRV EIK
```

Monoclonal antibody A32 recognizes a conformational epitope in the C1 region of HIV-1 Env gp120 (Wyatt et al. (1995) "*Involvement Of The V1/V2 Variable Loop Structure In The Exposure Of Human Immunodeficiency Virus Type 1 gp120 Epitopes Induced By Receptor Binding*," J. Virol. 69:5723-5733) and mediates potent ADCC activity and could block a significant proportion of ADCC-mediating Ab activity detectable in HIV-1 infected individuals (Ferrari, G. et al. (2011) "*An HIV-1 gp120 Envelope Human Monoclonal Antibody That Recognizes a C1 Conformational Epitope Mediates Potent Antibody Dependent Cellular Cytotoxicity (ADCC) Activity and Defines a Common ADCC Epitope in Human HIV-1 Serum*," J. Virol. 85(14): 7029-7036). Multiple VH Domains of Antibody A32 have been reported in the art that possess minor changes in framework regions 1 and/or 4 reported (see, e.g., Protein Data Base Accession number PDB: 4YBL_H, US 2015/0239961 and WO 2006/044410). Any of these variant Antibody A32 VH Domains may be employed in accordance with the present invention. The amino acid sequence of an illustrative VH Domain of A32 (SEQ ID NO:142) is shown below (CDR residues are shown underlined):

```
QVQLQESGPG LVKPSQTLSL SCTVSGGSSS SGAHYWSWIR

QYPGKGLEWI GYIHYSGNTY YNPSLKSRIT ISQHTSENQF

SLKLNSVTVA DTAVYYCARG TRLRTLRNAF DIWGQGTLVT

VSS
```

The amino acid sequence of the VL Domain of A32 (SEQ ID NO:143) is shown below (CDR residues are shown underlined):

```
QSALTQPPSA SGSPGQSVTI SCTGTSSDVG GYNYVSWYQH

HPGKAPKLII SEVNNRPSGV PDRFSGSKSG NTASLTVSGL

QAEDEAEYYC SSYTDIHNFV FGGGTKLTVL
```

The amino acid sequence of the VL Domain of A32 (SEQ ID NO:143) may be employed with the illustrative VH Domain of A32 (SEQ ID NO:142) or with any of the variant Antibody A32 VH Domains (see, e.g., Protein Data Base Accession number PDB: 4YBL_H, US 2015/0239961 and WO 2006/044410) to form an anti-HIV-1 Env gp120 Epitope Binding Site.

The present invention specifically includes and encompasses CD16×HIV Binding Molecules that comprise the VL and/or VH Domain, and/or 1, 2 or all 3 of the CDR$_L$s of the VL Region and/or 1, 2 or all 3 of the CDR$_H$s of the VH Domain of the anti-HIV monoclonal antibodies 7B2 or A32, or of any of the anti-HIV antibodies disclosed in WO 2016196975, WO 2016/149710, WO 2016/149698, WO 2016/149695, WO 2015/048610, WO 2012/030904, WO 2013/163427, WO 2013/192589, WO 2014/063059, WO 20170/11413, WO 2016/054101, WO 2014/159940, or WO 2017/011414.

The present application additionally specifically includes and encompasses CD16×HIV Binding Molecules that are capable of binding to HIV, to CD16 and to CD8, and particularly such trispecific binding molecules that comprise the VL and/or VH Domain, and/or 1, 2 or all 3 of the CDR$_L$s of the VL Region and/or 1, 2 or all 3 of the CDR$_H$s of the VH Domain of the anti-HIV monoclonal antibodies 7B2 or A32 or of any of the anti-HIV monoclonal antibodies provided in WO 2015/184203, WO 2016/054101, WO 2017/011413, WO 2017/011414.

2. Exemplary Anti-RSV Antibody

A further illustrative Pathogen-Associated Antigen is RSV glycoprotein F. An exemplary anti-RSV glycoprotein F antibody is Palivizumab (see, e.g., Protein Data Bank (PDB) ID No. 2HWZ). Alternative anti-RSV glycoprotein F antibodies include motavizumab (see, e.g., PDB ID No. 3IXT) and a variant of palivizumab (also referred to herein as "vPalivizumab") that has been engineered to remove a cysteine residue from palivizumab's CDR$_L$1. The amino acid sequence of the VH Domain of the variant of palivizumab (SEQ ID NO:144) is shown below (CDR residues are shown underlined):

```
QVTLRESGPA LVKPTQTLTL TCTFSGFSLS TSGMSVGWIR

QPPGKALEWL ADIWWDDKKD YNPSLKSRLT ISKDTSKNQV

VLKVTNMDPA DTATYYCARS MITNWYFDVW GAGTTVTVSS
```

The amino acid sequence of the VL Domain of the variant of palivizumab (SEQ ID NO:145) is shown below (CDR residues are shown underlined):

```
DIQMTQSPST LSASVGDRVT ITCRASQSVG YMHWYQQKPG

KAPKLLIYDT SKLASGVPSR FSGSGSGTEF TLTISSLQPD

DFATYYCFQG SGYPFTFGGG TKLEIK
```

The present invention specifically includes and encompasses CD16×RSV Binding Molecules that comprise the VL and/or VH Domain, and/or 1, 2 or all 3 of the CDR$_L$s of the VL Region and/or 1, 2 or all 3 of the CDR$_H$s of the VH Domain of the anti-RSV monoclonal antibody palivizumab or vPalivizumab.

VII. Exemplary Binding Molecules of the Present Invention

The principles of the present invention are illustrated by a series of exemplary CD16×DA Binding Molecules incorporating different murine or humanized anti-CD16 binding domains and having a Binding Domain that is immunospecific for a Disease Antigen. The covalent diabody structures and sequences of such illustrative CD16×DA Binding Molecules are summarized in Table 12, and are described in detail below. As will be recognized, analogous diabodies and other bispecific molecules may likewise be constructed (by employing the VL and VH domains of desired antibodies in lieu of the VL and VH domains used in the illustrative CD16×DA Binding Molecules.

TABLE 12

| Diabody Name | Polypeptide Chain | SEQ ID NO | Antibody | Domain | SEQ ID NO | Antibody | Domain | SEQ ID NO |
|---|---|---|---|---|---|---|---|---|
| DART-A | 1 | 151 | Trastuzumab | VL | 125 | CD16-M1 | VH | 64 |
|  | 2 | 152 | CD16-M1 | VL | 65 | Trastuzumab | VH | 124 |
|  | 3 | 153 | Common Diabody Polypeptide Chain | | | | | |
| DART-B | 1 | 154 | Trastuzumab | VL | 125 | CD16-M2 | VH | 75 |
|  | 2 | 155 | CD16-M2 | VL | 76 | Trastuzumab | VH | 124 |
|  | 3 | 153 | Common Diabody Polypeptide Chain | | | | | |
| DART-C | 1 | 156 | Trastuzumab | VL | 125 | hCD16-M1 | VH | 72 |
|  | 2 | 157 | hCD16-M1 | VL | 73 | Trastuzumab | VH | 124 |
|  | 3 | 153 | Common Diabody Polypeptide Chain | | | | | |
| DART-D | 1 | 158 | Trastuzumab | VL | 125 | hCD16-M2 | VH1 | 83 |
|  | 2 | 159 | hCD16-M2 | VL | 85 | Trastuzumab | VH | 124 |
|  | 3 | 153 | Common Diabody Polypeptide Chain | | | | | |
| DART-E | 1 | 160 | Trastuzumab | VL | 125 | hCD16-M2 | VH2 | 84 |
|  | 2 | 159 | hCD16-M2 | VL | 85 | Trastuzumab | VH | 124 |
|  | 3 | 153 | Common Diabody Polypeptide Chain | | | | | |
| DART-F | 1 | 161 | A32 | VL | 143 | hCD16-M1 | VH | 72 |
|  | 2 | 162 | hCD16-M1 | VL | 73 | A32 | VH | 142 |
|  | 3 | 153 | Common Diabody Polypeptide Chain | | | | | |
| DART-G | 1 | 163 | A32 | VL | 143 | hCD16-M2 | VH1 | 83 |
|  | 2 | 164 | hCD16-M2 | VL | 85 | A32 | VH | 142 |
|  | 3 | 153 | Common Diabody Polypeptide Chain | | | | | |
| DART-H | 1 | 165 | 7B2 | VL | 141 | hCD16-M1 | VH | 72 |
|  | 2 | 166 | hCD16-M1 | VL | 73 | 7B2 | VH | 140 |
|  | 3 | 153 | Common Diabody Polypeptide Chain | | | | | |
| DART-I | 1 | 186 | Trastuzumab | VL | 125 | hCD16-M1A | VH | 58 |
|  | 2 | 157 | hCD16-M1 | VL | 73 | Trastuzumab | VH | 124 |
|  | 3 | 153 | Common Diabody Polypeptide Chain | | | | | |
| DART-J | 1 | 156 | Trastuzumab | VL | 125 | hCD16-M1 | VH | 72 |
|  | 2 | 187 | hCD16-M1B | VL | 59 | Trastuzumab | VH | 124 |
|  | 3 | 153 | Common Diabody Polypeptide Chain | | | | | |
| DART-K | 1 | 186 | Trastuzumab | VL | 125 | hCD16-M1A | VH | 58 |
|  | 2 | 187 | hCD16-M1B | VL | 59 | Trastuzumab | VH | 124 |
|  | 3 | 153 | Common Diabody Polypeptide Chain | | | | | |
| DART-L | 1 | 188 | CD19 mAb 1 | VL | 139 | hCD16-M1 | VH | 72 |
|  | 2 | 189 | hCD16-M1 | VL | 73 | CD19 mAb 1 | VH | 138 |
|  | 3 | 153 | Common Diabody Polypeptide Chain | | | | | |
| DART-M | 1 | 188 | CD19 mAb 1 | VL | 139 | hCD16-M1 | VH | 72 |
|  | 2 | 190 | hCD16-M1B | VL | 59 | CD19 mAb 1 | VH | 138 |
|  | 3 | 153 | Common Diabody Polypeptide Chain | | | | | |
| DART-N | 1 | 191 | CD19 mAb 1 | VL | 139 | hCD16-M1A | VH | 58 |
|  | 2 | 190 | hCD16-M1B | VL | 59 | CD19 mAb 1 | VH | 138 |
|  | 3 | 153 | Common Diabody Polypeptide Chain | | | | | |
| DART-1 | 1 | 167 | Trastuzumab | VL | 125 | h3G8 | VH | 62 |
|  | 2 | 168 | h3G8 | VL | 63 | Trastuzumab | VH | 124 |
|  | 3 | 153 | Common Diabody Polypeptide Chain | | | | | |
| DART-2 | 1 | — | vPalivizumab | VL | 145 | h3G8 | VH | 62 |
|  | 2 | — | h3G8 | VL | 63 | vPalivizumab | VH | 144 |
|  | 3 | 153 | Common Diabody Polypeptide Chain | | | | | |
| DART-3 | 1 | 169 | vPalivizumab | VL | 145 | hCD16-M1 | VH | 72 |
|  | 2 | 170 | hCD16-M1 | VL | 73 | vPalivizumab | VH | 144 |
|  | 3 | 153 | Common Diabody Polypeptide Chain | | | | | |
| DART-4 | 1 | — | 7B2 | VL | 141 | h3G8 | VH | 62 |
|  | 2 | — | h3G8 | VL | 63 | 7B2 | VH | 140 |
|  | 3 | 153 | Common Diabody Polypeptide Chain | | | | | |
| DART-5 | 1 | — | vPalivizumab | VL | 145 | hCD16-M1 | VH | 72 |
|  | 2 | — | hCD16-M1 | VL | 73 | vPalivizumab | VH | 144 |
|  | 3 | 153 | Common Diabody Polypeptide Chain | | | | | |
| DART-6 | 1 | — | vPalivizumab | VL | 145 | hCD16-M1 | VH | 72 |
|  | 2 | — | hCD16-M1B | VL | 59 | vPalivizumab | VH | 144 |
|  | 3 | 153 | Common Diabody Polypeptide Chain | | | | | |
| DART-7 | 1 | — | vPalivizumab | VL | 145 | hCD16-M1A | VH | 58 |
|  | 2 | — | hCD16-M1B | VL | 59 | vPalivizumab | VH | 144 |
|  | 3 | 153 | Common Diabody Polypeptide Chain | | | | | |
| DART-X | 1 | 171 | 7B2 | VL | 141 | CD16-M1 | VH | 64 |
|  | 2 | 172 | CD16-M1 | VL | 65 | 7B2 | VH | 140 |
| DART-Y | 1 | 173 | 7B2 | VL | 141 | CD16-M2 | VH | 75 |
|  | 2 | 174 | CD16-M2 | VL | 76 | 7B2 | VH | 140 |
| DART-Z | 1 | — | A32 | VL | 143 | 4-LSN1 | VH | 175 |
|  | 2 | — | 4-LSN1 | VL | 176 | A32 | VH | 142 |
| DART-0 | 1 | — | 7B2 | VL | 141 | h3G8 | VH | 62 |
|  | 2 | — | h3G8 | VL | 63 | 7B2 | VH | 140 |

A. CD16×HER2/neu Binding Molecule, DART-A

The CD16×HER2/neu Binding Molecule designated "DART-A" is a first illustrative CD16×DA Binding Molecule. DART-A is an Fc Domain-containing, bispecific diabody capable of binding CD16 and the HER2/neu cancer antigen. DART-A is composed of three polypeptide chains and possesses one Binding Domain that comprises the VL and VH Domains of anti-human CD16 antibody CD16-M1 (and is thus immunospecific for an epitope of CD16) and one Binding Domain that comprises the VL and VH Domains of Trastuzumab (and is thus immunospecific for an epitope of the HER2/neu Cancer Antigen). The three polypeptide chains associate to form a covalently bonded DART® diabody capable of immunospecifically binding the epitope of CD16 and the epitope of the HER2/neu Cancer Antigen (see, e.g., FIG. 4A).

The first polypeptide chain of DART-A has the amino acid sequence of SEQ ID NO:151:

```
DIQMTQSPSS LSASVGDRVT ITCRASQDVN TAVAWYQQKP

GKAPKLLIYS ASFLYSGVPS RFSGSRSGTD FTLTISSLQP

EDFATYYCQQ HYTTPPTFGQ GTKVEIKGGG SGGGGEVKLV

ESGGTLVKPG GSLKLSCAAS GFTFNNYGMS WVRQTPEKRL

EWVATISGGG SYTFYPDSVK GRFTISRDNA KNSLYLQMSS

LRSEDTALYY CIRQSARAPE PYWGQGTLVT VSSASTKGEV

AACEKEVAAL EKEVAALEKE VAALEKGGGD KTHTCPPCPA

PEAAGGPSVF LFPPKPKDTL MISRTPEVTC VVVDVSHEDP

EVKFNWYVDG VEVHNAKTKP REEQYNSTYR VVSVLTVLHQ

DWLNGKEYKC KVSNKALPAP IEKTISKAKG QPREPQVYTL

PPSREEMTKN QVSLWCLVKG FYPSDIAVEW ESNGQPENNY

KTTPPVLDSD GSFFLYSKLT VDKSRWQQGN VFSCSVMHEA

LHNHYTQKSL SLSPGK
```

Residues 1-107 of the first polypeptide chain (SEQ ID NO:151) of such illustrative CD16×DA Binding Molecule correspond to the VL Domain of Trastuzumab (SEQ ID NO:125). Residues 108-115 (double underlined) of the first polypeptide chain correspond to Linker 1 (GGGSGGGG; SEQ ID NO:16). Residues 116-233 of the first polypeptide chain correspond to the VH Domain of anti-human CD16 antibody CD16-M1 (SEQ ID NO:64). Residues 234-238 correspond to a linker (SEQ ID NO:21, underlined). Residues 239-266 of the first polypeptide chain correspond to a cysteine-containing E-coil (SEQ ID NO:31). Residues 267-279 of the first polypeptide chain correspond to a linker (SEQ ID NO:43). Residues 280-496 of the first polypeptide chain correspond to a "knob-bearing" (SEQ ID NO:51), in which the final residue is lysine.

The second polypeptide chain of DART-A has the amino acid sequence of SEQ ID NO:152:

```
DIVMTQSQKF MSTSVGDRVS VTCKASQNVG THVAWYQQKS

GQSPKSLLYS ASYRYSGVPD RFSGSGSGTD FTLTISNVQS

EDLAEYFCQQ YKSYPLTFGA GTKLELKGGG SGGGGEVQLV
```
-continued
```
ESGGGLVQPG GSLRLSCAAS GFNIKDTYIH WVRQAPGKGL

EWVARIYPTN GYTRYADSVK GRFTISADTS KNTAYLQMNS

LRAEDTAVYY CSRWGGDGFY AMDYWGQGTL VTVSSASTKG

KVAACKEKVA ALKEKVAALK EKVAALKE
```

Residues 1-107 of the second polypeptide chain (SEQ ID NO:152) of such illustrative CD16×DA Binding Molecule correspond to the VL Domain of anti-human CD16 antibody CD16-M1 (SEQ ID NO:65). Residues 108-115 (double underlined) of the second polypeptide chain correspond to Linker 1 (GGGSGGGG; SEQ ID NO:16). Residues 116-235 of the second polypeptide chain correspond to the VH Domain of Trastuzumab (SEQ ID NO:124). Residues 236-240 of the second polypeptide chain correspond to a linker (SEQ ID NO:21, underlined). Residues 241-268 of the second polypeptide chain correspond to a cysteine-containing K-coil (SEQ ID NO:32).

The third polypeptide chain of the DART-A has the amino acid sequence of SEQ ID NO:153:

```
DKTHTCPPCP APEAAGGPSV FLFPPKPKDT LMISRTPEVT

CVVVDVSHED PEVKFNWYVD GVEVHNAKTK PREEQYNSTY

RVVSVLTVLH QDWLNGKEYK CKVSNKALPA PIEKTISKAK

GQPREPQVYT LPPSREEMTK NQVSLSCAVK GFYPSDIAVE

WESNGQPENN YKTTPPVLDS DGSFFLVSKL TVDKSRWQQG

NVFSCSVMHE ALHNRYTQKS LSLSPGK
```

Residues 1-10 of the third polypeptide chain (SEQ ID NO:153) of such illustrative CD16×DA Binding Molecule correspond to a linker (SEQ ID NO:40). Residues 11-227 of the third polypeptide chain correspond to a "hole-bearing" IgG1 CH2-CH3 Domain (SEQ ID NO:53), containing the H435R substitution (shown underlined), and in which the final residue is lysine. As stated above, the H435R substitution eliminates the ability of the molecule to bind to bind protein A.

As will be recognized, the third polypeptide chain of DART-A does not contain any Epitope Binding sites and may thus be employed in various CD16×DA Binding Molecules. Accordingly, the third polypeptide chain of DART-A is referred to as a "Common Diabody Polypeptide Chain."

B. CD16×HER2/neu Binding Molecule, "DART-B"

The CD16×Her2/neu Binding Molecule designated "DART-B" is a further illustrative CD16×DA Binding Molecule. DART-B is an Fc Domain-containing, bispecific diabody capable of binding CD16 and the HER2/neu Cancer Antigen. DART-B is composed of three polypeptide chains and possesses one Binding Domain that comprises the VL and VH Domains of anti-human CD16 antibody CD16-M2 (and is thus immunospecific for an epitope of CD16) and one Binding Domain that comprises the VL and VH Domains of Trastuzumab (and is thus immunospecific for an epitope of the HER2/neu Cancer Antigen). The three polypeptide chains associate to form a covalently bonded DART® diabody capable of immunospecifically binding the epitope of CD16 and the epitope of the HER2/neu Cancer Antigen (see, e.g., FIG. 4A).

The first polypeptide chain of DART-B has the amino acid sequence of SEQ ID NO:154:

```
DIQMTQSPSS LSASVGDRVT ITCRASQDVN TAVAWYQQKP

GKAPKLLIYS ASFLYSGVPS RFSGSRSGTD FTLTISSLQP

EDFATYYCQQ HYTTPPTFGQ GTKVEIKGGG SGGGGEVQLQ

QSGPELVKPG ASVKMSCKAS GYTFTSSAMH WVKKNPGQGL

EWIGYINHYN DGIKYNERFK GKATLTSDKS SSTAYMELSS

LTSEDSAVYY CATGYRYASW FASWGQGTLV TVSSASTKGE

VAACEKEVAA LEKEVAALEK EVAALEKGGG DKTHTCPPCP

APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGK
```

Residues 1-107 of the first polypeptide chain (SEQ ID NO:154) of such illustrative CD16×DA Binding Molecule correspond to the VL Domain of Trastuzumab (SEQ ID NO:125). Residues 108-115 (double underlined) of the first polypeptide chain correspond to Linker 1 (GGGSGGGG; SEQ ID NO:16). Residues 116-234 of the first polypeptide chain correspond to the VH Domain of anti-human CD16 antibody CD16-M2 (SEQ ID NO:75). Residues 235-239 correspond to a linker (SEQ ID NO:21, underlined). Residues 240-267 of the first polypeptide chain correspond to a cysteine-containing E-coil (SEQ ID NO:31). Residues 268-280 of the first polypeptide chain correspond to a linker (SEQ ID NO:43). Residues 281-497 of the first polypeptide chain correspond to a "knob-bearing" IgG1 CH2-CH3 Domain (SEQ ID NO:51), in which the final residue is lysine.

The second polypeptide chain of DART-B has the amino acid sequence of SEQ ID NO:155:

```
DILLTQSPAI LSVSPGERVS FSCRASQNIG TSIHWYQQRT

DGSPRLLIKS VSESISGIPS RFSGSGSGTD FTLTINGVES

GDISDYYCQQ SNSWPLTFGA GTKLELKGGG SGGGGEVQLV

ESGGGLVQPG GSLRLSCAAS GFNIKDTYIH WVRQAPGKGL

EWVARIYPTN GYTRYADSVK GRFTISADTS KNTAYLQMNS

LRAEDTAVYY CSRWGGDGFY AMDYWGQGTL VTVSSASTKG

KVAACEKEVA ALKEKVAALK EKVAALKE
```

Residues 1-107 of the second polypeptide chain (SEQ ID NO:155) of such illustrative CD16×DA Binding Molecule correspond to the VL Domain of anti-human CD16 antibody CD16-M2 (SEQ ID NO:76). Residues 108-115 (double underlined) of the second polypeptide chain correspond to Linker 1 (GGGSGGGG; SEQ ID NO:16). Residues 116-235 of the second polypeptide chain correspond to the VH Domain of Trastuzumab (SEQ ID NO:124). Residues 236-240 of the second polypeptide chain correspond to a linker (SEQ ID NO: 21, underlined). Residues 241-268 of the second polypeptide chain correspond to a cysteine-containing K-coil (SEQ ID NO:32).

The third polypeptide chain of DART-B has the amino acid sequence of the Common Diabody Polypeptide Chain (SEQ ID NO:153).

C. CD16×HER2/neu Binding Molecule "DART-C"

The CD16×HER2/neu Binding Molecule designated "DART-C" is a further illustrative CD16×DA Binding Molecule. DART-C is an Fc Domain-containing, bispecific diabody capable of binding CD16 and the HER2/neu Cancer Antigen. DART-C is composed of three polypeptide chains and possesses one Binding Domain that comprises the VL and VH Domains of humanized anti-human CD16 antibody hCD16-M1 (and is thus immunospecific for an epitope of CD16) and one Binding Domain that comprises the VL and VH Domains of Trastuzumab (and is thus immunospecific for an epitope of the HER2/neu Cancer Antigen). The three polypeptide chains associate to form a covalently bonded DART® diabody capable of immunospecifically binding the epitope of CD16 and the epitope of the HER2/neu Cancer Antigen (see, e.g., FIG. 4A).

The first polypeptide chain of DART-C has the amino acid sequence of SEQ ID NO:156:

```
DIQMTQSPSS LSASVGDRVT ITCRASQDVN TAVAWYQQKP

GKAPKLLIYS ASFLYSGVPS RFSGSRSGTD FTLTISSLQP

EDFATYYCQQ HYTTPPTFGQ GTKVEIKGGG SGGGGEVQLV

ESGGGLVKPG GSLRLSCAAS GFTFSNYGMS WVRQAPGKGL

EWVATISGGG SYTFYPDSVK GRFTISRDNA KNSLYLQMNS

LRTEDTALYY CVRQSARAPE PYWGQGTLVT VSSASTKGEV

AACEKEVAAL EKEVAALEKE VAALEKGGGD KTHTCPPCPA

PEAAGGPSVF LFPPKPKDTL MISRTPEVTC VVVDVSHEDP

EVKFNWYVDG VEVHNAKTKP REEQYNSTYR VVSVLTVLHQ

DWLNGKEYKC KVSNKALPAP IEKTISKAKG QPREPQVYTL

PPSREEMTKN QVSLWCLVKG FYPSDIAVEW ESNGQPENNY

KTTPPVLDSD GSFFLYSKLT VDKSRWQQGN VFSCSVMHEA

LHNHYTQKSL SLSPGK
```

Residues 1-107 of the first polypeptide chain (SEQ ID NO:156) of such illustrative CD16×DA Binding Molecule correspond to the VL Domain of Trastuzumab (SEQ ID NO:125). Residues 108-115 (double underlined) of the first polypeptide chain correspond to Linker 1 (GGGSGGGG; SEQ ID NO:16). Residues 116-233 of the first polypeptide chain correspond to the VH Domain of the humanized anti-human CD16 antibody hCD16-M1 (SEQ ID NO:72). Residues 234-238 correspond to a linker (SEQ ID NO:21, underlined). Residues 239-266 of the first polypeptide chain correspond to a cysteine-containing E-coil (SEQ ID NO:31). Residues 267-279 of the first polypeptide chain correspond to a linker (SEQ ID NO:43). Residues 280-496 of the first polypeptide chain correspond to a "knob-bearing" IgG1 CH2-CH3 Domain (SEQ ID NO:51), in which the final residue is lysine.

The second polypeptide chain of DART-C has the amino acid sequence of SEQ ID NO:157:

```
DIQMTQSPSF LSASVGDRVT ITCRASQNVG THVAWYQQKP
GKAPKSLLYS ASYRYSGVPS RFSGSGSGTD FTLTISSLQS
EDIATYYCQQ YKSYPLTFGQ GTKLEIKGGG SGGGGEVQLV
ESGGGLVQPG GSLRLSCAAS GFNIKDTYIH WVRQAPGKGL
EWVARIYPTN GYTRYADSVK GRFTISADTS KNTAYLQMNS
LRAEDTAVYY CSRWGGDGFY AMDYWGQGTL VTVSSASTKG
KVAACKEKVA ALKEKVAALK EKVAALKE
```

Residues 1-107 of the second polypeptide chain (SEQ ID NO:157) of such illustrative CD16×DA Binding Molecule correspond to the VL Domain of humanized anti-human CD16 antibody hCD16-M1 (SEQ ID NO:73). Residues 108-115 (double underlined) of the second polypeptide chain correspond to Linker 1 (GGGSGGGG; SEQ ID NO:16). Residues 116-235 of the second polypeptide chain correspond to the VH Domain of Trastuzumab (SEQ ID NO:124). Residues 236-240 of the second polypeptide chain correspond to a linker (SEQ ID NO:21, underlined). Residues 241-268 of the second polypeptide chain correspond to a cysteine-containing K-coil (SEQ ID NO:32).

The third polypeptide chain of DART-C has the amino acid sequence of the Common Diabody Polypeptide Chain (SEQ ID NO:153).

D. CD16×HER2/neu Binding Molecule "DART-D"

The CD16×HER2/neu Binding Molecule designated "DART-D" is a further illustrative CD16×DA Binding Molecule. DART-D is an Fc Domain-containing, bispecific diabody capable of binding CD16 and the HER2/neu Cancer Antigen. DART-D is composed of three polypeptide chains and possesses one Binding Domain that comprises the VL and VH Domains of humanized anti-human CD16 antibody hCD16-M2 (and is thus immunospecific for an epitope of CD16) and one Binding Domain that comprises the VL and VH Domains of Trastuzumab (and is thus immunospecific for an epitope of the HER2/neu Cancer Antigen). The three polypeptide chains associate to form a covalently bonded DART® diabody capable of immunospecifically binding the epitope of CD16 and the epitope of the HER2/neu Cancer Antigen (see, e.g., FIG. 4A).

The first polypeptide chain of DART-D has the amino acid sequence of SEQ ID NO:158:

```
DIQMTQSPSS LSASVGDRVT ITCRASQDVN TAVAWYQQKP
GKAPKLLIYS ASFLYSGVPS RFSGSRSGTD FTLTISSLQP
EDFATYYCQQ HYTTPPTFGQ GTKVEIKGGG SGGGGQVQLV
QSGAEVKKPG ASVKVSCKAS GYTFTSSAMH WVRQAPGQGL
EWMGYINHYN DGIKYNERFK GRVTITADKS TSTAYMELSS
LRSEDTAVYY CATGYRYASW FASWGQGTLV TVSSASTKGE
VAACEKEVAA LEKEVAALEK EVAALEKGGG DKTHTCPPCP
APEAAGGPSV FLFPPKPKDT LMISRTPEVT CVVVDVSHED
PEVKFNWYVD GVEVHNAKTK PREEQYNSTY RVVSVLTVLH
QDWLNGKEYK CKVSNKALPA PIEKTISKAK GQPREPQVYT
LPPSREEMTK NQVSLWCLVK GFYPSDIAVE WESNGQPENN
YKTTPPVLDS DGSFFLYSKL TVDKSRWQQG NVFSCSVMHE
ALHNHYTQKS LSLSPGK
```

Residues 1-107 of the first polypeptide chain (SEQ ID NO:158) of such illustrative CD16×DA Binding Molecule correspond to the VL Domain of Trastuzumab (SEQ ID NO:125). Residues 108-115 (double underlined) of the first polypeptide chain correspond to Linker 1 (GGGSGGGG; SEQ ID NO:16). Residues 116-234 of the first polypeptide chain correspond to the VH1 Domain of the humanized anti-human CD16 antibody hCD16-M2 (SEQ ID NO:83). Residues 235-239 correspond to a linker (SEQ ID NO:21, underlined). Residues 240-267 of the first polypeptide chain correspond to a cysteine-containing E-coil (SEQ ID NO:31). Residues 268-280 of the first polypeptide chain correspond to a linker (SEQ ID NO:43). Residues 281-497 of the first polypeptide chain correspond to a "knob-bearing" IgG1 CH2-CH3 Domain (SEQ ID NO:51), in which the final residue is lysine.

The second polypeptide chain of DART-D has the amino acid sequence of SEQ ID NO:159:

```
EIVLTQSPAT LSVSPGERAT LSCRASQNIG TSIHWYQQKP
DQSPKLLIKS VSESISGVPS RFSGSGSGTD FTLTINSLEA
EDFATYYCQQ SNSWPLTFGQ GTKLEIKGGG SGGGGEVQLV
ESGGGLVQPG GSLRLSCAAS GFNIKDTYIH WVRQAPGKGL
EWVARIYPTN GYTRYADSVK GRFTISADTS KNTAYLQMNS
LRAEDTAVYY CSRWGGDGFY AMDYWGQGTL VTVSSASTKG
KVAACKEKVA ALKEKVAALK EKVAALKE
```

Residues 1-107 of the second polypeptide chain (SEQ ID NO:159) of such illustrative CD16×DA Binding Molecule correspond to the VL1 Domain of humanized anti-human CD16 antibody hCD16-M2 (SEQ ID NO:85). Residues 108-115 (double underlined) of the second polypeptide chain correspond to Linker 1 (GGGSGGGG; SEQ ID NO:16). Residues 116-235 of the second polypeptide chain correspond to the VH Domain of Trastuzumab (SEQ ID NO:124). Residues 236-240 of the second polypeptide chain correspond to a linker (SEQ ID NO:21, underlined). Residues 241-268 of the second polypeptide chain correspond to a cysteine-containing K-coil (SEQ ID NO:32).

The third polypeptide chain of DART-D has the amino acid sequence of the Common Diabody Polypeptide Chain (SEQ ID NO:153).

E. CD16×HER2/Neu Binding Molecule "DART-E"

The CD16×HER2/neu Binding Molecule designated "DART-E" is a further illustrative CD16×DA Binding Molecule. DART-E is a bispecific diabody capable of binding CD16 and the HER2/neu Cancer Antigen. DART-E is composed of three polypeptide chains and possesses one Binding Domain that comprises the VL and VH Domains of humanized anti-human CD16 antibody hCD16-M2 (and is thus immunospecific for an epitope of CD16) and one Binding Domain that comprises the VL and VH Domains of Trastuzumab (and is thus immunospecific for an epitope of the HER2/neu Cancer Antigen). The three polypeptide chains associate to form a covalently bonded DART® diabody capable of immunospecifically binding the epitope of CD16 and the epitope of the HER2/neu Cancer Antigen (see, e.g., FIG. 4A).

The first polypeptide chain of DART-E has the amino acid sequence of SEQ ID NO:160:

```
DIQMTQSPSS LSASVGDRVT ITCRASQDVN TAVAWYQQKP
GKAPKLLIYS ASFLYSGVPS RFSGSRSGTD FTLTISSLQP
EDFATYYCQQ HYTTPPTFGQ GTKVEIKGGG SGGGGQVQLV
QSGAEVKKPG ASVKVSCKAS GYTFTSSAMH WVRQAPGQGL
EWMGYINHYN DGIKYNERFK GRVTITADKS TSTAYMELSS
LRSEDTAVYY CARGYRYASW FASWGQGTLV TVSSASTKGE
VAACEKEVAA LEKEVAALEK EVAALEKGGG DKTHTCPPCP
APEAAGGPSV FLFPPKPKDT LMISRTPEVT CVVVDVSHED
PEVKFNWYVD GVEVHNAKTK PREEQYNSTY RVVSVLTVLH
QDWLNGKEYK CKVSNKALPA PIEKTISKAK GQPREPQVYT
LPPSREEMTK NQVSLWCLVK GFYPSDIAVE WESNGQPENN
```

The second polypeptide chain of DART-E is identical in sequence to the second polypeptide chain of DART-D (SEQ ID NO:159).

The third polypeptide chain of DART-E has the amino acid sequence of the Common Diabody Polypeptide Chain (SEQ ID NO:153).

F. CD16×HIV Env Binding Molecule "DART-F"

The CD16×HIV env Binding Molecule designated "DART-F" is a further illustrative CD16×DA Binding Molecule. DART-F is a bispecific diabody capable of binding CD16 and the HIV env protein. DART-F is composed of three polypeptide chains and possesses one Binding Domain that comprises the VL and VH Domains of humanized anti-human CD16 antibody hCD16-M1 (and is thus immunospecific for an epitope of CD16) and one Binding Domain that comprises the VL and VH Domains of Antibody A32 (and is thus immunospecific for an epitope of the HIV env protein). The three polypeptide chains associate to form a covalently bonded DART® diabody capable of immunospecifically binding the epitope of CD16 and the epitope of the HIV env protein (see, e.g., FIG. 4A).

The first polypeptide chain of DART-F has the amino acid sequence of SEQ ID NO:161:

```
QSALTQPPSA SGSPGQSVTI SCTGTSSDVG GYNYVSWYQH HPGKAPKLII
SEVNNRPSGV PDRFSGSKSG NTASLTVSGL QAEDEAEYYC SSYTDIHNFV
FGGGTKLTVL GGGSGGGG EV QLVESGGGLV KPGGSLRLSC AASGFTFSNY
GMSWVRQAPG KGLEWVATIS GGGSYTFYPD SVKGRFTISR DNAKNSLYLQ
MNSLRTEDTA LYYCVRQSAR APEPYWGQGT LVTVSSASTK GEVAACEKEV
AALEKEVAAL EKEVAALEKG GGDKTHTCPP CPAPEAAGGP SVFLFPPKPK
DTLMISRTPE VTCVVVDVSH EDPEVKFNWY VDGVEVHNAK TKPREEQYNS
TYRVVSVLTV LHQDWLNGKE YKCKVSNKAL PAPIEKTISK AKGQPREPQV
YTLPPSREEM TKNQVSLWCL VKGFYPSDIA VEWESNGQPE NNYKTTPPVL
DSDGSFFLYS KLTVDKSRWQ QGNVFSCSVM HEALHNHYTQ KSLSLSPGK
```

-continued
```
YKTTPPVLDS DGSFFLYSKL TVDKSRWQQG NVFSCSVMHE
ALHNHYTQKS LSLSPGK
```

Residues 1-107 of the first polypeptide chain (SEQ ID NO:160) of such illustrative CD16×DA Binding Molecule correspond to the VL Domain of Trastuzumab (SEQ ID NO:125). Residues 108-115 (double underlined) of the first polypeptide chain correspond to Linker 1 (GGGSGGGG; SEQ ID NO:16). Residues 116-234 of the first polypeptide chain correspond to the VH2 Domain of the humanized anti-human CD16 antibody hCD16-M2 (SEQ ID NO:84). Residues 235-239 correspond to a linker (SEQ ID NO:21, underlined). Residues 240-267 of the first polypeptide chain correspond to a cysteine-containing E-coil (SEQ ID NO:31). Residues 268-280 of the first polypeptide chain correspond to a linker (SEQ ID NO:43). Residues 281-497 of the first polypeptide chain correspond to a "knob-bearing" IgG1 CH2-CH3 Domain (SEQ ID NO:51), in which the final residue is lysine.

Residues 1-110 of the first polypeptide chain (SEQ ID NO:161) of such illustrative CD16×DA Binding Molecule correspond to the VL Domain of Antibody A32 (SEQ ID NO:143). Residues 111-118 (double underlined) of the first polypeptide chain correspond to Linker 1 (GGGSGGGG; SEQ ID NO:16). Residues 119-236 of the first polypeptide chain correspond to the VH Domain of the humanized anti-human CD16 antibody hCD16-M1 (SEQ ID NO:72). Residues 237-241 correspond to a linker (SEQ ID NO:21, underlined). Residues 242-269 of the first polypeptide chain correspond to a cysteine-containing E-coil (SEQ ID NO:31). Residues 270-282 of the first polypeptide chain correspond to a linker (SEQ ID NO:43). Residues 283-499 of the first polypeptide chain correspond to a "knob-bearing" IgG1 CH2-CH3 Domain (SEQ ID NO:51), in which the final residue is lysine.

The second polypeptide chain of DART-F has the amino acid sequence of SEQ ID NO:162:

```
DIQMTQSPSF LSASVGDRVT ITCRASQNVG THVAWYQQKP GKAPKSLLYS

ASYRYSGVPS RFSGSGSGTD FTLTISSLQS EDIATYYCQQ YKSYPLTFGQ

GTKLEIKGGG SGGGGVQLQ ESGPGLVKPS QTLSLSCTVS GGSSSSGAHY

WSWIRQYPGK GLEWIGYIHY SGNTYYNPSL KSRITISQHT SENQFSLKLN

SVTVADTAVY YCARGTRLRT LRNAFDIWGQ GTLVTVSSAS TKGKVAACKE

KVAALKEKVA ALKEKVAALK E
```

Residues 1-107 of the second polypeptide chain (SEQ ID NO:162) of such illustrative CD16×DA Binding Molecule correspond to the VL Domain of humanized anti-human CD16 antibody hCD16-M1 (SEQ ID NO:73). Residues 108-115 (double underlined) of the second polypeptide chain correspond to Linker 1 (GGGSGGGG; SEQ ID NO:16). Residues 116-238 of the second polypeptide chain correspond to the VH Domain of Antibody A32 (SEQ ID NO:142). Residues 239-243 of the second polypeptide chain correspond to a linker (SEQ ID NO:21, underlined). Residues 244-271 of the second polypeptide chain correspond to a cysteine-containing K-coil (SEQ ID NO:32).

The third polypeptide chain of DART-F has the amino acid sequence of the Common Diabody Polypeptide Chain (SEQ ID NO:153).

G. CD16×HIV Env Binding Molecule "DART-G"

The CD16×HIV env Binding Molecule designated "DART-G" is a further illustrative CD16×DA Binding Molecule. DART-G is a bispecific diabody capable of binding CD16 and the HIV env protein. DART-G is composed of three polypeptide chains and possesses one Binding Domain that comprises the VL and VH Domains of humanized anti-human CD16 antibody hCD16-M2 (and is thus immunospecific for an epitope of CD16) and one Binding Domain that comprises the VL and VH Domains of Antibody A32 (and is thus immunospecific for an epitope of the HIV env protein). The three polypeptide chains associate to form a covalently bonded DART® diabody composed capable of immunospecifically binding the epitope of CD16 and the epitope of the HIV env protein (see, e.g., FIG. 4A).

The first polypeptide chain of the DART-G has the amino acid sequence of SEQ ID NO:163:

```
QSALTQPPSA SGSPGQSVTI SCTGTSSDVG GYNYVSWYQH HPGKAPKLII

SEVNNRPSGV PDRFSGSKSG NTASLTVSGL QAEDEAEYYC SSYTDIHNFV

FGGGTKLTVL GGGSGGGGQV QLVQSGAEVK KPGASVKVSC KASGYTFTSS

AMHWVRQAPG QGLEWMGYIN HYNDGIKYNE RFKGRVTITA DKSTSTAYME

LSSLRSEDTA VYYCATGYRY ASWFASWGQG TLVTVSSAST KGEVAACEKE

VAALEKEVAA LEKEVAALEK GGGDKTHTCP PCPAPEAAGG PSVFLFPPKP

KDTLMISRTP EVTCVVVDVS HEDPEVKFNW YVDGVEVHNA KTKPREEQYN

STYRVVSVLT VLHQDWLNGK EYKCKVSNKA LPAPIEKTIS KAKGQPREPQ

VYTLPPSREE MTKNQVSLWC LVKGFYPSDI AVEWESNGQP ENNYKTTPPV

LDSDGSFFLY SKLTVDKSRW QQGNVFSCSV MHEALHNHYT QKSLSLSPGK
```

Residues 1-110 of the first polypeptide chain (SEQ ID NO:163) of such illustrative CD16×DA Binding Molecule correspond to the VL Domain of Antibody A32 (SEQ ID NO:143). Residues 111-118 (double underlined) of the first polypeptide chain correspond to Linker 1 (GGGSGGGG; SEQ ID NO:16). Residues 119-237 of the first polypeptide chain correspond to the VH Domain of the humanized anti-human CD16 antibody hCD16-M2 (SEQ ID NO:83). Residues 238-242 correspond to a linker (SEQ ID NO:21, underlined). Residues 243-270 of the first polypeptide chain correspond to a cysteine-containing E-coil (SEQ ID NO:31). Residues 271-283 of the first polypeptide chain correspond to a linker (SEQ ID NO:43). Residues 284-500 of the first polypeptide chain correspond to a "knob-bearing" IgG1 CH2-CH3 Domain (SEQ ID NO:51), in which the final residue is lysine.

The second polypeptide chain of the DART-G has the amino acid sequence of SEQ ID NO:164:

```
EIVLTQSPAT LSVSPGERAT LSCRASQNIG TSIHWYQQKP DQSPKLLIKS

VSESISGVPS RFSGSGSGTD FTLTINSLEA EDFATYYCQQ SNSWPLTFGQ

GTKLEIKGGG SGGGGQVQLQ ESGPGLVKPS QTLSLSCTVS GGSSSSGAHY

WSWIRQYPGK GLEWIGYIHY SGNTYYNPSL KSRITISQHT SENQFSLKLN

SVTVADTAVY YCARGTRLRT LRNAFDIWGQ GTLVTVSSAS TKGKVAACKE

KVAALKEKVA ALKEKVAALK E
```

Residues 1-107 of the second polypeptide chain (SEQ ID NO:164) of such illustrative CD16xDA Binding Molecule correspond to the VL Domain of humanized anti-human CD16 antibody hCD16-M2 (SEQ ID NO:85). Residues 108-115 (double underlined) of the second polypeptide chain correspond to Linker 1 (GGGSGGGG; SEQ ID NO:16). Residues 116-238 of the second polypeptide chain correspond to the VH Domain of Antibody A32 (SEQ ID NO:142). Residues 239-243 of the second polypeptide chain correspond to a linker (SEQ ID NO:21, underlined). Residues 244-271 of the second polypeptide chain correspond to a cysteine-containing K-coil (SEQ ID NO:32).

The third polypeptide chain of DART-G has the amino acid sequence of the Common Diabody Polypeptide Chain (SEQ ID NO:153).

H. CD16xHIV Env Binding Molecule "DART-H"

The CD16xHIV env Binding Molecule designated "DART-H" is a further illustrative CD16xDA Binding Molecule. DART-H is a bispecific diabody capable of binding CD16 and the HIV env protein. DART-H is composed of three polypeptide chains and possesses one Binding Domain that comprises the VL and VH Domains of humanized anti-human CD16 antibody hCD16-M1 (and is thus immunospecific for an epitope of CD16) and one Binding Domain that comprises the VL and VH Domains of Antibody 7B2 (and is thus immunospecific for an epitope of the HIV env protein). The three polypeptide chains associate to form a covalently bonded DART® diabody capable of immunospecifically binding the epitope of CD16 and the epitope of the HIV env protein (see, e.g., FIG. 4A).

The first polypeptide chain of DART-H has the amino acid sequence of SEQ ID NO:165:

```
DIVMTQSPDS LAVSPGERAT IHCKSSQTLL YSSNNRHSIA WYQQRPGQPP

KLLLYWASMR LSGVPDRFSG SGSGTDFTLT INNLQAEDVA IYYCHQYSSH

PPTFGHGTRV EIKGGGSGGG GEVQLVESGG GLVKPGGSLR LSCAASGFTF

SNYGMSWVRQ APGKGLEWVA TISGGGSYTF YPDSVKGRFT ISRDNAKNSL

YLQMNSLRTE DTALYYCVRQ SARAPEPYWG QGTLVTVSSA STKGEVAACE

KEVAALEKEV AALEKEVAAL EKGGGDKTHT CPPCPAPEAA GGPSVFLFPP

KPKDTLMISR TPEVTCVVVD VSHEDPEVKF NWYVDGVEVH NAKTKPREEQ

YNSTYRVVSV LTVLHQDWLN GKEYKCKVSN KALPAPIEKT ISKAKGQPRE

PQVYTLPPSR EEMTKNQVSL WCLVKGFYPS DIAVEWESNG QPENNYKTTP

PVLDSDGSFF LYSKLTVDKS RWQQGNVFSC SVMHEALHNH YTQKSLSLSP
GK
```

Residues 1-113 of the first polypeptide chain (SEQ ID NO:165) of such illustrative CD16xDA Binding Molecule correspond to the VL Domain of Antibody 7B2 (SEQ ID NO:141). Residues 114-121 (double underlined) of the first polypeptide chain correspond to Linker 1 (GGGSGGGG; SEQ ID NO:16). Residues 122-239 of the first polypeptide chain correspond to the VH Domain of the humanized anti-human CD16 antibody hCD16-M1 (SEQ ID NO:72). Residues 240-244 correspond to a linker (SEQ ID NO:21, underlined). Residues 245-272 of the first polypeptide chain correspond to a cysteine-containing E-coil (SEQ ID NO:31). Residues 273-285 of the first polypeptide chain correspond to a linker (SEQ ID NO:43). Residues 286-502 of the first polypeptide chain correspond to a "knob-bearing" IgG1 CH2-CH3 Domain (SEQ ID NO:51), in which the final residue is lysine.

The second polypeptide chain of DART-H has the amino acid sequence of SEQ ID NO:166:

```
DIQMTQSPSF LSASVGDRVT ITCRASQNVG THVAWYQQKP GKAPKSLLYS

ASYRYSGVPS RFSGSGSGTD FTLTISSLQS EDIATYYCQQ YKSYPLTFGQ

GTKLEIKGGG SGGGGQVQLV QSGGGVFKPG GSLRLSCEAS GFTFTEYYMT

WVRQAPGKGL EWLAYISKNG EYSKYSPSSN GRFTISRDNA KNSVFLQLDR

LSADDTAVYY CARADGLTYF SELLQYIFDL WGQGARVTVS SASTKGKVAA

CKEKVAALKE KVAALKEKVA ALKE
```

Residues 1-107 of the second polypeptide chain (SEQ ID NO:166) of such illustrative CD16×DA Binding Molecule correspond to the VL Domain of humanized anti-human CD16 antibody hCD16-M1 (SEQ ID NO:73). Residues 108-115 (double underlined) of the second polypeptide chain correspond to Linker 1 (GGGSGGGG; SEQ ID NO:16). Residues 116-241 of the second polypeptide chain correspond to the VH Domain of Antibody 7B2 (SEQ ID NO:140). Residues 242-246 of the second polypeptide chain correspond to a linker (SEQ ID NO:21, underlined). Residues 247-274 of the second polypeptide chain correspond to a cysteine-containing K-coil (SEQ ID NO:32).

The third polypeptide chain of DART-H has the amino acid sequence of the Common Diabody Polypeptide Chain (SEQ ID NO:153).

I. CD16×HER2/Neu Binding Molecule "DART-I"

The CD16×HER2/neu Binding Molecule designated "DART-I" is a further illustrative CD16×DA Binding Molecule. DART-I is similar to the above-described DART-C, but contains the VH of hCD16-M1A (comprising a mutated $CDR_H3$). As indicated above, the VL Domain of hCD16-M1A has the same amino acid sequence as the VL Domain of hCD16-M1.

The first polypeptide chain of DART-I has the amino acid sequence of SEQ ID NO:186:

```
DIQMTQSPSS LSASVGDRVT ITCRASQDVN TAVAWYQQKP GKAPKLLIYS

ASFLYSGVPS RFSGSRSGTD FTLTISSLQP EDFATYYCQQ HYTTPPTFGQ

GTKVEIKGGG SGGGGEVQLV ESGGGLVKPG GSLRLSCAAS GFTFSNYGMS

WVRQAPGKGL EWVATISGGG SYTFYPDSVK GRFTISRDNA KNSLYLQMNS

LRTEDTALYY CVRQSANSPV PYWGQGTLVT VSSASTKGEV AACEKEVAAL

EKEVAALEKE VAALEKGGGD KTHTCPPCPA PEAAGGPSVF LFPPKPKDTL

MISRTPEVTC VVVDVSHEDP EVKFNWYVDG VEVHNAKTKP REEQYNSTYR

VVSVLTVLHQ DWLNGKEYKC KVSNKALPAP IEKTISKAKG QPREPQVYTL

PPSREEMTKN QVSLWCLVKG FYPSDIAVEW ESNGQPENNY KTTPPVLDSD

GSFFLYSKLT VDKSRWQQGN VFSCSVMHEA LHNHYTQKSL SLSPGK
```

Residues 1-107 of the first polypeptide chain (SEQ ID NO:186) of such illustrative CD16×DA Binding Molecule correspond to the VL Domain of Trastuzumab (SEQ ID NO:125). Residues 108-115 (double underlined) of the first polypeptide chain correspond to Linker 1 (GGGSGGGG; SEQ ID NO:16). Residues 116-233 of the first polypeptide chain correspond to the VH Domain of the optimized anti-human CD16 antibody hCD16-M1A (SEQ ID NO:58). Residues 234-238 correspond to a linker (SEQ ID NO:21, underlined). Residues 239-266 of the first polypeptide chain correspond to a cysteine-containing E-coil (SEQ ID NO:31). Residues 267-279 of the first polypeptide chain correspond to a linker (SEQ ID NO:43). Residues 280-496 of the first polypeptide chain correspond to a "knob-bearing" IgG1 CH2-CH3 Domain (SEQ ID NO:51), in which the final residue is lysine.

Since the VL Domain of hCD16-M1A is the same as that of hCD16-M1, the amino acid sequence of the second polypeptide chain of DART-I is the same as that of the second polypeptide chain of the DART-C (i.e., SEQ ID NO:157). Similarly, the third polypeptide chain of DART-I has the amino acid sequence of the Common Diabody Polypeptide Chain (SEQ ID NO:153).

J. CD16×HER2/Neu Binding Molecule "DART-J"

The CD16×HER2/neu Binding Molecule designated "DART-J" is a further illustrative CD16×DA Binding Molecule. DART-J is similar to the above-described DART-C, but contains the VL of hCD16-M1B (comprising a mutated $CDR_L3$). As indicated above, the VH Domain of hCD16-M1B has the same amino acid sequence as the VH Domain of hCD16-M1.

Since the VH Domain of hCD16-M1B is the same as that of hCD16-M1, the amino acid sequence of the first polypeptide chain of DART-J is the same as that of the first polypeptide chain of the DART-C (i.e., SEQ ID NO:156).

The second polypeptide chain of DART-J has the amino acid sequence of SEQ ID NO:187:

```
DIQMTQSPSF LSASVGDRVT ITCRASQNVG THVAWYQQKP GKAPKSLLYS

ASYRYSGVPS RFSGSGSGTD FTLTISSLQS EDIATYYCQD YTNYPLTFGQ

GTKLEIK GGG SGGGGEVQLV ESGGGLVQPG GSLRLSCAAS GFNIKDTYIH

WVRQAPGKGL EWVARIYPTN GYTRYADSVK GRFTISADTS KNTAYLQMNS

LRAEDTAVYY CSRWGGDGFY AMDYWGQGTL VTVSSASTKG KVAACKEKVA

ALKEKVAALK EKVAALKE
```

Residues 1-107 of the second polypeptide chain (SEQ ID NO:157) of such illustrative CD16×DA Binding Molecule correspond to the VL Domain of humanized anti-human CD16 antibody hCD16-M1B (SEQ ID NO:59). Residues 108-115 (double underlined) of the second polypeptide chain correspond to Linker 1 (GGGSGGGG; SEQ ID NO:16). Residues 116-235 of the second polypeptide chain correspond to the VH Domain of Trastuzumab (SEQ ID NO:124). Residues 236-240 of the second polypeptide chain correspond to a linker (SEQ ID NO:21, underlined). Residues 241-268 of the second polypeptide chain correspond to a cysteine-containing K-coil (SEQ ID NO:32).

The third polypeptide chain of DART-J has the amino acid sequence of the Common Diabody Polypeptide Chain (SEQ ID NO:153).

K. CD16×HER2/Neu Binding Molecule "DART-K"

The CD16×HER2/neu Binding Molecule designated "DART-K" is a further illustrative CD16×DA Binding Molecule. DART-K is similar to the above-described DART-J, but also contains VH of hCD16-M1A (comprising a mutated $CDR_H3$) Thus, DART-K contains the VL and VH of hCD16-M1AB (comprising a mutated $CDR_L3$ and a mutated $CDR_H3$).

Since DART-K contains the VH of hCD16-M1A the amino acid sequence of the first polypeptide chain of DART-K is the same as that of the first polypeptide chain of the DART-I (i.e., SEQ ID NO:186).

Since DART-K contains VL Domain of hCD16-M1B, the amino acid sequence of the second polypeptide chain of DART-K is the same as that of the second polypeptide chain of the DART-J (i.e., SEQ ID NO:187).

The third polypeptide chain of DART-J has the amino acid sequence of the Common Diabody Polypeptide Chain (SEQ ID NO:153).

L. CD16×CD19 Binding Molecule "DART-L"

The CD16×CD19 Binding Molecule designated "DART-L" is another illustrative CD16×DA Binding Molecule. DART-L is an Fc Domain-containing, bispecific diabody capable of binding CD16 and the CD19 B-cell tumor antigen. DART-L is composed of three polypeptide chains and possesses one Binding Domain that comprises the VL and VH Domains of anti-human CD16 antibody hCD16-M1 (and is thus immunospecific for an epitope of CD16) and one Binding Domain that comprises the VL and VH Domains of CD19 mAb 1 (and is thus immunospecific for an epitope of the CD19 Cancer Antigen). The three polypeptide chains associate to form a covalently bonded DART® diabody capable of immunospecifically binding the epitope of CD16 and the epitope of the CD19 Cancer Antigen (see, e.g., FIG. 4A).

The first polypeptide chain of DART-L has the amino acid sequence of SEQ ID NO:188:

```
ENVLTQSPAT LSVTPGEKAT ITCRASQSVS YMHWYQQKPG QAPRLLIYDA

SNRASGVPSR FSGSGSGTDH TLTISSLEAE DAATYYCFQG SVYPFTFGQG

TKLEIKGGGS GGGGEVQLVE SGGGLVKPGG SLRLSCAASG FTFSNYGMSW

VRQAPGKGLE WVATISGGGS YTFYPDSVKG RFTISRDNAK NSLYLQMNSL

RTEDTALYYC VRQSARAPEP YWGQGTLVTV SSGGCGGGEV AACEKEVAAL

EKEVAALEKE VAALEKGGGD KTHTCPPCPA PEAAGGPSVF LFPPKPKDTL

MISRTPEVTC VVVDVSHEDP EVKFNWYVDG VEVHNAKTKP REEQYNSTYR

VVSVLTVLHQ DWLNGKEYKC KVSNKALPAP IEKTISKAKG QPREPQVYTL

PPSREEMTKN QVSLWCLVKG FYPSDIAVEW ESNGQPENNY KTTPPVLDSD

GSFFLYSKLT VDKSRWQQGN VFSCSVMHEA LHNHYTQKSL SLSPGK
```

Residues 1-106 of the first polypeptide chain (SEQ ID NO:188) of such illustrative CD16×DA Binding Molecule correspond to the VL Domain of CD19 mAb 1 (SEQ ID NO:139). Residues 107-114 (double underlined) of the first polypeptide chain correspond to Linker 1 (GGGSGGGG; SEQ ID NO:16). Residues 115-232 of the first polypeptide chain correspond to the VH Domain of anti-human CD16 antibody hCD16-M1 (SEQ ID NO:72). Residues 233-238 correspond to a linker (SEQ ID NO:17, underlined). Residues 239-266 of the first polypeptide chain correspond to a cysteine-containing E-coil (SEQ ID NO:31). Residues 267-279 of the first polypeptide chain correspond to a linker (SEQ ID NO:43). Residues 280-496 of the first polypeptide chain correspond to a "knob-bearing" (SEQ ID NO:51), in which the final residue is lysine.

The second polypeptide chain of DART-L has the amino acid sequence of SEQ ID NO:189:

```
DIQMTQSPSF LSASVGDRVT ITCRASQNVG THVAWYQQKP GKAPKSLLYS

ASYRYSGVPS RFSGSGSGTD FTLTISSLQS EDIATYYCQQ YKSYPLTFGQ

GTKLEIKGGG SGGGGQVTLR ESGPALVKPT QTLTLTCTFS GFSLSTSGMG

VGWIRQPPGK ALEWLAHIWW DDDKRYNPAL KSRLTISKDT SKNQVFLTMT

NMDPVDTATY YCARMELWSY YFDYWGQGTT VTVSSGGCGG GKVAACKEKV

AALKEKVAAL KEKVAALKE
```

Residues 1-107 of the second polypeptide chain (SEQ ID NO:189) of such illustrative CD16×DA Binding Molecule correspond to the VL Domain of anti-human CD16 antibody hCD16-M1 (SEQ ID NO:73). Residues 108-115 (double underlined) of the second polypeptide chain correspond to Linker 1 (GGGSGGGG; SEQ ID NO:16). Residues 116-235 of the second polypeptide chain correspond to the VH Domain of CD19 mAb 1 (SEQ ID NO:138). Residues 236-241 of the second polypeptide chain correspond to a linker (SEQ ID NO:17, underlined). Residues 242-269 of the second polypeptide chain correspond to a cysteine-containing K-coil (SEQ ID NO:32).

The third polypeptide chain of DART-L has the amino acid sequence of the Common Diabody Polypeptide Chain (SEQ ID NO:153).

M. CD16×CD19 Binding Molecule "DART-M"

The CD16×CD19 Binding Molecule designated "DART-M" is a further illustrative CD16×DA Binding Molecule. DART-M is similar to the above-described DART-L, but contains the VL of hCD16-M1B (comprising a mutated $CDR_L3$). As indicated above, the VH Domain of hCD16-M1B has the same amino acid sequence as the VH Domain of hCD16-M1.

Since the VH Domain of hCD16-M1B is the same as that of hCD16-M1, the amino acid sequence of the first polypeptide chain of DART-M is the same as that of the first polypeptide chain of the DART-L (i.e., SEQ ID NO:188).

The second polypeptide chain of DART-M has the amino acid sequence of SEQ ID NO:190:

```
DIQMTQSPSF LSASVGDRVT ITCRASQNVG THVAWYQQKP GKAPKSLLYS

ASYRYSGVPS RFSGSGSGTD FTLTISSLQS EDIATYYCQD YTNYPLTFGQ

GTKLEIKGGG SGGGGQVTLR ESGPALVKPT QTLTLTCTFS GFSLSTSGMG

VGWIRQPPGK ALEWLAHIWW DDDKRYNPAL KSRLTISKDT SKNQVFLTMT

NMDPVDTATY YCARMELWSY YFDYWGQGTT VTVSSGGCGG GKVAACKEKV

AALKEKVAAL KEKVAALKE
```

Residues 1-107 of the second polypeptide chain (SEQ ID NO:190) of such illustrative CD16×DA Binding Molecule correspond to the VL Domain of anti-human CD16 antibody hCD16-M1B (SEQ ID NO:59). Residues 108-115 (double underlined) of the second polypeptide chain correspond to Linker 1 (GGGSGGGG; SEQ ID NO:16). Residues 116-235 of the second polypeptide chain correspond to the VH Domain of CD19 mAb 1 (SEQ ID NO:138). Residues 236-241 of the second polypeptide chain correspond to a linker (SEQ ID NO:17, underlined). Residues 242-269 of the second polypeptide chain correspond to a cysteine-containing K-coil (SEQ ID NO:32).

The third polypeptide chain of DART-M has the amino acid sequence of the Common Diabody Polypeptide Chain (SEQ ID NO:153).

N. CD16×CD19 Binding Molecule "DART-N"

The CD16×CD19 Binding Molecule designated "DART-N" is a further illustrative CD16×DA Binding Molecule. DART-N is similar to the above-described DART-M, but also contains the VH of hCD16-M1A (comprising a mutated $CDR_H3$). Thus, DART-N contains the VL and VH of hCD16-M1AB (comprising a mutated $CDR_L3$ and a mutated $CDR_H3$)).

The first polypeptide chain of DART-N has the amino acid sequence of SEQ ID NO:191:

```
ENVLTQSPAT LSVTPGEKAT ITCRASQSVS YMHWYQQKPG QAPRLLIYDA

SNRASGVPSR FSGSGSGTDH TLTISSLEAE DAATYYCFQG SVYPFTFGQG

TKLEIKGGGS GGGGEVQLVE SGGGLVKPGG SLRLSCAASG FTFSNYGMSW

VRQAPGKGLE WVATISGGGS YTFYPDSVKG RFTISRDNAK NSLYLQMNSL

RTEDTALYYC VRQSANSPVP YWGQGTLVTV SSGGCGGGEV AACEKEVAAL

EKEVAALEKE VAALEKGGGD KTHTCPPCPA PEAAGGPSVF LFPPKPKDTL

MISRTPEVTC VVVDVSHEDP EVKFNWYVDG VEVHNAKTKP REEQYNSTYR

VVSVLTVLHQ DWLNGKEYKC KVSNKALPAP IEKTISKAKG QPREPQVYTL

PPSREEMTKN QVSLWCLVKG FYPSDIAVEW ESNGQPENNY KTTPPVLDSD

GSFFLYSKLT VDKSRWQQGN VFSCSVMHEA LHNHYTQKSL SLSPGK
```

Residues 1-106 of the first polypeptide chain (SEQ ID NO:191) of such illustrative CD16×DA Binding Molecule correspond to the VL Domain of CD19 mAb 1 (SEQ ID NO:139). Residues 107-114 (double underlined) of the first polypeptide chain correspond to Linker 1 (GGGSGGGG; SEQ ID NO:16). Residues 115-232 of the first polypeptide chain correspond to the VH Domain of anti-human CD16 antibody hCD16-M1A (SEQ ID NO:58). Residues 233-238 correspond to a linker (SEQ ID NO:17, underlined). Residues 239-266 of the first polypeptide chain correspond to a cysteine-containing E-coil (SEQ ID NO:31). Residues 267-279 of the first polypeptide chain correspond to a linker (SEQ ID NO:43). Residues 280-496 of the first polypeptide chain correspond to a "knob-bearing" (SEQ ID NO:51), in which the final residue is lysine.

Since DART-N contains VL Domain of hCD16-M1B, the amino acid sequence of the second polypeptide chain of DART-N is the same as that of the second polypeptide chain of the DART-M (i.e., SEQ ID NO:190).

The third polypeptide chain of DART-N has the amino acid sequence of the Common Diabody Polypeptide Chain (SEQ ID NO:153).

O. CD16×HER2/Neu Binding Molecule "DART-1"

The CD16×HER2/neu Binding Molecule designated "DART-1" is a further illustrative CD16×DA Binding Molecule. DART-1 is a bispecific diabody capable of binding CD16 and the HER2/neu Cancer Antigen. DART-1 is essentially the same as DART-A, except that it possesses the VL and VH Domains of the humanized anti-human CD16 antibody h3G8 (see, e.g., U.S. Patent Publication No. 2004/0010124; PCT Publication No. WO 2017/142928; Li, W. et al. (2016) "*Identification Of High-Affinity Anti-CD16A Allotype Independent Human Antibody Domains*," Exp. Mol. Pathol. 101(2):281-289):

VH Domain of humanized Anti-Human CD16 mAb h3G8 (SEQ ID NO:62) is shown below (CDR$_H$ residues are shown underlined):

```
QVTLRESGPA LVKPTQTLTL TCTFSGFSLS TSGMGVGWIR QPPGKALEWL

AHIWWDDDKR YNPALKSRLT ISKDTSKNQV VLTMTNMDPV DTATYYCAQI

NPAWFAYWGQ GTLVTVSS
```

VL Domain of humanized CD16 mAb h3G8 (SEQ ID NO:63) is shown below (CDR$_L$ residues are shown underlined):

```
DIVMTQSPDS LAVSLGERAT INCKASQSVD FDGDSFMNWY QQKPGQPPKL

LIYTTSNLES GVPDRFSGSG SGTDFTLTIS SLQAEDVAVY YCQQSNEDPY

TFGQGTKLEI K
``` instead of the VH and VL Domains of anti-human CD16 antibody CD16-M1 (SEQ ID NO:64 and SEQ ID NO:65, respectively) that are present in the DART-A. The VH and VL Domains of h3G8 are used herein as a comparator CD16 binding site. DART-1 is composed of three polypeptide chains having two Binding Domains that comprises the VL and VH Domains of anti-human CD16 antibody CD16-M1 (and is thus immunospecific for an epitope of CD16) and one Binding Domain that comprises the VL and VH Domains of Trastuzumab (and is thus immunospecific for an epitope of the HER2/neu Cancer Antigen). The three polypeptide chains associate to form a covalently bonded DART® diabody capable of immunospecifically binding the epitope of CD16 and the epitope of the HER2/neu Cancer Antigen (see, e.g., FIG. 4A).

The first polypeptide chain of DART-1 has the amino acid sequence of SEQ ID NO:167:

```
DIQMTQSPSS LSASVGDRVT ITCRASQDVN TAVAWYQQKP GKAPKLLIYS

ASFLYSGVPS RFSGSRSGTD FTLTISSLQP EDFATYYCQQ HYTTPPTFGQ

GTKVEIKGGG SGGGGQVTLR ESGPALVKPT QTLTLTCTFS GFSLSTSGMG

VGWIRQPPGK ALEWLAHIWW DDDKRYNPAL KSRLTISKDT SKNQVVLTMT

NMDPVDTATY YCAQINPAWF AYWGQGTLVT VSSASTKGEV AACEKEVAAL

EKEVAALEKE VAALEKGGGD KTHTCPPCPA PEAAGGPSVF LFPPKPKDTL

MISRTPEVTC VVVDVSHEDP EVKFNWYVDG VEVHNAKTKP REEQYNSTYR

VVSVLTVLHQ DWLNGKEYKC KVSNKALPAP IEKTISKAKG QPREPQVYTL

PPSREEMTKN QVSLWCLVKG FYPSDIAVEW ESNGQPENNY KTTPPVLDSD

GSFFLYSKLT VDKSRWQQGN VFSCSVMHEA LHNHYTQKSL SLSPGK
```

Residues 1-107 of the first polypeptide chain (SEQ ID NO:167) of such illustrative CD16×DA Binding Molecule correspond to the VL Domain of Trastuzumab (SEQ ID NO:125). Residues 108-115 (double underlined) of the first polypeptide chain correspond to Linker 1 (GGGSGGGG; SEQ ID NO:16). Residues 116-233 of the first polypeptide chain correspond to the VH Domain of the humanized anti-human CD16 antibody h3G8 (SEQ ID NO:62). Residues 234-238 correspond to a linker (SEQ ID NO:21, underlined). Residues 239-266 of the first polypeptide chain correspond to a cysteine-containing E-coil (SEQ ID NO:31). Residues 267-279 of the first polypeptide chain correspond to a linker (SEQ ID NO:43). Residues 280-496 of the first polypeptide chain correspond to a "knob-bearing" IgG1 CH2-CH3 Domain (SEQ ID NO:51), in which the final residue is lysine.

The second polypeptide chain of DART-1 has the amino acid sequence of SEQ ID NO:168:

```
DIVMTQSPDS LAVSLGERAT INCKASQSVD FDGDSFMNWY

QQKPGQPPKL LIYTTSNLES GVPDRFSGSG SGTDFTLTIS

SLQAEDVAVY YCQQSNEDPY TFGQGTKLEI KGGGSGGGGE

VQLVESGGGL VQPGGSLRLS CAASGFNIKD TYIHWVRQAP

GKGLEWVARI YPTNGYTRYA DSVKGRFTIS ADTSKNTAYL

QMNSLRAEDT AVYYCSRWGG DGFYAMDYWG QGTLVTVSSA

STKGKVAACK EKVAALKEKV AALKEKVAAL KE
```

Residues 1-111 of the second polypeptide chain (SEQ ID NO:168) of such illustrative CD16×DA Binding Molecule correspond to the VL Domain of humanized anti-human CD16 antibody h3G8 (SEQ ID NO:63). Residues 112-119 (double underlined) of the second polypeptide chain correspond to Linker 1 (GGGSGGGG; SEQ ID NO:16). Residues 120-239 of the second polypeptide chain correspond to the VH Domain of Trastuzumab (SEQ ID NO:124). Residues 240-244 of the second polypeptide chain correspond to a linker (SEQ ID NO:21, underlined). Residues 244-272 of the second polypeptide chain correspond to a cysteine-containing K-coil (SEQ ID NO:32).

The third polypeptide chain of DART-1 has the amino acid sequence of the Common Diabody Polypeptide Chain (SEQ ID NO:153).

P. CD16×RSV Binding Molecule "DART-2"

The CD16×RSV Binding Molecule designated "DART-2" is a further illustrative CD16×DA Binding Molecule. DART-2 is a bispecific diabody capable of binding CD16 and the RSV glycoprotein F. DART-2 is essentially the same as the DART-1, except that it possesses the VH and VL Domains of the anti-RSV glycoprotein F antibody vPalivizumab (SEQ ID NO:144 and SEQ ID NO:145, respectively) instead of the VH and VL Domains of Trastuzumab (SEQ ID NO:124 and SEQ ID NO:125, respectively) that are present in DART-1 Diabody. Thus, DART-2 is composed of three polypeptide chains and possesses one Binding Domain that comprises the VL and VH Domains of the humanized anti-human CD16 antibody h3G8 (and is thus immunospecific for an epitope of CD16) and one Binding Domain that comprises the VL and VH Domains of vPalivizumab (and is thus immunospecific for an epitope of the RSV glycoprotein F). The third polypeptide chain has the amino acid sequence of the Common Diabody Polypeptide Chain (SEQ ID NO:153). The three polypeptide chains associate to form a covalently bonded DART® diabody capable of immunospecifically binding the epitope of CD16 and the epitope of RSV glycoprotein F (see, e.g., FIG. 4A). As noted above, the VH and VL Domains of h3G8 are used herein as a comparator CD16 binding site.

Q. CD16×RSV Binding Molecule "DART-3"

The CD16×RSV Binding Molecule designated "DART-3" is a further illustrative CD16×DA Binding Molecule. The CD16×RSV DART-3 is a bispecific diabody capable of binding CD16 and the RSV glycoprotein F. DART-3 is composed of three polypeptide chains and possesses one Binding Domain that comprises the VL and VH Domains of the humanized anti-human CD16 antibody hCD16-M1 (and is thus immunospecific for an epitope of CD16) and one Binding Domain that comprises the VL and VH Domains of vPalivizumab (and is thus immunospecific for an epitope of the RSV glycoprotein F). The three polypeptide chains associate to form a covalently bonded DART® diabody capable of immunospecifically binding the epitope of CD16 and the epitope of the RSV glycoprotein F (see, e.g., FIG. 4A).

The first polypeptide chain of DART-3 has the amino acid sequence of SEQ ID NO:169:

```
DIQMTQSPST LSASVGDRVT ITCRASQSVG YMHWYQQKPG
KAPKLLIYDT SKLASGVPSR FSGSGSGTEF TLTISSLQPD
DFATYYCFQG SGYPFTFGGG TKLEIKGGGS GGGGEVQLVE
SGGGLVKPGG SLRLSCAASG FTFSNYGMSW VRQAPGKGLE
WVATISGGGS YTFYPDSVKG RFTISRDNAK NSLYLQMNSL
RTEDTALYYC VRQSARAPEP YWGQGTLVTV SSASTKGEVA
ACEKEVAALE KEVAALEKEV AALEKGGGDK THTCPPCPAP
EAAGGPSVFL FPPKPKDTLM ISRTPEVTCV VVDVSHEDPE
VKFNWYVDGV EVHNAKTKPR EEQYNSTYRV VSVLTVLHQD
WLNGKEYKCK VSNKALPAPI EKTISKAKGQ PREPQVYTLP
PSREEMTKNQ VSLWCLVKGF YPSDIAVEWE SNGQPENNYK
TTPPVLDSDG SFFLYSKLTV DKSRWQQGNV FSCSVMHEAL
HNHYTQKSLS LSPGK
```

Residues 1-106 of the first polypeptide chain (SEQ ID NO:169) of such illustrative CD16×DA Binding Molecule correspond to the VL Domain of vPalivizumab (SEQ ID NO:145). Residues 107-114 (double underlined) of the first polypeptide chain correspond to Linker 1 (GGGSGGGG; SEQ ID NO:16). Residues 115-232 of the first polypeptide chain correspond to the VH Domain of the humanized anti-human CD16 antibody hCD16-M1 (SEQ ID NO:72). Residues 233-237 correspond to a linker (SEQ ID NO:21, underlined). Residues 238-265 of the first polypeptide chain correspond to a cysteine-containing E-coil (SEQ ID NO:31). Residues 266-278 of the first polypeptide chain correspond to a linker (SEQ ID NO:43). Residues 279-495 of the first polypeptide chain correspond to a "knob-bearing" IgG1 CH2-CH3 Domain (SEQ ID NO:51), in which the final residue is lysine.

The second polypeptide chain of DART-3 has the amino acid sequence of SEQ ID NO:170:

```
DIQMTQSPSF LSASVGDRVT ITCRASQNVG THVAWYQQKP
GKAPKSLLYS ASYRYSGVPS RFSGSGSGTD FTLTISSLQS
EDIATYYCQQ YKSYPLTFGQ GTKLEIKGGG SGGGGQVTLR
ESGPALVKPT QTLTLTCTFS GFSLSTSGMS VGWIRQPPGK
ALEWLADIWW DDKKDYNPSL KSRLTISKDT SKNQVVLKVT
NMDPADTATY YCARSMITNW YFDVWGAGTT VTVSSASTKG
KVAACKEKVA ALKEKVAALK EKVAALKE
```

Residues 1-107 of the second polypeptide chain (SEQ ID NO:170) of such illustrative CD16×DA Binding Molecule correspond to the VL Domain of humanized anti-human CD16 antibody hCD16-M1 (SEQ ID NO:73). Residues 108-115 (double underlined) of the second polypeptide chain correspond to Linker 1 (GGGSGGGG; SEQ ID NO:16). Residues 116-235 of the second polypeptide chain correspond to the VH Domain of vPalivizumab (SEQ ID NO:144). Residues 236-240 of the second polypeptide chain correspond to a linker (SEQ ID NO:21, underlined). Residues 241-268 of the second polypeptide chain correspond to a cysteine-containing K-coil (SEQ ID NO:32).

The third polypeptide chain of the DART-3 has the amino acid sequence of the Common Diabody Polypeptide Chain (SEQ ID NO:153).

R. CD16×HIV Env Binding Molecule "DART-4

The CD16×HIV env Binding Molecule designated "DART-4" is a further illustrative CD16×DA Binding Molecule. DART-4 is a bispecific diabody capable of binding CD16 and the HIV env protein. DART-4 is essentially the same as DART-1, except that it possesses the VH and VL Domains of the anti-HIV env protein antibody 7B2 (SEQ ID NO:140 and SEQ ID NO:141, respectively) instead of the VH and VL Domains of Trastuzumab (SEQ ID NO:124 and SEQ ID NO:125, respectively) that are present in DART-1. Thus, DART-4 is composed of three polypeptide chains and possesses one Binding Domain that comprises the VL and VH Domains of the humanized anti-human CD16 antibody h3G8 (and is thus immunospecific for an epitope of CD16) and one Binding Domain that comprises the VL and VH Domains of 7B2 (and is thus immunospecific for an epitope of the HIV Env protein). The third polypeptide chain has the amino acid sequence of the Common Diabody Polypeptide Chain (SEQ ID NO:153). The three polypeptide chains associate to form a covalently bonded DART® diabody capable of immunospecifically binding the epitope of CD16 and the epitope of the HIV env protein (see, e.g., FIG. 4A). As noted above, the VH and VL Domains of h3G8 are used herein as a comparator CD16 binding site.

S. CD16×RSV Binding Molecule "DART-5"

The CD16×RSV Binding Molecule designated "DART-5" is a further illustrative CD16×DA Binding Molecule. DART-5 is a bispecific diabody capable of binding CD16 and the RSV glycoprotein F. DART-5 is essentially the same as DART-L, except that it possesses the VL and VH Domains of the anti-RSV glycoprotein F antibody vPalivizumab (SEQ ID NO:144 and SEQ ID NO:145, respectively) instead of the VH and VL Domains of CD19 mAb 1 (SEQ ID NO:138 and SEQ ID NO:139, respectively) that are present in DART-L. Thus, DART-5 is composed of three polypeptide chains and possesses one Binding Domain that comprises the VL and VH Domains of the humanized anti-human CD16 antibody hCD16-M1 (and is thus immunospecific for an epitope of CD16) and one Binding Domain that comprises the VL and VH Domains of vPalivizumab (and is thus immunospecific for an epitope of the RSV glycoprotein F). The third polypeptide chain has the amino acid sequence of the Common Diabody Polypeptide Chain (SEQ ID NO:153). The three polypeptide chains associate to form a covalently bonded DART® diabody capable of immunospecifically binding the epitope of CD16 and the epitope of RSV glycoprotein F (see, e.g., FIG. 4A).

T. CD16×RSV Binding Molecule "DART-6"

The CD16×RSV Binding Molecule designated "DART-6" is a further illustrative CD16×DA Binding Molecule. DART-6 is a bispecific diabody capable of binding CD16 and the RSV glycoprotein F. DART-6 is essentially the same as DART-M, except that it possesses the VL and VH Domains of the anti-RSV glycoprotein F antibody vPalivizumab (SEQ ID NO:144 and SEQ ID NO:145, respectively) instead of the VH and VL Domains of CD19 mAb 1 (SEQ ID NO:138 and SEQ ID NO:139, respectively) that are present in DART-M. Thus, DART-6 is composed of three polypeptide chains and possesses one Binding Domain that comprises the VL and VH Domains of the optimized anti-human CD16 antibody hCD16-M1B (and is thus immunospecific for an epitope of CD16) and one Binding Domain that comprises the VL and VH Domains of vPalivizumab (and is thus immunospecific for an epitope of the RSV glycoprotein F). The third polypeptide chain has the amino acid sequence of the Common Diabody Polypeptide Chain (SEQ ID NO:153). The three polypeptide chains associate to form a covalently bonded DART® diabody capable of immunospecifically binding the epitope of CD16 and the epitope of RSV glycoprotein F (see, e.g., FIG. 4A).

U. CD16×RSV Binding Molecule "DART-7"

The CD16×RSV Binding Molecule designated "DART-7" is a further illustrative CD16×DA Binding Molecule. DART-7 is a bispecific diabody capable of binding CD16 and the RSV glycoprotein F. DART-7 is essentially the same as DART-N, except that it possesses the VL and VH Domains of the anti-RSV glycoprotein F antibody vPalivizumab (SEQ ID NO:144 and SEQ ID NO:145, respectively) instead of the VH and VL Domains of CD19 mAb 1 (SEQ ID NO:138 and SEQ ID NO:139, respectively) that are present in DART-N. Thus, DART-7 is composed of three polypeptide chains and possesses one Binding Domain that comprises the VL and VH Domains of the optimized anti-human CD16 antibody hCD16-M1AB (and is thus immunospecific for an epitope of CD16) and one Binding Domain that comprises the VL and VH Domains of vPalivizumab (and is thus immunospecific for an epitope of the RSV glycoprotein F). The third polypeptide chain has the amino acid sequence of the Common Diabody Polypeptide Chain (SEQ ID NO:153). The three polypeptide chains associate to form a covalently bonded DART® diabody capable of immunospecifically binding the epitope of CD16 and the epitope of RSV glycoprotein F (see, e.g., FIG. 4A).

V. CD16×HIV Env Molecule "DART-X"

The CD16×HIV env Binding Molecule designated "DART-X" is a further illustrative CD16×DA Binding Molecule. DART-X is a bispecific diabody capable of binding CD16 and the HIV env protein. DART-X is composed of two polypeptide chains and possesses one Binding Domain that comprises the VL and VH Domains of the anti-human CD16 antibody CD16-M1 (and is thus immunospecific for an epitope of CD16) and one Binding Domain that comprises the VL and VH Domains of 7B2 (and is thus immunospecific for an epitope of the HIV env protein). The two polypeptide chains associate to form a covalently bonded DART® diabody capable of immunospecifically binding the epitope of CD16 and the epitope of the HIV env protein (see, e.g., FIGS. 1A-1B).

The first polypeptide chain of DART-X has the amino acid sequence of SEQ ID NO:171:

```
DIVMTQSPDS LAVSPGERAT IHCKSSQTLL YSSNNRHSIA

WYQQRPGQPP KLLLYWASMR LSGVPDRFSG SGSGTDFTLT

INNLQAEDVA IYYCHQYSSH PPTFGHGTRV EIKGGGSGGG

GEVKLVESGG TLVKPGGSLK LSCAASGFTF NNYGMSWVRQ

TPEKRLEWVA TISGGGSYTF YPDSVKGRFT ISRDNAKNSL

YLQMSSLRSE DTALYYCIRQ SARAPEPYWG QGTLVTVSSA

STKGEVAACE KEVAALEKEV AALEKEVAAL EK
```

Residues 1-113 of the first polypeptide chain (SEQ ID NO:171) of such illustrative CD16×DA Binding Molecule correspond to the VL Domain of 7B2 (SEQ ID NO:141). Residues 114-121 (double underlined) of the first polypeptide chain correspond to Linker 1 (GGGSGGGG; SEQ ID NO:16). Residues 122-239 of the first polypeptide chain correspond to the VH Domain of the anti-human CD16 antibody CD16-M1 (SEQ ID NO:64). Residues 240-244 correspond to a linker (SEQ ID NO:21, underlined). Residues 245-272 of the first polypeptide chain correspond to a cysteine-containing E-coil (SEQ ID NO:31).

The second polypeptide chain of DART-X has the amino acid sequence of SEQ ID NO:172:

```
DIVMTQSQKF MSTSVGDRVS VTCKASQNVG THVAWYQQKS

GQSPKSLLYS ASYRYSGVPD RFSGSGSGTD FTLTISNVQS

EDLAEYFCQQ YKSYPLTFGA GTKLELKGGG SGGGGQVQLV

QSGGGVFKPG GSLRLSCEAS GFTFTEYYMT WVRQAPGKGL

EWLAYISKNG EYSKYSPSSN GRFTISRDNA KNSVFLQLDR

LSADDTAVYY CARADGLTYF SELLQYIFDL WGQGARVTVS

SASTKGKVAA CKEKVAALKE KVAALKEKVA ALKE
```

Residues 1-107 of the second polypeptide chain (SEQ ID NO:172) of such illustrative CD16×DA Binding Molecule correspond to the VL Domain of anti-human CD16 antibody CD16-M1 (SEQ ID NO:65). Residues 108-115 (double underlined) of the second polypeptide chain correspond to Linker 1 (GGGSGGGG; SEQ ID NO:16). Residues 116-241 of the second polypeptide chain correspond to the VH Domain of 7B2 (SEQ ID NO:140). Residues 242-246 of the second polypeptide chain correspond to a linker (SEQ ID NO:21, underlined). Residues 247-274 of the second polypeptide chain correspond to a cysteine-containing K-coil (SEQ ID NO:32).

W. CD16×HIV Env Binding Molecule "DART-Y"

The CD16×HIV env Binding Molecule designated "DART-Y" is a further illustrative CD16×DA Binding Molecule. DART-Y is a bispecific diabody capable of binding CD16 and the HIV env protein. DART-Y is composed of two polypeptide chains and possesses one Binding Domain that comprises the VL and VH Domains of the anti-human CD16 antibody CD16-M2 (and is thus immunospecific for an epitope of CD16) and one Binding Domain that comprises the VL and VH Domains of 7B2 (and is thus immunospecific for an epitope of the HIV env protein). The two polypeptide chains associate to form a covalently bonded DART® diabody capable of immunospecifically binding the epitope of CD16 and the epitope of the HIV env protein (see, e.g., FIG. 1B).

The first polypeptide chain of DART-Y has the amino acid sequence of SEQ ID NO:173:

```
DIVMTQSPDS LAVSPGERAT IHCKSSQTLL YSSNNRHSIA

WYQQRPGQPP KLLLYWASMR LSGVPDRFSG SGSGTDFTLT

INNLQAEDVA IYYCHQYSSH PPTFGHGTRV EIKGGGSGGG

GEVQLQQSGP ELVKPGASVK MSCKASGYTF TSSAMHWVKK

NPGQGLEWIG YINHYNDGIK YNERFKGKAT LTSDKSSSTA

YMELSSLTSE DSAVYYCATG YRYASWFASW GQGTLVTVSS

ASTKGEVAAC EKEVAALEKE VAALEKEVAA LEK
```

Residues 1-113 of the first polypeptide chain (SEQ ID NO:173) of such illustrative CD16xDA Binding Molecule correspond to the VL Domain of 7B2 (SEQ ID NO:141). Residues 114-121 (double underlined) of the first polypeptide chain correspond to Linker 1 (GGGSGGGG; SEQ ID NO:16). Residues 122-240 of the first polypeptide chain correspond to the VH Domain of the anti-human CD16 antibody CD16-M2 (SEQ ID NO:75). Residues 241-245 correspond to a linker (SEQ ID NO:21, underlined). Residues 246-273 of the first polypeptide chain correspond to a cysteine-containing E-coil (SEQ ID NO:31).

The second polypeptide chain of DART-Y has the amino acid sequence of SEQ ID NO:174:

```
DILLTQSPAI LSVSPGERVS FSCRASQNIG TSIHWYQQRT

DGSPRLLIKS VSESISGIPS RFSGSGSGTD FTLTINGVES

GDISDYYCQQ SNSWPLTFGA GTKLELKGGG SGGGGQVQLV

QSGGGVFKPG GSLRLSCEAS GFTFTEYYMT WVRQAPGKGL

EWLAYISKNG EYSKYSPSSN GRFTISRDNA KNSVFLQLDR

LSADDTAVYY CARADGLTYF SELLQYIFDL WGQGARVTVS

SASTKGKVAA CKEKVAALKE KVAALKEKVA ALKE
```

Residues 1-107 of the second polypeptide chain (SEQ ID NO:174) of such illustrative CD16xDA Binding Molecule correspond to the VL Domain of anti-human CD16 antibody CD16-M2 (SEQ ID NO:76). Residues 108-115 (double underlined) of the second polypeptide chain correspond to Linker 1 (GGGSGGGG; SEQ ID NO:16). Residues 116-241 of the second polypeptide chain correspond to the VH Domain of 7B2 (SEQ ID NO:140). Residues 242-246 of the second polypeptide chain correspond to a linker (SEQ ID NO:21, underlined). Residues 247-274 of the second polypeptide chain correspond to a cysteine-containing K-coil (SEQ ID NO:32).

X. CD16×HIV Env Binding Molecule "DART-0"

The CD16×HIV env Binding Molecule designated "DART-0 is a further illustrative CD16xDA Binding Molecule. DART-0 is a bispecific diabody capable of binding CD16 and the HIV env protein. DART-0 is essentially the same as DART-X, except that it possesses the VH and VL Domains of the humanized anti-human CD16 antibody h3G8 (SEQ ID NO:62 and SEQ ID NO:63, respectively) instead of the VH and VL Domains of anti-human CD16 antibody CD16-M1 (SEQ ID NO:64 and SEQ ID NO:65, respectively) that are present in the DART-X. Thus, DART-0 is composed of two polypeptide chains having one Binding Domain that comprises the VL and VH Domains of the humanized anti-human CD16 antibody h3G8 (and is thus immunospecific for an epitope of CD16) and one Binding Domain that comprises the VL and VH Domains of 7B2 (and is thus immunospecific for an epitope of the HIV Env protein). These polypeptide chains associate to form a covalently bonded DART® diabody composed of two polypeptide chains that possesses one Binding Domain immunospecific for the epitope of CD16 and one Binding Domain immunospecific for the epitope of the HIV env protein (see, e.g., FIG. 1A-1B). As noted above, the VH and VL Domains of h3G8 are used herein as a comparator CD16 binding site.

Y. CD16×HIV Env Binding Molecule "DART-Z"

The CD16×HIV env Binding Molecule designated "DART-Z" is a further illustrative CD16xDA Binding Molecule. DART-Z is a bispecific diabody capable of binding CD16 and the HIV env protein. DART-Z is essentially the same as DART-X, except that it possesses the VH and VL Domains of the anti-HIV env antibody A32 (SEQ ID NOs: 142 and 143, respectively) rather than the VH and VL Domains of the anti-HIV env antibody 7B2, and it possesses the VH and VL Domains of the anti-human CD16A scFv 4-LS21 (U.S. Patent Publn. No. 2015/0218275):

VH Domain of Anti-Human CD16A scFv 4-LS21 (SEQ ID NO:175):

```
EEVQLVQSGA EVKKPGESLK VSCKASGYTF TSYYMHWVRQ

APGQGLEWMG IINPSGGSTS YAQKFQGRVT MTRDTSTSTV

YMELSSLRSE DTAVYYCARG SAYYYDFADY WGQGTLVTVS S
```

VL Domain of Anti-Human CD16A scFv 4-LS21 (SEQ ID NO:176):

```
QPVLTQPSSV SVAPGQTATI SCGGHNIGSK NVHWYQQRPG

QSPVLVIYQD NKRPSGIPER FSGSNSGNTA TLTISGTQAM

DEADYYCQVW DNYSVLFGGG TKLTVL
``` instead of the VH and VL Domains of anti-human CD16 antibody CD16-M1 (SEQ ID NO:64 and SEQ ID NO:65, respectively) that are present in DART-X. Thus, DART-Z is composed of two polypeptide chains having one Binding Domain that comprises the VL and VH Domains of the anti-human CD16A scFv 4-LS21 (and is thus immunospecific for an epitope of CD16) and one Binding Domain that comprises the VL and VH Domains of A32 (and is thus immunospecific for an epitope of the HIV Env protein). These polypeptide chains associate to form a covalently bonded DART® diabody composed of two polypeptide chains that possesses one Binding Domain immunospecific for the epitope of CD16 and one Binding Domain immunospecific for the epitope of the HIV env protein (see, e.g., FIG. 1A-1B). The VH and VL Domains of 4-LS21 are used herein as a comparator CD16 binding sites.

Z. CD16×HIV Env×HIV Env Trivalent Molecules

The CD16xDA Binding Molecules of the present invention are further illustrated by Fc Domain-containing, bispecific or trispecific, CD16×HIV env×HIV env Trivalent Molecules that comprise two Binding Domains capable of binding to an epitope of the HIV env protein and one Binding Domain capable of binding to an epitope of CD16. Such epitopes of the HIV env protein may be the same (as in the CD16×HIV env×HIV env Trivalent Molecule "TRIDENT-A") or they may be different (as in the CD16×HIV env×HIV env Trivalent Molecule "TRIDENT-B"). The structures and sequences of illustrative Trivalent TRIDENT™ Molecules are summarized in Table 13, and are described in detail below.

TABLE 13

| Trivalent Molecule Name | Polypeptide Chain | SEQ ID NO | Antibody | Domain | SEQ ID NO | Antibody | Domain | SEQ ID NO |
|---|---|---|---|---|---|---|---|---|
| TRIDENT-A | 1 | 177 | A32 | VL | 143 | hCD16-M1 | VH | 72 |
|  | 2 | 178 | hCD16-M1 | VL | 73 | A32 | VH | 142 |
|  | 3 | 179 | A32 | VH | 142 |  |  |  |
|  | 4 | 180 | A32 | VL | 143 |  |  |  |
| TRIDENT-B | 1 | 177 | A32 | VL | 143 | hCD16-M1 | VH | 72 |
|  | 2 | 178 | hCD16-M1 | VL | 73 | A32 | VH | 142 |
|  | 3 | 181 | 7B2 | VH | 140 |  |  |  |
|  | 4 | 182 | 7B2 | VL | 141 |  |  |  |

1. CD16×HIV Env×HIV Env Trivalent Molecule "TRIDENT-A"

CD16×HIV env×HIV env Trivalent Molecule designated "TRIDENT-A" is composed of four polypeptide chains and possesses one Binding Domain that comprises the VL and VH Domains of anti-human CD16 antibody hCD16-M1 (and is thus immunospecific for an epitope of CD16) and two Binding Domains that each comprise the VL and VH Domains of A32 (and is thus immunospecific for the epitope of the HIV env protein recognized by antibody A32). The four polypeptide chains associate to form a covalently bonded TRIDENT™ molecule capable of immunospecifically binding one or two copies of the HIV env protein epitope recognized by antibody A32, and an epitope of CD16 (see FIG. 6A).

The first polypeptide chain of TRIDENT-A has the amino acid sequence of SEQ ID NO:177:

```
QSALTQPPSA SGSPGQSVTI SCTGTSSDVG GYNYVSWYQH
HPGKAPKLII SEVNNRPSGV PDRFSGSKSG NTASLTVSGL
QAEDEAEYYC SSYTDIHNFV FGGGTKLTVL GGGSGGGGEV
QLVESGGGLV KPGGSLRLSC AASGFTFSNY GMSWVRQAPG
KGLEWVATIS GGGSYTFYPD SVKGRFTISR DNAKNSLYLQ
MNSLRTEDTA LYYCVRQSAR APEPYWGQGT LVTVSSASTK
GEVAACEKEV AALEKEVAAL EKEVAALEKG GGDKTHTCPP
CPAPEAAGGP SVFLFPPKPK DTLMISRTPE VTCVVVDVSH
EDPEVKFNWY VDGVEVHNAK TKPREEQYNS TYRVVSVLTV
LHQDWLNGKE YKCKVSNKAL PAPIEKTISK AKGQPREPQV
YTLPPSREEM TKNQVSLWCL VKGFYPSDIA VEWESNGQPE
NNYKTTPPVL DSDGSFFLYS KLTVDKSRWQ QGNVFSCSVM
HEALHNHYTQ KSLSLSPGK
```

Residues 1-110 of the first polypeptide chain (SEQ ID NO:177) of such illustrative CD16×DA Binding Molecule correspond to the VL Domain of Antibody A32 (SEQ ID NO:143). Residues 111-118 (double underlined) of the first polypeptide chain correspond to Linker 1 (GGGSGGGG; SEQ ID NO:16). Residues 119-236 of the first polypeptide chain correspond to the VH Domain of anti-human CD16 antibody hCD16-M1 (SEQ ID NO:72). Residues 237-241 correspond to a linker (SEQ ID NO:21, underlined). Residues 242-269 of the first polypeptide chain correspond to a cysteine-containing E-coil (SEQ ID NO:31). Residues 270-282 of the first polypeptide chain correspond to a linker (SEQ ID NO:43). Residues 283-499 of the first polypeptide chain correspond to a "knob-bearing" IgG1 CH2-CH3 Domain (SEQ ID NO:51), in which the final residue is lysine.

The second polypeptide chain of TRIDENT-A has the amino acid sequence of SEQ ID NO:178:

```
DIQMTQSPSF LSASVGDRVT ITCRASQNVG THVAWYQQKP
GKAPKSLLYS ASYRYSGVPS RFSGSGSGTD FTLTISSLQS
EDIATYYCQQ YKSYPLTFGQ GTKLEIKGGG SGGGGQVQLQ
ESGPGLVKPS QTLSLSCTVS GGSSSSGAHY WSWIRQYPGK
GLEWIGYIHY SGNTYYNPSL KSRITISQHT SENQFSLKLN
SVTVADTAVY YCARGTRLRT LRNAFDIWGQ GTLVTVSSAS
TKGKVAACKE KVAALKEKVA ALKEKVAALK E
```

Residues 1-107 of the second polypeptide chain (SEQ ID NO:178) of such illustrative CD16×DA Binding Molecule correspond to the VL Domain of Antibody hCD16-M1 (SEQ ID NO:73). Residues 108-115 (double underlined) of the second polypeptide chain correspond to Linker 1 (GGGSGGGG; SEQ ID NO:16). Residues 116-238 of the second polypeptide chain correspond to the VH Domain of Antibody A32 (SEQ ID NO:142). Residues 239-243 of the second polypeptide chain correspond to a linker (SEQ ID NO:43). Residues 244-271 of the second polypeptide chain correspond to a cysteine-containing K-coil (SEQ ID NO:32).

The third polypeptide chain of TRIDENT-A has the amino acid sequence of SEQ ID NO:179:

```
QVQLQESGPG LVKPSQTLSL SCTVSGGSSS SGAHYWSWIR
QYPGKGLEWI GYIHYSGNTY YNPSLKSRIT ISQHTSENQF
SLKLNSVTVA DTAVYYCARG TRLRTLRNAF DIWGQGTLVT
```

-continued

```
VSSASTKGPS VFPLAPSSKS TSGGTAALGC LVKDYFPEPV

TVSWNSGALT SGVHTFPAVL QSSGLYSLSS VVTVPSSSLG

TQTYICNVNH KPSNTKVDKR VEPKSCDKTH TCPPCPAPEA

AGGPSVFLFP PKPKDTLMIS RTPEVTCVVV DVSHEDPEVK

FNWYVDGVEV HNAKTKPREE QYNSTYRVVS VLTVLHQDWL

NGKEYKCKVS NKALPAPIEK TISKAKGQPR EPQVYTLPPS

REEMTKNQVS LSCAVKGFYP SDIAVEWESN GQPENNYKTT

PPVLDSDGSF FLVSKLTVDK SRWQQGNVFS CSVMHEALHN

RYTQKSLSLS PGK
```

Residues 1-123 of the third polypeptide chain (SEQ ID NO:179) correspond to the VH Domain of Antibody A32 (SEQ ID NO:142). Residues 124-221 of the third polypeptide chain correspond to a human IgG1 CH1 Domain (SEQ ID NO:3). Residues 222-236 of the third polypeptide chain correspond to an IgG Hinge Domain (SEQ ID NO:7, underlined). Residues 237-453 of the third polypeptide chain correspond to a "hole-bearing" IgG1 CH2-CH3 Domain (SEQ ID NO:53), in which the final residue is lysine.

The fourth polypeptide chain of TRIDENT-A has the amino acid sequence of SEQ ID NO:180:

```
QSALTQPPSA SGSPGQSVTI SCTGTSSDVG GYNYVSWYQH

HPGKAPKLII SEVNNRPSGV PDRFSGSKSG NTASLTVSGL

QAEDEAEYYC SSYTDIHNFV FGGGTKLTVL RTVAAPSVFI

FPPSDEQLKS GTASVVCLLN NFYPREAKVQ WKVDNALQSG

NSQESVTEQD SKDSTYSLSS TLTLSKADYE KHKVYACEVT

HQGLSSPVTK SFNRGEC
```

Residues 1-110 of the fourth polypeptide chain (SEQ ID NO:180) correspond to the VL Domain of Antibody A32 (SEQ ID NO:143). Residues 111-217 of the fourth polypeptide chain correspond to a human CL Kappa Domain (SEQ ID NO:1).

2. CD16×HIV Env×HIV Env Trivalent Molecule "TRIDENT-B"

The illustrative CD16×HIV env×HIV env Trivalent Molecule designated "TRIDENT-B" is also composed of four polypeptide chains. It possesses one Binding Domain that comprises the VL and VH Domains of anti-human CD16 antibody hCD16-M1 (and is thus immunospecific for an epitope of CD16), a Binding Domain that comprises the VL and VH Domains of A32 (and is thus immunospecific for the epitope of the HIV env protein recognized by antibody A32) and a further Binding Domain that comprises the VL and VH Domains of 7B2 (and is thus immunospecific for the epitope of the HIV env protein recognized by antibody 7B2). The four polypeptide chains associate to form a covalently bonded TRIDENT™ molecule capable of immunospecifically binding the epitope of the HIV env protein recognized by antibody A32 and/or the epitope of the HIV env protein recognized by antibody 7B2, and an epitope of CD16 (see FIG. 6A).

The first polypeptide chain of TRIDENT-B is identical to the first polypeptide chain of TRIDENT-A (SEQ ID NO:177).

The second polypeptide chain of TRIDENT-B is identical to the second polypeptide chain of TRIDENT-A (SEQ ID NO:178).

The third polypeptide chain of TRIDENT-B has the amino acid sequence of SEQ ID NO:181:

```
QVQLVQSGGG VFKPGGSLRL SCEASGFTFT EYYMTWVRQA

PGKGLEWLAY ISKNGEYSKY SPSSNGRFTI SRDNAKNSVF

LQLDRLSADD TAVYYCARAD GLTYFSELLQ YIFDLWGQGA

RVTVSSASTK GPSVFPLAPS SKSTSGGTAA LGCLVKDYFP

EPVTVSWNSG ALTSGVHTFP AVLQSSGLYS LSSVVTVPSS

SLGTQTYICN VNHKPSNTKV DKRVEPKSCD KTHTCPPCPA

PEAAGGPSVF LFPPKPKDTL MISRTPEVTC VVVDVSHEDP

EVKFNWYVDG VEVHNAKTKP REEQYNSTYR VVSVLTVLHQ

DWLNGKEYKC KVSNKALPAP IEKTISKAKG QPREPQVYTL

PPSREEMTKN QVSLSCAVKG FYPSDIAVEW ESNGQPENNY

KTTPPVLDSD GSFFLVSKLT VDKSRWQQGN VFSCSVMHEA

LHNRYTQKSL SLSPGK
```

Residues 1-126 of the third polypeptide chain (SEQ ID NO:181) correspond to the VH Domain of Antibody 7B2 (SEQ ID NO:140). Residues 127-224 of the third polypeptide chain correspond to a human IgG1 CH1 Domain (SEQ ID NO:3). Residues 225-239 of the third polypeptide chain correspond to an IgG Hinge Domain (SEQ ID NO:7, underlined). Residues 240-456 of the third polypeptide chain correspond to a "hole-bearing" IgG1 CH2-CH3 Domain (SEQ ID NO:53), in which the final residue is lysine.

The fourth polypeptide chain of TRIDENT-B has the amino acid sequence of SEQ ID NO:182:

```
DIVMTQSPDS LAVSPGERAT IHCKSSQTLL YSSNNRHSIA

WYQQRPGQPP KLLLYWASMR LSGVPDRFSG SGSGTDFTLT

INNLQAEDVA IYYCHQYSSH PPTFGHGTRV EIKRTVAAPS

VFIFPPSDEQ LKSGTASVVC LLNNFYPREA KVQWKVDNAL

QSGNSQESVT EQDSKDSTYS LSSTLTLSKA DYEKHKVYAC

EVTHQGLSSP VTKSFNRGEC
```

Residues 1-113 of the fourth polypeptide chain (SEQ ID NO:182) correspond to the VL Domain of Antibody 7B2 (SEQ ID NO:141). Residues 114-220 of the fourth polypeptide chain correspond to a human CL Kappa Domain (SEQ ID NO:1).

VIII. Methods of Production

The molecules of the present invention are most preferably produced through the recombinant expression of nucleic acid molecules that encode such polypeptides, as is well-known in the art.

Polypeptides of the invention may be conveniently prepared using solid phase peptide synthesis (Merrifield, B. (1986) "*Solid Phase Synthesis*," Science 232(4748):341-347; Houghten, R. A. (1985) "*General Method For The Rapid Solid-Phase Synthesis Of Large Numbers Of Peptides: Specificity Of Antigen Antibody Interaction At The*

*Level Of Individual Amino Acids,"* Proc. Natl. Acad. Sci. (U.S.A.) 82(15):5131-5135; Ganesan, A. (2006) *"Solid-Phase Synthesis In The Twenty-First Century,"* Mini Rev. Med. Chem. 6(1):3-10).

Antibodies may be made recombinantly and expressed using any method known in the art. Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants (e.g., tobacco) or transgenic milk. Suitable methods for expressing antibodies recombinantly in plants or milk have been disclosed (see, for example, Peeters et al. (2001) *"Production Of Antibodies And Antibody Fragments In Plants,"* Vaccine 19:2756; Lonberg, N. et al. (1995) *"Human Antibodies From Transgenic Mice,"* Int. Rev. Immunol 13:65-93; and Pollock et al. (1999) *"Transgenic Milk As A Method For The Production Of Recombinant Antibodies,"* J. Immunol. Methods 231:147-157). Suitable methods for making derivatives of antibodies, e.g., humanized, single-chain, etc. are known in the art, and have been described above. In another alternative, antibodies may be made recombinantly by phage display technology (see, for example, U.S. Pat. Nos. 5,565, 332; 5,580,717; 5,733,743; 6,265,150; and Winter, G. et al. (1994) *"Making Antibodies By Phage Display Technology,"* Annu. Rev. Immunol. 12.433-455).

Vectors containing polynucleotides of interest (e.g., polynucleotides encoding the polypeptide chains of the binding molecules of the present invention) can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cell capable of overexpressing heterologous DNAs can be used for the purpose of expressing a polypeptide or protein of interest. Non-limiting examples of suitable mammalian host cells include but are not limited to COS, HeLa, and CHO cells.

The invention includes polypeptides comprising an amino acid sequence of a binding molecule of this invention. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available.

The invention includes variants of the disclosed binding molecules, including functionally equivalent polypeptides that do not significantly affect the properties of such molecules as well as variants that have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly or deleteriously change the functional activity, or use of chemical analogs. Amino acid residues that can be conservatively substituted for one another include but are not limited to: glycine/alanine; serine/threonine; valine/isoleucine/leucine; asparagine/glutamine; aspartic acid/glutamic acid; lysine/arginine; and phenylalanine/tyrosine. These polypeptides also include glycosylated and non-glycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the Variable Domain. Changes in the Variable Domain can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

In one embodiment, a fusion polypeptide is provided that comprises a Light Chain, a Heavy Chain or both a Light and Heavy Chain. In another embodiment, the fusion polypeptide contains a heterologous immunoglobulin constant region. In another embodiment, the fusion polypeptide contains a VH and a VL Domain of an antibody produced from a publicly-deposited hybridoma. For purposes of this invention, an antibody fusion protein contains polypeptide domains that enable the protein to immunospecifically bind both CD16 and a Disease Antigen, and which contains another amino acid sequence to which it is not attached in the native molecule, for example, a heterologous sequence or a homologous sequence from another region (e.g., a deimmunized albumin-binding domain, a Protein A recognition sequence, a peptide tag, etc.).

The present invention particularly encompasses such binding molecules (e.g., antibodies, diabodies, trivalent binding molecules, etc.) conjugated to a diagnostic or therapeutic moiety. For diagnostic purposes, the binding molecules of the invention may be coupled to a detectable substance. Such binding molecules are useful for monitoring and/or prognosing the development or progression of a disease as part of a clinical testing procedure, such as determining the efficacy of a particular therapy. Examples of detectable substances include various enzymes (e.g., horseradish peroxidase, beta-galactosidase, etc.), prosthetic groups (e.g., avidin/biotin), fluorescent materials (e.g., umbelliferone, fluorescein, or phycoerythrin), luminescent materials (e.g., luminol), bioluminescent materials (e.g., luciferase or aequorin), radioactive materials (e.g., carbon-14, manganese-54, strontium-85 or zinc-65), positron emitting metals, and nonradioactive paramagnetic metal ions. The detectable substance may be coupled or conjugated either directly to the binding molecule or indirectly, through an intermediate (e.g., a linker) using techniques known in the art.

For therapeutic purposes, the binding molecules of the invention may be conjugated to a therapeutic moiety such as a cytotoxin, (e.g., a cytostatic or cytocidal agent), a therapeutic agent or a radioactive metal ion, e.g., alpha-emitters. A cytotoxin or cytotoxic agent includes any agent that is detrimental to cells such as, for example, *Pseudomonas* exotoxin, Diptheria toxin, a botulinum toxin A through F, ricin abrin, saporin, and cytotoxic fragments of such agents.

A therapeutic agent includes any agent having a therapeutic effect to prophylactically or therapeutically treat a disorder. Such therapeutic agents may be chemical therapeutic agents, protein or polypeptide therapeutic agents, and include therapeutic agents that possess a desired biological activity and/or modify a given biological response. Examples of therapeutic agents include alkylating agents, angiogenesis inhibitors, anti-mitotic agents, hormone therapy agents, and antibodies useful for the treatment of cell proliferative disorders. The therapeutic moiety may be coupled or conjugated either directly to the binding molecule or indirectly, through an intermediate (e.g., a linker) using techniques known in the art.

IX. Uses of the Binding Molecules of the Present Invention

As discussed above, molecules capable of binding CD16 and a Disease Antigen are capable of mediating the redirected cell killing of a target cell (i.e., a cancer cell, or a pathogen-infected cell) that expresses such Disease Antigen on its cell surface. Such molecules may be used for therapeutic purposes, for example in subjects with cancer or an infection. Thus, binding molecules of the present invention have the ability to treat any disease or condition associated with or characterized by the expression of a Disease Antigen, particularly a Cancer Antigen or a Pathogen-Associated Antigen, on the surface of such target cell. Thus, without limitation, the binding molecules of the present invention may be employed in the treatment of cancer, particularly a cancer characterized by the expression of a Cancer Antigen. The binding molecules of the present invention may be employed in the treatment of infection, particularly an infection characterized by the expression of a Pathogen-Associated Antigen.

In particular, the present invention encompasses such methods wherein the molecule capable of binding CD16 comprises an Epitope-Binding Domain of an antibody that is capable of binding CD16 and also comprises an Epitope-Binding Domain capable of binding a Disease Antigen (in particular a Cancer Antigen or a Pathogen-Associated Antigen) on the surface of a target cell so as to mediate the redirected killing of the target cell (for example, by mediating redirected cell killing (e.g., redirected T-cell or redirected NK-cell cytotoxicity)).

In a specific embodiment, the molecule capable of binding CD16 and the Disease Antigen is a bispecific antibody, or the binding portions thereof, (including an scFv), a BiTe, a TandAb, and a CAR.

In a specific embodiment, the molecule capable of binding CD16 and the Disease Antigen is a bispecific diabody.

In a specific embodiment, the molecule capable of binding CD16 and the Disease Antigen is a trivalent binding molecule.

As used herein, the terms: "providing a therapy" and "treating" refer to any administration of a composition that is associated with any indicia of beneficial or desired result, including, without limitation, any clinical result such as decreasing symptoms resulting from the disease, attenuating a symptom of infection (e.g., viral load, fever, pain, sepsis, etc.) a shrinking of the size of a tumor (in the cancer context, for example, a tumor of breast, gastric or prostate cancer), a retardation of cancer cell growth, a delaying of the onset, development or progression of metastasis, a decreasing of a symptom resulting from the disease, an increasing of the quality of life of the recipient subject, a decreasing of the dose of other medications being provided to treat a subject's disease, an enhancing of the effect of another medication such as via targeting and/or internalization, a delaying of the progression of the disease, and/or a prolonging of the survival of recipient subject.

Subjects for treatment include animals, most preferably mammalian species such as non-primate (e.g., bovine, equine, feline, canine, rodent, etc.) or a primate (e.g., monkey such as, a cynomolgus monkey, human, etc.). In a preferred embodiment, the subject is a human.

Exemplary disorders that may be treated by various embodiments of the present invention include, but are not limited to, proliferative disorders, cell proliferative disorders, and cancer (especially a cancer expressing a Cancer Antigen bound by a molecule capable of mediating redirected cell killing), pathogen-associated diseases (especially a chronic viral infection associated with expression of a Pathogen-Associated Antigen bound by a molecule capable of mediating redirected cell killing). In various embodiments, the invention encompasses methods and compositions for treatment, prevention or management of a disease or disorder in a subject, comprising administering to the subject a therapeutically effective amount the binding molecules of the present invention. Such molecules are particularly useful for the prevention, inhibition, reduction of growth, or regression of primary tumors, and metastasis of tumors, and for reducing pathogen load, or eliminating pathogen-infected cells. Although not intending to be bound by a particular mechanism of action, such molecules may mediate effector function against target cells, promote the activation of the immune system against target cells, cross-link cell-surface antigens and/or receptors on target cells and enhance apoptosis or negative growth regulatory signaling, or a combination thereof, resulting in clearance and/or reduction in the number of target cells.

The cancers that may be treated by molecules of the present invention, and by the methods of the present invention, include, but are not limited to: an adrenal gland cancer, including but not limited to, a pheochromocytom or an adrenocortical carcinoma; an AIDS-associated cancer; an alveolar soft part sarcoma; an astrocytic tumor; a basal cancer; a bladder cancer, including but not limited to, a transitional cell carcinoma, a squamous cell cancer, an adenocarcinoma, or a carcinosarcoma; a bone and connective tissue sarcoma, such as but not limited to, a bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, or a synovial sarcoma; a brain cancer, including, but not limited to, a glioma, astrocytoma, brain stem glioma, ependymoma, oligodendroglioma, nonglial tumor, acoustic neurinoma, craniopharyngioma, medulloblastoma, meningioma, pineocytoma, pineoblastoma, or a primary brain lymphoma; a brain and spinal cord cancer; a breast cancer, including, but not limited to, an adenocarcinoma, lobular (small cell) carcinoma, intraductal carcinoma, medullary breast cancer, mucinous breast cancer, tubular breast cancer, papillary breast cancer, Paget's disease, or an inflammatory breast cancer; a carotid body tumor; a cervical cancer, including but not limited to, a squamous cell carcinoma, or a adenocarcinoma; a cholangiocarcinoma, including but not limited to, a papillary, nodular, or diffuse cholangiocarcinoma; a chondrosarcoma; a chordoma; a chromophobe renal cell carcinoma; a clear cell carcinoma; a colon cancer; a colorectal cancer; a cutaneous benign fibrous histiocytoma; a desmoplastic small round cell tumor; an ependymoma; an eye cancer, including, but not limited to, an ocular melanoma such as iris melanoma, choroidal melanoma, and cilliary body melanoma, and retinoblastoma; an esophageal cancer, including but not limited to, a squamous cancer, adenocarcinoma, adenoid cyctic carcinoma, mucoepidermoid carcinoma, adenosquamous carcinoma, sarcoma, melanoma, plasmacytoma, verrucous carcinoma, and an oat cell (small cell) carcinoma; a Ewing's tumor; an extraskeletal myxoid chondrosarcoma; a fibrogenesis imperfecta ossium; a fibrous dysplasia of the bone; a gallbladder or bile duct cancer, including but not limited to, an adenocarcinoma; a gastric cancer; a gestational trophoblastic disease; a germ cell tumor; a head and neck cancer; a hepatocellular carcinoma; Heavy Chain disease; an islet cell tumor; a Kaposi's sarcoma; a leukemia, including, but not limited to, an acute leukemia; acute lymphocytic leukemia; an acute myelocytic leukemia, such as, but not limited to, a myeloblastic, promyelocytic, myelomonocytic, monocytic, or erythroleukemia leukemia or a myelodysplastic syndrome; a chronic leukemia, such as but not limited to, a chronic myelocytic (granulocytic) leukemia, a chronic lymphocytic leukemia, a hairy cell leukemia; a lipoma/benign lipomatous tumor; a liposarcoma/malignant lipomatous tumor; a liver cancer, including but not limited to, a hepatocellular carcinoma, or a hepatoblastoma; a lymphoma, such as but not limited to, Hodgkin's disease; non-Hodgkin's disease; a lung cancer, including but not limited to, a non-small cell lung cancer, squamous cell carcinoma (epidermoid carcinoma), adenocarcinoma, large-cell carcinoma or a small-cell lung cancer; a medulloblastoma; a melanoma; a meningioma; a benign monoclonal gammopathy; a monoclonal gammopathy of undetermined significance; a multiple endocrine neoplasia; a multiple myeloma, such as but not limited to, a smoldering multiple myeloma, nonsecretory myeloma, osteosclerotic myeloma, plasma cell leukemia, solitary plasmacytoma and extramedullary plasmacytoma; a myelodysplastic syndrome; a neuroblastoma; a neuroendocrine tumor; an oral cancer, including but not limited to, a squamous cell carcinoma; an ovarian cancer; including, but not limited to, an ovarian epithelial carcinoma, borderline tumor, germ cell tumor, and stromal tumor; a pancreatic cancer, including but not limited to, an insulinoma, gastrinoma, glucagonoma, vipoma, somatostatin-secreting tumor, or a carcinoid or islet cell tumor; a parathyroid tumor; a pediatric cancer; a penal cancer; a peripheral nerve sheath tumor; a phaeochromocytoma; a pharynx cancer, including but not limited to, a squamous cell cancer, or a verrucous cancer; a pituitary cancer, including but not limited to, Cushing's disease, a prolactin-secreting tumor, acromegaly, or a diabetes insipius tumor; a prostate cancer, including but not limited to, an adenocarcinoma, leiomyosarcoma, or rhabdomyosarcoma; polycythemia vera; a posterious uveal melanoma; a rare hematologic disorder; a renal cancer, including but not limited to, an adenocarcinoma, hypernephroma, fibrosarcoma, a renal metastatic cancer, or a transitional cell cancer (renal pelvis and/or uterer); a rhabdoid tumor; a rhabdomyosarcoma; a salivary gland cancer, including but not limited to, an adenocarcinoma, mucoepidermoid carcinoma, or an adenoidcystic carcinoma; a sarcoma; a skin cancer, including but not limited to, a basal cell carcinoma, a squamous cell carcinoma and melanoma, a superficial spreading melanoma, a nodular melanoma, a lentigo malignant melanoma, or an acral lentiginous melanoma; a soft-tissue sarcoma; a squamous cell cancer; a stomach cancer, including but not limited to, an adenocarcinoma, a fungating (polypoid), ulcerating, superficial spreading, diffusely spreading, or malignant lymphoma, liposarcoma, fibrosarcoma, and carcinosarcoma; a synovial sarcoma; a testicular cancer, including but not limited to, a germinal tumor, seminoma, anaplastic, classic (typical), spermatocytic, non-seminoma, embryonal carcinoma, teratoma carcinoma, or a choriocarcinoma (yolk-sac tumor); a thymic carcinoma; a thymoma; a thyroid cancer, such as but not limited to, papillary or follicular thyroid cancer, metastatic thyroid cancer, medullary thyroid cancer or anaplastic thyroid cancer; a uterine cancer, including but not limited to, an endometrial carcinoma or a uterine sarcoma; a vaginal cancer, including but not limited to, a squamous cell carcinoma, adenocarcinoma, or melanoma; a vulvar cancer, including but not limited to, a squamous cell carcinoma, melanoma, adenocarcinoma, basal cell carcinoma, sarcoma, or Paget's disease; a Waldenström's macroglobulinemia, or Wilms' tumor. In addition, cancers include myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc.).

In particular, the binding molecules of the present invention may be used in the treatment of adrenal cancer, bladder cancer, breast cancer, colorectal cancer, gastric cancer, glioblastoma, kidney cancer, non-small-cell lung cancer, acute lymphocytic leukemia, acute myeloid leukemia, chronic lymphocytic leukemia, chronic myeloid leukemia, hairy cell leukemia, Burkett's lymphoma, diffuse large B cell lymphoma, follicular lymphoma, mantle cell lymphoma, marginal zone lymphoma, non-Hodgkin's lymphoma, small lymphocytic lymphoma, multiple myeloma, melanoma, ovarian cancer, pancreatic cancer, prostate cancer, skin cancer, renal cell carcinoma, testicular cancer, and uterine cancer.

Pathogen-associated diseases that may be treated by the CD16 Binding Molecules of the present invention include chronic viral, bacterial, fungal and parasitic infections. Chronic infections that may be treated by the CD16 Binding Molecules of the present invention include Epstein Barr virus, Hepatitis A Virus (HAV); Hepatitis B Virus (HBV); Hepatitis C Virus (HCV); herpes viruses (e.g. HSV-1, HSV-2, CMV), Human Immunodeficiency Virus (HIV), Vesicular Stomatitis Virus (VSV), Bacilli, *Citrobacter*, Cholera, Diphtheria, *Enterobacter*, Gonococci, *Helicobacter pylori, Klebsiella, Legionella*, Meningococci, mycobacteria, *Pseudomonas*, Pneumonococci, *rickettsia* bacteria, *Salmonella, Serratia*, Staphylococci, Streptococci, Tetanus, *Aspergillus (fumigatus, niger,* etc.), *Blastomyces dermatitidis, Candida (albicans, krusei, glabrata, tropicalis,* etc.), *Cryptococcus neoformans,* Genus Mucorales *(mucor, absidia, rhizopus), Sporothrix schenkii, Paracoccidioides brasiliensis, Coccidioides immitis, Histoplasma capsulatum,* Leptospirosis, *Borrelia burgdorferi,* helminth parasite (hookworm, tapeworms, flukes, flatworms (e.g. Schistosomia), Giardia Zambia, *trichinella, Dientamoeba Fragilis, Trypanosoma brucei, Trypanosoma cruzi,* and *Leishmania donovani*).

X. Pharmaceutical Compositions

The present invention encompasses compositions comprising a molecule capable of binding CD16 and also capable of binding to a Disease Antigen. The compositions of the invention include bulk drug compositions useful in the manufacture of pharmaceutical compositions (e.g., impure or non-sterile compositions) and pharmaceutical compositions (i.e., compositions that are suitable for administration to a subject or patient) that can be used in the preparation of unit dosage forms. Such compositions comprise a prophylactically or therapeutically effective amount of a molecule capable of binding CD16 and also capable of binding to a Disease Antigen so as to be capable of mediating the redirected killing of a target cell (e.g., a cancer cell, a pathogen-infected cell, etc.), or a combination of such agents and a pharmaceutically acceptable carrier. Preferably, compositions of the invention comprise a prophylactically or therapeutically effective amount of the binding molecules of the present invention and a pharmaceutically acceptable carrier. In a preferred aspect, such compositions are substantially purified (i.e., substantially free from substances that limit its effect or produce undesired side effects).

Various formulations of such compositions may be used for administration. In addition to the pharmacologically active agent(s), the compositions of the present invention may contain suitable pharmaceutically acceptable carriers comprising excipients and auxiliaries that are well-known in the art and are relatively inert substances that facilitate administration of a pharmacologically effective substance or which facilitate processing of the active compounds into preparations that can be used pharmaceutically for delivery to the site of action. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also provides a pharmaceutical pack or kit comprising one or more containers filled with a binding molecule of the present invention, alone or with such pharmaceutically acceptable carrier. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. A kit can comprise any of the binding molecules of the present invention. The kit can further comprise one or more other prophylactic and/or therapeutic agents useful for the treatment of cancer, in one or more containers.

XI. Methods of Administration

The compositions of the present invention may be provided for the treatment, prophylaxis, and amelioration of one or more symptoms associated with a disease, disorder or infection by administering to a subject an effective amount of a CD16×DA pharmaceutical composition of the present invention. In a preferred aspect, such compositions are substantially purified (i.e., substantially free from substances that limit its effect or produce undesired side effects). In a specific embodiment, the subject is an animal, preferably a mammal such as non-primate (e.g., bovine, equine, feline, canine, rodent, etc.) or a primate (e.g., monkey such as, a cynomolgus monkey, human, etc.). In a preferred embodiment, the subject is a human.

Methods of administering a CD16×DA Binding Molecule or pharmaceutical composition of the invention include, but are not limited to, parenteral administration (e.g., intradermal, intramuscular, intraperitoneal, intravenous and subcutaneous), epidural, and mucosal (e.g., intranasal and oral routes). In a specific embodiment, the binding molecules of the present invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local.

The invention also provides that preparations of the binding molecules of the present invention are packaged in a hermetically sealed container such as an ampoule or sachette indicating the quantity of the molecule. In one embodiment, such molecules are supplied as a dry sterilized lyophilized powder or water free concentrate in a hermetically sealed container and can be reconstituted, e.g., with water or saline to the appropriate concentration for administration to a subject. Preferably, the binding molecules of the present invention are supplied as a dry sterile lyophilized powder in a hermetically sealed container.

The lyophilized preparations of the binding molecules of the present invention should be stored at between 2° C. and 8° C. in their original container and the molecules should be administered within 12 hours, preferably within 6 hours, within 5 hours, within 3 hours, or within 1 hour after being reconstituted. In an alternative embodiment, such molecules are supplied in liquid form in a hermetically sealed container indicating the quantity and concentration of the molecule, fusion protein, or conjugated molecule. Preferably, such binding molecules, when provided in liquid form, are supplied in a hermetically sealed container.

The amount of such preparations of the invention that will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

As used herein, an "effective amount" of a pharmaceutical composition is an amount sufficient to effect beneficial or desired results including, without limitation, clinical results such as decreasing symptoms resulting from the disease, attenuating a symptom of infection (e.g., viral load, fever, pain, sepsis, etc.) or a symptom of cancer (e.g., the proliferation, of cancer cells, tumor presence, tumor metastases, etc.), thereby increasing the quality of life of those suffering from the disease, decreasing the dose of other medications required to treat the disease, enhancing the effect of another medication such as via targeting and/or internalization, delaying the progression of the disease, and/or prolonging survival of individuals. When applied to an individual active ingredient, administered alone, the term refers to that ingredient alone. When applied to a combination, the term refers to combined amounts of the active ingredients that result in the therapeutic effect, whether administered in combination, serially, or simultaneously.

An effective amount can be administered in one or more administrations. For purposes of this invention, an effective amount of drug, compound, or pharmaceutical composition is an amount sufficient: to kill and/or reduce the proliferation of cancer cells, and/or to eliminate, reduce and/or delay the development of metastasis from a primary site of cancer; or to reduce the proliferation of (or the effect of) an infectious pathogen and to reduce and/or delay the development of the pathogen-mediated disease, either directly or indirectly. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic agents, and a single agent may be considered to be given in an effective amount if, in conjunction with one or more other agents, a desirable result may be or is achieved. While individual needs vary, determination of optimal ranges of effective amounts of each component is within the skill of the art.

For the binding molecules encompassed by the invention, the dosage administered to a patient is preferably determined based upon the body weight (kg) of the recipient subject. For the binding molecules encompassed by the invention, the dosage administered to a patient is typically from about 0.01 µg/kg to about 30 mg/kg or more of the subject's body weight.

The dosage and frequency of administration of a binding molecule of the present invention may be reduced or altered by enhancing uptake and tissue penetration of the molecule by modifications such as, for example, lipidation.

The dosage of a binding molecule of the invention administered to a patient may be calculated for use as a single agent therapy. Alternatively, the molecule may be used in combination with other therapeutic compositions and the dosage administered to a patient are lower than when said molecules are used as a single agent therapy.

The pharmaceutical compositions of the invention may be administered locally to the area in need of treatment; this may be achieved by, for example, and not by way of limitation, local infusion, by injection, or by means of an implant, said implant being of a porous, non-porous, or gelatinous material, including membranes, such as SIALASTIC® membranes, or fibers. Preferably, when administering a molecule of the invention, care must be taken to use materials to which the molecule does not absorb.

The compositions of the invention can be delivered in a vesicle, in particular a liposome (See Langer (1990) "*New Methods Of Drug Delivery*," Science 249:1527-1533); Treat et al., in LIPOSOMES IN THE THERAPY OF INFECTIOUS DISEASE AND CANCER, Lopez-Berestein and Fidler (eds.), Liss, New York, pp. 353-365 (1989); Lopez-Berestein, ibid., pp. 317-327).

Treatment of a subject with a therapeutically or prophylactically effective amount of a binding molecule of the present invention can include a single treatment or, preferably, can include a series of treatments. In a preferred example, a subject is treated with a pharmaceutical composition of the invention for between about 1 to 10 weeks, preferably between 2 to 8 weeks, more preferably between about 3 to 7 weeks, and even more preferably for about 4, 5, or 6 weeks. The pharmaceutical compositions of the invention can be administered once a day with such administration occurring once a week, twice a week, once every two weeks, once a month, once every six weeks, once every two months, twice a year or once per year, etc. Alternatively, the pharmaceutical compositions of the invention can be administered twice a day with such administration occurring once a week, twice a week, once every two weeks, once a month, once every six weeks, once every two months, twice a year or once per year, etc. Alternatively, the pharmaceutical compositions of the invention can be administered three times a day with such administration occurring once a week, twice a week, once every two weeks, once a month, once every six weeks, once every two months, twice a year or once per year, etc. It will also be appreciated that the effective dosage of the molecules used for treatment may increase or decrease over the course of a particular treatment.

EXAMPLES

Having now generally described the invention, the same will be more readily understood through reference to the following examples, which are provided by way of illustration and are not intended to be limiting of the present invention unless specified.

Example 1

Characterization of CD16 Binding Molecules

As discussed above, a series of DART® Diabody CD16× DA Binding Molecules were generated incorporating different murine, humanized, or optimized anti-CD16 binding domains and having a Binding Domain that is immunospecific for either: (1) the HER2/neu tumor antigen (Binding Domain from Trastuzumab), (2) a Binding Domain that is immunospecific for an HIV antigen (Binding Domain from A32 or 7B2), (3) the CD19 B-cell antigen (Binding Domain from CD19 mAb 1), or (4) a Binding Domain that is immunospecific for an RSV antigen (Binding Domain from Palivizumab) (Table 14).

TABLE 14

| Designation | Specificities | CD16 VH/VL | Target VH/VL |
| --- | --- | --- | --- |
| DART-A | CD16 × HER2/neu | CD16-M1 | Trastuzumab |
| DART-B | CD16 × HER2/neu | CD16-M2 | Trastuzumab |
| DART-C | CD16 × HER2/neu | hCD16-M1 | Trastuzumab |
| DART-D | CD16 × HER2/neu | hCD16-M2 (VH1) | Trastuzumab |
| DART-E | CD16 × HER2/neu | hCD16-M2 (VH2) | Trastuzumab |
| DART-F | CD16 × HIV | hCD16-M1 | A32 |
| DART-G | CD16 × HIV | hCD16-M2 (VH1) | A32 |

TABLE 14-continued

| Designation | Specificities | CD16 VH/VL | Target VH/VL |
|---|---|---|---|
| DART-H | CD16 × HIV | hCD16-M1 | 7B2 |
| DART-I | CD16 × HER2/neu | hCD16-M1A | Trastuzumab |
| DART-J | CD16 × HER2/neu | hCD16-M1B | Trastuzumab |
| DART-K | CD16 × HER2/neu | hCD16-M1AB | Trastuzumab |
| DART-L | CD16 × CD19 | hCD16-M1 | CD19 mAb 1 |
| DART-M | CD16 × CD19 | hCD16-M1B | CD19 mAb 1 |
| DART-N | CD16 × CD19 | hCD16-M1AB | CD19 mAb 1 |
| DART-1 | CD16 × HER2/neu | h3G8 | Trastuzumab |
| DART-2 | CD16 × RSV | h3G8 | Palivizumab variant |
| DART-3 | CD16 × RSV | hCD16-M1 | vPalivizumab |
| DART-4 | CD16 × HIV | h3G8 | 7B2 |
| DART-5 | CD16 × RSV | hCD16-M1 | vPalivizumab |
| DART-6 | CD16 × RSV | hCD16-M1B | vPalivizumab |
| DART-7 | CD16 × RSV | hCD16-M1AB | vPalivizumab |
| DART-X | CD16 × HIV | CD16-M1 | 7B2 |
| DART-Y | CD16 × HIV | CD16-M2 | 7B2 |
| DART-Z | CD16 × HIV | 4-LSN1 | A32 |
| DART-0 | CD16 × HIV | h3G8 | 7B2 |

Competition studies were performed with the two chain diabodies (DART-X, DART-Y and DART-0) comprising murine antibody CD16-M1, murine antibody CD16-M2, humanized antibody 3G8 and two widely-available commercial antibodies: LNK16 and DJ130c (Abcam, etc.) A ProteOn analysis was conducted to assess the binding of test articles to CD16 molecules that had been immobilized on a chip. The CD16 molecules were first incubated with 5 nM CD16-Fc (human IgG2) Fusion captured, followed by incubation with 10 nM of a first test article (test article 1), followed by an incubation with 10 nM of a second test article (test article 2). Binding was detected using anti-human Fc F(ab')2 fragments.

This study revealed that the CD16-M1, CD16-M2, LNK16 and 3G8 binding domains each bound different epitopes of CD16. CD16-M2 was found to compete with antibody DJ130c for binding to CD16; DJ130c has been reported to bind CD16 at a site that is non-overlapping with CD16's Fc binding site (Tamm, A. et al. (1996) "*The Binding Epitopes Of Human CD16 (Fc Gamma RIII) Monoclonal Antibodies. Implications For Ligand Binding,*" J. Immunol. 157(4):1576-1581; Tamm, A. et al. (1996) "*The Igg Binding Site Of Human FcgammaRIIIB Receptor Involves CC' And FG Loops Of The Membrane-Proximal Domain,*" J. Biol. Chem. 271(7):3659-3666).

The ability of CD16-M1, DJ130c and LNK16 to bind CD16A in presence of IgG was evaluated. It was found that IgG presence inhibited binding by NK16, but that IgG presence did not inhibit binding between CD16 and CD16-M1 was not inhibited by the presence of IgG, whereas L. The 3G8 epitope has been reported to overlap with CD16's Fc binding site (Tamm, A. et al. (1996) J. Biol. Chem. 271(7): 3659-3666).

Figure 8:
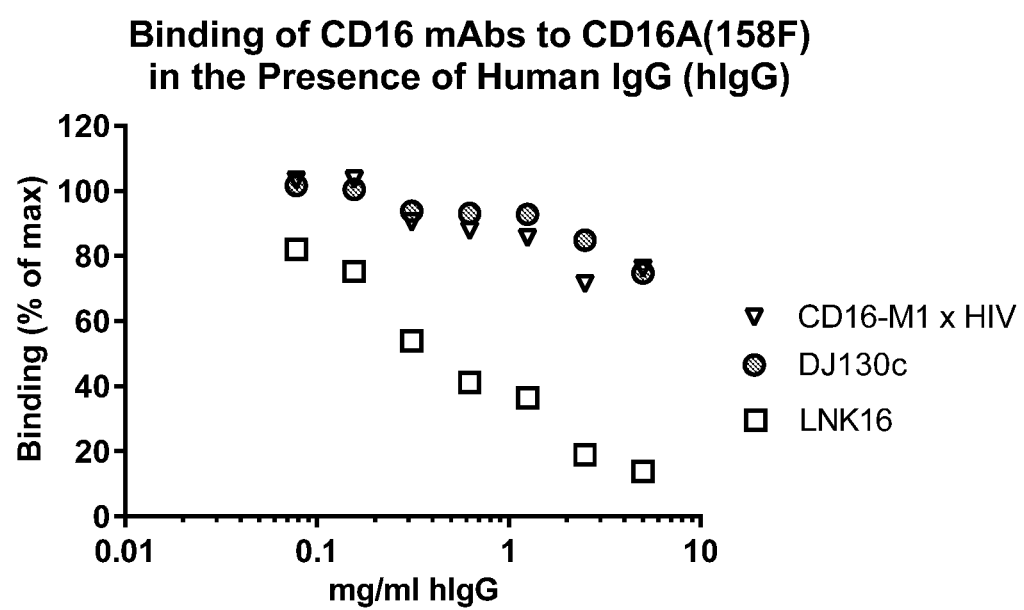
FIG. 8 shows the effect of increasing concentrations of human IgG on the ability of CD16 Binding Domains of LNK16, DJ130c and CD16-M1 to bind CD16.

Increasing concentrations of human IgG (hIgG) descreased the binding of antibody LNK16 to CD16, thus indicating that the epitope recognized by LNK16 overlaps with CD16's Fc binding site; in contrast, binding by the CD16 Binding domains of DJ130c or CD16-M1 was substantially unaffected, thus indicating that the CD16 epitopes recognized by these molecules did not overlap with CD16's Fc binding site (FIG. 8).

As discussed above, CD16A possesses two major allotypes, reflecting an 158F vs. 158V polymorphism. As shown in Table 15, CD16 Binding Domains of CD16-M1 and CD16-M2 were found to bind to both CD16 allotypes with similar high affinity (approximately 3-25-fold better than h3G8, which has a 10-fold lower affinity to the CD16 158F allotype, relative to the CD16 158V allotype. The binding domain of h3G8 was found to exhibit a fast off-rate. The analysis was conducted using a BIACORE® format in which the diabody molecules were captured on a goat (Fab')2 anti-human Fc surface, and the human CD16A V/F molecules (labeled with Avitag) were passed over the captured diabodies (normalized; 1:1 binding fit).

TABLE 15

| Molecule | ka | kd | $K_D$ (nM) |
|---|---|---|---|
| Human CD16A 158F | | | |
| DART-1 | $1.7 \times 10^6$ | $1.1 \times 10^{-1}$ | 65.9 |
| DART-C | $1.6 \times 10^6$ | $3.0 \times 10^{-4}$ | 0.2 |
| DART-D | $4.7 \times 10^5$ | $1.2 \times 10^{-3}$ | 2.5 |
| DART-F | $1.5 \times 10^6$ | $3.4 \times 10^{-4}$ | 0.2 |
| DART-G | $4.7 \times 10^5$ | $1.2 \times 10^{-3}$ | 2.6 |
| Human CD16A 158V | | | |
| DART-1 | $1.3 \times 10^6$ | $9.0 \times 10^{-3}$ | 6.9 |
| DART-C | $1.4 \times 10^6$ | $3.9 \times 10^{-4}$ | 0.3 |
| DART-D | $5.2 \times 10^5$ | $1.2 \times 10^{-3}$ | 2.3 |
| DART-F | $1.4 \times 10^6$ | $3.7 \times 10^{-4}$ | 0.3 |
| DART-G | $5.4 \times 10^5$ | $1.2 \times 10^{-3}$ | 2.2 |

A ProteOn analysis was conducted to assess the binding of the CD16 Binding Domains of the constructed diabodies to CD16-His tagged molecules (R&D Systems) that had been immobilized on a chip. The CD16 molecules were immobilized via an anti-PentaHis antibody, followed by incubation incubation with the diabodies. The results of the CD16 binding studies are summarized in Table 16 (the CD16 Binding Domain of DART-Z derives from scFv 4-LS21, which is specific for CD16A).

TABLE 16

| Molecule | ka | kd | $K_D$ (nM) |
|---|---|---|---|
| Human CD16A V158F | | | |
| DART-A | $4.2 \times 10^6$ | $3.3 \times 10^{-4}$ | 0.1 |
| DART-B | $2.9 \times 10^5$ | $4.8 \times 10^{-4}$ | 1.7 |
| DART-1 | $5.3 \times 10^5$ | $3.4 \times 10^{-2}$ | 63.1 |
| DART-C | $2.8 \times 10^6$ | $2.6 \times 10^{-4}$ | 0.1 |
| DART-D | $4.3 \times 10^5$ | $1.0 \times 10^{-3}$ | 2.4 |
| DART-E | $2.3 \times 10^5$ | $1.6 \times 10^{-3}$ | 7.2 |
| DART-F | $4.2 \times 10^6$ | $2.4 \times 10^{-4}$ | 0.1 |
| DART-G | $4.7 \times 10^5$ | $8.9 \times 10^{-4}$ | 1.9 |
| DART-H | $4.5 \times 10^6$ | $1.9 \times 10^{-4}$ | 0.04 |
| DART-4 | $6.1 \times 10^5$ | $4.7 \times 10^{-2}$ | 76.8 |
| DART-Z | $2.9 \times 10^5$ | $4.3 \times 10^{-3}$ | 15.2 |
| Human CD16A 158V | | | |
| DART-A | $3.9 \times 10^6$ | $4.5 \times 10^{-4}$ | 0.1 |
| DART-B | $3.2 \times 10^5$ | $4.1 \times 10^{-4}$ | 1.3 |
| DART-1 | $2.4 \times 10^5$ | $6.5 \times 10^{-3}$ | 26.7 |
| DART-C | $2.4 \times 10^6$ | $3.2 \times 10^{-4}$ | 0.1 |
| DART-D | $5.6 \times 10^5$ | $7.1 \times 10^{-4}$ | 1.3 |
| DART-E | $3.3 \times 10^5$ | $1.1 \times 10^{-3}$ | 3.3 |
| DART-F | $4.0 \times 10^6$ | $4.0 \times 10^{-4}$ | 0.1 |
| DART-G | $6.6 \times 10^5$ | $5.5 \times 10^{-4}$ | 0.8 |
| DART-H | $3.9 \times 10^6$ | $3.7 \times 10^{-4}$ | 0.1 |
| DART-4 | $2.9 \times 10^6$ | $6.9 \times 10^{-3}$ | 23.3 |
| DART-Z | $2.6 \times 10^5$ | $4.2 \times 10^{-3}$ | 15.7 |
| Human CD16B | | | |
| DART-A | $2.6 \times 10^6$ | $1.3 \times 10^{-3}$ | 0.5 |
| DART-B | $2.2 \times 10^5$ | $7.4 \times 10^{-4}$ | 3.3 |
| DART-1 | $8.9 \times 10^5$ | $5.5 \times 10^{-3}$ | 6.1 |
| DART-C | $1.5 \times 10^6$ | $6.9 \times 10^{-4}$ | 0.5 |
| DART-D | $3.5 \times 10^5$ | $1.3 \times 10^{-3}$ | 3.6 |
| DART-E | $1.5 \times 10^5$ | $1.9 \times 10^{-3}$ | 12.5 |

TABLE 16-continued

| DART-F | $2.8 \times 10^6$ | $1.1 \times 10^{-3}$ | 0.4 |
| DART-G | $4.6 \times 10^5$ | $1.2 \times 10^{-3}$ | 2.6 |
| DART-H | $2.5 \times 10^6$ | $8.9 \times 10^{-4}$ | 0.4 |
| DART-4 | $7.8 \times 10^5$ | $6.1 \times 10^{-3}$ | 7.8 |
| DART-Z | N/A* | N/A* | N/A* |

* The CD16 Binding Domain of DART-Z derives from scFv 4-LS21, which is specific for CD16A The results indicate that diabodies comprising CD16-M1 or CD16-M2 CD16 Binding Domains exhibited higher affinity to both alleles of CD16A and higher affinity than comparator molecules. Diabodies comprising hCD16-M2 (VH1) CD16 Binding Domains exhibited slightly better binding than diabodies comprising the hCD16-M2 (VH2) CD16 Binding Domains (compare DART-D vs. DART-E).

Example 2

Figure 9A:
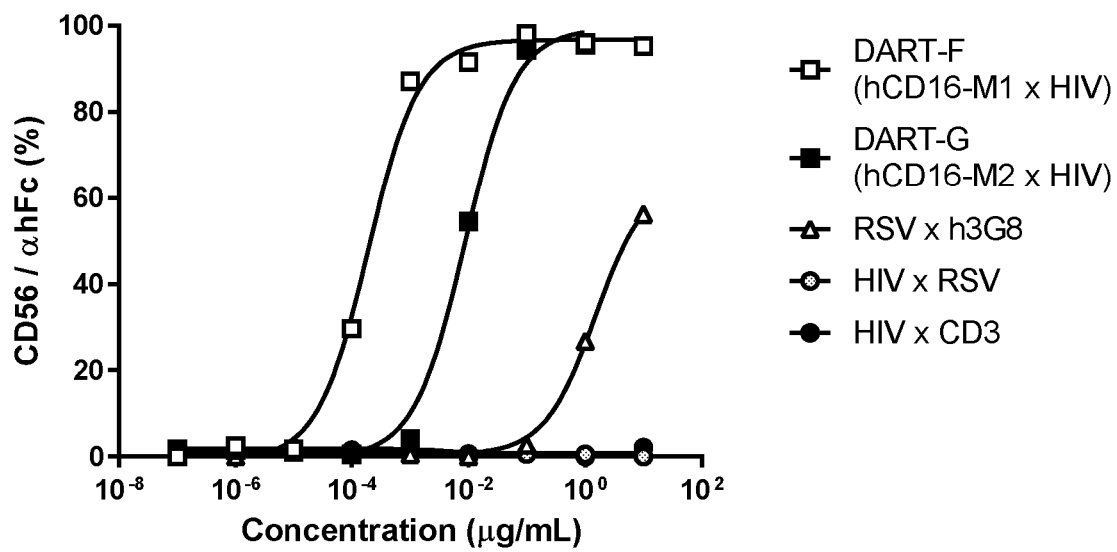
FIGS. 9A-9C show the ability of CD16 Binding Molecules: DART-F and DART-G to bind to NK cells (FIG. 9A; CD16A: na), neutrophils (FIG. 9B; CD16B:na, and T Cells (FIG. 9C) in whole blood of donor subjects, compared with an HIV×CD3 diabody (as a positive control for T-cell binding via its CD3 Binding Domain), an HIV×RSV diabody (as a negative control for all binding), and an h3G8× RSV diabody comparator molecule.
Figure 9B:
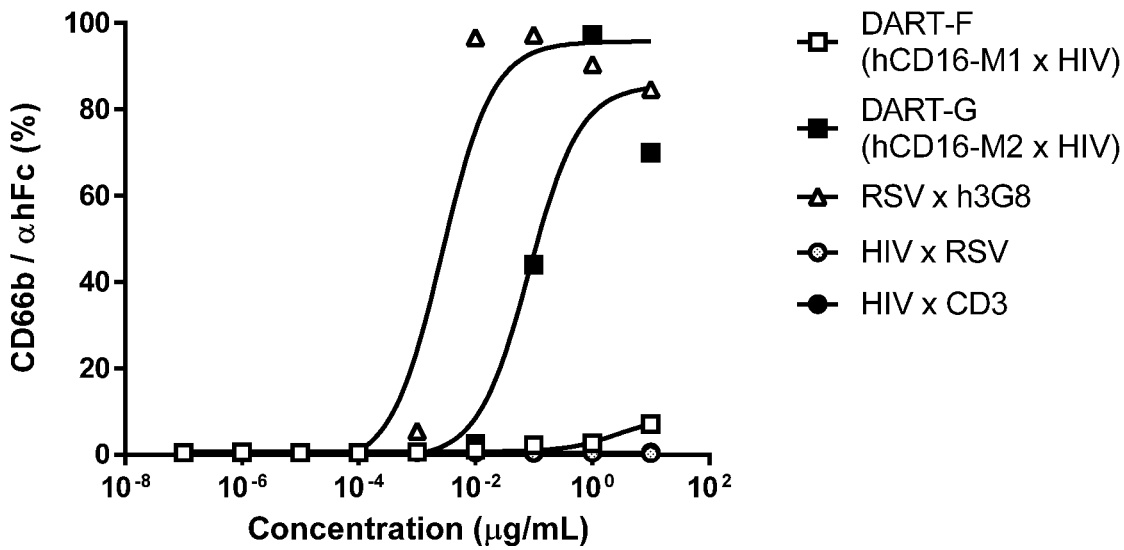
Figure 9C:
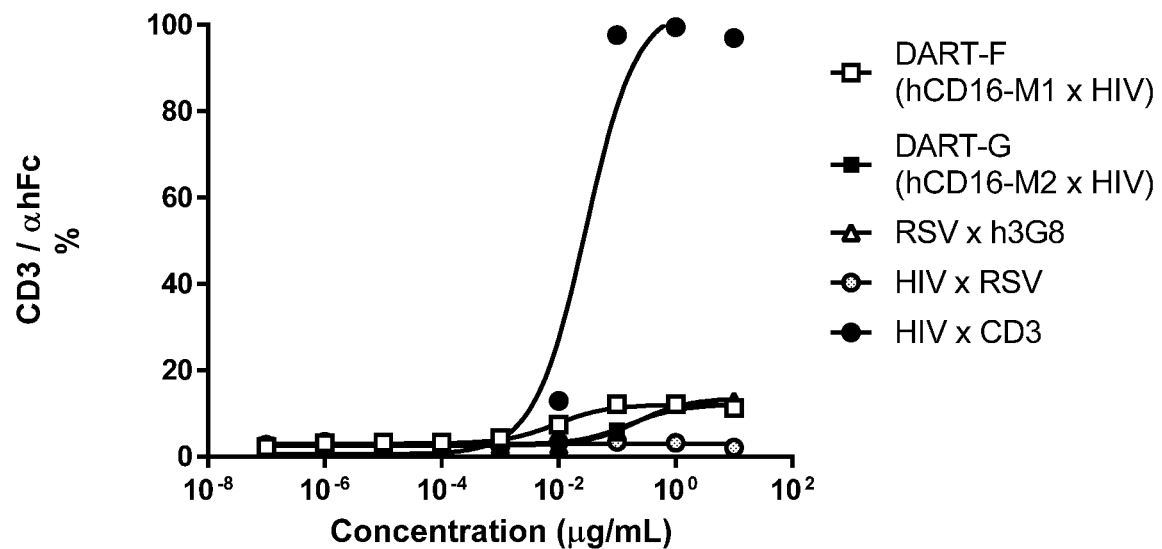

Binding of DART-F and DART-G CD16 Binding Molecules to NK Cells, Neutrophils and T Cells In order to demonstrate the ability of the CD16×DA Binding Molecules of the invention to bind CD16, whole blood of donor subjects was incubated in the presence of CD16-binding diabodies: DART-F and DART-G, an HIV× CD3 diabody (as a positive control for T-cell binding via its CD3 Binding Domain), an HIV×RSV diabody (as a negative control for all binding), and an h3G8×RSV diabody comparator molecule. Following incubation, the cells were labled with: anti-CD56-allophycocyanin (CD56 APC, NK cell marker), anti-CD66b-fluorescein isothiocyanate (CD66b FITC, neutrophil cell marker) and anti-CD3-peridinin chlorophyll protein-Cy5.5 (CD3 PerCP Cy5.5, T-cell marker), and anti-humanFc-Phycoerythrin (αhFc PE) to detect diabody binding and the cell surface. The labeled cells were analyzed by flow cytometry gated on NK cells. The co-staining results of the investigation for a first subject are shown in FIGS. 9A-9C, and indicate that DART-F (hCD16-M1) had a higher affinity for CD16A on the surface of NK cells relative to DART-G (hCD16-M2), both of which had a higher affinity than the h3G8×RSV diabody comparator molecule (FIG. 9A). In contrast, whereas the h3G8×RSV diabody comparator molecule was able to bind to CD16B of neutrophils, DART-G had lower binding ability, and DART-F had essentially no binding ability (FIG. 9B). As shown in FIG. 9C, the CD16 Binding Molecules were unable to bind to T cells.

Figure 10A:
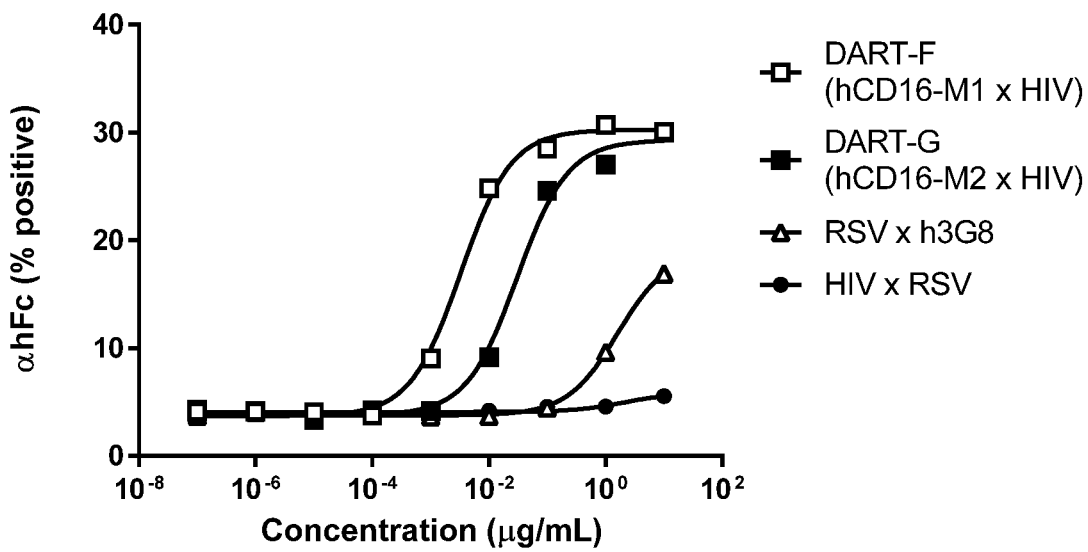
FIGS. 10A-10B show the ability of CD16 Binding Molecules: DART-F and DART-G to bind to CD16A-expressing cells of a gated lymphocyte population (FIG. 10A) and a gated granulocyte population (FIG. 10B), compared with an HIV×RSV diabody (as a negative control for all binding), and an h3G8×RSV diabody comparator molecule.
Figure 10B:
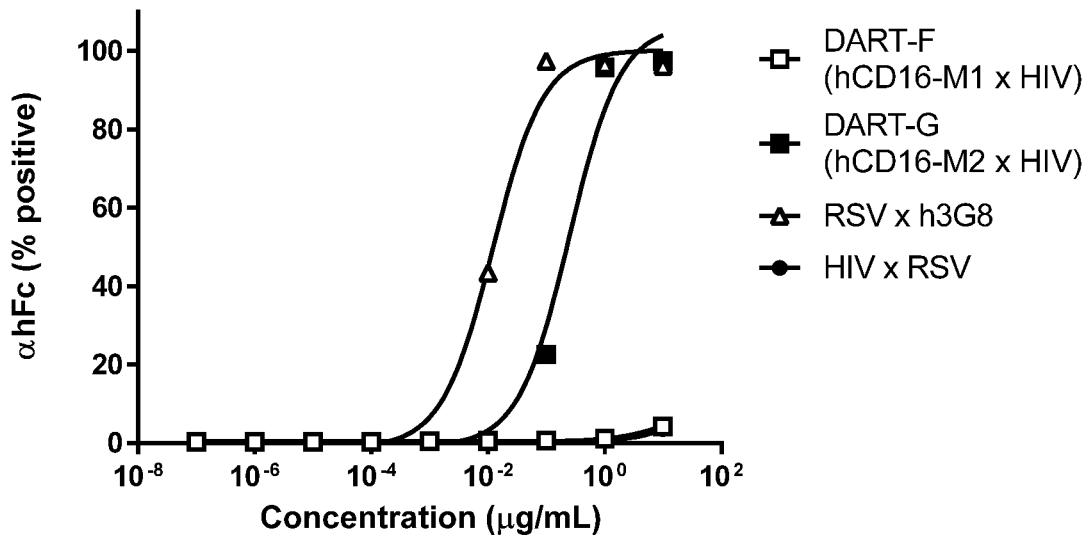

Similar binding was observed using whole blood of a second donor subject. Lymphocyte binding (CD16A F/V) and Neutrophil binding (CD16B, allotype undetermined) was assessed essentially as described using DART-F (hCD16-M1), DART-G (hCD16-M1), and the h3G8×RSV diabody comparator. The results of the investigation are shown in FIGS. 10A-10B. As shown in FIG. 10A, DART-F (hCD16-M1) and DART-G (hCD16-M1) both exhibited binding to CD16A-expressing cells of the gated lymphocyte population, with DART-F exhibiting greater binding; the h3G8×RSV diabody comparator molecule exhibited much weaker binding. As shown in FIG. 10B, DART-F failed to bind CD16B-expressing cells of the gated granulocyte population, in contrast to DART-G and the h3G8×RSV diabody comparator molecule, which both exhibited binding.

Example 3

CD16B Allotype Specificity of Anti-CD16 Binding Molecules CD16-M1 and CD16-M2

Figure 11A:
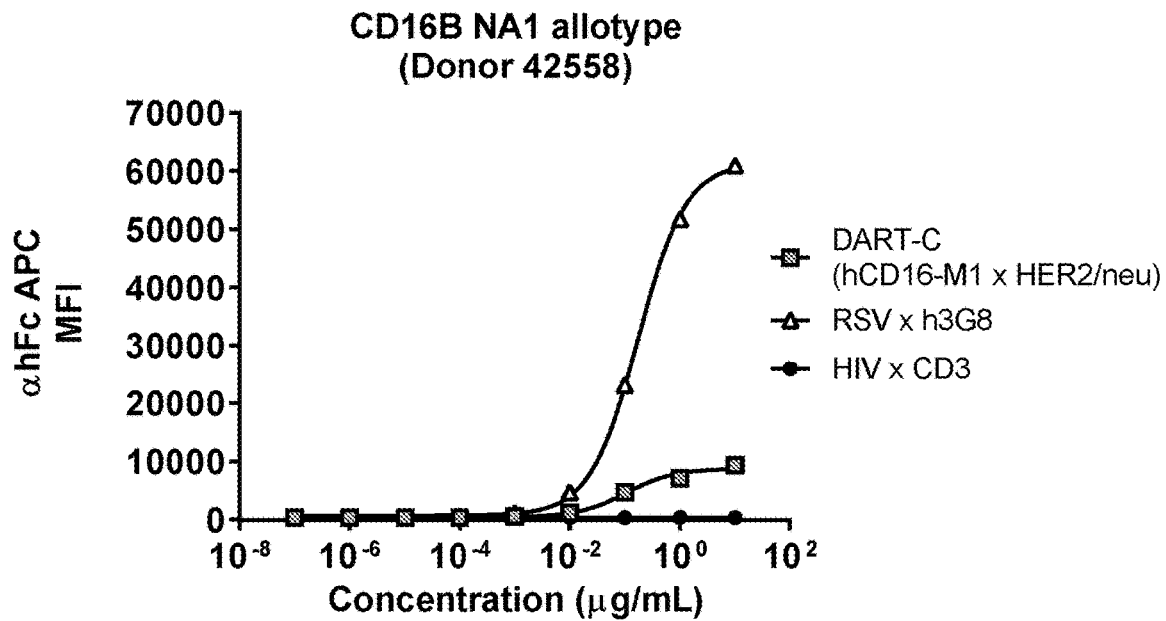
FIGS. 11A-11B show the ability of CD16 Binding Domains of CD16-M1 and h3G8 to distinguish glycosylation allotypes NA1 (FIG. 11A) and NA2 (FIG. 11B).
Figure 11B:
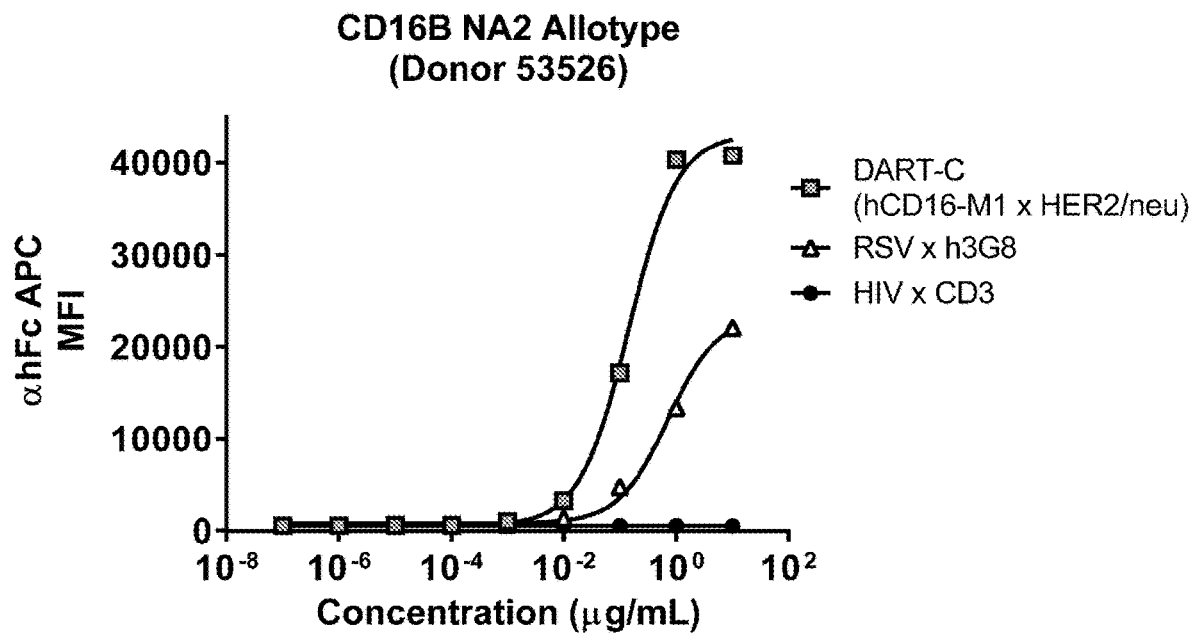

In order to demonstrate the ability of the CD16×DA Binding Molecules of the invention to distinguish glycosylation allotypes NA1 and NA2 of CD16B, DART-F (hCD16-M1) and the h3G8×RSV diabody comparator were incubated in the presence of whole blood and analyzed essentially as described above. The results show diabody staining of whole blood that had been gated on CD66b+ cells (i.e., neutrophils and eosinophils). FIGS. 11A-11B show the results of such an analysis, and indicate that the h3G8×RSV diabody comparator exhibited strong binding to NA1 and medium binding to NA2. In contrast, DART-F exhibited strong binding to NA2 and weak binding to NA1.

Example 4

CD16B Allotype Specificity of CD16 Binding Molecules CD16-M1 and CD16-M2

Figure 12:
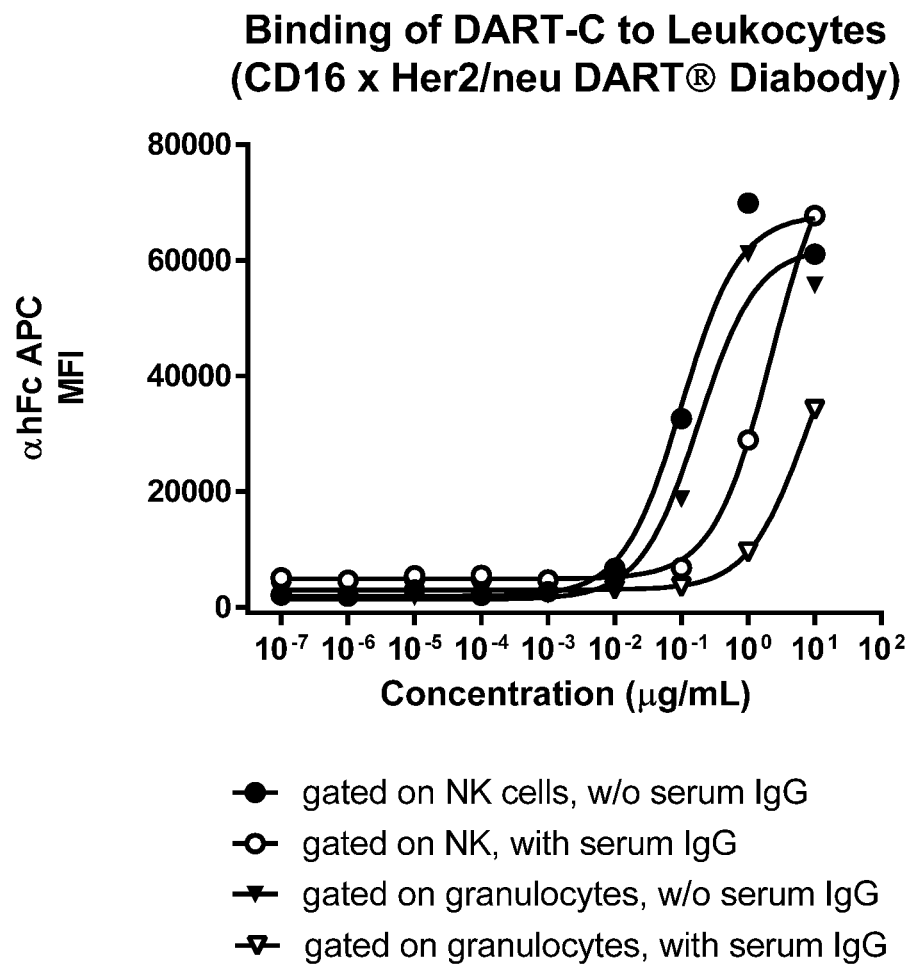
FIG. 12 shows the ability of CD16 Binding Domains of antibody hCD16-M1 (present in DART-C) to preferentially bind to NK cells in whole blood.

In order to further evaluate the ability of the CD16×DA Binding Molecules of the invention to bind leukocytes, the ability of CD16 Binding Domains of CD16-M1 to bind NK cells and granulocytes from whole blood was assessed. DART-C was incubated in the presence of whole blood leukocyte cells and analyzed essentially as described above. The results show diabody staining of whole blood that had been gated on NK cells (0.6% of leukocytres) or on granulocytes (49% of leukocytes). FIG. 12 shows the results of such an analysis, and indicates that CD16-M1 preferentially binds to NK cells.

Example 5

Binding of CD16 Binding Molecules to Human CD16, Cynomolgus Monkey CD16 and Murine CD16

Since the amino acid sequences of human CD16, cynomolgus monkey CD16 and murine CD16 share varying degrees of homology (FIG. 13; SEQ ID NOs:183, 184, and 185, respectively), the ability of CD16×DA Binding Molecules possessing CD16 Binding Domains of antibodies CD16-M1, CD16-M2 and 3G8 to bind human CD16, cynomolgus monkey CD16 and murine CD16 was investigated. The analysis was conducted using a BIACORE® format in which the diabodies molecules were captured on a Her2-His-tag surface, and the CD16 molecules (IgG2-Fc fusion proteins, 25 and 100 nM) were passed over the captured diabodies (normalized; bivalent binding fit estimate). The results of the investigation are summarized in Table 17.

TABLE 17

| CD16 Binding Molecule | CD16 Binding Domain | Human CD16 158F $K_D$ (nM) | Cynomolgus Monkey CD16 $K_D$ (nM) | Murine CD16 $K_D$ (nM) |
| --- | --- | --- | --- | --- |
| DART-1 | h3G8 | 13 | 29 | No Binding |
| DART-C | hCD16-M1 | 12 | 571 | No Binding |
| DART-D | hCD16-M2 | 4 | 597 | No Binding |

The CD16 binding domain of h3G8 was found to be able to bind CD16a of cynomolgus monkey with somewhat reduced affinity relative to its binding to human CD16a. The CD16 binding domains of DART-C (hCD16-M1) and DART-D (hCD16-M2) were found to have low affinity to cynomolgus monkey CD16. None of the tested CD16 binding molecules were found to be capable of binding to murine CD16, commensurate with its lower homology to human CD16.

Example 6

Figure 14A:
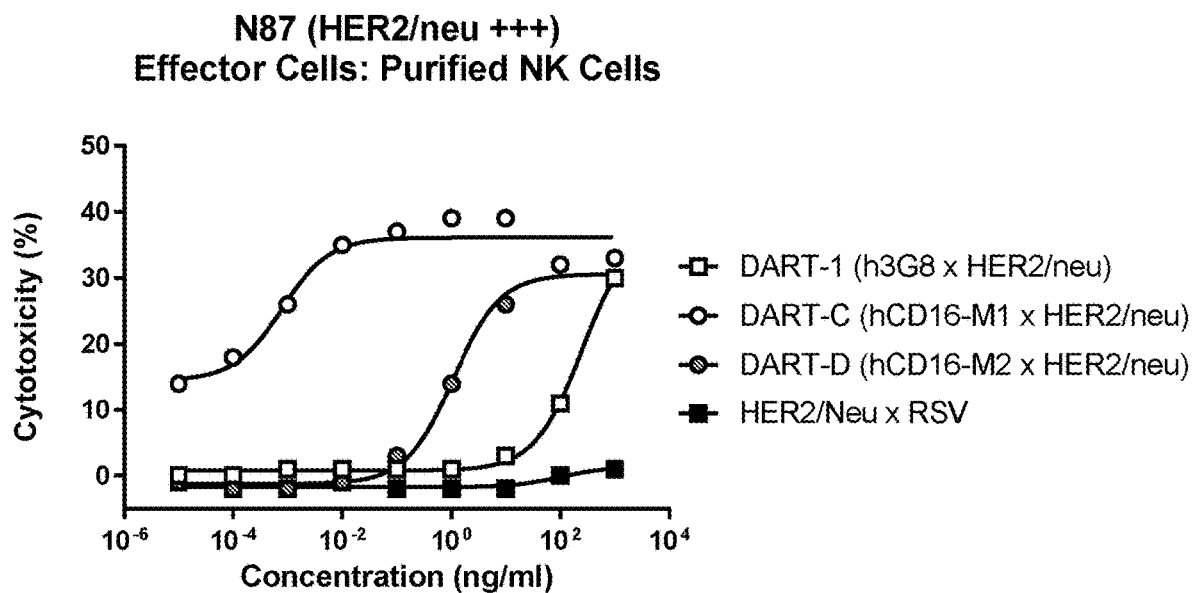
FIGS. 14A-14E show the percentage cytotoxicity resulting from a 24 hour incubation of target cancer cells expressing different levels of HER2/neu and Effector cells (either human PBMC (E:T=30:1) or purified human NK cells (E:T=2:1)) in the presence of the CD16×HER2/neu Binding Molecules: DART-C (having an hCD16-M1 CD16 Binding Domain), DART-D (having an hCD16-M2 CD16 Binding Domain), DART-1 (having an h3G8 CD16 Binding Domain), a negative control HER2/neu×RSV diabody or a positive h3G8×RSV diabody.
Figure 14B:
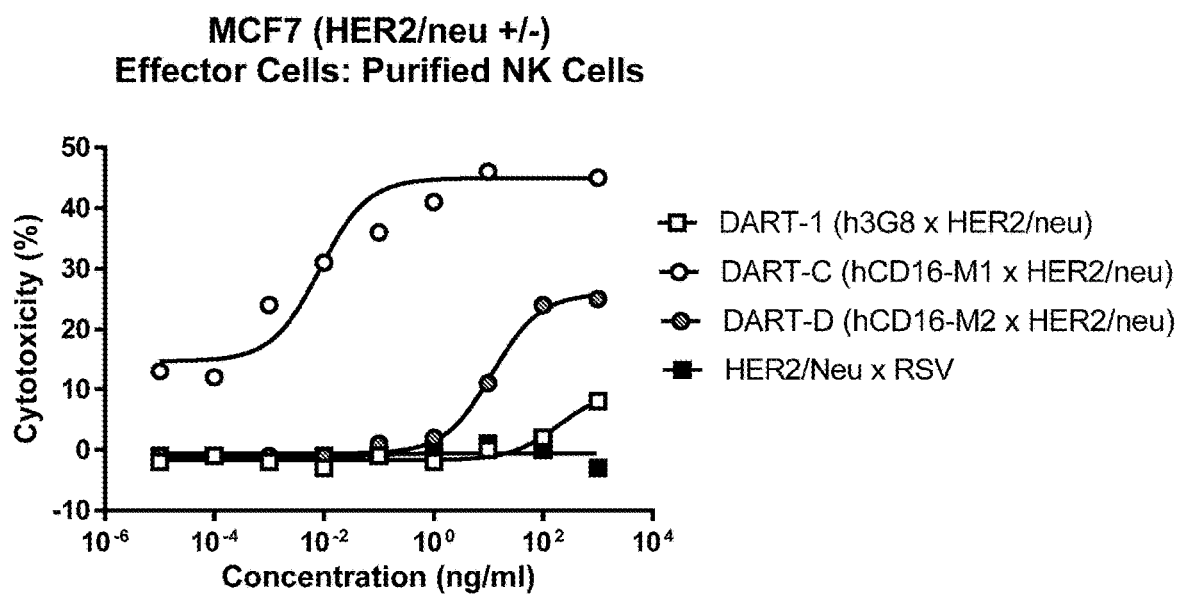
Figure 14C:
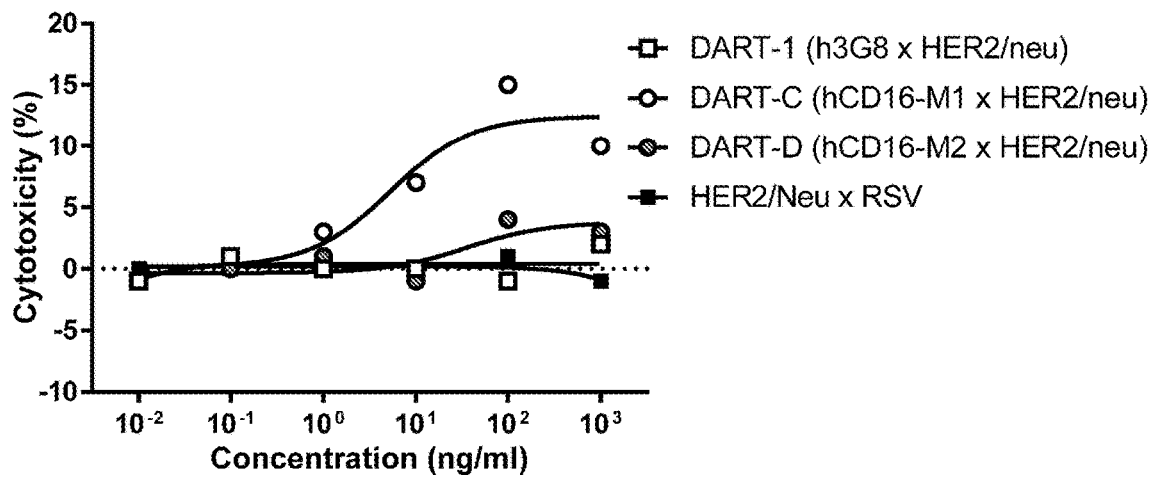
Figure 14D:
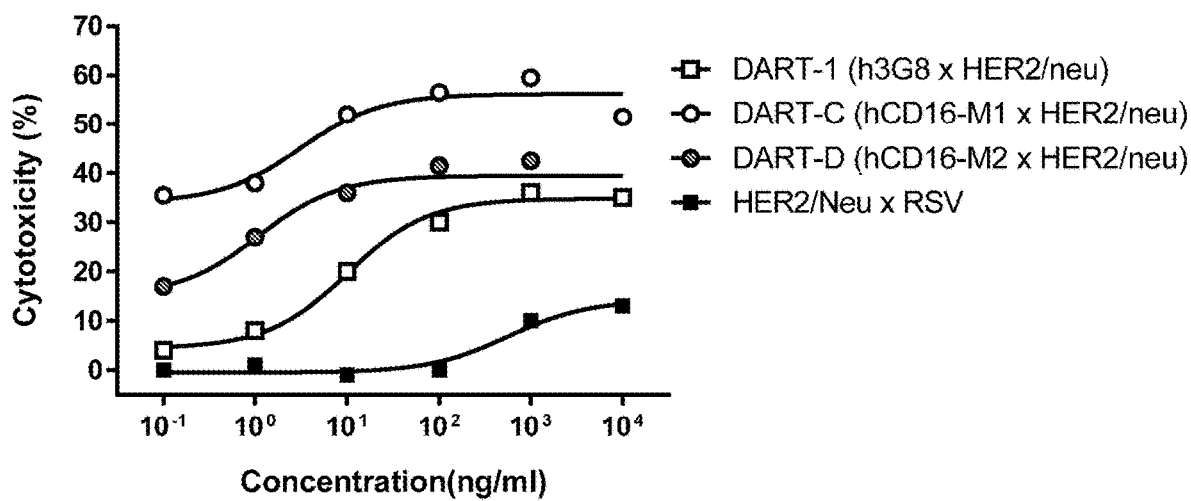
Figure 14E:
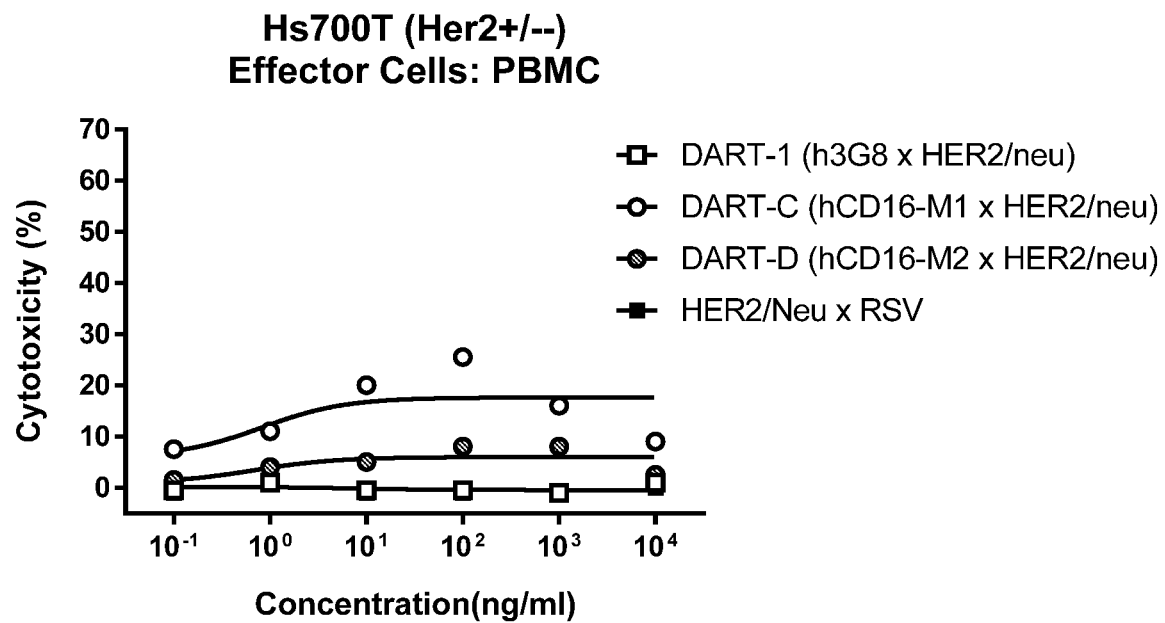

Evaluation of CD16 Binding Molecule-Mediated Cytotoxicity of HER2/Neu-Positive Cells In order to demonstrate the ability of the CD16×DA Binding Molecules of the invention to mediate cell killing, the CD16×HER2/neu Binding Molecules:
DART-C (having an hCD16-M1 CD16 Binding Domain);
DART-D (having an hCD16-M2 CD16 Binding Domain);
DART-1 (having an h3G8 CD16 Binding Domain);
or a HER2/Neux RSV diabody (negative control) were separately incubated with target cancer cells expressing different levels of HER2/neu in the presence of Effector cells (either human PBMC (E:T=30:1) or purified human NK cells (E:T=2:1)) for 24 hours. The percentage cytotoxicity (i.e., redirected cell killing) was determined by measuring the release of lactate dehydrogenase (LDH) into the media by damaged cells essentially as described below. The results of this investigation are shown in FIGS. 14A-14E. FIG. 14A shows the cytotoxicity exhibited against N87 HER2/neu target cells ((HER2/neu expression: +++) by purified NK cells; the CD16A allotype of such NK cells was 158F/158F. FIG. 14B shows the cytotoxicity exhibited against MCF7 HER2/neu target cells (HER2/neu expression: +/−) by purified NK cells; the CD16A allotype of such NK cells was 158F/158F. FIG. 14C shows the cytotoxicity exhibited against MDA-MB-231 HER2/neu target cells (HER2/neu expression: +/−) by PBMCs; the CD16A allotype of the NK cells of such PBMC preparation was not assessed. FIG. 14D shows the cytotoxicity exhibited against N87 HER2/neu target cells (HER2/neu expression: +++) by PBMCs; the CD16A allotype of the NK cells of such PBMC preparation was 158F/158V. FIG. 14E shows the cytotoxicity exhibited against Hs700T HER2/neu target cells (HER2/neu expression: +/−) by PBMCs; the CD16A allotype of the NK cells of such PBMC preparation was 158F/158V. The results show that CD16×DA Binding Molecules comprising the hCD16-M1 CD16 Binding Domain exhibited greater cytotoxicity against the HER2/neu-expressing cancer cells than CD16×DA Binding Molecules comprising the hCD16-M2 CD16 Binding Domain, and that molecules comprising such CD16 Binding Domains exhibited greater cytotoxicity than CD16×DA Binding Molecules comprising the h3G8 CD16 Binding Domain.

Example 7

Figure 15A:
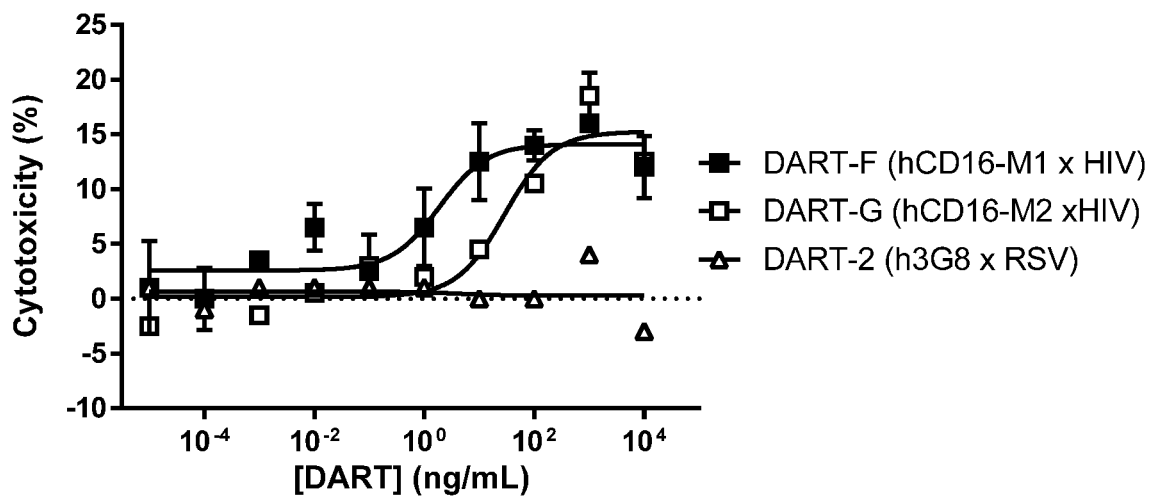
FIGS. 15A-15C show the percentage cytotoxicity resulting from a 24 hour incubation of HEK/D371 target cells expressing subtype HIV Env protein and Effector cells (either human PBMC (E:T=30:1) or purified human NK cells (E:T=3:1)) in the presence of the CD16×HIV env CD16 Binding Molecules: DART-F (having an hCD16-M1 CD16 Binding Domain), DART-G (having an hCD16-M2 CD16 Binding Domain), or DART-2 (having an h3G8 CD16 Binding Domain).
Figure 15B:
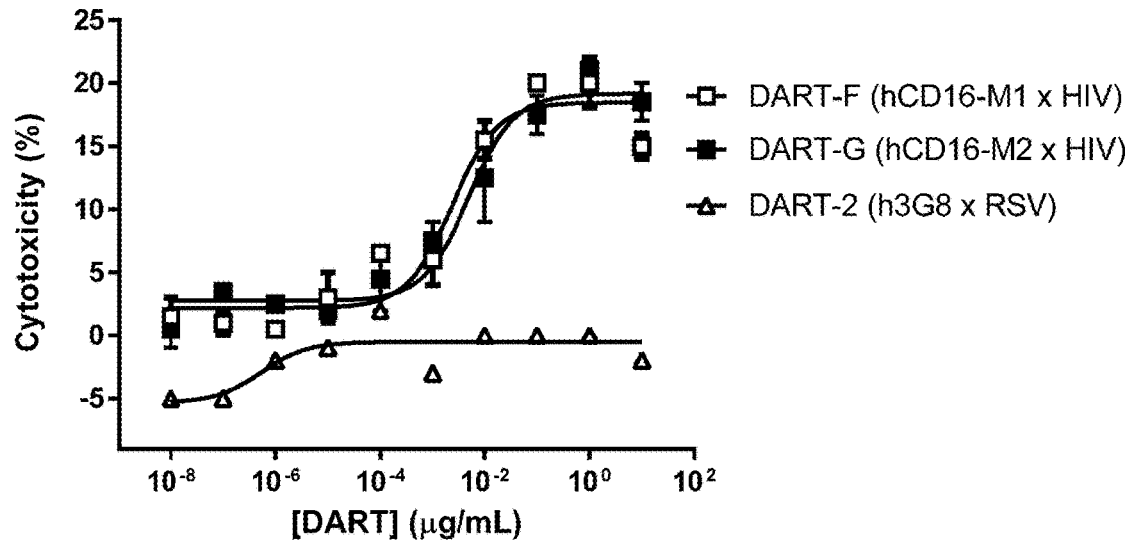
Figure 15C:
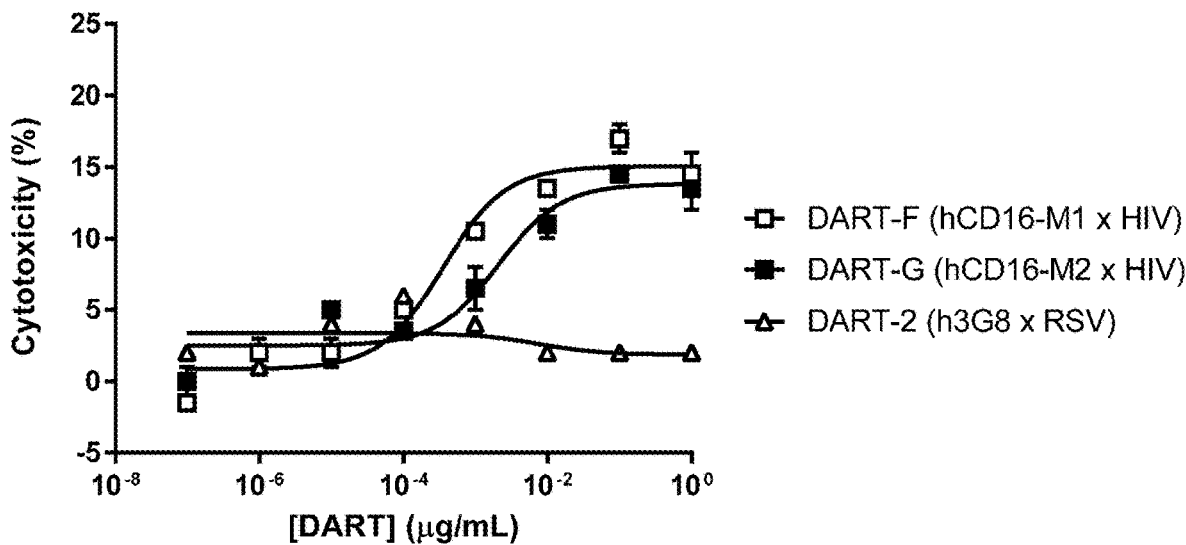

Evaluation of CD16 Binding Molecule-Mediated Cytotoxicity of HIV-Infected Cells In order to further demonstrate the ability of the CD16×DA Binding Molecules of the invention to mediate cell killing, the CD16×HIV env Binding Molecules:
DART-F (having an hCD16-M1 CD16 Binding Domain);
DART-G (having an hCD16-M2 CD16 Binding Domain);
or DART-2 (a h3G8×RSV diabody used as a negative control here)), were separately incubated with target 293HEK D371, which express HIV Env, in the presence of Effector cells (either human PBMC (E:T=30:1) or purified human NK cells (E:T=3:1) for 24 hours. The percentage cytotoxicity (i.e. redirected cell killing) was determined by measuring the release of lactate dehydrogenase (LDH) into the media by damaged cells using an LDH redirected cell killing assay essentially as described below. The results of this investigation are shown in FIGS. 15A-15C. FIG. 15A shows the cytotoxicity exhibited against the 293HEK D371 target cells by PBMCs of a first donor; the CD16A allotype the NK cells of such PBMC preparation was 158F/158V. FIG. 15B shows the cytotoxicity exhibited against the 293HEK D371 target cells by PBMCs of a second donor; the CD16A allotype of the NK cells of such PBMC preparation was 158F/158F. FIG. 15C shows the cytotoxicity exhibited against the 293HEK D371 target cells MC by purified NK cells; the CD16A allotype of the NK cells was 158F/158V. The results again showed that CD16×DA Binding Molecules comprising the hCD16-M1 CD16 Binding Domain exhibited greater cytotoxicity against the HIV env-espressing cells than CD16×DA Binding Molecules comprising the hCD16-M2 CD16 Binding Domain.

As indicated above, DART-F and DART-G are both Fc Domain-containing diabodies composed of three polypeptide chains. In order to demonstrate the ability of CD16×DA Binding Molecules of the invention that lack Fc Domains to mediate cell killing, the CD16×HIV env Binding Molecules:
DART-X (having an hCD16-M1 CD16 Binding Domain);
DART-Y (having an hCD16-M2 CD16 Binding Domain);
DART-0 (having an h3G8 CD16 Binding Domain);
or DART-3 (a CD16×RSV diabody having an hCD16-M1 CD16 Binding Domain used as a negative control here), were separately incubated with target HEK/D371 cells, which express the HIV env protein, in the presence of Effector cells (either Jurkat/CD16A 158F (FIG. 16A) or 158V/NFAT-Luc cells (FIG. 16B)). The percentage cytotoxicity (i.e. cell killing) was determined by measuring the release of lactate dehydrogenase (LDH) into the media by damaged cells using an LDH redirected cell killing assay essentially as described below. The results of this investigation are shown in FIGS. 16A-16B.

Figure 16A:
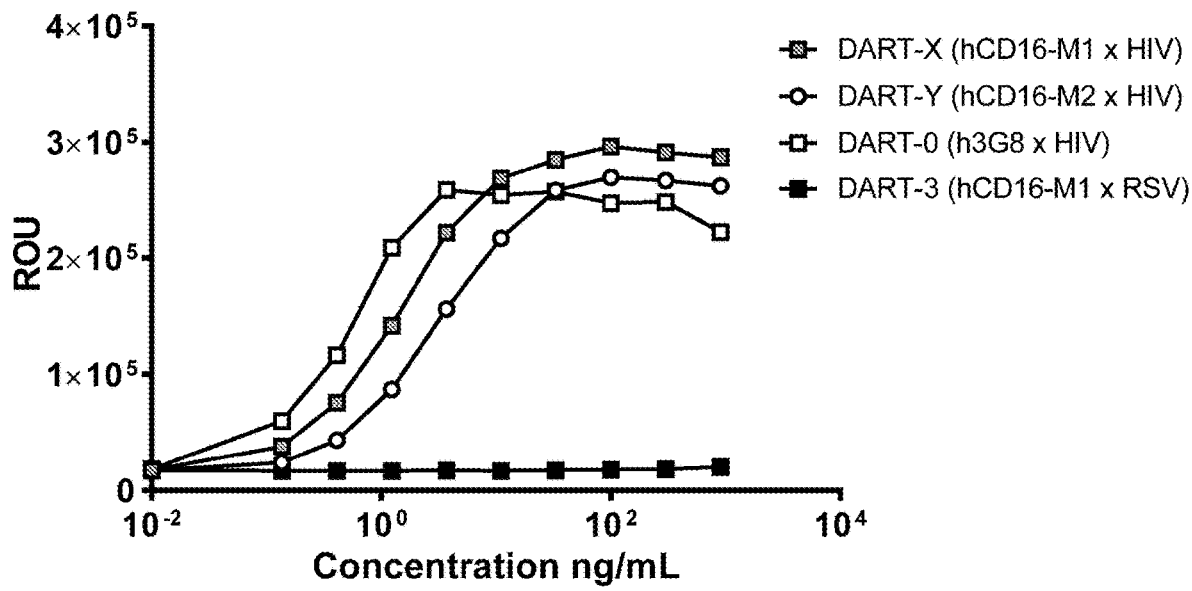
FIGS. 16A-16B show the percentage cytotoxicity of target HEK/D371 cells, which express the HIV env protein, in the presence of Effector cells (either Jurkat/CD16A 158F (FIG. 16A) or 158V/NFAT-Luc cells (FIG. 16B) upon incubation with DART-X (having an hCD16-M1 CD16 Binding Domain), DART-Y (having an hCD16-M2 CD16 Binding Domain), DART-0 (having an h3G8 CD16 Binding Domain) or DART-3 (a CD16×RSV diabody having an hCD16-M1 CD16 Binding Domain).
Figure 16B:
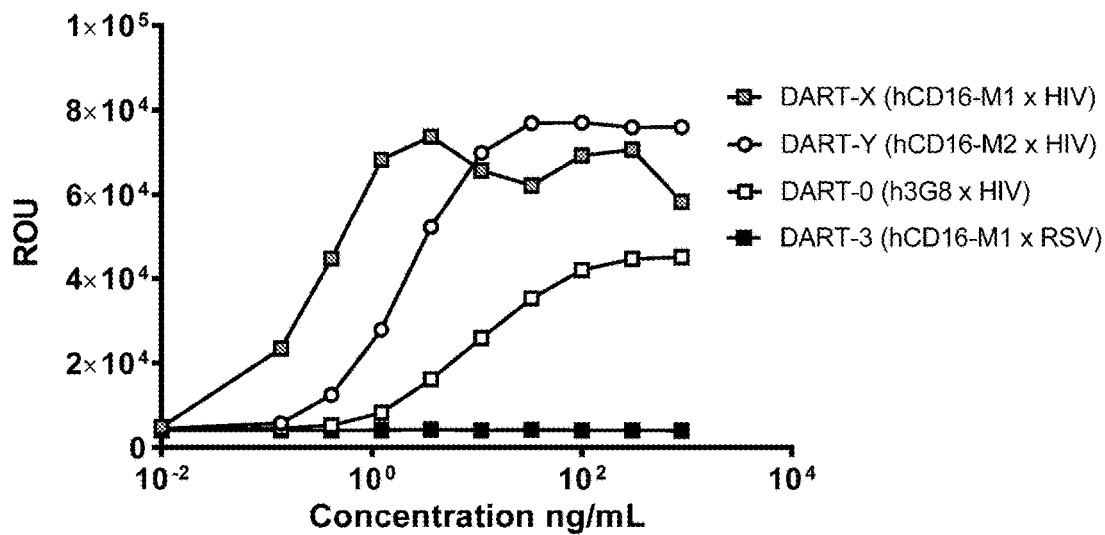

FIGS. 16A-16B show that DART-X (having an hCD16-M1 CD16 Binding Domain) exhibited a higher percentage cytotoxicity than DART-Y (having an hCD16-M2 CD16 Binding Domain). DART-0 (having an h3G8 CD16 Binding Domain) was found to mediate a higher level of cytotoxicity than DART-Y, but this effect was dependent on the effector cells having a 158V allotype (FIG. 16A vs. FIG. 16B). In contrast, the cytotoxicity mediated by DART-X or DART-Y was independent of CD16A allotype (FIG. 16A vs. FIG. 16B).

Example 8

Optimization of Binding to Non-Human Primate CD16

As noted above, hCD16-M1 was found to have low affinity to cynomolgus monkey CD16 (cynoCD16). Random mutagenesis was used to introduce substitutions within the $CDR_L3$ (Kabat positions 90-95) and $CDR_H3$ (Kabat positions 96-100) Domains of hCD16-M1. The mutants were screened to identify clones having enhanced binding to non-human primate CD16 (e.g., cynoCD16) and that retained binding affinity binding to both alleles of human CD16. A variant designated "hCD16-M1A" having a mutated $CDR_H3$, and a variant designated "hCD16-M1B" having a mutated $CDR_L3$ were selected for further analysis. In addition, a third variant combining the $CDR_H3$ and $CDR_L3$ mutations was generated and designated "hCD16-M1AB." The amino acid sequence of the CDRs and VH and VL Domains have been provided above (see, e.g., Table 8). Exemplary CD16×DA Binding Molecules incorporating the optimized anti-CD16 binding domains: hCD16-M1A, hCD16-M1B, or hCD16-M1AB, and having an anti-HER2/neu Binding Domain were generated and designated DART- I, DART-J, and DART-K, respectively (see, Table 12 for summary and above for detailed description and full amino acid sequences).

The ability of the exemplary CD16×HER2/neu Binding Molecules comprising the optimized hCD16-M1A, hCD16-M1B, and hCD16-M1AB, to bind CD16 expressed on the surface of human (FIG. 17A), cynomolgus monkey (FIG. 17B), and rhesus monkey (FIG. 17C) NK cells was examined by flow cytometry. Briefly, PBMCs were isolated and incubated in the presence of CD16-binding diabodies: DART-C (having the parental hCD16-M1 VH and VL domains); DART-I; DART-J; DART-K (having the optimized hCD16-M1A, hCD16-M1B, and hCD16-M1AB VH/VL Domains, respectively); a HER2/neu×RSV diabody (as a negative control for CD16 binding); DART-3 (a CD16×RSV diabody control having the having the parental hCD16-M1 VH and VL domains); or the DART-1 (h3G8× HER2/neu diabody) comparator molecule. Following incubation, the cells were labeled with: anti-CD56-allophycocyanin (CD56 APC, NK cell marker), and anti-CD3-peridinin chlorophyll protein-Cy5.5 (CD3 PerCP Cy5.5, T-cell marker), and anti-human Fc-Phycoerythrin (αhFc PE) to detect diabody binding and the cell surface. The labeled cells were analyzed by flow cytometry gated on NK cells.

Figure 17A:
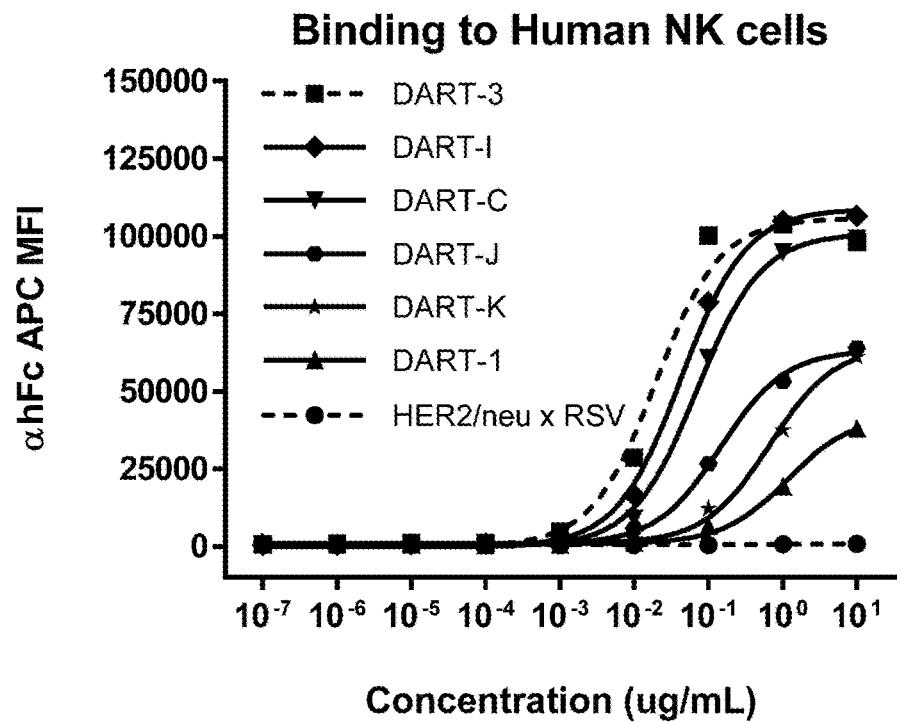
FIGS. 17A-17C show the ability of the optimized CD16 Binding Domains of hCD16-M1A (present in DART-I) hCD16-M1B (present in DART-J), hCD16-M1AB (present in DART-K), to bind to human NK cells (FIG. 17A), cynomolgus monkey NK cells (FIG. 17B), and rhesus monkey NK cells (FIG. 17C) present in PBMC samples as compared to parental CD16 Binding Domain of hCD16-M1 (present in DART-C an and DART-3) and the CD16 Binding Domain of h3G8 (present in DART-1). The HER2/neu×RSV diabody (lacking a CD16 Binding Domain) is included as a negative control.
Figure 17B:
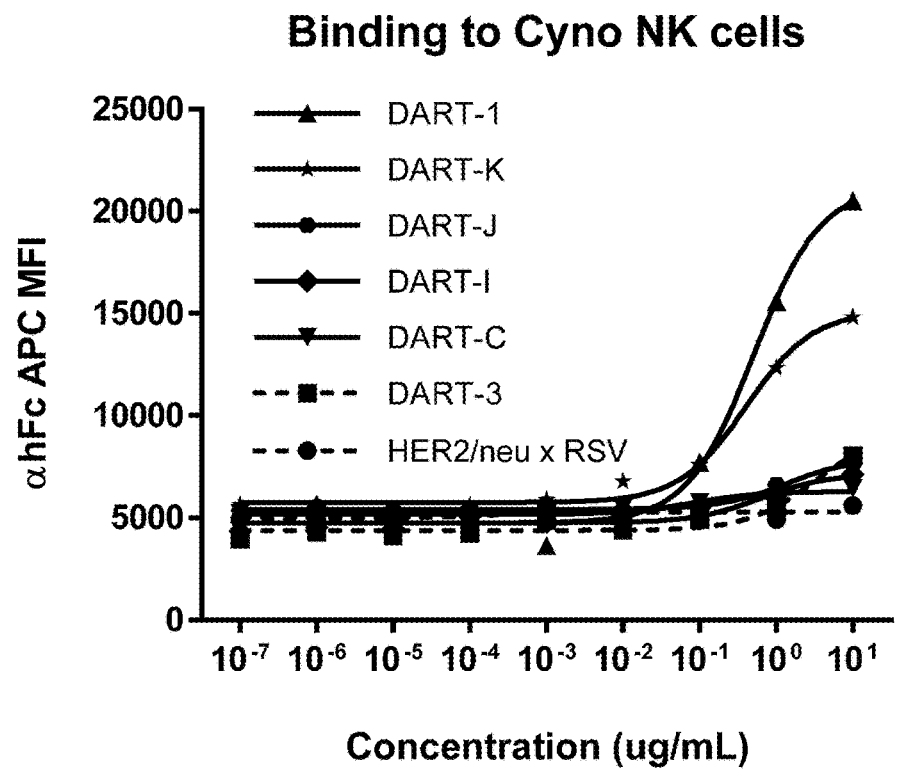
Figure 17C:
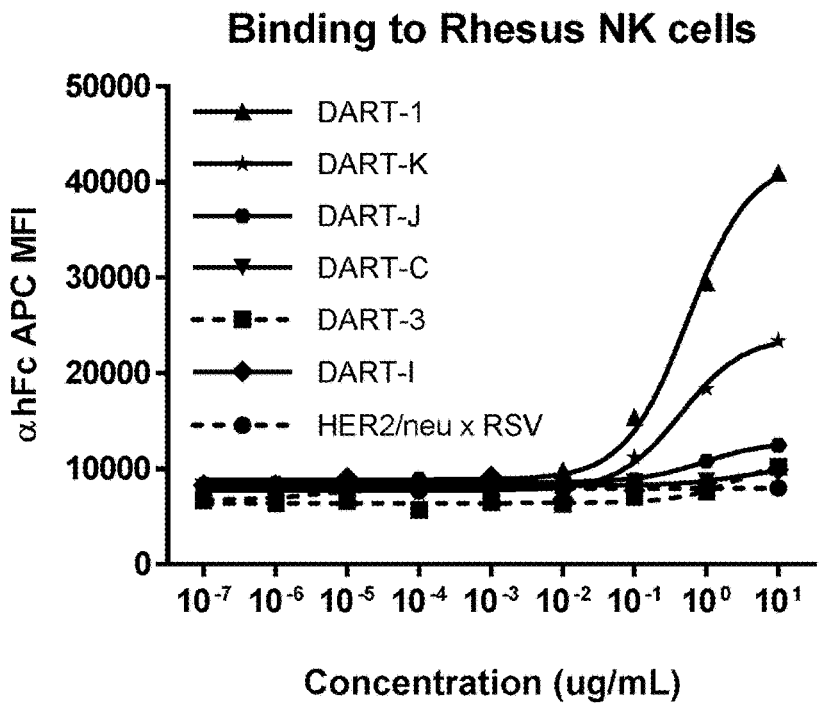

The co-staining results of the investigation are shown in FIGS. 17A-17C and indicate that the CD16×DA Binding Molecules comprising the optimized variants, particularly hCD16-M1AB (DART-K), exhibited improved affinity for non-human primate CD16 (FIGS. 17B-17C), although molecules comprising hCD16-M1B (DART-J) and hCD16-M1AB (DART-K) exhibited some reduction in binding to human CD16 (FIG. 17A) in this assay. No binding was observed by the negative control.

Figure 18A:
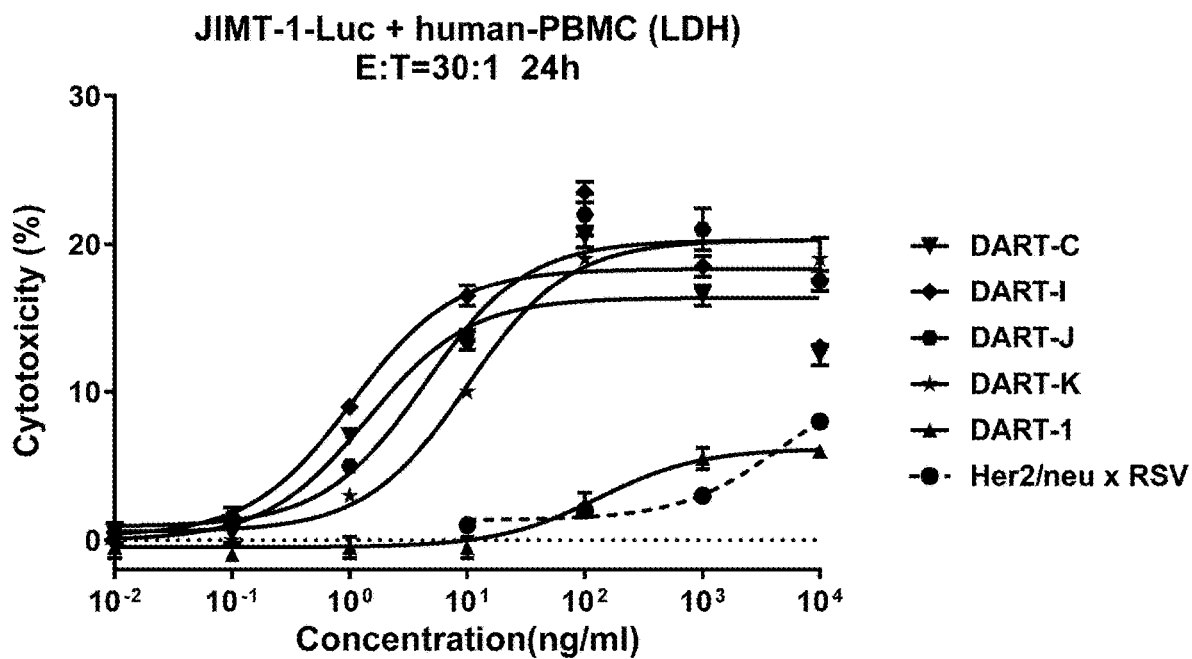
FIGS. 18A-18D show the ability of the optimized CD16 Binding Domains of hCD16-M1A (present in DART-I) hCD16-M1B (present in DART-J), and hCD16-M1AB (present in DART-K) to mediate redirected cell killing of HER2/neu expressing target cells with both human and cynomolgus monkey Effector cells. Plotted is the cytotoxicity resulting from a 24 hour incubation of JIMT-1-Luc target cancer cells and Effector cells (either human PBMCs (FIGS. 18A-18B) or cynomolgus monkey PMBCs (FIGS. 18C-18D)) (E:T=30:1) in the presence of the CD16×HER2/ neu Binding Molecules: DART-C (having an hCD16-M1 CD16 Binding Domain), DART-I (having an hCD16-M1A CD16 Binding Domain), DART-J (having a hCD16-M1B Binding Domain), DART-K (having a hCD16-M1AB Binding Domain), DART-1 (having an h3G8 CD16 Binding Domain), or a negative control HER2/neu×RSV diabody as measured in an LDH redirected cell killing assay (plotted as percent cytotoxicity, FIGS. 18A and 18C) or a LUM redirected cell killing assay (luminescence (LUM) is plotted in relative light units (RLU), FIGS. 18B and 18D).
Figure 18B:
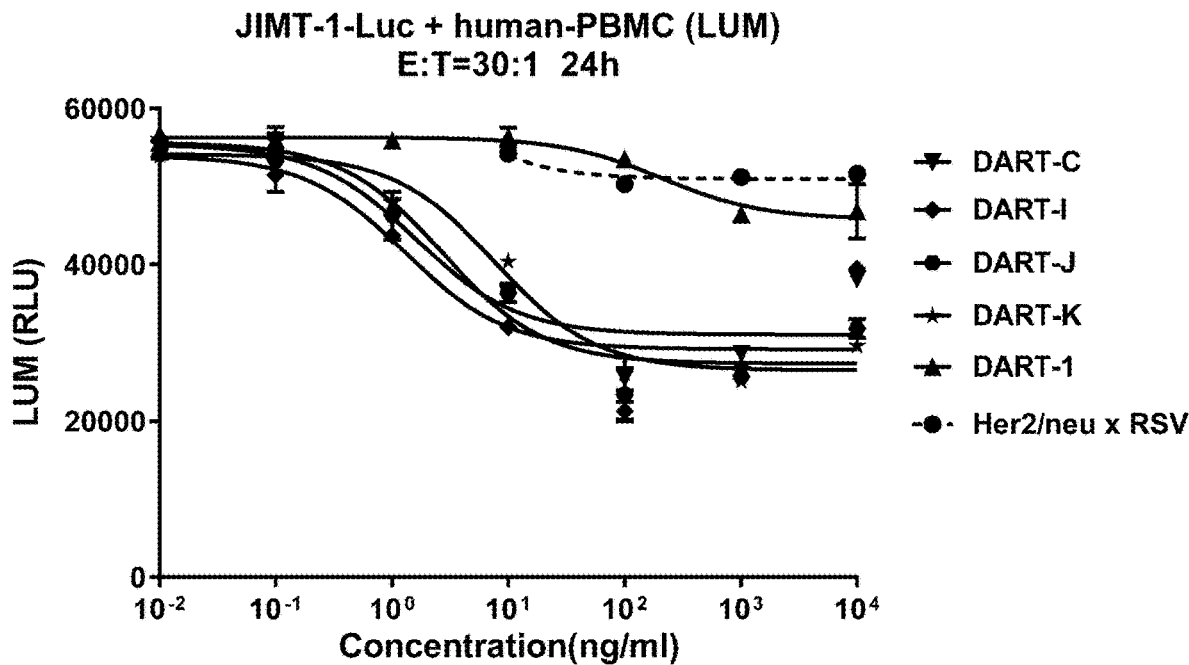
Figure 18C:
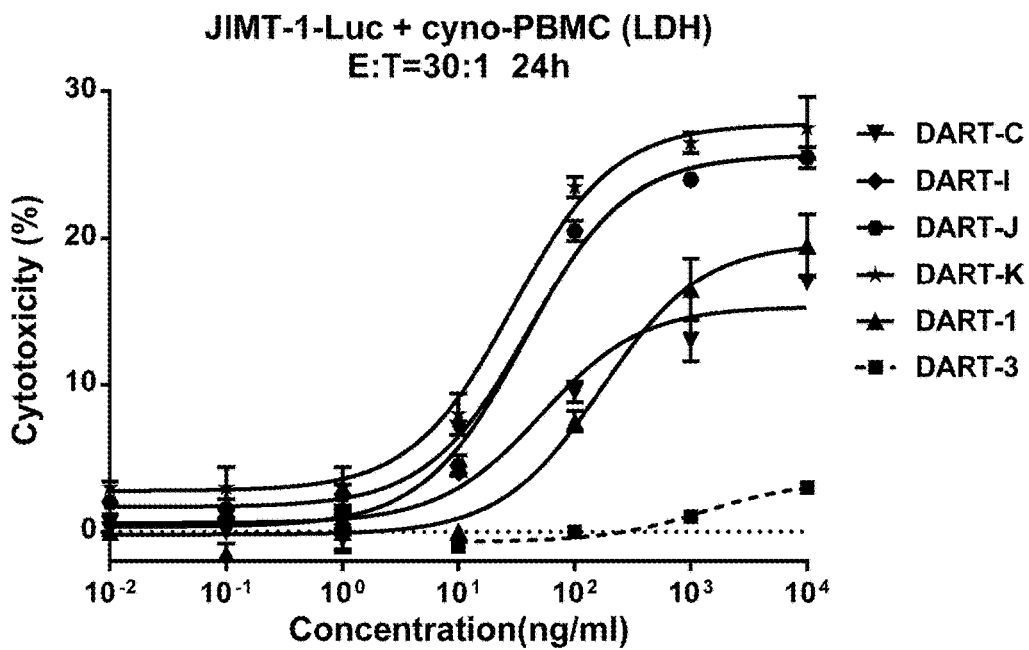
Figure 18D:
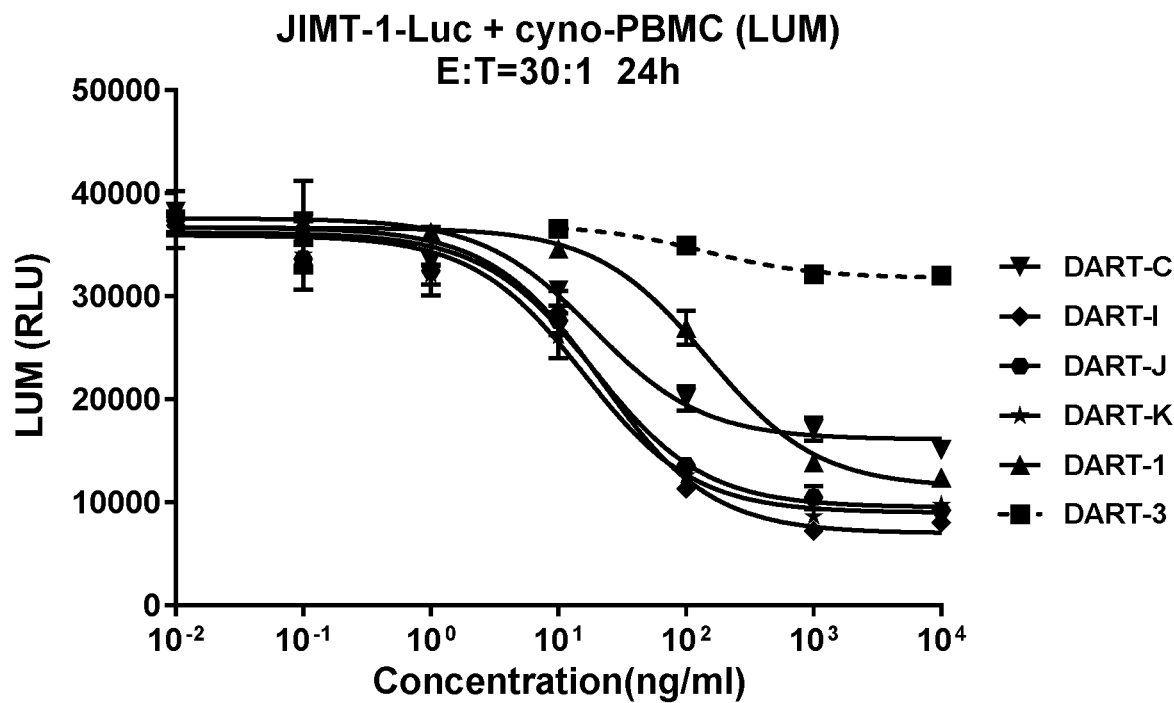

The ability of CD16×DA Binding Molecules having optimized hCD16-M1A, hCD16-M1B, and hCD16-M1AB binding domains, to mediate redirected cell killing of JIMT-1-Luc target cells with human PBMCs (huPBMCs) or cynomolgus monkey PBMC (cynoPBMCs) effector cells from several donors was evaluated using two different redirected cell killing assays. Representative data from these studies are presented in FIGS. 18A-18D and summarized in Table 18. In both assays, DART-C (having the parental hCD16-M1 VH and VL domains), DART-I, DART-J, or DART-K (having the optimized hCD16-M1A, hCD16-M1B, and hCD16-M1AB VH/VL Domains, respectively); a negative control (either HER2/neu×RSV diabody or the CD16×RSV diabody, DART-3); or DART-1 (h3G8×HER2/neu diabody) comparator molecule, were incubated with huPMBCs (FIG. 18A-18B) or cynoPBMCs (FIGS. 18C-18D) and JIMT-1-Luc target tumor cells at an E:T ration of 30:1 and the percentage cytotoxicity (i.e., cell killing) was determined. In one assay cell killing was determined by measuring the release of lactate dehydrogenase (LDH) into the media by damaged cells using an LDH redirected cell killing assay essentially as described below (FIGS. 18A and 18C)). In another assay cytotoxicity was determined by luminescence (LUM) assay measuring cellular luciferase activity of the target cells using a LUM redirected cell killing assay essentially as described below (FIGS. 18B and 18D). The EC50 values (ng/mL) for the LDH assay after 24 hour and 48 hour incubation is presented in Table 18.

TABLE 18

| | 24 hour Assay/LDH EC50, ng/mL | | 48 hour Assay/LDH EC50, ng/mL | |
| --- | --- | --- | --- | --- |
| | HuPBMCs | CynoPBMCs | HuPBMCs | CynoPBMCs |
| DART-1 | 131 | 170 | 156.1 | 101 |
| DART-C | 1.42 | 51.47 | 0.822 | 70.6 |
| DART-I | 1.05 | 36.98 | 0.492 | 13.31 |
| DART-J | 4.4 | 39.91 | 1.06 | 10.88 |
| DART-K | 10.8 | 29.44 | 2.24 | 6.66 |

These data show that, although the CD16×DA Binding Molecule comprising the CD16 binding domain of hCD16-M1 (DART-C) binds cynoCD16 with apparent low affinity, it is capable of mediating redirected cell killing. In addition, CD16×DA Binding Molecules comprising the optimized CD16 binding domains hCD16-M1A (DART-I), hCD16-M1B (DART-J), or hCD16-M1AB (DART-K) exhibited improved cytotoxicity with CynoPBMCs while exhibiting only a slight reduction in cytotoxicity with huPBMCs as compared to the same molecule comprising hCD16-M1 (DART-C).

Example 9

CD16×CD19 Binding Molecules

In further studies, exemplary CD16×DA Binding Molecules having an anti-CD19 Binding Domain and incorporating the anti-CD16 binding domain of hCD16-M1, or the optimized anti-CD16 binding domain of hCD16-M1B or hCD16-M1AB, were generated and designated DART-L, DART-M, and DART-N, respectively (see, Table 12 for summary and above for detailed description and full amino acid sequences). Three additional molecules were generated and designated DART-5 (comprising hCD16-M1), DART-6 (comprising hCD16-M1A), and DART-7 (comprising hCD16-M1AB), in which the CD19 Binding Domain was replaced with an anti-RSV binding domain (see, Table 12 for summary and above for detailed description), such exemplary CD16×RSV Binding Molecules are used below as negative controls for CD19 binding.

Figure 19A:
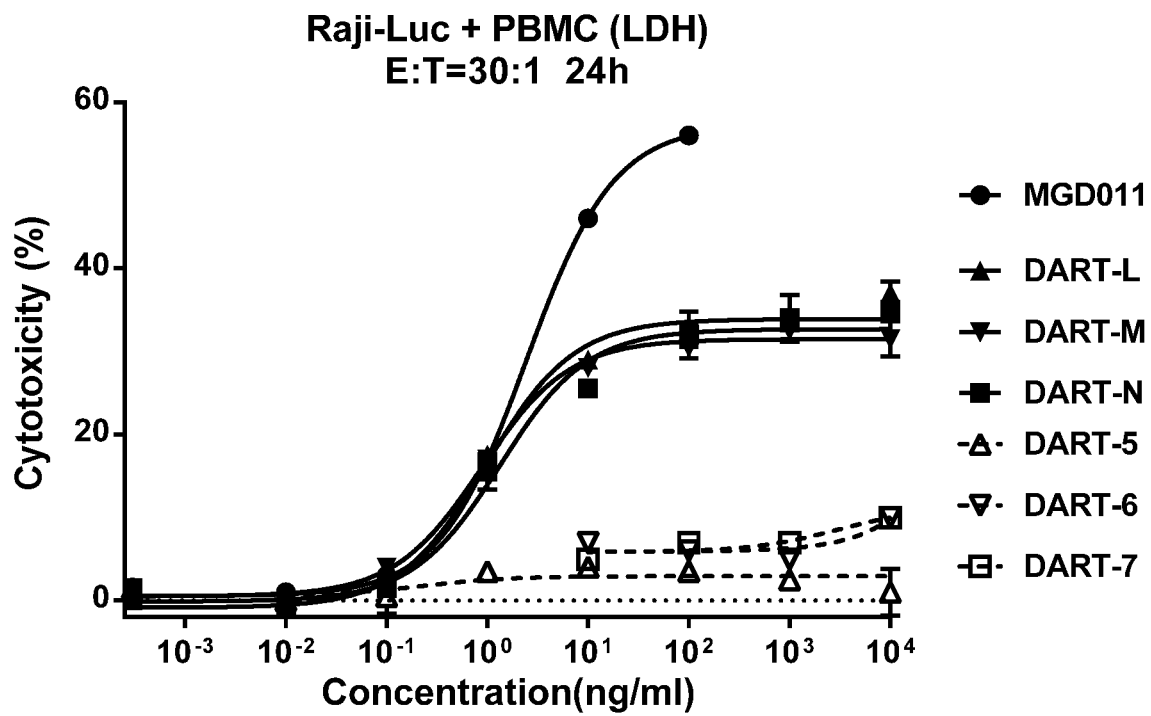
FIGS. 19A-19D show the ability of the optimized CD16 Binding Domains of hCD16-M1B (present in DART-M), and hCD16-M1AB (present in DART-N) to mediate redirected cell killing of CD19 expressing target cells with human Effector cells. Cytotoxicity measured after 24 hour (FIGS. 19A and 19C) and 48 hour incubations (FIGS. 19B and 19D) of Raji-Luc target cancer cells and human PBMC Effector cells (E:T=30:1) in the presence of the CD16× CD19 Binding Molecules: DART-L (having an hCD16-M1 CD16 Binding Domain), DART-M (having a hCD16-M1B Binding Domain), DART-N (having a hCD16-M1AB Binding Domain), duvortuxizumab (a positive control CD3× CD19 diabody), or negative control CD16×RSV diabodies DART-5 (having an hCD16-M1 CD16 Binding Domain), DART-6 (having a hCD16-M1B Binding Domain), DART-7 (having a hCD16-M1AB Binding Domain), as measured in an LDH redirected cell killing assay (plotted as percent cytotoxicity, FIGS. 19A and 19B) or a LUM redirected cell killing assay (LUM is plotted in RLU, FIGS. 19C and 19D).
Figure 19B:
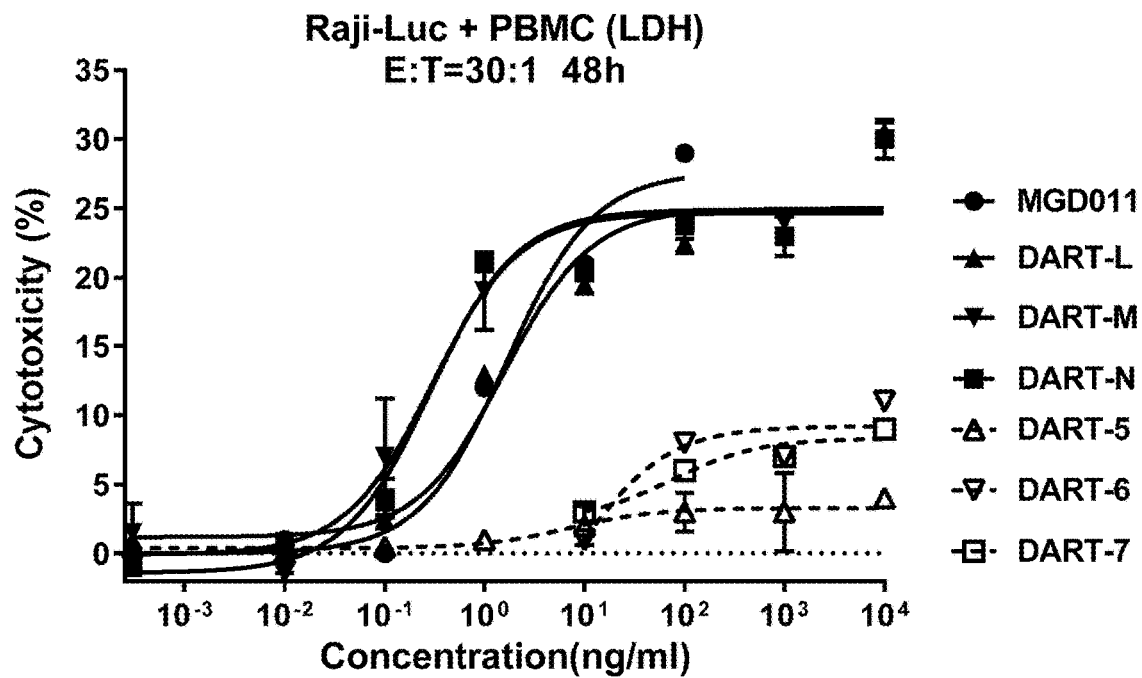
Figure 19C:
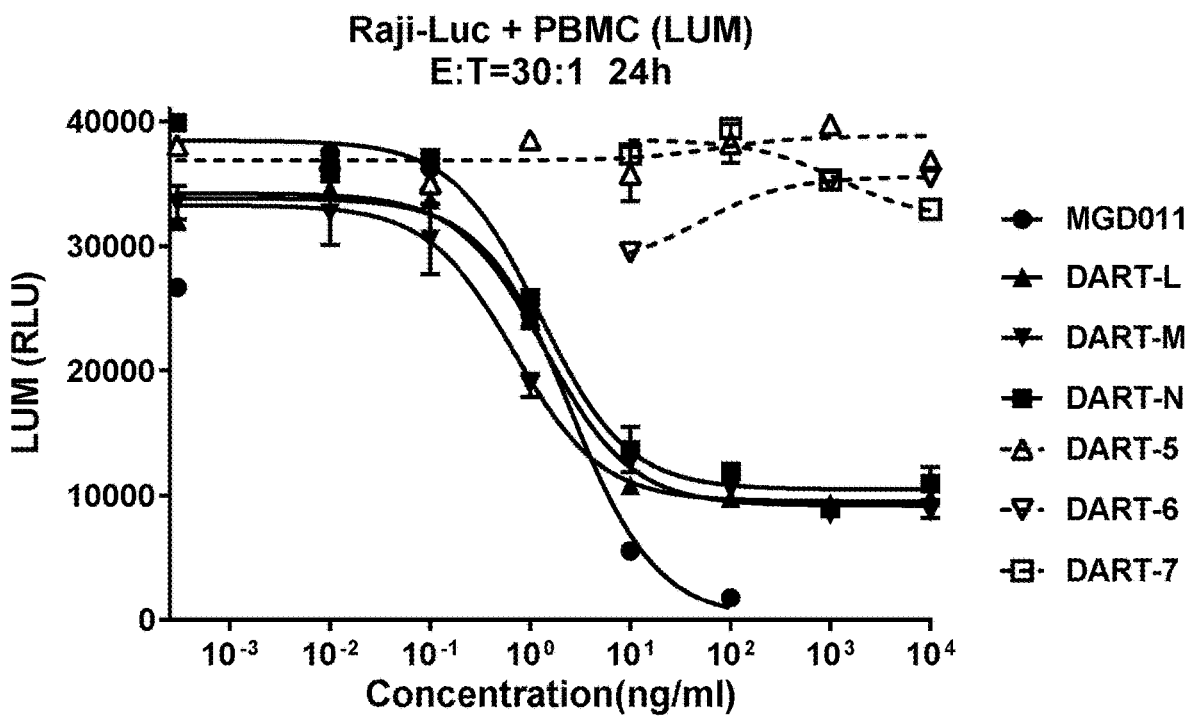
Figure 19D:
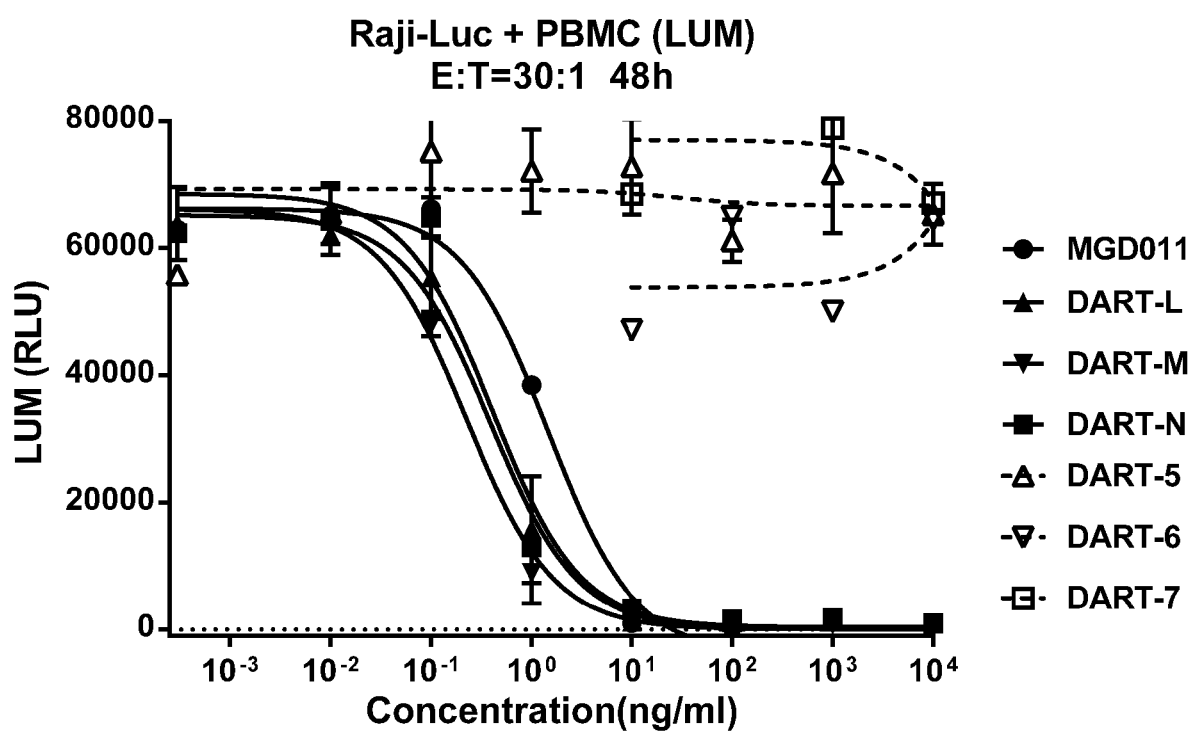

The ability of: DART-L, DART-M, and DART-N; the control molecules: DART-5, DART-6, and DART-7; or the CD3×CD19 DART® diabody duvortuxizumab (also known as MGD011; amino acid sequence found in WHO Drug Information, 2016, Proposed INN: List 116, 30(4):627-629) to mediate redirected cell killing of Raji-Luc target cells with human PBMCs (huPBMCs) effector cells (E:T=30:1) was evaluated in the LDH and LUM cell killing assays essentially as described below. Representative data from these studies are presented in FIGS. 19A-19D. The results of the LDH assays show that after 24 hours (FIG. 19A) and 48 hour (FIG. 19B) incubations the CD16×DA Binding Molecules exhibited similar cytotoxicity activity as MGD011, with the CD16×DA Binding Molecules comprising the optimized CD16 binding domains hCD16-M1B (DART-M), or hCD16-M1AB (DART-N), exhibiting similar cytotoxicity with huPBMCs as compared to the same molecule comprising hCD16-M1 (DART-L). Similar results were observed after 24 hours (FIG. 19C) and 48 hours (FIG. 19D) in the LUM assays. Minimal cytotoxicity was observed for the control molecules lacking a CD19 binding domain (DART-5, DART-6, and DART-7) in these studies.

Figure 20A:
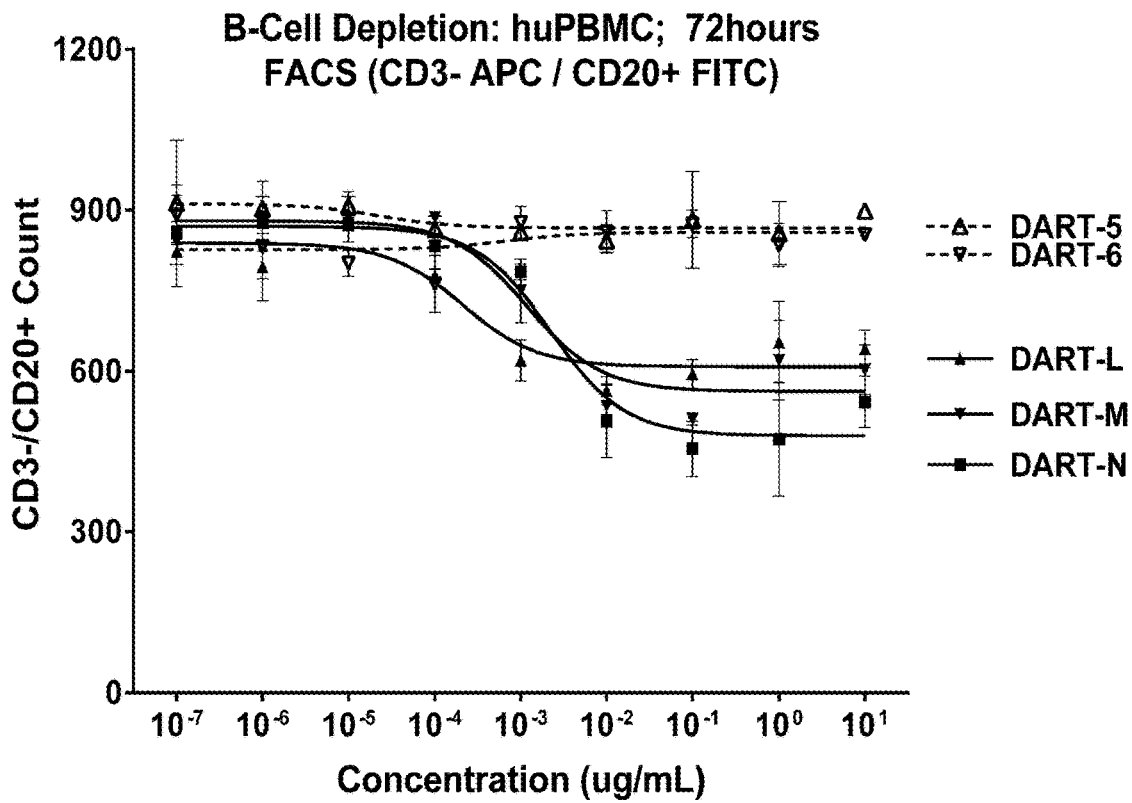
FIGS. 20A-20D show the ability of the optimized CD16 Binding Domains of hCD16-M1B (present in DART-M), and hCD16-M1AB (present in DART-N) to mediate autologous B-cell depletion in vitro both human and cynomolgus monkey PBMC samples. The B-cell counts (CD3$^-$/CD20$^+$ cells) after 72 hour (FIGS. 20A and 20C), 96 hour (FIG. 20B), and 144 hour (FIG. 20D) incubations of human (FIGS. 20A-20B) or cynomolgus monkey (FIGS. 20C-20D) PBMCs presence of the CD16×CD19 Binding Molecules: DART-L (having an hCD16-M1 CD16 Binding Domain), DART-M (having a hCD16-M1B Binding Domain), DART-N (having a hCD16-M1AB Binding Domain), or negative control CD16×RSV diabodies DART-5 (having an hCD16-M1 CD16 Binding Domain), DART-6 (having a hCD16-M1B Binding Domain) as measured by flow cytometry.
Figure 20B:
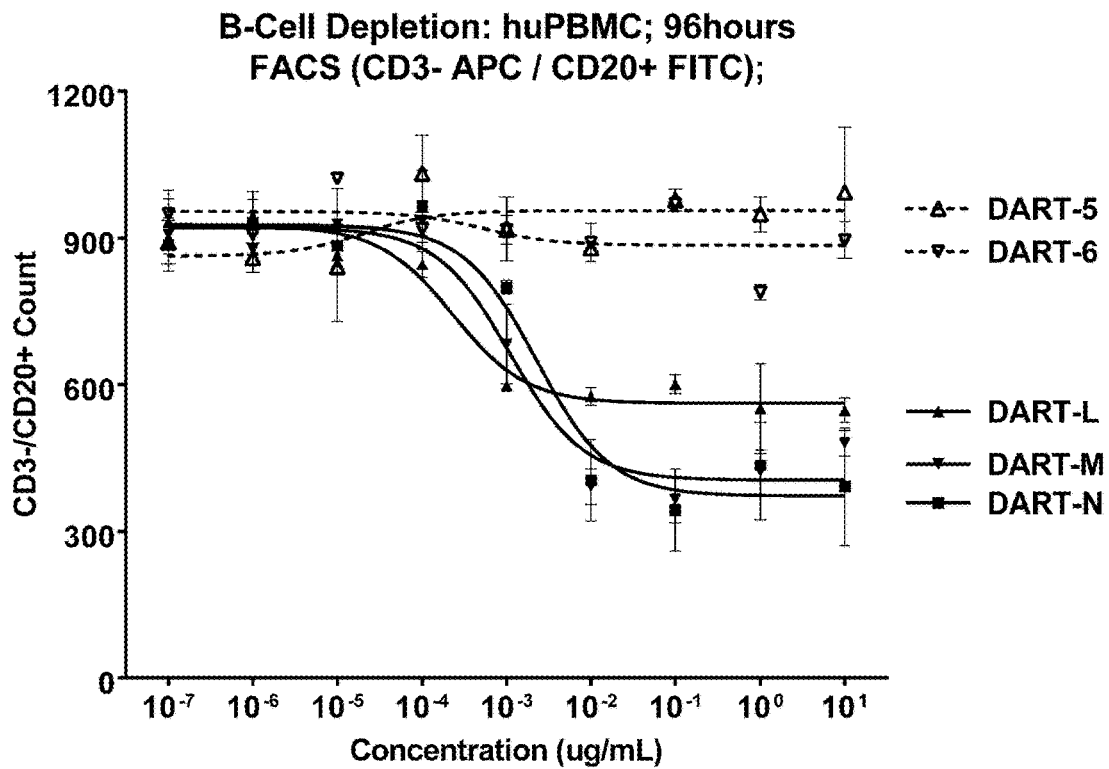
Figure 20C:
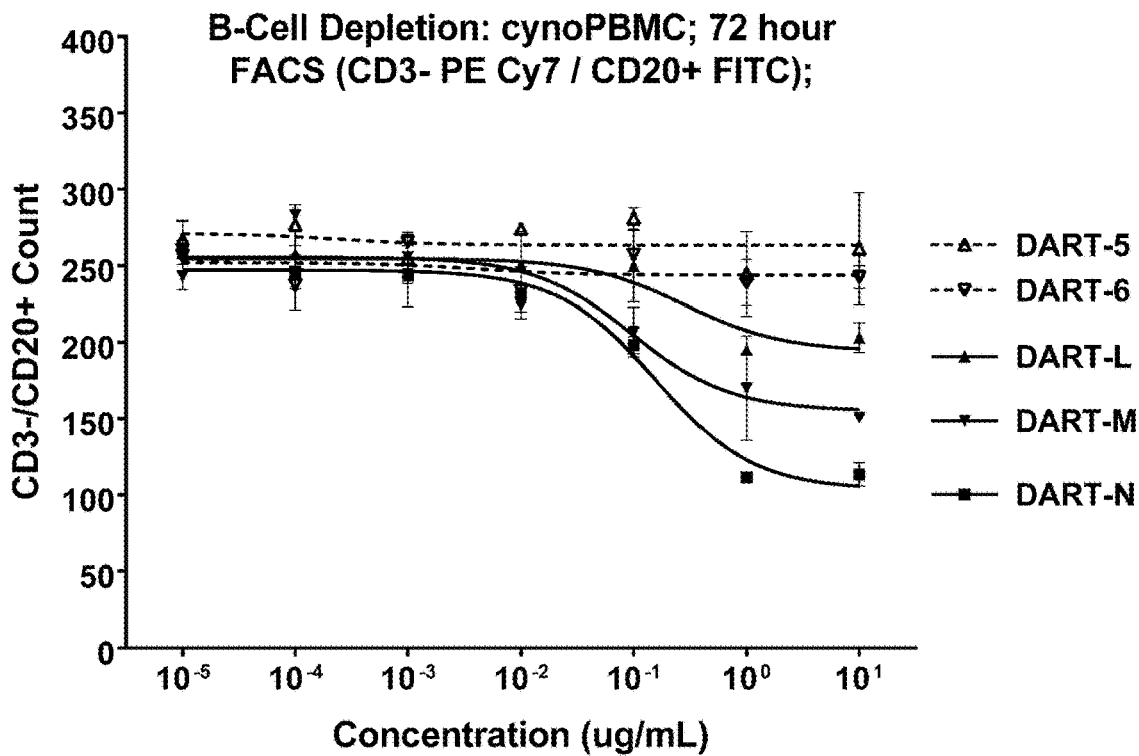
Figure 20D:
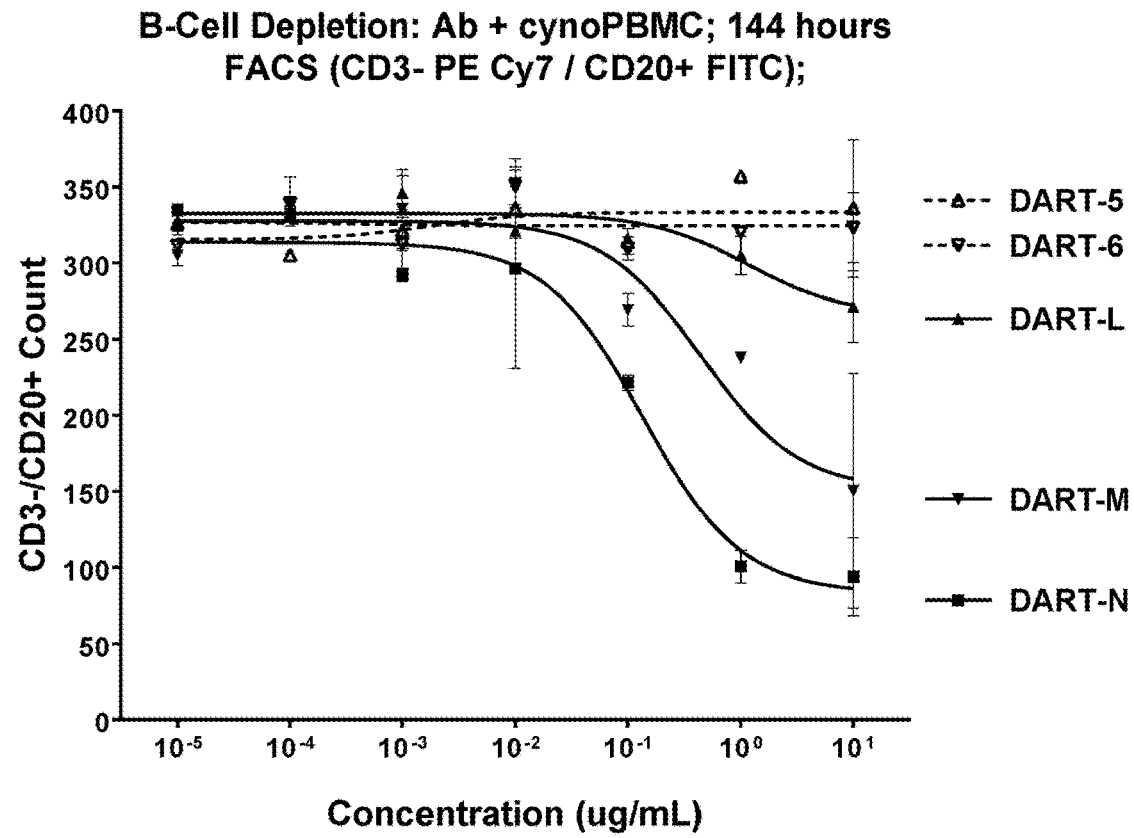

The exemplary CD16×DA Binding Molecules DART-L, DART-M, DART-N (having a binding site for the B-cell antigen CD19) and the negative controls: DART-5 and DART-6 (having a binding site for CD16 and a binding site for RSV) were evaluated for their ability to mediate autologous B-cell depletion in vitro. Briefly, PMBCs isolated from human or cynomolgus monkey were incubated in supplemented medium in the presence of increasing concentrations DART-L, DART-M, DART-N and the control molecules lacking a CD19 binding domain DART-5 and DART-6. B-cell levels were analyzed by flow cytometry (using CD3 for negative selection and CD20 as a B-cell marker; CD3/CD20$^+$) at 72 hours and 96 hours post incubation for huPBMCs (FIGS. 20A-20B, respectively) and at 72 hours and 144 hours post incubation for cynoPBMCs (FIGS. 20C-20D, respectively). Representative data from these studies are presented in FIGS. 20A-20D, and show that all the CD16xDA Binding Molecules were able to deplete autologous B-cells from both huPBMCs (FIGS. 20A-20B) and cynoPBMCs (FIGS. 20C-20D).

CD16xDA Binding Molecules comprising the optimized CD16 binding domains hCD16-M1B (DART-M), or hCD16-M1AB (DART-N), mediated a larger reduction in B-cells, with both huPBMCs and cynoPBMCs as compared to the same molecule comprising hCD16-M1 (DART-L). However, higher concentrations were required to deplete B-cells from cynoPBMCs. This trend was observed for multiple PBMC donors. Minimal B-cell depletion was observed for the control molecules lacking a CD19 binding domain (DART-5 and DART-6).

Example 10

Exemplary Redirected Cell Killing Assays

LDH redirected cell killing assay: These assays may be performed using the CytoTox 96® Non-Radioactive Cytotoxicity Assay Kit (Promega), or similar, that quantitatively measures LDH release essentially as described below. Target cells (e.g., tumor target cells) are resuspended at a density of 4×10$^5$ cells/mL (or appropriate density to achieve the desired E:T ratio) in assay media (e.g., RPMI 1640 without phenol red, 10% FBS, 1% pen/strep) and preferably a viability of higher than 90% at assay initiation, and isolated purified effector cells (e.g., PBMC or NK cells purified from human or non-human primate (e.g., cynomolgus monkey) donor) suspended in the assay media at the appropriate density (e.g., 4×10$^5$ cells/mL) to achieve an effector-to-target (E:T) cell ratio of 10:1, or 30:1 (or other desired E:T ratio) are used. An aliquot of target cell suspension (e.g., 50 µL, 20,000 cells), an aliquot of effector cell suspension (e.g., 100 µL, 200,000 cells for 10:1 E:T ratio), and an aliquot (e.g., 50 µL) of serially diluted test article (e.g., 5 fold, or 10 fold) are added to duplicate wells of a microtiter plate and incubated (37° C. with 5% CO2) for 24-96 hours, or longer if desired. At the end of the incubation an aliquot of lysis solution (e.g., 30 µL) is added and the plates are incubated for ~10 minutes to completely lyse the target cells. The plates are then centrifuged to pellet the cell debris (e.g., 212×g for 5 minutes) and an aliquot (e.g., 40 µL) of supernatant of is transferred from each well of the assay plate to a flat-bottom ELISA plate and an aliquot (e.g., 40 µL) of LDH substrate solution is added to each well. Plates are incubated for 10-20 minutes at room temperature in the dark and an aliquot (e.g., 40 µL) of stop solution (Promega Cat #G183A) is added. The optical density is measured at 490 nm within 1 hour on a Victor2 Multilabel plate reader (Perkin Elmer #1420-014), or similar. Specific cell lysis is calculated from optical density (OD) data using the following formula:

$$\text{Cytotoxicity (\%)} = \frac{100 \times (OD \text{ of Sample} - OD \text{ of } AICC)}{OD \text{ of } MR - OD \text{ of } SR}$$

wherein "AICC" is antibody-independent cellular cytotoxicity, "MR" is maximal release and "SR" is spontaneous release. The dose-response curves are generated using GraphPad Prism 6 software (or similar) by curve fitting the cytotoxicity values to the sigmoidal dose-response function.

Luminescence (LUM) redirected cell killing assay: These assays may be performed using the Steady-Glo luciferase substrate (Promega), or a similar sustrate, and quantitatively measure celluar luciferase activity in living target cells engineered to express the luciferase (luc) reporter gene (e.g., JIMT-1-Luc, Raji-Luc cells) essentially as described below. The preparation and set up for these assays is essentially identical to the LDH assay described above. Following incubation, an aliquot (e.g., 100 µL) of culture medium is removed from each well and an aliquot (e.g., 100 µL) of Steady-Glo luciferase substrate ((Promega), or similar) is subsequently added to each well, followed by pipetting up/down several times for complete lysis of target cells. The plates are incubated at room temperature in the dark for 10 minutes and then luminescence intensity is measured using a VictorX4 Multilabel plate reader (Perkin Elmer #1420-014, or similar) with luminescence relative light unit (RLU) as the read-out. RLU is indicative of relative viability of the target cells. Dose-response curves are generated using GraphPad Prism 6 software (or similar) by curve fitting the RLU values to the sigmoidal dose-response function.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

SEQUENCE LISTING

<160> NUMBER OF SEQ ID NOS: 191

<210> SEQ ID NO 1
<211> LENGTH: 107
<212> TYPE: PRT
<213> ORGANISM: Homo sapiens -continued

```
<220> FEATURE:
<221> NAME/KEY: MISC_FEATURE
<222> LOCATION: (1)..(107)
<223> OTHER INFORMATION: Human IgG CL Kappa Domain

<400> SEQUENCE: 1
```

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

```
<210> SEQ ID NO 2
<211> LENGTH: 104
<212> TYPE: PRT
<213> ORGANISM: Homo sapiens
<220> FEATURE:
<221> NAME/KEY: MISC_FEATURE
<222> LOCATION: (1)..(104)
<223> OTHER INFORMATION: Human IgG CL Lambda Domain

<400> SEQUENCE: 2
```

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

```
<210> SEQ ID NO 3
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG1 CH1 Domain

<400> SEQUENCE: 3
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Arg Val

<210> SEQ ID NO 4
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG2 CH1 Domain

<400> SEQUENCE: 4

Ala Ser Thr Lys Gly Pro Ser Val Phe Pro Leu Ala Pro Cys Ser Arg
1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                 85                  90                  95

Thr Val

<210> SEQ ID NO 5
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG3 CH1 Domain

<400> SEQUENCE: 5

Ala Ser Thr Lys Gly Pro Ser Val Phe Pro Leu Ala Pro Cys Ser Arg
1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                 85                  90                  95

Arg Val

```
<210> SEQ ID NO 6
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: Human IgG4 CH1 Domain

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 7
<211> LENGTH: 15
<212> TYPE: PRT
<213> ORGANISM: Homo sapiens
<220> FEATURE:
<221> NAME/KEY: MISC_FEATURE
<222> LOCATION: (1)..(15)
<223> OTHER INFORMATION: Human IgG1 Hinge Domain

<400> SEQUENCE: 7

Glu Pro Lys Ser Cys Asp Lys Thr His Thr Cys Pro Pro Cys Pro
1               5                   10                  15

<210> SEQ ID NO 8
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Human IgG2 Hinge Domain

<400> SEQUENCE: 8

Glu Arg Lys Cys Cys Val Glu Cys Pro Pro Cys Pro
1               5                   10

<210> SEQ ID NO 9
<211> LENGTH: 62
<212> TYPE: PRT
<213> ORGANISM: Homo sapiens
<220> FEATURE:
<221> NAME/KEY: MISC_FEATURE
<222> LOCATION: (1)..(62)
<223> OTHER INFORMATION: Human IgG3 Hinge Domain

<400> SEQUENCE: 9

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30
```

```
Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro
 50                  55                  60

<210> SEQ ID NO 10
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: Human IgG4 Hinge Domain

<400> SEQUENCE: 10

Glu Ser Lys Tyr Gly Pro Pro Cys Pro Ser Cys Pro
 1               5                  10

<210> SEQ ID NO 11
<211> LENGTH: 12
<212> TYPE: PRT
<213> ORGANISM: Artificial Sequence
<220> FEATURE:
<223> OTHER INFORMATION: IgG4 Hinge Domain Comprising Stabilizing S228P
      Substitution

<400> SEQUENCE: 11

Glu Ser Lys Tyr Gly Pro Pro Cys Pro Pro Cys Pro
 1               5                  10

<210> SEQ ID NO 12
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: Exemplary IgG1 CH2-CH3 Domain
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 12

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
             35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
```

```
                145                 150                 155                 160

Tyr Lys Thr Thr Pro Pro Val Leu Asp Ser Asp Gly Ser Phe Phe Leu
                    165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 13
<211> LENGTH: 216
<212> TYPE: PRT
<213> ORGANISM: Homo sapiens
<220> FEATURE:
<221> NAME/KEY: MISC_FEATURE
<222> LOCATION: (1)..(216)
<223> OTHER INFORMATION: Exemplary IgG2 CH2-CH3 Domain
<220> FEATURE:
<221> NAME/KEY: MISC_FEATURE
<222> LOCATION: (216)..(216)
<223> OTHER INFORMATION: Xaa is Lysine (K) or is Absent

<400> SEQUENCE: 13

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
                20                  25                  30

Val Asp Val Ser His Glu Asp Pro Glu Val Gln Phe Asn Trp Tyr Val
            35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
    130                 135                 140

Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Xaa
    210                 215

<210> SEQ ID NO 14
<211> LENGTH: 217
<212> TYPE: PRT
<213> ORGANISM: Homo sapiens
<220> FEATURE:
<221> NAME/KEY: MISC_FEATURE
```

```
<222> LOCATION: (1)..(217)
<223> OTHER INFORMATION: Exemplary IgG3 CH2-CH3 Domain
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 14

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly Xaa
    210                 215

<210> SEQ ID NO 15
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: Exemplary IgG4 CH2-CH3 Domain
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 15

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60
```

```
Gln Phe Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
    210                 215
```

<210> SEQ ID NO 16
<211> LENGTH: 8
<212> TYPE: PRT
<213> ORGANISM: Artificial Sequence
<220> FEATURE:
<223> OTHER INFORMATION: Linker 1 Spacer Peptide

<400> SEQUENCE: 16

```
Gly Gly Gly Ser Gly Gly Gly Gly
1               5
```

<210> SEQ ID NO 17
<211> LENGTH: 6
<212> TYPE: PRT
<213> ORGANISM: Artificial Sequence
<220> FEATURE:
<223> OTHER INFORMATION: Preferred Linker 2 Cysteine-Containing Spacer
      Peptide

<400> SEQUENCE: 17

```
Gly Gly Cys Gly Gly Gly
1               5
```

<210> SEQ ID NO 18
<211> LENGTH: 4
<212> TYPE: PRT
<213> ORGANISM: Artificial Sequence
<220> FEATURE:
<223> OTHER INFORMATION: Alternative Linker 2 Cysteine-Containing
      Spacer Peptide

<400> SEQUENCE: 18

```
Gly Gly Gly Ser
1
```

<210> SEQ ID NO 19
<211> LENGTH: 6
<212> TYPE: PRT
<213> ORGANISM: Artificial Sequence
<220> FEATURE:
<223> OTHER INFORMATION: Alternative Linker 2 Cysteine-Containing
      Spacer Peptide

```
<400> SEQUENCE: 19

Leu Gly Gly Gly Ser Gly
1               5

<210> SEQ ID NO 20
<211> LENGTH: 11
<212> TYPE: PRT
<213> ORGANISM: Artificial Sequence
<220> FEATURE:
<223> OTHER INFORMATION: Alternative Linker 2 Cysteine-Containing
      Spacer Peptide

<400> SEQUENCE: 20

Gly Gly Gly Ser Gly Gly Gly Ser Gly Gly Gly
1               5                   10

<210> SEQ ID NO 21
<211> LENGTH: 5
<212> TYPE: PRT
<213> ORGANISM: Artificial Sequence
<220> FEATURE:
<223> OTHER INFORMATION: Alternative Linker 2 Cysteine-Containing
      Spacer Peptide

<400> SEQUENCE: 21

Ala Ser Thr Lys Gly
1               5

<210> SEQ ID NO 22
<211> LENGTH: 6
<212> TYPE: PRT
<213> ORGANISM: Artificial Sequence
<220> FEATURE:
<223> OTHER INFORMATION: Alternative Linker 2 Cysteine-Containing
      Spacer Peptide

<400> SEQUENCE: 22

Leu Glu Pro Lys Ser Ser
1               5

<210> SEQ ID NO 23
<211> LENGTH: 5
<212> TYPE: PRT
<213> ORGANISM: Artificial Sequence
<220> FEATURE:
<223> OTHER INFORMATION: Alternative Linker 2 Cysteine-Containing
      Spacer Peptide

<400> SEQUENCE: 23

Ala Pro Ser Ser Ser
1               5

<210> SEQ ID NO 24
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: Cysteine-Containing Heterodimer-Promoting
      Domain

<400> SEQUENCE: 24

Gly Val Glu Pro Lys Ser Cys
1               5
```

```
<210> SEQ ID NO 25
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: Cysteine-Containing Heterodimer-Promoting
      Domain

<400> SEQUENCE: 25

Val Glu Pro Lys Ser Cys
1               5

<210> SEQ ID NO 26
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: Cysteine-Containing Heterodimer-Promoting
      Domain

<400> SEQUENCE: 26

Ala Glu Pro Lys Ser Cys
1               5

<210> SEQ ID NO 27
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: Cysteine-Containing Heterodimer-Promoting
      Domain

<400> SEQUENCE: 27

Gly Phe Asn Arg Gly Glu Cys
1               5

<210> SEQ ID NO 28
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: Cysteine-Containing Heterodimer-Promoting
      Domain

<400> SEQUENCE: 28

Phe Asn Arg Gly Glu Cys
1               5

<210> SEQ ID NO 29
<211> LENGTH: 28
<212> TYPE: PRT
<213> ORGANISM: Artificial Sequence
<220> FEATURE:
<223> OTHER INFORMATION: "E-coil" Heterodimer-Promoting Domain

<400> SEQUENCE: 29

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25
```

<210> SEQ ID NO 30
<211> LENGTH: 28
<212> TYPE: PRT
<213> ORGANISM: Artificial Sequence
<220> FEATURE:
<223> OTHER INFORMATION: "K-coil" Heterodimer-Promoting Domain

<400> SEQUENCE: 30

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 31
<211> LENGTH: 28
<212> TYPE: PRT
<213> ORGANISM: Artificial Sequence
<220> FEATURE:
<223> OTHER INFORMATION: Cysteine-Containing "E-coil" Heterodimer-
      Promoting Domain

<400> SEQUENCE: 31

Glu Val Ala Ala Cys Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 32
<211> LENGTH: 28
<212> TYPE: PRT
<213> ORGANISM: Artificial Sequence
<220> FEATURE:
<223> OTHER INFORMATION: Cysteine-Containing "K-coil" Heterodimer-
      Promoting Domain

<400> SEQUENCE: 32

Lys Val Ala Ala Cys Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 33
<211> LENGTH: 46
<212> TYPE: PRT
<213> ORGANISM: Streptococcus dysgalactiae
<220> FEATURE:
<221> NAME/KEY: MISC_FEATURE
<222> LOCATION: (1)..(46)
<223> OTHER INFORMATION: Albumin-Binding Domain 3 (ABD3) of protein G
      of Streptococcus strain G148

<400> SEQUENCE: 33

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
            20                  25                  30

Gly Val Lys Ala Leu Ile Asp Glu Ile Leu Ala Ala Leu Pro
        35                  40                  45

<210> SEQ ID NO 34
<211> LENGTH: 46
<212> TYPE: PRT
<213> ORGANISM: Artificial Sequence
<220> FEATURE:
<223> OTHER INFORMATION: Variant Deimmunized Albumin-Binding Domain 3

(ABD3) of protein G of Streptococcus strain G148

<400> SEQUENCE: 34

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
            20                  25                  30

Gly Val Lys Ala Leu Ile Asp Glu Ile Leu Ala Ala Leu Pro
        35                  40                  45

<210> SEQ ID NO 35
<211> LENGTH: 46
<212> TYPE: PRT
<213> ORGANISM: Artificial Sequence
<220> FEATURE:
<223> OTHER INFORMATION: Variant Deimmunized Albumin-Binding Domain 3
      (ABD3) of protein G of Streptococcus strain G148

<400> SEQUENCE: 35

Leu Ala Glu Ala Lys Val Leu Ala Asn Arg Glu Leu Asp Lys Tyr Gly
1               5                   10                  15

Val Ser Asp Tyr Tyr Lys Asn Ala Ala Asn Asn Ala Lys Thr Val Glu
            20                  25                  30

Gly Val Lys Ala Leu Ile Ala Glu Ile Leu Ala Ala Leu Pro
        35                  40                  45

<210> SEQ ID NO 36
<211> LENGTH: 46
<212> TYPE: PRT
<213> ORGANISM: Artificial Sequence
<220> FEATURE:
<223> OTHER INFORMATION: Variant Deimmunized Albumin-Binding Domain 3
      (ABD3) of protein G of Streptococcus strain G148

<400> SEQUENCE: 36

Leu Ala Glu Ala Lys Val Leu Ala Asn Arg Glu Leu Asp Lys Tyr Gly
1               5                   10                  15

Val Ser Asp Tyr Tyr Lys Asn Leu Ile Ser Asn Ala Lys Ser Val Glu
            20                  25                  30

Gly Val Lys Ala Leu Ile Ala Glu Ile Leu Ala Ala Leu Pro
        35                  40                  45

<210> SEQ ID NO 37
<211> LENGTH: 8
<212> TYPE: PRT
<213> ORGANISM: Artificial Sequence
<220> FEATURE:
<223> OTHER INFORMATION: Linker Peptide

<400> SEQUENCE: 37

Ala Pro Ser Ser Ser Pro Met Glu
1               5

<210> SEQ ID NO 38
<211> LENGTH: 16
<212> TYPE: PRT
<213> ORGANISM: Artificial Sequence
<220> FEATURE:
<223> OTHER INFORMATION: Linker Peptide

<400> SEQUENCE: 38

Val Glu Pro Lys Ser Ala Asp Lys Thr His Thr Cys Pro Pro Cys Pro
1               5                   10                  15

```
<210> SEQ ID NO 39
<211> LENGTH: 16
<212> TYPE: PRT
<213> ORGANISM: Artificial Sequence
<220> FEATURE:
<223> OTHER INFORMATION: Linker Peptide

<400> SEQUENCE: 39

Leu Glu Pro Lys Ser Ala Asp Lys Thr His Thr Cys Pro Pro Cys Pro
1               5                   10                  15

<210> SEQ ID NO 40
<211> LENGTH: 10
<212> TYPE: PRT
<213> ORGANISM: Artificial Sequence
<220> FEATURE:
<223> OTHER INFORMATION: Linker Peptide

<400> SEQUENCE: 40

Asp Lys Thr His Thr Cys Pro Pro Cys Pro
1               5                   10

<210> SEQ ID NO 41
<211> LENGTH: 15
<212> TYPE: PRT
<213> ORGANISM: Artificial Sequence
<220> FEATURE:
<223> OTHER INFORMATION: scFv Linker Peptide

<400> SEQUENCE: 41

Gly Gly Gly Gly Ser Gly Gly Gly Gly Ser Gly Gly Gly Gly Ser
1               5                   10                  15

<210> SEQ ID NO 42
<211> LENGTH: 12
<212> TYPE: PRT
<213> ORGANISM: Artificial Sequence
<220> FEATURE:
<223> OTHER INFORMATION: "Long" Linker Peptide

<400> SEQUENCE: 42

Gly Gly Gly Gly Ser Gly Gly Gly Ser Gly Gly Gly
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Alternative Linker Peptide

<400> SEQUENCE: 43

Gly Gly Gly Asp Lys Thr His Thr Cys Pro Pro Cys Pro
1               5                   10

<210> SEQ ID NO 44
<211> LENGTH: 16
<212> TYPE: PRT
<213> ORGANISM: Artificial Sequence
<220> FEATURE:
<223> OTHER INFORMATION: Alternative Linker Peptide

<400> SEQUENCE: 44

Leu Glu Pro Lys Ser Ser Asp Lys Thr His Thr Cys Pro Pro Cys Pro
1               5                   10                  15
```

```
<210> SEQ ID NO 45
<211> LENGTH: 217
<212> TYPE: PRT
<213> ORGANISM: Artificial Sequence
<220> FEATURE:
<223> OTHER INFORMATION: IgG1 CH2-CH3 Domain Having L234A/L235A
      Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 45

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 46
<211> LENGTH: 217
<212> TYPE: PRT
<213> ORGANISM: Artificial Sequence
<220> FEATURE:
<223> OTHER INFORMATION: IgG1 CH2-CH3 Domain Having S442C Substitution
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 46

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45
```

```
Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Cys Leu Ser Pro Gly Xaa
210                 215

<210> SEQ ID NO 47
<211> LENGTH: 217
<212> TYPE: PRT
<213> ORGANISM: Artificial Sequence
<220> FEATURE:
<223> OTHER INFORMATION: IgG1 CH2-CH3 Domain Having L234A/L235A/S442C
      Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 47

Ala Pro Glu Ala Ala Gly Gly Pro Ser Val Phe Leu Phe Pro Pro Lys
 1                5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
```

-continued

```
                165                 170                 175
Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Cys Leu Ser Pro Gly Xaa
    210                 215

<210> SEQ ID NO 48
<211> LENGTH: 217
<212> TYPE: PRT
<213> ORGANISM: Artificial Sequence
<220> FEATURE:
<223> OTHER INFORMATION: IgG1 CH2-CH3 Domain Having M252Y/S254T/T256E
      Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 48

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 49
<211> LENGTH: 217
<212> TYPE: PRT
<213> ORGANISM: Artificial Sequence
<220> FEATURE:
<223> OTHER INFORMATION: IgG1 CH2-CH3 Domain Having
      L234A/L235A/M252Y/S254T/T256E Substitutions
<220> FEATURE:
<221> NAME/KEY: MISC_FEATURE
<222> LOCATION: (217)..(217)
```

<223> OTHER INFORMATION: Xaa is Lysine (K) or is Absent

<400> SEQUENCE: 49

```
Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215
```

<210> SEQ ID NO 50
<211> LENGTH: 217
<212> TYPE: PRT
<213> ORGANISM: Artificial Sequence
<220> FEATURE:
<223> OTHER INFORMATION: IgG1 CH2-CH3 Domain Having
      L234A/L235A/M252Y/S254T/T256E/S442C Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 50

```
Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

```
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Cys Leu Ser Pro Gly Xaa
    210                 215

<210> SEQ ID NO 51
<211> LENGTH: 217
<212> TYPE: PRT
<213> ORGANISM: Artificial Sequence
<220> FEATURE:
<223> OTHER INFORMATION: "Knob-bearing" IgG1 CH2-CH3 Domain
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 51

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215
```

<210> SEQ ID NO 52
<211> LENGTH: 217
<212> TYPE: PRT
<213> ORGANISM: Artificial Sequence
<220> FEATURE:
<223> OTHER INFORMATION: "Knob-bearing" IgG1 CH2-CH3 Domain Having
      L234A/L235A/M252Y/S254T/T256E Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 52

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215

<210> SEQ ID NO 53
<211> LENGTH: 217
<212> TYPE: PRT
<213> ORGANISM: Artificial Sequence
<220> FEATURE:
<223> OTHER INFORMATION: "Hole-bearing" IgG1 CH2-CH3 Domain Having
      L234A/L235A Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 53

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

```
Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
            115                 120                 125

Thr Lys Asn Gln Val Ser Leu Ser Cys Ala Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
            195                 200                 205

Lys Ser Leu Ser Leu Ser Pro Gly Xaa
            210                 215
```

```
<210> SEQ ID NO 54
<211> LENGTH: 217
<212> TYPE: PRT
<213> ORGANISM: Artificial Sequence
<220> FEATURE:
<223> OTHER INFORMATION: "Hole-bearing" IgG1 CH2-CH3 Domain Having
      L234A/L235A/M252Y/S254T/T256E Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 54
```

```
Ala Pro Glu Ala Ala Gly Gly Pro Ser Val Phe Leu Phe Pro Pro Lys
 1               5                  10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
            115                 120                 125

Thr Lys Asn Gln Val Ser Leu Ser Cys Ala Val Lys Gly Phe Tyr Pro
130                 135                 140

Ser Asp Ile Ala Val Glu Trp Glu Ser Asn Gly Gln Pro Glu Asn Asn
```

```
145                 150                 155                 160
Tyr Lys Thr Thr Pro Pro Val Leu Asp Ser Asp Gly Ser Phe Phe Leu
                    165                 170                 175

Val Ser Lys Leu Thr Val Asp Lys Ser Arg Trp Gln Gln Gly Asn Val
                180                 185                 190

Phe Ser Cys Ser Val Met His Glu Ala Leu His Asn Arg Tyr Thr Gln
            195                 200                 205

Lys Ser Leu Ser Leu Ser Pro Gly Xaa
        210                 215
```

<210> SEQ ID NO 55
<211> LENGTH: 217
<212> TYPE: PRT
<213> ORGANISM: Artificial Sequence
<220> FEATURE:
<223> OTHER INFORMATION: IgG4 CH2-CH3 Domain Having M252Y/S254T/T256E
      Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 55

```
Ala Pro Glu Phe Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
                20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
        50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
                100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
            210                 215
```

<210> SEQ ID NO 56
<211> LENGTH: 217
<212> TYPE: PRT
<213> ORGANISM: Artificial Sequence
<220> FEATURE:
<223> OTHER INFORMATION: "Knob-bearing" IgG4 CH2-CH3 Domain Having
      M252Y/S254T/T256E Substitutions

```
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 56

Ala Pro Glu Phe Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
    210                 215

<210> SEQ ID NO 57
<211> LENGTH: 217
<212> TYPE: PRT
<213> ORGANISM: Artificial Sequence
<220> FEATURE:
<223> OTHER INFORMATION: "Hole-bearing" IgG1 CH2-CH3 Domain Having
      M252Y/S254T/T256E Substitutions
<220> FEATURE:
<221> NAME/KEY: MISC_FEATURE
<222> LOCATION: (217)..(217)
<223> OTHER INFORMATION: Xaa is Lysine (K) or is Absent

<400> SEQUENCE: 57

Ala Pro Glu Phe Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80
```

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Arg Leu Thr Val Asp Lys Ser Arg Trp Gln Glu Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Leu Gly Xaa
    210                 215

<210> SEQ ID NO 58
<211> LENGTH: 118
<212> TYPE: PRT
<213> ORGANISM: Artificial Sequence
<220> FEATURE:
<223> OTHER INFORMATION: Optimized VH Domain of Anti-human CD16
      monoclonal antibody hCD16-M1A

<400> SEQUENCE: 58

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Ser Tyr Thr Phe Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Leu Tyr Tyr Cys
                85                  90                  95

Val Arg Gln Ser Ala Asn Ser Pro Val Pro Tyr Trp Gly Gln Gly Thr
            100                 105                 110

Leu Val Thr Val Ser Ser
        115

<210> SEQ ID NO 59
<211> LENGTH: 107
<212> TYPE: PRT
<213> ORGANISM: Artificial Sequence
<220> FEATURE:
<223> OTHER INFORMATION: Optimized VL Domain of Anti-human CD16
      monoclonal antibody hCD16-M1B

<400> SEQUENCE: 59

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asn Val Gly Thr His
            20                  25                  30

Val Ala Trp Tyr Gln Gln Lys Pro Gly Lys Ala Pro Lys Ser Leu Leu
         35                  40                  45

Tyr Ser Ala Ser Tyr Arg Tyr Ser Gly Val Pro Ser Arg Phe Ser Gly
 50                  55                  60

Ser Gly Ser Gly Thr Asp Phe Thr Leu Thr Ile Ser Ser Leu Gln Ser
 65                  70                  75                  80

Glu Asp Ile Ala Thr Tyr Tyr Cys Gln Asp Tyr Thr Asn Tyr Pro Leu
                 85                  90                  95

Thr Phe Gly Gln Gly Thr Lys Leu Glu Ile Lys
             100                 105

<210> SEQ ID NO 60
<211> LENGTH: 9
<212> TYPE: PRT
<213> ORGANISM: Artificial Sequence
<220> FEATURE:
<223> OTHER INFORMATION: CDR3 of Heavy Chain of Optimized Anti-Human
      CD16 Monoclonal Antibodiies hCD16-M1A and hCD16-M1AB

<400> SEQUENCE: 60

Gln Ser Ala Asn Ser Pro Val Pro Tyr
1               5

<210> SEQ ID NO 61
<211> LENGTH: 9
<212> TYPE: PRT
<213> ORGANISM: Artificial Sequence
<220> FEATURE:
<223> OTHER INFORMATION: CDR3 of Light Chain of Optimized Anti-Human
      CD16 Monoclonal Antibodiies hCD16-M1B and hCD16-M1AB

<400> SEQUENCE: 61

Gln Asp Tyr Thr Asn Tyr Pro Leu Thr
1               5

<210> SEQ ID NO 62
<211> LENGTH: 118
<212> TYPE: PRT
<213> ORGANISM: Artificial Sequence
<220> FEATURE:
<223> OTHER INFORMATION: VH Domain of Humanized Anti-Human CD16 mAb h3G8

<400> SEQUENCE: 62

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
             20                  25                  30

Gly Met Gly Val Gly Trp Ile Arg Gln Pro Pro Gly Lys Ala Leu Glu
         35                  40                  45

Trp Leu Ala His Ile Trp Trp Asp Asp Asp Lys Arg Tyr Asn Pro Ala
 50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Gln Ile Asn Pro Ala Trp Phe Ala Tyr Trp Gly Gln Gly Thr
             100                 105                 110

Leu Val Thr Val Ser Ser
        115

<210> SEQ ID NO 63

```
<211> LENGTH: 111
<212> TYPE: PRT
<213> ORGANISM: Artificial Sequence
<220> FEATURE:
<223> OTHER INFORMATION: VL Domain of Humanized Anti-Human CD16 mAb h3G8

<400> SEQUENCE: 63

Asp Ile Val Met Thr Gln Ser Pro Asp Ser Leu Ala Val Ser Leu Gly
 1               5                  10                  15

Glu Arg Ala Thr Ile Asn Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys
            100                 105                 110

<210> SEQ ID NO 64
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: VH Domain of Murine Anti-human CD16 Monoclonal
      Antibody CD16-M1

<400> SEQUENCE: 64

Glu Val Lys Leu Val Glu Ser Gly Gly Thr Leu Val Lys Pro Gly Gly
 1               5                  10                  15

Ser Leu Lys Leu Ser Cys Ala Ala Ser Gly Phe Thr Phe Asn Asn Tyr
            20                  25                  30

Gly Met Ser Trp Val Arg Gln Thr Pro Glu Lys Arg Leu Glu Trp Val
        35                  40                  45

Ala Thr Ile Ser Gly Gly Gly Ser Tyr Thr Phe Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ser Glu Asp Thr Ala Leu Tyr Tyr Cys
                85                  90                  95

Ile Arg Gln Ser Ala Arg Ala Pro Glu Pro Tyr Trp Gly Gln Gly Thr
            100                 105                 110

Leu Val Thr Val Ser Ser
        115

<210> SEQ ID NO 65
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: VH Domain of Murine Anti-human CD16 Monoclonal
      Antibody CD16-M1

<400> SEQUENCE: 65
```

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr His
            20                  25                  30

Val Ala Trp Tyr Gln Gln Lys Ser Gly Gln Ser Pro Lys Ser Leu Leu
        35                  40                  45

Tyr Ser Ala Ser Tyr Arg Tyr Ser Gly Val Pro Asp Arg Phe Ser Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Lys Ser Tyr Pro Leu
                85                  90                  95

Thr Phe Gly Ala Gly Thr Lys Leu Glu Leu Lys
            100                 105
```

<210> SEQ ID NO 66
<211> LENGTH: 5
<212> TYPE: PRT
<213> ORGANISM: Artificial Sequence
<220> FEATURE:
<223> OTHER INFORMATION: CDR1 of Heavy Chain of Humanized Anti-human
      CD16 Monoclonal Antibody hCD16-M1, hCD16-M1A, hCD16-M1B and HCD16-
      M1AB

<400> SEQUENCE: 66

```
Asn Tyr Gly Met Ser
1               5
```

<210> SEQ ID NO 67
<211> LENGTH: 17
<212> TYPE: PRT
<213> ORGANISM: Artificial Sequence
<220> FEATURE:
<223> OTHER INFORMATION: CDR2 of Heavy Chain of Humanized Anti-human
      CD16 Monoclonal Antibody hCD16-M1, hCD16-M1A, hCD16-M1B and HCD16-
      M1AB

<400> SEQUENCE: 67

```
Thr Ile Ser Gly Gly Gly Ser Tyr Thr Phe Tyr Pro Asp Ser Val Lys
1               5                   10                  15

Gly
```

<210> SEQ ID NO 68
<211> LENGTH: 9
<212> TYPE: PRT
<213> ORGANISM: Artificial Sequence
<220> FEATURE:
<223> OTHER INFORMATION: CDR3 of Heavy Chain of Humanized Anti-human
      CD16 Monoclonal Antibody hCD16-M1 and HCD16-M1B

<400> SEQUENCE: 68

```
Gln Ser Ala Arg Ala Pro Glu Pro Tyr
1               5
```

<210> SEQ ID NO 69
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: CDR1 of Light Chain of Anti-human CD16
      Monoclonal Antibody CD16-M1

<400> SEQUENCE: 69

```
<210> SEQ ID NO 70
<211> LENGTH: 7
<212> TYPE: PRT
<213> ORGANISM: Artificial Sequence
<220> FEATURE:
<223> OTHER INFORMATION: CDR2 of Light Chain of Humanized Anti-human
      CD16 Monoclonal Antibody hCD16-M1, hCD16-M1A, hCD16-M1B and HCD16-
      M1AB

<400> SEQUENCE: 70

Ser Ala Ser Tyr Arg Tyr Ser
1               5

<210> SEQ ID NO 71
<211> LENGTH: 9
<212> TYPE: PRT
<213> ORGANISM: Artificial Sequence
<220> FEATURE:
<223> OTHER INFORMATION: CDR3 of Light Chain of Humanized Anti-human
      CD16 Monoclonal Antibody hCD16-M1 and hCD16-M1A

<400> SEQUENCE: 71

Gln Gln Tyr Lys Ser Tyr Pro Leu Thr
1               5

<210> SEQ ID NO 72
<211> LENGTH: 118
<212> TYPE: PRT
<213> ORGANISM: Artificial Sequence
<220> FEATURE:
<223> OTHER INFORMATION: VH Domain of Humanized Derivative of Murine
      Anti-human CD16 monoclonal antibody CD16-M1

<400> SEQUENCE: 72

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Ser Tyr Thr Phe Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Leu Tyr Tyr Cys
                85                  90                  95

Val Arg Gln Ser Ala Arg Ala Pro Glu Pro Tyr Trp Gly Gln Gly Thr
            100                 105                 110

Leu Val Thr Val Ser Ser
        115

<210> SEQ ID NO 73
<211> LENGTH: 107
<212> TYPE: PRT
<213> ORGANISM: Artificial Sequence
<220> FEATURE:
<223> OTHER INFORMATION: VL Domain of Humanized Derivative of Murine
      Anti-human CD16 monoclonal antibody CD16-M1

<400> SEQUENCE: 73
```

Lys Ala Ser Gln Asn Val Gly Thr His Val Ala
1               5                   10

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asn Val Gly Thr His
            20                  25                  30

Val Ala Trp Tyr Gln Gln Lys Pro Gly Lys Ala Pro Lys Ser Leu Leu
            35                  40                  45

Tyr Ser Ala Ser Tyr Arg Tyr Ser Gly Val Pro Ser Arg Phe Ser Gly
        50                  55                  60

Ser Gly Ser Gly Thr Asp Phe Thr Leu Thr Ile Ser Ser Leu Gln Ser
65                  70                  75                  80

Glu Asp Ile Ala Thr Tyr Tyr Cys Gln Gln Tyr Lys Ser Tyr Pro Leu
                85                  90                  95

Thr Phe Gly Gln Gly Thr Lys Leu Glu Ile Lys
            100                 105
```

<210> SEQ ID NO 74
<211> LENGTH: 11
<212> TYPE: PRT
<213> ORGANISM: Artificial Sequence
<220> FEATURE:
<223> OTHER INFORMATION: CDR1 of Light Chain of Anti-human CD16
      Monoclonal Antibody hCD16-M1, hCD16-M1A, hCD16-M1B and HCD16-M1AB

<400> SEQUENCE: 74

```
Arg Ala Ser Gln Asn Val Gly Thr His Val Ala
1               5                   10
```

<210> SEQ ID NO 75
<211> LENGTH: 119
<212> TYPE: PRT
<213> ORGANISM: Mus musculus
<220> FEATURE:
<221> NAME/KEY: MISC_FEATURE
<222> LOCATION: (1)..(119)
<223> OTHER INFORMATION: VH Domain of Murine Anti-human CD16 Monoclonal
      Antibody CD16-M2

<400> SEQUENCE: 75

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Ser
            20                  25                  30

Ala Met His Trp Val Lys Lys Asn Pro Gly Gln Gly Leu Glu Trp Ile
            35                  40                  45

Gly Tyr Ile Asn His Tyr Asn Asp Gly Ile Lys Tyr Asn Glu Arg Phe
        50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Thr Gly Tyr Arg Tyr Ala Ser Trp Phe Ala Ser Trp Gly Gln Gly
            100                 105                 110

Thr Leu Val Thr Val Ser Ser
        115
```

<210> SEQ ID NO 76
<211> LENGTH: 107
<212> TYPE: PRT
<213> ORGANISM: Mus musculus
<220> FEATURE:
<221> NAME/KEY: MISC_FEATURE

```
<222> LOCATION: (1)..(107)
<223> OTHER INFORMATION: VL Domain of Murine Anti-human CD16 Monoclonal
      Antibody CD16-M2

<400> SEQUENCE: 76

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Asn Ile Gly Thr Ser
            20                  25                  30

Ile His Trp Tyr Gln Gln Arg Thr Asp Gly Ser Pro Arg Leu Leu Ile
        35                  40                  45

Lys Ser Val Ser Glu Ser Ile Ser Gly Ile Pro Ser Arg Phe Ser Gly
    50                  55                  60

Ser Gly Ser Gly Thr Asp Phe Thr Leu Thr Ile Asn Gly Val Glu Ser
65                  70                  75                  80

Gly Asp Ile Ser Asp Tyr Tyr Cys Gln Gln Ser Asn Ser Trp Pro Leu
                85                  90                  95

Thr Phe Gly Ala Gly Thr Lys Leu Glu Leu Lys
            100                 105

<210> SEQ ID NO 77
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDR1 of Heavy Chain of Anti-human CD16
      Monoclonal Antibody CD16-M2 and hCD16-M2

<400> SEQUENCE: 77

Ser Ser Ala Met His
1               5

<210> SEQ ID NO 78
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDR2 of Heavy Chain of Anti-human CD16
      Monoclonal Antibody CD16-M2 and hCD16-M2

<400> SEQUENCE: 78

Tyr Ile Asn His Tyr Asn Asp Gly Ile Lys Tyr Asn Glu Arg Phe Lys
1               5                   10                  15

Gly

<210> SEQ ID NO 79
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: CDR3 of Heavy Chain of Anti-human CD16
      Monoclonal Antibody CD16-M2 and hCD16-M2

<400> SEQUENCE: 79

Gly Tyr Arg Tyr Ala Ser Trp Phe Ala Ser
1               5                   10

<210> SEQ ID NO 80
```

```
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: CDR1 of Light Chain of Anti-human CD16
      Monoclonal Antibody CD16-M2 and hCD16-M2

<400> SEQUENCE: 80

Arg Ala Ser Gln Asn Ile Gly Thr Ser Ile His
1               5                   10

<210> SEQ ID NO 81
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDR2 of Light Chain of Anti-human CD16
      Monoclonal Antibody CD16-M2 and hCD16-M2

<400> SEQUENCE: 81

Ser Val Ser Glu Ser Ile Ser
1               5

<210> SEQ ID NO 82
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDR3 of Light Chain of Anti-human CD16
      Monoclonal Antibody CD16-M2 and hCD16-M2

<400> SEQUENCE: 82

Gln Gln Ser Asn Ser Trp Pro Leu Thr
1               5

<210> SEQ ID NO 83
<211> LENGTH: 119
<212> TYPE: PRT
<213> ORGANISM: Artificial Sequence
<220> FEATURE:
<223> OTHER INFORMATION: VH Domain of Humanized Anti-human CD16
      Monoclonal Antibody hCD16-M2 VH1

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Ala Met His Trp Val Arg Gln Ala Pro Gly Gln Gly Leu Glu Trp Met
        35                  40                  45

Gly Tyr Ile Asn His Tyr Asn Asp Gly Ile Lys Tyr Asn Glu Arg Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Tyr Arg Tyr Ala Ser Trp Phe Ala Ser Trp Gly Gln Gly
            100                 105                 110

Thr Leu Val Thr Val Ser Ser
```

<210> SEQ ID NO 84
<211> LENGTH: 119
<212> TYPE: PRT
<213> ORGANISM: Artificial Sequence
<220> FEATURE:
<223> OTHER INFORMATION: VH Domain of Humanized Anti-human CD16
      Monoclonal Antibody hCD16-M2 VH2

<400> SEQUENCE: 84

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser
            20                  25                  30

Ala Met His Trp Val Arg Gln Ala Pro Gly Gln Gly Leu Glu Trp Met
        35                  40                  45

Gly Tyr Ile Asn His Tyr Asn Asp Gly Ile Lys Tyr Asn Glu Arg Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Arg Tyr Ala Ser Trp Phe Ala Ser Trp Gly Gln Gly
            100                 105                 110

Thr Leu Val Thr Val Ser Ser
        115

<210> SEQ ID NO 85
<211> LENGTH: 107
<212> TYPE: PRT
<213> ORGANISM: Artificial Sequence
<220> FEATURE:
<223> OTHER INFORMATION: VL Domain of Humanized Anti-human CD16
      Monoclonal Antibody hCD16-M2 VL1

<400> SEQUENCE: 85

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Asn Ile Gly Thr Ser
            20                  25                  30

Ile His Trp Tyr Gln Gln Lys Pro Asp Gln Ser Pro Lys Leu Leu Ile
        35                  40                  45

Lys Ser Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Phe Ala Thr Tyr Tyr Cys Gln Gln Ser Asn Ser Trp Pro Leu
                85                  90                  95

Thr Phe Gly Gln Gly Thr Lys Leu Glu Ile Lys
            100                 105

<210> SEQ ID NO 86
<211> LENGTH: 118
<212> TYPE: PRT
<213> ORGANISM: Artificial Sequence
<220> FEATURE:
<223> OTHER INFORMATION: VH Domain of Anti-NKG2D Monoclonal Antibody
      KYK-1.0

<400> SEQUENCE: 86

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Lys Tyr
65                  70                  75                  80

Leu Gln Met Asn Ser Leu Arg Ala Glu Asp Thr Ala Val Tyr Tyr Cys
                85                  90                  95

Ala Lys Asp Arg Phe Gly Tyr Tyr Leu Asp Tyr Trp Gly Gln Gly Thr
            100                 105                 110

Leu Val Thr Val Ser Ser
            115
```

```
<210> SEQ ID NO 87
<211> LENGTH: 108
<212> TYPE: PRT
<213> ORGANISM: Artificial Sequence
<220> FEATURE:
<223> OTHER INFORMATION: VL Domain of Anti-NKG2D Monoclonal Antibody
      KYK-1.0

<400> SEQUENCE: 87
```

```
Gln Pro Val Leu Thr Gln Pro Ser Ser Val Ser Ala Pro Gly Glu
1               5                   10                  15

Thr Ala Arg Ile Pro Cys Gly Gly Asp Asp Ile Glu Thr Lys Ser Val
            20                  25                  30

His Trp Tyr Gln Gln Lys Pro Gly Gln Ala Pro Val Leu Val Ile Tyr
        35                  40                  45

Asp Asp Asp Asp Arg Pro Ser Gly Ile Pro Glu Arg Phe Phe Gly Ser
    50                  55                  60

Asn Ser Gly Asn Thr Ala Thr Leu Ser Ile Ser Arg Val Glu Ala Gly
65                  70                  75                  80

Asp Glu Ala Asp Tyr Tyr Cys Gln Val Trp Asp Asp Asn Asn Asp Glu
                85                  90                  95

Trp Val Phe Gly Gly Gly Thr Gln Leu Thr Val Leu
            100                 105
```

```
<210> SEQ ID NO 88
<211> LENGTH: 121
<212> TYPE: PRT
<213> ORGANISM: Artificial Sequence
<220> FEATURE:
<223> OTHER INFORMATION: VH Domain of Anti-NKG2D Monoclonal Antibody
      KYK-2.0

<400> SEQUENCE: 88
```

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Leu Gly Asp Gly Thr Tyr Phe Asp Tyr Trp Gly
            100                 105                 110

Gln Gly Thr Thr Val Thr Val Ser Ser
            115                 120

<210> SEQ ID NO 89
<211> LENGTH: 110
<212> TYPE: PRT
<213> ORGANISM: Artificial Sequence
<220> FEATURE:
<223> OTHER INFORMATION: VL Domain of Anti-NKG2D Monoclonal Antibody
      KYK-2.0

<400> SEQUENCE: 89

Gln Ser Ala Leu Thr Gln Pro Ala Ser Val Ser Gly Ser Pro Gly Gln
1               5                   10                  15

Ser Ile Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Phe Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110

<210> SEQ ID NO 90
<211> LENGTH: 118
<212> TYPE: PRT
<213> ORGANISM: Artificial Sequence
<220> FEATURE:
<223> OTHER INFORMATION: VH Domain of Anti-human CD2 Monoclonal
      Antibody CD2 mAb Lo-CD2a

<400> SEQUENCE: 90

Glu Val Gln Leu Gln Gln Ser Gly Pro Glu Leu Gln Arg Pro Gly Ala
1               5                   10                  15

Ser Val Lys Leu Ser Cys Lys Ala Ser Gly Tyr Ile Phe Thr Glu Tyr
            20                  25                  30

Tyr Met Tyr Trp Val Lys Gln Arg Pro Lys Gln Gly Leu Glu Leu Val
        35                  40                  45

Gly Arg Ile Asp Pro Glu Asp Gly Ser Ile Asp Tyr Val Glu Lys Phe
    50                  55                  60

Lys Lys Lys Ala Thr Leu Thr Ala Asp Thr Ser Ser Asn Thr Ala Tyr
65                  70                  75                  80

Met Gln Leu Ser Ser Leu Thr Ser Glu Asp Thr Ala Thr Tyr Phe Cys
                85                  90                  95

Ala Arg Gly Lys Phe Asn Tyr Arg Phe Ala Tyr Trp Gly Gln Gly Thr
            100                 105                 110

Leu Val Thr Val Ser Ser
            115
```

<210> SEQ ID NO 91
<211> LENGTH: 112
<212> TYPE: PRT
<213> ORGANISM: Artificial Sequence
<220> FEATURE:
<223> OTHER INFORMATION: VL Domain of Anti-human CD2 Monoclonal
      Antibody CD2 mAb Lo-CD2a

<400> SEQUENCE: 91

Asp Val Val Leu Thr Gln Thr Pro Pro Thr Leu Leu Ala Thr Ile Gly
1               5                   10                  15

Gln Ser Val Ser Ile Ser Cys Arg Ser Ser Gln Ser Leu Leu His Ser
            20                  25                  30

Ser Gly Asn Thr Tyr Leu Asn Trp Leu Leu Gln Arg Thr Gly Gln Ser
        35                  40                  45

Pro Gln Pro Leu Ile Tyr Leu Val Ser Lys Leu Glu Ser Gly Val Pro
    50                  55                  60

Asn Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Tyr Cys Met Gln Phe
                85                  90                  95

Thr His Tyr Pro Tyr Thr Phe Gly Ala Gly Thr Lys Leu Glu Leu Lys
            100                 105                 110

<210> SEQ ID NO 92
<211> LENGTH: 120
<212> TYPE: PRT
<213> ORGANISM: Artificial Sequence
<220> FEATURE:
<223> OTHER INFORMATION: VH Domain of Anti-human CD8 Monoclonal
      Antibody OKT8

<400> SEQUENCE: 92

Gln Val Gln Leu Leu Glu Ser Gly Pro Glu Leu Leu Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Tyr Pro Tyr Thr Gly Gly Thr Gly Tyr Asn Gln Lys Phe
    50                  55                  60

Lys Asn Lys Ala Thr Leu Thr Val Asp Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asn Phe Arg Tyr Thr Tyr Trp Tyr Phe Asp Val Trp Gly Gln
            100                 105                 110

Gly Thr Thr Val Thr Val Ser Ser
        115                 120

<210> SEQ ID NO 93
<211> LENGTH: 112
<212> TYPE: PRT
<213> ORGANISM: Artificial Sequence
<220> FEATURE:
<223> OTHER INFORMATION: VL Domain of Anti-human CD8 Monoclonal
      Antibody OKT8

<400> SEQUENCE: 93

```
Asp Ile Val Met Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Asp Asn Ser Leu Met His Trp Tyr Gln Gln Lys Pro Gly Gln Pro Pro
        35                  40                  45

Lys Val Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys Arg
            100                 105                 110
```

```
<210> SEQ ID NO 94
<211> LENGTH: 121
<212> TYPE: PRT
<213> ORGANISM: Artificial Sequence
<220> FEATURE:
<223> OTHER INFORMATION: VH Domain of Anti-human CD8 Monoclonal
      Antibody TRX2

<400> SEQUENCE: 94

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asp Phe
            20                  25                  30

Gly Met Asn Trp Val Arg Gln Ala Pro Gly Lys Gly Leu Glu Trp Val
        35                  40                  45

Ala Leu Ile Tyr Tyr Asp Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro His Tyr Asp Gly Tyr Tyr His Phe Phe Asp Ser Trp Gly
            100                 105                 110

Gln Gly Thr Leu Val Thr Val Ser Ser
            115                 120
```

```
<210> SEQ ID NO 95
<211> LENGTH: 106
<212> TYPE: PRT
<213> ORGANISM: Artificial Sequence
<220> FEATURE:
<223> OTHER INFORMATION: VL Domain of Anti-human CD8 Monoclonal
      Antibody TRX2

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Gly Ser Gln Asp Ile Asn Asn Tyr
            20                  25                  30

Leu Ala Trp Tyr Gln Gln Lys Pro Gly Lys Ala Pro Lys Leu Leu Ile
        35                  40                  45

Tyr Asn Thr Asp Ile Leu His Thr Gly Val Pro Ser Arg Phe Ser Gly
    50                  55                  60
```

```
Ser Gly Ser Gly Thr Asp Phe Thr Phe Thr Ile Ser Ser Leu Gln Pro
 65                  70                  75                  80

Glu Asp Ile Ala Thr Tyr Tyr Cys Tyr Gln Tyr Asn Asn Gly Tyr Thr
                 85                  90                  95

Phe Gly Gln Gly Thr Lys Val Glu Ile Lys
            100                 105
```

<210> SEQ ID NO 96
<211> LENGTH: 120
<212> TYPE: PRT
<213> ORGANISM: Artificial Sequence
<220> FEATURE:
<223> OTHER INFORMATION: VH Domain of Anti-human B7-H3 Monoclonal
      Antibody B7-H3 mAb-B VH1

<400> SEQUENCE: 96

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                 20                  25                  30

Trp Met Gln Trp Val Arg Gln Ala Pro Gly Gln Gly Leu Glu Trp Met
             35                  40                  45

Gly Thr Ile Tyr Pro Gly Asp Gly Asp Thr Arg Tyr Thr Gln Lys Phe
         50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Gly Ile Pro Arg Leu Trp Tyr Phe Asp Val Trp Gly Gln
                100                 105                 110

Gly Thr Thr Val Thr Val Ser Ser
            115                 120
```

<210> SEQ ID NO 97
<211> LENGTH: 120
<212> TYPE: PRT
<213> ORGANISM: Artificial Sequence
<220> FEATURE:
<223> OTHER INFORMATION: VH Domain of Anti-human B7-H3 Monoclonal
      Antibody B7-H3 mAb-B VH2

<400> SEQUENCE: 97

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                 20                  25                  30

Trp Met Gln Trp Val Arg Gln Ala Pro Gly Gln Gly Leu Glu Trp Met
             35                  40                  45

Gly Thr Ile Tyr Pro Gly Gly Gly Asp Thr Arg Tyr Thr Gln Lys Phe
         50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Gly Ile Pro Arg Leu Trp Tyr Phe Asp Val Trp Gly Gln
                100                 105                 110

Gly Thr Thr Val Thr Val Ser Ser
            115                 120
```

<210> SEQ ID NO 98
<211> LENGTH: 107
<212> TYPE: PRT
<213> ORGANISM: Artificial Sequence
<220> FEATURE:
<223> OTHER INFORMATION: VL Domain of Anti-human B7-H3 Monoclonal
      Antibody B7-H3 mAb-B VL1

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Pro
                85                  90                  95

Thr Phe Gly Gly Gly Thr Lys Leu Glu Ile Lys
            100                 105

<210> SEQ ID NO 99
<211> LENGTH: 107
<212> TYPE: PRT
<213> ORGANISM: Artificial Sequence
<220> FEATURE:
<223> OTHER INFORMATION: VL Domain of Anti-human B7-H3 Monoclonal
      Antibody B7-H3 mAb-B VL2

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Pro
                85                  90                  95

Thr Phe Gly Gly Gly Thr Lys Leu Glu Ile Lys
            100                 105

<210> SEQ ID NO 100
<211> LENGTH: 117
<212> TYPE: PRT
<213> ORGANISM: Artificial Sequence
<220> FEATURE:
<223> OTHER INFORMATION: VH Domain of Anti-human B7-H3 Monoclonal
      Antibody B7-H3 mAb-C

<400> SEQUENCE: 100

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr

```
                    20                  25                  30
Gly Met Ser Trp Val Arg Gln Ala Pro Gly Lys Gly Leu Glu Trp Val
            35                  40                  45

Ala Thr Ile Asn Ser Gly Gly Ser Asn Thr Tyr Tyr Pro Asp Ser Leu
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Asp Gly Gly Ala Met Asp Tyr Trp Gly Gln Gly Thr Thr
            100                 105                 110

Val Thr Val Ser Ser
        115

<210> SEQ ID NO 101
<211> LENGTH: 108
<212> TYPE: PRT
<213> ORGANISM: Artificial Sequence
<220> FEATURE:
<223> OTHER INFORMATION: VL Domain of Anti-human B7-H3 Monoclonal
      Antibody B7-H3 mAb-C

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Tyr Ser Tyr
            20                  25                  30

Leu Ala Trp Tyr Gln Gln Lys Pro Gly Lys Ala Pro Lys Leu Leu Val
        35                  40                  45

Tyr Asn Thr Lys Thr Leu Pro Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Pro
                85                  90                  95

Trp Thr Phe Gly Gln Gly Thr Arg Leu Glu Ile Lys
            100                 105

<210> SEQ ID NO 102
<211> LENGTH: 119
<212> TYPE: PRT
<213> ORGANISM: Artificial Sequence
<220> FEATURE:
<223> OTHER INFORMATION: VH Domain of Anti-human B7-H3 Monoclonal
      Antibody B7-H3 mAb-D

<400> SEQUENCE: 102

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Gly Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
```

```
                         85                  90                  95

Ala Arg His Gly Tyr Arg Tyr Glu Gly Phe Asp Tyr Trp Gly Gln Gly
                100                 105                 110

Thr Thr Val Thr Val Ser Ser
            115

<210> SEQ ID NO 103
<211> LENGTH: 107
<212> TYPE: PRT
<213> ORGANISM: Artificial Sequence
<220> FEATURE:
<223> OTHER INFORMATION: VL Domain of Anti-human B7-H3 Monoclonal
      Antibody B7-H3 mAb-D

<400> SEQUENCE: 103

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
                20                  25                  30

Val Ala Trp Tyr Gln Gln Lys Pro Gly Lys Ala Pro Lys Ala Leu Ile
            35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Glu Tyr Phe Cys Gln Gln Tyr Asn Asn Tyr Pro Phe
                85                  90                  95

Thr Phe Gly Gln Gly Thr Lys Leu Glu Ile Lys
                100                 105

<210> SEQ ID NO 104
<211> LENGTH: 122
<212> TYPE: PRT
<213> ORGANISM: Artificial Sequence
<220> FEATURE:
<223> OTHER INFORMATION: VH Domain of Anti-human B7-H3 Monoclonal
      Antibody Enoblituzumab

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Gly Met His Trp Val Arg Gln Ala Pro Gly Lys Gly Leu Glu Trp Val
            35                  40                  45

Ala Tyr Ile Ser Ser Asp Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Gly Arg Gly Arg Glu Asn Ile Tyr Tyr Gly Ser Arg Leu Asp Tyr Trp
                100                 105                 110

Gly Gln Gly Thr Thr Val Thr Val Ser Ser
            115                 120

<210> SEQ ID NO 105
<211> LENGTH: 107
<212> TYPE: PRT
```

```
<213> ORGANISM: Artificial Sequence
<220> FEATURE:
<223> OTHER INFORMATION: VL Domain of Anti-human B7-H3 Monoclonal
      Antibody Enoblituzumab

<400> SEQUENCE: 105

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys
            100                 105

<210> SEQ ID NO 106
<211> LENGTH: 121
<212> TYPE: PRT
<213> ORGANISM: Artificial Sequence
<220> FEATURE:
<223> OTHER INFORMATION: VH Domain of Humanized anti-CEACAM5 / CEACAM6
      Monoclonal Antibody 16C3

<400> SEQUENCE: 106

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Leu Ile Ser Thr Tyr Ser Gly Asp Thr Lys Tyr Asn Gln Asn Phe
50                  55                  60

Lys Gly Lys Ala Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120

<210> SEQ ID NO 107
<211> LENGTH: 107
<212> TYPE: PRT
<213> ORGANISM: Artificial Sequence
<220> FEATURE:
<223> OTHER INFORMATION: VL Domain of Humanized anti-CEACAM5 / CEACAM6
      Monoclonal Antibody 16C3

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30
```

```
Leu Asn Trp Tyr Gln Arg Lys Pro Gly Lys Ser Pro Lys Leu Leu Ile
        35                  40                  45

Trp Gly Ala Ser Asn Leu Ala Asp Gly Met Pro Ser Arg Phe Ser Gly
    50                  55                  60

Ser Gly Ser Gly Arg Gln Tyr Thr Leu Thr Ile Ser Ser Leu Gln Pro
65                  70                  75                  80

Glu Asp Val Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105
```

<210> SEQ ID NO 108
<211> LENGTH: 121
<212> TYPE: PRT
<213> ORGANISM: Artificial Sequence
<220> FEATURE:
<223> OTHER INFORMATION: VH Domain of Humanized anti-CEACAM5 / CEACAM6
      Monoclonal Antibody hMN15

<400> SEQUENCE: 108

```
Gln Val Gln Leu Val Glu Ser Gly Gly Gly Val Val Gln Pro Gly Arg
1               5                   10                  15

Ser Leu Arg Leu Ser Cys Ser Ser Gly Phe Ala Leu Thr Asp Tyr
            20                  25                  30

Tyr Met Ser Trp Val Arg Gln Ala Pro Gly Lys Gly Leu Glu Trp Leu
        35                  40                  45

Gly Phe Ile Ala Asn Lys Ala Asn Gly His Thr Thr Asp Tyr Ser Pro
    50                  55                  60

Ser Val Lys Gly Arg Phe Thr Ile Ser Arg Asp Asn Ser Lys Asn Thr
65                  70                  75                  80

Leu Phe Leu Gln Met Asp Ser Leu Arg Pro Glu Asp Thr Gly Val Tyr
                85                  90                  95

Phe Cys Ala Arg Asp Met Gly Ile Arg Trp Asn Phe Asp Val Trp Gly
            100                 105                 110

Gln Gly Thr Pro Val Thr Val Ser Ser
        115                 120
```

<210> SEQ ID NO 109
<211> LENGTH: 107
<212> TYPE: PRT
<213> ORGANISM: Artificial Sequence
<220> FEATURE:
<223> OTHER INFORMATION: VL Domain of Humanized anti-CEACAM5 / CEACAM6
      Monoclonal Antibody hMN15

<400> SEQUENCE: 109

```
Asp Ile Gln Leu Thr Gln Ser Pro Ser Ser Leu Ser Ala Ser Val Gly
1               5                   10                  15

Asp Arg Val Thr Met Thr Cys Ser Ala Ser Ser Arg Val Ser Tyr Ile
            20                  25                  30

His Trp Tyr Gln Gln Lys Pro Gly Lys Ala Pro Lys Arg Trp Ile Tyr
        35                  40                  45

Gly Thr Ser Thr Leu Ala Ser Gly Val Pro Ala Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Tyr Asn Pro Pro Thr
                85                  90                  95
```

Phe Gly Gln Gly Thr Lys Val Glu Ile Lys Arg
            100                 105

<210> SEQ ID NO 110
<211> LENGTH: 119
<212> TYPE: PRT
<213> ORGANISM: Artificial Sequence
<220> FEATURE:
<223> OTHER INFORMATION: VH Domain of Chimeric Anti-human EGFR
      Monoclonal Antibody Cetuximab

<400> SEQUENCE: 110

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 111
<211> LENGTH: 108
<212> TYPE: PRT
<213> ORGANISM: Artificial Sequence
<220> FEATURE:
<223> OTHER INFORMATION: VL Domain of Chimeric Anti-human EGFR
      Monoclonal Antibody Cetuximab

<400> SEQUENCE: 111

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg
            100                 105

<210> SEQ ID NO 112
<211> LENGTH: 119
<212> TYPE: PRT
<213> ORGANISM: Artificial Sequence
<220> FEATURE:
<223> OTHER INFORMATION: VH Domain of Chimeric Anti-human EGFR
      Monoclonal Antibody Panitumumab

<400> SEQUENCE: 112

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser
            115

<210> SEQ ID NO 113
<211> LENGTH: 108
<212> TYPE: PRT
<213> ORGANISM: Artificial Sequence
<220> FEATURE:
<223> OTHER INFORMATION: VL Domain of Chimeric Anti-human EGFR
      Monoclonal Antibody Panitumumab

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg
            100                 105

<210> SEQ ID NO 114
<211> LENGTH: 118
<212> TYPE: PRT
<213> ORGANISM: Artificial Sequence
<220> FEATURE:
<223> OTHER INFORMATION: VH Domain of Anti-human EphA2 Monoclonal
      Antibody EphA2 mAb 1

<400> SEQUENCE: 114

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Ser Val His Trp Val Arg Gln Pro Pro Gly Lys Gly Leu Glu Trp Leu
        35                  40                  45

```
Gly Met Ile Trp Gly Gly Gly Ser Thr Asp Tyr Asn Ser Ala Leu Lys
    50              55                  60
Ser Arg Leu Ser Ile Ser Lys Asp Asn Ser Lys Ser Gln Val Phe Leu
65              70                  75                  80
Lys Met Asn Ser Leu Gln Thr Asp Asp Thr Ala Met Tyr Tyr Cys Ala
                85                  90                  95
Arg Lys His Gly Asn Tyr Tyr Thr Met Asp Tyr Trp Gly Gln Gly Thr
            100                 105                 110
Ser Val Thr Val Ser Ser
            115
```

<210> SEQ ID NO 115
<211> LENGTH: 106
<212> TYPE: PRT
<213> ORGANISM: Artificial Sequence
<220> FEATURE:
<223> OTHER INFORMATION: VL Domain of Anti-human EphA2 Monoclonal
      Antibody EphA2 mAb 1

<400> SEQUENCE: 115

```
Asp Ile Gln Met Thr Gln Thr Thr Ser Ser Leu Ser Ala Ser Leu Gly
1               5                   10                  15
Asp Arg Ile Thr Ile Ser Cys Arg Ala Ser Gln Asp Ile Ser Asn Tyr
                20                  25                  30
Leu Asn Trp Tyr Gln Leu Lys Pro Asp Gly Thr Val Lys Leu Leu Ile
            35                  40                  45
Tyr Tyr Thr Ser Arg Leu His Ser Gly Val Pro Ser Arg Phe Ser Gly
        50                  55                  60
Ser Gly Ser Gly Thr Asp Tyr Ser Leu Thr Ile Ser Asn Leu Glu Gln
65                  70                  75                  80
Glu Asp Ile Ala Thr Tyr Phe Cys Gln Gln Gly Tyr Thr Leu Tyr Thr
                85                  90                  95
Phe Gly Gly Gly Thr Lys Leu Glu Ile Lys
            100                 105
```

<210> SEQ ID NO 116
<211> LENGTH: 118
<212> TYPE: PRT
<213> ORGANISM: Artificial Sequence
<220> FEATURE:
<223> OTHER INFORMATION: VH Domain of Anti-human EphA2 Monoclonal
      Antibody EphA2 mAb2

<400> SEQUENCE: 116

```
Gln Ile Gln Leu Val Gln Ser Gly Pro Glu Leu Lys Lys Pro Gly Glu
1               5                   10                  15
Thr Val Lys Ile Ser Cys Lys Ala Ser Gly Phe Thr Phe Thr Asn Tyr
                20                  25                  30
Gly Met Asn Trp Val Lys Gln Ala Pro Gly Lys Gly Leu Lys Trp Met
            35                  40                  45
Gly Trp Ile Asn Thr Tyr Ile Gly Glu Pro Thr Tyr Ala Asp Asp Phe
        50                  55                  60
Lys Gly Arg Phe Val Phe Ser Leu Glu Thr Ser Ala Ser Thr Ala Tyr
65                  70                  75                  80
Leu Gln Ile Asn Asn Leu Lys Asn Glu Asp Met Ala Thr Tyr Phe Cys
                85                  90                  95
Ala Arg Glu Leu Gly Pro Tyr Tyr Phe Asp Tyr Trp Gly Gln Gly Thr
            100                 105                 110
```

Thr Leu Thr Val Ser Ser
         115

<210> SEQ ID NO 117
<211> LENGTH: 111
<212> TYPE: PRT
<213> ORGANISM: Artificial Sequence
<220> FEATURE:
<223> OTHER INFORMATION: VL Domain of Anti-human EphA2 Monoclonal
      Antibody EphA2 mAb2

<400> SEQUENCE: 117

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Ser Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Thr Phe Gly Ser Gly Thr Lys Leu Glu Ile Lys
            100                 105                 110

<210> SEQ ID NO 118
<211> LENGTH: 118
<212> TYPE: PRT
<213> ORGANISM: Artificial Sequence
<220> FEATURE:
<223> OTHER INFORMATION: VH Domain of Anti-human EphA2 Monoclonal
      Antibody EphA2 mAb3

<400> SEQUENCE: 118

Glu Val Gln Leu Val Glu Ser Gly Gly Gly Ser Val Lys Pro Gly Gly
1               5                   10                  15

Ser Leu Lys Leu Ser Cys Ala Ala Ser Gly Phe Thr Phe Thr Asp His
            20                  25                  30

Tyr Met Tyr Trp Val Arg Gln Thr Pro Glu Lys Arg Leu Glu Trp Val
        35                  40                  45

Ala Thr Ile Ser Asp Gly Gly Ser Phe Thr Ser Tyr Pro Asp Ser Val
    50                  55                  60

Lys Gly Arg Phe Thr Ile Ser Arg Asp Ile Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Thr Arg Asp Glu Ser Asp Arg Pro Phe Pro Tyr Trp Gly Gln Gly Thr
            100                 105                 110

Leu Val Thr Val Ser Ser
         115

<210> SEQ ID NO 119
<211> LENGTH: 107
<212> TYPE: PRT
<213> ORGANISM: Artificial Sequence
<220> FEATURE:
<223> OTHER INFORMATION: VL Domain of Anti-human EphA2 Monoclonal
      Antibody EphA2 mAb3

```
<400> SEQUENCE: 119

Asp Ile Val Leu Thr Gln Ser His Arg Ser Met Ser Thr Ser Val Gly
1               5                   10                  15

Asp Arg Val Asn Ile Thr Cys Lys Ala Ser Gln Asp Val Thr Thr Ala
            20                  25                  30

Val Ala Trp Tyr Gln Gln Lys Pro Gly Gln Ser Pro Lys Leu Leu Ile
        35                  40                  45

Phe Trp Ala Ser Thr Arg His Ala Gly Val Pro Asp Arg Phe Thr Gly
50                  55                  60

Ser Gly Ser Gly Thr Asp Phe Thr Leu Thr Ile Ser Ser Val Gln Ala
65                  70                  75                  80

Gly Asp Leu Ala Leu Tyr Tyr Cys Gln Gln His Tyr Ser Thr Pro Tyr
                85                  90                  95

Thr Phe Gly Gly Gly Thr Lys Leu Glu Ile Lys
            100                 105

<210> SEQ ID NO 120
<211> LENGTH: 119
<212> TYPE: PRT
<213> ORGANISM: Artificial Sequence
<220> FEATURE:
<223> OTHER INFORMATION: VH Domain of Anti-human gpA33 Monoclonal
      Antibody gpA33 mAb 1

<400> SEQUENCE: 120

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Glu Thr Asn Tyr Asn Gly Lys Phe
50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Tyr Gly Asn Asn Val Tyr Phe Asp Val Trp Gly Gln Gly
            100                 105                 110

Thr Thr Val Thr Val Ser Ser
        115

<210> SEQ ID NO 121
<211> LENGTH: 106
<212> TYPE: PRT
<213> ORGANISM: Artificial Sequence
<220> FEATURE:
<223> OTHER INFORMATION: VL Domain of Anti-human gpA33 Monoclonal
      Antibody gpA33 mAb 1

<400> SEQUENCE: 121

Asp Ile Gln Leu Thr Gln Ser Pro Ser Phe Leu Ser Ala Ser Val Gly
1               5                   10                  15

Asp Arg Val Thr Ile Thr Cys Ser Ala Arg Ser Ser Ile Ser Phe Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
```

-continued

```
                50                  55                  60
Gly Ser Gly Thr Glu Phe Thr Leu Thr Ile Ser Ser Leu Glu Ala Glu
 65                  70                  75                  80

Asp Ala Ala Thr Tyr Tyr Cys Gln Gln Trp Ser Ser Tyr Pro Leu Thr
                 85                  90                  95

Phe Gly Gln Gly Thr Lys Leu Glu Ile Lys
            100                 105

<210> SEQ ID NO 122
<211> LENGTH: 120
<212> TYPE: PRT
<213> ORGANISM: Artificial Sequence
<220> FEATURE:
<223> OTHER INFORMATION: VH Domain of Anti-human HER2/neu Monoclonal
      Antibody Margetuximab

<400> SEQUENCE: 122

Gln Val Gln Leu Gln Gln Ser Gly Pro Glu Leu Val Lys Pro Gly Ala
 1               5                  10                  15

Ser Leu Lys Leu Ser Cys Thr Ala Ser Gly Phe Asn Ile Lys Asp Thr
                20                  25                  30

Tyr Ile His Trp Val Lys Gln Arg Pro Glu Gln Gly Leu Glu Trp Ile
            35                  40                  45

Gly Arg Ile Tyr Pro Thr Asn Gly Tyr Thr Arg Tyr Asp Pro Lys Phe
 50                  55                  60

Gln Asp Lys Ala Thr Ile Thr Ala Asp Thr Ser Ser Asn Thr Ala Tyr
 65                  70                  75                  80

Leu Gln Val Ser Arg Leu Thr Ser Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Ala Ser Val Thr Val Ser Ser
        115                 120

<210> SEQ ID NO 123
<211> LENGTH: 107
<212> TYPE: PRT
<213> ORGANISM: Artificial Sequence
<220> FEATURE:
<223> OTHER INFORMATION: VL Domain of Anti-human HER2/neu Monoclonal
      Antibody Margetuximab

<400> SEQUENCE: 123

Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Asn Thr Ala
                20                  25                  30

Val Ala Trp Tyr Gln Gln Lys Pro Gly His Ser Pro Lys Leu Leu Ile
            35                  40                  45

Tyr Ser Ala Ser Phe Arg Tyr Thr Gly Val Pro Asp Arg Phe Thr Gly
 50                  55                  60

Ser Arg Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Thr Thr Pro Pro
                 85                  90                  95

Thr Phe Gly Gly Gly Thr Lys Val Glu Ile Lys
            100                 105
```

```
<210> SEQ ID NO 124
<211> LENGTH: 120
<212> TYPE: PRT
<213> ORGANISM: Artificial Sequence
<220> FEATURE:
<223> OTHER INFORMATION: VH Domain of Anti-human HER2/neu Monoclonal
      Antibody Trastuzumab

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 125
<211> LENGTH: 107
<212> TYPE: PRT
<213> ORGANISM: Artificial Sequence
<220> FEATURE:
<223> OTHER INFORMATION: VL Domain of Anti-human HER2/neu Monoclonal
      Antibody Trastuzumab

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 126
<211> LENGTH: 119
<212> TYPE: PRT
<213> ORGANISM: Artificial Sequence
<220> FEATURE:
<223> OTHER INFORMATION: VH Domain of Anti-human HER2/neu Monoclonal
      Antibody Pertuzumab

<400> SEQUENCE: 126

Glu Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 127
<211> LENGTH: 107
<212> TYPE: PRT
<213> ORGANISM: Artificial Sequence
<220> FEATURE:
<223> OTHER INFORMATION: VL Domain of Anti-human HER2/neu Monoclonal
      Antibody Pertuzumab

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 128
<211> LENGTH: 123
<212> TYPE: PRT
<213> ORGANISM: Artificial Sequence
<220> FEATURE:
<223> OTHER INFORMATION: VH Domain of Anti-human VEGF Monoclonal
      Antibody Bevacizumab

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80
```

-continued

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 129
<211> LENGTH: 108
<212> TYPE: PRT
<213> ORGANISM: Artificial Sequence
<220> FEATURE:
<223> OTHER INFORMATION: VL Domain of Anti-human VEGF Monoclonal
      Antibody Bevacizumab

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg
            100                 105

<210> SEQ ID NO 130
<211> LENGTH: 118
<212> TYPE: PRT
<213> ORGANISM: Artificial Sequence
<220> FEATURE:
<223> OTHER INFORMATION: VH Domain of Anti-human 5T4 Monoclonal
      Antibody 5T4 mAb 1

<400> SEQUENCE: 130

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Met His Trp Val Arg Gln Ala Pro Gly Gln Gly Leu Glu Trp Met
        35                  40                  45

Gly Arg Ile Asp Pro Asn Arg Gly Gly Thr Glu Tyr Asn Glu Lys Ala
    50                  55                  60

Lys Ser Arg Val Thr Met Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Asn Pro Tyr Tyr Pro Met Asp Tyr Trp Gly Gln Gly Thr
            100                 105                 110

Thr Val Thr Val Ser Ser
        115

<210> SEQ ID NO 131

<211> LENGTH: 107
<212> TYPE: PRT
<213> ORGANISM: Artificial Sequence
<220> FEATURE:
<223> OTHER INFORMATION: VL Domain of Anti-human 5T4 Monoclonal
      Antibody 5T4 mAb 1

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Arg Ala Asn Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Tyr Asp Asp Phe Pro Trp
                85                  90                  95

Thr Phe Gly Gln Gly Thr Lys Leu Glu Ile Lys
            100                 105

<210> SEQ ID NO 132
<211> LENGTH: 127
<212> TYPE: PRT
<213> ORGANISM: Artificial Sequence
<220> FEATURE:
<223> OTHER INFORMATION: VH Domain of Anti-human 5T4 Monoclonal
      Antibody 5T4 mAb 2

<400> SEQUENCE: 132

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Thr Trp Val Lys Gln Arg Pro Gly Gln Gly Leu Glu Trp Ile
        35                  40                  45

Gly Asp Ile Tyr Pro Gly Ser Gly Arg Ala Asn Tyr Asn Glu Lys Phe
50                  55                  60

Lys Ser Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Asn Cys
                85                  90                  95

Ala Arg Tyr Gly Pro Leu Phe Thr Thr Val Val Asp Pro Asn Ser Tyr
            100                 105                 110

Ala Met Asp Tyr Trp Gly Gln Gly Thr Ser Val Thr Val Ser Ser
        115                 120                 125

<210> SEQ ID NO 133
<211> LENGTH: 112
<212> TYPE: PRT
<213> ORGANISM: Artificial Sequence
<220> FEATURE:
<223> OTHER INFORMATION: VL Domain of Anti-human 5T4 Monoclonal
      Antibody 5T4 mAb 2

<400> SEQUENCE: 133

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Ser
              20                  25                  30

Asn Gly Asn Thr Tyr Leu Glu Trp Tyr Leu Gln Lys Pro Gly Gln Ser
          35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                  85                  90                  95

Ser His Val Pro Phe Thr Phe Gly Ser Gly Thr Lys Leu Glu Ile Lys
              100                 105                 110

<210> SEQ ID NO 134
<211> LENGTH: 122
<212> TYPE: PRT
<213> ORGANISM: Artificial Sequence
<220> FEATURE:
<223> OTHER INFORMATION: VH Domain of Anti-human IL13R(alpha)2
      Monoclonal Antibody hu08

<400> SEQUENCE: 134

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Asn
              20                  25                  30

Gly Met Ser Trp Val Arg Gln Ala Pro Gly Lys Gly Leu Glu Trp Val
          35                  40                  45

Ala Thr Val Ser Ser Gly Gly Ser Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                  85                  90                  95

Ala Arg Gln Gly Thr Thr Ala Leu Ala Thr Arg Phe Phe Asp Val Trp
              100                 105                 110

Gly Gln Gly Thr Leu Val Thr Val Ser Ser
          115                 120

<210> SEQ ID NO 135
<211> LENGTH: 107
<212> TYPE: PRT
<213> ORGANISM: Artificial Sequence
<220> FEATURE:
<223> OTHER INFORMATION: VL Domain of Anti-human IL13R(alpha)2
      Monoclonal Antibody hu08

<400> SEQUENCE: 135

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Gly Thr Ala
              20                  25                  30

Val Ala Trp Tyr Gln Gln Lys Pro Gly Lys Ala Pro Lys Leu Leu Ile
          35                  40                  45

Tyr Ser Ala Ser Tyr Arg Ser Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

```
Glu Asp Phe Ala Thr Tyr Tyr Cys Gln His Tyr Ser Ala Pro Trp
            85                  90                  95

Thr Phe Gly Gly Gly Thr Lys Val Glu Ile Lys
            100                 105

<210> SEQ ID NO 136
<211> LENGTH: 120
<212> TYPE: PRT
<213> ORGANISM: Artificial Sequence
<220> FEATURE:
<223> OTHER INFORMATION: VH Domain of Anti-human CD123 Monoclonal
      Antibody CD123 mAb 1

<400> SEQUENCE: 136

Glu Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met Lys Trp Val Arg Gln Ala Pro Gly Gln Gly Leu Glu Trp Ile
            35                  40                  45

Gly Asp Ile Ile Pro Ser Asn Gly Ala Thr Phe Tyr Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser
        115                 120

<210> SEQ ID NO 137
<211> LENGTH: 113
<212> TYPE: PRT
<213> ORGANISM: Artificial Sequence
<220> FEATURE:
<223> OTHER INFORMATION: VL Domain of Anti-human CD123 Monoclonal
      Antibody CD123 mAb 1

<400> SEQUENCE: 137

Asp Phe Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 138
<211> LENGTH: 120
<212> TYPE: PRT
```

-continued

<213> ORGANISM: Artificial Sequence
<220> FEATURE:
<223> OTHER INFORMATION: VH Domain of Anti-human CD19 Monoclonal
      Antibody CD19 mAb 1

<400> SEQUENCE: 138

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Arg Tyr Asn Pro Ala
50                  55                  60

Leu Lys Ser Arg Leu Thr Ile Ser Lys Asp Thr Ser Lys Asn Gln Val
65                  70                  75                  80

Phe Leu Thr Met Thr Asn Met Asp Pro Val Asp Thr Ala Thr Tyr Tyr
                85                  90                  95

Cys Ala Arg Met Glu Leu Trp Ser Tyr Tyr Phe Asp Tyr Trp Gly Gln
            100                 105                 110

Gly Thr Thr Val Thr Val Ser Ser
        115                 120

<210> SEQ ID NO 139
<211> LENGTH: 106
<212> TYPE: PRT
<213> ORGANISM: Artificial Sequence
<220> FEATURE:
<223> OTHER INFORMATION: VL Domain of Anti-human CD19 Monoclonal
      Antibody CD19 mAb 1

<400> SEQUENCE: 139

Glu Asn Val Leu Thr Gln Ser Pro Ala Thr Leu Ser Val Thr Pro Gly
1               5                   10                  15

Glu Lys Ala Thr Ile Thr Cys Arg Ala Ser Gln Ser Val Ser Tyr Met
            20                  25                  30

His Trp Tyr Gln Gln Lys Pro Gly Gln Ala Pro Arg Leu Leu Ile Tyr
        35                  40                  45

Asp Ala Ser Asn Arg Ala Ser Gly Val Pro Ser Arg Phe Ser Gly Ser
    50                  55                  60

Gly Ser Gly Thr Asp His Thr Leu Thr Ile Ser Ser Leu Glu Ala Glu
65                  70                  75                  80

Asp Ala Ala Thr Tyr Tyr Cys Phe Gln Gly Ser Val Tyr Pro Phe Thr
                85                  90                  95

Phe Gly Gln Gly Thr Lys Leu Glu Ile Lys
            100                 105

<210> SEQ ID NO 140
<211> LENGTH: 126
<212> TYPE: PRT
<213> ORGANISM: Artificial Sequence
<220> FEATURE:
<223> OTHER INFORMATION: VH Domain of Anti-HIV env Monoclonal Antibody
      7B2

<400> SEQUENCE: 140

Gln Val Gln Leu Val Gln Ser Gly Gly Gly Val Phe Lys Pro Gly Gly
1               5                   10                  15

Ser Leu Arg Leu Ser Cys Glu Ala Ser Gly Phe Thr Phe Thr Glu Tyr
            20                  25                  30

Tyr Met Thr Trp Val Arg Gln Ala Pro Gly Lys Gly Leu Glu Trp Leu
            35                  40                  45

Ala Tyr Ile Ser Lys Asn Gly Glu Tyr Ser Lys Tyr Ser Pro Ser Ser
 50                  55                  60

Asn Gly Arg Phe Thr Ile Ser Arg Asp Asn Ala Lys Asn Ser Val Phe
65                  70                  75                  80

Leu Gln Leu Asp Arg Leu Ser Ala Asp Thr Ala Val Tyr Tyr Cys
                85                  90                  95

Ala Arg Ala Asp Gly Leu Thr Tyr Phe Ser Glu Leu Leu Gln Tyr Ile
            100                 105                 110

Phe Asp Leu Trp Gly Gln Gly Ala Arg Val Thr Val Ser Ser
            115                 120                 125

<210> SEQ ID NO 141
<211> LENGTH: 113
<212> TYPE: PRT
<213> ORGANISM: Artificial Sequence
<220> FEATURE:
<223> OTHER INFORMATION: VL Domain of Anti-HIV env Monoclonal Antibody
      7B2

<400> SEQUENCE: 141

Asp Ile Val Met Thr Gln Ser Pro Asp Ser Leu Ala Val Ser Pro Gly
1               5                   10                  15

Glu Arg Ala Thr Ile His Cys Lys Ser Ser Gln Thr Leu Leu Tyr Ser
            20                  25                  30

Ser Asn Asn Arg His Ser Ile Ala Trp Tyr Gln Gln Arg Pro Gly Gln
        35                  40                  45

Pro Pro Lys Leu Leu Leu Tyr Trp Ala Ser Met Arg Leu Ser Gly Val
 50                  55                  60

Pro Asp Arg Phe Ser Gly Ser Gly Ser Gly Thr Asp Phe Thr Leu Thr
65                  70                  75                  80

Ile Asn Asn Leu Gln Ala Glu Asp Val Ala Ile Tyr Tyr Cys His Gln
                85                  90                  95

Tyr Ser Ser His Pro Pro Thr Phe Gly His Gly Thr Arg Val Glu Ile
            100                 105                 110

Lys

<210> SEQ ID NO 142
<211> LENGTH: 123
<212> TYPE: PRT
<213> ORGANISM: Artificial Sequence
<220> FEATURE:
<223> OTHER INFORMATION: VH Domain of Anti-HIV env gp120 Monoclonal
      Antibody A32

<400> SEQUENCE: 142

Gln Val Gln Leu Gln Glu Ser Gly Pro Gly Leu Val Lys Pro Ser Gln
1               5                   10                  15

Thr Leu Ser Leu Ser Cys Thr Val Ser Gly Gly Ser Ser Ser Gly
            20                  25                  30

Ala His Tyr Trp Ser Trp Ile Arg Gln Tyr Pro Gly Lys Gly Leu Glu
        35                  40                  45

Trp Ile Gly Tyr Ile His Tyr Ser Gly Asn Thr Tyr Tyr Asn Pro Ser
 50                  55                  60

Leu Lys Ser Arg Ile Thr Ile Ser Gln His Thr Ser Glu Asn Gln Phe
65                  70                  75                  80

Ser Leu Lys Leu Asn Ser Val Thr Val Ala Asp Thr Ala Val Tyr Tyr
                85                  90                  95

Cys Ala Arg Gly Thr Arg Leu Arg Thr Leu Arg Asn Ala Phe Asp Ile
            100                 105                 110

Trp Gly Gln Gly Thr Leu Val Thr Val Ser Ser
        115                 120

<210> SEQ ID NO 143
<211> LENGTH: 110
<212> TYPE: PRT
<213> ORGANISM: Artificial Sequence
<220> FEATURE:
<223> OTHER INFORMATION: VL Domain of Anti-HIV env gp120 Monoclonal
      Antibody A32

<400> SEQUENCE: 143

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln His Pro Gly Lys Ala Pro Lys Leu
        35                  40                  45

Ile Ile Ser Glu Val Asn Asn Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Glu Tyr Tyr Cys Ser Ser Tyr Thr Asp Ile
                85                  90                  95

His Asn Phe Val Phe Gly Gly Gly Thr Lys Leu Thr Val Leu
            100                 105                 110

<210> SEQ ID NO 144
<211> LENGTH: 120
<212> TYPE: PRT
<213> ORGANISM: Artificial Sequence
<220> FEATURE:
<223> OTHER INFORMATION: VH Domain of Anti-RSV glycoprotein F
      Monoclonal Antibody Variant of Palivizumab

<400> SEQUENCE: 144

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser
        115                 120

<210> SEQ ID NO 145
<211> LENGTH: 106

```
<212> TYPE: PRT
<213> ORGANISM: Artificial Sequence
<220> FEATURE:
<223> OTHER INFORMATION: VL Domain of Anti-RSV glycoprotein F
      Monoclonal Antibody Variant of Palivizumab

<400> SEQUENCE: 145

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 146
<211> LENGTH: 192
<212> TYPE: PRT
<213> ORGANISM: Homo sapiens
<220> FEATURE:
<221> NAME/KEY: MISC_FEATURE
<222> LOCATION: (1)..(192)
<223> OTHER INFORMATION: Extracellular Domain (ECD) of the 158F
      Allotype of Human CD16A

<400> SEQUENCE: 146

Gly Met Arg Thr Glu Asp Leu Pro Lys Ala Val Val Phe Leu Glu Pro
1               5                   10                  15

Gln Trp Tyr Arg Val Leu Glu Lys Asp Ser Val Thr Leu Lys Cys Gln
            20                  25                  30

Gly Ala Tyr Ser Pro Glu Asp Asn Ser Thr Gln Trp Phe His Asn Glu
        35                  40                  45

Ser Leu Ile Ser Ser Gln Ala Ser Ser Tyr Phe Ile Asp Ala Ala Thr
    50                  55                  60

Val Asp Asp Ser Gly Glu Tyr Arg Cys Gln Thr Asn Leu Ser Thr Leu
65                  70                  75                  80

Ser Asp Pro Val Gln Leu Glu Val His Ile Gly Trp Leu Leu Leu Gln
                85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
        115                 120                 125

Gly Lys Gly Arg Lys Tyr Phe His His Asn Ser Asp Phe Tyr Ile Pro
    130                 135                 140

Lys Ala Thr Leu Lys Asp Ser Gly Ser Tyr Phe Cys Arg Gly Leu Phe
145                 150                 155                 160

Gly Ser Lys Asn Val Ser Ser Glu Thr Val Asn Ile Thr Ile Thr Gln
                165                 170                 175

Gly Leu Ala Val Ser Thr Ile Ser Ser Phe Phe Pro Pro Gly Tyr Gln
            180                 185                 190
```

<210> SEQ ID NO 147
<211> LENGTH: 192
<212> TYPE: PRT
<213> ORGANISM: Homo sapiens
<220> FEATURE:
<221> NAME/KEY: MISC_FEATURE
<222> LOCATION: (1)..(192)
<223> OTHER INFORMATION: Extracellular Domain (ECD) of the 158V
      Allotype of Human CD16A

<400> SEQUENCE: 147

```
Gly Met Arg Thr Glu Asp Leu Pro Lys Ala Val Val Phe Leu Glu Pro
1               5                   10                  15

Gln Trp Tyr Arg Val Leu Glu Lys Asp Ser Val Thr Leu Lys Cys Gln
            20                  25                  30

Gly Ala Tyr Ser Pro Glu Asp Asn Ser Thr Gln Trp Phe His Asn Glu
        35                  40                  45

Ser Leu Ile Ser Ser Gln Ala Ser Ser Tyr Phe Ile Asp Ala Ala Thr
    50                  55                  60

Val Asp Asp Ser Gly Glu Tyr Arg Cys Gln Thr Asn Leu Ser Thr Leu
65                  70                  75                  80

Ser Asp Pro Val Gln Leu Glu Val His Ile Gly Trp Leu Leu Leu Gln
                85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
        115                 120                 125

Gly Lys Gly Arg Lys Tyr Phe His His Asn Ser Asp Phe Tyr Ile Pro
    130                 135                 140

Lys Ala Thr Leu Lys Asp Ser Gly Ser Tyr Phe Cys Arg Gly Leu Val
145                 150                 155                 160

Gly Ser Lys Asn Val Ser Ser Glu Thr Val Asn Ile Thr Ile Thr Gln
                165                 170                 175

Gly Leu Ala Val Ser Thr Ile Ser Phe Phe Pro Pro Gly Tyr Gln
            180                 185                 190
```

<210> SEQ ID NO 148
<211> LENGTH: 184
<212> TYPE: PRT
<213> ORGANISM: Homo sapiens
<220> FEATURE:
<221> NAME/KEY: MISC_FEATURE
<222> LOCATION: (1)..(184)
<223> OTHER INFORMATION: Extracellular Domain (ECD) of the NA1 Allotype
      of Human CD16B

<400> SEQUENCE: 148

```
Gly Met Arg Thr Glu Asp Leu Pro Lys Ala Val Val Phe Leu Glu Pro
1               5                   10                  15

Gln Trp Tyr Arg Val Leu Glu Lys Asp Ser Val Thr Leu Lys Cys Gln
            20                  25                  30

Gly Ala Tyr Ser Pro Glu Asp Asn Ser Thr Gln Trp Phe His Asn Asn
        35                  40                  45

Ser Leu Ile Ser Ser Gln Ala Ser Ser Tyr Phe Ile Asp Ala Ala Thr
    50                  55                  60

Val Asp Asp Ser Gly Glu Tyr Arg Cys Gln Thr Asn Leu Ser Thr Leu
65                  70                  75                  80

Ser Asp Pro Val Gln Leu Glu Val His Val Gly Trp Leu Leu Leu Gln
                85                  90                  95
```

```
Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
        115                 120                 125

Gly Lys Asp Arg Lys Tyr Phe His His Asn Ser Asp Phe His Ile Pro
    130                 135                 140

Lys Ala Thr Leu Lys Asp Ser Gly Ser Tyr Phe Cys Arg Gly Leu Val
145                 150                 155                 160

Gly Ser Lys Asn Val Ser Ser Glu Thr Val Asn Ile Thr Ile Thr Gln
                165                 170                 175

Gly Leu Ala Val Ser Thr Ile Ser
            180
```

<210> SEQ ID NO 149
<211> LENGTH: 184
<212> TYPE: PRT
<213> ORGANISM: Homo sapiens
<220> FEATURE:
<221> NAME/KEY: MISC_FEATURE
<222> LOCATION: (1)..(184)
<223> OTHER INFORMATION: Extracellular Domain (ECD) of the NA2 Allotype of Human CD16B

<400> SEQUENCE: 149

```
Gly Met Arg Thr Glu Asp Leu Pro Lys Ala Val Val Phe Leu Glu Pro
1               5                   10                  15

Gln Trp Tyr Ser Val Leu Glu Lys Asp Ser Val Thr Leu Lys Cys Gln
            20                  25                  30

Gly Ala Tyr Ser Pro Glu Asp Asn Ser Thr Gln Trp Phe His Asn Glu
        35                  40                  45

Ser Leu Ile Ser Ser Gln Ala Ser Ser Tyr Phe Ile Asp Ala Ala Thr
    50                  55                  60

Asn Asp Asp Ser Gly Glu Tyr Arg Cys Gln Thr Asn Leu Ser Thr Leu
65                  70                  75                  80

Ser Asp Pro Val Gln Leu Glu Val His Ile Gly Trp Leu Leu Leu Gln
                85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
        115                 120                 125

Gly Lys Asp Arg Lys Tyr Phe His His Asn Ser Asp Phe His Ile Pro
    130                 135                 140

Lys Ala Thr Leu Lys Asp Ser Gly Ser Tyr Phe Cys Arg Gly Leu Val
145                 150                 155                 160

Gly Ser Lys Asn Val Ser Ser Glu Thr Val Asn Ile Thr Ile Thr Gln
                165                 170                 175

Gly Leu Ala Val Ser Thr Ile Ser
            180
```

<210> SEQ ID NO 150
<211> LENGTH: 184
<212> TYPE: PRT
<213> ORGANISM: Macaca fascicularis
<220> FEATURE:
<221> NAME/KEY: MISC_FEATURE
<222> LOCATION: (1)..(184)
<223> OTHER INFORMATION: Extracellular Domain (ECD) of the CD16 of Cynomolgus Monkey

<400> SEQUENCE: 150

```
Gly Met Arg Ala Glu Asp Leu Pro Arg Ala Val Val Phe Leu Glu Pro
1               5                   10                  15

Gln Trp Tyr Arg Val Leu Glu Lys Asp Arg Val Thr Leu Lys Cys Gln
            20                  25                  30

Gly Ala Tyr Ser Pro Glu Asp Asn Ser Thr Arg Trp Phe His Asn Glu
        35                  40                  45

Ser Leu Ile Ser Ser Gln Thr Ser Ser Tyr Phe Ile Ala Ala Ala Arg
50                  55                  60

Val Asn Asn Ser Gly Glu Tyr Arg Cys Gln Thr Ser Leu Ser Thr Leu
65                  70                  75                  80

Ser Asp Pro Val Gln Leu Glu Val His Ile Gly Trp Leu Leu Leu Gln
                85                  90                  95

Ala Pro Arg Trp Val Phe Lys Glu Glu Ser Ile His Leu Arg Cys
            100                 105                 110

His Ser Trp Lys Asn Thr Leu Leu His Lys Val Thr Tyr Leu Gln Asn
            115                 120                 125

Gly Lys Gly Arg Lys Tyr Phe His Gln Asn Ser Asp Phe Tyr Ile Pro
130                 135                 140

Lys Ala Thr Leu Lys Asp Ser Gly Ser Tyr Phe Cys Arg Gly Leu Ile
145                 150                 155                 160

Gly Ser Lys Asn Val Ser Ser Glu Thr Val Asn Ile Thr Ile Thr Gln
                165                 170                 175

Asp Leu Ala Val Ser Ser Ile Ser
                180

<210> SEQ ID NO 151
<211> LENGTH: 496
<212> TYPE: PRT
<213> ORGANISM: Artificial Sequence
<220> FEATURE:
<223> OTHER INFORMATION: First Polypeptide Chain of the CD16 x HER2/neu
      Binding Molecule "DART-A"

<400> SEQUENCE: 151

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Ser Gly
            100                 105                 110

Gly Gly Gly Glu Val Lys Leu Val Glu Ser Gly Gly Thr Leu Val Lys
            115                 120                 125

Pro Gly Gly Ser Leu Lys Leu Ser Cys Ala Ala Ser Gly Phe Thr Phe
130                 135                 140

Asn Asn Tyr Gly Met Ser Trp Val Arg Gln Thr Pro Glu Lys Arg Leu
145                 150                 155                 160

Glu Trp Val Ala Thr Ile Ser Gly Gly Gly Ser Tyr Thr Phe Tyr Pro
```

165                 170                 175
Asp Ser Val Lys Gly Arg Phe Thr Ile Ser Arg Asp Asn Ala Lys Asn
            180                 185                 190

Ser Leu Tyr Leu Gln Met Ser Ser Leu Arg Ser Glu Asp Thr Ala Leu
            195                 200                 205

Tyr Tyr Cys Ile Arg Gln Ser Ala Arg Ala Pro Glu Pro Tyr Trp Gly
            210                 215                 220

Gln Gly Thr Leu Val Thr Val Ser Ser Ala Ser Thr Lys Gly Glu Val
225                 230                 235                 240

Ala Ala Cys Glu Lys Glu Val Ala Ala Leu Glu Lys Glu Val Ala Ala
            245                 250                 255

Leu Glu Lys Glu Val Ala Ala Leu Glu Lys Gly Gly Gly Asp Lys Thr
            260                 265                 270

His Thr Cys Pro Pro Cys Pro Ala Pro Glu Ala Ala Gly Gly Pro Ser
            275                 280                 285

Val Phe Leu Phe Pro Pro Lys Pro Lys Asp Thr Leu Met Ile Ser Arg
            290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
            325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
            355                 360                 365

Lys Cys Lys Val Ser Asn Lys Ala Leu Pro Ala Pro Ile Glu Lys Thr
            370                 375                 380

Ile Ser Lys Ala Lys Gly Gln Pro Arg Glu Pro Gln Val Tyr Thr Leu
385                 390                 395                 400

Pro Pro Ser Arg Glu Glu Met Thr Lys Asn Gln Val Ser Leu Trp Cys
            405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
            435                 440                 445

Ser Asp Gly Ser Phe Phe Leu Tyr Ser Lys Leu Thr Val Asp Lys Ser
            450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
            485                 490                 495

<210> SEQ ID NO 152
<211> LENGTH: 268
<212> TYPE: PRT
<213> ORGANISM: Artificial Sequence
<220> FEATURE:
<223> OTHER INFORMATION: Second Polypeptide Chain of the CD16 x HER2/neu
      Binding Molecule "DART-A"

<400> SEQUENCE: 152

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr His
            20                  25                  30

-continued

Val Ala Trp Tyr Gln Gln Lys Ser Gly Gln Ser Pro Lys Ser Leu Leu
            35                  40                  45

Tyr Ser Ala Ser Tyr Arg Tyr Ser Gly Val Pro Asp Arg Phe Ser Gly
 50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Lys Ser Tyr Pro Leu
                85                  90                  95

Thr Phe Gly Ala Gly Thr Lys Leu Glu Leu Lys Gly Gly Gly Ser Gly
            100                 105                 110

Gly Gly Gly Glu Val Gln Leu Val Glu Ser Gly Gly Gly Leu Val Gln
            115                 120                 125

Pro Gly Gly Ser Leu Arg Leu Ser Cys Ala Ala Ser Gly Phe Asn Ile
130                 135                 140

Lys Asp Thr Tyr Ile His Trp Val Arg Gln Ala Pro Gly Lys Gly Leu
145                 150                 155                 160

Glu Trp Val Ala Arg Ile Tyr Pro Thr Asn Gly Tyr Thr Arg Tyr Ala
                165                 170                 175

Asp Ser Val Lys Gly Arg Phe Thr Ile Ser Ala Asp Thr Ser Lys Asn
            180                 185                 190

Thr Ala Tyr Leu Gln Met Asn Ser Leu Arg Ala Glu Asp Thr Ala Val
        195                 200                 205

Tyr Tyr Cys Ser Arg Trp Gly Gly Asp Gly Phe Tyr Ala Met Asp Tyr
210                 215                 220

Trp Gly Gln Gly Thr Leu Val Thr Val Ser Ser Ala Ser Thr Lys Gly
225                 230                 235                 240

Lys Val Ala Ala Cys Lys Glu Lys Val Ala Ala Leu Lys Glu Lys Val
                245                 250                 255

Ala Ala Leu Lys Glu Lys Val Ala Ala Leu Lys Glu
            260                 265

<210> SEQ ID NO 153
<211> LENGTH: 227
<212> TYPE: PRT
<213> ORGANISM: Artificial Sequence
<220> FEATURE:
<223> OTHER INFORMATION: Third Polypeptide Chain of the CD16 x HER2/neu
      Binding Molecule "DART-A" ("Common Diabody Polypeptide Chain")

<400> SEQUENCE: 153

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

```
Tyr Thr Leu Pro Pro Ser Arg Glu Glu Met Thr Lys Asn Gln Val Ser
        130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn Arg Tyr Thr Gln Lys Ser Leu Ser Leu Ser
    210                 215                 220
Pro Gly Lys
225

<210> SEQ ID NO 154
<211> LENGTH: 497
<212> TYPE: PRT
<213> ORGANISM: Artificial Sequence
<220> FEATURE:
<223> OTHER INFORMATION: First Polypeptide Chain of the CD16 x HER2/neu
      Binding Molecule "DART-B"

<400> SEQUENCE: 154

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Gly Gly Gly Ser Gly
            100                 105                 110
Gly Gly Gly Glu Val Gln Leu Gln Gln Ser Gly Pro Glu Leu Val Lys
        115                 120                 125
Pro Gly Ala Ser Val Lys Met Ser Cys Lys Ala Ser Gly Tyr Thr Phe
    130                 135                 140
Thr Ser Ser Ala Met His Trp Val Lys Lys Asn Pro Gly Gln Gly Leu
145                 150                 155                 160
Glu Trp Ile Gly Tyr Ile Asn His Tyr Asn Asp Gly Ile Lys Tyr Asn
                165                 170                 175
Glu Arg Phe Lys Gly Lys Ala Thr Leu Thr Ser Asp Lys Ser Ser Ser
            180                 185                 190
Thr Ala Tyr Met Glu Leu Ser Ser Leu Thr Ser Glu Asp Ser Ala Val
        195                 200                 205
Tyr Tyr Cys Ala Thr Gly Tyr Arg Tyr Ala Ser Trp Phe Ala Ser Trp
    210                 215                 220
Gly Gln Gly Thr Leu Val Thr Val Ser Ser Ala Ser Thr Lys Gly Glu
225                 230                 235                 240
Val Ala Ala Cys Glu Lys Glu Val Ala Ala Leu Glu Lys Glu Val Ala
```

```
                    245                 250                 255
Ala Leu Glu Lys Glu Val Ala Ala Leu Glu Lys Gly Gly Gly Asp Lys
            260                 265                 270

Thr His Thr Cys Pro Pro Cys Pro Ala Pro Glu Ala Ala Gly Gly Pro
            275                 280                 285

Ser Val Phe Leu Phe Pro Pro Lys Pro Lys Asp Thr Leu Met Ile Ser
            290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
                340                 345                 350

Val Ser Val Leu Thr Val Leu His Gln Asp Trp Leu Asn Gly Lys Glu
            355                 360                 365

Tyr Lys Cys Lys Val Ser Asn Lys Ala Leu Pro Ala Pro Ile Glu Lys
            370                 375                 380

Thr Ile Ser Lys Ala Lys Gly Gln Pro Arg Glu Pro Gln Val Tyr Thr
385                 390                 395                 400

Leu Pro Pro Ser Arg Glu Glu Met Thr Lys Asn Gln Val Ser Leu Trp
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
            435                 440                 445

Asp Ser Asp Gly Ser Phe Phe Leu Tyr Ser Lys Leu Thr Val Asp Lys
            450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys

<210> SEQ ID NO 155
<211> LENGTH: 268
<212> TYPE: PRT
<213> ORGANISM: Artificial Sequence
<220> FEATURE:
<223> OTHER INFORMATION: Second Polypeptide Chain of the CD16 x HER2/neu
      Binding Molecule "DART-B"

<400> SEQUENCE: 155

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Asn Ile Gly Thr Ser
            20                  25                  30

Ile His Trp Tyr Gln Gln Arg Thr Asp Gly Ser Pro Arg Leu Leu Ile
        35                  40                  45

Lys Ser Val Ser Glu Ser Ile Ser Gly Ile Pro Ser Arg Phe Ser Gly
    50                  55                  60

Ser Gly Ser Gly Thr Asp Phe Thr Leu Thr Ile Asn Gly Val Glu Ser
65                  70                  75                  80

Gly Asp Ile Ser Asp Tyr Tyr Cys Gln Gln Ser Asn Ser Trp Pro Leu
                85                  90                  95

Thr Phe Gly Ala Gly Thr Lys Leu Glu Leu Lys Gly Gly Gly Ser Gly
```

```
                100             105                 110
Gly Gly Gly Glu Val Gln Leu Val Glu Ser Gly Gly Leu Val Gln
            115                 120                 125

Pro Gly Gly Ser Leu Arg Leu Ser Cys Ala Ala Ser Gly Phe Asn Ile
            130                 135             140

Lys Asp Thr Tyr Ile His Trp Val Arg Gln Ala Pro Gly Lys Gly Leu
145                 150                 155                 160

Glu Trp Val Ala Arg Ile Tyr Pro Thr Asn Gly Tyr Thr Arg Tyr Ala
                165                 170                 175

Asp Ser Val Lys Gly Arg Phe Thr Ile Ser Ala Asp Thr Ser Lys Asn
                180                 185                 190

Thr Ala Tyr Leu Gln Met Asn Ser Leu Arg Ala Glu Asp Thr Ala Val
            195                 200                 205

Tyr Tyr Cys Ser Arg Trp Gly Gly Asp Gly Phe Tyr Ala Met Asp Tyr
        210                 215                 220

Trp Gly Gln Gly Thr Leu Val Thr Val Ser Ser Ala Ser Thr Lys Gly
225                 230                 235                 240

Lys Val Ala Ala Cys Lys Glu Lys Val Ala Ala Leu Lys Glu Lys Val
                245                 250                 255

Ala Ala Leu Lys Glu Lys Val Ala Ala Leu Lys Glu
                260                 265

<210> SEQ ID NO 156
<211> LENGTH: 496
<212> TYPE: PRT
<213> ORGANISM: Artificial Sequence
<220> FEATURE:
<223> OTHER INFORMATION: First Polypeptide Chain of the CD16 x HER2/neu
      Binding Molecule "DART-C"

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Ser Gly
            100                 105                 110

Gly Gly Gly Glu Val Gln Leu Val Glu Ser Gly Gly Gly Leu Val Lys
            115                 120                 125

Pro Gly Gly Ser Leu Arg Leu Ser Cys Ala Ala Ser Gly Phe Thr Phe
            130                 135                 140

Ser Asn Tyr Gly Met Ser Trp Val Arg Gln Ala Pro Gly Lys Gly Leu
145                 150                 155                 160

Glu Trp Val Ala Thr Ile Ser Gly Gly Gly Ser Tyr Thr Phe Tyr Pro
                165                 170                 175

Asp Ser Val Lys Gly Arg Phe Thr Ile Ser Arg Asp Asn Ala Lys Asn
                180                 185                 190
```

```
Ser Leu Tyr Leu Gln Met Asn Ser Leu Arg Thr Glu Asp Thr Ala Leu
            195                 200                 205

Tyr Tyr Cys Val Arg Gln Ser Ala Arg Ala Pro Glu Pro Tyr Trp Gly
        210                 215                 220

Gln Gly Thr Leu Val Thr Val Ser Ser Ala Ser Thr Lys Gly Glu Val
225                 230                 235                 240

Ala Ala Cys Glu Lys Glu Val Ala Ala Leu Glu Lys Glu Val Ala Ala
                245                 250                 255

Leu Glu Lys Glu Val Ala Ala Leu Glu Lys Gly Gly Asp Lys Thr
                260                 265                 270

His Thr Cys Pro Pro Cys Pro Ala Pro Glu Ala Ala Gly Gly Pro Ser
            275                 280                 285

Val Phe Leu Phe Pro Pro Lys Pro Lys Asp Thr Leu Met Ile Ser Arg
        290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
370                 375                 380

Ile Ser Lys Ala Lys Gly Gln Pro Arg Glu Pro Gln Val Tyr Thr Leu
385                 390                 395                 400

Pro Pro Ser Arg Glu Glu Met Thr Lys Asn Gln Val Ser Leu Trp Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

<210> SEQ ID NO 157
<211> LENGTH: 268
<212> TYPE: PRT
<213> ORGANISM: Artificial Sequence
<220> FEATURE:
<223> OTHER INFORMATION: Second Polypeptide Chain of the CD16 x HER2/neu
      Binding Molecule "DART-C"

<400> SEQUENCE: 157

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asn Val Gly Thr His
            20                  25                  30

Val Ala Trp Tyr Gln Gln Lys Pro Gly Lys Ala Pro Lys Ser Leu Leu
        35                  40                  45

Tyr Ser Ala Ser Tyr Arg Tyr Ser Gly Val Pro Ser Arg Phe Ser Gly
    50                  55                  60
```

```
Ser Gly Ser Gly Thr Asp Phe Thr Leu Thr Ile Ser Ser Leu Gln Ser
 65                  70                  75                  80

Glu Asp Ile Ala Thr Tyr Tyr Cys Gln Gln Tyr Lys Ser Tyr Pro Leu
                 85                  90                  95

Thr Phe Gly Gln Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
            115                 120                 125

Pro Gly Gly Ser Leu Arg Leu Ser Cys Ala Ala Ser Gly Phe Asn Ile
130                 135                 140

Lys Asp Thr Tyr Ile His Trp Val Arg Gln Ala Pro Gly Lys Gly Leu
145                 150                 155                 160

Glu Trp Val Ala Arg Ile Tyr Pro Thr Asn Gly Tyr Thr Arg Tyr Ala
                165                 170                 175

Asp Ser Val Lys Gly Arg Phe Thr Ile Ser Ala Asp Thr Ser Lys Asn
                180                 185                 190

Thr Ala Tyr Leu Gln Met Asn Ser Leu Arg Ala Glu Asp Thr Ala Val
            195                 200                 205

Tyr Tyr Cys Ser Arg Trp Gly Gly Asp Gly Phe Tyr Ala Met Asp Tyr
210                 215                 220

Trp Gly Gln Gly Thr Leu Val Thr Val Ser Ser Ala Ser Thr Lys Gly
225                 230                 235                 240

Lys Val Ala Ala Cys Lys Glu Lys Val Ala Ala Leu Lys Glu Lys Val
                245                 250                 255

Ala Ala Leu Lys Glu Lys Val Ala Ala Leu Lys Glu
            260                 265

<210> SEQ ID NO 158
<211> LENGTH: 497
<212> TYPE: PRT
<213> ORGANISM: Artificial Sequence
<220> FEATURE:
<223> OTHER INFORMATION: First Polypeptide Chain of the CD16 x HER2/neu
      Binding Molecule "DART-D"

<400> SEQUENCE: 158

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Gly Gly Gly Ser Gly
            100                 105                 110

Gly Gly Gly Gln Val Gln Leu Val Gln Ser Gly Ala Glu Val Lys Lys
            115                 120                 125

Pro Gly Ala Ser Val Lys Val Ser Cys Lys Ala Ser Gly Tyr Thr Phe
130                 135                 140

Thr Ser Ser Ala Met His Trp Val Arg Gln Ala Pro Gly Gln Gly Leu
```

-continued

```
            145                 150                 155                 160
        Glu Trp Met Gly Tyr Ile Asn His Tyr Asn Asp Gly Ile Lys Tyr Asn
                        165                 170                 175

Glu Arg Phe Lys Gly Arg Val Thr Ile Thr Ala Asp Lys Ser Thr Ser
                        180                 185                 190

Thr Ala Tyr Met Glu Leu Ser Ser Leu Arg Ser Glu Asp Thr Ala Val
                        195                 200                 205

Tyr Tyr Cys Ala Thr Gly Tyr Arg Tyr Ala Ser Trp Phe Ala Ser Trp
                210                 215                 220

Gly Gln Gly Thr Leu Val Thr Val Ser Ser Ala Ser Thr Lys Gly Glu
        225                 230                 235                 240

Val Ala Ala Cys Glu Lys Glu Val Ala Ala Leu Glu Lys Glu Val Ala
                        245                 250                 255

Ala Leu Glu Lys Glu Val Ala Ala Leu Glu Lys Gly Gly Gly Asp Lys
                        260                 265                 270

Thr His Thr Cys Pro Pro Cys Pro Ala Pro Glu Ala Ala Gly Gly Pro
                        275                 280                 285

Ser Val Phe Leu Phe Pro Pro Lys Pro Lys Asp Thr Leu Met Ile Ser
                290                 295                 300

Arg Thr Pro Glu Val Thr Cys Val Val Val Asp Val Ser His Glu Asp
        305                 310                 315                 320

Pro Glu Val Lys Phe Asn Trp Tyr Val Asp Gly Val Glu Val His Asn
                        325                 330                 335

Ala Lys Thr Lys Pro Arg Glu Glu Gln Tyr Asn Ser Thr Tyr Arg Val
                        340                 345                 350

Val Ser Val Leu Thr Val Leu His Gln Asp Trp Leu Asn Gly Lys Glu
                        355                 360                 365

Tyr Lys Cys Lys Val Ser Asn Lys Ala Leu Pro Ala Pro Ile Glu Lys
                        370                 375                 380

Thr Ile Ser Lys Ala Lys Gly Gln Pro Arg Glu Pro Gln Val Tyr Thr
        385                 390                 395                 400

Leu Pro Pro Ser Arg Glu Glu Met Thr Lys Asn Gln Val Ser Leu Trp
                        405                 410                 415

Cys Leu Val Lys Gly Phe Tyr Pro Ser Asp Ile Ala Val Glu Trp Glu
                        420                 425                 430

Ser Asn Gly Gln Pro Glu Asn Asn Tyr Lys Thr Thr Pro Pro Val Leu
                        435                 440                 445

Asp Ser Asp Gly Ser Phe Phe Leu Tyr Ser Lys Leu Thr Val Asp Lys
        450                 455                 460

Ser Arg Trp Gln Gln Gly Asn Val Phe Ser Cys Ser Val Met His Glu
        465                 470                 475                 480

Ala Leu His Asn His Tyr Thr Gln Lys Ser Leu Ser Leu Ser Pro Gly
                        485                 490                 495

Lys
```

<210> SEQ ID NO 159
<211> LENGTH: 268
<212> TYPE: PRT
<213> ORGANISM: Artificial Sequence
<220> FEATURE:
<223> OTHER INFORMATION: Second Polypeptide Chain of the CD16 x HER2/neu Binding Molecule "DART-D"

<400> SEQUENCE: 159

Glu Ile Val Leu Thr Gln Ser Pro Ala Thr Leu Ser Val Ser Pro Gly

-continued

```
                1               5              10              15

Glu Arg Ala Thr Leu Ser Cys Arg Ala Ser Gln Asn Ile Gly Thr Ser
                         20              25              30

Ile His Trp Tyr Gln Gln Lys Pro Asp Gln Ser Pro Lys Leu Leu Ile
                         35              40              45

Lys Ser Val Ser Glu Ser Ile Ser Gly Val Pro Ser Arg Phe Ser Gly
                         50              55              60

Ser Gly Ser Gly Thr Asp Phe Thr Leu Thr Ile Asn Ser Leu Glu Ala
         65                      70              75                      80

Glu Asp Phe Ala Thr Tyr Tyr Cys Gln Gln Ser Asn Ser Trp Pro Leu
                                 85              90              95

Thr Phe Gly Gln Gly Thr Lys Leu Glu Ile Lys Gly Gly Gly Ser Gly
                         100             105             110

Gly Gly Gly Glu Val Gln Leu Val Glu Ser Gly Gly Gly Leu Val Gln
                         115             120             125

Pro Gly Gly Ser Leu Arg Leu Ser Cys Ala Ala Ser Gly Phe Asn Ile
                 130             135             140

Lys Asp Thr Tyr Ile His Trp Val Arg Gln Ala Pro Gly Lys Gly Leu
         145                     150             155                     160

Glu Trp Val Ala Arg Ile Tyr Pro Thr Asn Gly Tyr Thr Arg Tyr Ala
                         165             170             175

Asp Ser Val Lys Gly Arg Phe Thr Ile Ser Ala Asp Thr Ser Lys Asn
                         180             185             190

Thr Ala Tyr Leu Gln Met Asn Ser Leu Arg Ala Glu Asp Thr Ala Val
                         195             200             205

Tyr Tyr Cys Ser Arg Trp Gly Gly Asp Gly Phe Tyr Ala Met Asp Tyr
                 210             215             220

Trp Gly Gln Gly Thr Leu Val Thr Val Ser Ser Ala Ser Thr Lys Gly
         225                     230             235                     240

Lys Val Ala Ala Cys Lys Glu Lys Val Ala Ala Leu Lys Glu Lys Val
                         245             250             255

Ala Ala Leu Lys Glu Lys Val Ala Ala Leu Lys Glu
                         260             265

<210> SEQ ID NO 160
<211> LENGTH: 497
<212> TYPE: PRT
<213> ORGANISM: Artificial Sequence
<220> FEATURE:
<223> OTHER INFORMATION: First Polypeptide Chain of the CD16 x HER2/neu
      Binding Molecule "DART-E"

<400> SEQUENCE: 160

Asp Ile Gln Met Thr Gln Ser Pro Ser Ser Leu Ser Ala Ser Val Gly
         1               5              10              15

Asp Arg Val Thr Ile Thr Cys Arg Ala Ser Gln Asp Val Asn Thr Ala
                         20              25              30

Val Ala Trp Tyr Gln Gln Lys Pro Gly Lys Ala Pro Lys Leu Leu Ile
                         35              40              45

Tyr Ser Ala Ser Phe Leu Tyr Ser Gly Val Pro Ser Arg Phe Ser Gly
                         50              55              60

Ser Arg Ser Gly Thr Asp Phe Thr Leu Thr Ile Ser Ser Leu Gln Pro
         65                      70              75                      80

Glu Asp Phe Ala Thr Tyr Tyr Cys Gln Gln His Tyr Thr Thr Pro Pro
                                 85              90              95
```

Thr Phe Gly Gln Gly Thr Lys Val Glu Ile Lys Gly Gly Ser Gly
                100                 105                 110

Gly Gly Gly Gln Val Gln Leu Val Gln Ser Gly Ala Glu Val Lys Lys
            115                 120                 125

Pro Gly Ala Ser Val Lys Val Ser Cys Lys Ala Ser Gly Tyr Thr Phe
    130                 135                 140

Thr Ser Ser Ala Met His Trp Val Arg Gln Ala Pro Gly Gln Gly Leu
145                 150                 155                 160

Glu Trp Met Gly Tyr Ile Asn His Tyr Asn Asp Gly Ile Lys Tyr Asn
                165                 170                 175

Glu Arg Phe Lys Gly Arg Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Arg Gly Tyr Arg Tyr Ala Ser Trp Phe Ala Ser Trp
    210                 215                 220

Gly Gln Gly Thr Leu Val Thr Val Ser Ser Ala Ser Thr Lys Gly Glu
225                 230                 235                 240

Val Ala Ala Cys Glu Lys Glu Val Ala Ala Leu Glu Lys Glu Val Ala
                245                 250                 255

Ala Leu Glu Lys Glu Val Ala Ala Leu Glu Lys Gly Gly Gly Asp Lys
            260                 265                 270

Thr His Thr Cys Pro Pro Cys Pro Ala Pro Glu Ala Ala Gly Gly Pro
        275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Pro Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Arg Glu Glu Met Thr Lys Asn Gln Val Ser Leu Trp
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
    450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys

<210> SEQ ID NO 161

<211> LENGTH: 499
<212> TYPE: PRT
<213> ORGANISM: Artificial Sequence
<220> FEATURE:
<223> OTHER INFORMATION: First Polypeptide Chain of the CD16 x HIV env
      Binding Molecule "DART-F"

<400> SEQUENCE: 161

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln His Pro Gly Lys Ala Pro Lys Leu
        35                  40                  45

Ile Ile Ser Glu Val Asn Asn Arg Pro Ser Gly Val Pro Asp Arg Phe
50 55 60

Ser Gly Ser Lys Ser Gly Asn Thr Ala Ser Leu Thr Val Ser Gly Leu
65 70 75 80

Gln Ala Glu Asp Glu Ala Glu Tyr Tyr Cys Ser Ser Tyr Thr Asp Ile
85 90 95

His Asn Phe Val Phe Gly Gly Gly Thr Lys Leu Thr Val Leu Gly Gly
100 105 110

Gly Ser Gly Gly Gly Gly Glu Val Gln Leu Val Glu Ser Gly Gly Gly
115 120 125

Leu Val Lys Pro Gly Gly Ser Leu Arg Leu Ser Cys Ala Ala Ser Gly
130 135 140

Phe Thr Phe Ser Asn Tyr Gly Met Ser Trp Val Arg Gln Ala Pro Gly
145 150 155 160

Lys Gly Leu Glu Trp Val Ala Thr Ile Ser Gly Gly Gly Ser Tyr Thr
165 170 175

Phe Tyr Pro Asp Ser Val Lys Gly Arg Phe Thr Ile Ser Arg Asp Asn
180 185 190

Ala Lys Asn Ser Leu Tyr Leu Gln Met Asn Ser Leu Arg Thr Glu Asp
195 200 205

Thr Ala Leu Tyr Tyr Cys Val Arg Gln Ser Ala Arg Ala Pro Glu Pro
210 215 220

Tyr Trp Gly Gln Gly Thr Leu Val Thr Val Ser Ser Ala Ser Thr Lys
225 230 235 240

Gly Glu Val Ala Ala Cys Glu Lys Glu Val Ala Ala Leu Glu Lys Glu
245 250 255

Val Ala Ala Leu Glu Lys Glu Val Ala Ala Leu Glu Lys Gly Gly Gly
260 265 270

Asp Lys Thr His Thr Cys Pro Pro Cys Pro Ala Pro Glu Ala Ala Gly
275 280 285

Gly Pro Ser Val Phe Leu Phe Pro Pro Lys Pro Lys Asp Thr Leu Met
290 295 300

Ile Ser Arg Thr Pro Glu Val Thr Cys Val Val Val Asp Val Ser His
305 310 315 320

Glu Asp Pro Glu Val Lys Phe Asn Trp Tyr Val Asp Gly Val Glu Val
325 330 335

His Asn Ala Lys Thr Lys Pro Arg Glu Glu Gln Tyr Asn Ser Thr Tyr
340 345 350

Arg Val Val Ser Val Leu Thr Val Leu His Gln Asp Trp Leu Asn Gly
355 360 365

Lys Glu Tyr Lys Cys Lys Val Ser Asn Lys Ala Leu Pro Ala Pro Ile

```
                370                 375                 380
Glu Lys Thr Ile Ser Lys Ala Lys Gly Gln Pro Arg Glu Pro Gln Val
385                 390                 395                 400

Tyr Thr Leu Pro Pro Ser Arg Glu Glu Met Thr Lys Asn Gln Val Ser
                405                 410                 415

Leu Trp Cys Leu Val Lys Gly Phe Tyr Pro Ser Asp Ile Ala Val Glu
                420                 425                 430

Trp Glu Ser Asn Gly Gln Pro Glu Asn Asn Tyr Lys Thr Thr Pro Pro
                435                 440                 445

Val Leu Asp Ser Asp Gly Ser Phe Phe Leu Tyr Ser Lys Leu Thr Val
                450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys

<210> SEQ ID NO 162
<211> LENGTH: 271
<212> TYPE: PRT
<213> ORGANISM: Artificial Sequence
<220> FEATURE:
<223> OTHER INFORMATION: Second Polypeptide Chain of the CD16 x HIV env
      Binding Molecule "DART-F"

<400> SEQUENCE: 162

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asn Val Gly Thr His
                20                  25                  30

Val Ala Trp Tyr Gln Gln Lys Pro Gly Lys Ala Pro Lys Ser Leu Leu
                35                  40                  45

Tyr Ser Ala Ser Tyr Arg Tyr Ser Gly Val Pro Ser Arg Phe Ser Gly
                50                  55                  60

Ser Gly Ser Gly Thr Asp Phe Thr Leu Thr Ile Ser Ser Leu Gln Ser
65                  70                  75                  80

Glu Asp Ile Ala Thr Tyr Tyr Cys Gln Gln Tyr Lys Ser Tyr Pro Leu
                85                  90                  95

Thr Phe Gly Gln Gly Thr Lys Leu Glu Ile Lys Gly Gly Gly Ser Gly
                100                 105                 110

Gly Gly Gly Gln Val Gln Leu Gln Glu Ser Gly Pro Gly Leu Val Lys
                115                 120                 125

Pro Ser Gln Thr Leu Ser Leu Ser Cys Thr Val Ser Gly Gly Ser Ser
                130                 135                 140

Ser Ser Gly Ala His Tyr Trp Ser Trp Ile Arg Gln Tyr Pro Gly Lys
145                 150                 155                 160

Gly Leu Glu Trp Ile Gly Tyr Ile His Tyr Ser Gly Asn Thr Tyr Tyr
                165                 170                 175

Asn Pro Ser Leu Lys Ser Arg Ile Thr Ile Ser Gln His Thr Ser Glu
                180                 185                 190

Asn Gln Phe Ser Leu Lys Leu Asn Ser Val Thr Val Ala Asp Thr Ala
                195                 200                 205

Val Tyr Tyr Cys Ala Arg Gly Thr Arg Leu Arg Thr Leu Arg Asn Ala
                210                 215                 220

Phe Asp Ile Trp Gly Gln Gly Thr Leu Val Thr Val Ser Ser Ala Ser
```

```
                225                 230                 235                 240
Thr Lys Gly Lys Val Ala Ala Cys Lys Glu Lys Val Ala Ala Leu Lys
                    245                 250                 255

Glu Lys Val Ala Ala Leu Lys Glu Lys Val Ala Ala Leu Lys Glu
                260                 265                 270

<210> SEQ ID NO 163
<211> LENGTH: 500
<212> TYPE: PRT
<213> ORGANISM: Artificial Sequence
<220> FEATURE:
<223> OTHER INFORMATION: First Polypeptide Chain of the CD16 x HIV env
      Binding Molecule "DART-G"

<400>

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Ala Leu Pro Ala Pro
    370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Glu Glu Met Thr Lys Asn Gln Val
                405                 410                 415

Ser Leu Trp Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly Lys
            500

<210> SEQ ID NO 164
<211> LENGTH: 271
<212> TYPE: PRT
<213> ORGANISM: Artificial Sequence
<220> FEATURE:
<223> OTHER INFORMATION: Second Polypeptide Chain of the CD16 x HIV env
      Binding Molecule "DART-G"

<400> SEQUENCE: 164

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Asn Ile Gly Thr Ser
            20                  25                  30

Ile His Trp Tyr Gln Gln Lys Pro Asp Gln Ser Pro Lys Leu Leu Ile
        35                  40                  45

Lys Ser Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Phe Ala Thr Tyr Tyr Cys Gln Gln Ser Asn Ser Trp Pro Leu
                85                  90                  95

Thr Phe Gly Gln Gly Thr Lys Leu Glu Ile Lys Gly Gly Gly Ser Gly
            100                 105                 110

Gly Gly Gly Gln Val Gln Leu Gln Glu Ser Gly Pro Gly Leu Val Lys
        115                 120                 125

Pro Ser Gln Thr Leu Ser Leu Ser Cys Thr Val Ser Gly Gly Ser Ser
    130                 135                 140

Ser Ser Gly Ala His Tyr Trp Ser Trp Ile Arg Gln Tyr Pro Gly Lys
145                 150                 155                 160

Gly Leu Glu Trp Ile Gly Tyr Ile His Tyr Ser Gly Asn Thr Tyr Tyr
                165                 170                 175

```
Asn Pro Ser Leu Lys Ser Arg Ile Thr Ile Ser Gln His Thr Ser Glu
            180                 185                 190

Asn Gln Phe Ser Leu Lys Leu Asn Ser Val Thr Val Ala Asp Thr Ala
            195                 200                 205

Val Tyr Tyr Cys Ala Arg Gly Thr Arg Leu Arg Thr Leu Arg Asn Ala
    210                 215                 220

Phe Asp Ile Trp Gly Gln Gly Thr Leu Val Thr Val Ser Ser Ala Ser
225                 230                 235                 240

Thr Lys Gly Lys Val Ala Ala Cys Lys Glu Lys Val Ala Ala Leu Lys
                245                 250                 255

Glu Lys Val Ala Ala Leu Lys Glu Lys Val Ala Ala Leu Lys Glu
            260                 265                 270

<210> SEQ ID NO 165
<211> LENGTH: 502
<212> TYPE: PRT
<213> ORGANISM: Artificial Sequence
<220> FEATURE:
<223> OTHER INFORMATION: First Polypeptide Chain of the CD16 x HIV env
      Binding Molecule "DART-H"

<400> SEQUENCE: 165

Asp Ile Val Met Thr Gln Ser Pro Asp Ser Leu Ala Val Ser Pro Gly
1               5                   10                  15

Glu Arg Ala Thr Ile His Cys Lys Ser Ser Gln Thr Leu Leu Tyr Ser
            20                  25                  30

Ser Asn Asn Arg His Ser Ile Ala Trp Tyr Gln Gln Arg Pro Gly Gln
        35                  40                  45

Pro Pro Lys Leu Leu Leu Tyr Trp Ala Ser Met Arg Leu Ser Gly Val
    50                  55                  60

Pro Asp Arg Phe Ser Gly Ser Gly Ser Gly Thr Asp Phe Thr Leu Thr
65                  70                  75                  80

Ile Asn Asn Leu Gln Ala Glu Asp Val Ala Ile Tyr Tyr Cys His Gln
                85                  90                  95

Tyr Ser Ser His Pro Pro Thr Phe Gly His Gly Thr Arg Val Glu Ile
            100                 105                 110

Lys Gly Gly Gly Ser Gly Gly Gly Gly Glu Val Gln Leu Val Glu Ser
        115                 120                 125

Gly Gly Gly Leu Val Lys Pro Gly Gly Ser Leu Arg Leu Ser Cys Ala
    130                 135                 140

Ala Ser Gly Phe Thr Phe Ser Asn Tyr Gly Met Ser Trp Val Arg Gln
145                 150                 155                 160

Ala Pro Gly Lys Gly Leu Glu Trp Val Ala Thr Ile Ser Gly Gly Gly
                165                 170                 175

Ser Tyr Thr Phe Tyr Pro Asp Ser Val Lys Gly Arg Phe Thr Ile Ser
            180                 185                 190

Arg Asp Asn Ala Lys Asn Ser Leu Tyr Leu Gln Met Asn Ser Leu Arg
        195                 200                 205

Thr Glu Asp Thr Ala Leu Tyr Tyr Cys Val Arg Gln Ser Ala Arg Ala
    210                 215                 220

Pro Glu Pro Tyr Trp Gly Gln Gly Thr Leu Val Thr Val Ser Ser Ala
225                 230                 235                 240

Ser Thr Lys Gly Glu Val Ala Ala Cys Glu Lys Glu Val Ala Ala Leu
                245                 250                 255

Glu Lys Glu Val Ala Ala Leu Glu Lys Glu Val Ala Ala Leu Glu Lys
```

```
                260                 265                 270
Gly Gly Gly Asp Lys Thr His Thr Cys Pro Pro Cys Pro Ala Pro Glu
            275                 280                 285

Ala Ala Gly Gly Pro Ser Val Phe Leu Phe Pro Pro Lys Pro Lys Asp
        290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
        355                 360                 365

Leu Asn Gly Lys Glu Tyr Lys Cys Lys Val Ser Asn Lys Ala Leu Pro
370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Glu Glu Met Thr Lys Asn
                405                 410                 415

Gln Val Ser Leu Trp Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly Lys
            500

<210> SEQ ID NO 166
<211> LENGTH: 274
<212> TYPE: PRT
<213> ORGANISM: Artificial Sequence
<220> FEATURE:
<223> OTHER INFORMATION: Second Polypeptide Chain of the CD16 x HIV env
      Binding Molecule "DART-H"

<400> SEQUENCE: 166

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asn Val Gly Thr His
            20                  25                  30

Val Ala Trp Tyr Gln Gln Lys Pro Gly Lys Ala Pro Lys Ser Leu Leu
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Ser
65                  70                  75                  80

Glu Asp Ile Ala Thr Tyr Tyr Cys Gln Gln Tyr Lys Ser Tyr Pro Leu
                85                  90                  95

Thr Phe Gly Gln Gly Thr Lys Leu Glu Ile Lys Gly Gly Gly Ser Gly
            100                 105                 110
```

```
Gly Gly Gly Gln Val Gln Leu Val Gln Ser Gly Gly Val Phe Lys
            115                 120                 125

Pro Gly Gly Ser Leu Arg Leu Ser Cys Glu Ala Ser Gly Phe Thr Phe
        130                 135                 140

Thr Glu Tyr Tyr Met Thr Trp Val Arg Gln Ala Pro Gly Lys Gly Leu
145                 150                 155                 160

Glu Trp Leu Ala Tyr Ile Ser Lys Asn Gly Glu Tyr Ser Lys Tyr Ser
                165                 170                 175

Pro Ser Ser Asn Gly Arg Phe Thr Ile Ser Arg Asp Asn Ala Lys Asn
            180                 185                 190

Ser Val Phe Leu Gln Leu Asp Arg Leu Ser Ala Asp Thr Ala Val
        195                 200                 205

Tyr Tyr Cys Ala Arg Ala Asp Gly Leu Thr Tyr Phe Ser Glu Leu Leu
        210                 215                 220

Gln Tyr Ile Phe Asp Leu Trp Gly Gln Gly Ala Arg Val Thr Val Ser
225                 230                 235                 240

Ser Ala Ser Thr Lys Gly Lys Val Ala Ala Cys Lys Glu Lys Val Ala
                245                 250                 255

Ala Leu Lys Glu Lys Val Ala Ala Leu Lys Glu Lys Val Ala Ala Leu
            260                 265                 270

Lys Glu

<210> SEQ ID NO 167
<211> LENGTH: 496
<212> TYPE: PRT
<213> ORGANISM: Artificial Sequence
<220> FEATURE:
<223> OTHER INFORMATION: First Polypeptide Chain of the CD16 x HER2/neu
      Binding Molecule "DART-1"

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Ser Gly
            100                 105                 110

Gly Gly Gly Gln Val Thr Leu Arg Glu Ser Gly Pro Ala Leu Val Lys
        115                 120                 125

Pro Thr Gln Thr Leu Thr Leu Thr Cys Thr Phe Ser Gly Phe Ser Leu
    130                 135                 140

Ser Thr Ser Gly Met Gly Val Gly Trp Ile Arg Gln Pro Pro Gly Lys
145                 150                 155                 160

Ala Leu Glu Trp Leu Ala His Ile Trp Trp Asp Asp Lys Arg Tyr
                165                 170                 175

Asn Pro Ala Leu Lys Ser Arg Leu Thr Ile Ser Lys Asp Thr Ser Lys
            180                 185                 190
```

```
Asn Gln Val Val Leu Thr Met Thr Asn Met Asp Pro Val Asp Thr Ala
            195                 200                 205

Thr Tyr Tyr Cys Ala Gln Ile Asn Pro Ala Trp Phe Ala Tyr Trp Gly
            210                 215                 220

Gln Gly Thr Leu Val Thr Val Ser Ser Ala Ser Thr Lys Gly Glu Val
225                 230                 235                 240

Ala Ala Cys Glu Lys Glu Val Ala Ala Leu Lys Glu Val Ala Ala
            245                 250                 255

Leu Glu Lys Glu Val Ala Ala Leu Glu Lys Gly Gly Asp Lys Thr
            260                 265                 270

His Thr Cys Pro Pro Cys Pro Ala Pro Glu Ala Ala Gly Gly Pro Ser
            275                 280                 285

Val Phe Leu Phe Pro Pro Lys Pro Lys Asp Thr Leu Met Ile Ser Arg
            290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
            355                 360                 365

Lys Cys Lys Val Ser Asn Lys Ala Leu Pro Ala Pro Ile Glu Lys Thr
            370                 375                 380

Ile Ser Lys Ala Lys Gly Gln Pro Arg Glu Pro Gln Val Tyr Thr Leu
385                 390                 395                 400

Pro Pro Ser Arg Glu Glu Met Thr Lys Asn Gln Val Ser Leu Trp Cys
                405                 410                 415

Leu Val Lys Gly Phe Tyr Pro Ser Asp Ile Ala Val Glu Trp Glu Ser
                420                 425                 430

Asn Gly Gln Pro Glu Asn Asn Tyr Lys Thr Thr Pro Pro Val Leu Asp
            435                 440                 445

Ser Asp Gly Ser Phe Phe Leu Tyr Ser Lys Leu Thr Val Asp Lys Ser
450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

<210> SEQ ID NO 168
<211> LENGTH: 272
<212> TYPE: PRT
<213> ORGANISM: Artificial Sequence
<220> FEATURE:
<223> OTHER INFORMATION: Second Polypeptide Chain of the CD16 x HER2/neu
      Binding Molecule "DART-1"

<400> SEQUENCE: 168

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Val Pro Asp
50                  55                  60
```

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Gly
            100                 105                 110

Gly Gly Ser Gly Gly Gly Gly Glu Val Gln Leu Val Glu Ser Gly Gly
            115                 120                 125

Gly Leu Val Gln Pro Gly Gly Ser Leu Arg Leu Ser Cys Ala Ala Ser
    130                 135                 140

Gly Phe Asn Ile Lys Asp Thr Tyr Ile His Trp Val Arg Gln Ala Pro
145                 150                 155                 160

Gly Lys Gly Leu Glu Trp Val Ala Arg Ile Tyr Pro Thr Asn Gly Tyr
                165                 170                 175

Thr Arg Tyr Ala Asp Ser Val Lys Gly Arg Phe Thr Ile Ser Ala Asp
            180                 185                 190

Thr Ser Lys Asn Thr Ala Tyr Leu Gln Met Asn Ser Leu Arg Ala Glu
        195                 200                 205

Asp Thr Ala Val Tyr Tyr Cys Ser Arg Trp Gly Gly Asp Gly Phe Tyr
    210                 215                 220

Ala Met Asp Tyr Trp Gly Gln Gly Thr Leu Val Thr Val Ser Ser Ala
225                 230                 235                 240

Ser Thr Lys Gly Lys Val Ala Ala Cys Lys Glu Lys Val Ala Ala Leu
                245                 250                 255

Lys Glu Lys Val Ala Ala Leu Lys Glu Lys Val Ala Ala Leu Lys Glu
            260                 265                 270

<210> SEQ ID NO 169
<211> LENGTH: 495
<212> TYPE: PRT
<213> ORGANISM: Artificial Sequence
<220> FEATURE:
<223> OTHER INFORMATION: First Polypeptide Chain of the CD16 x RSV
      Binding Molecule "DART-3"

<400> SEQUENCE: 169

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Gly Tyr Met
                20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Gly Gly Gly Ser Gly Gly
            100                 105                 110

Gly Gly Glu Val Gln Leu Val Glu Ser Gly Gly Gly Leu Val Lys Pro
        115                 120                 125

Gly Gly Ser Leu Arg Leu Ser Cys Ala Ala Ser Gly Phe Thr Phe Ser
    130                 135                 140

Asn Tyr Gly Met Ser Trp Val Arg Gln Ala Pro Gly Lys Gly Leu Glu

-continued 145 150 155 160

Trp Val Ala Thr Ile Ser Gly Gly Gly Ser Tyr Thr Phe Tyr Pro Asp
165 170 175

Ser Val Lys Gly Arg Phe Thr Ile Ser Arg Asp Asn Ala Lys Asn Ser
180 185 190

Leu Tyr Leu Gln Met Asn Ser Leu Arg Thr Glu Asp Thr Ala Leu Tyr
195 200 205

Tyr Cys Val Arg Gln Ser Ala Arg Ala Pro Glu Pro Tyr Trp Gly Gln
210 215 220

Gly Thr Leu Val Thr Val Ser Ser Ala Ser Thr Lys Gly Glu Val Ala
225 230 235 240

Ala Cys Glu Lys Glu Val Ala Ala Leu Glu Lys Glu Val Ala Ala Leu
245 250 255

Glu Lys Glu Val Ala Ala Leu Glu Lys Gly Gly Gly Asp Lys Thr His
260 265 270

Thr Cys Pro Pro Cys Pro Ala Pro Glu Ala Ala Gly Gly Pro Ser Val
275 280 285

Phe Leu Phe Pro Pro Lys Pro Lys Asp Thr Leu Met Ile Ser Arg Thr
290 295 300

Pro Glu Val Thr Cys Val Val Val Asp Val Ser His Glu Asp Pro Glu
305 310 315 320

Val Lys Phe Asn Trp Tyr Val Asp Gly Val Glu Val His Asn Ala Lys
325 330 335

Thr Lys Pro Arg Glu Glu Gln Tyr Asn Ser Thr Tyr Arg Val Val Ser
340 345 350

Val Leu Thr Val Leu His Gln Asp Trp Leu Asn Gly Lys Glu Tyr Lys
355 360 365

Cys Lys Val Ser Asn Lys Ala Leu Pro Ala Pro Ile Glu Lys Thr Ile
370 375 380

Ser Lys Ala Lys Gly Gln Pro Arg Glu Pro Gln Val Tyr Thr Leu Pro
385 390 395 400

Pro Ser Arg Glu Glu Met Thr Lys Asn Gln Val Ser Leu Trp Cys Leu
405 410 415

Val Lys Gly Phe Tyr Pro Ser Asp Ile Ala Val Glu Trp Glu Ser Asn
420 425 430

Gly Gln Pro Glu Asn Asn Tyr Lys Thr Thr Pro Pro Val Leu Asp Ser
435 440 445

Asp Gly Ser Phe Phe Leu Tyr Ser Lys Leu Thr Val Asp Lys Ser Arg
450 455 460

Trp Gln Gln Gly Asn Val Phe Ser Cys Ser Val Met His Glu Ala Leu
465 470 475 480

His Asn His Tyr Thr Gln Lys Ser Leu Ser Leu Ser Pro Gly Lys
485 490 495

<210> SEQ ID NO 170
<211> LENGTH: 268
<212> TYPE: PRT
<213> ORGANISM: Artificial Sequence
<220> FEATURE:
<223> OTHER INFORMATION: Second Polypeptide Chain of the CD16 x RSV
Binding Molecule “DART-3”

<400> SEQUENCE: 170

Asp Ile Gln Met Thr Gln Ser Pro Ser Phe Leu Ser Ala Ser Val Gly
1 5 10 15

```
Asp Arg Val Thr Ile Thr Cys Arg Ala Ser Gln Asn Val Gly Thr His
            20                  25                  30

Val Ala Trp Tyr Gln Gln Lys Pro Gly Lys Ala Pro Lys Ser Leu Leu
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Ser
65                  70                  75                  80

Glu Asp Ile Ala Thr Tyr Tyr Cys Gln Gln Tyr Lys Ser Tyr Pro Leu
                85                  90                  95

Thr Phe Gly Gln Gly Thr Lys Leu Glu Ile Lys Gly Gly Gly Ser Gly
            100                 105                 110

Gly Gly Gly Gln Val Thr Leu Arg Glu Ser Gly Pro Ala Leu Val Lys
        115                 120                 125

Pro Thr Gln Thr Leu Thr Leu Thr Cys Thr Phe Ser Gly Phe Ser Leu
    130                 135                 140

Ser Thr Ser Gly Met Ser Val Gly Trp Ile Arg Gln Pro Pro Gly Lys
145                 150                 155                 160

Ala Leu Glu Trp Leu Ala Asp Ile Trp Trp Asp Asp Lys Lys Asp Tyr
                165                 170                 175

Asn Pro Ser Leu Lys Ser Arg Leu Thr Ile Ser Lys Asp Thr Ser Lys
            180                 185                 190

Asn Gln Val Val Leu Lys Val Thr Asn Met Asp Pro Ala Asp Thr Ala
        195                 200                 205

Thr Tyr Tyr Cys Ala Arg Ser Met Ile Thr Asn Trp Tyr Phe Asp Val
    210                 215                 220

Trp Gly Ala Gly Thr Thr Val Thr Val Ser Ser Ala Ser Thr Lys Gly
225                 230                 235                 240

Lys Val Ala Ala Cys Lys Glu Lys Val Ala Ala Leu Lys Glu Lys Val
                245                 250                 255

Ala Ala Leu Lys Glu Lys Val Ala Ala Leu Lys Glu
            260                 265
```

<210> SEQ ID NO 171
<211> LENGTH: 272
<212> TYPE: PRT
<213> ORGANISM: Artificial Sequence
<220> FEATURE:
<223> OTHER INFORMATION: First Polypeptide Chain of the CD16 x HIV env Binding Molecule "DART-X"

<400> SEQUENCE: 171

```
Asp Ile Val Met Thr Gln Ser Pro Asp Ser Leu Ala Val Ser Pro Gly
1               5                   10                  15

Glu Arg Ala Thr Ile His Cys Lys Ser Ser Gln Thr Leu Leu Tyr Ser
            20                  25                  30

Ser Asn Asn Arg His Ser Ile Ala Trp Tyr Gln Gln Arg Pro Gly Gln
        35                  40                  45

Pro Pro Lys Leu Leu Leu Tyr Trp Ala Ser Met Arg Leu Ser Gly Val
    50                  55                  60

Pro Asp Arg Phe Ser Gly Ser Gly Ser Gly Thr Asp Phe Thr Leu Thr
65                  70                  75                  80

Ile Asn Asn Leu Gln Ala Glu Asp Val Ala Ile Tyr Tyr Cys His Gln
                85                  90                  95

Tyr Ser Ser His Pro Pro Thr Phe Gly His Gly Thr Arg Val Glu Ile
            100                 105                 110
```

```
Lys Gly Gly Gly Ser Gly Gly Gly Glu Val Lys Leu Val Glu Ser
        115                 120                 125
Gly Gly Thr Leu Val Lys Pro Gly Gly Ser Leu Lys Leu Ser Cys Ala
    130                 135                 140
Ala Ser Gly Phe Thr Phe Asn Asn Tyr Gly Met Ser Trp Val Arg Gln
145                 150                 155                 160
Thr Pro Glu Lys Arg Leu Glu Trp Val Ala Thr Ile Ser Gly Gly Gly
                165                 170                 175
Ser Tyr Thr Phe Tyr Pro Asp Ser Val Lys Gly Arg Phe Thr Ile Ser
            180                 185                 190
Arg Asp Asn Ala Lys Asn Ser Leu Tyr Leu Gln Met Ser Ser Leu Arg
        195                 200                 205
Ser Glu Asp Thr Ala Leu Tyr Tyr Cys Ile Arg Gln Ser Ala Arg Ala
    210                 215                 220
Pro Glu Pro Tyr Trp Gly Gln Gly Thr Leu Val Thr Val Ser Ser Ala
225                 230                 235                 240
Ser Thr Lys Gly Glu Val Ala Ala Cys Glu Lys Val Ala Ala Leu
                245                 250                 255
Glu Lys Glu Val Ala Ala Leu Glu Lys Glu Val Ala Ala Leu Glu Lys
        260                 265                 270

<210> SEQ ID NO 172
<211> LENGTH: 274
<212> TYPE: PRT
<213> ORGANISM: Artificial Sequence
<220> FEATURE:
<223> OTHER INFORMATION: Second Polypeptide Chain of the CD16 x HIV env
      Binding Molecule "DART-X"

<400> SEQUENCE: 172

Asp Ile Val Met Thr Gln Ser Gln Lys Phe

```
        195                 200                 205

Tyr Tyr Cys Ala Arg Ala Asp Gly Leu Thr Tyr Phe Ser Glu Leu Leu
    210                 215                 220

Gln Tyr Ile Phe Asp Leu Trp Gly Gln Gly Ala Arg Val Thr Val Ser
225                 230                 235                 240

Ser Ala Ser Thr Lys Gly Lys Val Ala Ala Cys Lys Glu Lys Val Ala
                245                 250                 255

Ala Leu Lys Glu Lys Val Ala Ala Leu Lys Glu Lys Val Ala Ala Leu
            260                 265                 270

Lys Glu

<210> SEQ ID NO 173
<211> LENGTH: 273
<212> TYPE: PRT
<213> ORGANISM: Artificial Sequence
<220> FEATURE:
<223> OTHER INFORMATION: First Polypeptide Chain of the CD16 x HIV env
      Binding Molecule "DART-Y"

<400> SEQUENCE: 173

Asp Ile Val Met Thr Gln Ser Pro Asp Ser Leu Ala Val Ser Pro Gly
1               5                   10                  15

Glu Arg Ala Thr Ile His Cys Lys Ser Ser Gln Thr Leu Leu Tyr Ser
            20                  25                  30

Ser Asn Asn Arg His Ser Ile Ala Trp Tyr Gln Gln Arg Pro Gly Gln
        35                  40                  45

Pro Pro Lys Leu Leu Leu Tyr Trp Ala Ser Met Arg Leu Ser Gly Val
    50                  55                  60

Pro Asp Arg Phe Ser Gly Ser Gly Ser Gly Thr Asp Phe Thr Leu Thr
65                  70                  75                  80

Ile Asn Asn Leu Gln Ala Glu Asp Val Ala Ile Tyr Tyr Cys His Gln
                85                  90                  95

Tyr Ser Ser His Pro Pro Thr Phe Gly His Gly Thr Arg Val Glu Ile
            100                 105                 110

Lys Gly Gly Gly Ser Gly Gly Gly Gly Glu Val Gln Leu Gln Gln Ser
        115                 120                 125

Gly Pro Glu Leu Val Lys Pro Gly Ala Ser Val Lys Met Ser Cys Lys
    130                 135                 140

Ala Ser Gly Tyr Thr Phe Thr Ser Ser Ala Met His Trp Val Lys Lys
145                 150                 155                 160

Asn Pro Gly Gln Gly Leu Glu Trp Ile Gly Tyr Ile Asn His Tyr Asn
                165                 170                 175

Asp Gly Ile Lys Tyr Asn Glu Arg Phe Lys Gly Lys Ala Thr Leu Thr
            180                 185                 190

Ser Asp Lys Ser Ser Ser Thr Ala Tyr Met Glu Leu Ser Ser Leu Thr
        195                 200                 205

Ser Glu Asp Ser Ala Val Tyr Tyr Cys Ala Thr Gly Tyr Arg Tyr Ala
    210                 215                 220

Ser Trp Phe Ala Ser Trp Gly Gln Gly Thr Leu Val Thr Val Ser Ser
225                 230                 235                 240

Ala Ser Thr Lys Gly Glu Val Ala Ala Cys Glu Lys Glu Val Ala Ala
                245                 250                 255

Leu Glu Lys Glu Val Ala Ala Leu Glu Lys Glu Val Ala Ala Leu Glu
            260                 265                 270

Lys
```

```
<210> SEQ ID NO 174
<211> LENGTH: 274
<212> TYPE: PRT
<213> ORGANISM: Artificial Sequence
<220> FEATURE:
<223> OTHER INFORMATION: Second Polypeptide Chain of the CD16 x HIV env
      Binding Molecule "DART-Y"

<400> SEQUENCE: 174

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Asn Ile Gly Thr Ser
            20                  25                  30

Ile His Trp Tyr Gln Gln Arg Thr Asp Gly Ser Pro Arg Leu Leu Ile
        35                  40                  45

Lys Ser Val Ser Glu Ser Ile Ser Gly Ile Pro Ser Arg Phe Ser Gly
    50                  55                  60

Ser Gly Ser Gly Thr Asp Phe Thr Leu Thr Ile Asn Gly Val Glu Ser
65                  70                  75                  80

Gly Asp Ile Ser Asp Tyr Tyr Cys Gln Gln Ser Asn Ser Trp Pro Leu
                85                  90                  95

Thr Phe Gly Ala Gly Thr Lys Leu Glu Leu Lys Gly Gly Gly Ser Gly
            100                 105                 110

Gly Gly Gly Gln Val Gln Leu Val Gln Ser Gly Gly Gly Val Phe Lys
        115                 120                 125

Pro Gly Gly Ser Leu Arg Leu Ser Cys Glu Ala Ser Gly Phe Thr Phe
130                 135                 140

Thr Glu Tyr Tyr Met Thr Trp Val Arg Gln Ala Pro Gly Lys Gly Leu
145                 150                 155                 160

Glu Trp Leu Ala Tyr Ile Ser Lys Asn Gly Glu Tyr Ser Lys Tyr Ser
                165                 170                 175

Pro Ser Ser Asn Gly Arg Phe Thr Ile Ser Arg Asp Asn Ala Lys Asn
            180                 185                 190

Ser Val Phe Leu Gln Leu Asp Arg Leu Ser Ala Asp Asp Thr Ala Val
        195                 200                 205

Tyr Tyr Cys Ala Arg Ala Asp Gly Leu Thr Tyr Phe Ser Glu Leu Leu
    210                 215                 220

Gln Tyr Ile Phe Asp Leu Trp Gly Gln Gly Ala Arg Val Thr Val Ser
225                 230                 235                 240

Ser Ala Ser Thr Lys Gly Lys Val Ala Ala Cys Lys Glu Lys Val Ala
                245                 250                 255

Ala Leu Lys Glu Lys Val Ala Ala Leu Lys Glu Lys Val Ala Ala Leu
            260                 265                 270

Lys Glu

<210> SEQ ID NO 175
<211> LENGTH: 121
<212> TYPE: PRT
<213> ORGANISM: Artificial Sequence
<220> FEATURE:
<223> OTHER INFORMATION: VH Domain of Anti-Human CD16A scFv 4-LS21

<400> SEQUENCE: 175

Glu Glu Val Gln Leu Val Gln Ser Gly Ala Glu Val Lys Lys Pro Gly
1               5                   10                  15

Glu Ser Leu Lys Val Ser Cys Lys Ala Ser Gly Tyr Thr Phe Thr Ser
```

-continued

```
            20                  25                  30

Tyr Tyr Met His Trp Val Arg Gln Ala Pro Gly Gln Gly Leu Glu Trp
        35                  40                  45

Met Gly Ile Ile Asn Pro Ser Gly Gly Ser Thr Ser Tyr Ala Gln Lys
    50                  55                  60

Phe Gln Gly Arg Val Thr Met Thr Arg Asp Thr Ser Thr Ser Thr Val
65                  70                  75                  80

Tyr Met Glu Leu Ser Ser Leu Arg Ser Glu Asp Thr Ala Val Tyr Tyr
                85                  90                  95

Cys Ala Arg Gly Ser Ala Tyr Tyr Tyr Asp Phe Ala Asp Tyr Trp Gly
            100                 105                 110

Gln Gly Thr Leu Val Thr Val Ser Ser
        115                 120

<210> SEQ ID NO 176
<211> LENGTH: 106
<212> TYPE: PRT
<213> ORGANISM: Artificial Sequence
<220> FEATURE:
<223> OTHER INFORMATION: VL Domain of Anti-Human CD16A scFv 4-LS21

<400> SEQUENCE: 176

Gln Pro Val Leu Thr Gln Pro Ser Ser Val Ser Val Ala Pro Gly Gln
1               5                   10                  15

Thr Ala Thr Ile Ser Cys Gly Gly His Asn Ile Gly Ser Lys Asn Val
            20                  25                  30

His Trp Tyr Gln Gln Arg Pro Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Val Trp Asp Asn Tyr Ser Val Leu
                85                  90                  95

Phe Gly Gly Gly Thr Lys Leu Thr Val Leu
            100                 105

<210> SEQ ID NO 177
<211> LENGTH: 499
<212> TYPE: PRT
<213> ORGANISM: Artificial Sequence
<220> FEATURE:
<223> OTHER INFORMATION: First Polypeptide Chain of the CD16 x HIV env x
      HIV env Trivalent Binding Molecule "TRIDENT-A"

<400> SEQUENCE: 177

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln His His Pro Gly Lys Ala Pro Lys Leu
        35                  40                  45

Ile Ile Ser Glu Val Asn Asn Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Glu Tyr Tyr Cys Ser Ser Tyr Thr Asp Ile
                85                  90                  95
```

```
His Asn Phe Val Phe Gly Gly Thr Lys Leu Thr Val Leu Gly Gly
            100                 105                 110

Gly Ser Gly Gly Gly Glu Val Gln Leu Val Glu Ser Gly Gly Gly
        115                 120                 125

Leu Val Lys Pro Gly Gly Ser Leu Arg Leu Ser Cys Ala Ala Ser Gly
130                 135                 140

Phe Thr Phe Ser Asn Tyr Gly Met Ser Trp Val Arg Gln Ala Pro Gly
145                 150                 155                 160

Lys Gly Leu Glu Trp Val Ala Thr Ile Ser Gly Gly Ser Tyr Thr
            165                 170                 175

Phe Tyr Pro Asp Ser Val Lys Gly Arg Phe Thr Ile Ser Arg Asp Asn
            180                 185                 190

Ala Lys Asn Ser Leu Tyr Leu Gln Met Asn Ser Leu Arg Thr Glu Asp
            195                 200                 205

Thr Ala Leu Tyr Tyr Cys Val Arg Gln Ser Ala Arg Ala Pro Glu Pro
        210                 215                 220

Tyr Trp Gly Gln Gly Thr Leu Val Thr Val Ser Ser Ala Ser Thr Lys
225                 230                 235                 240

Gly Glu Val Ala Ala Cys Glu Lys Glu Val Ala Ala Leu Glu Lys Glu
                245                 250                 255

Val Ala Ala Leu Glu Lys Glu Val Ala Ala Leu Glu Lys Gly Gly Gly
            260                 265                 270

Asp Lys Thr His Thr Cys Pro Pro Cys Pro Ala Pro Glu Ala Ala Gly
        275                 280                 285

Gly Pro Ser Val Phe Leu Phe Pro Pro Lys Pro Lys Asp Thr Leu Met
        290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Glu Glu Met Thr Lys Asn Gln Val Ser
                405                 410                 415

Leu Trp Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
        450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
            485                 490                 495

Pro Gly Lys
```

-continued

<210> SEQ ID NO 178
<211> LENGTH: 271
<212> TYPE: PRT
<213> ORGANISM: Artificial Sequence
<220> FEATURE:
<223> OTHER INFORMATION: Second Polypeptide Chain of the CD16 x HIV env x HIV env Trivalent Binding Molecule "TRIDENT-A"

<400> SEQUENCE: 178

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asn Val Gly Thr His
            20                  25                  30

Val Ala Trp Tyr Gln Gln Lys Pro Gly Lys Ala Pro Lys Ser Leu Leu
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Ser
65                  70                  75                  80

Glu Asp Ile Ala Thr Tyr Tyr Cys Gln Gln Tyr Lys Ser Tyr Pro Leu
                85                  90                  95

Thr Phe Gly Gln Gly Thr Lys Leu Glu Ile Lys Gly Gly Gly Ser Gly
            100                 105                 110

Gly Gly Gly Gln Val Gln Leu Gln Glu Ser Gly Pro Gly Leu Val Lys
        115                 120                 125

Pro Ser Gln Thr Leu Ser Leu Ser Cys Thr Val Ser Gly Gly Ser Ser
    130                 135                 140

Ser Ser Gly Ala His Tyr Trp Ser Trp Ile Arg Gln Tyr Pro Gly Lys
145                 150                 155                 160

Gly Leu Glu Trp Ile Gly Tyr Ile His Tyr Ser Gly Asn Thr Tyr Tyr
                165                 170                 175

Asn Pro Ser Leu Lys Ser Arg Ile Thr Ile Ser Gln His Thr Ser Glu
            180                 185                 190

Asn Gln Phe Ser Leu Lys Leu Asn Ser Val Thr Val Ala Asp Thr Ala
        195                 200                 205

Val Tyr Tyr Cys Ala Arg Gly Thr Arg Leu Arg Thr Leu Arg Asn Ala
    210                 215                 220

Phe Asp Ile Trp Gly Gln Gly Thr Leu Val Thr Val Ser Ser Ala Ser
225                 230                 235                 240

Thr Lys Gly Lys Val Ala Ala Cys Lys Glu Lys Val Ala Ala Leu Lys
                245                 250                 255

Glu Lys Val Ala Ala Leu Lys Glu Lys Val Ala Ala Leu Lys Glu
            260                 265                 270
```

<210> SEQ ID NO 179
<211> LENGTH: 453
<212> TYPE: PRT
<213> ORGANISM: Artificial Sequence
<220> FEATURE:
<223> OTHER INFORMATION: Third Polypeptide Chain of the CD16 x HIV env x HIV env Trivalent Binding Molecule "TRIDENT-A"

<400> SEQUENCE: 179

```
Gln Val Gln Leu Gln Glu Ser Gly Pro Gly Leu Val Lys Pro Ser Gln
1               5                   10                  15

Thr Leu Ser Leu Ser Cys Thr Val Ser Gly Gly Ser Ser Ser Ser Gly
            20                  25                  30

Ala His Tyr Trp Ser Trp Ile Arg Gln Tyr Pro Gly Lys Gly Leu Glu
```

```
                35                  40                  45
Trp Ile Gly Tyr Ile His Tyr Ser Gly Asn Thr Tyr Tyr Asn Pro Ser
 50                  55                  60

Leu Lys Ser Arg Ile Thr Ile Ser Gln His Thr Ser Glu Asn Gln Phe
 65                  70                  75                  80

Ser Leu Lys Leu Asn Ser Val Thr Val Ala Asp Thr Ala Val Tyr Tyr
                     85                  90                  95

Cys Ala Arg Gly Thr Arg Leu Arg Thr Leu Arg Asn Ala Phe Asp Ile
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                    165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Ser Cys Ala Val Lys Gly Phe Tyr Pro Ser Asp Ile Ala
                370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn Arg Tyr Thr Gln Lys Ser Leu Ser
                435                 440                 445

Leu Ser Pro Gly Lys
                450
```

-continued

<210> SEQ ID NO 180
<211> LENGTH: 217
<212> TYPE: PRT
<213> ORGANISM: Artificial Sequence
<220> FEATURE:
<223> OTHER INFORMATION: Fourth Polypeptide Chain of the CD16 x HIV
    env x HIV env Trivalent Binding Molecule "TRIDENT-A"

<400> SEQUENCE: 180

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln His His Pro Gly Lys Ala Pro Lys Leu
        35                  40                  45

Ile Ile Ser Glu Val Asn Asn Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Glu Tyr Tyr Cys Ser Ser Tyr Thr Asp Ile
                85                  90                  95

His Asn Phe Val Phe Gly Gly Gly Thr Lys Leu Thr Val Leu Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 181
<211> LENGTH: 456
<212> TYPE: PRT
<213> ORGANISM: Artificial Sequence
<220> FEATURE:
<223> OTHER INFORMATION: Third Polypeptide Chain of the CD16 x HIV env x HIV env Trivalent Binding Molecule "TRIDENT-B"

<400> SEQUENCE: 181

```
Gln Val Gln Leu Val Gln Ser Gly Gly Gly Val Phe Lys Pro Gly Gly
1               5                   10                  15

Ser Leu Arg Leu Ser Cys Glu Ala Ser Gly Phe Thr Phe Thr Glu Tyr
            20                  25                  30

Tyr Met Thr Trp Val Arg Gln Ala Pro Gly Lys Gly Leu Glu Trp Leu
        35                  40                  45

Ala Tyr Ile Ser Lys Asn Gly Glu Tyr Ser Lys Tyr Ser Pro Ser Ser
    50                  55                  60

Asn Gly Arg Phe Thr Ile Ser Arg Asp Asn Ala Lys Asn Ser Val Phe
65                  70                  75                  80
```

Leu Gln Leu Asp Arg Leu Ser Ala Asp Asp Thr Ala Val Tyr Tyr Cys
            85                  90                  95

Ala Arg Ala Asp Gly Leu Thr Tyr Phe Ser Glu Leu Leu Gln Tyr Ile
            100                 105                 110

Phe Asp Leu Trp Gly Gln Gly Ala Arg Val Thr Val Ser Ser Ala Ser
            115                 120                 125

Thr Lys Gly Pro Ser Val Phe Pro Leu Ala Pro Ser Ser Lys Ser Thr
            130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
            195                 200                 205

Cys Asn Val Asn His Lys Pro Ser Asn Thr Lys Val Asp Lys Arg Val
            210                 215                 220

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
            290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
            355                 360                 365

Lys Asn Gln Val Ser Leu Ser Cys Ala Val Lys Gly Phe Tyr Pro Ser
            370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
            405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn Arg Tyr Thr Gln Lys
            435                 440                 445

Ser Leu Ser Leu Ser Pro Gly Lys
    450                 455

<210> SEQ ID NO 182
<211> LENGTH: 220
<212> TYPE: PRT
<213> ORGANISM: Artificial Sequence
<220> FEATURE:

<223> OTHER INFORMATION: Fourth Polypeptide Chain of the CD16 x HIV
      env x HIV env Trivalent Binding Molecule "TRIDENT-B"

<400> SEQUENCE: 182

Asp Ile Val Met Thr Gln Ser Pro Asp Ser Leu Ala Val Ser Pro Gly
1 5 10 15

Glu Arg Ala Thr Ile His Cys Lys Ser Ser Gln Thr Leu Leu Tyr Ser
20 25 30

Ser Asn Asn Arg His Ser Ile Ala Trp Tyr Gln Gln Arg Pro Gly Gln
35 40 45

Pro Pro Lys Leu Leu Leu Tyr Trp Ala Ser Met Arg Leu Ser Gly Val
50 55 60

Pro Asp Arg Phe Ser Gly Ser Gly Ser Gly Thr Asp Phe Thr Leu Thr
65 70 75 80

Ile Asn Asn Leu Gln Ala Glu Asp Val Ala Ile Tyr Tyr Cys His Gln
85 90 95

Tyr Ser Ser His Pro Pro Thr Phe Gly His Gly Thr Arg Val Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys
210 215 220

<210> SEQ ID NO 183
<211> LENGTH: 254
<212> TYPE: PRT
<213> ORGANISM: Homo sapiens
<220> FEATURE:
<221> NAME/KEY: MISC_FEATURE
<222> LOCATION: (1)..(254)
<223> OTHER INFORMATION: Human CD16

<400> SEQUENCE: 183

Met Trp Gln Leu Leu Leu Pro Thr Ala Leu Leu Leu Leu Val Ser Ala
1 5 10 15

Gly Met Arg Thr Glu Asp Leu Pro Lys Ala Val Val Phe Leu Glu Pro
20 25 30

Gln Trp Tyr Arg Val Leu Glu Lys Asp Ser Val Thr Leu Lys Cys Gln
35 40 45

Gly Ala Tyr Ser Pro Glu Asp Asn Ser Thr Gln Trp Phe His Asn Glu
50 55 60

Ser Leu Ile Ser Ser Gln Ala Ser Ser Tyr Phe Ile Asp Ala Ala Thr
65 70 75 80

Val Asp Asp Ser Gly Glu Tyr Arg Cys Gln Thr Asn Leu Ser Thr Leu
85 90 95

Ser Asp Pro Val Gln Leu Glu Val His Ile Gly Trp Leu Leu Leu Gln
100 105 110

```
Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
        210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 184
<211> LENGTH: 254
<212> TYPE: PRT
<213> ORGANISM: Macaca fascicularis
<220> FEATURE:
<221> NAME/KEY: MISC_FEATURE
<222> LOCATION: (1)..(254)
<223> OTHER INFORMATION: Cynomolgus monkey CD16

<400> SEQUENCE: 184

Met Trp Gln Leu Leu Pro Thr Ala Leu Leu Leu Val Ser Ala
1               5                   10                  15

Gly Met Arg Ala Glu Asp Leu Pro Arg Ala Val Val Phe Leu Glu Pro
            20                  25                  30

Gln Trp Tyr Arg Val Leu Glu Lys Asp Arg Val Thr Leu Lys Cys Gln
        35                  40                  45

Gly Ala Tyr Ser Pro Glu Asp Asn Ser Thr Arg Trp Phe His Asn Glu
    50                  55                  60

Ser Leu Ile Ser Ser Gln Thr Ser Ser Tyr Phe Ile Ala Ala Ala Arg
65                  70                  75                  80

Val Asn Asn Ser Gly Glu Tyr Arg Cys Gln Thr Ser Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Glu Ser Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His Gln Asn Ser Asp Phe Tyr Ile Pro
145                 150                 155                 160

Lys Ala Thr Leu Lys Asp Ser Gly Ser Tyr Phe Cys Arg Gly Leu Ile
                165                 170                 175

Gly Ser Lys Asn Val Ser Ser Glu Thr Val Asn Ile Thr Ile Thr Gln
                180                 185                 190

Asp Leu Ala Val Ser Ser Ile Ser Ser Phe Phe Pro Pro Gly Tyr Gln
        195                 200                 205
```

```
Val Ser Phe Cys Leu Val Met Val Leu Leu Phe Ala Val Asp Thr Gly
    210                 215                 220

Leu Tyr Phe Ser Met Lys Lys Ser Ile Pro Ser Ser Thr Arg Asp Trp
225                 230                 235                 240

Glu Asp His Lys Phe Lys Trp Ser Lys Asp Pro Gln Asp Lys
                245                 250

<210> SEQ ID NO 185
<211> LENGTH: 267
<212> TYPE: PRT
<213> ORGANISM: Mus musculus
<220> FEATURE:
<221> NAME/KEY: MISC_FEATURE
<222> LOCATION: (1)..(267)
<223> OTHER INFORMATION: Murine CD16

<400> SEQUENCE: 185

Met Thr Leu Asp Thr Gln Met Phe Gln Asn Ala His Ser Gly Ser Gln
1               5                   10                  15

Trp Leu Leu Pro Pro Leu Thr Ile Leu Leu Phe Ala Phe Ala Asp
            20                  25                  30

Arg Gln Ser Ala Ala Leu Pro Lys Ala Val Val Lys Leu Asp Pro Pro
            35                  40                  45

Trp Ile Gln Val Leu Lys Glu Asp Met Val Thr Leu Met Cys Glu Gly
    50                  55                  60

Thr His Asn Pro Gly Asn Ser Ser Thr Gln Trp Phe His Asn Trp Ser
65                  70                  75                  80

Ser Ile Arg Ser Gln Val Gln Ser Ser Tyr Thr Phe Lys Ala Thr Val
                85                  90                  95

Asn Asp Ser Gly Glu Tyr Arg Cys Gln Met Glu Gln Thr Arg Leu Ser
            100                 105                 110

Asp Pro Val Asp Leu Gly Val Ile Ser Asp Trp Leu Leu Leu Gln Thr
        115                 120                 125

Pro Gln Arg Val Phe Leu Glu Gly Glu Thr Ile Thr Leu Arg Cys His
    130                 135                 140

Ser Trp Arg Asn Lys Leu Leu Asn Arg Ile Ser Phe Phe His Asn Glu
145                 150                 155                 160

Lys Ser Val Arg Tyr His His Tyr Lys Ser Asn Phe Ser Ile Pro Lys
                165                 170                 175

Ala Asn His Ser His Ser Gly Asp Tyr Tyr Cys Lys Gly Ser Leu Gly
            180                 185                 190

Ser Thr Gln His Gln Ser Lys Pro Val Thr Ile Thr Val Gln Asp Pro
        195                 200                 205

Ala Thr Thr Ser Ser Ile Ser Leu Val Trp Tyr His Thr Ala Phe Ser
    210                 215                 220

Leu Val Met Cys Leu Leu Phe Ala Val Asp Thr Gly Leu Tyr Phe Tyr
225                 230                 235                 240

Val Arg Arg Asn Ile Gln Thr Pro Arg Asp Tyr Trp Arg Lys Ser Leu
                245                 250                 255

Ser Ile Arg Lys His Gln Ala Pro Gln Asp Lys
            260                 265

<210> SEQ ID NO 186
<211> LENGTH: 496
<212> TYPE: PRT
<213> ORGANISM: Artificial Sequence
<220> FEATURE:
<223> OTHER INFORMATION: First Polypeptide Chain of the CD16 x HER2/neu
```

Binding Molecule "DART-I"

<400> SEQUENCE: 186

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Ser Gly
            100                 105                 110

Gly Gly Gly Glu Val Gln Leu Val Glu Ser Gly Gly Leu Val Lys
        115                 120                 125

Pro Gly Gly Ser Leu Arg Leu Ser Cys Ala Ala Ser Gly Phe Thr Phe
    130                 135                 140

Ser Asn Tyr Gly Met Ser Trp Val Arg Gln Ala Pro Gly Lys Gly Leu
145                 150                 155                 160

Glu Trp Val Ala Thr Ile Ser Gly Gly Gly Ser Tyr Thr Phe Tyr Pro
                165                 170                 175

Asp Ser Val Lys Gly Arg Phe Thr Ile Ser Arg Asp Asn Ala Lys Asn
            180                 185                 190

Ser Leu Tyr Leu Gln Met Asn Ser Leu Arg Thr Glu Asp Thr Ala Leu
        195                 200                 205

Tyr Tyr Cys Val Arg Gln Ser Ala Asn Ser Pro Val Pro Tyr Trp Gly
210                 215                 220

Gln Gly Thr Leu Val Thr Val Ser Ser Ala Ser Thr Lys Gly Glu Val
225                 230                 235                 240

Ala Ala Cys Glu Lys Glu Val Ala Ala Leu Glu Lys Glu Val Ala Ala
                245                 250                 255

Leu Glu Lys Glu Val Ala Ala Leu Glu Lys Gly Gly Gly Asp Lys Thr
            260                 265                 270

His Thr Cys Pro Pro Cys Pro Ala Pro Glu Ala Ala Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
    370                 375                 380

Ile Ser Lys Ala Lys Gly Gln Pro Arg Glu Pro Gln Val Tyr Thr Leu
385                 390                 395                 400
```

```
Pro Pro Ser Arg Glu Glu Met Thr Lys Asn Gln Val Ser Leu Trp Cys
                405                 410                 415
Leu Val Lys Gly Phe Tyr Pro Ser Asp Ile Ala Val Glu Trp Glu Ser
            420                 425                 430
Asn Gly Gln Pro Glu Asn Asn Tyr Lys Thr Thr Pro Pro Val Leu Asp
        435                 440                 445
Ser Asp Gly Ser Phe Phe Leu Tyr Ser Lys Leu Thr Val Asp Lys Ser
    450                 455                 460
Arg Trp Gln Gln Gly Asn Val Phe Ser Cys Ser Val Met His Glu Ala
465                 470                 475                 480
Leu His Asn His Tyr Thr Gln Lys Ser Leu Ser Leu Ser Pro Gly Lys
                485                 490                 495

<210> SEQ ID NO 187
<211> LENGTH: 268
<212> TYPE: PRT
<213> ORGANISM: Artificial Sequence
<220> FEATURE:
<223> OTHER INFORMATION: Second Polypeptide Chain of the CD16 x HER2/neu
      Binding Molecule "DART-J"

<400> SEQUENCE: 187

Asp Ile Gln Met Thr Gln Ser Pro Ser Phe Leu Ser Ala Ser Val Gly
1               5                   10                  15
Asp Arg Val Thr Ile Thr Cys Arg Ala Ser Gln Asn Val Gly Thr His
            20                  25                  30
Val Ala Trp Tyr Gln Gln Lys Pro Gly Lys Ala Pro Lys Ser Leu Leu
        35                  40                  45
Tyr Ser Ala Ser Tyr Arg Tyr Ser Gly Val Pro Ser Arg Phe Ser Gly
    50                  55                  60
Ser Gly Ser Gly Thr Asp Phe Thr Leu Thr Ile Ser Ser Leu Gln Ser
65                  70                  75                  80
Glu Asp Ile Ala Thr Tyr Tyr Cys Gln Asp Tyr Thr Asn Tyr Pro Leu
                85                  90                  95
Thr Phe Gly Gln Gly Thr Lys Leu Glu Ile Lys Gly Gly Gly Ser Gly
            100                 105                 110
Gly Gly Gly Glu Val Gln Leu Val Glu Ser Gly Gly Gly Leu Val Gln
        115                 120                 125
Pro Gly Gly Ser Leu Arg Leu Ser Cys Ala Ala Ser Gly Phe Asn Ile
    130                 135                 140
Lys Asp Thr Tyr Ile His Trp Val Arg Gln Ala Pro Gly Lys Gly Leu
145                 150                 155                 160
Glu Trp Val Ala Arg Ile Tyr Pro Thr Asn Gly Tyr Thr Arg Tyr Ala
                165                 170                 175
Asp Ser Val Lys Gly Arg Phe Thr Ile Ser Ala Asp Thr Ser Lys Asn
            180                 185                 190
Thr Ala Tyr Leu Gln Met Asn Ser Leu Arg Ala Glu Asp Thr Ala Val
        195                 200                 205
Tyr Tyr Cys Ser Arg Trp Gly Gly Asp Gly Phe Tyr Ala Met Asp Tyr
    210                 215                 220
Trp Gly Gln Gly Thr Leu Val Thr Val Ser Ser Ala Ser Thr Lys Gly
225                 230                 235                 240
Lys Val Ala Ala Cys Lys Glu Lys Val Ala Ala Leu Lys Glu Lys Val
                245                 250                 255
Ala Ala Leu Lys Glu Lys Val Ala Ala Leu Lys Glu
            260                 265
```

-continued

<210> SEQ ID NO 188
<211> LENGTH: 496
<212> TYPE: PRT
<213> ORGANISM: Artificial Sequence
<220> FEATURE:
<223> OTHER INFORMATION: First Polypeptide Chain of the CD16 x CD19
      Binding Molecule "DART-L"

<400> SEQUENCE: 188

Glu Asn Val Leu Thr Gln Ser Pro Ala Thr Leu Ser Val Thr Pro Gly
1               5                   10                  15

Glu Lys Ala Thr Ile Thr Cys Arg Ala Ser Gln Ser Val Ser Tyr Met
            20                  25                  30

His Trp Tyr Gln Gln Lys Pro Gly Gln Ala Pro Arg Leu Leu Ile Tyr
        35                  40                  45

Asp Ala Ser Asn Arg Ala Ser Gly Val Pro Ser Arg Phe Ser Gly Ser
    50                  55                  60

Gly Ser Gly Thr Asp His Thr Leu Thr Ile Ser Ser Leu Glu Ala Glu
65                  70                  75                  80

Asp Ala Ala Thr Tyr Tyr Cys Phe Gln Gly Ser Val Tyr Pro Phe Thr
                85                  90                  95

Phe Gly Gln Gly Thr Lys Leu Glu Ile Lys Gly Gly Gly Ser Gly Gly
            100                 105                 110

Gly Gly Glu Val Gln Leu Val Glu Ser Gly Gly Gly Leu Val Lys Pro
        115                 120                 125

Gly Gly Ser Leu Arg Leu Ser Cys Ala Ala Ser Gly Phe Thr Phe Ser
    130                 135                 140

Asn Tyr Gly Met Ser Trp Val Arg Gln Ala Pro Gly Lys Gly Leu Glu
145                 150                 155                 160

Trp Val Ala Thr Ile Ser Gly Gly Gly Ser Tyr Thr Phe Tyr Pro Asp
                165                 170                 175

Ser Val Lys Gly Arg Phe Thr Ile Ser Arg Asp Asn Ala Lys Asn Ser
            180                 185                 190

Leu Tyr Leu Gln Met Asn Ser Leu Arg Thr Glu Asp Thr Ala Leu Tyr
        195                 200                 205

Tyr Cys Val Arg Gln Ser Ala Arg Ala Pro Glu Pro Tyr Trp Gly Gln
    210                 215                 220

Gly Thr Leu Val Thr Val Ser Ser Gly Gly Cys Gly Gly Gly Glu Val
225                 230                 235                 240

Ala Ala Cys Glu Lys Glu Val Ala Ala Leu Glu Lys Glu Val Ala Ala
                245                 250                 255

Leu Glu Lys Glu Val Ala Ala Leu Glu Lys Gly Gly Gly Asp Lys Thr
            260                 265                 270

His Thr Cys Pro Pro Cys Pro Ala Pro Glu Ala Ala Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr

```
                355                 360                 365
Lys Cys Lys Val Ser Asn Lys Ala Leu Pro Ala Pro Ile Glu Lys Thr
            370                 375                 380

Ile Ser Lys Ala Lys Gly Gln Pro Arg Glu Pro Gln Val Tyr Thr Leu
385                 390                 395                 400

Pro Pro Ser Arg Glu Glu Met Thr Lys Asn Gln Val Ser Leu Trp Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Val Leu Asp
            435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
            485                 490                 495

<210> SEQ ID NO 189
<211> LENGTH: 269
<212> TYPE: PRT
<213> ORGANISM: Artificial Sequence
<220> FEATURE:
<223> OTHER INFORMATION: Second Polypeptide Chain of the CD16 x CD19
      Binding Molecule "DART-L"

<400> SEQUENCE: 189

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asn Val Gly Thr His
            20                  25                  30

Val Ala Trp Tyr Gln Gln Lys Pro Gly Lys Ala Pro Lys Ser Leu Leu
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Ser
65                  70                  75                  80

Glu Asp Ile Ala Thr Tyr Tyr Cys Gln Gln Tyr Lys Ser Tyr Pro Leu
                85                  90                  95

Thr Phe Gly Gln Gly Thr Lys Leu Glu Ile Lys Gly Gly Gly Ser Gly
            100                 105                 110

Gly Gly Gly Gln Val Thr Leu Arg Glu Ser Gly Pro Ala Leu Val Lys
        115                 120                 125

Pro Thr Gln Thr Leu Thr Leu Thr Cys Thr Phe Ser Gly Phe Ser Leu
    130                 135                 140

Ser Thr Ser Gly Met Gly Val Gly Trp Ile Arg Gln Pro Pro Gly Lys
145                 150                 155                 160

Ala Leu Glu Trp Leu Ala His Ile Trp Trp Asp Asp Lys Arg Tyr
                165                 170                 175

Asn Pro Ala Leu Lys Ser Arg Leu Thr Ile Ser Lys Asp Thr Ser Lys
            180                 185                 190

Asn Gln Val Phe Leu Thr Met Thr Asn Met Asp Pro Val Asp Thr Ala
        195                 200                 205

Thr Tyr Tyr Cys Ala Arg Met Glu Leu Trp Ser Tyr Tyr Phe Asp Tyr
    210                 215                 220
```

```
Trp Gly Gln Gly Thr Thr Val Thr Val Ser Ser Gly Gly Cys Gly Gly
225                 230                 235                 240

Gly Lys Val Ala Ala Cys Lys Glu Lys Val Ala Ala Leu Lys Glu Lys
                245                 250                 255

Val Ala Ala Leu Lys Glu Lys Val Ala Ala Leu Lys Glu
                260                 265

<210> SEQ ID NO 190
<211> LENGTH: 269
<212> TYPE: PRT
<213> ORGANISM: Artificial Sequence
<220> FEATURE:
<223> OTHER INFORMATION: Second Polypeptide Chain of the CD16 x CD19
      Binding Molecule "DART-M"

<400> SEQUENCE: 190

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asn Val Gly Thr His
                20                  25                  30

Val Ala Trp Tyr Gln Gln Lys Pro Gly Lys Ala Pro Lys Ser Leu Leu
            35                  40                  45

Tyr Ser Ala Ser Tyr Arg Tyr Ser Gly Val Pro Ser Arg Phe Ser Gly
        50                  55                  60

Ser Gly Ser Gly Thr Asp Phe Thr Leu Thr Ile Ser Ser Leu Gln Ser
65                  70                  75                  80

Glu Asp Ile Ala Thr Tyr Tyr Cys Gln Asp Tyr Thr Asn Tyr Pro Leu
                85                  90                  95

Thr Phe Gly Gln Gly Thr Lys Leu Glu Ile Lys Gly Gly Gly Ser Gly
            100                 105                 110

Gly Gly Gly Gln Val Thr Leu Arg Glu Ser Gly Pro Ala Leu Val Lys
        115                 120                 125

Pro Thr Gln Thr Leu Thr Leu Thr Cys Thr Phe Ser Gly Phe Ser Leu
130                 135                 140

Ser Thr Ser Gly Met Gly Val Gly Trp Ile Arg Gln Pro Pro Gly Lys
145                 150                 155                 160

Ala Leu Glu Trp Leu Ala His Ile Trp Trp Asp Asp Lys Arg Tyr
                165                 170                 175

Asn Pro Ala Leu Lys Ser Arg Leu Thr Ile Ser Lys Asp Thr Ser Lys
            180                 185                 190

Asn Gln Val Phe Leu Thr Met Thr Asn Met Asp Pro Val Asp Thr Ala
        195                 200                 205

Thr Tyr Tyr Cys Ala Arg Met Glu Leu Trp Ser Tyr Tyr Phe Asp Tyr
    210                 215                 220

Trp Gly Gln Gly Thr Thr Val Thr Val Ser Ser Gly Gly Cys Gly Gly
225                 230                 235                 240

Gly Lys Val Ala Ala Cys Lys Glu Lys Val Ala Ala Leu Lys Glu Lys
                245                 250                 255

Val Ala Ala Leu Lys Glu Lys Val Ala Ala Leu Lys Glu
                260                 265

<210> SEQ ID NO 191
<211> LENGTH: 496
<212> TYPE: PRT
<213> ORGANISM: Artificial Sequence
<220> FEATURE:
<223> OTHER INFORMATION: First Polypeptide Chain of the CD16 x CD19
      Binding Molecule "DART-N"
```

```
<400> SEQUENCE: 191

Glu Asn Val Leu Thr Gln Ser Pro Ala Thr Leu Ser Val Thr Pro Gly
1               5                   10                  15

Glu Lys Ala Thr Ile Thr Cys Arg Ala Ser Gln Ser Val Ser Tyr Met
            20                  25                  30

His Trp Tyr Gln Gln Lys Pro Gly Gln Ala Pro Arg Leu Leu Ile Tyr
        35                  40                  45

Asp Ala Ser Asn Arg Ala Ser Gly Val Pro Ser Arg Phe Ser Gly Ser
    50                  55                  60

Gly Ser Gly Thr Asp His Thr Leu Thr Ile Ser Ser Leu Glu Ala Glu
65                  70                  75                  80

Asp Ala Ala Thr Tyr Tyr Cys Phe Gln Gly Ser Val Tyr Pro Phe Thr
                85                  90                  95

Phe Gly Gln Gly Thr Lys Leu Glu Ile Lys Gly Gly Ser Gly Gly
                100                 105                 110

Gly Gly Glu Val Gln Leu Val Glu Ser Gly Gly Leu Val Lys Pro
            115                 120                 125

Gly Gly Ser Leu Arg Leu Ser Cys Ala Ala Ser Gly Phe Thr Phe Ser
130                 135                 140

Asn Tyr Gly Met Ser Trp Val Arg Gln Ala Pro Gly Lys Gly Leu Glu
145                 150                 155                 160

Trp Val Ala Thr Ile Ser Gly Gly Gly Ser Tyr Thr Tyr Pro Asp
                165                 170                 175

Ser Val Lys Gly Arg Phe Thr Ile Ser Arg Asp Asn Ala Lys Asn Ser
            180                 185                 190

Leu Tyr Leu Gln Met Asn Ser Leu Arg Thr Glu Asp Thr Ala Leu Tyr
                195                 200                 205

Tyr Cys Val Arg Gln Ser Ala Asn Ser Pro Val Pro Tyr Trp Gly Gln
        210                 215                 220

Gly Thr Leu Val Thr Val Ser Ser Gly Gly Cys Gly Gly Gly Glu Val
225                 230                 235                 240

Ala Ala Cys Glu Lys Glu Val Ala Ala Leu Glu Lys Glu Val Ala Ala
                245                 250                 255

Leu Glu Lys Glu Val Ala Ala Leu Glu Lys Gly Gly Gly Asp Lys Thr
                260                 265                 270

His Thr Cys Pro Pro Cys Pro Ala Pro Glu Ala Ala Gly Gly Pro Ser
            275                 280                 285

Val Phe Leu Phe Pro Pro Lys Pro Lys Asp Thr Leu Met Ile Ser Arg
    290                 295                 300

Thr Pro Glu Val Thr Cys Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
        370                 375                 380

Ile Ser Lys Ala Lys Gly Gln Pro Arg Glu Pro Gln Val Tyr Thr Leu
385                 390                 395                 400

Pro Pro Ser Arg Glu Glu Met Thr Lys Asn Gln Val Ser Leu Trp Cys
```

|   |   |   |   |   | 405 |   |   |   | 410 |   |   |   |   | 415 |   |
|---|---|---|---|---|---|---|---|---|---|---|---|---|---|---|---|
| Leu | Val | Lys | Gly<br>420 | Phe | Tyr | Pro | Ser | Asp<br>425 | Ile | Ala | Val | Glu | Trp<br>430 | Glu | Ser |
| Asn | Gly | Gln<br>435 | Pro | Glu | Asn | Asn<br>440 | Tyr | Lys | Thr | Thr | Pro<br>445 | Pro | Val | Leu | Asp |
| Ser | Asp<br>450 | Gly | Ser | Phe | Phe<br>455 | Leu | Tyr | Ser | Lys | Leu<br>460 | Thr | Val | Asp | Lys | Ser |
| Arg<br>465 | Trp | Gln | Gln | Gly | Asn<br>470 | Val | Phe | Ser | Cys<br>475 | Ser | Val | Met | His | Glu<br>480 | Ala |
| Leu | His | Asn | His | Tyr<br>485 | Thr | Gln | Lys | Ser<br>490 | Leu | Ser | Leu | Ser | Pro | Gly<br>495 | Lys |

What is claimed is:

1. A CD16×Disease Antigen (CD16×DA) Binding Molecule comprising a CD16 Binding Domain capable of binding an epitope of CD16 and also a Disease Antigen-Binding Domain capable of binding an epitope of a Disease Antigen, wherein said CD16 Binding Domain and said Disease Antigen-Binding Domain each comprise:
an antibody Variable Heavy Chain (VH) Domain that comprises a $CDR_H1$ Domain, a $CDR_H2$ Domain, and a $CDR_H3$ Domain; and
an antibody Variable Light Chain (VL) Domain that comprises a $CDR_L1$ Domain, a $CD_RL2$ Domain, and a $CDR_L3$ Domain;
wherein said CD16 Binding Domain comprises:
(1) (A) a $CDR_H1$ Domain comprising the amino acid sequence of SEQ ID NO:66;
(B) a $CDR_H2$ Domain comprising the amino acid sequence of SEQ ID NO:67;
(C) a $CDR_H3$ Domain comprising the amino acid sequence of SEQ ID NO:68 or SEQ ID NO:60;
(D) a $CDR_L1$ Domain comprising the amino acid sequence of SEQ ID NO:69 or SEQ ID NO:74;
(E) a $CDR_L2$ Domain comprising the amino acid sequence of SEQ ID NO:70; and
(F) a $CDR_L3$ Domain comprising the amino acid sequence of SEQ ID NO:71 or SEQ ID NO:61; or
(2) (A) a $CDR_H1$ Domain comprising the amino acid sequence of SEQ ID NO:77;
(B) a $CDR_H2$ Domain comprising the amino acid sequence of SEQ ID NO:78;
(C) a $CDR_H3$ Domain comprising the amino acid sequence of SEQ ID NO:79;
(D) a $CDR_L1$ Domain comprising the amino acid sequence of SEQ ID NO:80;
(E) a $CDR_L2$ Domain comprising the amino acid sequence of SEQ ID NO:81; and
(F) a $CDR_L3$ Domain comprising the amino acid sequence of SEQ ID NO:82; or
(3) a VH Domain comprising the amino acid sequence of SEQ ID NO:64 and a VL Domain comprising the amino acid sequence of SEQ ID NO:65; or
(4) a VH Domain comprising the amino acid sequence of SEQ ID NO:72 and a VL Domain comprising the amino acid sequence of SEQ ID NO:73; or
(5) a VH Domain comprising the amino acid sequence of SEQ ID NO:58 and a VL Domain comprising the amino acid sequence of SEQ ID NO:73; or
(6) a VH Domain comprising the amino acid sequence of SEQ ID NO:72 and a VL Domain comprising the amino acid sequence of SEQ ID NO:59; or
(7) a VH Domain comprising the amino acid sequence of SEQ ID NO:58 and a VL Domain comprising the amino acid sequence of SEQ ID NO:59; or
(8) a VH Domain comprising the amino acid sequence of SEQ ID NO:75 and a VL Domain comprising the amino acid sequence of SEQ ID NO:76; or
(9) a VH Domain comprising the amino acid sequence of SEQ ID NO:83 or SEQ ID NO:84 and a VL Domain comprising the amino acid sequence of SEQ ID NO:85; and
(II) said Disease Antigen Binding Domain comprises:
(1) the VL and VH Domains of margetuximab, wherein said VH Domain comprises the amino acid sequence of SEQ ID NO:122 and said VL Domain comprises the amino acid sequence of SEQ ID NO:123; or
(2) the VL and VH Domains of trastuzumab, wherein said VH Domain comprises the amino acid sequence of SEQ ID NO:124 and said VL Domain comprises the amino acid sequence of SEQ ID NO:125; or
(3) the VL and VH Domains of pertuzumab, wherein said VH Domain comprises the amino acid sequence of SEQ ID NO:126 and said VL Domain comprises the amino acid sequence of SEQ ID NO:127; or
(4) the VL and VH Domains of bevacizumab, wherein said VH Domain comprises the amino acid sequence of SEQ ID NO:128 and said VL Domain comprises the amino acid sequence of SEQ ID NO:129; or
(5) the VL and VH Domains of 5T4 mAb 1, wherein said VH Domain comprises the amino acid sequence of SEQ ID NO:130 and said VL Domain comprises the amino acid sequence of SEQ ID NO:131; or
(6) the VL and VH Domains of 5T4 mAb 2, wherein said VH Domain comprises the amino acid sequence of SEQ ID NO:132 and said VL Domain comprises the amino acid sequence of SEQ ID NO:133; or
(7) the VL and VH Domains of hu08, wherein said VH Domain comprises the amino acid sequence of SEQ ID NO:134 and said VL Domain comprises the amino acid sequence of SEQ ID NO:135; or
(8) the VL and VH Domains of CD123 mAb 1, wherein said VH Domain comprises the amino acid sequence of SEQ ID NO:136 and said VL Domain comprises the amino acid sequence of SEQ ID NO:137; or
(9) the VL and VH Domains of CD19 mAb 1, wherein said VH Domain comprises the amino acid sequence of SEQ ID NO:138 and said VL Domain comprises the amino acid sequence of SEQ ID NO:139; or
(10) the VL and VH Domains of 7B2, wherein said VH Domain comprises the amino acid sequence of SEQ ID NO:140 and said VL Domain comprises the amino acid sequence of SEQ ID NO:141; or
(11) the VL and VH Domains of A32, wherein said VH Domain comprises the amino acid sequence of SEQ ID NO:142 and said VL Domain comprises the amino acid sequence of SEQ ID NO:143; or
(12) the VL and VH Domains of vPalivizumab, wherein said VH Domain comprises the amino acid sequence of SEQ ID NO:144 and said VL Domain comprises the amino acid sequence of SEQ ID NO:145; or
(13) the VL and VH Domains of Enoblituzumab, wherein said VH Domain comprises the amino acid sequence of SEQ ID NO:104 and said VL Domain comprises the amino acid sequence of SEQ ID NO:105.

2. The CD16×Disease Antigen Binding Molecule of claim 1, wherein said Molecule is a bispecific antibody, a bispecific diabody, a bispecific TandAb, a bispecific trivalent molecule, or a bispecific CAR.

3. The CD16×Disease Antigen Binding Molecule of claim 1, wherein said CD16 Binding Domain comprises:
(A) a $CDR_H1$ Domain comprising the amino acid sequence of SEQ ID NO:66;
(B) a $CDR_H2$ Domain comprising the amino acid sequence of SEQ ID NO:67;
(C) a $CDR_H3$ Domain comprising the amino acid sequence of SEQ ID NO:68, or SEQ ID NO:60;
(D) a $CDR_L1$ Domain comprising the amino acid sequence of SEQ ID NO:69 or SEQ ID NO:74;
(E) a $CDR_L2$ Domain comprising the amino acid sequence of SEQ ID NO:70; and
(F) a $CDR_L3$ Domain comprising the amino acid sequence of SEQ ID NO:71, or SEQ ID NO:61.

4. The CD16×Disease Antigen Binding Molecule of claim 1, wherein said CD16 Binding Domain comprises:
(A) a VH Domain comprising the amino acid sequence of SEQ ID NO:72 and a VL Domain comprising the amino acid sequence of SEQ ID NO:73;
(B) a VH Domain comprising the amino acid sequence of SEQ ID NO:58 and a VL Domain comprising the amino acid sequence of SEQ ID NO:73;
(C) a VH Domain comprising the amino acid sequence of SEQ ID NO:72 and a VL Domain comprising the amino acid sequence of SEQ ID NO:59; or
(D) a VH Domain comprising the amino acid sequence of SEQ ID NO:58 and a VL Domain comprising the amino acid sequence of SEQ ID NO:59.

5. The CD16×Disease Antigen Binding Molecule of claim 1, wherein said CD16 Binding Domain comprises:
(A) a $CDR_H1$ Domain comprising the amino acid sequence of SEQ ID NO:77;
(B) a $CDR_H2$ Domain comprising the amino acid sequence of SEQ ID NO:78;
(C) a $CDR_H3$ Domain comprising the amino acid sequence of SEQ ID NO:79;
(D) a $CDR_L1$ Domain comprising the amino acid sequence of SEQ ID NO:80;
(E) a $CDR_L2$ Domain comprising the amino acid sequence of SEQ ID NO:81; and
(F) a $CDR_L3$ Domain comprising the amino acid sequence of SEQ ID NO:82.

6. The CD16×Disease Antigen Binding Molecule of claim 1, wherein said CD16 Binding Domain comprises a VH Domain comprising the amino acid sequence of SEQ ID NO:83 or SEQ ID NO:84 and a VL Domain comprising the amino acid sequence of SEQ ID NO:85.

7. The CD16×Disease Antigen Binding Molecule of claim 1, wherein said Disease Antigen Binding Domain comprises:
(1) said VL and VH Domains of margetuximab;
(2) said VL and VH Domains of trastuzumab;
(3) said VL and VH Domains of pertuzumab;
(4) said VL and VH Domains of bevacizumab,
(5) said VL and VH Domains of 5T4 mAb 1;
(6) said VL and VH Domains of 5T4 mAb 2;
(7) said VL and VH Domains of hu08;
(8) said VL and VH Domains of CD123 mAb 1;
(9) said VL and VH Domains of CD19 mAb 1; or
(10) said VL and VH Domains of Enoblituzumab.

8. The CD16×Disease Antigen Binding Molecule of claim 1, wherein said Disease Antigen Binding Domain comprises:
(1) said VL and VH Domains of 7B2;
(2) said VL and VH Domains of A32; or
(3) said VL and VH Domains of vPalivizumab.

9. The CD16×Disease Antigen Binding Molecule of claim 1, wherein said molecule is:
(A) a diabody, said diabody being a covalently bonded complex of polypeptide chains; or
(B) a trivalent binding molecule, said trivalent binding molecule being a covalently bonded complex of polypeptide chains, or
(C) a bispecific antibody.

10. The CD16×Disease Antigen Binding Molecule of claim 9, wherein said molecule comprises an Fc Region.

11. The CD16×Disease Antigen Binding Molecule of claim 10, wherein said Fc Region is of the IgG1, IgG2, IgG3, or IgG4 isotype.

12. The CD16×Disease Antigen Binding Molecule of claim 10, wherein said Fc Region is a variant Fc Region that comprises:
(A) one or more amino acid modifications that reduces the affinity of the variant Fc Region for an FcγR; and/or
(B) one or more amino acid modifications that enhances the serum half-life of the variant Fc Region.

13. The CD16×Disease Antigen Binding Molecule of claim 12, wherein:
(A) said one or more amino acid modifications that reduces the affinity of the variant Fc Region for an FcγR comprise the substitution of L234A; L235A; or L234A and L235A; and/or
(B) said one or more amino acid modifications that enhances the serum half-life of the variant Fc Region comprise the substitution of M252Y; M252Y and S254T; M252Y and T256E; M252Y, S254T and T256E; or K288D and H435K,
wherein said numbering is that of the EU index as in Kabat.

14. A CD16 Binding Molecule, that comprises:
(A) a $CDR_H1$ Domain comprising the amino acid sequence of SEQ ID NO:66;
(B) a $CDR_H2$ Domain comprising the amino acid sequence of SEQ ID NO:67;
(C) a $CDR_H3$ Domain comprising the amino acid sequence of SEQ ID NO:68, or SEQ ID NO:60;
(D) a $CDR_L1$ Domain comprising the amino acid sequence of SEQ ID NO:69 or SEQ ID NO:74;
(E) a $CDR_L2$ Domain comprising the amino acid sequence of SEQ ID NO:70; and
(F) a $CDR_L3$ Domain comprising the amino acid sequence of SEQ ID NO:71, or SEQ ID NO:61.

15. The CD16 Binding Molecule of claim 14, wherein said molecule comprises:

(A) a VH Domain comprising the amino acid sequence of SEQ ID NO:64 and a VL Domain comprising the amino acid sequence of SEQ ID NO:65; or
(B) a VH Domain comprising the amino acid sequence of SEQ ID NO:72 and a VL Domain comprising the amino acid sequence of SEQ ID NO:73; or
(C) a VH Domain comprising the amino acid sequence of SEQ ID NO:58 and a VL Domain comprising the amino acid sequence of SEQ ID NO:73; or
(D) a VH Domain comprising the amino acid sequence of SEQ ID NO:72 and a VL Domain comprising the amino acid sequence of SEQ ID NO:59; or
(E) a VH Domain comprising the amino acid sequence of SEQ ID NO:58 and a VL Domain comprising the amino acid sequence of SEQ ID NO:59; or
(F) a VH Domain comprising the amino acid sequence of SEQ ID NO:75 and a VL Domain comprising the amino acid sequence of SEQ ID NO:76.

16. A CD16 Binding Molecule that comprises:
(A) a $CDR_H1$ Domain comprising the amino acid sequence of SEQ ID NO:77;
(B) a $CDR_H2$ Domain comprising the amino acid sequence of SEQ ID NO:78;
(C) a $CDR_H3$ Domain comprising the amino acid sequence of SEQ ID NO:79;
(D) a $CDR_L1$ Domain comprising the amino acid sequence of SEQ ID NO:80;
(E) a $CDR_L2$ Domain comprising the amino acid sequence of SEQ ID NO:81; and
(F) a $CDR_L3$ Domain comprising the amino acid sequence of SEQ ID NO:82.

17. The CD16 Binding Molecule of claim 16, wherein said molecule comprises a VH Domain comprising the amino acid sequence of SEQ ID NO:83 or SEQ ID NO:84 and a VL Domain comprising the amino acid sequence of SEQ ID NO:85.

18. The CD16 Binding Molecule of claim 14, wherein said molecule is selected from the group consisting of: an antibody, a multispecific antibody, a Fab' fragment, a $F(ab')_2$ fragment, a (Fv) fragment, a single-chain (scFv), a single-chain antibody, a disulfide-linked bispecific Fv (sdFv), a diabody, a trivalent binding molecule, and a CAR-T molecule.

19. A pharmaceutical composition that comprises the CD16×Disease Antigen Binding Molecule of claim 1 and a pharmaceutically acceptable carrier.

20. A pharmaceutical composition that comprises the CD16 Binding Molecule of claim 14 and a pharmaceutically acceptable carrier.

* * * * *